US011596676B2

(12) United States Patent
Mondal et al.

(10) Patent No.: US 11,596,676 B2
(45) Date of Patent: *Mar. 7, 2023

(54) METHODS OF TREATING NONALCOHOLIC STEATOHEPATITIS COMPRISING ADMINISTERING AN ANTI-HUMAN BETA KLOTHO ANTIBODY OR BINDING FRAGMENT THEREOF

(71) Applicant: NGM Biopharmaceuticals, Inc., South San Francisco, CA (US)

(72) Inventors: Kalyani Mondal, San Mateo, CA (US); Betty Chan Li, Millbrae, CA (US); Yu Chen, Foster City, CA (US); Taruna Arora, Palo Alto, CA (US); Hugo Matern, San Mateo, CA (US); Wenyan Shen, Redwood City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 16/928,862

(22) Filed: Jul. 14, 2020

(65) Prior Publication Data
US 2021/0030857 A1    Feb. 4, 2021

Related U.S. Application Data

(63) Continuation of application No. 16/103,613, filed on Aug. 14, 2018, now Pat. No. 10,744,191, which is a continuation of application No. 15/659,177, filed on Jul. 25, 2017, now Pat. No. 10,093,735, which is a continuation of application No. 14/604,592, filed on Jan. 23, 2015, now Pat. No. 9,738,716.

(60) Provisional application No. 61/931,531, filed on Jan. 24, 2014.

(51) Int. Cl.
*A61K 39/395* (2006.01)
*A61K 39/00* (2006.01)
*C07K 16/28* (2006.01)
*G01N 33/66* (2006.01)

(52) U.S. Cl.
CPC ...... *A61K 39/001154* (2018.08); *C07K 16/28* (2013.01); *A61K 2039/505* (2013.01); *C07K 2317/24* (2013.01); *C07K 2317/34* (2013.01); *C07K 2317/75* (2013.01); *G01N 33/66* (2013.01)

(58) Field of Classification Search
None
See application file for complete search history.

(56) References Cited

U.S. PATENT DOCUMENTS

| | | |
|---|---|---|
| 6,579,850 B1 | 6/2003 | Nabesliima |
| 6,635,468 B2 | 10/2003 | Ashkenazi |
| 6,716,626 B1 | 4/2004 | Itoh |
| 6,806,352 B2 | 10/2004 | Desnoyers |
| 6,812,339 B1 | 11/2004 | Venter |
| 6,987,121 B2 | 1/2006 | Kliewer |
| 7,115,415 B2 | 10/2006 | Goddard |
| 7,129,072 B1 | 10/2006 | Schlessinger |
| 7,208,312 B1 | 4/2007 | Desnoyers |
| 7,259,248 B2 | 8/2007 | Itoh |
| 7,288,406 B2 | 10/2007 | Bogin |
| 7,390,879 B2 | 6/2008 | Ashkenazi |
| 7,459,540 B1 | 12/2008 | Thomason |
| 7,491,697 B2 | 2/2009 | Beals |
| 7,537,902 B2 | 5/2009 | Kuro-o |
| 7,576,190 B2 | 8/2009 | Glaesner |
| 7,582,607 B2 | 9/2009 | Frye |
| 7,622,445 B2 | 11/2009 | Frye |
| 7,655,627 B2 | 2/2010 | Frye |
| 7,667,005 B2 | 2/2010 | Nabeshima |
| 7,667,008 B2 | 2/2010 | Thomason |
| 7,705,195 B2 | 4/2010 | French |
| 7,723,297 B2 | 5/2010 | Itoh |
| 7,947,866 B2 | 5/2011 | Sparks |
| 8,012,931 B2 | 9/2011 | Cujec |
| 8,034,770 B2 | 10/2011 | Belouski |
| 8,188,040 B2 | 5/2012 | Belouski |
| 8,324,160 B2 | 12/2012 | Li |
| 8,361,963 B2 | 1/2013 | Belouski |
| 8,372,952 B2 | 2/2013 | Smith |
| 8,383,365 B2 | 2/2013 | Cujec |
| 8,410,051 B2 | 4/2013 | Belouski |
| 8,420,088 B2 | 4/2013 | Glass |
| 8,481,031 B2 | 7/2013 | Glass |

(Continued)

FOREIGN PATENT DOCUMENTS

| | | |
|---|---|---|
| CN | 102858802 A | 1/2013 |
| DE | 10100588 | 7/2002 |

(Continued)

OTHER PUBLICATIONS

Davidson et al., "A high-throughput shotgun mutagenesis approach to mapping B-cell antibody epitopes," Immunology, Sep. 2014, 143(1):13-20.

(Continued)

*Primary Examiner* — Christine J Saoud

(74) *Attorney, Agent, or Firm* — Fish & Richardson P.C.

(57) ABSTRACT

The present disclosure provides binding proteins, such as antibodies and binding fragments thereof, that bind beta klotho, including human beta klotho, and methods of their use, including in the treatment of nonalcoholic steatohepatitis. The present disclosure also provides exemplary specific sequences of complementarity determining regions, variable regions, heavy chains, and light chains of the antibodies and/or binding fragments thereof.

21 Claims, 23 Drawing Sheets

Specification includes a Sequence Listing.

(56) References Cited

U.S. PATENT DOCUMENTS

| | | |
|---|---|---|
| 8,535,912 B2 | 9/2013 | Sonoda |
| 8,541,369 B2 | 9/2013 | Dickinson |
| 8,580,936 B2 | 11/2013 | Williams |
| 8,618,053 B2 | 12/2013 | Belouski |
| 8,642,546 B2 | 2/2014 | Belouski |
| 8,673,860 B2 | 3/2014 | Schellenberger |
| 8,741,841 B2 | 6/2014 | Darling |
| 8,795,985 B2 | 8/2014 | Belouski |
| 8,802,697 B2 | 8/2014 | Bifulco |
| 8,809,499 B2 | 8/2014 | Fan |
| 8,835,385 B2 | 9/2014 | Belouski |
| 8,883,726 B2 | 11/2014 | Dickinson |
| 8,889,426 B2 | 11/2014 | Mohammadi |
| 8,889,621 B2 | 11/2014 | Mohammadi |
| 8,927,492 B2 | 1/2015 | Darling |
| 8,932,589 B2 | 1/2015 | Glass |
| 8,951,966 B2 | 2/2015 | Ling |
| 8,962,557 B2 | 2/2015 | Blaber |
| 8,975,223 B2 | 3/2015 | Vignati |
| 8,993,727 B2 | 3/2015 | Walker |
| 8,999,929 B2 | 4/2015 | Mohammadi |
| 9,006,400 B2 | 4/2015 | Boettcher |
| 9,089,525 B1 | 7/2015 | Ling |
| 9,273,107 B2 | 3/2016 | Ling |
| 9,290,557 B2 | 3/2016 | Ling |
| 9,580,483 B2 | 2/2017 | Ling |
| 9,670,260 B2 | 6/2017 | Ling |
| 9,738,716 B2 | 8/2017 | Mondal |
| 9,751,924 B2 | 9/2017 | Ling |
| 9,878,008 B2 | 1/2018 | Ling |
| 9,878,009 B2 | 1/2018 | Ling |
| 9,889,177 B2 | 2/2018 | Ling |
| 9,889,178 B2 | 2/2018 | Ling |
| 9,895,416 B2 | 2/2018 | Ling |
| 9,925,242 B2 | 3/2018 | Ling |
| 10,093,735 B2 | 10/2018 | Mondal et al. |
| 10,744,191 B2 | 8/2020 | Moitdal et al. |
| 10,800,843 B2 | 8/2020 | Mondal et al. |
| 2002/0012961 A1 | 1/2002 | Botstein |
| 2002/0042367 A1 | 4/2002 | Stewart |
| 2002/0082205 A1 | 6/2002 | Itoh |
| 2002/0151496 A1 | 10/2002 | Bringmann |
| 2002/0155543 A1 | 10/2002 | Adams |
| 2003/0045489 A1 | 3/2003 | Murphy |
| 2003/0065140 A1 | 4/2003 | Vernet |
| 2003/0105302 A1 | 6/2003 | Itoh |
| 2003/0113718 A1 | 6/2003 | Ashkenazi |
| 2003/0119112 A1 | 6/2003 | Baker |
| 2003/0125521 A1 | 7/2003 | Baker |
| 2003/0166051 A1 | 9/2003 | Desnoyers |
| 2003/0170822 A1 | 9/2003 | Itoh |
| 2003/0180890 A1 | 9/2003 | Conklin |
| 2003/0185846 A1 | 10/2003 | Ashkenazi |
| 2003/0220246 A1 | 11/2003 | Conklin |
| 2004/0014658 A1 | 1/2004 | Bogin |
| 2004/0126852 A1 | 7/2004 | Stewart |
| 2004/0146908 A1 | 7/2004 | Adams |
| 2004/0185494 A1 | 9/2004 | Itoh |
| 2005/0026243 A1 | 2/2005 | Stewart |
| 2005/0026832 A1 | 2/2005 | Adams |
| 2005/0107475 A1 | 5/2005 | Jones |
| 2005/0153305 A1 | 7/2005 | Vernet |
| 2005/0181375 A1 | 8/2005 | Aziz |
| 2005/0196842 A1 | 9/2005 | Botstein |
| 2006/0160181 A1 | 7/2006 | Luethy |
| 2006/0172386 A1 | 8/2006 | Itoh |
| 2006/0246540 A1 | 11/2006 | Ashkenazi |
| 2006/0275794 A1 | 12/2006 | Carrino |
| 2006/0281679 A1 | 12/2006 | Itoh |
| 2007/0037165 A1 | 2/2007 | Venter |
| 2007/0042395 A1 | 2/2007 | Botstein |
| 2007/0077626 A1 | 4/2007 | Botstein |
| 2007/0238657 A1 | 10/2007 | Itoh |
| 2007/0253966 A1 | 11/2007 | Glaesner |
| 2008/0057076 A1 | 3/2008 | Bringmann |
| 2008/0124759 A1 | 5/2008 | Conklin |
| 2008/0261236 A1 | 10/2008 | Kuro-o |
| 2009/0081658 A1 | 3/2009 | Belouchi |
| 2009/0098603 A1 | 4/2009 | Botstein |
| 2009/0196876 A1 | 8/2009 | Sparks |
| 2009/0226459 A1 | 9/2009 | Powers |
| 2009/0312265 A1 | 12/2009 | Schmidtchen |
| 2010/0158914 A1 | 6/2010 | Desnoyers |
| 2010/0184665 A1 | 7/2010 | Suzuki |
| 2010/0215657 A1 | 8/2010 | Glass |
| 2010/0239554 A1 | 9/2010 | Schellenberger |
| 2010/0240587 A1 | 9/2010 | Schlein |
| 2010/0323954 A1 | 12/2010 | Li |
| 2010/0330062 A1 | 12/2010 | Koeffler |
| 2011/0015345 A1 | 1/2011 | Pinkstaff |
| 2011/0053787 A1 | 3/2011 | Brulliard |
| 2011/0104152 A1 | 5/2011 | Sonoda |
| 2011/0107439 A1 | 5/2011 | De Wit |
| 2011/0135657 A1 | 6/2011 | Hu |
| 2011/0150903 A1 | 6/2011 | Bautin |
| 2011/0190207 A1 | 8/2011 | Mohammadi |
| 2011/0195077 A1 | 8/2011 | Glass |
| 2011/0195895 A1 | 8/2011 | Walker |
| 2011/0207912 A1 | 8/2011 | Botstein |
| 2011/0306129 A1 | 12/2011 | Nistor |
| 2011/0312881 A1 | 12/2011 | Silverman |
| 2012/0003216 A1 | 1/2012 | Belouski |
| 2012/0064544 A1 | 3/2012 | Econs |
| 2012/0172314 A1 | 7/2012 | Koeffler |
| 2012/0178699 A1 | 7/2012 | Wolf |
| 2012/0288886 A1 | 11/2012 | Mohammadi |
| 2012/0294861 A1 | 11/2012 | Sonoda |
| 2012/0308580 A1 | 12/2012 | Bertoletti |
| 2012/0328616 A1 | 12/2012 | Li |
| 2013/0004492 A1 | 1/2013 | Marshall |
| 2013/0023474 A1 | 1/2013 | Ling |
| 2013/0116171 A1 | 5/2013 | Jonker |
| 2013/0122004 A1 | 5/2013 | Glass |
| 2013/0122020 A1 | 5/2013 | Liu |
| 2013/0129725 A1 | 5/2013 | Fachini |
| 2013/0143796 A1 | 6/2013 | Li |
| 2013/0172275 A1 | 7/2013 | Mohammadi |
| 2013/0183294 A1 | 7/2013 | Pai |
| 2013/0183319 A1 | 7/2013 | Bange |
| 2013/0184211 A1 | 7/2013 | Mohammadi |
| 2013/0231277 A1 | 9/2013 | Mohammadi |
| 2013/0324458 A1 | 12/2013 | Glass |
| 2013/0324701 A1 | 12/2013 | Williams |
| 2013/0331317 A1 | 12/2013 | Mohammadi |
| 2013/0331325 A1 | 12/2013 | Mohammadi |
| 2014/0094406 A1 | 4/2014 | Mohammadi |
| 2014/0148388 A1 | 5/2014 | Sonoda |
| 2014/0155316 A1 | 6/2014 | Mohammadi |
| 2014/0189893 A1 | 7/2014 | Li |
| 2014/0194352 A1 | 7/2014 | Ling |
| 2014/0243260 A1 | 8/2014 | Mohammadi |
| 2014/0243266 A1 | 8/2014 | Ling |
| 2014/0363435 A1 | 12/2014 | Desnoyers |
| 2015/0079065 A1 | 3/2015 | Wolf |
| 2015/0111821 A1 | 4/2015 | Suh |
| 2015/0210764 A1 | 7/2015 | Mondal |
| 2015/0284442 A1 | 10/2015 | Ling |
| 2015/0291677 A1 | 10/2015 | Ling |
| 2016/0045565 A1 | 2/2016 | Ling |
| 2016/0166642 A1 | 6/2016 | Ling |
| 2016/0168215 A1 | 6/2016 | Ling |
| 2016/0168216 A1 | 6/2016 | Ling |
| 2016/0168217 A1 | 6/2016 | Ling |
| 2016/0168218 A1 | 6/2016 | Ling |
| 2016/0168219 A1 | 6/2016 | Ling |
| 2016/0168220 A1 | 6/2016 | Ling |
| 2016/0168221 A1 | 6/2016 | Ling |
| 2016/0168222 A1 | 6/2016 | Ling |
| 2016/0200788 A1 | 7/2016 | Ling |
| 2016/0252497 A1 | 9/2016 | Ling |
| 2017/0182122 A1 | 6/2017 | Ling |
| 2017/0182123 A1 | 6/2017 | Ling |
| 2017/0232067 A1 | 8/2017 | Lindhout |
| 2017/0327551 A1 | 11/2017 | Ling |

(56) References Cited

U.S. PATENT DOCUMENTS

| | | |
|---|---|---|
| 2018/0100014 A1 | 4/2018 | Mondal et al. |
| 2019/0106490 A1 | 4/2019 | Mondal et al. |
| 2019/0338046 A1 | 11/2019 | Mondal et al. |
| 2021/0115133 A1 | 4/2021 | Mondal et al. |

FOREIGN PATENT DOCUMENTS

| | | |
|---|---|---|
| DE | 10100587 | 11/2002 |
| EP | 2163626 A1 | 3/2010 |
| EP | 2510009 B1 | 4/2017 |
| JP | 2001072607 A | 3/2001 |
| JP | 2002112772 A | 4/2002 |
| JP | 2003334088 A | 11/2003 |
| JP | 2006158339 A | 6/2006 |
| JP | 2006240990 | 9/2006 |
| JP | 2009039117 A | 2/2009 |
| JP | 2013194049 A | 9/2013 |
| NZ | 602702 | 3/2014 |
| WO | WO 1998/029544 | 7/1998 |
| WO | WO 2000/060085 | 10/2000 |
| WO | WO 2001/018209 A1 | 3/2001 |
| WO | WO 2001/038529 A1 | 5/2001 |
| WO | WO 2001/049740 A1 | 7/2001 |
| WO | WO 2001/049849 A1 | 7/2001 |
| WO | WO 2001/061007 A2 | 8/2001 |
| WO | WO 2002/036732 A2 | 5/2002 |
| WO | WO 2002/041911 A2 | 5/2002 |
| WO | WO 2002/055693 A2 | 7/2002 |
| WO | WO 2003/080803 A2 | 10/2003 |
| WO | WO 2004/026228 A2 | 4/2004 |
| WO | WO 2004/063355 A2 | 7/2004 |
| WO | WO 2006/004076 A1 | 1/2006 |
| WO | WO 2006/048291 A2 | 5/2006 |
| WO | WO 2006/049854 A2 | 5/2006 |
| WO | WO 2008/021196 A2 | 2/2008 |
| WO | WO 2008/030273 A2 | 3/2008 |
| WO | WO 2008/123625 A1 | 10/2008 |
| WO | WO 2008/135993 A1 | 11/2008 |
| WO | WO 2009/009173 A2 | 1/2009 |
| WO | WO 2009/076478 A2 | 6/2009 |
| WO | WO 2009/090553 A2 | 7/2009 |
| WO | WO 2009/095372 A1 | 8/2009 |
| WO | WO 2009/116861 A2 | 9/2009 |
| WO | WO 2010/004204 A2 | 1/2010 |
| WO | WO 2010/006214 A1 | 1/2010 |
| WO | WO 2010/042747 A2 | 4/2010 |
| WO | WO 2010/065439 A1 | 6/2010 |
| WO | WO 2010/080976 A1 | 7/2010 |
| WO | WO 2010/083051 A2 | 7/2010 |
| WO | WO 2010/12 9600 A2 | 11/2010 |
| WO | WO 2010/139741 A1 | 12/2010 |
| WO | WO 2010/142665 A1 | 12/2010 |
| WO | WO 2010/148142 A1 | 12/2010 |
| WO | WO 2011/047267 A1 | 4/2011 |
| WO | WO 2011/068893 A1 | 6/2011 |
| WO | WO 2011/071783 A1 | 6/2011 |
| WO | WO 2011/084808 A2 | 7/2011 |
| WO | WO 2011/089203 A1 | 7/2011 |
| WO | WO 2011/092234 A1 | 8/2011 |
| WO | WO 2011/130417 A2 | 10/2011 |
| WO | WO 2011/130729 A2 | 10/2011 |
| WO | WO 2011/154349 A2 | 12/2011 |
| WO | WO 2012/010553 A1 | 1/2012 |
| WO | WO 2012/031603 A2 | 3/2012 |
| WO | WO 2012/062078 A1 | 5/2012 |
| WO | WO 2012/066075 A1 | 5/2012 |
| WO | WO 2012/086809 A1 | 6/2012 |
| WO | WO 2012/138919 A2 | 10/2012 |
| WO | WO 2012/140650 A2 | 10/2012 |
| WO | WO 2012/154263 A1 | 11/2012 |
| WO | WO 2012/158704 A1 | 11/2012 |
| WO | WO 2012/170438 A2 | 12/2012 |
| WO | WO 2012/170704 A2 | 12/2012 |
| WO | WO 2012/177481 A2 | 12/2012 |
| WO | WO 2013/006486 A2 | 1/2013 |
| WO | WO 2013/010780 A1 | 1/2013 |
| WO | WO 2013/027191 A1 | 2/2013 |
| WO | WO 2013/033452 A2 | 3/2013 |
| WO | WO 2013/049234 A2 | 4/2013 |
| WO | WO 2013/109856 A2 | 7/2013 |
| WO | WO 2013/131091 A1 | 9/2013 |
| WO | WO 2013/151671 A1 | 10/2013 |
| WO | WO 2013/173158 A1 | 11/2013 |
| WO | WO 2013/184958 A1 | 12/2013 |
| WO | WO 2013/184960 A2 | 12/2013 |
| WO | WO 2013/184962 A1 | 12/2013 |
| WO | WO 2013/188182 A1 | 12/2013 |
| WO | WO 2014/031420 A1 | 2/2014 |
| WO | WO 2014/037373 A1 | 3/2014 |
| WO | WO 2014/085365 A2 | 6/2014 |
| WO | WO 2014/105939 A1 | 7/2014 |
| WO | WO 2014/130659 A1 | 8/2014 |
| WO | WO 2014/149699 A1 | 9/2014 |
| WO | WO 2014/152090 A1 | 9/2014 |
| WO | WO 2015/065897 A1 | 5/2015 |
| WO | WO 2/15/100366 | 7/2015 |
| WO | WO 2015/112886 A2 | 7/2015 |
| WO | WO 2015/183890 A2 | 12/2015 |
| WO | WO 2015/195509 A2 | 12/2015 |
| WO | WO 2016/065106 A1 | 4/2016 |
| WO | WO 2016/073855 A1 | 5/2016 |
| WO | WO 2017/083276 A1 | 5/2017 |
| WO | WO 2018/039557 A1 | 3/2018 |
| WO | WO 2018/044778 A1 | 3/2018 |

OTHER PUBLICATIONS

Adams et al., "FGF21 requires B klotho to act in vivo," PloS One, 2012, 7(11):e49977.

Aranha et al., "Bile acid levels are increased in the liver of patients with steatohepatitis," Eur. J. Gastroenterol. Hepatol., 2008, 20(6):519-525.

Beenken et al., "The FGF family: biology, pathophysiology and therapy," Nat. Rev. Drug Discov., 2009, 8:235-253.

Beuers et al., "Medical treatment of primary sclerosing cholangitis: a role for novel bile acids and other (post-) transcriptional modulators?" Clin. Rev. Allergy Immunol., 2009, 36(1):52-61.

Bromberg et al., "Stat3 as an oncogene," Cell, 1999, 98:295-303.

Calvisi et al., "Ubiquitous activation of Ras and Jak/Stat pathways in human HCC," Gastroenterol., 2006, 130:1117-1128.

Camilleri et al., "Measurement of Serum 7α-hydroxy-4-cholesten-3-one (or 7αC4), a Surrogate Test for Bile Acid Malabsorption in Health, Ileal Disease and Irritable Bowel Syndrome using Liquid Chromatography-Tandem Mass Spectrometry," Neurogastroenterol, 2009, Motil., 21(7):734-43.

Casset et al., "A peptide mimetic of an anti-CD4 monoclonal antibody by rational design," Biochem. Biophys. Res. Commun., 2003, 307:198-205.

Chazouilleres, "Primary sclerosing cholangitis and bile acids," Clinics and Research in Hepatology and Gastroenterology, 2012, 36:S21-S25.

Chen et al., "Selection and Analysis of an Optimized Anti-VEGF Antibody: Crystal Structure of an Affinity-matured Fab in Complex with Antigen," J. Mol. Biol., 1999, 293:865-881.

Chen et al., "Soluble FGFR4 extracellular domain inhibits FGF19-induced activation of FGFR4 signaling and prevents nonalcoholic fatty liver disease," Biochem. Biophys. Res. Comm., 2011, 409:651-656.

Chen et al., "Sorafenib overcomes TRAIL resistance of hepatocellular carcinoma cells through the inhibition of STAT3," Clin. Cancer Res., 2010, 16:5189-5199.

Claudel et al., "Role of Nuclear Receptors for Bile Acid Metabolism, Bile Secretion, Cholestasis, and Gallstone Disease," Biochim. Biophys. Acta, 2011, 1812:867-878.

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., 2002, 169:3076-3084.

(56) References Cited

OTHER PUBLICATIONS

Desnoyers et al., "Targeting FGF19 inhibits tumor growth in colon cancer xenograft and FGF19 transgenic hepatocellular carcinoma models," Oncogene, 2008, 27:85-97.
Durovcová et al., "Plasma Concentration of Fibroblast Growth Factors 21 and 19 in Patients with Cushing's Syndrome," Physiol. Res., 2010, 59:415-422.
Foltz et al., "Supplementary Materials for: Treating Diabetes and Obesity with an FGF21-Mimetic Antibody Activating the βKlotho/FGFR1c Receptor Complex," Sci. Transl. Med., 2012, 4:162ra153, 1-13.
Foltz et al., "Treating Diabetes and Obesity with an FGF21-Mimetic Antibody Activating the βKlotho/FGFR1c Receptor Complex," Sci. Transl. Med., 2012, 4(162):1-10.
French et al., "Targeting FGFR4 Inhibits Hepatocellular Carcinoma in Preclimcai Mouse Models," PLoS One, 2012, 7(5):e36713, 1-12.
Fukumoto et al., "FGF23 is a hormone-regulating phosphate metabolism—unique biological characteristics of FGF23," Bone, 2007, 40(5):1190-1195.
Ge et al., "Characterization of a FGF19 Variant with Altered Receptor Specificity Revealed a Central Role for FGFR1c in the Regulation of Glucose Metabolism," PLoS One, 2012, 7(3):e33603, 1-9.
GenBank EHH53620.1: Beta-klotho (Macaca fascicularis)[online] Nov. 4, 2011 [retrieved Mar. 28, 2015], Available on the internet: <URL: http://www.ncbi.nlm.nih.gov/protein/355749221?sat=37&satkey=109028311, 2 pages.
Goetz et al., "Molecular insights into the klotho-dependent, endocrine mode of action of fibroblast growth factor 19 subfamily members." Mol. Cell. Biol., 2007, 27(9):3417-3428.
Harmer et al., "The Crystal Structure of Fibroblast Growth Factor (FGF) 19 Reveals Novel Features of the FGF Family and Offers a Structural Basis for Its Unusual Receptor Affinity'," Biochemistry, 2004, 43:629-640.
Hasegawa, "The expansion of PROMININ-1-positive epithelial-mesenchymal cells within periportal fibrosis of rotavirus induced biliaiy atresia," Hepatol., 2013, 58:802A.
He et al., "Hepatocyte IKKbeta/NF-kappaB inhibits tumor promotion and progression by preventing oxidative stress-driven STAT3 activation," Cancer Cell, 2010, 17:286-297.
He et al., "Identification of liver cancer progenitors whose malignant progression depends on autocrine IL-6 signaling," Cell, 2013, 155:384-396.
He et al., "NF-κB and STAT3—key players in liver inflammation and cancer," Cell Res., 2011, 21:159-168.
Hofmann et al., "Chronic diarrhea due to excessive bile acid synthesis and not defective ileal transport: A new syndrome of defective FGF19 release." Clin. Gastroenterol. Hepatol., 2009, 7(11):1151-1154.
Holm et al., "Functional mapping and single drain construction of the anti-cytokeratin 8 monoclonal antibody TS1," Mol. Immunol., 2007, 44:1075-1084.
Holt et al., "Definition of a novel growth factor-dependent signal cascade for the suppression of bile acid biosynthesis," Genes Dev., 2003, 17:1581-1591.
Ikeda et al., "Leptin receptor somatic mutations are frequent in HCV-infected cirrhotic liver and associated with hepatocellular carcinoma," Gastroenterol., 2014, 146:222-232.
Inagaki et al., "Fibroblast Growth Factor 15 Functions as an Enterohepatic Signal to Regulate Bile Acid Homeostasis," Cell Metabolism, 2005, 2:217-225.
Ito et al., "Molecular cloning and expression analyses of mouse beta klotho, which encodes a novel Klotho family protein," Mech. Dev., 2000, 98(1-2):115-119.
Kakumu et al., "Interleukin 6 production by peripheral blood mononuclear cells in patients with chronic hepatitis B virus infection and primary biliaiy cirrhosis," Gastroenterologia Japonica, 1993, 28:18-24.

Karras et al., "STAT3 regulates the growth and immunoglobulin production of BCL(1) B cell lymphoma through control of cell cycle progression," Cellular Immunol., 2000, 202:124-135.
Kenakin et al., "Signalling bias in new drug discovery: detection, quantification and therapeutic impact," Nat. Rev. Drug Discov., 2013, 12:205-216.
Kir et al., "Roles of FGF19 in Liver Metabolism," Cold Spring Harb. Symp. Quant. Biol., 2011, 76:139-144.
Kumar et al., "Molecular cloning and expression of the Fabs of human autoantibodies in *Escherichia coli*. Determination of the heavy or light chain contribution to the anti-DNA/-cardiolipin activity of the Fab," J. Biol. Chem., 2000, 275:35129-35136.
Kuro-O; Endocrine FGFs andKlothos, Springer-Verlag, New York, chapter 2, pp. 25-40 (2012).
Kurosu et al., "Regulation of fibroblast growth factor-23 signaling bv klotho," J. Biol. Chem., 2006, 281(10):6120-6123.
Kurosu et al., "Supplemental Data For: Tissue-specific Expression of βKlotho and Fibroblast Growth Factor (FGF) Receptor Isoforms Determines Metabolic Activity of FGF19 and FGF21," J. Biol. Chem., (2007) (available at: http://www.jbc.org/content/suppl/2007/07/11/M704165200.DC1/Kurosu_Suppl_Data.pdf (last visited Jul. 23, 2014), 2 pages.
Kurosu et al., "Tissue-specific Expression of βKlotho and Fibroblast Growth Factor (FGF) Receptor Isoforms Determines Metabolic Activity of FGF19 and FGF21," J. Biol. Chem., 2007, 282(37):26687-26695.
Lee et al., "Structures of β-klotho reveal a 'zip code'-like mechanism for endocrine FGF signaling," Nature, 2018, 553:501-505, Extended Data.
Lin et al., "Liver-specific Activities of FGF19 Require Klotho beta," J. Biol. Chem., 2007, 282(37):27277-27284.
Lin et al., "The STAT3 inhibitor NSC 74859 is effective in hepatocellular cancers with disrupted TGF-beta signaling." Oncogene, 2009, 28:961-972.
Lindor, "Ursodeoxycholic acid for the treatment of primary biliary cirrhosis," New Engl. J Med., 2007, 357:1524-1529.
Ling et al., "Identification of Gut Factors that Mimic the Metabolic Benefits Seen After Gastric Bypass Surgery," American Diabetes Association, 72nd Scientific Sessions, Jun. 8-12, 2012, Philadelphia, PA, http://www.abstactsonline.com.
Ling et al., NGM Biopharmaceuticals, Identification of Gut Factors that Mimic the Metabolic Benefits of Gastric Bypass Surgery, p. 1, Jun. 8-12, 2012, Abstract.
Luo et al., "A nontumorigenic variant of FGF19 treats cholestatic liver diseases," Sci. Transl. Med., 2014, 6:247ra100, 1-11.
MacCallum et al., "Antibody-antigen Interactions: Contact Analysis and Binding Site Topography," J. Mol.Biol., 1996, 262:732-745.
Mellor, "Targeted inhibition of the FGF19-FGFR4 pathway in hepatocellular carcinoma; translational safety considerations," Liver Int., 2014, e1-e9.
Micanovic et al., "Different roles of N- and C-termini in the functional activity of FGF21," J. Cell. Physiol., 2009, 219:227-234.
Miyata et al., "Involvement of Multiple Elements in FXR-mediated Transcriptional Activation of FGF19," J. Steroid Biochm. Mol. Biol., 2012, 132:41-47.
Moyers et al., "Molecular determinants of FGF-21 activity-synergy and cross-talk with PPARgamma signaling," J. Cell. Physiol., 2007, 210(1):1-6.
NCBI Reference Sequence: NP_783864.1: beta-klotho (*Homo sapiens*) [online] Nov. 2, 2013 [retrieved Mar. 28, 2015], Available on the internet: URL:http://www.uniprot.org/uniprot/Q86Z14.txt?version=93, 3 pages.
Nicholes et al., "A Mouse Model of Hepatocellular Carcinoma: Ectopic Expression of Fibroblast Growth Factor in Skeletal Muscle of Transgenic Mice," Amer. J. Pathol., 2002, 160:2295-2307.
Ogawa et al., "Beta Klotho is Required for Metabolic Activity of Fibroblast Growth Factor 21," Proc. Natl. Acad. Sci, USA, 2007, 104:7432-7437.
Pai et al., "Antibody-Mediated Inhibition of Fibroblast Growth Factor 19 Results in Increased Bile Acids Synthesis and Ileal Malabsorption of Bile Acids in Cynomolgus Monkeys," Toxicological Sciences, 2012, 126(2):446-456.

(56) References Cited

OTHER PUBLICATIONS

Pattni et al., "Fibroblast Growth Factor 19 and 7α-Hydroxy-4-Cholesten-3-one in the Diagnosis of Patients With Possible Bile Acid Diarrhea," Clinical and Translational Gastroenterology, 2012, 3:e18, 7 pages.
Potthoff et al., "Endocrine Fibroblast Growth Factors 15/19 and 21: From Feast to Famine," Genes Dev., 2012, 26:312-324.
Pusl et al., "Intrahepatic cholestasis of pregnancy," Orphanet. J Rare Diseases, 2007, 2:26.
R&D Systems, "Monoclonal Anti-human/mouse Klotho β Antibody," catalog No. MAB3738, Feb. 6, 2007, 1 page.
Rose et al., "Molecular Control of Systemic Bile Acid Homeostasis by the Liver Glucocorticoid Receptor," Cell Metabolism, 2011, 14:123-130.
Rossi et al., "Ngm282. a Novel Specific Inhibitor of Cyp7a1-Mediated Bile Acid Synthesis, is Safe and Well Tolerated with Predictable Pharmacokinetics in Healthy Human Subjects," Journal of Hepatology, 2014, 60(1): S533.
Ryan et al., "FXR is a Molecular Target for the Effects of Vertical Sleeve Gastroectomy," Nature, 509(7499):183-188, 2014, epub ahead of print Mar. 26, 2014.
Sawey et al., "Identification of a Therapeutic Strategy Targeting Amplified FGF19 in Liver Cancer by Oncogenomic Screening," Cancer Cell. 2011. 19(3):347-358.
Schaap et al., "High expression of the bile salt-homeostatic hormone fibroblast growth factor 19 in the liver of patients with extrahepatic cholestasis," Hepatol., 2009, 49:1228-1235.
Schaap, "Role of Fibroblast Growth Factor 19 in the Control of Glucose Homeostasis," Curr. Opin. Clin. Nutr. Metab. Care, 2012, 15(4):386-391.
Smith et al., "FGF21 Can be Mimicked In Vitro and In Vivo by a Novel Anti-FGFR1c/b-Klotho Bispecific Protein," PLoS One, 2013, 8(4):1-11.
Smith-Gill et al., "Contributions of Immunoglobulin Heavy and Light Chains to Antibody Specificity for Lysozyme and Two Haptens," J. Immunol., 1987, 139:4135-4144.
Song et al., "Light Chain of Natural Antibody Plays a Dominant Role in Protein Antigen Binding," Biochem. Biophys. Res. Comm., 2000, 268:390-394.
Tartaglia et al., "Identification and expression cloning of a leptin receptor, OB-R," Cell, 1995, 83:1263-1271.
Tomlinson et al., "Transgenic Mice Expressing Human Fibroblast Growth Factor-19 Display Increased Metabolic Rate and Decreased Adiposity," Endocrinology, 2002, 143(5):1741-1747.
Urakawa et al., "Klotho converts canonical FGF receptor into a specific receptor for FGF23," Nature, 2006, 444(7210):770-774.
Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.
Walters et al., "Managing bile acid diarrhoea," Ther. Adv. Gastroenterol., 2010, 3(6):349-357.
Walters, "A variant of FGF19 for treatment of disorders of cholestasis and bile acid metabolism," Ann. Transl. Med., 2015, 3(S1):S7.
Wang et al., "Leptin in hepatocellular carcinoma," World J. Gastroenterol., 2010, 16:5801-5809.
Wu et al., "FGF19 Regulates Cell Proliferation, Glucose and Bile Acid Metabolism via FGFR4-Dependent and Independent Pathways," PLoS One, 2011, 6(3):e17868, 1-11.
Wu et al., "C-tenninal Tail of FGF19 Determines Its Specificity toward Klotho C-receptors," J. Biol. Chem., 2008, 283(48):33304-33309.
Wu et al., "FGF19-induced Hepatocyte Proliferation is Mediated Through FGFR4 Activation," J. Biol. Chem., 2010, 285(8):5165-5170.
Wu et al., "Humanization of a Murine Monoclonal Antibody by Simultaneous Optimization of Framework and CDR Residues," J. Mol. Biol., 1999, 294:151-162.
Wu et al., "Role of FGF 19 Induced FGFR4 Activation in the Regulation of Glucose Homeostasis," Aging, 2009, 1(12):1023-1027.
Wu et al., "Selective Activation of FGFR4 by an FGF19 Variant Does Not improve Glucose Metabolism in ob/ob Mice," Proc. Natl. Acad. Sci. USA, 2009, 106(34):14379-14384.
Wu et al., "Separating Mitogenic and Metabolic Activities of Fibroblast Growth Factor 19 (FGF19)," Proc. Natl. Acad. Sci. USA, 2010, 107(32):14158-14163.
Wu et al., "Therapeutic Utilities of Fibroblast Growth Factor 19," Expert Opin. Ther. Targets, 2011, 15(11):1307-1316.
Xie et al., "FGF-19, A Novel Fibroblast Growth Factor with Unique Specificity for FGFR4," Cytokine, 1999, 11(10):729-735.
Zhang et al., "Adenovirus-adeno-associated virus hybrid for large-scale recombinant adeno-associated virus production," Hum. Gene Ther., 2009, 20:922-929.
Zhang et al., "Fibroblast growth factor 21 analogs for treating metabolic disorders," Front Endocrinol., 2015, 6(168):1-9.
Zhou et al., "Engineered fibroblast growth factor 19 reduces liver injury and resolves sclerosing cholangitis in Mdr2-deficient mice," Hepatology, 2016, 63(3):914-929.
Zhou et al., "Separating Tumorigenicity from Bile Acid Regulatory Activity for Endocrine Hormone FGF19," Cancer Research, 2014, 74(12):3306-3316.

```
Kabat    1          10          22              31-----35       40              50---abc------60---65
AbM      1          10          22         26-----35            40              50---abc------58      65
Chothia  1          10          22         26-----32            40                   abc----55        65
Contact  1          10          22              30-----35       40              50---abc------58      65
IMGT     1          10          23         27-----38  41                             56------65        74
AHon     1                      23              27         42         47-----57                       76

5H23  QVQLQQSGPELVKPGALVKISCKAS GYTFTS-YDIN WVKQRPGQGLEWIG WIYP--GDGSTKYNEKFKG
1C17  QVQLQESGPGLVKPSQSLSLTCSVT GYSITSGYYWN WIRQFPGNKLEWMG YIN----YDGNSNYTPSLKN
1D19  QVQPESGPELVKPGALVKISCKAS GYTFTR-YDIN WMKQRPGQGLEWIG WIYP--GDSSTKFNENFKD
2L12  QVQLQESGPELVKPGALVKISCKAS GYTFTR-YDIN WVKKRPGQGLEWIG WIYP--GDDSTKYNEKFKG
3L3   QVQPQESGPELVKPGTLVKISCKAS GYTFTS-YDIN WVKQRPGQGLEWIG WIYP--GDGSPKYDEKFKG
3N20  QVQLQESGAELARPGASVKLSCKVS GYIFTN-YGIS WVKQRTGQGLEWIG EIYP--RSGNTYYNEKFKG
4P5   QVQLQQSGPELVKPGALVKISCKAS GYTFTR-YDIN WVKKRPGQGLEWIG WIYP----GDDSTKYNEKFKG
5C23  QVQPQESGPELVKPGALVKISCKAS GYTFTR-YDIN WVKKRPGQGLEWIG WIYP--GDGSTKYNEKFEG
5F7   QVQPQESGPELVKPGALVKISCKAS GYTFTR-YDIN WVKQRPGQGLEWIG WIYP--GDISTKYNEKFKG
1G19  QVQLQESGPGLVKPSQSLSLTCSVT GYSITSGYYWN WIRQFPGNKLEWMG YIN----YGGSNNYNPSLKN

Kabat    70         80        abc     90         95---100-----102               110
AbM      70         80        abc     90         95---100-----102               110
Chothia  70         80        abc     90         96-100----101                  110
Contact  70         80        abc     90    93---100----101                     110
IMGT     75                            89  105-------------117
AHon                                 106 109                  138

5H23  KATLTADKSSRTAYMQLSSLTSENSAVYFCAR SDYYGSRSF--AY WGQGTLVTVSA  (SEQ ID NO:25)
1C17  RISITRDTSKNQFFLKLNSVTPEDTATYYCAR KGAYYSNYDSFDV WGTGTTVTVSS  (SEQ ID NO:51)
1D19  KATLTADKSSSTAYMQLSSLTSENSTVYFCAR SDYYGSRSF---TY WGQGTLVTVSA (SEQ ID NO:77)
2L12  KATLTADKSSSTAYMQLSSLTSENSAVYFCAR SDYYGSRSF---VY WGQGTLVTVSA (SEQ ID NO:103)
3L3   KATLTADKSSSTAYMQLSSLTSENSAVYFCAR SDYYGSRSF---VY WGQGTSLTVSS (SEQ ID NO:129)
3N20  KATLTADMSSSTAYMDLRSLTSEDSAVYFCAR HWDGVLDYF--DY WGQGTSLTVSS  (SEQ ID NO:155)
4P5   KATLTADKSSSTAYMQLSSLTSENSAVYFCAR SDYYGSRSF--VY WGQGTLVTVSA  (SEQ ID NO:181)
5C23  KATLTADKSSSTAYMQLSSLTSENSAVYFCAR SDYYGSRSF---VY WGQGTLVTVSA (SEQ ID NO:207)
5F7   KATLTADKSSSTAYMQLSSLTSENSAVYFCAR SDYYGSRSF---VY WGQGTLVTVSA (SEQ ID NO:233)
1G19  RISITRDTSKNQFFLKLTSVTTEDTATYYCAR RGAYYSNYDSFDV WGTGTTVTVSS  (SEQ ID NO:259)
```

FIGURE 1A

```
Kabat     1           10          20            24-27abcd----34          40       50-----56
AbM       1           10          20            24----30abcd----34       40       50-----56
Chothia   1           10          20            26--30abcd----32         40       50--
Contact   1           10          20                    30abcd------36   40              46-----55
IMGT      1                          23        27----------38    41                       56-65 69
                                                                                              1-

AHon      1                          23                42                58                      72
5H23      DIVLTQSPASLAVSLGQRATISC RASKSVST----SGYVYMH WNQQKPGQPPKLLIY LASYLES
1C17      DIKMTQSPSSMYASLGERVTITC KASQDINS-------YLS  WVQQKPGKSPKTLIY RANRLVD
1D19      DIVLTQSPASLAVSLGQRATISC RASKSVST--SGYSYMH   WYQQKPGQPPKLLIY LASNLES
2L12      DIVLTQSPASLPVSLGQRATISC RASKSVST--SGYSYLH   WYQQKPGQPPKLLIY LASNLES
3L3       DIVLTQSPASLAVSLGQRATISC RASKSVST--SGYSYVH   WYQQKPGQPPKLLIY LASNLES
3N20      DIVMTQSPSSLSVSAGEKVTMSC KSSQSLLNSGNQKNYLA   WYQQKPGQPPKLLIY GASTRES
4P5       DILLTQSPASLAVSLGQRATISC RASKSVST--SGYSYMH   WYQQKPGQPPKLLIY LASNLES
5C23      DIVLTQSPDSLTVSLGQRATISC RASKSVST--SGYSYMH   WYQQKPGQPPKLLIY LASNLES
5F7       DIVLTQSPASLAVSLGQRATISC RASKSVST--SGYSYMH   WYQQKPGQPPKLLIY LASNLES
1G19      DIKMTQSPSSMYASLGERVTITC KASQDINS-------YLS  WFQQKPGKSPKTLIY RANRLVD

Kabat           60              70              80              89-----97
AbM             60              70              80              89-----97
Chothia         60              70              80                91----96
Contact         60              70              80              89-----96
IMGT            70              89                              105-----117
AHon            73              91                              107    138
5H23      GVPARFSGSGSGSGTDFTLNIHPVEEEDAATYYC QHSRDLTFP FGGGTKLEIK  (SEQ ID NO:26)
1C17      GVPSRFSGSGSGSGTDYSLTISSLEYEDMGIYYC LQYDEFPFT FGSGTKLEIK  (SEQ ID NO:52)
1D19      GVPARFSGSGSGSGTDFTLNIHPVEEEDAATYYC QHSRELPYT FGGGTKLEIK  (SEQ ID NO:78)
2L12      GVPARFSGSGSGSGTDFTLNIHPVEEEDAATYYC QHSGELPYT FGGGTKLEIK  (SEQ ID NO:104)
3L3       GVPDRFTGSGSGSGTDFTLTISSVQAEDLAVYYC QHSGELPYT FGAGTKLELK  (SEQ ID NO:130)
3N20      GVPARFSGRGSGSGTDFTLNIHPVEEEDAATYYC LNDHSYPFT FGGGTKLEIK  (SEQ ID NO:156)
4P5       GVPARFSGSGSGSGTDFTLNIHPVEEEDAATYYC HHSGELPYT FGGGTKLEIK  (SEQ ID NO:182)
5C23      GVPSRFSGSGSGSGTDFTLNIHPVEEEDAATYYC QHSRELPYT FGGGTKLEIK  (SEQ ID NO:208)
5F7       GVPARFSGSGSGSGTDFTLNIHPVEEEDAATYYC QHSRELPYT FGGGTKVEIK  (SEQ ID NO:234)
1G19      GVPSRFSGSGSGSGQDYSLTISSLEYEEMGIYYC LQYDEFPYT FGGGTKLEIK  (SEQ ID NO:260)
```

FIGURE 1B

```
VH Domain
Kabat     1        22                 31-----35        40          50--abc------60----65
AbM       1  10    22            26-----35             40          50--abc------58    65
Chothia   1  10    22            26-----32             40                 abc--55     65
Contact   1  10    22                 30-----35        40          47------abc--58    65
IMGT      1  10    23            27-----38             41                 56--------65 74
AHon      1        23                 27              42                  57              76
5H23      QVQLQQSGPELVKPGALVKISCKAS GYTFTS--YDIN WVKQRPGQGLEWIG WIYP--GDGNSTKYNEKFKG
1D19      QVQPQESGPELVKPGALVKISCKAS GYTFTR--YDIN WMKQRPGQGLEWIG WIYP--GDSSTKFNENFKD
2L12      QVQLQQSGPELVKPGALVKISCKAS GYTFTR--YDIN WVKKRPGQGLEWIG WIYP--GDDSTKYNEKFKG
3L3       QVQPQESGPELVKPGTLVKISCKAS GYTFTS--YDIN WVKKRPGQGLEWIG WIYP--GDGSFKYDEKFKG
4P5       QVQLQQSGPELVKPGALVKISCKAS GYTFTR--YDIN WVKKRPGQGLEWIG WIYP--GDDSTKYNEKFKG
5C23      QVQPQESGPELVKPGALVKISCKAS GYTFTR--YDIN WVKQRPGQGLEWIG WIYP--GDGSTKYNEKFEG
5F7       QVQPQESGPELVKPGALVKISCKAS GYTFTR--YDIN WVKQRPGQGLEWIG WIYP--GDISTKYNEKFKG
consensus                           GYTFTR-YDIN                 WIYP--GDX$_1$STKYNEKFKG
                                    (SEQ ID NO:1)                where X$_1$ = G,D,S,I
                                                                 (SEQ ID NO:262)
or
consensus                           GYTFT X$_1$-YDIN             WIYP--GDX$_1$STKYNEKFKG
                                    where X$_1$ = R,S            where X$_1$ = G,D,S,I
                                    (SEQ ID NO:261)              (SEQ ID NO:262)

1C17      QVQLQESGPGLVKPSQSLSLTCSVT GYSITSGYYWN WIRQFPGNKLEWMG YIN---YDGNSNYTPSLKN
1G19      QVQLQESGPGLVKPSQSLSLTCSVT GYSITSGYYWN WIRQFPGNKLEWMG YIN---YGGSNNYNPSLKN
consensus                           GYSITSGYYWN                YIN---YX$_1$GX$_2$X$_3$NYX$_4$PSLKN
                                    (SEQ ID NO:27)             where X$_1$ = D,G
                                                               where X$_2$ = N,S
                                                               where X$_3$ = S,N
                                                               where X$_4$ = T,N
                                                               (SEQ ID NO:264)

3N20      QVQLQESGAELARPGASVKLSCKVS GYIFTN--YGIS WVKQRTGQGLEWIG EIYP--RSGNTYYNEKFKG
```

FIGURE 2A-1

```
VH Domain (continued)

Kabat     70           80  abc             90            95--100----102              110
AbM       70           80  abc             90            95--100----102              110
Chothia   70           80  abc             90            96-100----101               110
Contact   70           80  abc             90            ---100---101                110
IMGT      75           89                  93----------105--------------117
AHon                                             106 109                 138
5H23   KATLTADKSSRTAYMQLSSLTSENSAVYFCAR SDYYGSRSF--AY WGQGTLVTVSA (SEQ ID NO:25)
1D19   KATLTADKSSSTAYMQLSSLTSENSTVYFCAR SDYYGSRSF--TY WGQGTLVTVSA (SEQ ID NO:77)
2L12   KATLTADKSSSTAYMQLSSLTSENSAVYFCAR SDYYGSRSF--VY WGQGTLVTVSA (SEQ ID NO:103)
3L3    KATLTADKSSSTAYMQLSSLTSENSAVYFCAR SDYYGSRSF---VY WGQGTLVTVSA (SEQ ID NO:129)
4P5    KATLTADKSSSTAYMQLSSLTSENSAVYFCAR SDYYGSRSF---VY WGQGTLVTVSA (SEQ ID NO:181)
5C23   KATLTADKSSSTAYMQLSSLTSENSAVYFCAR SDYYGSRSF--VY WGQGTLVTVSA (SEQ ID NO:207)
5F7    KATLTADKSSSTAYMQLNSLTSENSAVYFCAR SDYYGSRSF--VY WGQGTLVTVSA (SEQ ID NO:233)
consensus                               SDYYGSRSF--VY
or                                      (SEQ ID NO:81)

consensus                               SDYYGSRSF--X1Y where X1 = V,T,A
1C17   RISITRDTSKNQFFLKLNSVTPEDTATYYCAR KGAYYSNYDSFDV WGTGTTVTVSS (SEQ ID NO:51)
1G19   RISITRDTSKNQFFLKLITSVTTEDTATYYCAR RGAYYSNYDSFDV WGTGTTVTVSS (SEQ ID NO:259)
consensus                              X1GAYYSNYDSFDV where X1 = K,R
                                       (SEQ ID NO:265)

3N20   KATLTADMSSSTAYMDLRSLTSEDSAVYFCAR HWDGVLDYF--DY WGQGTSLTVSS (SEQ ID NO:155)
```

FIGURE 2A-2

```
VL Domain

Kabat     1           10           20           24--27abcd------34           40                  50-----56
AbM       1           10           20           24----30abcd----34           40                  50-----56
Chothia   1           10           20           26--30abcd----32             40                  50---
Contact   1           10           20                30abcd------36          40                  46-----55
IMGT      1                                     27---------38   41                               56-65 69
                                                                                                 |    |
AHon      1           23                        23                42                             58   72
5H23      DIVLTQSPASLAVSLGQRATISC    RASKSVST---SGYVYMH    WNQQKPGQPPKLLIY    LASYLES
1D19      DIVLTQSPASLAVSLGQRATISC    RASKSVST---SGYSYMH    WYQQKPGQPPKLLIY    LASNLES
2L12      DIVLTQSPASLPVSLGQRATISC    RASKSVST---SGYSLH     WYQQKPGQPPKLLIY    LASNLES
3L3       DIVLTQSPASLAVSLGQRATISC    RASKSVST---SGYSYVH    WYQQKPGQPPKLLIY    LASNLES
4P5       DILLTQSPASLAVSLGQRATISC    RASKSVST---SGYSYMH    WYQQKPGQPPKLLIY    LASNLES
5C23      DIVLTQSPDSLTVSLGQRATISC    RASKSVST---SGYSYMH    WYQQKPGQPPKLLIY    LASNLES
5F7       DIVLTQSPASLAVSLGQRATISC    RASKSVST---SGYSYMH    WYQQKPGQPPKLLIY    LASNLES
consensus                            RASKSVST---SGYSYMH                       LASNLES
or                                    (SEQ ID NO:56)                          (SEQ ID NO: 57)

consensus                            RASKSVST---SGYSYX₁H                      LASNLES
                                     where X₁ = M,L,V                         (SEQ ID NO: 57)
                                      (SEQ ID NO:266)

1C17      DIKMTQSPSSMYASLGERVTITC    KASQDINS-------YLS    WVQQKPGKSPKTLIY    RANRLVD
1G19      DIKMTQSPSSMYASLGERVTITC    KASQDINS-------YLS    WFQQKPGKSPKTLIY    RANRLVD
consensus                            KASQDINS-------YLS                       RANRLVD
or                                    (SEQ ID NO:30)                          (SEQ ID NO: 31)
3N20      DIVMTQSPSSLSVSAGEKVTMSC    KSSQSLLNSGNQKNYLA    WYQQKPGQPPKLLIY    GASTRES
```

FIGURE 2B-1

```
VL Domain (continued)

Kabat      60              70              80              89-------97
AbM        60              70              80              89-------97
Chothia    60              70              80              91----96
Contact    60              70              80              89----96
IMGT          70              89              105------117
AHon          73              91              107      138
5H23       GVPARFSGSGSGTDFTLNIHPVEEEDAAIYYC QHSRDLTFP  FGGGTKLEIK  (SEQ ID NO:26)
1D19       GVPARFSGSGSGTDFTLNIHPVEEEDAATYYC QHSRELPYT  FGSGTKLEIK  (SEQ ID NO:78)
2L12       GVPARFSGSGSGTDFTLNIHPVEEEDAATYYC QHSGELPYT  FGGGTKLEIK  (SEQ ID NO:104)
3L3        GVPARFSGRGSGTDFTLNIHPVEEEDAATYYC QHSGELPYT  FGGGTKLEIK  (SEQ ID NO:130)
4P5        GVPARFSGRGSGTDFTLNIHPVEEEDAATYYC HHSGELPYT  FGGGTKLEIK  (SEQ ID NO:182)
5C23       GVPARFSGSGSGTDFTLNIHPVEEEDAATYYC QHSRELPYT  FGGGTKLEIK  (SEQ ID NO:208)
5F7        GVPARFSGSGSGTDFTLNIHPVEEEDAATYYC QHSRELPYT  FGGGTKVEIK  (SEQ ID NO:234)
consensus                                  X₁HSX₂ELPYT where X₁ = Q,H; where X₂ = R,G
                                           (SEQ ID NO:267)

1C17       GVPSRFSGSGSGQDYSLTISSLEYEDMGIYYC LQYDEFPFT  FGSGTKLEIK  (SEQ ID NO:52)
1G19       GVPSRFSGSGSGQDYSLTISSLEYEEMGIYYC LQYDEFPYT  FGGGTKLEIK  (SEQ ID NO:260)
consensus                                  LQYDEFPX₁T where X₁ = F,Y
                                           (SEQ ID NO:268)

3N20       GVPDRFTGSGSGTDFTLTISSVQAEDLAVYYC LNDHSYPFT  FGAGTKLELK  (SEQ ID NO:156)
```

FIGURE 2B-2

| VH Domain | | | | | | | | | |
|---|---|---|---|---|---|---|---|---|---|
| Kabat | 1 | 10 | 22 | | 31----35 | | 40 | 50---a------60----65 | |
| AbM | 1 | 10 | 22 | 26-----35 | | | 40 | 50---a------58 | 65 |
| Chothia | 1 | 10 | 22 | 26-----32 | | | 40 | a-55 | 65 |
| Contact | 1 | 10 | 22 | | 30----38 | | 40 | 47------------58 | 65 |
| IMGT | 1 | | 23 | 27-----38 | | 41 | | 56------65 | 74 |
| AHon | 1 | | 23 | 27 | | 42 | | 57 | 76 |
| 5H23 | | | QVQLQQSGPELVKPGALVKISCKAS | GYTFTSYDIN | | WVKQRPGQGLEWIG | | WIYPGDGSTKYNEKFKG | |
| 5H23v1-3 | | | QVQLVQSGAEVKKPGASVKVSCKAS | GYTFTSYDIN | | WVRQAPGQGLEWMG | | WIYPGDGSTKYNEKFKG | |
| vH1 | | | QVQLVQSGAEVKKPGASVKVSCKAS | GYTFTSYDIN | | WVRQAPGQGLEWMG | | WIYPGDGSTKYNEKFKG | |
| vH2 | | | QVQLVQSGPEVKKPGASVKVSCKAS | GYTFTSYDIN | | WVRQPGQGLEWMG | | WIYPGDGSTKYNEKFKG | |
| vH3 | | | QVQLQQSGAEVKKPGASVKVSCKAS | GYTFTSYDIN | | WVRQAPGQGLEWIG | | WIYPGDGSTKYNEKFKG | |
| vH4 | | | QVQLVQSGPEVKKPGASVKVSCKAS | GYTFTSYDIN | | WVRQPGQGLEWIG | | WIYPGDGSTKYNEKFKG | |
| vH5 | | | QVQLVQSGAEVKKPGASVKVSCKAS | GYTFTSYDIN | | WVRQAPGQGLEWIG | | WIYPGDGSTKYNEKFKG | |
| vH6 | | | QVQLVQSGAEVKKPGASVKVSCKAS | GYTFTSYDIN | | WVKQAPGQGLEWIG | | WIYPGDGSTKYNEKFKG | |
| 5H23v1-69 | | | QVQLVQSGAEVKKPGSSVKVSCKAS | GYTFTSYDIN | | WVRQAPGQGLEWMG | | WIYPGDGSTKYNEKFKG | |
| vH7 | | | QVQLVQSGAEVKKPGSSVKVSCKAS | GYTFTSYDIN | | WVRQAPGQGLEWIG | | WIYPGDGSTKYNEKFKG | |
| vH8 | | | QVQLVQSGAEVKKPGSSVKVSCKAS | GYTFTSYDIN | | WVRQAPGQGLEWIG | | WIYPGDGSTKYNEKFKG | |
| vH9 | | | QVQLVQSGAEVKKPGSSVKVSCKAS | GYTFTSYDIN | | WVRQAPGQGLEWIG | | WIYPGDGSTKYNEKFKG | |

FIGURE 3A-1

```
VH Domain (continued)

Kabat            70              80  abc            90      95--100--102         110
AbM              70              80  abc            90      95--100--102         110
Chothia          70              80  abc            90      96-100-101           110
Contact          70              80  abc            90   93-----100-101          110
IMGT                      75                  89                105--------117
AHon                                                        106 109      138
5H23       KATLTADKSSRTAYMQLSSLTSENSAVYFCAR SDYYGSRSFAY WGQGTLVTVSS  (SEQ ID NO:25)
5H23v1-3   RVTITRDTSASTAYMELSSLRSEDTAVYYCAR SDYYGSRSFAY WGQGTLVTVSS  (SEQ ID NO:323)
vH1        RVTITRDTSASTAYMELSSLRSEDTAVYYCAR SDYYGSRSFAY WGQGTLVTVSS  (SEQ ID NO:269)
vH2        RVTITADKSARTAYMELSSLTSEDTAVYYCAR SDYYGSRSFAY WGQGTLVTVSS  (SEQ ID NO:270)
vH3        KATITRDTSASTAYMELSSLTSEDTAVYFCAR SDYYGSRSFAY WGQGTLVTVSS  (SEQ ID NO:271)
vH4        RVTITADKSARTAYMELSSLTSEDTAVYYCAR SDYYGSRSFAY WGQGTLVTVSS  (SEQ ID NO:272)
vH5        KATLTADTSASTAYMELSSLRSENTAVYFCAR SDYYGSRSFAY WGQGTLVTVSS  (SEQ ID NO:273)
vH6        KATLTADKSARTAYMELSSLRSENTAVYFCAR SDYYGSRSFAY WGQGTLVTVSS  (SEQ ID NO:274)

5H23v1-69  RVTITADESTSTAYMELSSLRSEDTAVYYCAR SDYYGSRSFAY WGQGTLVTVSS  (SEQ ID NO:414)
vH7        RATLTADKSTSTAYMELSSLRSEDTAVYYCAR SDYYGSRSFAY WGQGTLVTVSS  (SEQ ID NO:320)
vH8        RATLTADKSTRTAYMELSSLRSEDTAVYYCAR SDYYGSRSFAY WGQGTLVTVSS  (SEQ ID NO:321)
vH9        RATITTADKSTSTAYMELSSLRSEDTAVYYCAR SDYYGSRSFAY WGQGTLVTVSS (SEQ ID NO:322)
```

FIGURE 3A-2

VL Domain

```
Kabat      1          10          20          24-27abcd----34           40              50------56
AbM        1          10          20          24-----30ab----34         40              50------56
Chothia    1          10          20          26---30ab----32           40              50---
Contact    1          10          20                  30ab------36      40              
IMGT       1                                  27--------38     41                       46----------55
                                 23
AHon       1                                                   42                       56-65    69
                                 23                                                       58        72
5H23       DIVLTQSPASLAVSLGQRATISC RASKSVSTSGYVYMH WNQQKPGQPPKLLIY LASYLES
5H23v4-1   DIVMTQSPDSLAVSLGERATINC RASKSVSTSGYVYMH WYQQKPGQPPKLLIY LASYLES
vL1        DIVLTQSPDSLAVSLGERATINC RASKSVSTSGYVYMH WNQQKPGQPPKLLIY LASYLES
vL2        DIVMTQSPDSLAVSLGERATINC RASKSVSTSGYVYMH WYQQKPGQPPKLLIY LASYLES
vL3        DIVMTQSPDSLAVSLGERATINC RASKSVSTSGYVYMH WNQQKPGQPPKLLIY LASYLES
vL4        DIVLTQSPDSLAVSLGERATINC RASKSVSTSGYVYMH WNQQKPGQPPKLLIY LASYLES
vL5        DIVMTQSPDSLAVSLGERATINC RASKSVSTSGYVYMH WNQQKPGQPPKLLIY LASYLES Kabat      60          70          80          89-----97
AbM        60          70          80          89-----97
Chothia    60          70          80             91-----96
Contact    60          70          80          89-----96
IMGT       70                     89                           105------117
AHon       73                     91                                    107   138
5H23       GVPARFSGSGSGTDFTLNIHPVEEEDAAIYYC  QHSRDLTFP  FGGGTKLEIK  (SEQ ID NO:26)
5H23v4-1   GVPDRFSGSGSGTDFTLTISSLQAEDVAVYYC  QHSRDLTFP  FGGGTKLEIK  (SEQ ID NO:355)
vL1        GVPDRFSGSGSGTDFTLTISSVQAEDAAIYYC  QHSRDLTFP  FGGGTKLEIK  (SEQ ID NO:275)
vL2        GVPDRFSGSGSGTDFTLTISSVQAEDVAVYYC  QHSRDLTFP  FGGGTKLEIK  (SEQ ID NO:276)
vL3        GVPDRFSGSGSGTDFTLTISSLQAEDVAIYYC  QHSRDLTFP  FGGGTKLEIK  (SEQ ID NO:277)
vL4        GVPDRFSGSGSGTDFTLTISSVQAEDVAVYYC  QHSRDLTFP  FGGGTKVEIK  (SEQ ID NO:325)
vL5        GVPDRFSGSGSGTDFTLTISSLQAEDVAVYYC  QHSRDLTFP  FGGGTKVEIK  (SEQ ID NO:326)
```

FIGURE 3B

| VL Domain | | | | | | |
|---|---|---|---|---|---|---|
| Kabat | 1 | 10 | 20 | 24-27abcd----34 | 40 | 50------56 |
| AbM | 1 | 10 | 20 | 24----30ab----34 | 40 | 50------56 |
| Chothia | 1 | 10 | 20 | 26--30ab--32 | 40 | 50--- |
| Contact | 1 | 10 | 20 | 30ab-------36 | 40 | 46------55 |
| IMGT | 1 | | 23 | 27--------38 | 41 | 56-65 69 |
| | | | | | | |
| AHon | 1 | | 23 | 42 | | 58 72 |
| 5H23 | DIVLTQSPASLAVSLGQRATISC | | | RASKSVSTSGYVYMH | WNQQKPGQPPKLLIY | LASYLES |
| 5H23v1-39 | DIQMTQSPSSLSASVGDRVTITC | | | RASKSVSTSGYVYMH | WYQQKPGKAPKLLIY | LASYLES |
| v1-39a | DIQMTQSPSSLSASVGDRVTITC | | | RASKSVSTSGYVYMH | WYQQKPGKAPKLLIY | LASYLES |
| v1-39b | DIQMTQSPSSLSASVGDRVTITC | | | RASKSVSTSGYVYMH | WYQQKPGKAPKLLIY | LASYLES |
| v1-39c | DIQMTQSPSSLSASVGDRVTITC | | | RASKSVSTSGYVYMH | WNQQKPGKAPKLLIY | LASYLES |
| v1-39d | DIQMTQSPSSLSASVGDRVTITC | | | RASKSVSTSGYVYMH | WYQQKPGKAPKLLIY | LASYLES |
| v1-39e | DIQLTQSPSSLSASVGDRVTITC | | | RASKSVSTSGYVYMH | WYQQKPGKAPKLLIY | LASYLES |
| v1-39f | DIQMTQSPSSLSASVGDRVTITC | | | RASKSVSTSGYVYMH | WYQQKPGKPPKLLIY | LASYLES |
| v1-39g | DIQLTQSPSSLSASVGDRVTITC | | | RASKSVSTSGYVYMH | WYQQKPGKPPKLLIY | LASYLES |
| v1-39h | DIQMTQSPSSLSASVGDRVTITC | | | RASKSVSTSGYVYMH | WNQQKPGKPPKLLIY | LASYLES |
| v1-39i | DIQMTQSPSSLSASVGDRVTITC | | | RASKSVSTSGYVYMH | WYQQKPGKAPKLLIY | LASYLES |
| v1-39j | DIQMTQSPSSLSASVGDRVTITC | | | RASKSVSTSGYVYMH | WYQQKPGKAPKLLIY | LASYLES |
| v1-39k | DIQLTQSPSSLSASVGDRVTITC | | | RASKSVSTSGYVYMH | WNQQKPGKPPKLLIY | LASYLES |
| v1-39l | DIQMTQSPSSLSASVGDRVTITC | | | RASKSVSTSGYVYMH | WNQQKPGKPPKLLIY | LASYLES |
| v1-39m | DIQMTQSPSSLSASVGDRVTITC | | | RASKSVSTSGYVYMH | WYQQKPGKPPKLLIY | LASYLES |
| v1-39n | DIQMTQSPSSLSASVGDRVTITC | | | RASKSVSTSGYVYMH | WYQQKPGKPPKLLIY | LASYLES |
| v1-39o | DIQMTQSPSSLSASVGDRVTITC | | | RASKSVSTSGYVYMH | WYQQKPGKPPKLLIY | LASYLES |
| v1-39p | DIQMTQSPSSLSASVGDRVTITC | | | RASKSVSTSGYVYMH | WYQQKPGKPPKLLIY | LASYLES |

FIGURE 3C-1

VL Domain (continued)

| | | | | | | | |
|---|---|---|---|---|---|---|---|
| Kabat | 60 | 70 | 80 | | 89------97 | | |
| AbM | 60 | 70 | 80 | | 89------97 | | |
| Chothia | 60 | 70 | 80 | | 91----96 | | |
| Contact | 60 | 70 | 80 | | 89----96 | | |
| IMGT | 70 | 89 | | | 105------117 | | |
| AHon | 73 | 91 | | | 107    138 | | |
| 5H23 | GVPARFSGSGSGTDFTLNIHPVEEEDAATYYC | QHSRDLTFP | FGGGTKLEIK | (SEQ ID NO:26) |
| 5H23v1-39 | GVPSRFSGSGSGTDFTLTISSLQPEDFATYYC | QHSRDLTFP | FGGGTKLEIK | (SEQ ID NO:353) |
| v1-39a | GVPSRFSGSGSGTDFTLTISSLQPEDFATYYC | QHSRDLTFP | FGQGTKLEIK | (SEQ ID NO:327) |
| v1-39b | GVPSRFSGSGSGTDFTLTISSVQPEDFATYYC | QHSRDLTFP | FGGGTKLEIK | (SEQ ID NO:328) |
| v1-39c | GVPSRFSGSGSGTDFTLTISSLQPEDFATYYC | QHSRDLTFP | FGGGTKLEIK | (SEQ ID NO:329) |
| v1-39d | GVPSRFSGSGSGTDFTLTISSLQPEDFATYYC | QHSRDLTFP | FGGGTKLEIK | (SEQ ID NO:330) |
| v1-39e | GVPSRFSGSGSGTDFTLTISSVQPEDFATYYC | QHSRDLTFP | FGGGTKLEIK | (SEQ ID NO:331) |
| v1-39f | GVPSRFSGSGSGTDFTLTISSVQPEDFATYYC | QHSRDLTFP | FGGGTKLEIK | (SEQ ID NO:332) |
| v1-39g | GVPSRFSGSGSGTDFTLTISSVQPEDFATYYC | QHSRDLTFP | FGGGTKLEIK | (SEQ ID NO:333) |
| v1-39h | GVPSRFSGSGSGTDFTLTISSVQPEDFATYYC | QHSRDLTFP | FGGGTKLEIK | (SEQ ID NO:334) |
| v1-39i | GVPSRFSGSGSGTDFTLTISSLQPEDFATYYC | QHSRDLTFP | FGGGTKLEIK | (SEQ ID NO:335) |
| v1-39j | GVPSRFSGSGSGTDFTLTISSVQEEDFATYYC | QHSRDLTFP | FGGGTKLEIK | (SEQ ID NO:336) |
| v1-39k | GVPSRFSGSGSGTDFTLTISSVQEEDFATYYC | QHSRDLTFP | FGGGTKLEIK | (SEQ ID NO:337) |
| v1-39l | GVPSRFSGSGSGTDFTLTISSVQEEDFATYYC | QHSRDLTFP | FGGGTKLEIK | (SEQ ID NO:338) |
| v1-39m | GVPSRFSGSGSGTDFTLTISSVQEEDFAATYYC | QHSRDLTFP | FGGGTKLEIK | (SEQ ID NO:339) |
| v1-39n | GVPSRFSGSGSGTDFTLTISSVQEEDFAATYYC | QHSRDLTFP | FGGGTKLEIK | (SEQ ID NO:340) |
| v1-39o | GVPSRFSGSGSGTDFTLTISSVQPEDFATYYC | QHSRDLTFP | FGQGTKLEIK | (SEQ ID NO:341) |
| v1-39p | GVPSRFSGSGSGTDFTLTISSVQEEDFATYYC | QHSRDLTFP | FGQGTKLEIK | (SEQ ID NO:342) |

FIGURE 3C-2

VL Domain

| | | | | | | | |
|---|---|---|---|---|---|---|---|
| Kabat | 1 | | 10 | | 20 | 24-27abcd----34 | 40 | 50-----56 |
| AbM | 1 | | 10 | | 20 | 24----30ab----34 | 40 | 50-----56 |
| Chothia | 1 | | 10 | | 20 | 26--30ab--32 | 40 | 50--- |
| Contact | 1 | | 10 | | 20 | 30ab------36 | 40 | 46------55 |
| IMGT | 1 | | | | 23 | 27-------38 | 41 | 56-65 69 |

| | | | | |
|---|---|---|---|---|
| AHon | 1 | | 23 | 42 | 58 72 |
| 5H23 | EIVLTQSPASLAVSLGQRATISC | RASKSVSTSGYVYMH | WNQQKPGQPPKLLIY | LASYLES |
| 5H23v3-20 | EIVLTQSPATLSLSPGERATLSC | RASKSVSTSGYVYMH | WYQQKPGQAPRLLIY | LASYLES |
| v3-20a | EIVLTQSPATLSLSPGERATLSC | RASKSVSTSGYVYMH | WYQQKPGQAPRLLIY | LASYLES |
| v3-20b | EIVLTQSPATLSLSPGERATLSC | RASKSVSTSGYVYMH | WYQQKPGQAPRLLIY | LASYLES |
| v3-20c | EIVLTQSPATLSLSPGERATLSC | RASKSVSTSGYVYMH | WNQQKPGQAPRLLIY | LASYLES |
| v3-20d | EIVLTQSPATLSLSPGERATLSC | RASKSVSTSGYVYMH | WYQQKPGQPPRLLIY | LASYLES |
| v3-20e | EIVLTQSPATLSLSPGERATLSC | RASKSVSTSGYVYMH | WYQQKPGQAPRLLIY | LASYLES |
| v3-20f | EIVLTQSPATLSLSPGERATLSC | RASKSVSTSGYVYMH | WNQQKPGQAPRLLIY | LASYLES |
| v3-20g | EIVLTQSPATLSLSPGERATLSC | RASKSVSTSGYVYMH | WYQQKPGQAPRLLIY | LASYLES |
| v3-20h | EIVLTQSPATLSLSPGERATLSC | RASKSVSTSGYVYMH | WYQQKPGQPPRLLIY | LASYLES |
| v3-20i | EIVLTQSPATLSLSPGERATLSC | RASKSVSTSGYVYMH | WNQQKPGQAPRLLIY | LASYLES |
| v3-20j | EIVLTQSPATLSLSPGERATLSC | RASKSVSTSGYVYMH | WNQQKPGQPPRLLIY | LASYLES |

FIGURE 3D-1

VL Domain (continued)

```
Kabat            60              70              80              89-------97
AbM              60              70              80              89-------97
Chothia          60              70              80              91-------96
Contact          60              70              80              89-------96
IMGT      70                             89                             105------117
AHon      73                             91                             107      138
5H23      GVPARFSGSGSGTDFTLNIHPVEEDAAIYYC QHSRDLTFP FGGGTKLEIK (SEQ ID NO:26)
5H23v3-20 GIPARFSGSGSGTDFTLTISRLEPEDFAVYYC QHSRDLTFP FGGGTKLEIK (SEQ ID NO:354)
v3-20a    GIPARFSGSGSGTDFTLTISRLEPEDFAVYYC QHSRDLTFP FGQGTKLEIK (SEQ ID NO:343)
v3-20b    GIPARFSGSGSGTDFTLTISRVEPEDFAVYYC QHSRDLTFP FGGGTKLEIK (SEQ ID NO:344)
v3-20c    GIPARFSGSGSGTDFTLTISRVEPEDFAVYYC QHSRDLTFP FGGGTKLEIK (SEQ ID NO:345)
v3-20d    GIPARFSGSGSGTDFTLTISRLEPEDFAVYYC QHSRDLTFP FGGGTKLEIK (SEQ ID NO:346)
v3-20e    GIPARFSGSGSGTDFTLTISRLEPEDAAVYYC QHSRDLTFP FGGGTKLEIK (SEQ ID NO:347)
v3-20f    GIPARFSGSGSGTDFTLTISRVEPEDFAVYYC QHSRDLTFP FGGGTKLEIK (SEQ ID NO:348)
v3-20g    GIPARFSGSGSGTDFTLTISRVEPEDFAVYYC QHSRDLTFP FGGGTKLEIK (SEQ ID NO:349)
v3-20h    GIPARFSGSGSGTDFTLTISRLEEEDFAVYYC QHSRDLTFP FGGGTKLEIK (SEQ ID NO:350)
v3-20i    GIPARFSGSGSGTDFTLTISRVEEEDFAVYYC QHSRDLTFP FGGGTKLEIK (SEQ ID NO:351)
v3-20j    GIPARFSGSGSGTDFTLTISRVEEEDAAVYYC QHSRDLTFP FGGGTKLEIK (SEQ ID NO:352)
```

```
              40                                                        80
human   MKPGCAAGSPGNEWIFFSTDEITTRYRNTMSNGGLQRSVILSALILLRAVTGFSGDGRAIWSKNPNFTPVNESQLFLYDT
chMoHu  MKTGCAAGSPGNEWIFFSSDERNTRSRKTMSNRALQRSAVLSAFVLLRAVTGFSGDGKAIWDKKQYVSPVNPSQLFLYDT
chHuMo  MKPGCAAGSPGNEWIFFSTDEITTRYRNTMSNGGLQRSVILSALILLRAVTGFSGDGRAIWSKNPNFTPVNESQLFLYDT
mouse   MKTGCAAGSPGNEWIFFSSDERNTRSRKTMSNRALQRSAVLSAFVLLRAVTGFSGDGKAIWDKKQYVSPVNPSQLFLYDT 120                                                       160
human   FPKNFFWGIGTGALQVEGSWKKDGKGPSIWDHFIHTHLKNVSSTNGSSDSYIFLEKDLSALDFIGVSFYQFSISWPRLFP
chMoHu  FPKNFSWGVGTGAFQVEGSWKTDGRGPSIWDRYVYSHLRGVNGTDRSTDSYIFLEKDLLALDFLGVSFYQFSISWPRLFP
chHuMo  FPKNFFWGIGTGALQVEGSWKKDGKGPSIWDHFIHTHLKNVSSTNGSSDSYIFLEKDLSALDFIGVSFYQFSISWPRLFP
mouse   FPKNFSWGVGTGAFQVEGSWKTDGRGPSIWDRYVYSHLRGVNGTDRSTDSYIFLEKDLLALDFLGVSFYQFSISWPRLFP 200                                                       240
human   DGIVTVANAKGLQYYSTLLDALVLRNIEPIVTLYHWDLPLALQEKYGGWKNDTIIDIFNDYATYCFQMFGDRVKYWITIH
chMoHu  NGTVAAVNAQGLRYYRALLDSIVLRNIEPIVTLYHWDLPLTLQEEYGGWKNATMIDLFNDYATYCFQTFGDRVKYWITIH
chHuMo  DGIVTVANAKGLQYYSTLLDALVLRNIEPIVTLYHWDLPLALQEKYGGWKNDTIIDIFNDYATYCFQMFGDRVKYWITIH
mouse   NGTVAAVNAQGLRYYRALLDSIVLRNIEPIVTLYHWDLPLTLQEEYGGWKNATMIDLFNDYATYCFQTFGDRVKYWITIH 280                                                       320
human   NPYLVAWHGYGTGMHAPGEKGNLAAVYTVGHNLIKAHSKVWHNYNTHFRPHQKGWLSITTLGSHWIEPNRSENTMDIFKCQ
chMoHu  NPYLVAWHGFGTGMHAPGEKGNLTAVYTVGHNLIKAHSKVWHNTYDKNFRPHQKGWLSITLGSHWIEPNRTDNMEDVINCQ
chHuMo  NPYLVAWHGYGTGMHAPGEKGNLAAVYTVGHNLIKAHSKVWHNYNTHFRPHQKGWLSITTLGSHWIEPNRSENTMDIFKCQ
mouse   NPYLVAWHGFGTGMHAPGEKGNLTAVYTVGHNLIKAHSKVWHNTYDKNFRPHQKGWLSITLGSHWIEPNRTDNMEDVINCQ 360                                                       400
human   QSMVSVLGWFANPIHGDGDYPEGMRKKLFSVLPIFSEAEKHEMRGTADFFAFSFGPNNFKPLNTMAKMGQNVSLNLREAL
chMoHu  HSMSSVLGWFTDGDGDYPEFMKTG--AMIPEFSEAEKEEVRGTADFFAFSFGPNNFRPSNTVVKMGQNVSLNLRQVL
chHuMo  QSMVSVLGWFANPIHGDGDYPEGMRKKLFSVLPIFSEAEKHEMRGTADFFAFSFGPNNFKPLNTMAKMGQNVSLNLREAL
mouse   HSMSSVLGWFTDGDGDYPEFMKTG--AMIPEFSEAEKEEVRGTADFFAFSFGPNNFRPSNTVVKMGQNVSLNLRQVL 440                                                       480
human   NWIKLEYNNPRILIAENGWFTDSRVKTEDTTAIYMMKNFLSQVLQAIRLDEIRVFGYTAWSLLDGFEWQDAYTIRRGLFY
chMoHu  NWIKLEYDDPQILISENGWFTDSYIKTEDTTAIYMMKNFLNQVLQAIKFDEIRVFGYTAWTLLDGFEWQDAYTTRRGLFY
chHuMo  NWIKLEYNNPRILIAENGWFTDSRVKTEDTTAIYMMKNFLSQVLQAIRLDEIRVFGYTAWSLLDGFEWQDAYTIRRGLFY
mouse   NWIKLEYDDPQILISENGWFTDSYIKTEDTTAIYMMKNFLNQVLQAIKFDEIRVFGYTAWTLLDGFEWQDAYTTRRGLFY
```

FIGURE 4B

```
human    VDFNSKQKERKPKSSAHYYKQIIRENGFSLKESTPDVQGQFPCDFSWGVTESVLKPESVASSPQFSDPHLYVWNATGNRL
chMoHu   VDFNSEQKERKPKSSAHYYKQIIQDNGFSLKESTPDVQGQFPCDFSWGVTESVLKPESVASSPQFSDPHLYVWNATGNRL
chHuMo   LYRVEGVRLKTRPSQCTDYVSIKKRVEMLAKMKVTHYQFALDWTSILPTGNLSAVNRQALRYYRCVVSEGLKLGISAMVT
mouse    VDFNSKQKERKPKSSAHYYKQIIQDNGFPLKESTPDMKGRFPCDFSWGVTESVLKPEFTVSSPQFTDPHLYVWNVTGNRL
                                      520                540                 560 human    LHRVEGVRLKTRPAQCTDFVNIKKQLEMLARMKVTHYRFALDWASVLPTGNLSAVNRQALRYYRCVVSEGLKLGISAMVT
chMoHu   LHRVEGVRLKTRPAQCTDFVNIKKQLEMLARMKVTHYRFALDWASVLPTGNLSAVNRQALRYYRCVVSEGLKLGISAMVT
chHuMo   LYRVEGVRLKTRPSQCTDYVSIKKRVEMLAKMKVTHYQFALDWTSILPTGNLSKVNRQVLRYYRCVLRYYRCVVSEGLKLGVFPMVT
mouse    LYRVEGVRLKTRPSQCTDYVSIKKRVEMLAKMKVTHYQFALDWTSILPTGNLSKVNRQVLRYYRCVVSEGLKLGVFPMVT
                                      600                620                 640 human    LYYPTHAHLGLPEPLLHADGWLNPSTAEAFQAYAGLCFQELGDLVKLWITINEPNRLSDIYNRSGNDTYGAAHNLLVAHA
chMoHu   LYYPTHAHLGLPEPLLHADGWLNPSTAEAFQAYAGLCFQELGDLVKLWITINEPNRLSDIYNRSGNDTYGAAHNLLVAHA
chHuMo   LYHPTHSHIGLPLPLLSSGGWLNMNTAKAFQDYAELCFRELGDLVKLWITINEPNRLSDMYNRTSNDTYRAAHNLMIAHA
mouse    LYHPTHSHIGLPLPLLSSGGWLNMNTAKAFQDYAELCFRELGDLVKLWITINEPNRLSDMYNRTSNDTYRAAHNLMIAHA
                                      680                700                 720 human    LAWRLYDRQFRPSQRGAVSLSLHADWAEPANPYADSHWRAAERFLQFEIAWFAEPLFKTGDYPAAMREYIASKHRRGLSS
chMoHu   LAWRLYDRQFRPSQRGAVSLSLHADWAEPANPYADSHWRAAERFLQFEIAWFAEPLFKTGDYPAAMREYIASKHRRGLSS
chHuMo   QVWHLYDRQYRPVQHGAVSLSLHCDWAEPANPFVDSHWKAAERFLQFEIAWFADDPLFKTGDYPSVMKEYIASKNQRGLSS
mouse    QVWHLYDRQYRPVQHGAVSLSLHCDWAEPANPFVDSHWKAAERFLQFEIAWFADPLFKTGDYPSVMKEYIASKNQRGLSS
                                      760                780                 800 human    SALPRLTEAERRLLKGTVDFCALNHFTTRFVMHEQLAGSRYDSDRDIQFLQDITRLSSPTRLAVIPWGVRKLLRWVRRNY
chMoHu   SALPRLTEAERRLLKGTVDFCALNHFTTRFVMHEQLAGSRYDSDRDIQFLQDITRLSSPTRLAVIPWGVRKLLRWVRRNY
chHuMo   SVLPRFTAKESRLVKGTVDFYALNHFTTRFVIHKQLNTNRSVADRDVQFLQDITRLSSPSRLAVTPWGVRKLLAWIRRNY
mouse    SVLPRFTAKESRLVKGTVDFYALNHFTTRFVIHKQLNTNRSVADRDVQFLQDITRLSSPSRLAVTPWGVRKLLAWIRRNY
                                      840                860                 880 human    GDMDIYITASGIDDQALEDDRLRKYLGKYLQEVLKAYLIDKVRIKGYYAFKLAEEKSKPRFGFETSDFKAKSSIQFYNK
chMoHu   GDMDIYITASGIDDQALEDDRLRKYLGKYLQEVLKAYLIDKVRIKGYYAFKLAEEKSKPRFGFFTSDFKAKSSIQFYNK
chHuMo   RDRDIYITTANGIDDLALEDDQIRKYYLEKYVQEALKAYLIDKVKIKGYYAFKLTEEKSKPRFGFFTSDFRAKSSVQFYSK
mouse    RDRDIYITTANGIDDLALEDDQIRKYYLEKYVQEALKAYLIDKVKIKGYYAFKLTEEKSKPRFGFFTSDFRAKSSVQFYSK
                                      920                940                 960
```

FIGURE 4C

```
                                  1000                                          1040
human  VISSRGFPFENSSSRCSQTQENTECTVCLFLVQKKPLIFLGCCFFSTLVLLLSIAIFQRQKRRKFWKAKNLQHIPLKKGK
chMoHu VISSRGFPFENSSSRCSQTQENTECTVCLFLVQKKPLIFLGCCFFSTLVLLLSIAIFQRQKRRKFWKAKNLQHIPLKKGK
chHuMo LISSSGLPAENRSPACGQPAEDTDCTICSFLVEKKPLIFFGCCFISTLAVLLSITVFHHQKRRKFQKARNLQNIPLKKGH
mouse  LISSSGLPAENRSPACGQPAEDTDCTICSFLVEKKPLIFFGCCFISTLAVLLSITVFHHQKRRKFQKARNLQNIPLKKGH human  -RVVS (SEQUENCE ID 297)
chMoHu -RVVS (SEQUENCE ID 376)
chHuMo *SRVFS* (SEQUENCE ID 374)
mouse  *SRVFS* (SEQUENCE ID 301)
```

FIGURE 5A

```
                                   30                                            60
human    MKPGCAAGSPGNEWIFFSTDEITTRYRNTMSNGGLQRSVILSALILLRAVTGFSGDGRAI
cyno     MKPGCAAGSPGNEWIFFSTDEITIRYRNTMSNGGLQRSVILSALTLLRAVTGFSGDGRAV
mouse    MKTGCAAGSPGNEWIFFSSDERNTRSRKTMSNRALQRSAVLSAFVLLRAVTGFSGDGKAI
rabbit   MKPGCAAGSPGNEWIFFSSDERNRRCRETMSSGRLRRSVMLSAFILLRAVTGFPGDGRAV
hamster  MKAGCAAGSPGNEWIFLSSYERNTRSKKTMSNRALQRSVVLSAFVLLRAVTGLSGDGKAI
rat      MKTGCAAGSPGNEWVFFSSDERSTRSRKTMSNGALQRSAVLSALVLLRAVTGFSGDGKAI
dog      MKPGCAAGSPGNEWIFLSTDESNTHYRKTMCNHGLQRSVILSAFILLGAVPGFSGDGRAI
         *  ********** *  *        *   * ***    **** **** **  **** *** *

90                                           120
human    WSKNPNFTPVNESQLFLYDTFPKNFFWGIGTGALQVEGSWKKDGKGPSIWDHFIHTHLKN
cyno     WSKNPNFTPVNESQLFLYDTFPKNFFWGIGTGALQVEGSWKKDGKGPSIWDHFVHTHLKN
mouse    WDKKQYVSPVNPSQLFLYDTFPKNFFWGVGTGAFQVEGSWKTDGRGPSIWDRYVSHLRG
rabbit   WSQNPNLSPVNESQLFLYDTFPKNFFWGVGTGAFQVEGSWKKDGKGLSVWDHFIATHLN-
hamster  WDKKQYVSPVNASQLFLYDTFPKNFFWGVGTGAFQVEGNWQADGRGPSIWDRFIYTHLRD
rat      WDKKQYVSPVNPGQLFLYDTFPKNFFWGVGTGAFQVEGNWKADGRGPSIWDRYVDSHLRG
dog      WSKNPHFSPVNESQLFLYDTFPKNFFWGVGTGAFQVEGNWKTDGKGPSIWDHFIHTHLKN
         *   *  ** * * ************* **** **  ****   **  * ****   **

150                                           180
human    VSSTNGSSDSYIFLEKDLSALDFIGVSFYQFSISWPRLFPDGIVTTVANAKGLQYYSTLLD
cyno     VSSTNGSSDSYIFLEKDLSALDFIGVSFYQFSISWPRLFPDGIVTVANAKGLQYYNTLLD
mouse    VNGTDRSTDSYIFLEKDLSALDFLGVSFYQFSISWPRLFPNGTVAAVNAQGLRYRALLD
rabbit   VSSRDGSSDSYIFLEKDLSALDFLGVSFYQFSISWPRLFPDGTVAVANAKGLQYNRLLD
hamster  VSITEKSADSYIFLEKDLLALDFLGVSFYQFSISWPRLFPDGTVASVNAKGLQYYNKLLD
rat      VNSTDRSTDSYVFLEKDLLALDFLGVSFYQFSISWPRLFPNGTVAAVNAKGLQYYRALLD
dog      VNSMNSSSDSYIFLEKDLSALDFIGVSFYQFSISWPRLFPDGIAAVANAKGLQYYNSLLD
         *    *  *** ******  **** ****************  *     ****** *  ***
```

FIGURE 5B

```
                                                             210                                                                         240
human     ALVLRNIEPIVTLYHWDLPLALQEKYGGWKNDTIIDIFNDYATYCFQMFGDRVKYWITIH
cyno      SLVLRNIEPIVTLYHWDLPLALQEKYGGWKNDTIIDIFNDYATYCFQTFGDRVKYWITIH
mouse     SLVLRNIEPVVTLYHWDLPLTLQEEYGGWKNATMIDLFNDYATYCFQTFGDRVKYWITIH
rabbit    SLLLRNIEPVVTLYHWDLPWALQEKYGGWKNETLIDLFNDYATYCFQTFGDRVKYWITIH
hamster   SLLLRNIEPVVTLYHWDLPLALQEDYGGWKNATMIDLFNDYATYCFQTFGDRVKYWITIH
rat       SLVLRNIEPIVTLYHWDLPLTLQEEYGGWKNATMIDLFNDYATYCFQTFGDRVKYWITIH
dog       ALVLRNIEPIVTLYHWDLPLALQEKYGGWKNETITDIFNDYATYCFQTFGDRVKYWITIH
          * ******** ******** * ** ****** *  * ****************** ***

270                                                                         300
human     NPYLVAWHGYGTGMHAPGEKGNLAAVYTVGHNLIKAHSKVWHNYNTHFRPHQKGWLSITL
cyno      NPYLVAWHGYGTGMHAPGEKGNLAAVYTVGHNLIKAHSKVWHNYNTHFRPHQKGWLSITL
mouse     NPYLVAWHGFGTGMHAPGEKGNLTAVYTVGHNLIKAHSKVWHNYDKNFRPHQKGWLSITL
rabbit    NPYLVAWHGYGTGMHAPGEKGNVAAVYTVGHNLLKAHSKVWHNYNRNFRPHQKGWLSITL
hamster   NPYLVAWHGFATGMHAPGETGNLTAVYIVGHNLTAVYTVGHNLIKAHSKVWHNYDKNFRPHQKGLLSITL
rat       NPYLVAWHGFGTGMHAPGEKGNLTAVYTVGHNLIKAHSKVWHNYDKNFRPHQKGWLSITL
dog       NPYLVAWHGYGTGMHAPGEKGNLAAVYTVGHNLIKAHSKVWHNYNTNFRPYQKGLLSITL
          ********* ******** ** **** *****  * ***************    ****

330                                                                         360
human     GSHWIEPNRSENTMDIFKCQQSMVSVLGWFANPIHGDGDYPEGMRKKLFSVLPIFSEAEK
cyno      GSHWIEPNRSENTMDILKCQQSMVSVLGWFANPIHGDGDYPEGMKKKLLSILPLFSEAEK
mouse     GSHWIEPNRTDNMEDVINCQHSMSSVLGWFANPIHGDGDYPEFMKT--GAMIPEFSEAEK
rabbit    GSHWIEPNRAESIVDILKCQQSMVSVLGWFANPIHGDGDYPEVMTKKLLSVLPAFSEAEK
hamster   GSHWIEPNKTENMADTISCQHSMAFVLGWFANPIHADGDYPEFMKT--LSTMPVFSEAEK
rat       GSHWIEPNRTENMEDVINCQHSMSSVLGWFANPIHGDGDYPEFMKT--SSVIPEFSEAEK
dog       GSHWIEPNRSENMMDILKCQQSMVSVLGWFANPIHGNGDYPEVMKKKLLSTILPLFSEAEK
          ********    *  *  ** **  ***********  ****  *      * *****
```

FIGURE 5C

```
                                                                                390                                                420
human    HEMRGTADFFAFSFGPNNFKPLNTMAKMGQNVSLNLREALNWIKLEYNNPRILIAENGWF
cyno     NEVRGTADFFAFSFGPNNFKPLNTMAKMGQNVSLNLREALNWIKLEYNNPRILIAENGWF
mouse    EEVRGTADFFAFSFGPNNFRPSNTVVKMGQNVSLNLRQVLNWIKLEYDDPQILISENGWF
rabbit   NEVRGTADFFAFSFGPNNFKPLNTMAKMGQNVSLNLRQVLNWIKLEYGNPRILIAENGWF
hamster  EEVRGTADFFAFSFGPNNFRPSNTVVKMGQNVSLNLRQVLNWIKLEYDNPRILISENGWF
rat      EEVRGTADFFAFSFGPNNFRPSNTVVKMGQNVSLNLRQVLNWIKLEYDNPRILISENGWF
dog      NEVRGTADFFAFSFGPNNFKPQNTMAKMGQNVSLNREVLNWIKLEYGNPRILIAENGWF
         * ****************** *   ***********   *******  *** *  *****

450                                                480
human    TDSRVKTEDTTAIYMMKNFLSQVLQAIRLDEIRVFGYTAWSLLDGFEWQDAYTIRRGLFY
cyno     TDSHVKTEDTTAIYMMKNFLSQVLQAIRLDEIRVFGYTAWSLLDGFEWQDAYTIRRGLFY
mouse    TDSYIKTEDTTAIYMMKNFLNQVLQAIKFDEIRVFGYTAWTLLDGFEWQDAYTTRRGLFY
rabbit   TDSYVQTEDTTAIYMMKNFLNQVLQAIRLDGVRVFGYTAWSLLDGFEWQDAYNTRRGLFY
hamster  TDSDIKTEDTTAIYMMKHFLNQVLQAIQFDEIRVFGYTAWSLLDGFEWQYAYTSRRGLFY
rat      TDSYIKTEDTTAIYMMKNFLNQVLQAIKFDEIQVFGYTAWTLLDGFEWQDAYTTRRGLFY
dog      TDSHVKTEDTTAIYMMKNFLNQVLQAIRFDEIQVFGYTAWSLLDGFEWQDAYSTRRGLFY
         ***  ************ ** ***** *  *** ****** ****** *   ******

510                                                540
human    VDFNSKQKERKPKSSAHYYKQIIRENGFSLKESTPDVQGQFPCDFSWGVTESVLKPESVA
cyno     VDFNSKQKERKPKSSAHYYKQIIRENGFSLKEATPDVQGQFPCDFSWGVTESVLKPESVA
mouse    VDFNSEQKERKPKSSAHYYKQIIQDNGFPLKESTPDMKGRFPCDFSWGVTESVLKPEFTV
rabbit   VDFNSEQRERRPKSSAHYYKQVIGENGFTLREATPDLQGQFPCDFSWGVTESVLKPESVA
hamster  VDFNSEQKERKPKTSAHYYKQIIQENGFPLKESTPDMQGQFPCDFSWGVTESVLKPEFMV
rat      VDFNSEQKERKPKSSAHYYKQIIQDNGFPLQESTPDMKGQFPCDFSWGVTESVLKPEFTV
dog      VDFNSKQKERKPKSSAYYYKQIIQENGFTFKESTPDVQGQFPCDFSWGVTESVLKPKVVA
         ***** * ** ** ** ****  * **    * *** *  ****************
```

FIGURE 5D

```
                                                                          600
                        570
human    SSPQFSDPHLYVWNATGNRLLHRVEGVRLLKTRPAQCTDFVNIKKQLEMLARMKVTHYRFA
cyno     SSPQFSDPYLYVWNATGNRLLHRVEGVRLLKTRPAQCTDFVNIKKQLEMLARMKVTHYRFA
mouse    SSPQFTDPHLYVWNVTGNRLLYRVEGVRLLKTRPSQCTDYVSIKKRVEMLAKMKVTHYQFA
rabbit   SSPQFSDPHLYVWNATGNRLHRVEGVRLLKTRPAQCTDFITIKKQLEMLARMKVTHFRFA
hamster  SSPQFTDPHLYVWNATGNRLLHRVEGVRLLQRVEGVRLLKTKPSHCTDYVSIKKRVEMLAKMKVTHYQFA
rat      SSPQFTDPHLYVWNVTGNRLLYRVEGVRLLKTRPSQCTDYVSIKKRVEMLAKMKVTHYQFA
dog      SSPQFSDPHLYVWNVTGNRLLHRVEGVRLLKTRPAQCTDFVSIKRQLEMLARMNVTHYRFA
         ****  ** ***** *****  ****    ** ***   ***   * *** *****  **

660
                        630
human    LDWASVLPTGNLSAVNRQALRYYRCVVSEGLKLGISAMVTLYYPTHAHLGLPEPLLHADG
cyno     LDWASVLPTGNLSAVNRQALRYYRCVVSEGLKLGISAMVTLYYPTHAHLGLPEPLLHAGG
mouse    LDWTSILPTGNLSKVNRQVLRYYRCVVSEGLKLGVFPMVTLYHPTHSHLGLPLPLLSSGG
rabbit   LDWASVLPTGNLSEVNRQALRYYRCVVTEGLKLNISPMVTLYYPTHAHLGLPAPLLHSGG
hamster  LDWATILPTGNLSEVNRQVLRYYRCVVSEGLKLGVSPMVTLYHPTHSHLGLPEPLLNSGG
rat      LDWTSILPTGNLSKINRQVLRYYRCVVSEGLKLGISPMVTLYHPTHSHLGLPMPLLSSGG
dog      LDWPSILPTGNLSTVNRQALRYYRCVVSESLKLSISPMVTLYYPTHAHLGLPSPLLHSGG
         ***    ***** ***   *********     ** *  ** ** ** ***   **

720
                        690
human    WLNPSTAEAFQAYAGLCFQELGDLVKLWITTINEPNRLSDIYNRSGNDTYGAAHNLLVAHA
cyno     WLNPSTVEAFQAYAGLCFQELGDLVKLWITTINEPNRLSDIYNRSGNDTYGAAHNLLVAHA
mouse    WLNMNTAKAFQDYAELCFRELGDLVKLWITTINEPNRLSDMYNRTSNDTYRAAHNLMIAHA
rabbit   WLDPSTAKAFRDYAGLCFRELGDLVKLWITTINEPNRLSDVYNRTSNDTYQAAHNLLIAHA
hamster  WLNTYTAKAFQDYAGLCFKELGDLVKLWITTINEPNRLSDMYNRTSNDTYRAAHNLMIAHA
rat      WLNTNTAKAFQDYAGLCFRELGDLVKLWITTINEPNRLSDMYNRTSNDTYRAAHNLMIAHA
dog      WLNASTARAFQDYAGLCFQELGDLVKLWITTINEPNRLSDVYSHTSSDTYRAAHNLLIAHA
         **     ** *** *** *************** ** *** ***     ****
```

FIGURE 5E

```
                                        750                         780
human    LAWRLVDRQFRPSQRGAVSLSLHADWAEPANPYADSHWRAAERFLQFEIAWFAEPLFKTG
cyno     LAWRLVDRQFRPSQRGAVSLSLHADWAEPANPYADSHWRAAERFLQFEIAWFAEPLFKTG
mouse    QVWHLYDRQYRPVQHGAVSLSLHCDWAEPANPFVDSHWKAAERFLQEIAWFADPLFKTG
rabbit   LVWHLYDRQYRPSQRGALSLSLHSDWAEPANPYVASHWQAAERFLQFEIAWFAEPLFKTG
hamster  QVWHLYDRQYRPVQHGAVSLSLHSDWVEPANPYVDSHWKAAERFLLFEIAWFADPLFKTG
rat      QVWHLYDRQYRPVQHGAVSLSLHSDWAEPANPYVESHWKAAERFLQFEIAWFADPLFKTG
dog      LVWHLYDRRYRPAQRGAVSLSLHSDWAEPANPYADSHWKAAERFLQFEIAWFAEPLFKTG
           *  * ****    ***** **  ** **** * *** ****  ****** *****
                                        810                         840
human    DYPAAMREYIASKHRRGLSSSALPRLTEAERRLLKGTVDFCALNHFTTRFVMHEQLAGSR
cyno     DYPAAMREYIASKHRRGLSSSALPRLTEAERRLLKGTVDFCALNHFTTRFVMHEQLAGSR
mouse    DYPSVMKEYIASKNQRGLSSSVLPRFTAKESRLVKGTVDFYALNHFTTRFVIHKQLNTNR
rabbit   DYPVAMREYIASKTRRGLSSSVLPRFSDAERRLVKGAADFYALNHFTTRFVMHEQQNGSR
hamster  DYPLAMKEYIASKNQQGLSRSVLPRFTPEESRLVKGTIDFYALNHFTTRFVIHKQLNSSR
rat      DYPLAMKEYIASKKQRGLSSSVLPRFTLKESRLVKGTIDFYALNHFTTRFVIHKQLNTNC
dog      DYPPAMREYIASKNRQGLSRSTLPRFTDEERRLVKGAADFYALNHFTTRFVMHARQNGSR
         ***  * ***** * *** * *** *      ** ** * * ********** *
                                        870                         900
human    YDSDRDIQFLQDITRLSSPTRLAVIPWGVRKLLRWVRRNYGDMDIYITASGIDDQALEDD
cyno     YDSDRDIQFLQDITRLSSPTRLAVIPWGVRKLLRWVRRNYGDMDIYITASGIDDQALEDD
mouse    SVADRDVQFLQDITRLSSPSRLAVTPWGVRKLLAWIRRNYRDRDIYITANGIDDLALEDD
rabbit   YDSDRDVQFLQDITRLASPSRLRWMPWGEGKLLRWMRNNYGDLDVYITANGIDDQALQND
hamster  SMADRDVQFLQDITRLSSPSRLAVMPWGARKLLGWIQRNYGDMDIYITANGIDDLALEND
rat      SVADRDVQFLQDITRLSPSRLAVTPWGMRKLLGWIRRNYRDMDIYVTANGIDDLALEDD
dog      YDADRDVQFLQDITCLSSPSRLAVLPWGERKVLRWIQKNYGDVDVYITASGIDDQSLEND
           ***  ******  * ** *  ***  *   * *  *    *  *** **** *
```

FIGURE 5F

```
                        930                                              960
human     RLRKYYLGKYLQEVLKAYLIDKVRIKGYYAFKLAEEKSKPREGFFTSDFKAKSSIQFYNK
cyno      RLRKYYLEKYLQEVLKAYLIDKVRIKGYYAFKLAEEKSKPREGFFTSDFKAKSSIQFYNK
mouse     QIRKYYLEKYVQEALKAYLIDKVKIKGYYAFKLTEEKSKPREGFFTSDFRAKSSVQFYSK
rabbit    QLRQYYLEKYVQEALKAYLIDKIKIKGYYAFKLTEEKSKPREGFFTSDFKAKSSIQFYNK
hamster   GIRKYYLEKYIQEALKAYLIDKVKIKGYYAFKLTEEKSKPREGFFTSDFKAKSSVEFYSK
rat       QIRKYYLEKYVQEALKAYLIDKVKIKGYYAFKLTEEKSKPREGFFTSDFKAKSSVQFYSK
dog       ELRKYYLEKYIQEALKAHLIDKVKVKGYYAFKLTEEKSKPREGFFTSEFKAKSSVQLYNK
            *** **** ** *** **** *  ***** *** ***** ****** ****  * *

990                                             1020
human     VISSRGFPFENSSSRCSQTQENTECTVCLFLVQKKPLIFLGCCFFSTLVLLLSIAIFQRQ
cyno      MISSGFPSENSSSRCSQTQKNTECTVCLFLVQKKPLIFLGCCFFSTLVLLLSITIFHRQ
mouse     LISSSGLPAENRSPACGQPAEDTDCTICSFLVEKKPLIEKKPLIFFGCCFFISTLAVLLSITVFHHQ
rabbit    LITSNGFPSENGGPRCNQTQGNPECTVCLLLLQKKPLIFFSCCFFCTLVLLSITIFHRR
hamster   LISRSGFPSETSNPACGQPPEDTDCTICSFFTQKKSLIFFGCCFISTLAVLLSITIFHHR
rat       LISSSGFSSENRSPACGQPPEDTECAICSFLTQKKPLIFFGCCFISTLAALLSITIFHHR
dog       LISNSGFPSENRSPRCSETQRNTECMVCLFLVQKKPLIFFSCCFFSSCCFISTLVLLSSITILHKR
          *  *  *  *  *     *    **  ** * *** ***  *** ** * *  *

1045
human     KRRKFWKAKNLQHIPLKKGKRVVS-       (SEQ ID NO:297)
cyno      KRRKFWKAKNLQHIPLKKGKRVLS-       (SEQ ID NO:299)
mouse     KRRKFQKARNLQNIPLKKGHSRVFS       (SEQ ID NO:301)
rabbit    KRRKFWKAKDIQHIPLKKGHKRVLS       (SEQ ID NO:410)
hamster   KRR-FHKSKNLENIPLKEGHSRVLS       (SEQ ID NO:408)
rat       KRRKFQKARNLQHIPLKKGHSRVFS       (SEQ ID NO:356)
dog       KRRKIWKAKNLQHIPLKKSKNSLQS       (SEQ ID NO:412)
          ***     *  *  ****
```

METHODS OF TREATING NONALCOHOLIC STEATOHEPATITIS COMPRISING ADMINISTERING AN ANTI-HUMAN BETA KLOTHO ANTIBODY OR BINDING FRAGMENT THEREOF

CROSS-REFERENCE TO RELATED APPLICATIONS

This application is a continuation of U.S. patent application Ser. No. 16/103,613, filed Aug. 14, 2018, now U.S. Pat. No. 10,744,191, which is a continuation of U.S. patent application Ser. No. 15/659,177, filed Jul. 25, 2017, now U.S. Pat. No. 10,093,735, which is a continuation of U.S. patent application Ser. No. 14/604,592, filed Jan. 23, 2015, now U.S. Pat. No. 9,738,716, which claims the benefit of priority of U.S. Provisional Application Ser. No. 61/931,531, filed Jan. 24, 2014, the entire contents of which are each incorporated herein by reference.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Jul. 13, 2020, is named 47702-0002004_SEQ_LISTING.txt and is 377000 bytes in size.

FIELD

The present disclosure relates generally to binding proteins, such as antibodies, that bind to beta klotho, including human beta klotho, and methods of their use.

BACKGROUND

Beta klotho, which belongs to the Klotho family, is a single-pass type I membrane protein. Beta klotho has an extracellular domain consisting of two internal repeats which share homology with members of the family 1 glycosidases but lack glucosidase catalytic activity. Beta klotho expression is primarily detected in the liver, pancreas and adipose tissue. Ito and colleagues have reported that beta klotho-deficient (KLB−/−) mice have elevated mRNA levels of CYP7A1 and CY8B1 and exhibit increased synthesis and excretion of bile acid (Ito et al., 2005, J Clin Invest 115: 2202-2208). Beta klotho forms a complex with fibroblast growth factor (FGF) receptors and functions as a co-receptor for FGFs, including FGF19 and FGF21.

Twenty-two members of the human FGF family have been identified and four tyrosine kinase receptors that bind to FGF (FGFR1-FGFR4) have been identified. The interaction between FGF and its receptor results in FGFR dimerization, which enables the cytoplasmic domains of the receptor to transphosphorylate and become activated, which in turn leads to the phosphorylation and activation of downstream signaling molecules.

The high affinity receptor for FGF19 is FGFR4 and the binding of FGF19 to FGFR4 is facilitated by beta klotho. It has been reported that FGF19 transgenic mice have decreased adiposity, increased metabolic rate, reduced liver triglycerides, increased fatty acid oxidation, reduced glucose levels and increased insulin sensitivity (Tomlinson et al., 2002, Endocrinology 143: 1741-1747). In addition, these transgenic mice were reported not to become obese or diabetic on a high-fat diet (Tomlinson et al., 2002, Endocrinology 143: 1741-1747). It has also been reported that FGF19 treatment prevented or reversed diabetes in mice made obese by genetic ablation of brown adipose tissue or the genetic absence of leptin (Fu et al., 2004, Endocrinology 145: 2594-2603).

FGF21 acts through the interaction of FGFRs and beta klotho. FGFR1 is an abundant receptor in white adipose tissue and is most likely the main functional receptor for FGF21 in white adipose tissue. FGF21 expression is detected in the liver, thymus, adipose tissue, and islet beta-cells in the pancreas. It has been reported that the interaction of FGF21 with the beta klotho-FGFR complex stimulates glucose uptake, decreases glucagon secretion, improves insulin sensitivity and glucose clearance, promotes white adipose tissue in response to fasting, increases ketogenesis in liver in response to fasting, reduces plasma triglyceride levels, and increases energy expenditure (Iglesias et al., 2012, European Journal of Endocrinology 167: 301-309).

Since FGF19 and FGF21 require both FGFRs and beta klotho for cell signaling, agents which mimic FGF19 and/or FGF21 may be desirable for their effects or glucose metabolism or lipid metabolism. However, it is not clear what features are required for an agent to confer FGF19-like or FGF21-like cell signaling activity.

SUMMARY

The present disclosure provides proteins that bind to beta klotho, including binding proteins such as antibodies that bind to beta klotho. Such binding proteins including antibodies, may bind to a beta klotho polypeptide, a beta klotho fragment and/or a beta klotho epitope. Such binding proteins, including antibodies, may be agonists (e.g., induce FGF19-like or FGF21-like signaling of a FGF receptor or activate a beta klotho/FGF receptor complex).

The present disclosure also provides binding proteins, including antibodies or fragments thereof, that (i) bind to human beta klotho, (ii) induce FGF19-like signaling and/or FGF21-like signaling, and (iii) do not compete with FGF19 and/or FGF21 for the interaction with beta klotho.

In some embodiments, the anti-beta klotho antibodies are humanized antibodies that bind to a beta klotho polypeptide, a beta klotho fragment, or a beta klotho epitope. In certain embodiments, an anti-beta klotho antibody comprises a VH CDR1, VH CDR2, VH CDR3, VL CDR1, VL CDR2, and/or VL CDR3 of a monoclonal antibody designated 5H23, 1C17, 1D19, 2L12, 3L3, 3N20, 4P5, 5C23, 5F7 or 1G19 as described herein, or a humanized variant thereof. In certain embodiments, an anti-beta klotho antibody can further comprise a VH FR1, VH FR2, VH FR3, VH FR4, VL FR1, VL FR2, VL FR3, and/or VL FR4 of a human immunoglobulin amino acid sequence or a variant thereof.

In some embodiments, a binding protein (e.g., an anti-beta klotho antibody) comprises six CDRs or less than six CDRs. In some embodiments, a binding protein (e.g., an anti-beta klotho antibody) comprises one, two, three, four, five, or six CDRs selected from VH CDR1, VH CDR2, VH CDR3, VL CDR1, VL CDR2, and/or VL CDR3. In some embodiments, a binding protein (e.g., an anti-beta klotho antibody) comprises one, two, three, four, five, or six CDRs selected from VH CDR1, VH CDR2, VH CDR3, VL CDR1, VL CDR2, and/or VL CDR3 of a monoclonal antibody designated as 5H23, 1C17, 1D19, 2L12, 3L3, 3N20, 4P5, 5C23, 5F7 or 1G19 as described herein, or a humanized variant thereof. In some embodiments, a binding protein (e.g., an anti-beta klotho antibody) further comprises a scaffold region or frame work region, including a VH FR1, VH FR2, VH FR3, VH FR4, VL FR1, VL FR2, VL FR3, and/or VL FR4 of a human immunoglobulin amino acid sequence or a variant thereof.

In some embodiments, the antibody is a humanized antibody, a monoclonal antibody, a recombinant antibody, an antigen binding fragment or any combination thereof. In some embodiments, the antibody is a humanized monoclonal antibody, or antigen binding fragment thereof, that binds to a beta klotho polypeptide (e.g., a cell surface-expressed or soluble beta klotho), a beta klotho fragment, or a beta klotho epitope.

The present disclosure also provides binding proteins such as anti-beta klotho antibodies (i) that competitively block (e.g., in a dose-dependent manner) an anti-beta klotho antibody provided herein from binding to a beta klotho polypeptide (e.g., a cell surface-expressed or soluble beta klotho), a beta klotho fragment, or a beta klotho epitope and/or (ii) that bind to a beta klotho epitope that is bound by an anti-beta klotho antibody provided herein. In other embodiments, the binding proteins such as anti-beta klotho antibody competitively blocks (e.g., in a dose-dependent manner) monoclonal antibody 5H23 or 1G19 described herein or a humanized variant thereof from binding to a beta klotho polypeptide (e.g., a cell surface-expressed or soluble beta klotho), a beta klotho fragment, or a beta klotho epitope. In other embodiments, the binding proteins such as anti-beta klotho antibody binds to a beta klotho epitope that is bound (e.g., recognized) by monoclonal antibody 5H23, or 1G19 described herein or a humanized variant thereof.

The present disclosure also provides binding proteins, including antibodies or fragments thereof, that (i) bind to an epitope of human beta klotho and cynomologous monkey beta klotho recognized by an antibody comprising a heavy chain variable region having the amino acid sequence of SEQ ID NO:25 and a light chain variable region having the amino acid sequence of SEQ ID NO:26; or (ii) compete for the binding to human beta klotho with an antibody comprising a heavy chain variable region having the amino acid sequence of SEQ ID NO:25 and a light chain variable region having the amino acid sequence of SEQ ID NO:26.1n some embodiments, binding proteins, including antibodies or fragments thereof, are provided herein that bind to a region, including an epitope, of human beta klotho or cyno beta klotho. In some embodiments, binding proteins, including antibodies or fragments thereof, bind to a region of human beta klotho or cycno beta klotho including, for example, those that bind to: (i) a KLB2 domain of human beta klotho comprising amino acid residues 509 to 1044 of SEQ ID NO:297; (ii) a glycosyl hydrolase 1 region of a KLB2 domain of human beta klotho comprising amino acid residues 517 to 967 of SEQ ID NO:297; (iii) a region of human beta klotho comprising amino acid residues 657 to 703 of SEQ ID NO:297; or (iv) a region of cyno beta klotho comprising amino acid residues 657 to 703 of SEQ ID NO:299.

In some embodiments, binding proteins, including antibodies or fragments thereof, are provided herein that bind to a specific epitope of human beta klotho, including, for example, those that bind to: (i) an epitope of human beta klotho comprising at least one of amino acid residues 657, 701 and/or 703 of human beta klotho (SEQ ID NO: 297); (ii) an epitope of human beta klotho comprising at least amino acid residue 657 of SEQ ID NO: 297; (iii) an epitope of human beta klotho comprising at least amino acid residue 701 of SEQ ID NO: 297; (iv) an epitope of human beta klotho comprising at least amino acid residue 703 of SEQ ID NO: 297; (v) an epitope of human beta klotho comprising at least amino acid residues 657 and 701 of SEQ ID NO: 297; (vi) an epitope of human beta klotho comprising at least amino acid residues 657 and 703 of SEQ ID NO: 297; (vii) an epitope of human beta klotho comprising at least amino acid residues 701 and 703 of SEQ ID NO: 297; or (viii) an epitope of human beta klotho comprising at least amino acid residues 657, 701 and 703 of SEQ ID NO: 297. Such antibodies provided above can, in some embodiments, induce FGF19-like signaling and/or FGF21-like signaling or activate a beta klotho/FGF receptor complex in a cell that expresses human beta klotho and an FGF receptor. Additionally, in some embodiments, the antibody is a monoclonal antibody, for example, a humanized, human or chimeric antibody.

In some embodiments, the binding proteins such as antibeta klotho antibodies provided herein are conjugated or recombinantly linked to a diagnostic agent, detectable agent or therapeutic agent. In some aspects, the therapeutic agent is a drug, including one or more drugs such as biguanides and sulphonylureas (e.g., metformin tolbutamide, chlorpropamide, acetohexamide, tolazamide, glibenclamide, glyburide, and glipizide), thiazolidinediones (e.g., rosiglitazone, pioglitazone), GLP-1 analogues, PPAR gamma agonists (e.g., pioglitazone and rosiglitazone), dipeptidyl peptidase-4 (DPP-4) inhibitors, (e.g., JANUVIN®, ONGLYZA®) bromocriptine formulations and bile acid sequestrants (e.g., colesevelam), and insulin (e.g., bolus and basal analogs), alpha glucosidase inhibitors (e.g., acarbose, roglibose), metformin (e.g., metformin hydrochloride) with or without a thiazolidinedione (TZD), SGLT-2 inhibitors, appetite suppression or weight loss drugs (e.g., Meridia®/sibutramine, Xenical®/ortistat). In some aspects, the detectable agent is a radioisotope, an enzyme, a fluorescent compound, a bioluminescent compound or a chemiluminescent compound.

In certain embodiments, compositions are provided comprising a binding protein such as an anti-beta klotho antibody described herein. Also provided herein are pharmaceutical compositions comprising a binding protein such as an beta klotho antibody as described herein.

The present disclosure also provides isolated nucleic acid molecules encoding an immunoglobulin heavy chain, an immunoglobulin light chain, VH region, VL region, VH CDR1, VH CDR2, VH CDR3, VL CDR1, VL CDR2, and/or VL CDR3 of binding proteins (e.g., anti-beta klotho antibodies) that bind to a beta klotho polypeptide, a beta klotho polypeptide fragment, or a beta klotho epitope. In some embodiments, the nucleic acid molecule encodes a VH region, VL region, VH CDR1, VH CDR2, VH CDR3, VL CDR1, VL CDR2, and/or VL CDR3 of a monoclonal antibody designated as 5H23, 1C17, 1D19, 2L12, 3L3, 3N20, 4P5, 5C23, 5F7 or 1G19 as described herein, or a humanized variant thereof. In some embodiments, the nucleic acid molecule further encodes a scaffold region or a framework region, including VH FR1, VH FR2, VH FR3, VH FR4, VL FR1, VL FR2, VL FR3, and/or VL FR4 of a human immunoglobulin amino acid sequence or a variant thereof. Also provided herein are vectors and host cells comprising the nucleic acid molecules encoding an a binding protein such as anti-beta klotho antibody, as well as methods of producing a binding protein such as an anti-beta klotho antibody by culturing the host cells provided herein under conditions that promote the production of a binding protein such as an anti-beta klotho antibody.

The present disclosure also provides methods of treating, preventing or alleviating a disease, disorder or condition (e.g., one or more symptoms) comprising administering a therapeutically effective amount of a binding protein such as an anti-beta klotho antibody provided herein to a subject, including a subject in need thereof, thereby treating, preventing or alleviating the disease, disorder or condition. In some embodiments, the disease, disorder or condition is caused by or otherwise associated with beta klotho, such as those related to FGF19-like and/or FGF21-like signaling in a subject. In certain embodiments, the disease is treatable by lowering blood glucose, insulin or serum lipid levels (e.g., Type 2 diabetes, obesity, dyslipidemia, NASH, cardiovascular disease, metabolic syndrome).

In some embodiments, the disease, disorder or condition is related to glucose metabolism or lipid metabolism. In some embodiments, the disease, disorder or condition is selected from the group of a hyperglycemic condition. (e.g., diabetes, such as Type I diabetes, Type 2 diabetes, gestational diabetes, insulin resistance, hyperinsulinemia, glucose intolerance, metabolic syndrome, or obesity).

In some embodiments, the methods of treating, preventing or ameliorating include methods of improving glucose metabolism and/or methods of improving lipid metabolism. In some embodiments, the methods of treating, preventing or ameliorating result in reduced glucose levels (e.g., reduced blood glucose), increased insulin sensitivity, reduced insulin resistance, reduced glycogen, improved glucose tolerance, improved glucose tolerance, improved glucose metabolism, improved homeostasis, improved pancreatic function, reduced triglycerides, reduced cholesterol, reduced IDL, reduced LDL, reduced VLDL, decreased blood pressure, decreased internal thickening of a blood vessel and/or decreased body mass or weight gain.

The present disclosure provides methods of treating a disease, disorder or condition associated with human FGF19 and/or human FGF21, which includes any disease, disorder or condition whose onset in a subject (e.g., a patient) is caused by, at least in part, the induction of FGF19-like and/or FGF21-like signaling, which is initiated in vivo by the formation of a complex comprising FGFR1c, FGFR2c, FGFR3c or FGFR4 and beta klotho and FGF19 or FGF21. The severity of the disease or condition can also be decreased by the induction of FGF19-like and/or FGF21-like signaling. Examples of diseases and conditions that can be treated with the binding proteins such as anti-beta klotho antibodies include type 2 diabetes, obesity, dyslipidemia, NASH, cardiovascular disease, and metabolic syndrome.

As such, the binding proteins such as anti-beta klotho antibodies described herein can be used to treat type 2 diabetes, obesity, dyslipidemia (e.g., hypertriglyceridemia), NASH, cardiovascular disease, and/or metabolic syndrome, as well as any disease, disorder, or condition in which it is desirable to mimic or augment the in vivo effects of FGF19 and/or FGF21, or can be employed as a prophylactic treatment administered, for example, daily, weekly, biweekly, monthly, bimonthly, biannually, etc. to prevent or reduce the frequency and/or severity of symptoms (e.g., elevated plasma glucose levels, elevated triglycerides and cholesterol levels), including, for example, to thereby provide an improved glycemic and/or cardiovascular risk factor profile. The present disclosure provides methods of improving metabolic parameters by administering to a subject a binding protein, including an antibody or fragment thereof as described herein or an pharmaceutical composition described herein, including, for example, wherein the improvement includes a decrease in body weight, body mass index, abdominal circumference, skinfold thickness, glucose, insulin and/or triglycerides.

The present disclosure also provides methods of inducing FGF19-like or FGF21-like signaling of cells having cell surface expression of beta klotho and one or more FGF receptors, such as FGFR1, FGFR2, FGFR3, or FGFR4 comprising contacting the cells with an effective amount of a binding protein (e.g., an antibody) that binds to beta klotho as described herein. In some embodiments, the cell is an adipocyte or hepatocyte. In other embodiments, the cell is a cell transfected with a gene encoding beta klotho and optionally a gene encoding an FGF receptor. Additional methods provided include using an anti-beta klotho antibody as described herein, with activity to mediate FGF19-like and/or FGF21 like signaling effects.

The present disclosure also provides methods of modulating an FGF19-like or FGF21-like signaling in a subject comprising administering an effective amount of a binding protein such as an anti-beta klotho antibody as described herein to a subject, including a subject in need thereof. In some embodiments, the modulating comprises FGF19-like activation. In some embodiments, the modulating comprises FGF21-like activation. In some embodiments, the modulating comprises increasing glucose metabolism (e.g., reducing glucose levels such as blood glucose levels).

The present disclosure also provides methods for detecting beta klotho in a sample comprising contacting the sample with a binding protein such as an anti-beta klotho antibody as described herein, that comprises a detectible agent. In certain embodiments, the sample comprises a cell expressing beta klotho on its surface.

The present disclosure also provides kits comprising a binding protein such as an anti-beta klotho antibody that binds to a beta klotho polypeptide, a beta klotho fragment or a beta klotho epitope as described herein.

BRIEF DESCRIPTION OF THE FIGURES

FIG. 1A-1B shows a sequence alignment of the heavy chain variable regions and light chain variable regions of the anti-beta klotho antibodies designated 5H23, 1C17, 1D19, 2L12, 3L3, 3N20, 4P5, 5C23, 5F7 and 1G19. Boundaries of CDRs are indicated by Kabat, AbM, Chothia, Contact and IMGT numbering.

FIGS. 2A-1 and 2A-2 shows sequence alignments of the heavy chain variable regions of the anti-beta klotho antibodies providing consensus CDR sequences. Top grouping consists of antibodies designated 5H23, 1D19, 2L12, 3L3, 4P5, 5C23 and 5F7. Lower grouping consists of antibodies designated 1C17 and 1G19. Bottom grouping consists only of the antibody designated 3N20 Variable residues are presented by "X." Boundaries of CDRs are indicated by Kabat, AbM, Chothia, Contact and IMGT numbering.

FIGS. 2B-1 and 2B-2 shows sequence alignments of the light chain variable regions of the anti-beta klotho antibodies providing consensus CDR sequences. Top grouping consists of antibodies designated 5H23, 1D19, 2L12, 3L3, 4P5, 5C23 and 5F7. Lower grouping consists of antibodies designated 1C17 and 1G19. Bottom grouping consists only of the antibody designated 3N20. Variable residues are presented by "X." Boundaries of CDRs are indicated by Kabat, AbM, Chothia, Contact and IMGT numbering.

FIGS. 3A-1 and 3A-2 shows a sequence alignment of the heavy chain variable region of anti-beta klotho antibody designated 5H23 with the humanized sequences (vH1-vH9). Residues that are bolded indicate exemplary residues that have been modified from the original antibody. Residues that are bolded and underlined indicate residues altered back to a mouse residue.

FIG. 3B shows a sequence alignment of the light chain variable region of anti-beta klotho antibody designated 5H23 with the humanized sequences (vL1-vL5). Residues that are bolded indicate exemplary residues that have been modified. Residues that are bolded and underlined indicate residues altered back to a mouse residue.

FIGS. 3C-1 and 3C-2 shows a sequence alignment of the light chain variable region of anti-beta klotho antibody designated 5H23 with the humanized sequences (v1-39a-v1-39p). Residues that are bolded indicate exemplary residues that have been modified.

FIGS. 3D-1 and 3D-2 shows a sequence alignment of a light chain variable region of anti-beta klotho antibody designated 5H23 with various humanized sequences (v3-20a-v3-20j). Residues that are bolded indicate exemplary residues that have been modified.

FIG. 4A-4C shows a sequence alignment between human, mouse and chimeric beta klotho polypeptides. Chimeric polypeptide chMoHu indicates mouse KLB(M1-F506)-human KLB(S509-S1044). Chimeric polypeptide chHuMo indicates human KLB (M1-F508)-mouse KLB (P507-S1043). Residues corresponding to mouse residues are bolded and italicized.

FIG. 5A-5F shows a sequence alignment between beta klotho polypeptides from various species described herein.

DETAILED DESCRIPTION

Figure 6:
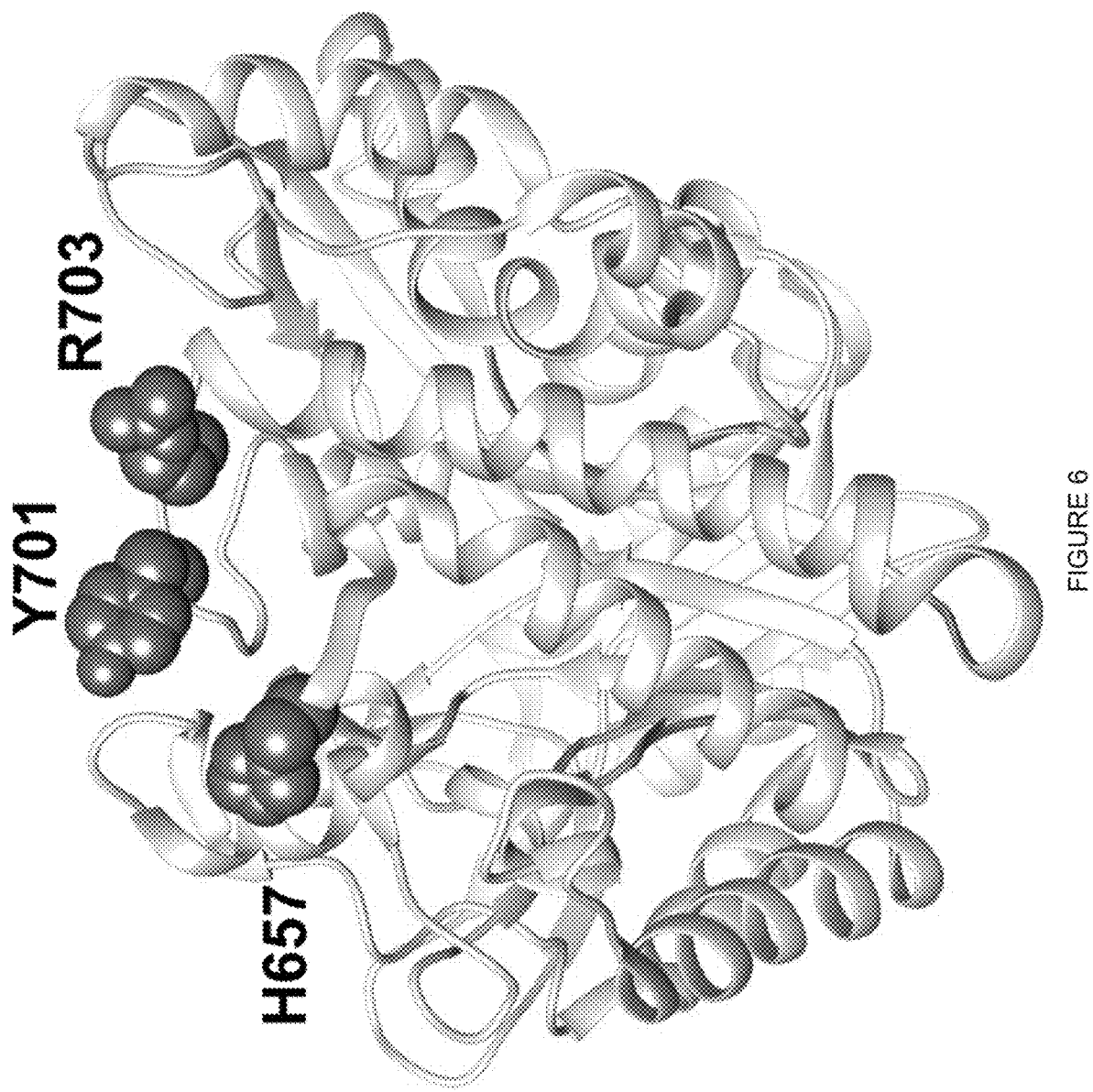
FIG. 6 shows a three-dimensional model of the three identified binding residues (dark spheres) at the equivalent positions on human cytosolic beta-glucosidase. The structure shows the equivalent of Klotho-beta residues 521-963.

Binding proteins, such as antibodies that bind beta klotho, including human and/or cyno beta klotho, are provided herein. A unique property of such binding proteins, including antibodies disclosed herein, is their agonistic nature, including the ability to mimic the in vivo effect of FGF19 and/or FGF21 and to induce FGF19-like signaling and/or FGF21-like signaling. More remarkably and specifically, some of the binding proteins such as antibodies to beta klotho disclosed herein (i) bind to human and cyno beta klotho, (ii) do not compete for binding with FGF19 and/or FGF21, and (iii) induce FGF19-like signaling and/or FGF21-like signaling, including, for example, in several in vitro cell-based assays. Such assays may include (1) an ELK-luciferase reporter assay (see, e.g., Example 4); (2) a recombinant FGF19 receptor mediated cell assay for ERK-phosphorylation (see, e.g., Example 4); and (3) a human adipocyte assay for ERK-phosphorylation (see, e.g., Example 5). Binding proteins such as anti-beta klotho antibodies, as described herein, therefore are expected to exhibit activities in vivo that are consistent with the natural biological function of FGF19 and/or FGF21. This property makes the disclosed binding proteins, including anti-beta klotho antibodies, viable therapeutics for the treatment of metabolic diseases (e.g., Type 2 diabetes, obesity, dyslipidemia, NASH, cardiovascular disease, metabolic syndrome) and broadly any disease, disorder, or condition in which it is desirable to mimic or augment the in vivo effects of FGF19 and/or FGF21.

The binding proteins, such as antibodies that bind beta klotho, that are provided herein share the common feature of competing with each other for the binding of beta klotho (see, e.g., Example 3 describing antibodies in the 5H23 epitope bin). This competitive inhibition indicates that each antibody binds to the same region of beta klotho (e.g., the same epitope), thereby asserting similar effects. The anti-beta klotho antibodies provided herein include humanized anti-beta klotho antibodies, including humanized anti-beta klotho antibodies derived from or based on 5H23, 1C17, 1D19, 2L12, 3L3, 3N20, 4P5, 5C23, 5F7 and/or 1G19 having CDR sequence as described in Tables 1-10 or FIGS. 1-3, such as anti-beta klotho antibodies, including humanized anti-beta klotho antibodies, bind to a specific domain of human beta klotho (e.g., KL2 (residues S509-S1044); see Example 9). Moreover, such binding can be largely attributed to particular amino acid residues within the KL2 region (e.g., H657, Y701 and R703), which comprise the epitope recognized by the anti-beta klotho antibodies described herein. Taken together, the results described herein demonstrate that the effects observed for an anti-beta klotho antibody that is derived from or based on 5H23 or an antibody in the 5H23 eptitope bin, including an antibody having one or more CDRs described in Tables 1-10 or FIGS. 1-3, can be extrapolated to other anti-beta klotho antibodies described herein having the same or similar eptitope specificity (e.g., the same or similar CDRs). For example, the in vitro activities of antibodies as shown in Examples 4-7 and 9, as well as the in vivo effects demonstrated in Example 8 for an exemplary humanized anti-beta klotho antibody, are representative of the activities and effects of the anti-beta klotho antibodies described herein.

In some embodiments of the present disclosure, the binding proteins such as anti-beta klotho antibodies may comprise immunoglobulin variable regions which comprise one or more complementary determining regions (CDRs) as described in Tables 1-10. In such binding proteins (e.g., anti-beta klotho antibodies), the CDRs may be joined with one or more scaffold regions or framework regions, which orient(s) the CDR(s) such that the proper antigen binding properties of the CDR(s) is achieved. Such binding proteins, including anti-beta klotho antibodies as described herein, can facilitate or enhance the interaction between FGFR1c and beta klotho, and can induce FGF19-like and/or FGF21-like signaling.

General Techniques

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (F. M. Ausubel, et al. eds., (2003)); Therapeutic Monoclonal Antibodies: From Bench to Clinic, Z. An, ed, Wiley, Hoboken N.J. (2009); Monoclonal Antibodies: Methods and Protocols, M. Albitar, ed., Humana Press, Totawa, N.J. (2010); and Antibody Engineering, 2nd Ed., Vols 1 and 2, Kontermann and Dubel, eds., Springer-Verlag, Heidelberg, 2010.

Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications and other publications are incorporated by reference in their entirety. In the event that any description of terms set forth conflicts with any document incorporated herein by reference, the description of term set forth below shall control.

The term "beta klotho" or "beta klotho polypeptide" and similar terms refers to a polypeptide ("polypeptide," and "protein" are used interchangeably herein) or any native beta klotho from any vertebrate source, including mammals such as primates (e.g., humans, cynomolgus monkey (cyno)), dogs, and rodents (e.g., mice and rats), unless otherwise indicated, and, in certain embodiments, included related beta klotho polypeptides, including SNP variants thereof. Beta klotho comprises two domains, beta klotho 1 (KLB1) and beta klotho 2 (KLB2). Each beta klotho domain comprises a glycosyl hydrolase 1 region. For example, the KLB1 domain of human beta klotho comprises amino acid residues 1-508 with the glycosyl hydrolase 1 region comprising amino acid residues 77-508, and the KLB2 domain of human beta klotho comprises amino acid residues 509-1044 with the glycosyl hydrolase 1 region comprising amino acid residues 517-967. The amino acid sequence of human beta klotho is provided below:

```
                                               (SEQ ID NO: 297)
   1 MKPGCAAGSP GNEWIFFSTD EITTRYRNTM SNGGLQRSVI LSALILLRAV

51 TGFSGDGRAI WSKNPNFTPV NESQLFLYDT FPKNFFWGIG TGALQVEGSW

101 KKDGKGPSIW DHFIHTHLKN VSSTNGSSDS YIFLEKDLSA LDFIGVSFYQ

151 FSISWPRLFP DGIVTVANAK GLQYYSTLLD ALVLRNIEPI VTLYHWDLPL

201 ALQEKYGGWK NDTIIDIFND YATYCFQMFG DRVKYWITIH NPYLVAWHGY

251 GTGMHAPGEK GNLAAVYTVG HNLIKAHSKV WHNYNTHFRP HQKGWLSITL

301 GSHWIEPNRS ENTMDIFKCQ QSMVSVLGWF ANPIHGDGDY PEGMRKKLFS

351 VLPIFSEAEK HEMRGTADFF AFSFGPNNFK PLNTMAKMGQ NVSLNLREAL

401 NWIKLEYNNP RILIAENGWF TDSRVKTEDT TAIYMMKNFL SQVLQAIRLD

451 EIRVFGYTAW SLLDGFEWQD AYTIRRGLFY VDFNSKQKER KPKSSAHYYK

501 QIIRENGFSL KESTPDVQGQ FPCDFSWGVT ESVLKPESVA SSPQFSDPHL

551 YVWNATGNRL LHRVEGVRLK TRPAQCTDFV NIKKQLEMLA RMKVTHYRFA

601 LDWASVLPTG NLSAVNRQAL RYYRCVVSEG LKLGISAMVT LYYPTHAHLG

651 LPEPLLHADG WLNPSTAEAF QAYAGLCFQE LGDLVKLWIT INEPNRLSDI

701 YNRSGNDTYG AAHNLLVAHA LAWRLYDRQF RPSQRGAVSL SLHADWAEPA

751 NPYADSHWRA AERFLQFEIA WFAEPLFKTG DYPAAMREYI ASKHRRGLSS

801 SALPRLTEAE RRLLKGTVDF CALNHFTTRF VMHEQLAGSR YDSDRDIQFL

851 QDITRLSSPT RLAVIPWGVR KLLRWVRRNY GDMDIYITAS GIDDQALEDD

901 RLRKYYLGKY LQEVLKAYLI DKVRIKGYYA FKLAEEKSKP RFGFFTSDFK

951 AKSSIQFYNK VISSRGFPFE NSSSRCSQTQ ENTECTVCLF LVQKKPLIFL

1001 GCCFFSTLVL LLSIAIFQRQ KRRKFWKAKN LQHIPLKKGK RVVS
```

An encoding nucleic acid sequence of human beta klotho is provided below:

```
                                       (SEQ ID NO: 298)
atgaagccaggctgtgcggcaggatctccagggaatgaatggattttctt cagcactgatgaaataaccacacgctataggaatacaatgtccaacgggg gattgcaaagatctgtcatcctgtcagcacttattctgctacgagctgtt actggattctctggagatggaagagctatatggtctaaaaatcctaattt tactccggtaaatgaaagtcagctgtttctctatgacactttccctaaaa acttttctggggtattgggactggagcattgcaagtggaagggagttgg aagaaggatggaaaaggaccttctatatgggatcatttcatccacacaca ccttaaaaatgtcagcagcacgaatggttccagtgacagttatattttc tggaaaaagacttatcagccctggattttataggagttctttttatcaa ttttcaatttcctggccaaggcttttccccgatggaatagtaacagttgc caacgcaaaaggtctgcagtactacagtactcttctggacgctctagtgc ttagaaacattgaacctatagttactttataccactgggatttgcctttg gcactacaagaaaaatatgggggtggaaaaatgataccataatagatat cttcaatgactatgccacatactgtttccagatgtttggggaccgtgtca aatattggattacaattcacaacccatatctagtggcttggcatgggtat gggacaggtatgcatgccctggagagaaggaaatttagcagctgtcta cactgtgggacacaacttgatcaaggctcactcgaaagtttggcataact acaacacacatttccgcccacatcagaagggttggttatcgatcacgttg ggatctcattggatcgagccaaaccggtcggaaaacacgatggatatatt caaatgtcaacaatccatggtttctgtgcttggatggtttgccaaccta
``` tccatggggatggcgactatccagaggggatgagaagaagttgttctcc gttctacccattttctctgaagcagagaagcatgagatgagaggcacagc tgatttctttgccttttcttttggacccaacaacttcaagcccctaaaca ccatggctaaaatgggacaaaatgtttcacttaatttaagagaagcgctg aactggattaaactggaatacaacaaccctcgaatcttgattgctgagaa tggctggttcacagacagtcgtgtgaaaacagaagacaccacggccatct acatgatgaagaatttcctcagccaggtgcttcaagcaataaggttagat gaaatacgagtgtttggttatactgcctggtctctcctggatggctttga atggcaggatgcttacaccatccgccgaggattattttatgtggatttta acagtaaacagaaagagcggaaacctaagtcttcagcacactactacaaa cagatcatacgagaaatggttttctttaaaagagtccacgccagatgt gcagggccagtttcctgtgacttctcctgggtgtcactgaatctgttc ttaagcccgagtctgtggcttcgtcccacagttcagcgatcctcatctg tacgtgtggaacgccactggcaacagactgttgcaccgagtggaagggt gaggctgaaaacacgacccgctcaatgcacagattttgtaaacatcaaaa aacaacttgagatgttggcaagaatgaaagtcacccactaccggtttgct ctggattgggcctcggtccttcccactggcaacctgtccgcggtgaaccg acaggccctgaggtactacaggtgcgtggtcagtgaggggctgaagcttg gcatctccgcgatggtcacccctgtattatccgacccacgccacctaggc ctccccgagcctctgttgcatgccgacgggtggctgaacccatcgacggc cgaggccttccaggcctacgctgggctgtgcttccaggagctgggggacc tggtgaagctctggatcaccatcaacgagcctaaccggctaagtgacatc tacaaccgctctggcaacgacacctacggggcggcgcacaacctgctggt ggcccacgccctggcctggcgcctctacgaccggcagttcaggccctcac agcgcggggccgtgtcgctgtcgctgcacgcggactgggcggaacccgcc aaccccatgctgactcgcactggagggcggccgagcgcttcctgcagtt cgagatcgcctggttcgccgagccgctcttcaagaccggggactaccccg cggccatgagggaatacattgcctccaagcaccgacgggggctttccagc tcggccctgccgcgcctcaccgaggccgaaaggaggctgctcaagggcac ggtcgacttctgcgcgctcaaccacttcaccactaggttcgtgatgcacg agcagctggccggcagccgctacgactcggacagggacatccagtttctg caggacatcacccgcctgagctcccacgcgcctggctgtgattccctg gggggtgcgcaagctgctgcggtgggtccggaggaactacggcgacatgg acatttacatcaccgccagtggcatcgacgaccaggctctggaggatgac cggctccggaagtactacctagggaagtaccttcaggaggtgctgaaagc atacctgattgataaagtcagaatcaaaggctattatgcattcaaactgg ctgaagagaaatctaaacccagatttggattcttcacatctgattttaaa gctaaatcctcaatacaattttacaacaaagtgatcagcagcagggggctt cccttttgagaacagtagttctagatgcagtcagacccaagaaaatacag agtgcactgtctgcttattccttgtgcagaagaaaccactgatattcctg ggttgttgcttcttctccaccctggttctactcttatcaattgccatttt tcaaaggcagaagagaagaaagttttggaaagcaaaaaacttacaacaca taccattaaagaaaggcaagagagttgttagc The amino acid sequence of beta klotho from cynomolgus monkey (cyno), scientific name *Macaca fascicularis*, is provided below:

```
                                          (SEQ ID NO: 299)
  1 MKPGCAAGSP GNEWIFFSTD EITIRYRNTM SNGGLQRSVI LSALTLLRAV

51 TGFSGDGRAV WSKNPNFTPV NESQLFLYDT FPKNFFWGVG TGALQVEGSW

101 KKDGKGPSIW DHFVHTHLKN VSSTNGSSDS YIFLEKDLSA LDFIGVSFYQ

151 FSISWPRLFP DGIVTVANAK GLQYYNTLLD SLVLRNIEPI VTLYHWDLPL

201 ALQEKYGGWK NDTIIDIFND YATYCFQTFG DRVKYWITIH NPYLVAWHGY

251 GTGMHAPGEK GNLAAVYTVG HNLIKAHSKV WHNYNTHFRP HQKGWLSITL

301 GSHWIEPNRS ENTMDILKCQ QSMVSVLGWF ANPIHGDGDY PEGMKKKLLS

351 ILPLFSEAEK NEVRGTADFF AFSFGPNNFK PLNTMAKMGQ NVSLNLREAL

401 NWIKLEYNNP RILIAENGWF TDSHVKTEDT TAIYMMKNFL SQVLQAIRLD

451 EIRVFGYTAW SLLDGFEWQD AYTIRRGLFY VDFNSKQKER KPKSSAHYYK

501 QIIRENGFSL KEATPDVQGQ FPCDFSWGVT ESVLKPESVA SSPQFSDPYL

551 YVWNATGNRL LHRVEGVRLK TRPAQCTDFV NIKKQLEMLA RMKVTHYRFA

601 LDWASVLPTG NLSAVNRQAL RYYRCVVSEG LKLGISAMVT LYYPTHAHLG

651 LPEPLLHAGG WLNPSTVEAF QAYAGLCFQE LGDLVKLWIT INEPNRLSDI

701 YNRSGNDTYG AAHNLLVAHA LAWRLYDRQF RPSQRGAVSL SLHADWAEPA

751 NPYADSHWRA AERFLQFEIA WFAEPLFKTG DYPAAMREYI ASKHRRGLSS
```

```
 801 SALPRLTEAE RRLLKGTVDF CALNHFTTRF VMHEQLAGSR YDSDRDIQFL

851 QDITRLSSPT RLAVIPWGVR KLLRWVRRNY GDMDIYITAS GIDDQALEDD

901 RLRKYYLEKY LQEVLKAYLI DKVRIKGYYA FKLAEEKSKP RFGFFTSDFK

951 AKSSIQFYNK MISSSGFPSE NSSSRCSQTQ KNTECTVCLF LVQKKPLIFL

1001 GCCFFSTLVL LLSITIFHRQ KRRKFWKAKN LQHIPLKKGK RVLS
```

An encoding nucleic acid sequence of cyno beta klotho is provided below:

(SEQ ID NO: 300)
atgaagcctggatgtgccgccggaagcccggcaacgagtggatcttctt
cagcaccgacgagatcaccatccggtacagaaacaccatgagcaacggcg
gcctgcagcggagcgtgatcctgtctgctctgaccctgctgagagccgtg
accggcttcagcggagatggcagagccgtgtggtccaagaaccccaactt
cacccccgtgaacgagagccagctgttcctgtacgataccttccccaaga
acttcttctggggcgtgggcacaggcgccctgcaggtggaaggatcctgg
aagaaggacggcaagggccccagcatctgggaccactttgtgcacaccca
cctgaagaacgtgtccagcaccacggcagcagcgacagctacatctttct
ggaaaaggacctgagcgccctggacttcatcggcgtgtccttctaccagt
tcagcatcagctggcccagactgttccccgacggcatcgtgacagtggcc
aatgccaagggcctgcagtactacaacaccctgctggacagcctggtgct
gcggaacatcgagcccatcgtgaccctgtaccactgggacctgccactgg
ctctgcaggagaaatacggcggctggaagaacgacaccatcatcgacatc
ttcaacgactacgccacctactgcttccagaccttcggcgacagagtgaa
gtactggatcacaatccacaaccctacctggtggcctggcacggctatg
gcaccggaatgcatgccctggcgagaagggaaatctggccgccgtgtac
accgtgggccacaacctgatcaaggcccacagcaaagtgtggcacaacta
caatacccacttccggccccaccagaagggctggctgtctatcacactgg
gcagccactggatcgagcctaaccgcagcgagaacaccatggacatcctg
aagtgccagcagagcatggtgtccgtgctgggatggttcgccaaccccat
tcacggcgacggcgattaccccgagggcatgaagaagaagctgctgagca
tcctgcccctgttcagcgaggccgagaagaacgaagtgcggggcaccgcc
gatttcttcgcctttagcttcggccccaacaacttcaagcccctgaatac
catggccaagatgggccagaatgtgtccctgaacctgagagaggccctga
actggatcaagctggagtacaacaaccccggatcctgatcgccgagaac
ggctggttcaccgacgccacgtgaaaaccgaggacaccaccgccatcta
tatgatgaagaacttcctgagccaggtgctgcaggctatccggctggatg
agatccgggtgttcggctacaccgcctggtcactgctggacggcttcgaa
tggcaggacgcctacaccatcagacggggcctgttctacgtggacttcaa
cagcaagcagaaagagcggaagcccaagagcagcgcccactactacaagc
agatcatcagagagaatggcttcagcctgaaagaggccaccccgacgtg
cagggccagttcccttgtgatttctcttggggcgtgaccgagagcgtgct gaagcctgaaagcgtggccagcagcccccagttcagcgaccccttacctgt
acgtgtggaacgccaccggcaaccggctgctgcatagagtggaaggcgtg
cggctgaaaaccagacccgcccagtgcaccgacttcgtgaacatcaagaa
acagctggaaatgctggcccggatgaaagtgacccactacagattcgccc
tggactgggccagcgtgctgcctaccggaaatctgagcgccgtgaacaga
caggccctgcggtactacagatgcgtggtgtccgagggcctgaagctggg
catcagcgccatggtcaccctgtactacctaccacgcccacctgggac
tgcctgaacctctgctgcatgctggcggctggctgaaccctagcaccgtg
gaagcctttcaggcctacgccgggctgtgcttccaggaactgggcgacct
cgtgaagctgtggatcaccatcaacgagcccaacagactgagcgacatct
acaacagaagcggcaacgacacctacggcgctgcccacaatctgctggtg
gctcatgccctggcttggcggctgtacgacagacagttccggccttctca
gcggggagccgtgtctctgtctctgcatgccgattgggccgagcccgcca
acccttacgccgactctcattggagagccgccgagcggttcctgcagttc
gagatcgcttggtttgccgagcccctgttcaagaccggcgattaccctgc
cgccatgagagagtatatcgccagcaagcacagacggggcctgagcagct
ctgccctgcctagactgaccgaggccgagcggagactgctgaagggaacc
gtggatttctgcgccctgaaccacttcaccaccagattcgtgatgcacga
gcagctggccggcagcagatacgacagcgaccgggacatccagtttctgc
aggacatcacccggctgagcagccctacaagactggccgtgatcccttgg
ggagtgcggaagctgctgagatgggtgcgcagaaactacggcgacatgga
tatctacatcaccgccagcggcatcgacgaccaggccctggaagatgacc
ggctgcggaagtactacctggaaaagtacctgcaggaagtgctgaaggcc
tacctgatcgacaaagtgcggatcaagggctactacgccttcaagctggc
cgaggaaagagcaagcccagattcggcttcttcaccagcgacttcaagg
ccaagagcagcatccagttctacaacaagatgatcagcagcagcggcttc
cccagcgagaacagcagctccagatgcagccagacccagaaaaacaccga
gtgtaccgtgtgcctgttcctggtgcagaagaagcccctgatcttcctgg
gctgctgcttctttagcaccctggtgctgctgctgtccatcaccatcttc
caccggcagaagcggaaagttctggaaggccaaaaacctgcagcacat
cccctgaagaaaggcaagcgggtgctgagctga The amino acid sequence of beta klotho homolog from mouse, scientific name *Mus musculus*, is provided below:

(SEQ ID NO: 301)

```
  1 MKTGCAAGSP GNEWIFFSSD ERNTRSRKTM SNRALQRSAV LSAFVLLRAV
 51 TGFSGDGKAI WDKKQYVSPV NPSQLFLYDT FPKNFSWGVG TGAFQVEGSW
101 KTDGRGPSIW DRYVYSHLRG VNGTDRSTDS YIFLEKDLLA LDFLGVSFYQ
151 FSISWPRLFP NGTVAAVNAQ GLRYYRALLD SLVLRNIEPI VTLYHWDLPL
201 TLQEEYGGWK NATMIDLFND YATYCFQTFG DRVKYWITIH NPYLVAWHGF
251 GTGMHAPGEK GNLTAVYTVG HNLIKAHSKV WHNYDKNFRP HQKGWLSITL
301 GSHWIEPNRT DNMEDVINCQ HSMSSVLGWF ANPIHGDGDY PEFMKTGAMI
351 PEFSEAEKEE VRGTADFFAF SFGPNNFRPS NTVVKMGQNV SLNLRQVLNW
401 IKLEYDDPQI LISENGWFTD SYIKTEDTTA IYMMKNFLNQ VLQAIKFDEI
451 RVFGYTAWTL LDGFEWQDAY TTRRGLFYVD FNSEQKERKP KSSAHYYKQI
501 IQDNGFPLKE STPDMKGRFP CDFSWGVTES VLKPEFTVSS PQFTDPHLYV
551 WNVTGNRLLY RVEGVRLKTR PSQCTDYVSI KKRVEMLAKM KVTHYQFALD
601 WTSILPTGNL SKVNRQVLRY YRCVVSEGLK LGVFPMVTLY HPTHSHLGLP
651 LPLLSSGGWL NMNTAKAFQD YAELCFRELG DLVKLWITIN EPNRLSDMYN
701 RTSNDTYRAA HNLMIAHAQV WHLYDRQYRP VQHGAVSLSL HCDWAEPANP
751 FVDSHWKAAE RFLQFEIAWF ADPLFKTGDY PSVMKEYIAS KNQRGLSSSV
801 LPRFTAKESR LVKGTVDFYA LNHFTTRFVI HKQLNTNRSV ADRDVQFLQD
851 ITRLSSPSRL AVTPWGVRKL LAWIRRNYRD RDIYITANGI DDLALEDDQI
901 RKYYLEKYVQ EALKAYLIDK VKIGYYAFK LTEEKSKPRF GFFTSDFRAK
951 SSVQFYSKLI SSSGLPAENR SPACGQPAED TDCTICSFLV EKKPLIFFGC
1001 CFISTLAVLL SITVFHHQKR RKFQKARNLQ NIPLKKGHSR VFS
```

An encoding nucleic acid sequence of mouse beta klotho is provided below:

(SEQ ID NO: 302)

```
atgaagacaggctgtgcagcagggtctccggggaatgaatggattttc
ttcagctctgatgaaagaaacacacgctctaggaaaacaatgtccaac
agggcactgcaaagatctgccgtgctgtctgcgtttgttctgctgcga
gctgttaccggcttctccggagacgggaaagcaatatggataaaaaa
cagtacgtgagtccggtaaacccaagtcagctgttcctctatgacact
ttccctaaaaacttttcctggggcgttgggaccggagcatttcaagtg
gaagggagttggaagacagatggaagaggaccctcgatctgggatcgg
tacgtctactcacacctgagaggtgtcaacggcacagacagatccact
gacagttacatctttctggaaaaagacttgttggctctggatttttta
ggagtttcttttatcagttctcaatctcctggccacggttgtttccc
aatggaacagtagcagcagtgaatgcgcaaggtctccggtactaccgt
gcacttctggactcgctggtacttaggaatatcgagcccattgttacc
ttgtaccattgggatttgcctctgacgctccaggaagaatatgggggc
tggaaaaatgcaactatgatagatctcttcaacgactatgccacatac
tgcttccagacccttggagaccgtgtcaaatattggattacaattcac
aaccccttaccttgttgcttggcatgggtttggcacaggtatgcatgca
ccaggagagaagggaaatttaacagctgtctacactgtgggacacaac
ctgatcaaggcacattcgaaagtgtggcataactacgacaaaaacttc
cgccctcatcagaagggttggctctccatcaccttggggtcccattgg
atagagccaaacagaacagacaacatggaggacgtgatcaactgccag
cactccatgtcctctgtgcttggatggttcgccaaccccatccacggg
gacggcgactaccctgagttcatgaagacgggcgccatgatccccgag
ttctctgaggcagagaaggaggaggtgaggggcacggctgatttctttt
gccttttccttcgggcccaacaacttcaggccctcaaacaccgtggtg
aaaatgggacaaaatgtatcactcaacttaaggcaggtgctgaactgg
attaaactggaatacgatgaccctcaaatcttgatttcggagaacggc
tggttcacagatagctatataaagacagaggacaccacggccatctac
atgatgaagaatttcctaaaccaggttcttcaagcaataaaatttgat
gaaatccgcgtgtttggttatacggcctggactctcctggatggcttt
gagtggcaggatgcctatacgacccgacgagggctgttttatgtggac
tttaacagtgagcagaaagagaggaaacccaagtcctcggctcattac
tacaagcagatcatacaagacaacggcttcccttttgaaagagtccacg
ccagacatgaagggtcggttcccctgtgatttctcttggggagtcact
```

-continued

```
gagtctgttcttaagcccgagtttacggtctcctcccgcagtttacc
gatcctcacctgtatgtgtggaatgtcactggcaacagattgctctac
cgagtggaaggggtaaggctgaaaacaagaccatcccagtgcacagat
tatgtgagcatcaaaaaacgagttgaaatgttggcaaaaatgaaagtc
acccactaccagtttgctctggactggacctctatccttcccactggc
aatctgtccaaagttaacagacaagtgttaaggtactataggtgtgtg
gtgagcgaaggactgaagctgggcgtcttccccatggtgacgttgtac
cacccaacccactcccatctcggcctcccctgccacttctgagcagt
gggggggtggctaaacatgaacacagccaaggccttccaggactacgct
gagctgtgcttccgggagttgggggacttggtgaagctctggatcacc
atcaatgagcctaacaggctgagtgacatgtacaaccgcacgagtaat
gacacctaccgtgcagcccacaacctgatgatcgcccatgcccaggtc
tggcacctctatgataggcagtataggccggtccagcatggggctgtg
tcgctgtccttacattgcgactgggcagaacctgccaaccccttgtg
gattcacactggaaggcagccgagcgcttcctccagtttgagatcgcc
tggtttgcagatccgctcttcaagactggcgactatccatcggttatg
aaggaatacatcgcctccaagaaccagcgagggctgtctagctcagtc
ctgccgcgcttcaccgcgaaggagagcaggctggtgaagggtaccgtc
gacttctacgcactgaaccacttcactacgaggttcgtgatacacaag
cagctgaacaccaaccgctcagttgcagacagggacgtccagttcctg
caggacatcacccgcctaagctcgcccagccgcctggctgtaacaccc
tggggagtgcgcaagctccttgcgtggatccggaggaactacagagac
agggatatctacatcacagccaatggcatcgatgacctggctctagag
gatgatcagatccgaaagtactacttggagaagtatgtccaggaggct
ctgaaagcatatctcattgacaaggtcaaaatcaaaggctactatgca
ttcaaactgactgaagagaaatctaagcctagatttggattttttcacc
tctgacttcagagctaagtcctctgtccagttttacagcaagctgatc
agcagcagtggcctccccgctgagaacagaagtcctgcgtgtggtcag
cctgcggaagacacagactgcaccattttgctcattctcgtggagaag
aaaccactcatcttcttcggttgctgcttcatctccactctggctgta
ctgctatccatcaccgttttcatcatcaaaagagaagaaattccag
aaagcaaggaacttacaaaatataccattgaagaaaggccacagcaga
gttttcagc
```

The amino acid sequence of beta klotho from rat, scientific name *Rattus norvegicus*, is provided below:

```
                                  (SEQ ID NO: 356)
MKTGCAAGSPGNEVVVFFSSDERSTRSRKTMSNGALQRSAVLSALVLLR

AVTGFSGDGKAIWDKKQYVSPVNPGQLFLYDTFPKNFSWGVGTGAFQVE

GSWKADGRGPSIWDRYVDSHLRGVNSTDRSTDSYVFLEKDLLALDFLGV

SFYQFSISWPRLFPNGTVAAVNAKGLQYYRALLDSLVLRNIEPIVTLYH

WDLPLTLQEEYGGWKNATMIDLFNDYATYCFQTFGDRVKYWITIHNPYL
```

-continued

```
VAWHGFGTGMHAPGEKGNLTAVYTVGHNLIKAHSKVWHNYDKNFRPHQK

GWLSITLGSHWIEPNRTENMEDVINCQHSMSSVLGWFANPIHGDGDYPE

FMKTSSVIPEFSEAEKEEVRGTADFFAFSFGPNNFRPSNTVVKMGQNVS

LNLRQVLNWIKLEYDNPRILISENGWFTDSYIKTEDTTAIYMMKNFLNQ

VLQAIKFDEIQVFGYTAVVTLLDGFEWQDAYTTRRGLFYVDFNSEQKER

KPKSSAHYYKQIIQDNGFPLQESTPDMKGQFPCDFSWGVTESVLKPEFT

VSSPQFTDPHLYVWNVTGNRLLYRVEGVRLKTRPSQCTDYVSIKKRVEM

LAKMKVTHYQFALDVVTSILPTGNLSKINRQVLRYYRCVVSEGLKLGIS

PMVTLYHPTHSHLGLPMPLLSSGGWLNTNTAKAFQDYAGLCFKELGDLV

KLWITINEPNRLSDMYNRTSNDTYRAAHNLMIAHAQVWHLYDRQYRPVQ

HGAVSLSLHSDWAEPANPYVESHWKAAERFLQFEIAWFADPLFKTGDYP

LAMKEYIASKKQRGLSSSVLPRFTLKESRLVKGTIDFYALNHFTTRFVI

HKQLNTNCSVADRDVQFLQDITRLSSPSRLAVTPWGMRKLLGWIRRNYR

DMDIYVTANGIDDLALEDDQIRKYYLEKYVQEALKAYLIDKVKIKGYYA

FKLTEEKSKPRFGFFTSDFKAKSSVQFYSKLISSSGFSSENRSPACGQP

PEDTECAICSFLTQKKPLIFFGCCFISTLAALLSITIFHHRKRRKFQKA

RNLQNIPLKKGHSRVFS
```

An encoding nucleic acid sequence of rat beta klotho is provided below:

```
                                  (SEQ ID NO: 357)
ATGAAGACAGGCTGTGCAGCAGGGTCTCCAGGGAATGAATGGGTTTTCTT

CAGCTCTGATGAAAGAAGCACACGCTCTAGGAAAACAATGTCCAACGGAG

CACTGCAAAGATCTGCCGTGCTGTCTGCATTGGTTCTGCTGCGAGCTGTT

ACCGGCTTCTCTGGAGACGGAAAAGCAATATGGGATAAAAAACAATACGT

GAGTCCGGTAAACCCAGGTCAGCTGTTCCTCTATGACACTTTCCCTAAAA

ACTTTTCCTGGGGCGTTGGGACCGGAGCATTTCAAGTGGAAGGGAGTTGG

AAGGCAGATGGAAGAGGACCCTCGATCTGGGACCGTTATGTCGACTCACA

CCTGAGAGGTGTCAACAGCACAGACAGATCCACTGACAGTTATGTCTTTC

TGGAAAAGGACTTGCTGGCTCTGGATTTTTTAGGAGTTTCTTTTTATCAG

TTCTCAATCTCCTGGCCGCGGTTGTTCCCCAACGGAACAGTAGCAGCTGT

GAATGCAAAAGGTCTCCAGTACTACAGAGCACTTCTGGACTCGCTGGTAC

TTAGGAATATCGAACCCATTGTTACCTTATACCATTGGGATTTGCCTTTG

ACGCTACAGGAAGAATATGGGGGCTGGAAAAATGCAACTATGATAGATCT

CTTCAATGACTATGCCACATACTGCTTCCAGACCTTTGGAGACCGTGTCA

AATATTGGATTACAATTCACAACCCTTACCTCGTTGCTTGGCATGGGTTT

GGCACAGGTATGCATGCGCCAGGAGAGAAGGGAAATTTAACAGCTGTCTA

CACTGTGGGACACAACCTGATCAAGGCGCATTCGAAAGTGTGGCATAACT

ACGACAAAAACTTCCGCCCTCATCAGAAGGGTTGGCTCTCCATCACCTTG

GGGTCCCATTGGATAGAACCAAACAGAACAGAAAACATGGAGGACGTGAT

CAACTGCCAGCACTCCATGTCTTCTGTGCTCGGATGGTTTGCCAACCCCA
```

-continued
```
TCCACGGAGACGGCGACTACCCCGAGTTCATGAAGACGAGCTCCGTAATC
CCTGAGTTCTCTGAGGCAGAGAAGGAGGAGGTGCGGGGCACTGCTGACTT
CTTTGCCTTTTCCTTCGGGCCCAACAATTTCAGGCCCTCGAACACCGTGG
TAAAAATGGACAAAATGTATCACTCAACTTAAGACAGGTGCTGAACTGG
ATTAAACTAGAATATGACAACCCTCGAATCTTGATTTCGGAGAACGGCTG
GTTCACAGATAGTTATATAAAGACGGAAGATACCACGGCCATCTACATGA
TGAAGAATTTCCTCAACCAGGTTCTTCAAGCAATAAAGTTTGATGAAATA
CAAGTGTTTGGTTATACGGCTTGGACTCTCCTGGATGGCTTTGAGTGGCA
GGATGCCTACACGACCCGACGAGGGCTGTTTTATGTGGACTTTAATAGTG
AGCAGAAAGAGAGGAAACCCAAGTCCTCCGCTCATTACTACAAACAGATT
ATACAAGACAACGGTTTCCCTTTGCAAGAATCCACACCAGACATGAAGGG
TCAGTTTCCCTGTGACTTCTCCTGGGGAGTCACTGAGTCTGTTCTTAAGC
CGGAGTTTACGGTGTCCTCCCCACAGTTTACTGATCCTCACCTGTATGTG
TGGAATGTCACTGGCAACAGATTGCTATACCGAGTGGAAGGAGTCAGGCT
AAAAACAAGACCGTCCCAATGCACAGATTATGTGAGCATCAAAAAACGAG
TTGAAATGTTGGCCAAAATGAAAGTCACCCACTACCAGTTTGCTCTGGAC
TGGACCTCTATCCTCCCTACCGGAAATCTGTCTAAAATTAATAGACAAGT
GTTGAGGTACTATAGGTGTGTGGTGAGCGAAGGACTGAAGCTGGGCATCT
CCCCTATGGTGACGTTGTACCACCCGACCCACTCCCATCTAGGCCTCCCC
ATGCCACTTCTGAGCAGTGGGGATGGCTAAACACCAACACAGCCAAGGC
CTTCCAGGACTACGCAGGCCTGTGCTTCAAGGAGCTGGGGGACTTGGTAA
AGCTCTGGATCACCATCAATGAACCCAATAGGCTGAGTGACATGTACAAC
CGCACGAGTAACGACACCTACCGTGCGGCCCACAACCTGATGATCGCCCA
TGCCCAGGTCTGGCACCTCTATGATAGGCAGTATAGGCCGGTCCAGCACG
GGGCTGTGTCGCTGTCCTTACATTCCGACTGGGCAGAACCTGCCAACCCC
TATGTGGAGTCTCACTGGAAGGCAGCCGAGCGCTTCCTCCAGTTTGAGAT
CGCCTGGTTTGCGGATCCACTCTTCAAGACTGGTGACTACCCGCTGGCCA
TGAAGGAATACATCGCCTCCAAGAAGCAGCGAGGGCTGTCTAGCTCAGTC
CTGCCGCGCTTTACCTTGAAGGAGAGCAGGCTGGTGAAGGGGACCATCGA
CTTTTACGCACTGAACCACTTCACTACTAGATTCGTGATACACAAGCAGT
TGAATACCAACTGCTCAGTGGCAGACAGGGACGTCCAGTTCCTGCAGGAC
ATCACCCGCCTGAGCTCGCCCAGTCGCCTAGCCGTAACGCCCTGGGGAAT
GCGCAAGCTCCTTGGGTGGATCCGGAGGAACTACAGAGACATGGATATCT
ACGTCACAGCCAATGGCATTGATGATCTTGCTCTAGAGGACGATCAGATT
AGAAAGTACTACTTGGAGAAGTACGTCCAGGAGGCTCTGAAAGCATATCT
GATTGACAAGGTCAAAATCAAAGGCTACTATGCATTCAAACTGACTGAAG
AGAAATCTAAGCCTAGATTTGGATTTTTCACATCTGACTTCAAAGCTAAA
TCTTCTGTACAGTTTTATAGCAAGCTGATCAGCAGCAGCGGCTTCTCCTC
TGAGAACAGAAGTCCTGCCTGTGGTCAGCCTCCAGAAGACACAGAATGCG
CCATTTGCTCCTTCCTTACACAGAAGAAACCACTCATCTTCTTTGGTTGT
TGCTTCATCTCCACTCTGGCTGCACTGCTATCAATCACTATTTTTCATCA
TCGGAAGAGAAGAAAATTCCAGAAAGCAAGGAACTTACAAAATATACCAT
TGAAGAAAGGGCACAGCAGAGTTTTTAGCTAA
```

The amino acid sequence of beta klotho from Hamster, scientific name *Cricetulus griseus*, is provided below:

(SEQ ID NO: 408)
```
MKAGCAAGSPGNEWIFLSSYERNTRSKKTMSNRALQRSVVLSAFVLLRAV
TGLSGDGKAIWDKKQYVSPVNASQLFLYDTFPKNFFWGVGTGAFQVEGNW
QADGRGPSIWDRFIYTHLRDVSITEKSADSYIFLEKDLLALDFLGVSFYQ
FSISWPRLFPNGTVASVNAKGLQYYNKLLDSLILRNIEPVVTLYHWDLPL
ALQEDYGGWKNATMIDLFNDYATYCFQTFGDRVKYWITIHNPYLVAWHGF
ATGMHAPGETGNLTAVYIVGHNLIKAHSKVWHNYDKNFRPHQKGLLSITL
GSHWIEPNKTENMADTISCQHSMAFVLGWFANPIHADGDYPEFMKTLSTM
PVFSEAEKEEVRGTADFFAFSFGPNNFRPSNTVVKMGQNVSLNLRQVLNW
IKLEYDNPRILISENGWFTDSDIKTEDTTAIYMMKHFLNQVLQAIQFDEI
RVFGYTAWSLLDGFEWQYAYTSRRGLFYVDFNSEQKERKPKTSAHYYKQI
IQENGFPLKESTPDMQGQFPCDFSWGVTESVLKPEFMVSSPQFTDPHLYV
WNATGNRLLQRVEGVRLKTKPSHCTDYVSIKKRVEMLAKMKVTHYQFALD
WATILPTGNLSEVNRQVLRYYRCVVSEGLKLGVSPMVTLYHPTHSHLGLP
EPLLNSGGWLNTYTAKAFQDYAGLCFQELGDLVKLWITINEPNRLSDMYN
RTSNDTYRAAHNLMIAHAQVWRLYDRQYRPVQHGAVSLSLHSDWVEPANP
YVDSHWKAAERFLLFEIAWFADPLFKTGDYPLAMKEYIASKNQQGLSRSV
LPRFTPEESRLVKGTIDFYALNHFTTRFVIHKQLNSSRSMADRDVQFLQD
ITRLSSPSRLAVMPWGARKLLGWIQRNYGDMDIYITANGIDDLALENDGI
RKYYLEKYIQEALKAYLIDKVKIKGYYAFKLTEEKSKPRFGFFTSDFKAK
SSVEFYSKLISRSGFPSETSNPACGQPPEDTDCTICSFFTQKKSLIFFGC
CFISTLAVLLSITIFHHRKRRFHKSKNLENIPLKEGHSRVLS
```

An encoding nucleic acid sequence of Hamster beta klotho is provided below:

(SEQ ID NO: 409)
```
atgtccaacagggcactgcaaagatctgtcgtgctgtcagcgtttgttct
gctgcgagctgttaccggattgtctggagacgggaaagcgatatgggata
aaaaacagtacgtgagtccggtgaatgcaagtcagctgtttctctatgac
actttccctaaaaacttttctggggtgttggaactggagcatttcaagt
ggaagggaattggcaggcagacggaagaggaccctcgatttgggatcgtt
tcatctacacacacctgagagatgtcagcatcacagagaaatccgccgac
agttacattttctggaaaaagatttgttggctctggattttttaggagt
ttcttttttatcagttctcaatctcctggccacggttgttccccaatggaa
cagtagcatccgtgaatgcaaaaggtctccaatactacaacaaacttctg
gactcgctgatacttaggaatattgagcccgttgttaccttataccattg
ggatttgcctttggcgctacaggaagactatgggggttggaaaaatgcaa
```

```
ctatgatagatctcttcaatgactatgccacatactgcttccagaccttt
ggagaccgtgtcaagtattggattacaattcacaaccccttacctggttgc
ttggcatgggtttgccacaggtatgcatgcgccaggagagacgggaaatt
taacagctgtctacattgtgggacacaacctgatcaaggctcattcgaaa
gtgtggcataactacgacaaaaacttccgcccccatcagaagggtttgct
gtccattaccttggggtcccactggatagaaccaaacaaaacagaaaaca
tggccgatacaatcagctgccagcactctatggcttttgtgcttgggtgg
tttgccaacccatccatgcagacggcgactaccctgagttcatgaaaac
attgtccaccatgccagtgttctctgaggcagagaaggagggggtgaggg
gcacagctgacttctttgccttttcctttgggcccaacaatttcaggccc
tcgaacactgtagtgaaaatgggacaaaatgtatcactcaacttaagaca
ggtgctgaactggattaaattagaatatgacaaccctcgaatcttgattt
cggagaatggctggttcacagatagtgacataaagacagaggacaccaca
gccatctacatgatgaagcatttcctcaaccaggttcttcaagcaataca
gtttgatgaaatacgagtgtttggttacacggcctggtctctcctgatg
gctttgaatggcagtatgcctacacgtctcgccgaggactgttttatgtg
gactttaatagtgaacagaaagaaaggaaacccaagacctcggcacatta
ctacaaacagatcatacaagaaatggtttcccttgaaagagtccacgc
cagacatgcagggtcagtttccctgtgacttctcctgggggtcaccgag
tctgttcttaagccggagtttatggtttcctccccacagtttaccgaccc
tcacctgtatgtgtggaatgccactggcaacagattgctacagcgagtag
aaggagtaaggctaaaaacaaaaccatcccactgcacagactatgttagc
atcaaaaaacgagttgagatgttggccaaaatgaaagtcacccactacca
gtttgctctggactgggccaccatccttcccactggcaatctgtctgaag
ttaatagacaagtactaaggtactataggtgtgtggtgagcgaaggactg
aagctgggcgtctctcccatggtgacgttgtaccaccccacccactccca
tctaggcctccctgagccgcttcttaacagtgggggatggctaaacactt
acaccgccaaggccttccaggactacgcaggactgtgcttccaggaacta
ggggacttggtgaagctctggatcaccatcaatgagcctaataggctgag
tgacatgtacaaccgcacgagtaatgacacctaccgtgcagcccataacc
tgatgattgccatgcccaggtctggcgtctctacgacaggcagtataggg
ccagtccagcatggagctgtgtcgctgtccctacattctgactgggtgga
acctgccaaccctatgtggactcacactggaaggcagcggagcgcttcc
tcctgtttgagatcgcctggttcgctgatccgctcttcaagactggcgac
tatccactggccatgaaggagtacatcgcctccaagaaccagcaagggct
gtcccgctcagtcctgccgcgcttcaccccagaggagagcaggctggtga
agggcaccatcgacttctacgcactgaaccacttcactactaggttcgtg
atacacaaacagctcaacagcagccgctctatggcagacagggacgtcca
gttcctgcaggacatcacccgcctgagctcgcccagccgcctggctgtta
tgccctggggagcacgcaagctgctttgggtggatccagaggaactatggg
gacatggacatctacatcacagccaatggcatcgatgatctggctctgga
``` gaatgatgggatccgaaagtactacttggagaagtacatccaggaggctc tgaaagcatacctcattgacaaagtcaaaatcaaaggctattatgcattc aaactgactgaagagaaatctaagcctagatttggatttttcacatctga cttcaaagctaagtcatctgtagagttttatagcaagttgatcagcagaa gtggcttcccctctgagactagcaatcccgcatgtggtcagcctccagaa gacacagactgcaccatctgctcatttttcactcagaagaaatctctgat cttctttggttgttgcttcatctccactctggctgtactgctgtcaatca ccattttcatcatcgaaagagaagatttcataaatcaaagaacttagaa aatataccattgaaggaaggccacagtagagttcttagctaa The amino acid sequence of beta klotho from rabbit, scientific name *Oryctolagus cuniculus*, is provided below:

(SEQ ID NO: 410)
MKPGCAAGSPGNEWVSFCTDERNRRCRETMSSGRLRRSVMLSAFILLRAV
TGFPGDGRAVWSQNPNLSPVNESQLFLYDTFPKNFFWGVGTGAFQVEGSW
KKDGKGLSVWDHFIATHLNVSSRDGSSDSYIFLEKDLSALDFLGVSFYQF
SISWPRLFPDGTVAVANAKGLQYYNRLLDSLLLRNIEPVVTLYHWDLPWA
LQEKYGGWKNETLIDLFNDYATYCFQTFGDRVKYWITIHNPYLVAWHGYG
TGLHAPGEKGNVAAVYTVGHNLLKAHSKVWHNYNRNFRPHQKGWLSITLG
SHWIEPNRAESIVDILKCQQSMVSVLGWFANPIHGDGDYPEVMTKKLLSV
LPAFSEAEKNEVRGTADFFAFSFGPNNFKPLNTMAKMGQNVSLNLRQVLN
WIKLEYGNPRILIAENGWFTDSYVQTEDTTAIYMMKNFLNQVLQAIRLDG
VRVFGYTAWSLLDGFEWQDAYNTRRGLFYVDFNSEQRERRPKSSAHYYKQ
VIGENGFTLREATPDLQGQFPCDFSWGVTESVLKPESVASSPQFSDPHLY
VWNATGNRMLHRVEGVRLKTRPAQCTDFITIKKQLEMLARMKVTHFRFAL
DWASVLPTGNLSEVNRQALRYYRCVVTEGLKLNISPMVTLYYPTHAHLGL
PAPLLHSGGWLDPSTAKAFRDYAGLCFRELGDLVKLWITINEPNRLSDVY
NRTSNDTYQAAHNLLIAHALVWHLYDRQYRPSQRGALSLSLHSDWAEPAN
PYVASHWQAAERFLQFEIAWFAEPLFKTGDYPVAMREYIASKTRRGLSSS
VLPRFSDAERRLVKGAADFYALNHFTTRFVMHEQQNGSRYDSDRDVQFLQ
DITRLASPSRLAVMPWGEGKLLRWMRNNYGDLDVYITANGIDDQALQNDQ
LRQYYLEKYVQEALKAYLIDKIKIKGYYAFKLTEEKSKPRFGFFTSDFKA
KSSIQFYNKLITSNGFPSENGGPRCNQTQGNPECTVCLLLLQKKPLIFFS
CCFFCTLVLLSSITIFHRRKRRKFWKAKDLQHIPLKKGHKRVLS

An encoding nucleic acid sequence of rabbit beta klotho is provided below:

(SEQ ID NO: 411)
tgaagccgtgataagacggtcccgcagttcgtggcaaatgaagccaggct gtgcggcaggatctccaggggaatgaatgggtttccttctgcaccgatgaa agaaacagacgctgtagggaaacgatgtccagcggacgcctgcggagatc tgtcatgctgtcagccttcatcctgctgcgagccgtgactgggttccccg -continued

```
gagacggaagagctgtatggtcgcaaaatcctaatttgagtccggtaaac
gaaagtcagctgtttctctatgacactttcccaaaaaacttttttctgggg
tgtggggactggagccttccaagtggaagggagttggaagaaggatggga
aaggactctctgtatgggatcatttcatcgctacacacctgaacgtcagc
agccgcgatggctccagtgacagctacatttttttggagaaagacttatc
ggcgctggattttttaggagtctcttttttatcagttttcaatttcctggc
caagactgttcccggatggcacagtagcagtcgccaatgcaaaaggtctc
cagtactataatcggctcctggactctctgctacttagaaacattgaacc
tgtagtcactttataccattgggatctgccttgggcgctacaagaaaaat
acgggggtggaaaaacgagacgttgattgatttattcaatgactatgcc
acctactgtttccagacgtttggggaccgtgtcaaatactggatcaccat
tcacaatccctatctggtggcttggcatggctacgggacaggtctgcatg
ctccgggagagaaggggaatgtggcagctgtctacactgtgggacacaac
ctgcttaaggctcattcaaaagtctggcacaactacaacaggaatttccg
cccgcatcagaaaggctggctgtcgatcacgctgggatcccactggattg
agccaaacagagcggaaagcatcgtggacatactcaagtgccagcagtcc
atggtctcggtgctgggctggtttgccaacccgatccacggggacgggga
ctacccagaggtgatgacaaagaagctgctctccgtcctgcccgctttct
cagaagcagagaagaacgaggtacgaggcaccgcagacttctttgccttt
tcgtttggaccaacaacttcaagcccttaaacaccatggctaaaatggg
gcagaatgtgtcactcaatctaagacaggtgctgaactggattaaactgg
aatatggcaaccctcgaatcctgatcgctgagaacggctggttcacagac
agttacgtgcaaacagaagacaccacagccatctacatgatgaagaattt
cctcaaccaggttcttcaagcaataaggttggatggagtccgagtgtttg
gctacactgctggtctctcctggatggcttcgaatggcaggacgcttac
aacacccgccgtggactgttttatgtggacttcaacagcgaacagagaga
aagaaggcccaagtcctcggcgcattactataaacaggtcataggagaaa
acggcttcacgctcagagaggccaccccggatctgcaggggcagtttccc
tgtgacttctcctggggcgtcaccgagtctgttcttaagcccgagtcggt
ggcttcctcgccacagttcagcgaccctcacctctacgtgtggaacgcca
ctggcaaccgaatgcttcaccgggtggaaggggtgaggctgaaaacacgg
cccgctcagtgcacagatttcatcaccatcaagaaacaactcgagatgtt
ggcaagaatgaaagtcacccacttccggtttgctctggactgggcctcgg
tccttcccacgggcaacctgtccgaggtgaaccgacaagccctgaggtac
tacaggtgtgtggtcaccgaggggctgaagctcaacatctcgcccatggt
caccttgtactacccgacccatgcccacctgggcctgcccgccgctgc
tgcacagcgggggggtggctggacccatccacggccaaggccttccgcgac
tacgcagggctgtgcttccgggagctgggggacctggtgaagctctggat
caccatcaacgagcccaacggctgagcgacgtctacaaccgcaccagca
acgacacctaccaggccgcccacaacctgctgatcgcgcacgcgctcgtg
tggcacctgtacgaccgccagtaccggccgtcgcagcgcggggcgctgtc
```

-continued

```
gctgtccctgcactcggactgggccgagcccgccaaccctacgtggcct
cgcactggcaggcggccgagcgcttcctgcagttcgagattgcgtggttc
gccgagcccctgttcaagaccggggactaccggtggccatgagggagta
catccgcctccaagacccggcgcgggctctccagctccgtgctgccccgct
tcagcgacgccgagcggcggctggtcaagggcgccgccgacttctacgcc
ctcaaccacttccaccaccaggttcgtgatgcacgagcagcagaacggcag
ccgctacgactcggacagggacgtgcagttcctgcaggacatcacccgcc
tggcctcacccagccgcctggccgtgatgccctgggggcgagggcaagctg
ctgcggtggatgcggaacaactacggagacctggacgtctacatcacggc
caatggcatcgacgaccaggccctgcagaacgaccagcttcgccagtact
acctggagaagtacgtccaggaggctctgaaagcatatctgatagataaa
ataaaaatcaaaggctattatgcattcaaactgactgaagaaaaatctaa
acccaggtttggattcttcacctctgatttcaaagccaagtcttcaatac
agttttacaacaaactaattaccagcaacggcttcccgtctgagaacggc
ggtcctagatgcaatcagactcaaggaaatcccgagtgcaccgtctgctt
actcctcctgcagaagaagccgctgatattctttagctgctgcttcttct
gcaccctggttctactctcatcaattaccatctttcacagacggaagaga
agaaaattttggaaagcaaaggacttacaacacataccattaaagaaagg
ccacaagagagtccttagctaaagtgaacttatttctctctgaagagtttt
agaaattcactccagttccatatgctggtaacacaaaagacatacccgta
ttgtacacagagtatttgagatactgtgctaaccaaggcgatgacaatca
aaacctctgccatgtggttgaatgcattttcccttaagcggtgacaatca
gcgaactcagttcttggttctaaaggaggcttcgcactgccactaggcta
tgagtattacctgacgcattgctttgtcaagtttgatgagctgtttcgca
tcattctctagctttctttagataccaatagctactatggtaaaagttgt
ttttaaaagtcaaactctgtaaggcttcacagcagatttaaaactattct
ttacactggatctgtgattttgtcactcgtagcaaggtgctttcccctttt
tggtcctagtggctctcaaatagaaagcaaacacatcttagggtaatcta
cttatctatagccaatcacagcactgacccacaactacacaaatccgtta
gctcttctccataaaacacctaattttgtgatcttttaagtaatctgaaa
tgtaaaagtatgacttccgtaacccatctcatgaaagatcgactaagga
gagccatacccagctgtgaggacaatttagtcactaatctcaccgtactg
caacttcctcctttagagcaggcattccttaccattttttgtaagatgaca
tgatttagcatctagaacccctatctgcagtttctttctatggcttacct
acatttcaagaatattgaacggaaaatttcagaaagatttccaagttta
aattgtgtactagcattagtgcatgatgaaatctcattttctttgctcca
tcctgcacaggatgtgaaacatccctctgtccagcaagtccaagctacct
atattactcacttgatagtcaccatggttatccagctgttattacttgct
catacccaggtaacccttttttatttttaatatagctccaaagtataagac
tagtgatgaaaaggaggtaagtcatcaaatatggaaggacagattaactc
```

```
tggcactaagtgggaatgctgcaggttttacaggaaaacaaaattcagtc
agtggtttaaagcatcctctgaggtacctggggcacaatctccacagata
aggggaaagagcactgacaaagactaaacatcctaaaaagacgcaatgtt
ctacttactggccatcagaataatggccaaggaccctatacttgcttgc
tctctagccaagtttcgctgcacataggtgtagaatgcagcgactgaccc
tggatgcgattcagaatgctgatctgagtgaactagtttttttatacagca
cttttttaaagcctagaattcttccatctgaacttgggagttttgacttt
ttgaaattaattgtgcttaagatttattcagtgattctaaacactggagg
tagaaaactgtatacccattatgcctattaattttttcttgattagccaac
atttaaataaccacaaagtggccagtcgttgtctttcccttttcaggaatt
taagtcaaaggatgctgctgcctgcgatgctggcacttcatagggtgac
agtttgtgtccctgcggttccacttcctatccagctccctgctaatggct
tgggagagccctgcacccacatgggagacccaaaagcagatcctgctgct
ttcagcctgctgcggccacttggagtatgaaccagtggatggaagatcaa
tgtctctcccaacaattctttgaataaattttttcaaagtcaaaataaa
attctccagctcaaaaagctttagtagaaaacgatcctacattaaggcgg
ttgtgattgtatcccaagtgcatctacgttacaaaccaaattgagtatgc
aattcagtatgctactagactataaggagaaaacagccaattcaaacaaa
ataccaaagtcacgtgcagttaatttgctttctggttggccaaatgtttt
ttttctcttcttgccaccactgttttacatgtactttagaagaaattttg
acttttttgcttcctttgagaaatcactattatcaaaggcaattcataatt
acaagtggtccattgtcttaagagctcaagattatagcccttcaaacttg
ccaaactcctcaaatagtgaagctcctaacgaagggtttacaacatcctg
ttccttaggggttatattttttaagtgactgtaattacctaacaaattta
atctggctatctattggtaatacatgtaatattcaggtttatcataaacc
cacttaaaaactaaaggttaagtggaagttgctgcttttcaaagtaacag
gcttctcaggggaaaatatcaccttagcgtccacctggtactacatctcg
tgtattcactgtaacccatctttccgaacatgtctgatatatatggaaac
aacactagtgcttagcctctggaaatgaggccaggattttgtgattaaat
gtctaatttattccaaataaactgatttacgccaata
```

The amino acid sequence of beta klotho from dog, scientific name *Canis lupus familiaris*, is provided below:

(SEQ ID NO: 412)
MKPGCAAGSPGNEWIFLSTDESNTHYRKTMCNHGLQRSVILSAFILLGAV
PGFSGDGRAIWSKNPHFSPVNESQLFLYDTFPKNFFWGVGTGAFQVEGNW
KTDGKGPSIWDHFIHTHLKNVNSMNSSSDSYIFLEKDLSALDFIGVSFYQ
FSISWPRLFPDGIAAVANAKGLQYYNSLLDALVLRNIEPIVTLYHWDLPL
ALQEKYGGWKNETITDIFNDYATYCFQTFGDRVKYWITIHNPYLVAWHGY
GTGMHAPGEKGNLAAVYTVGHNLIKAHSKVWHNYNTNFRPYQKGLLSITL
GSHWIEPNRSENMMDILKCQQSMVSVLGWFANPIHGNGDYPEVMKKKLLS
TLPLFSEAEKNEVRGTADFFAFSFGPNNFKPQNTMAKMGQNVSLNLREVL
NWIKLEYGNPRILIAENGWFTDSHVKTEDTTAIYMMKNFLNQVLQAIRFD
EIQVFGYTAWSLLDGFEWQDAYSTRRGLFYVDFNSKQKERKPKSSAYYYK
QIIQENGFTFKESTPDVQGQFPCDFSWGVTESVLKPKWASSPQFSDPHLY
VWNVTGNRLLHRVEGVRLKTRPAQCTDFVSIKRQLEMLARMNVTHYRFAL
DWPSILPTGNLSTVNRQALRYYRCVVSESLKLSISPMVTLYYPTHAHLGL
PSPLLHSGGWLNASTARAFQDYAGLCFQELGDLVKLWITINEPNRLSDVY
SHTSSDTYRAAHNLLIAHALVWHLYDRRYRPAQRGAVSLSLHSDWAEPAN
PYADSHWKAAERFLQFEIAWFAEPLFKTGDYPPAMREYIASKNRQGLSRS
TLPRFTDEERRLVKGAADFYALNHFTTRFVMHARQNGSRYDADRDVQFLQ
DITCLSSPSRLAVLPWGERKVLRWIQKNYGDVDVYITASGIDDQSLENDE
LRKYYLEKYIQEALKAHLIDKVKVKGYYAFKLTEEKSKPRFGFFTSEFKA
KSSVQLYNKLISNSGFPSENRSPRCSETQRNTECMVCLFLVQKKPLIFFS
CCFFSTLVLLSSITILHKRKRRKIWKAKNLQHIPLKKSKNSLQS

An encoding nucleic acid sequence of dog beta klotho is provided below:

(SEQ ID NO: 413)
```
acaatcacaagcttttactgaagcgttgataagacaggcgagcagttagt
ggcaaatgaagccaggctgtgcggctggatctccagggaatgaatggatt
ttcctcagcaccgatgaaagcaacacacactataggaaaacaatgtgcaa
ccacgggctacagagatctgtcatcctgtcagcatttattctcctaggag
ctgttcctggattctctggagacggaagagctatatggtctaaaatcct
cattttagtccggtaaatgaaagtcagctgtttctctatgacactttcc
taaaaacttttttgggcgtgggactggagcatttcaagtggaaggga
attggaagacagatggaaaaggaccctctatatgggatcatttcatccac
acacaccttaaaaatgtcaacagcatgaatagttccagtgacagttacat
ttttctggaaaaagacctatcagccctggattttatcggagtttcttttt
atcaattttcaatttcctggccaaggcttttccccgatggaatagcagca
gttgccaacgcaaaaggtctccagtactacaattctcttctcgatgctct
agtacttaggaacattgaacctatagttactttataccattgggatttgc
ctttggcactacaagaaaaatatggggggtggaaaaatgaaaccataacg
gatatcttcaatgactatgccacctactgtttccagacgttcggggatcg
tgtcaaatactggattacaattcacaatccatatctagttgcttggcatg
ggtatgggacaggtatgcacgcgcctggagagaagggaaacttagcagct
gtctacactgtgggacacaacctaatcaaggctcattcgaaagtttggca
taactacaacacaaatttccgcccatatcagaagggtttgttatcaatca
cgttgggatcccattggattgaaccaaacagatcagaaaacatgatggat
atactcaaatgtcaacaatccatggtttcagtgctcgggtggtttgccaa
ccccatccatgggaatggagactatccagaagtgatgaaaaagaagttgc
tctccactctaccccttttctctgaagcagagaagaatgaagtgaggggc
acagctgacttctttgccttttcctttggacccaacaatttcaagcccca
```

-continued

```
gaacaccatggctaaaatgggacaaaatgtgtcactcaatttaagagaag
tgctgaattggattaaactggaatatggcaaccccccgaatcttgattgct
gagaatggctggttcacagacagtcatgtgaaaacagaagataccacagc
catttacatgatgaagaatttcctcaaccaggttcttcaagcaataaggt
ttgacgaaatacaagtgtttggctacactgcttggtctctcctggatggc
tttgaatggcaggatgcttactccactcgccgaggattattttatgtgga
ttttaatagtaaacaaaagaaagaaagcccaagtcttcggcatattact
ataaacagatcatacaagaaaatggttttactttcaaagagtccacccca
gatgtgcagggtcagtttcctgtgacttctcatggggtgtcaccgaatc
tgtccttaagcccaaagtcgtggcttcctccccacagttcagcgaccctc
acctgtacgtgtggaatgtgacaggcaacagactgttgcaccgagtggaa
ggggtgaggctgaagacacggccggctcaatgcacagattttgtcagcat
caaaagacaacttgagatgttggcgaggatgaacgtcactcactacaggt
ttgctctggactggccctccatccttcccaccggcaacctgtccacggtt
aaccgacaagccctgaggtactacaggtgtgtggtcagcgagtcgctgaa
gctcagcatctccccgatggtcacgctgtactacccgacccacgccacc
tgggcctcccctcgccgctgctgcacagcgggggctggctgaacgcgtcc
accgcccgcgccttccaggactatgccgggctgtgcttccaggagctggg
ggacctggtgaagctctggatcaccatcaatgagcccaaccggctgagtg
acgtctacagccacaccagcagcgacacctaccgggcagcgcacaacctg
ctgatcgcccacgcccggtgtggcacctgtacgaccggcggtaccggcc
ggcgcagcgcggggccgtgtcgctgtccctgcactcggactgggcggagc
ccgccaacccctacgccgactcgcactggaaggcggccgagcgcttcctg
cagttcgaaatcgcctggttcgccgagccgctcttcaagaccggggacta
cccgccggccatgagggagtacatcgcctccaagaacaggcagggqctct
cgcgctccaccctgcccgcttcaccgacgaggagaggaggctggtcaag
ggcgccgccgacttctacgcgctgaaccacttcaccaccaggttcgtgat
gcacgcgcgccagaacggcagccgctacgacgcggaccgcgacgtccagt
tcctgcaggacatcacctgcctgagctcccccagccgcctggccgtcctg
ccctgggggagcgcaaggtgctcaggtggatccagaagaactacggaga
cgtggacgtgtacatcacggccagtggcatcgatgaccagtctctggaaa
atgatgagctcagaaaatactacttggagaaatacatccaggaggctctg
aaagcacacctaattgataaagtcaaagtcaaaggctattatgcattcaa
actgactgaagaaaatctaaacccagatttggattcttcacgtctgaat
tcaaagctaaatcctcagttcagctttacaacaaactgatcagcaacagt
ggcttcccttctgagaacaggagtcctagatgcagtgagactcaaagaaa
cacagagtgcatggtctgctttatttcttgtgcaaaagaaaccactgatat
tctttagttgttgcttcttctctaccctggttctactttcatcgattacc
attcttcataagcgaaagagaagaaaaatttggaaagcaagaacttaca
acatataccattaaagtgaggccacagaaagttcttagtgaaactgatcc
tatttctgtctgcatgatagaaagtctaaaaattcactccagtcccaaat
``` actggtaacatagaagacaatttgaaacactagtagtaaccaaggtgatg
acaatcaaggtctctgctgtgtggtccaaatgaattttccattaggtgtt
gacatcactgaatacagttttagatctgaagactaagatctagagagta
agctaggattatctgatacaatgcttcattaagtttaataagctgttatc
catcattcttctctggcttccttctagaaataccaatagctaattatagc
aacttagaaaaaagtgcaacttttgctagactccatagcagaaatctaaa
actcttaacactggatattcagtgattattctatcacttctaacaaggtg
cttttccccttagaagatatacaatagggtaaatagtgctcctttatca
tccattccagcacttttttttccagcatagactcttaaacacattgatc
ctagttttttctcaatagaaataaaaaatcatttagaaaacatggaatttt
gtgaggtctctccttgcattagatctgagttttttttaaaaaaaagactt
aacttccataacccatctcatgggaagatcacaggactaagattaaggag
agttagacccatcaactgcctgaggagacagcactcaacctcacagtaca
gcaaattccttgggacaaactgacagcaatcttccgcacttggattgttg
aggcagcacacaagatcttaacatacttaggaaagttaaatattctaaaa
agatgtaaagttttattttttattatcaagtcttcaaaggaccatattatt
ccataagacttgctctctcctgagttccactcttctgacactatgtgtat
atggggacactcaaactgcaccttgacattgcaactttggatacaattca
gaatgtaaatgtttgaaggacttaaaactttctccactgcacctttgaa
gctgggattaagtaaatacgaactgggagtttgactttttgaactctgt
gcttgatttattcactgtattctaaatttttaaggaaaacctgaatgtaaa
cccattcatacccttctttgggttagtaaacatttaaccacccatttc
a.

The amino acid sequence of human/mouse beta klotho chimeric protein (human KLB (M1-F508)-mouse KLB (P507-S1043)) is provided below:

(SEQ ID NO: 374)
MKPGCAAGSPGNEWIFFSTDEITTRYRNTMSNGGLQRSVILSALILLRAV

TGFSGDGRAIWSKNPNFTPVNESQLFLYDTFPKNFFWGIGTGALQVEGSW

KKDGKGPSIWDHFIHTHLKNVSSTNGSSDSYIFLEKDLSALDFIGVSFYQ

FSISWPRLFPDGIVTVANAKGLQYYSTLLDALVLRNIEPIVTLYHWDLPL

ALQEKYGGWKNDTIIDIFNDYATYCFQMFGDRVKYWITIHNPYLVAWHGY

GTGMHAPGEKGNLAAVYTVGHNLIKAHSKVWHNYNTHFRPHQKGWLSITL

GSHWIEPNRSENTMDIFKCQQSMVSVLGWFANPIHGDGDYPEGMRKKLFS

VLPIFSEAEKHEMRGTADFFAFSFGPNNFKPLNTMAKMGQNVSLNLREAL

NWIKLEYNNPRILIAENGWFTDSRVKTEDTTAIYMMKNFLSQVLQAIRLD

EIRVFGYTAWSLLDGFEWQDAYTIRRGLFYVDFNSKQKERKPKSSAHYYK

QIIRENGFPLKESTPDMKGRFPCDFSWGVTESVLKPEFTVSSPQFTDPHL

YVWNVTGNRLLYRVEGVRLKTRPSQCTDYVSIKKRVEMLAKMKVTHYQFA

LDWTSILPTGNLSKVNRQVLRYYRCVVSEGLKLGVFPMVTLYHPTHSHLG

LPLPLLSSGGWLNMNTAKAFQDYAELCFRELGDLVKLWITINEPNRLSDM

YNRTSNDTYRAAHNLMIAHAQVWHLYDRQYRPVQHGAVSLSLHCDWAEPA

NPFVDSHWKAAERFLQFEIAWFADPLFKTGDYPSVMKEYIASKNQRGLSS

SVLPRFTAKESRLVKGTVDFYALNHFTTRFVIHKQLNTNRSVADRDVQFL

QDITRLSSPSRLAVTPWGVRKLLAWIRRNYRDRDIYITANGIDDLALEDD

QIRKYYLEKYVQEALKAYLIDKVKIKGYYAFKLTEEKSKPRFGFFTSDFR

AKSSVQFYSKLISSSGLPAENRSPACGQPAEDTDCTICSFLVEKKPLIFF

GCCFISTLAVLLSITVFHHQKRRKFQKARNLQNIPLKKGHSRVFS.

An encoding nucleic acid sequence of human/mouse beta klotho chimeric protein is provided below:

(SEQ ID NO: 375)
ATGAAGCCAGGCTGTGCGGCAGGATCTCCAGGGAATGAATGGATTTTCTT

CAGCACTGATGAAATAACCACACGCTATAGGAATACAATGTCCAACGGGG

GATTGCAAAGATCTGTCATCCTGTCAGCACTTATTCTGCTACGAGCTGTT

ACTGGATTCTCTGGAGATGGAAGAGCTATATGGTCTAAAAATCCTAATTT

TACTCCGGTAAATGAAAGTCAGCTGTTTCTCTATGACACTTTCCCTAAAA

ACTTTTTCTGGGGTATTGGACTGGAGCATTGCAAGTGGAAGGGAGTTGG

AAGAAGGATGGAAAAGGACCTTCTATATGGGATCATTTCATCCACACACA

CCTTAAAAATGTCAGCAGCACGAATGGTTCCAGTGACAGTTATATTTTTC

TGGAAAAAGACTTATCAGCCCTGGATTTTATAGGAGTTTCTTTTTATCAA

TTTTCAATTTCCTGGCCAAGGCTTTTCCCCGATGGAATAGTAACAGTTGC

CAACGCAAAAGGTCTGCAGTACTACAGTACTCTTCTGGACGCTCTAGTGC

TTAGAAACATTGAACCTATAGTTACTTTATACCACTGGGATTTGCCTTTG

GCACTACAAGAAAAATATGGGGGGTGGAAAAATGATACCATAATAGATAT

CTTCAATGACTATGCCACATACTGTTTCCAGATGTTTGGGGACCGTGTCA

AATATTGGATTACAATTCACAACCCATATCTAGTGGCTTGGCATGGGTAT

GGGACAGGTATGCATGCCCCTGGAGAGAAGGGAAATTTAGCAGCTGTCTA

CACTGTGGGACACAACTTGATCAAGGCTCACTCGAAAGTTTGGCATAACT

ACAACACACATTTCCGCCCACATCAGAAGGGTTGGTTATCGATCACGTTG

GGATCTCATTGGATCGAGCCAAACCGGTCGGAAAACACGATGGATATATT

CAAATGTCAACAATCCATGGTTTCTGTGCTTGGATGGTTTGCCAACCCTA

TCCATGGGGATGGCGACTATCCAGAGGGGATGAGAAAGAAGTTGTTCTCC

GTTCTACCCATTTTCTCTGAAGCAGAGAAGCATGAGATGAGAGGCACAGC

TGATTTCTTTGCCTTTTCTTTTGGACCCAACAACTTCAAGCCCCTAAACA

CCATGGCTAAAATGGGACAAAATGTTTCACTTAATTTAAGAGAAGCGCTG

AACTGGATTAAACTGGAATACAACAACCCTCGAATCTTGATTGCTGAGAA

TGGCTGGTTCACAGACAGTCGTGTGAAAACAGAAGACACCACGGCCATCT

ACATGATGAAGAATTTCCTCAGCCAGGTGCTTCAAGCAATAAGGTTAGAT

GAAATACGAGTGTTTGGTTATACTGCCTGGTCTCTCCTGGATGGCTTTGA

ATGGCAGGATGCTTACACCATCCGCCGAGGATTATTTTATGTGGATTTTA

ACAGTAAACAGAAAGAGCGGAAACCTAAGTCTTCAGCACACTACTACAAA

CAGATCATACGAGAAATGGTTTTCCTTTGAAAGAGTCCACGCCAGACAT

GAAGGGTCGGTTCCCCTGTGATTTCTCTTGGGGAGTCACTGAGTCTGTTC

TTAAGCCCGAGTTTACGGTCTCCTCCCCGCAGTTTACCGATCCTCACCTG

TATGTGTGGAATGTCACTGGCAACAGATTGCTCTACCGAGTGGAAGGGGT

AAGGCTGAAAACAAGACCATCCCAGTGCACAGATTATGTGAGCATCAAA

AACGAGTTGAAATGTTGGCAAAAATGAAAGTCACCCACTACCAGTTTGCT

CTGGACTGGACCTCTATCCTTCCCACTGGCAATCTGTCCAAAGTTAACAG

ACAAGTGTTAAGGTACTATAGGTGTGTGGTGAGCGAAGGACTGAAGCTGG

GCGTCTTCCCCATGGTGACGTTGTACCACCCAACCCACTCCCATCTCGGC

CTCCCCCTGCCACTTCTGAGCAGTGGGGGTGGCTAAACATGAACACAGC

CAAGGCCTTCCAGGACTACGCTGAGCTGTGCTTCCGGGAGTTGGGGGACT

TGGTGAAGCTCTGGATCACCATCAATGAGCCTAACAGGCTGAGTGACATG

TACAACCGCACGAGTAATGACACCTACCGTGCAGCCCACAACCTGATGAT

CGCCCATGCCCAGGTCTGGCACCTCTATGATAGGCAGTATAGGCCGGTCC

AGCATGGGGCTGTGTCGCTGTCCTTACATTGCGACTGGGCAGAACCTGCC

AACCCCTTTGTGGATTCACACTGGAAGGCAGCCGAGCGCTTCCTCCAGTT

TGAGATCGCCTGGTTTGCAGATCCGCTCTTCAAGACTGGCGACTATCCAT

CGGTTATGAAGGAATACATCGCCTCCAAGAACCAGCGAGGGCTGTCTAGC

TCAGTCCTGCCCGCGCTTCACCGCGAAGGAGAGCAGGCTGGTGAAGGGTAC

CGTCGACTTCTACGCACTGAACCACTTCACTACGAGGTTCGTGATACACA

AGCAGCTGAACACCAACCGCTCAGTTGCAGACAGGGACGTCCAGTTCCTG

CAGGACATCACCCGCCTAAGCTCGCCCAGCCGCCTGGCTGTAACACCCTG

GGGAGTGCGCAAGCTCCTTGCGTGGATCCGGAGGAACTACAGAGACAGGG

ATATCTACATCACAGCCAATGGCATCGATGACCTGGCTCTAGAGGATGAT

CAGATCCGAAAGTACTACTTGGAGAAGTATGTCCAGGAGGCTCTGAAAGC

ATATCTCATTGACAAGGTCAAAATCAAAGGCTACTATGCATTCAAACTGA

CTGAAGAGAAATCTAAGCCTAGATTTGGATTTTTCACCTCTGACTTCAGA

GCTAAGTCCTCTGTCCAGTTTTACAGCAAGCTGATCAGCAGCAGTGGCCT

CCCCGCTGAGAACAGAAGTCCTGCGTGTGGTCAGCCTGCGGAAGACACAG

ACTGCACCATTTGCTCATTTCTCGTGGAGAAGAAACCACTCATCTTCTTC

GGTTGCTGCTTCATCTCCACTCTGGCTGTACTGCTATCCATCACCGTTTT

TCATCATCAAAAGAGAAGAAAATTCCAGAAAGCAAGGAACTTACAAAATA

TACCATTGAAGAAAGGCCACAGCAGAGTTTTCAGCTGA

The amino acid sequence of mouse/human beta klotho chimeric protein (mouse KLB (M1-F506)-human KLB (S509-S1044)) is provided below:

(SEQ ID NO: 376)
MKTGCAAGSPGNEWIFFSSDERNTRSRKTMSNRALQRSAVLSAFVLLRAV

TGFSGDGKAIWDKKQYVSPVNPSQLFLYDTFPKNFSWGVGTGAFQVEGSW

KTDGRGPSIWDRYVYSHLRGVNGTDRSTDSYIFLEKDLLALDFLGVSFYQ

FSISWPRLFPNGTVAAVNAQGLRYYRALLDSLVLRNIEPIVTLYHWDLPL

TLQEEYGGWKNATMIDLFNDYATYCFQTFGDRVKYWITIHNPYLVAWHGF
GTGMHAPGEKGNLTAVYTVGHNLIKAHSKVWHNYDKNFRPHQKGWLSITL
GSHWIEPNRTDNMEDVINCQHSMSSVLGWFANPIHGDGDYPEFMKTGAMI
PEFSEAEKEEVRGTADFFAFSFGPNNFRPSNTVVKMGQNVSLNLRQVLNW
IKLEYDDPQILISENGWFTDSYIKTEDTTAIYMMKNFLNQVLQAIKFDEI
RVFGYTAWTLLDGFEWQDAYTTRRGLFYVDFNSEQKERKPKSSAHYYKQI
IQDNGFSLKESTPDVQGQFPCDFSWGVTESVLKPESVASSPQFSDPHLYV
WNATGNRLLHRVEGVRLKTRPAQCTDFVNIKKQLEMLARMKVTHYRFALD
WASVLPTGNLSAVNRQALRYYRCVVSEGLKLGISAMVTLYYPTHAHLGLP
EPLLHADGWLNPSTAEAFQAYAGLCFQELGDLVKLWITINEPNRLSDIYN
RSGNDTYGAAHNLLVAHALAWRLYDRQFRPSQRGAVSLSLHADWAEPANP
YADSHWRAAERFLQFEIAWFAEPLFKTGDYPAAMREYIASKHRRGLSSSA
LPRLTEAERRLLKGTVDFCALNHFTTRFVMHEQLAGSRYDSDRDIQFLQD
ITRLSSPTRLAVIPWGVRKLLRWVRRNYGDMDIYITASGIDDQALEDDRL
RKYYLGKYLQEVLKAYLIDKVRIKGYYAFKLAEEKSKPRFGFFTSDFKAK
SSIQFYNKVISSRGFPFENSSSRCSQTQENTECTVCLFLVQKKPLIFLGC
CFFSTLVLLLSIAIFQRQKRRKFWKAKNLQHIPLKKGKRVVS

An encoding nucleic acid sequence of mouse/human beta klotho chimeric protein is provided below:

(SEQ ID NO: 377)
ATGAAGACAGGCTGTGCAGCAGGGTCTCCGGGGAATGAATGGATTTTCTT
CAGCTCTGATGAAAGAAACACACGCTCTAGGAAAACAATGTCCAACAGGG
CACTGCAAAGATCTGCCGTGCTGTCTGCGTTTGTTCTGCTGCGAGCTGTT
ACCGGCTTCTCCGGAGACGGGAAAGCAATATGGGATAAAAAACAGTACGT
GAGTCCGGTAAACCCAAGTCAGCTGTTCCTCTATGACACTTTCCCTAAAA
ACTTTTCCTGGGGCGTTGGGACCGGAGCATTTCAAGTGGAAGGGAGTTGG
AAGACAGATGGAAGAGGACCCTCGATCTGGGATCGGTACGTCTACTCACA
CCTGAGAGGTGTCAACGGCACAGACAGATCCACTGACAGTTACATCTTTC
TGGAAAAAGACTTGTTGGCTCTGGATTTTTTAGGAGTTTCTTTTTATCAG
TTCTCAATCTCCTGGCCACGGTTGTTTCCCAATGGAACAGTAGCAGCAGT
GAATGCGCAAGGTCTCCGGTACTACCGTGCACTTCTGGACTCGCTGGTAC
TTAGGAATATCGAGCCCATTGTTACCTTGTACCATTGGGATTTGCCTCTG
ACGCTCCAGGAAGAATATGGGGCTGGAAAAATGCAACTATGATAGATCT
CTTCAACGACTATGCCACATACTGCTTCCAGACCTTTGGAGACCGTGTCA
AATATTGGATTACAATTCACAACCCTTACCTTGTTGCTTGGCATGGGTTT
GGCACAGGTATGCATGCACCAGGAGAGAAGGGAAATTTAACAGCTGTCTA
CACTGTGGGACACAACCTGATCAAGGCACATTCGAAAGTGTGGCATAACT
ACGACAAAAACTTCCGCCCTCATCAGAAGGGTTGGCTCTCCATCACCTTG
GGGTCCCATTGGATAGAGCCAAACAGAACAGACAACATGGAGGACGTGAT
CAACTGCCAGCACTCCATGTCCTCTGTGCTTGGATGGTTCGCCAACCCCA
TCCACGGGGACGGCGACTACCCTGAGTTCATGAAGACGGGCGCCATGATC

CCCGAGTTCTCTGAGGCAGAGAAGGAGGAGGTGAGGGGCACGGCTGATTT
CTTTGCCTTTTCCTTCGGGCCCAACAACTTCAGGCCCTCAAACACCGTGG
TGAAAATGGGACAAAATGTATCACTCAACTTAAGGCAGGTGCTGAACTGG
ATTAAACTGGAATACGATGACCCTCAAATCTTGATTTCGGAGAACGGCTG
GTTCACAGATAGCTATATAAAGACAGAGGACACCACGGCCATCTACATGA
TGAAGAATTTCCTAAACCAGGTTCTTCAAGCAATAAAATTTGATGAAATC
CGCGTGTTTGGTTATACGGCCTGGACTCTCCTGGATGGCTTTGAGTGGCA
GGATGCCTATACGACCCGACGAGGGCTGTTTTATGTGGACTTTAACAGTG
AGCAGAAAGAGAGGAAACCCAAGTCCTCGGCTCATTACTACAAGCAGATC
ATACAAGACAACGCTTCTCTTTAAAAGAGTCCACGCCAGATGTGCAGGG
CCAGTTTCCCTGTGACTTCTCCTGGGGTGTCACTGAATCTGTTCTTAAGC
CCGAGTCTGTGGCTTCGTCCCCACAGTTCAGCGATCCTCATCTGTACGTG
TGGAACGCCACTGGCAACAGACTGTTGCACCGAGTGGAAGGGGTGAGGCT
GAAAACACGACCCGCTCAATGCACAGATTTTGTAAACATCAAAAAACAAC
TTGAGATGTTGGCAAGAATGAAAGTCACCCACTACCGGTTTGCTCTGGAT
TGGGCCTCGGTCCTTCCCACTGGCAACCTGTCCGCGGTGAACCGACAGGC
CCTGAGGTACTACAGGTGCGTGGTCAGTGAGGGGCTGAAGCTTGGCATCT
CCGCGATGGTCACCCTGTATTATCCGACCCACGCCCACCTAGGCCTCCCC
GAGCCTCTGTTGCATGCCGACGGGTGGCTGAACCCATCGACGGCCGAGGC
CTTCCAGGCCTACGCTGGGCTGTGCTTCCAGGAGCTGGGGGACCTGGTGA
AGCTCTGGATCACCATCAACGAGCCTAACCGGCTAAGTGACATCTACAAC
CGCTCTGGCAACGACACCTACGGGGCGGCGCACAACCTGCTGGTGGCCCA
CGCCCTGGCCTGGCGCCTCTACGACCGGCAGTTCAGGCCCTCACAGCGCG
GGGCCGTGTCGCTGTCGCTGCACGCGGACTGGGCGGAACCCGCCAACCCC
TATGCTGACTCGCACTGGAGGGCGGCCGAGCGCTTCCTGCAGTTCGAGAT
CGCCTGGTTCGCCGAGCCGCTCTTCAAGACCGGGGACTACCCCGCGGCCA
TGAGGGAATACATTGCCTCCAAGCACCGACGGGGCTTTCCAGCTCGGCC
CTGCCGCGCCTCACCGAGGCCGAAAGGAGGCTGCTCAAGGGCACGGTCGA
CTTCTGCGCGCTCAACCACTTCACCACTAGGTTCGTGATGCACGAGCAGC
TGGCCGGCAGCCGCTACGACTCGGACAGGGACATCCAGTTTCTGCAGGAC
ATCACCCGCCTGAGCTCCCCACGCGCCTGGCTGTGATTCCTGGGGGT
GCGCAAGCTGCTGCGGTGGGTCCGGAGGAACTACGGCGACATGGACATTT
ACATCACCGCCAGTGGCATCGACGACCAGGCTCTGGAGGATGACCGGCTC
CGGAAGTACTACCTAGGGAAGTACCTTCAGGAGGTGCTGAAAGCATACCT
GATTGATAAAGTCAGAATCAAAGGCTATTATGCATTCAAACTGGCTGAAG
AGAAATCTAAACCCAGATTTGGATTCTTCACATCTGATTTTAAAGCTAAA
TCCTCAATACAATTTTACAACAAAGTGATCAGCAGCAGGGGCTTCCCTTT
TGAGAACAGTAGTTCTAGATGCAGTCAGACCCAAGAAAATACAGAGTGCA
CTGTCTGCTTATTCCTTGTGCAGAAGAAACCACTGATATTCCTGGGTTGT
TGCTTCTTCTCCACCCTGGTTCTACTCTTATCAATTGCCATTTTTCAAAG

```
-continued
GCAGAAGAGAAGAAAGTTTTGGAAAGCAAAAAACTTACAACACATACCAT

TAAAGAAAGGCAAGAGAGTTGTTAGCTAG
```

Related beta klotho polypeptides include allelic variants (e.g., SNP variants); splice variants; fragments; derivatives; substitution, deletion, and insertion variants; fusion polypeptides; and interspecies homologs, preferably, which retain beta klotho activity and/or are sufficient to generate an anti-beta klotho immune response. As those skilled in the art will appreciate, an anti-beta klotho antibody provided herein can bind to a beta klotho polypeptide, a beta klotho polypeptide fragment, a beta klotho antigen, and/or a beta klotho epitope. An epitope may be part of a larger beta klotho antigen, which may be part of a larger beta klotho polypeptide fragment, which, in turn, may be part of a larger beta klotho polypeptide. Beta klotho may exist in a native or denatured form. Beta klotho polypeptides described herein may be isolated from a variety of sources, such as from human tissue types or from another source, or prepared by recombinant or synthetic methods. A beta klotho polypeptide may comprise a polypeptide having the same amino acid sequence as a corresponding beta klotho polypeptide derived from nature. Beta klotho polypeptides encompass truncated or secreted forms of a beta klotho polypeptide (e.g., an extracellular domain sequence), variant forms (e.g., alternatively spliced forms) and allelic variants of the polypeptide. Orthologs to the beta klotho polypeptide are also well known in the art.

The term "beta klotho" encompasses "full-length," unprocessed beta klotho as well as any form of beta klotho that results from processing in the cell. The term also encompasses naturally occurring variants or mutations of beta klotho (e.g., splice variants, allelic variants, SNP variants and isoforms). The beta klotho polypeptides described herein may be isolated from a variety of sources, such as from human tissue types or from another source, or prepared by recombinant or synthetic methods.

The terms "FGF19-like signaling" and "induces FGF19-like signaling," when applied to a binding protein such an antibody that binds to beta klotho of the present disclosure, means that the binding protein (e.g., antibody) mimics, or modulates, an in vivo biological effect induced by the binding of (i) beta klotho; (ii) FGFR1c, FGFR2c, FGFR3c, and FGFR4; or (iii) a complex comprising beta klotho and one of FGFR1c, FGFR2c, FGFR3c, and FGFR4 and induces a biological response that otherwise would result from FGF19 binding to (i) beta klotho; (ii) FGFR1c, FGFR2c, FGFR3c or FGFR4; or (iii) a complex comprising beta klotho and one of FGFR1c, FGFR2c, FGFR3c, and FGFR4 in vivo. In assessing the binding and specificity of anti-beta klotho antibody, for example, an antibody or fragment thereof, that binds to beta klotho (e.g., human beta klotho), an antibody or fragment thereof is deemed to induce a biological response when the response is equal to or greater than 5%, and preferably equal to or greater than 10%, 15%, 20%, 25%, 30%, 35%, 40%, 45%, 50%, 55%, 60%, 65%, 70%, 75%, 80%, 85%, 90% or 95%, of the activity of a wild type FGF19 standard comprising the mature form of SEQ ID NO:304 (e.g., the mature form of human FGF19) and has the following properties: exhibiting an efficacy level of equal to or more than 5% of an FGF19 standard, with an EC50 of equal to or less than 100 nM, e.g., 90 nM, 80 nM, 70 nM, 60 nM, 50 nM, 40 nM, 30 nM, 20 nM or 10 nM in (1) a recombinant FGF19 receptor mediated luciferase-reporter cell assay (see, e.g., Example 4); (2) ERK-phosphorylation in a recombinant FGF19 receptor mediated cell assay (see, e.g., Example 4); or (3) ERK-phosphorylation in human adipocytes (see, e.g., Example 5).

The term "FGF19R" may refer to a multimeric receptor complex that FGF19 is known or suspected to form in vivo. In various embodiments, FGF19R comprises (i) an FGFR, e.g., FGFR1c, FGFR2c, FGFR3c or FGFR4, and (ii) beta klotho.

The terms "FGF21-like signaling" and "induces FGF21-like signaling," when applied to a binding protein such an antibody that binds to beta klotho of the present disclosure, means that the binding protein (e.g., antibody) mimics, or modulates, an in vivo biological effect induced by the binding of (i) beta klotho, (ii) FGFR1c, FGFR2c, FGFR3c, and FGFR4; or (iii) a complex comprising beta klotho and one of FGFR1c, FGFR2c, FGFR3c, and FGFR4 and induces a biological response that otherwise would result from FGF21 binding to (i) beta klotho; (ii) FGFR1c, FGFR2c, FGFR3c or FGFR4; or (iii) a complex comprising beta klotho and one of FGFR1c, FGFR2c, FGFR3c, and FGFR4 in vivo. In assessing the binding and specificity of anti-beta klotho antibody, for example, an antibody or fragment thereof that binds to beta klotho (e.g., human beta klotho), an antibody or fragment thereof is deemed to induce a biological response when the response is equal to or greater than 5%, and preferably equal to or greater than 10%, 15%, 20%, 25%, 30%, 35%, 40%, 45%, 50%, 55%, 60%, 65%, 70%, 75%, 80%, 85%, 90% or 95%, of the activity of a wild type FGF21 standard comprising the mature form of SEQ ID NO:306 or 429 (e.g., the mature form of the human FGF21 sequence) and has the following properties: exhibiting an efficacy level of equal to or more than 5% of an FGF21 standard, with an EC50 of equal to or less than 100 nM, e.g., 90 nM, 80 nM, 70 nM, 60 nM, 50 nM, 40 nM, 30 nM, 20 nM or 10 nM in (1) a recombinant FGF21 receptor mediated luciferase-reporter cell assay (see, e.g., Example 4); (2) ERK-phosphorylation in the recombinant FGF21 receptor mediated cell assay (see, e.g., Example 4); or (3) ERK-phosphorylation in human adipocytes (see, e.g., Example 5).

The term "FGF21R" may refer to a multimeric receptor complex that FGF21 is known or suspected to form in vivo. In various embodiments, FGF21R comprises (i) an FGFR, e.g., FGFR1c, FGFR2c, FGFR3c or FGFR4, and (ii) beta klotho.

The term "binding protein" refers to a protein comprising a portion (e.g., one or more binding regions such as CDRs) that binds to beta klotho, including human and/or cyno beta klotho and, optionally, a scaffold or framework portion (e.g., one or more scaffold or framework regions) that allows the binding portion to adopt a conformation that promotes binding of the binding protein to a beta klotho polypeptide, fragment or epitope. Examples of such binding proteins include antibodies, such as a human antibody, a humanized antibody; a chimeric antibody; a recombinant antibody; a single chain antibody; a diabody; a triabody; a tetrabody; a Fab fragment; a F(ab') 2 fragment; an IgD antibody; an IgE antibody; an IgM antibody; an IgG1 antibody; an IgG2 antibody; an IgG3 antibody; or an IgG4 antibody, and fragments thereof. The binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, Proteins: Structure, Function, and Bioinformatics, 53(1):

121-129 (2003); Roque et al., Biotechnol. Prog. 20:639-654 (2004). In addition, peptide antibody mimetics ("PAMs") can be used, as well as scaffolds based on antibody mimetics utilizing fibronectin components as a scaffold. In the context of the present disclosure, a binding protein is said to specifically bind or selectively bind to beta klotho, for example, when the dissociation constant ($K_D$) is $\leq 10^{-8}$ M. The binding protein (e.g., antibody) may specifically bind beta klotho with high affinity when the $K_D$ is $\leq 10^{-9}$ M or $K_D$ is $\leq 10^{-10}$ M. In some embodiments, the binding proteins (e.g., antibodies) may bind to beta klotho or a complex comprising FGFR1c and beta klotho, including with a $K_D$ of between about $10^{-7}$ M and about $10^{-12}$ M and in other embodiments, the binding proteins (e.g., antibodies) may bind with a $K_D$ of $1-2 \times 10^{-9}$ M.

The term "antibody" and "immunoglobulin" or "Ig" are used interchangeably herein, and is used in the broadest sense and specifically covers, for example, individual anti-beta klotho monoclonal antibodies (including agonist, antagonist, neutralizing antibodies, full length or intact monoclonal antibodies), anti-beta klotho antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-beta klotho antibodies, and fragments of anti-beta klotho antibodies, as described below. An antibody can be human, humanized, chimeric and/or affinity matured as well as an antibody from other species, for example mouse, rabbit etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See, Borrebaeck (ed.) (1995) Antibody Engineering, Second Ed., Oxford University Press.; Kuby (1997) Immunology, Third Ed., W.H. Freeman and Company, New York). In specific embodiments, the specific molecular antigen can be bound by an antibody provided herein includes a beta klotho polypeptide, beta klotho fragment or beta klotho epitope. Antibodies also include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments (e.g., antigens-binding fragments such as beta klotho binding fragments) of any of the above, which refers a portion of an antibody heavy or light chain polypeptide that retains some or all of the binding activity of the antibody from which the fragment was derived. Non-limiting examples of functional fragments (e.g., antigens-binding fragments such as beta klotho binding fragments) include single-chain Fvs (scFv) (e.g., including monospecific, bispecific, etc.), Fab fragments, F(ab') fragments, F(ab)2 fragments, F(ab')2 fragments, disulfide-linked Fvs (sdFv), Fd fragments, Fv fragments, diabody, triabody, tetrabody and minibody. In particular, antibodies provided herein include immunoglobulin molecules and immunologically active portions of immunoglobulin molecules, for example, antigen binding domains or molecules that contain an antigen-binding site that binds to a beta klotho antigen (e.g., one or more complementarity determining regions (CDRs) of an anti-beta klotho antibody). Such antibody fragments can be found described in, for example, Harlow and Lane, Antibodies: A Laboratory Manual, Cold Spring Harbor Laboratory, New York (1989); Myers (ed.), Molec. Biology and Biotechnology: A Comprehensive Desk Reference, New York: VCH Publisher, Inc.; Huston et al., Cell Biophysics, 22:189-224 (1993); Plückthun and Skerra, Meth. Enzymol., 178:497-515 (1989) and in Day, E. D., Advanced Immunochemistry, Second Ed., Wiley-Liss, Inc., New York, N.Y. (1990). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. Anti-beta klotho antibodies may be agonistic antibodies or antagonistic antibodies. Provided herein are agonistic antibodies to beta klotho, including antibodies that induce FGF19-like signaling and/or FGF21-like signaling. Preferred agonistic antibodies to beta klotho do not compete for the binding of FGF19 and/or FGF21 to an FGF receptor including, for example, FGFR1c, FGFR2c, FGFR3c, or FGFR4c.

The term "fibroblast growth factors" refers to a family of growth factors, including twenty-two members of the human FGF family. The FGF19 subfamily of fibroblast growth factors consists of human FGF21, FGF23 and FGF19 and mouse FGF15. The effects of FGF family members are the result of their heparin-dependent binding to one or more members of the FGF receptor tyrosine kinase (FGFR) family, which includes four members each having a tyrosine kinase domain, FGFR1, FGFR2, FGFR3 and FGFR4, as well as two splice variants each of FGFR1, FGFR2 and FGFR3. These splice variants, which occur in exon 3 of FGFR1, FGFR2 and FGFR3, are designated as "b" and "c" variants (e.g., FGFR1b, FGFR2b, FGFR3c, FGFR1c, FGFR2c and FGFR3c, which are also known as FGFR1(III)b, FGFR2(III)b, FGFR3(III)c, FGFR1(III)c, FGFR2(III)c and FGFR3(III)c, respectively). For example, FGF19 targets and has effects on both adipocytes and hepatocytes. Mice treated with recombinant human FGF19 (rhFGF19), despite being on a high-fat diet, show increased metabolic rates, increased lipid oxidation, a lower respiratory quotient and weight loss. Moreover, such mice showed lower serum levels of leptin, insulin, cholesterol and triglycerides, and normal levels of blood glucose despite the high-fat diet and without appetite diminishment. In addition, obese mice that lacked leptin but included a FGF19 transgene showed weight loss, lowered cholesterol and triglycerides, and did not develop diabetes. In addition, obese, diabetic mice that lack leptin, when injected with rhFGF19, showed reversal of their metabolic characteristics in the form of weight loss and lowered blood glucose. For example, FGF21 is expressed primarily by the liver and has metabolic effects similar to that of FGF19, such as increased metabolism via its effects on adipose tissue, weight loss, lowered blood glucose levels, and resistance to obesity and diabetes. FGF21-transgenic mice were also resistant to diet-induced obesity, and, in diabetic rodent models, FGF21 administration lowered blood glucose and triglyceride levels. FGF19 and FGF21 metabolic effects occur via their binding FGF receptors, including the FGFR1c, FGFR2c and FGFR3c receptors, and required beta klotho for the binding. for the binding. The binding of FGF19 and FGF21 to FGFR1c and FGFR2c are significant. FGF19 has also been shown to have metabolic effects distinct from FGF21, including regulating bile production by the liver via its liver-specific effects, negatively regulating bile production in response to postprandial bile-production, and liver mitogenic effects that are not observed with respect to FGF21. For example, FGF19 transgenic mice develop hepatic adenocarcinoma due to increased proliferation and dysplasia of hepatocytes, and rhFGF19-treated mice exhibit hepatocyte proliferation of hepatocytes. These additional activities of FGF19 appear to be mediated via its binding to FGFR4. FGF19 can bind FGFR4 in both a beta klotho-dependent and beta klotho-independent manner. Although FGF21 has also been shown to bind FGFR4 in a beta klotho-dependent manner, efficient signaling has not previously been observed from the binding of FGF21 to FGFR4.

Binding proteins, such as anti-beta klotho antibodies, as disclosed herein can induce FGF19-like signaling, as described herein. In vivo, the mature form of FGF19 is the active form of the molecule. A nucleic acid sequence encoding full length FGF19 is provided below; the nucleotides encoding the signal sequence are underlined.

(SEQ ID NO: 303)
atgcggagcgggtgtgtggtggtccacgtatggatcctggccggcctctg gctggccgtggccgggcgcccctcgccttctcggacgcggggccccacg tgcactacggctggggcgacccatccgcctgcggcacctgtacacctcc ggccccacgggctctccagct*gct*tcctgcgcatccgtgccgacggcgt cgtggactgcgcgcgggcagagcgcgcacagtttgctggagatcaagg cagtcgctctgcggaccgtggccatcaagggcgtgcacagcgtgcggtac ctctgcatggg*cgcc*gacggcaagatgcaggggctgcttcagtactcgga ggaagactgtgctttcgaggaggagatccgcccagatggctacaatgtgt accgatccgagaagcac*cgc*ctcccggtctccctgagcagtgccaaacag cggcagctgtacaagaacagaggctttcttccactctctcatttcctgcc catgctgcccatggtcccagaggagcctgaggacctcaggggccacttgg aatctgacatgttctcttcgcccctggagaccgacagcatggacccattt gggcttgtcaccggact*ggaggcc*gtgaggagtcccagctttgagaagta
a The amino acid sequence of full length FGF19 is provided; the amino acids that make up the signal sequence are underlined:

(SEQ ID NO: 304)
mrsgcvvvhvwilaglwlavag*RPLAFSDAGPHVHYGW*GDPIRLRHLYTS

GPHGLSSCFLRIRADGVVDCARGQSAHSLLEIKAVA*LRTV*AIKGVHS*VRY*

LCMGADGKMQGLLQYSEEDCAFEEEIRPDGYNVYRSEKHRLPVSLSSAKQ

RQLYKNRGFLPLSHFLPMLPMVPEEPEDLRGHLESDMFSSPLETDSMDPF

GLVTGLEAVRSPSFEK

Binding proteins, such as anti-beta klotho antibodies, as described herein can induce FGF21-like signaling, as described herein. In vivo, the mature form of FGF21 is the active form of the molecule. A nucleic acid sequence encoding a full length FGF21 is provided below; the nucleotides encoding the signal sequence are underlined:

(SEQ ID NO: 305)
atg gac tcg gac gag acc ggg ttc gag cac tca gga ctg tgg gtt tct gtg ctg gct ggt ctt ctg ctg gga gcc tgc cag gca cac ccc atc cct gac tcc agt cct ctc ctg caa ttc ggg ggc caa gtc cgg cag cgg tac ctc tac aca gat gat gcc cag cag aca gaa gcc cac ctg gag atc agg gag gat ggg acg gtg ggg ggc gct gct gac cag agc ccc gaa agt ctc ctg cag ctg aaa gcc ttg aag ccg gga gtt att caa atc ttg gga gtc aag aca tcc agg ttc ctg tgc cag cgg cca gat ggg gcc ctg tat gga tcg ctc cac ttt gac cct gag gcc tgc agc ttc cgg gag ctg ctt ctt gag gac gga tac aat gtt tac cag tcc gaa gcc cac ggc ctc ccg ctg cac ctg cca ggg aac aag tcc cca cac cgg gac cct gca ccc cga gga cca gct cgc ttc ctg cca cta cca ggc ctg ccc ccc gca ccc ccg gag cca ccc gga atc ctg gcc ccc cag ccc ccc gat gtg ggc tcc tcg gac cct ctg agc atg gtg gga cct tcc cag ggc cga agc ccc agc tac gct tcc tga.

An amino acid sequence of a full length FGF21 is provided below; the amino acids that make up the signal sequence are underlined:

(SEQ ID NO: 306)
m d s d e t g f e h s g l w v s v l a g l l l g a c g a H P I P D S S P L L Q F G G Q V R Q R Y

L Y T D D A Q Q T E A H L E I R E D G T V G G A

A D Q S P E S L L Q L K A L K P G V I Q I L G V

K T S R F L C Q R P D G A L Y G S L H F D P E A

C S F R E L L L E D G Y N V Y Q S E A H G L P L

H L P G N K S P H R D P A P R G P A R F L P L P

G L P P A P P E P P G I L A P Q P P D V G S S D

P L S M V G P S Q G R S P S Y A S.

A nucleic acid sequence also encoding a full length FGF21 is provided; the nucleotides encoding the signal sequence are underlined:

(SEQ ID NO: 428)
atggactcggacgagaccgggttcgagcactcaggactgtgggtttctgt gctggctggtcttctgctgggagcctgccaggcaCACCCCATCCCTGACT

CCAGTCCTCTCCTGCAATTCGGGGGCCAAGTCCGGCAGCGGTACCTCTAC

ACAGATGATGCCCAGCAGACAGAAGCCCACCTGGAGATCAGGGAGGATGG

GACGGTGGGGGGCGCTGCTGACCAGAGCCCCGAAAGTCTCCTGCAGCTGA

AAGCCTTGAAGCCGGGAGTTATTCAAATCTTGGGAGTCAAGACATCCAGG

```
TTCCTGTGCCAGCGGCCAGATGGGGCCCTGTATGGATCGCTCCACTTTGA

CCCTGAGGCCTGCAGCTTCCGGGAGCTGCTTCTTGAGGACGGATACAATG

TTTACCAGTCCGAAGCCCACGGCCTCCCGCTGCACCTGCCAGGGAACAAG

TCCCCACACCGGGACCCTGCACCCCGAGGACCAGCTCGCTTCCTGCCACT

ACCAGGCCTGCCCCCGCACTCCCGGAGCCACCCGGAATCCTGGCCCCCC

AGCCCCCCGATGTGGGCTCCTCGGACCCTCTGAGCATGGTGGGACCTTCC

CAGGGCCGAAGCCCCAGCTACGCTTCCTGA.
```

An amino acid sequence also encoding a full length FGF21 is provided; the amino acids encoding the signal sequence are underlined:

(SEQ ID NO: 429)
<u>mdsdetgfehsglwvsvlaglllgacga</u>HPIPDSSPLLQFGGQVRQRYLY

TDDAQQTEAHLEIREDGTVGGAADQSPESLLQLKALKPGVIQILGVKTSR

FLCQRPDGALYGSLHFDPEACSFRELLLEDGYNVYQSEAHGLPLHLPGNK

SPHRDPAPRGPARFLPLPGLPPALPEPPGILAPQPPDVGSSDPLSMVGPS

QGRSPSYAS

Binding proteins, such as anti-beta klotho antibodies, as described herein bind to beta klotho alone or in complex with an FGF receptor, such as FGFR1c. An encoding nucleic acid sequence of human FGFR1c (GenBank Accession Number NM 023110; also designated FGFRαIIIc) is provided below:

(SEQ ID NO: 307)
```
atgtggagctggaagtgcctcctcttctgggctgtgctggtcacagcc acactctgcaccgctaggccgtccccgaccttgcctgaacaagcccag ccctggggagcccctgtggaagtggagtccttcctggtccaccccggt gacctgctgcagcttcgctgtcggctgcgggacgatgtgcagagcatc aactggctgcgggacggggtgcagctggcggaaagcaaccgcacccg cat cacaggggaggaggtggaggtgcaggactccgtgcccgcagact ccggcctctatgcttgcgtaaccagcagcccctcgggcagtgacacca cctacttctccgtcaatgtttcagatgctctcccctcctcggaggatga tgatgatgatgactcctcttcagaggagaaagaaacagataaca ccaaaccaaaccgtatgcccgtagctccatattggacatcaccagaaa agatggaaagaaattgcatgcagtgccggctgccaagacagtgaag ttcaaatgcccttccagtgggacaccaaacccaacactgcgctggttg aaaaatggcaaagaattcaaacctgaccacagaattggaggctacaa ggtccgttatgccacctggagcatcataatggactctgtggtgccctc tgacaagggcaactacacctgcattgtggagaatgagtacgcagca tcaaccacacataccagctggatgtcgtggagcggtcccctcaccggc ccatcctgcaagcagggttgcccgccaacaaaacagtggccctggt agcaacgtggagttcatgtgtaaggtgtacagtgacccgcagccgcac atccagtggctaaagcacatcgaggtgaatggagcaagattggcc agacaacctgccttatgtccagatcttgaagactgctggagttaatac caccgacaaagagatggaggtgcttcacttaagaaatgtctcctttga ggacgcaggggagtatacgtgcttggcgggtaactctatcggactctc ccatcactctgcatggttgaccgttctggaagccctggaagagaggcc ggcagtgatgacctcgcccctgtacctggagatcatcatctattgcac aggggccttcctcatctcctgcatggtggggtcggtcatcgtctacaa gatgaagagtggtaccaagaagagtgacttccacagccagatggctg tgcacaagctggccaagagcatccctctgcgcagacaggtaacagtg tctgctgactccagtgcatccatgaactctggggttcttctggttcggc catcacggctctcctccagtgggactcccatgctagcaggggtctctg agtatgagcttcccgaagaccctcgctgggagctgcctcgggacagac tggtcttaggcaaaccctgggagagggctgctttgggcaggtggtgt tggcagaggctatcgggctggacaaggacaaacccaaccgtgtgacc aaagtggctgtgaagatgttgaagtcggacgcaacagagaaagactt gtcagacctgatctcagaaatggagatgatgaagatgatcgggaagc ataagaatatcatcaacctgctgggggcctgcacgcaggatggtccct tgtatgtcatcgtggagtatgcctccaagggcaacctgcgggagtacc tgcaggcccggaggccccagggctggaatactgctacaacccagc cacaacccagaggagcagctctcctccaaggacctggtgtcctgcgcc taccaggtggcccgaggcatggagtatctggcctccaagaagtgcata caccgagacctggcagccaggaatgtcctggtgacagaggacaatgt gatgaagatagcagactttggcctcgcacgggacattcaccacatcga ctactataaaaagacaaccaacggccgactgcctgtgaagtggatgg cacccgaggcattatttgaccggatctacacccaccagagtgatgtgt ggtctttcggggtgctcctgtgggagatcttcactctgggcggctcccc ataccccggtgtgcctgtggaggaacttttcaagctgctgaaggaggg tcaccgcatggacaagcccagtaactgcaccaacgagctgtacatgat gatgcgggactgctggcatgcagtgccctcacagagacccaccttcaa gcagctggtggaagacctggaccgcatcgtggccttgacctccaacca ggagtacctggacctgtccatgccctggaccagtactccccagctt tcccgacacccggagctctacgtgctcctcaggggaggattccgtctt ctctcatgagccgctgcccgaggagccctgcctgccccgacacccagc ccagcttgccaatggcggactcaaacgccgctga.
```

The amino acid sequence of human FGFR1c (GenBank Accession Number NP 075598) (also designated FGFRαIIIC) is provided below:

(SEQ ID NO: 308)
MWSWKCLLFWAVLVTATLCTARPSPTLPEQAQPWGAPVEVESFLVHPG

DLLQLRCRLRDDVQSINWLRDGVQLAESNRTRITGEEVEVQDSVPADS

GLYACVTSSPSGSDTTYFSVNVSDALPSSEDDDDDDSSSEEKETDNT

KPNRMPVAPYWTSPEKMEKKLHAVPAAKTVKFKCPSSGTPNPTLRWLK

NGKEFKPDHRIGGYKVRYATWSIIMDSVVPSDKGNYTCIVENEYGSIN

HTYQLDVVERSPHRPILQAGLPANKTVALGSNVEFMCKVYSDPQPHIQ

WLKHIEVNGSKIGPDNLPYVQILKTAGVNTTDKEMEVLHLRNVSFEDA

GEYTCLAGNSIGLSHHSAWLTVLEALEERPAVMTSPLYLEIIIYCTGA

FLISCMVGSVIVYKMKSGTKKSDFHSQMAVHKLAKSIPLRRQVTVSAD

SSASMNSGVLLVRPSRLSSSGTPMLAGVSEYELPEDPRWELPRDRLVL

GKPLGEGCFGQVVLAEAIGLDKDKPNRVTKVAVKMLKSDATEKDLSDL

ISEMEMMKMIGKHKNIINLLGACTQDGPLYVIVEYASKGNLREYLQAR

RPPGLEYCYNPSHNPEEQLSSKDLVSCAYQVARGMEYLASKKCIHRDL

AARNVLVTEDNVMKIADFGLARDIHHIDYYKKTTNGRLPVKWMAPEAL

FDRIYTHQSDVWSFGVLLWEIFTLGGSPYPGVPVEELFKLLKEGHRMD

KPSNCTNELYMMMRDCWHAVPSQRPTFKQLVEDLDRIVALTSNQEYLD

LSMPLDQYSPSFPDTRSSTCSSGEDSVFSHEPLPEEPCLPRHPAQLAN

GGLKRR.

Binding proteins, such as anti-beta klotho antibodies, described herein may bind to beta klotho in complex with the extracellular portion of an FGF receptor such as FGFR1c. An example of an extracellular region of FGFR1c is:

(SEQ ID NO: 309)
MWSWKCLLFWAVLVTATLCTARPSPTLPEQAQPWGAPVEVESFLVHPGD

LLQLRCRLRDDVQSINWLRDGVQLAESNRTRITGEEVEVQDSVPADSGL

YACVISSPSGSDITYFSVNVSDALPSSEDDDDDDDSSSEEKETDNTKPN

RMPVAPYWTSPEKMEKKLHAVPAAKTVKFKCPSSGTPNPTLRWLKNGKE

FKPDHRIGGYKVRYATWSIIMDSVVPSDKGNYTCIVENEYGSINHTYQL

DVVERSPHRPILQAGLPANKTVALGSNVEFMCKVYSDPQPHIQWLKHIE

VNGSKIGPDNLPYVQILKTAGVNTTDKEMEVLHLRNVSFEDAGEYTCLA

GNSIGLSHHSAWLTVLEALEERPAVMTSPLY.

An example of an extracellular region of FGFR1c (αIIIc) is:

(SEQ ID NO: 427)
RPSPTLPEQAQPWGAPVEVESFLVHPGDLLQLRCRLRDDVQSINWLRDGV

QLAESNRTRITGEEVEVQDSVPADSGLYACVTSSPSGSDTTYFSVNVSDA

LPSSEDDDDDDDSSSEEKETDNTKPNRMPVAPYWTSPEKMEKKLHAVPAA

KTVKFKCPSSGTPNPTLRWLKNGKEFKPDHRIGGYKVRYATWSIIMDSVV

PSDKGNYTCIVENEYGSINHTYQLDVVERSPHRPILQAGLPANKTVALGS

NVEFMCKVYSDPQPHIQWLKHIEVNGSKIGPDNLPYVQILKTAGVNTTDK

EMEVLHLRNVSFEDAGEYTCLAGNSIGLSHHSAWLTVLEALEERPAVMTS

PLYE.

An example of an extracellular region of FGFR1c (βIIIc) is:

(SEQ ID NO: 426)
RPSPTLPEQDALPSSEDDDDDDDSSSEEKETDNTKPNPVAPYWTSPEKME

KKLHAVPAAKTVKFKCPSSGTPNPTLRWLKNGKEFKPDHRIGGYKVRYAT

WSIIMDSVVPSDKGNYTCIVENEYGSINHTYQLDVVERSPHRPILQAGLP

ANKTVALGSNVEFMCKVYSDPQPHIQWLKHIEVNGSKIGPDNLPYVQILK

TAGVNTTDKEMEVLHLRNVSFEDAGEYTCLAGNSIGLSHHSAWLTVLEAL

EERPAVMTSPLYLE.

As described herein, FGFR1c proteins can also include fragments. As used herein, the terms are used interchangeably to mean a receptor, in particular and unless otherwise specified, a human receptor, that upon association with beta klotho and FGF21 induces FGF21-like signaling activity.

The term FGFR1c also includes post-translational modifications of the FGFR1c amino acid sequence, for example, possible N-linked glycosylation sites. Thus, the antigen binding proteins can bind to or be generated from proteins glycosylated at one or more of the positions.

Binding proteins, such as anti-beta klotho antibodies, as described herein bind to beta klotho alone or in complex with an FGF receptor, such as FGFR2c. An encoding nucleic acid sequence of human FGFR2c is provided below:

(SEQ ID NO: 310)
atggtcagctggggtcgtttcatctgcctggtcgtggtcaccatggcaacc ttgtccctggcccggccctccttcagtttagttgaggataccacattagag ccagaagagccaccaaccaaataccaaatctctcaaccagaagtgtacgtg gctgcgccaggggagtcgctagaggtgcgctgcctgttgaaagatgccgcc gtgatcagttggactaaggatggggtgcacttggggcccaacaataggaca gtgcttattggggagtacttgcagataaagggcgccacgcctagagactcc ggcctctatgcttgtactgccagtaggactgtagacagtgaaacttggtac ttcatggtgaatgtcacagatgccatctcatccggagatgatgaggatgac accgatggtgcggaagattttgtcagtgagaacagtaacaacaagagagca ccatactggaccaacacagaaaagatggaaaagcggctccatgctgtgcct gcggccaacactgtcaagtttcgctgcccagccggggggaacccaatgcca accatgcggtggctgaaaaacgggaaggagtttaagcaggagcatcgcatt ggaggctacaaggtacgaaaccagcactggagcctcattatggaaagtgtg gtcccatctgacaagggaaattatacctgtgtagtggagaatgaatacggg tccatcaatcacacgtaccacctggatgttgtggagcgatcgcctcaccgg cccatcctccaagccggactgccggcaaatgcctccacagtggtcggagga gacgtagagtttgtctgcaaggtttacagtgatgcccagccccacatccag tggatcaagcacgtggaaaagaacggcagtaaatacgggcccgacgggctg ccctacctcaaggttctcaaggccgccggtgttaacaccacggacaaagag attgaggttctctatattcggaagtaacttttgaggacgctggggaatata cgtgcttggcgggtaattctattgggatatcctttcactctgcatggttga cagtctgccagcgcctggaagagaaaaggagattacagcttccccagact -continued

```
acctggagatagccatttactgcatagggggtcttcttaatcgcctgtatgg tggtaacagtcatcctgtgccgaatgaagaacacgaccaagaagccagact tcagcagccagccggctgtgcacaagctgaccaaacgtatcccctgcgga gacaggtaacagtttcggctgagtccagctcctccatgaactccaacaccc cgctggtgaggataacaacacgcctctcttcaacggcagacaccccatgc tggcagggggtctccgagtatgaacttccagaggacccaaaatgggagtttc caagagataagctgacactgggcaagcccctgggagaaggttgctttgggc aagtggtcatggcgaagcagtgggaattgacaaagacaagcccaaggagg cggtcaccgtggccgtgaagatgttgaaagatgatgccacagagaaagacc tttctgatctggtgtcagagatggagatgatgaagatgattgggaaacaca agaatatcataaatcttcttggagcctgcacacaggatgggcctctctatg tcatagttgagtatgcctcaaaggcaacctccgagaatacctccgagccc ggaggccacccgggatggagtactcctatgacattaacgtgttcctgagg agcagatgaccttcaaggacttggtgtcatgcacctaccagctggccagag gcatggagtacttggcttcccaaaaatgtattcatcgagatttagcagcca gaaatgttttggtaacagaaaacaatgtgatgaaaatagcagactttggac tcgccagagatatcaacaatatagactattacaaaaagaccaccaatgggc ggcttccagtcaagtggatggctccagaagccctgtttgatagagtataca ctcatcagagtgatgtctggtccttcggggtgttaatgtgggagatcttca ctttaggggggctcgccctacccagggattcccgtggaggaacttttttaagc tgctgaaggaaggacacagaatggataagccagccaactgcaccaacgaac tgtacatgatgatgagggactgttggcatgcagtgccctcccagagaccaa cgttcaagcagttggtagaagacttggatcgaattctcactctcacaacca atgaggaatacttggacctcagccaacctctcgaacagtattcacctagtt accctgacacaagaagttcttgttcttcaggagatgattctgttttttctc cagaccccatgccttacgaaccatgccttcctcagtatccacacataaacg gcagtgttaaaacatga
```

The amino acid sequence of human FGFR2c is provided below; the amino acids that make up the signal sequence are underlined:

(SEQ ID NO: 311)
mvswgrficlvvytmatlslaRPSFSLVEDTTLEPEEPPIKYQISQPEVYV

AAPGESLEVRCLLKDAAVISWTKDGVHLGPNNRTVLIGEYLQIKGATPRDS

GLYACTASRTVDSETWYFMVNVTDAISSGDDEDDIDGAEDFVSENSNNKRA

PYWINTEKMEKRLHAVPAANTVKFRCPAGGNPMPIMRWLKNGKEFKQEHRI

GGYKVRNQHWSLIMESVVPSDKGNYTCVVENEYGSINHTYHLDVVERSPHR

PILQAGLPANASTVVGGDVEFVCKVYSDAQPHIQWIKHVEKNGSKYGPDGL

PYLKVLKAAGVNTTDKEIEVLYIRNVTFEDAGEYTCLAGNSIGISFHSAWL

TVLPAPGREKEITASPDYLEIAIYCIGVFLIACMVVTVILCRMKNTTKKPD

FSSQPAVHKLTKRIPLRRQVTVSAESSSSMNSNTPLVRITTRLSSTADTPM

LAGVSEYELPEDPKWEFPRDKLTLGKPLGEGCFGQVVMAEAVGIDKDKPKE

AVTVAVKMLKDDATEKDLSDLVSEMEMMKMIGKHKNIINLLGACTQDGPLY

VIVEYASKGNLREYLRARRPPGMEYSYDINRVPEEQMTFKDLVSCTYQLAR

GMEYLASQKCIHRDLAARNVLVTENNVMKIADFGLARDINNIDYYKKTING

RLPVKWMAPEALFDRVYTHQSDVWSFGVLMWEIFTLGGSPYPGIPVEELFK

LLKEGHRMDKPANCTNELYMMMRDCWHAVPSQRPTFKQLVEDLDRILTLTT

NEEYLDLSQPLEQYSPSYPDTRSSCSSGDDSVFSPDPMPYEPCLPQYPHIN

GSVKT

Binding proteins, such as anti-beta klotho antibodies, as described herein bind to beta klotho alone or in complex with an FGF receptor, such as FGFR3c. An encoding nucleic acid sequence of human FGFR3c (GenBank Accession Number NP 000133) is provided below:

(SEQ ID NO: 312)
```
atgggcgcccctgcctgcgccctcgcgctctgcgtggccgtggccatcgtg gccggcgcctcctcggagtccttggggacggagcagcgcgtcgtggggcga gcggcagaagtcccgggcccagagcccggccagcaggagcagttggtcttc ggcagcggggatgctgtggagctgagctgtcccccgcccggggggtggtccc atgggcccactgtctgggtcaaggatggcacagggctggtgccctcggag cgtgtcctggtggggcccagcggctgcaggtgctgaatgcctcccacgag gactccggggcctacagctgccggcagcggctcacgcagcgcgtactgtgc cacttcagtgtgcgggtgacagacgctccatcctcgggagatgacgaagac ggggaggacgaggctgaggacacaggtgtggacacagggcgcccttactgg acacggcccgagcggatggacaagaagctgctggccgtgccggccgccaac accgtccgcttccgctgcccagccgctggcaaccccactccctccatctcc tggctgaagaacggcagggagttccgcggcgagcaccgcattggaggcatc aagctgcggcatcagcagtggagcctggtcatggaaagcgtggtgccctcg gaccgcggcaactacacctgcgtcgtggagaacaagtttggcagcatccgg cagacgtacacgctggacgtgctggagcgccccgcaccggcccatcctgc aggcggggctgccggccaaccagacggcggtgctgggcagcgacgtggagt tccactgcaaggtgtacagtgacgcacagcccccatccagtggctcaagc acgtggaggtgaatggcagcaaggtgggcccggacggcacaccctacgtta ccgtgctcaagacggcgggcgctaacaccaccgacaaggagctagaggttc tctccttgcacaacgtcacctttgaggacgccggggagtacacctgcctgg cgggcaattctattgggttttctcatcactctgcgtggctggtggtgctgc cagccgaggaggagctggtggaggctgacgaggcgggcagtgtgtatgcag gcatcctcagctacgggggtgggcttcttcctgttcatcctggtggtgggcgg ctgtgacgctctgccgcctgcgcagcccccccaagaaaggcctgggctccc ccaccgtgcacaagatctcccgcttcccgctcaagcgacaggtgtccctgg agtccaacgcgtccatgagctccaacacaccactggtgcgcatcgcaaggc tgtcctcaggggagggccccacgctggccaatgtctccgagctcgagctgc ctgccgaccccaaatgggagctgtctcggggcccggctgaccctgggcaagc
```

```
ccccttggggagggctgcttcggccaggtggtcatggcggaggccatcggca ttgacaaggaccgggccgccaagcctgtcaccgtagccgtgaagatgctga aagacgatgccactgacaaggacctgtcggacctggtgtctgagatggaga tgatgaagatgatcgggaaacacaaaaacatcatcaacctgctgggcgcct gcacgcagggcgggcccctgtacgtgctggtggagtacgcggccaagggta acctgcgggagtttctgcggcgcggcggccccccgggcctggactactcct tcgacacctgcaagccgcccgaggagcagctcaccttcaaggacctggtgt cctgtgcctaccaggtggcccggggcatggagtacttggcctcccagaagt gcatccacagggacctggctgcccgcaatgtgctggtgaccgaggacaacg tgatgaagatcgcagacttcgggctggcccgggacgtgcacaacctcgact actacaagaagacaaccaacggccggctgcccgtgaagtggatggcgcctg aggccttgtttgaccgagtctacactcaccagagtgacgtctggtcctttg gggtcctgctctgggagatcttcacgctgggggctccccgtaccccggca tccctgtggaggagctcttcaagctgctgaaggagggccaccgcatggaca agcccgccaactgcacacacgacctgtacatgatcatgcgggagtgctggc atgccgcgcctcccagaggcccaccttcaagcagctggtggaggacctgg accgtgtccttaccgtgacgtccaccgacgagtacctggacctgtcggcgc ctttcgagcagtactccccgggtggccaggacaccccagctccagctcct caggggacgactccgtgtttgcccacgacctgctgccccggccccaccca gcagtgggggctcgcggacgtga
```

The amino acid sequences of human FGFR3c is provided below; the amino acids that make-up the signal sequence are underlined:

(SEQ ID NO: 313)
<u>mgapacalalcvavaivagass</u>ESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGFSHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMEMMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTDEYLDLSA
PFEQYSPGGQDTPSSSSSGDDSVFAHDLLPPAPPSSGGSRT Binding proteins, such as anti-beta klotho antibodies, as described herein bind to beta klotho alone or in complex with an FGF receptor, such as FGFR4. An encoding nucleic acid sequence of human FGFR4 is provided below:

(SEQ ID NO: 314)
```
atgcggctgctgctggccctgttgggggtcctgctgagtgtgcctgggcct ccagtcttgtccctggaggcctctgaggaagtggagcttgagccctgcctg gctcccagcctggagcagcaagagcaggagctgacagtagcccttgggcag cctgtgcgtctgtgctgtgggcgggctgagcgtggtggccactggtacaag gagggcagtcgcctggcacctgctggccgtgtacggggctggaggggccgc ctagagattgccagcttcctacctgaggatgctggccgctacctctgcctg gcacgaggctccatgatcgtcctgcagaatctcaccttgattacaggtgac tccttgacctccagcaacgatgatgaggaccccaagtcccatagggacccc tcgaataggcacagttaccccagcaagcaccctactggacacaccccag cgcatggagaagaaactgcatgcagtacctgcggggaacaccgtcaagttc cgctgtccagctgcaggcaaccccacgccaccatccgctggcttaaggat ggacaggcctttcatggggagaaccgcattggaggcattcggctgcgccat cagcactggagtctcgtgatggagagcgtggtgccctcggaccgcggcaca tacacctgcctggtagagaacgctgtgggcagcatccgctataactacctg ctagatgtgctggagcggtccccgcaccggcccatcctgcaggccgggctc ccggccaacaccacagccgtggtgggcagcgacgtggagctgctgtgcaag gtgtacagcgatgcccagccccacatccagtggctgaagcacatcgtcatc aacggcagcagcttcggagccgacggtttccctatgtgcaagtcctaaag actgcagacatcaatagctcagaggtggaggtcctgtacctgcggaacgtg tcagccgaggacgcaggcgagtacacctgcctcgcaggcaattccatcggc ctctcctaccagtctgcctggctcacggtgctgccagaggaggacccacac tggaccgcagcagcgcccgaggccaggtatacggacatcatcctgtacgcg tcgggctccctggccttggctgtgctcctgctgctggccgggctgtatcga gggcaggcgctccacggccggcacccccgcccgcccgccactgtgcagaag ctctcccgcttccctctggcccgacagttctccctggagtcaggctcttcc ggcaagtcaagctcatccctggtacgaggcgtgcgtctctcctccagcggc cccgccttgctcgccggcctcgtgagtctagatctacctctcgacccacta tgggagttcccccgggacaggctggtgcttgggaagcccctaggcgagggc tgctttggccaggtagtacgtgcagaggcctttggcatggaccctgcccgg cctgaccaagccagcactgtggccgtcaagatgctcaaagacaacgcctct gacaaggacctggccgacctggtctcggagatggaggtgatgaagctgatc ggccgacacaagaacatcatcaacctgcttggtgtctgcacccaggaaggg cccctgtacgtgatcgtggagtgcgccgccaaggaaacctgcgggagttc ctgcgggcccggcgcccccaggccccgacctcagcccgacggtcctcgg agcagtgaggggccgctctccttcccagtcctggtctcctgcgcctaccag gtggcccgaggcatgcagtatctggagtcccggaagtgtatccaccgggac ctggctgccgcaatgtgctggtgactgaggacaatgtgatgaagattgct gactttgggctggcccgcggcgtccaccacattgactactataagaaaacc
```

```
agcaacggccgcctgcctgtgaagtggatggcgcccgaggccttgtttgac cgggtgtacacacaccagagtgacgtgtggtcttttgggatcctgctatgg gagatcttcaccctcgggggctcccgtatcctggcatcccggtggaggag ctgttctcgctgctgcgggagggacatcggatggaccgaccccacactgc cccccagagctgtacgggctgatgcgtgagtgctggcacgcagcgccctcc cagaggcctaccttcaagcagctggtggaggcgctggacaaggtcctgctg gccgtctctgaggagtacctcgacctccgcctgaccttcggaccctattcc ccctctggtggggacgccagcagcacctgctcctccagcgattctgtcttc agccacgaccccctgccattgggatccagctccttcccttcgggtctggg gtgcagacatga
```

The amino acid sequence of human FGFR4 (GenBank Accession Number NP. 002002.3) is provided below; the amino acids that make-up the signal sequence are underlined:

(SEQ ID NO: 315)
<u>mrlllallgyllsvpgppvls</u>LEASEEVELEPCLAPSLEQQEQELTVALGQ

PVRLCCGRAERGGHWYKEGSRLAPAGRVRGWRGRLEIASFLPEDAGRYLCL

ARGSMIVLQNLTLITGDSLTSSNDDEDPKSHRDPSNRHSYPQQAPYWTHPQ

RMEKKLHAVPAGNTVKFRCPAAGNPTPTIRWLKDGQAFHGENRIGGIRLRH

QHWSLVMESVVPSDRGTYTCLVENAVGSIRYNYLLDVLERSPHRPILQAGL

PANTTAVVGSDVELLCKVYSDAQPHIQWLKHIVINGSSFGADGFPYVQVLK

TADINSSEVEVLYLRNVSAEDAGEYTCLAGNSIGLSYQSAWLTVLPEEDPT

WTAAAPEARYTDIILYASGSLALAVLLLLAGLYRGQALHGRHPRPPATVQK

LSRFPLARQFSLESGSSGKSSSSLVRGVRLSSSGPALLAGLVSLDLPLDPL

WEFPRDRLVLGKPLGEGCFGQVVRAEAFGMDPARPDQASTVAVKMLKDNAS

DKDLADLVSEMEVMKLIGRHKNIINLLGVCTQEGPLYVIVECAAKGNLREF

LRARRPPGPDLSPDGPRSSEGPLSFPVLVSCAYQVARGMQYLESRKCIHRD

LAARNVLVTEDNVMKIADFGLARGVHHIDYYKKTSNGRLPVKWMAPEALFD

RVYTHQSDVWSFGILLWEIFTLGGSPYPGIPVEELFSLLREGHRMDRPPHC

PPELYGLMRECWHAAPSQRPTFKQLVEALDKVLLAVSEEYLDLRLTFGPYS

PSGGDASSTCSSSDSVFSHDPLPLGSSSFPFGSGVQT

An "antigen" is a predetermined antigen to which an antibody can selectively bind. A target antigen may be a polypeptide, carbohydrate, nucleic acid, lipid, hapten or other naturally occurring or synthetic compound. Preferably, the target antigen is a polypeptide.

The term "antigen binding fragment," "antigen binding domain," "antigen binding region," and similar terms refer to that portion of an antibody which comprises the amino acid residues that interact with an antigen and confer on the binding agent its specificity and affinity for the antigen (e.g., the complementarity determining regions (CDRs)).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. The strength of the total non-covalent interactions between a single antigen-binding site on an antibody and a single epitope of a target molecule, such as beta klotho, is the affinity of the antibody or functional fragment for that epitope. The ratio of association (k1) to dissociation (k−1) of an antibody to a monovalent antigen (k1/k−1) is the association constant K, which is a measure of affinity. The value of K varies for different complexes of antibody and antigen and depends on both k1 and k−1. The association constant K for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent beta klotho, come in contact with antibodies containing multiple binding sites, the interaction of antibody with antigen at one site will increase the probability of a reaction at a second site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The terms "antibodies that specifically bind to beta klotho," "antibodies that specifically bind to a beta klotho epitope," and analogous terms are also used interchangeably herein and refer to antibodies that specifically bind to a beta klotho polypeptide, such as a beta klotho antigen, or fragment, or epitope (e.g., human beta klotho such as a human beta klotho polypeptide, antigen or epitope). An antibody that specifically binds to beta klotho, (e.g., human beta klotho) may bind to the extracellular domain or peptide derived from the extracellular domain of beta klotho beta klotho. An antibody that specifically binds to a beta klotho antigen (e.g., human beta klotho) may be cross-reactive with related antigens (e.g., cyno beta klotho). In certain embodiments, an antibody that specifically binds to a beta klotho antigen does not cross-react with other antigens. An antibody that specifically binds to a beta klotho antigen can be identified, for example, by immunoassays, Biacore, or other techniques known to those of skill in the art. An antibody binds specifically to a beta klotho antigen when it binds to a beta klotho antigen with higher affinity than to any cross reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., Paul, ed., 1989, *Fundamental Immunology Second Edition*, Raven Press, New York at pages 332 336 for a discussion regarding antibody specificity. An antibody "which binds" an antigen of interest (e.g., a target antigen such as beta klotho) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein, for example, as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-6}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope. In certain embodiments, an antibody that binds to beta klotho has a dissociation constant (Kd) of less than or equal to 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. The lower the $K_D$, the higher the affinity of the anti-beta klotho antibody. In certain embodiments, anti-beta klotho antibody binds to an epitope of beta klotho that is conserved among beta klotho from different species (e.g., between human and cyno beta klotho).

The term "compete" when used in the context of anti-beta klotho antibodies (e.g., agonistic antibodies and binding proteins that bind to (i) beta klotho; or (ii) a complex comprising beta klotho and one of FGFR1c, FGFR2c, FGFR3c, and FGFR4) that compete for the same epitope or binding site on a target means competition between as determined by an assay in which the antibody (or binding fragment) thereof under study prevents or inhibits the specific binding of a reference molecule (e.g., a reference ligand, or reference antigen binding protein, such as a reference antibody) to a common antigen (e.g., beta klotho or a fragment thereof). Numerous types of competitive binding assays can be used to determine if a test antibody competes with a reference antibody for binding to beta klotho (e.g., human beta klotho). Examples of assays that can be employed include solid phase direct or indirect radioimmunoassay (RIA), solid phase direct or indirect enzyme immunoassay (EIA), sandwich competition assay (see, e.g., Stahli et al., (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane, (1988) Antibodies, A Laboratory Manual, Cold Spring Harbor Press); solid phase direct label RIA using 1-125 label (see, e.g., Morel et al., (1988) Molec. Immunol. 25:7-15); solid phase direct biotin-avidin EIA (see, e.g., Cheung, et al., (1990) Virology 176:546-552); and direct labeled RIA (Moldenhauer et al., (1990) Scand. J. Immunol. 32:77-82). Typically, such an assay involves the use of a purified antigen (e.g., beta klotho such as human beta klotho) bound to a solid surface or cells bearing either of an unlabelled test antigen binding protein (e.g., test anti-beta klotho antibody) or a labeled reference antigen binding protein (e.g., reference anti-beta klotho antibody). Competitive inhibition may be measured by determining the amount of label bound to the solid surface or cells in the presence of the test antigen binding protein. Usually the test antigen binding protein is present in excess. Antibodies identified by competition assay (competing antibodies) include antibodies binding to the same epitope as the reference antibody and/or antibodies binding to an adjacent epitope sufficiently proximal to the epitope bound by the reference for antibodies steric hindrance to occur. Additional details regarding methods for determining competitive binding are described herein. Usually, when a competing antibodies protein is present in excess, it will inhibit specific binding of a reference antibodies to a common antigen by at least 23%, for example 40%, 45%, 50%, 55%, 60%, 65%, 70% or 75%]]. In some instance, binding is inhibited by at least 80%, 85%, 90%, 95%, 96% or 97%, 98%, 99% or more.

The term "anti-beta klotho antibody" or "an antibody that binds to beta klotho" includes an antibody that is capable of binding beta klotho with sufficient affinity such that the antibody is useful as a diagnostic and/or therapeutic agent in targeting beta klotho. Preferably, the extent of binding of an anti-beta klotho antibody to an unrelated, non-beta klotho protein is less than about 10% of the binding of the antibody to beta klotho as measured, for example, by fluorescence activated cell sorting (FACS) analysis or an immunoassay such as a radioimmunoassay (RIA). An antibody that "specifically binds to" or is "specific for" beta klotho is Illustrated above. In certain embodiments, an antibody that binds to beta klotho, as described herein has a dissociation constant (Kd) of less than or equal to 10 nM, 9 nM, 8 nM, 7 nM, 6 nM, 5 nM, 4 nM, 0.9 nM, 0.8 nM, 0.7 nM, 0.6 nM, 0.5 nM, 0.4 nM, 0.3 nM, 0.2 nM, or 0.1 nM, and/or is greater than or equal to 0.1 nM. In certain embodiments, anti-beta klotho antibody binds to an epitope of beta klotho that is conserved among beta klotho from different species (e.g., between human and cyno beta klotho).

An "isolated" antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 25%, 20%, 15%, 10%, 5%, or 1% (by dry weight) of heterologous protein (also referred to herein as a "contaminating protein"). In certain embodiments, when the antibody is recombinantly produced, it is substantially free of culture medium, e.g., culture medium represents less than about 20%, 15%, 10%, 5%, or 1% of the volume of the protein preparation. In certain embodiments, when the antibody is produced by chemical synthesis, it is substantially free of chemical precursors or other chemicals, for example, it is separated from chemical precursors or other chemicals which are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 1951), such as 96%, 97%, 98%, or 99%, by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In specific embodiments, antibodies provided herein are isolated.

A 4-chain antibody unit is a heterotetrameric glycoprotein composed of two identical light (L) chains and two identical heavy (H) chains. In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for p and c isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The term "variable region" or "variable domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases forming part of, the β sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, Md., 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. The variability in sequence is concentrated in the CDRs while the less variable portions in the variable region are referred to as framework regions (FR). The CDRs of the light and heavy chains are primarily responsible for the interaction of the antibody with antigen. In specific embodiments, the variable region is a human variable region.

The term "variable region residue numbering as in Kabat" or "amino acid position numbering as in Kabat", and variations thereof, refers to the numbering system used for heavy chain variable regions or light chain variable regions of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc, according to Kabat) after heavy chain FR residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, including, for example, by AbM, Chothia, Contact, IMGT and AHon. Various numbers systems are illustrated in FIGS. 1-3.

An "intact" antibody is one comprising an antigen-binding site as well as a CL and at least heavy chain constant regions, CH1, CH2 and CH3. The constant regions may include human constant regions or amino acid sequence variants thereof. Preferably, an intact antibody has one or more effector functions.

"Antibody fragments" comprise a portion of an intact antibody, preferably the antigen binding or variable region of the intact antibody. Examples of antibody fragments include, without limitation, Fab, Fab', F(ab')2, and Fv fragments; diabodies and di-diabodies (see, e.g., Holliger, P. et al., (1993) Proc. Natl. Acad. Sci. 90:6444-8; Lu, D. et al., (2005) J. Biol. Chem. 280:19665-72; Hudson et al., Nat. Med. 9:129-134 (2003); WO 93/11161; and U.S. Pat. Nos. 5,837,242 and 6,492,123); single-chain antibody molecules (see, e.g., U.S. Pat. Nos. 4,946,778; 5,260,203; 5,482,858 and 5,476,786); dual variable domain antibodies (see, e.g., U.S. Pat. No. 7,612,181); single variable domain antibodies (SdAbs) (see, e.g., Woolven et al., Immunogenetics 50: 98-101, 1999; Streltsov et al., Proc Natl Acad Sci USA.

101:12444-12449, 2004); and multispecific antibodies formed from antibody fragments.

A "functional fragment" or "binding fragment" or "antigen binding fragment" of a therapeutic antibody will exhibit at least one if not some or all of the biological functions attributed to the intact antibody, the function comprising at least binding to the target antigen, (e.g., a beta klotho binding fragment or fragment that binds to beta klotho).

The term "fusion protein" as used herein refers to a polypeptide that comprises an amino acid sequence of an antibody and an amino acid sequence of a heterologous polypeptide or protein (e.g., a polypeptide or protein not normally a part of the antibody (e.g., a non-anti-beta klotho antigen binding antibody)). The term "fusion" when used in relation to beta klotho or to an anti-beta klotho antibody refers to the joining of a peptide or polypeptide, or fragment, variant and/or derivative thereof, with a heterologous peptide or polypeptide. In certain embodiments, the fusion protein retains the biological activity of the beta klotho or anti-beta klotho antibody. In certain embodiments, the fusion protein comprises a beta klotho antibody VH region, VL region, VH CDR (one, two or three VH CDRs), and/or VL CDR (one, two or three VL CDRs), wherein the fusion protein binds to a beta klotho epitope, a beta klotho fragment and/or a beta klotho polypeptide.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, (e.g., isotypes) referred to as alpha ($\alpha$), delta ($\delta$), epsilon ($\epsilon$), gamma ($\gamma$) and mu ($\mu$), based on the amino acid sequence of the heavy chain constant region. The distinct heavy chains differ in size: $\alpha$, $\delta$ and $\gamma$ contain approximately 450 amino acids, while p and c contain approximately 550 amino acids. When combined with a light chain, these distinct types of heavy chains give rise to five well known classes (e.g., isotypes) of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa ($\kappa$) of lambda ($\lambda$) based on the amino acid sequence of the constant domains. Light chain amino acid sequences are well known in the art. A light chain can be a human light chain.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "monoclonal antibody" as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell, wherein the antibody binds to only a beta klotho epitope as determined, for example, by ELISA or other antigen-binding or competitive binding assay known in the art. The term "monoclonal" is not limited to any particular method for making the antibody. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). Exemplary methods of producing monoclonal antibodies are provided in the Examples herein.

The term "native" when used in connection with biological materials such as nucleic acid molecules, polypeptides, host cells, and the like, refers to those which are found in nature and not manipulated, modified, and/or changed (e.g., isolated, purified, selected) by a human being.

The antibodies provided herein can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)).

"Humanized" forms of nonhuman (e.g., murine) antibodies are chimeric antibodies that include human immunoglobulins (e.g., recipient antibody) in which the native CDR residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., Nature, 321:522-525 (1986); Riechmann et al., Nature, 332:323-329 (1988); and Presta, Curr. Op. Struct. Biol., 2:593-596 (1992); Carter et al., Proc. Natl. Acd. Sci. USA 89:4285-4289 (1992); and U.S. Pat. No. 6,800,738 (issued Oct. 5, 2004), 6,719,971 (issued Sep. 27, 2005), 6,639,055

(issued Oct. 28, 2003), 6,407,213 (issued Jun. 18, 2002), and 6,054,297 (issued Apr. 25, 2000).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (Hoogenboom and Winter, J. Mol. Biol., 227:381 (1991); Marks et al., J. Mol. Biol., 222:581 (1991) and yeast display libraries (Chao et al., Nature Protocols 1: 755-768 (2006)). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., mice (see, e.g., Jakobovits, A., Curr. Opin. Biotechnol. 1995, 6(5):561-6; Bruggemann and Taussing, Curr. Opin. Biotechnol. 1997, 8(4):455-8; and U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., J. Biol. Chem. 252:6609-6616 (1977); Kabat, Adv. Prot. Chem. 32:1-75 (1978)). CDR region sequences also have been defined structurally by Chothia as those residues that are not part of the conserved β-sheet framework, and thus are able to adapt different conformations (Chothia and Lesk, J. Mol. Biol. 196:901-917 (1987)). Both terminologies are well recognized in the art. CDR region sequences have also been defined by AbM, Contact and IMGT. CDR region sequences are illustrated in FIGS. 1-3. The positions of CDRs within a canonical antibody variable region have been determined by comparison of numerous structures (Al-Lazikani et al., J. Mol. Biol. 273:927-948 (1997); Morea et al., Methods 20:267-279 (2000)). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra (1997)). Such nomenclature is similarly well known to those skilled in the art.

The term "hypervariable region", "HVR", or "HV", when used herein refers to the regions of an antibody variable region that are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (see, e.g., Kabat et al., Sequences of Proteins of Immunological Interest, 5th Ed. Public Health Service, National Institutes of Health, Bethesda, Md. (1991)). Chothia refers instead to the location of the structural loops (see, e.g., Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B, if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). The "contact" hypervariable regions are based on an analysis of the available complex crystal structures. The residues from each of these hypervariable regions or CDRs are noted below.

Recently, a universal numbering system has been developed and widely adopted, ImMunoGeneTics (IMGT) Information System® (Lafranc et al., Dev. Comp. Immunol. 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Plückthun, J. Mol. Biol. 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra) and is also illustrated in FIGS. 1-3. An Exemplary system, shown herein, combines Kabat and Chothia.

|  | Exemplary | IMGT | Kabat | AbM | Chothia | Contact |
| --- | --- | --- | --- | --- | --- | --- |
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (L1), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. As used herein, the terms "HVR" and "CDR" are used interchangeably.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CH1, CH2 and CH3 regions of the heavy chain and the CL region of the light chain.

The term "framework" or "FR" residues are those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

An "affinity matured" antibody is one with one or more alterations (e.g., amino acid sequence variations, including changes, additions and/or deletions) in one or more HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. For review, see Hudson and Souriau, Nature Medicine 9:129-134 (2003); Hoogenboom, Nature Biotechnol. 23: 1105-1116 (2005); Quiroz and Sinclair, Revista Ingeneria Biomedia 4: 39-51 (2010).

A "blocking" antibody or an "antagonist" antibody is one which inhibits or reduces biological activity of the antigen it binds. For example, blocking antibodies or antagonist antibodies may substantially or completely inhibit the biological activity of the antigen.

An "agonist antibody" is an antibody that triggers a response, e.g., one that mimics at least one of the functional activities of a polypeptide of interest (e.g., FGF19 or FGF21). An agonist antibody includes an antibody that is a ligand mimetic, for example, wherein a ligand binds to a cell surface receptor and the binding induces cell signaling or activities via an intercellular cell signaling pathway and wherein the antibody induces a similar cell signaling or activation.

An "agonist" of beta klotho refers to a molecule that is capable of activating or otherwise increasing one or more of the biological activities of beta klotho, such as in a cell expressing beta klotho and a FGF receptor. In some embodiments, an agonist of beta klotho (e.g., an agonistic antibody as described herein) may, for example, act by activating or otherwise increasing the activation and/or cell signaling pathways of a cell expressing a beta klotho protein and a FGF receptor, thereby increasing a beta klotho-mediated biological activity of the cell relative to the beta klotho-mediated biological activity in the absence of agonist. In some embodiments the antibodies provided herein are agonistic anti-beta klotho antibodies, including antibodies that induce FGF19-like signaling and/or FGF21-like signaling.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein.

Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$," or "$K_D$ value" may be measured by assays known in the art, for example by a binding assay. The $K_D$ may be measured in a radiolabeled antigen binding assay (RIA), for example, performed with the Fab version of an antibody of interest and its antigen (Chen, et al., (1999) J. Mol Biol 293:865-881). The $K_D$ or $K_D$ value may also be measured by using surface plasmon resonance assays by Biacore, using, for example, a BIAcore™-2000 or a BIAcore™-3000 BIAcore, Inc., Piscataway, N.J.), or by biolayer interferometry using, for example, the OctetQK384 system (ForteBio, Menlo Park, Calif.). An "on-rate" or "rate of association" or "association rate" or "kon" may can also be determined with the same surface plasmon resonance or biolayer interferometry techniques described above using, for example, a BIAcore™-2000 or a BIAcore™-3000 (BIAcore, Inc., Piscataway, N.J.), or the OctetQK384 system (ForteBio, Menlo Park, Calif.).

The phrase "substantially similar" or "substantially the same" denotes a sufficiently high degree of similarity between two numeric values (e.g., one associated with an antibody of the present disclosure and the other associated with a reference antibody) such that one of skill in the art would consider the difference between the two values to be of little or no biological and/or statistical significance within the context of the biological characteristic measured by the values (e.g., $K_D$ values). For example, the difference between the two values may be less than about 50%, less than about 40%, less than about 30%, less than about 20%, less than about 10%, less than about 5%, as a function of the value for the reference antibody.

The phrase "substantially reduced," or "substantially different", as used herein, denotes a sufficiently high degree of difference between two numeric values (e.g., one associated with an antibody of the present disclosure and the other associated with a reference antibody) such that one of skill in the art would consider the difference between the two values to be of statistical significance within the context of the biological characteristic measured by the values. For example, the difference between said two values may be preferably greater than about 10%, greater than about 20%, greater than about 30%, greater than about 40%, greater than about 50% as a function of the value for the reference antibody.

Antibody "effector functions" refer to those biological activities attributable to the Fc region (e.g., a native sequence Fc region or amino acid sequence variant Fc region) of an antibody, and vary with the antibody isotype. Examples of antibody effector functions include: Cl q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding region or binding domain (e.g., an antibody variable region or domain) and can be assessed using various assays as disclosed.

A "native sequence Fc region" comprises an amino acid sequence identical to the amino acid sequence of an Fc region found in nature, and not manipulated, modified, and/or changed (e.g., isolated, purified, selected, including or combining with other sequences such as variable region sequences) by a human. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, (e.g., substituting, addition, or deletion) preferably one or more amino acid substitution(s). Preferably, the variant Fc region has at least one amino acid substitution compared to a native sequence Fc region or to the Fc region of a parent polypeptide, for example, from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and more preferably at least about 90% homology therewith, for example, at least about 95% homology therewith. For example, a variant with two amino acid changes to alanine at two positions in the human IgG1 Fc sequence are shown bolded in the amino acid sequence provided below:

(SEQ ID NO: 316)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPALAGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPGK

Such a variant sequence may be used in humanized heavy chain constructs such as shown below for a humanized 5H23-vH3 (see, e.g., Example 7) designated 5H23(vH3)-hIgG1(E233A)(L235A) as provided below; the amino acids that make up the signal sequence are underlined and the variable region sequence is bolded:

(SEQ ID NO: 317)
<u>mdmrvpaqllglllllwlrgarc</u>QVQLQQSGAEVKKPGASVKVSCKASGYT

FTSYDINWVRQAPGQGLEWIGWIYPGDGSTKYNEKFKGKATITRDTSAST

AYMELSSLRSEDTAVYFCARSDYYGSRSFAYWGQGTLVTVSSASTKGPSV

FPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHT

CPPCPAPALAGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSC

SVMHEALHNHYTQKSLSLSPGK

A "light chain constant region" includes kappa and lambda constant regions. An exemplary kappa constant region is provided below:

(SEQ ID NO: 318)
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC

Such a kappa constant region sequence may be used in humanized light chain constructs such as shown below for a humanized 5H23-vL2 (see, e.g., Example 7) as provided below; the amino acids that make up the signal sequence are underlined and the variable region sequence is bolded:

(SEQ ID NO: 319)
<u>mdmrvpaqllglllllwlrgarc</u>DIVMTQSPDSLAVSLGERATINCRASKS

VSTSGYVYMHWYQQKPGQPPKLLIYLASYLESGVPDRFSGSGSGTDFTLT

ISSVQAEDVAVYYCQHSRDLTFPFGGGTKLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC

The term "variant" when used in relation to beta klotho or to an anti-beta klotho antibody may refer to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified beta klotho sequence. For example, a beta klotho variant may result from one or more (such as, for example, about 1 to about 25, about 1 to about 20, about 1 to about 15, about 1 to about 10, or about 1 to about 5) changes to an amino acid sequence of a native beta klotho. Also by way of example, a variant of an anti-beta klotho antibody may result from one or more (such as, for example, about 1 to about 25, about 1 to about 20, about 1 to about 15, about 1 to about 10, or about 1 to about 5) changes to an amino acid sequence of a native or previously unmodified anti-beta klotho antibody. Variants may be naturally occurring, such as allelic or splice variants, or may be artificially constructed. Polypeptide variants may be prepared from the corresponding nucleic acid molecules encoding the variants. In specific embodiments, the beta klotho variant or anti-beta klotho antibody variant at least retains beta klotho or anti-beta klotho antibody functional activity, respectively. In specific embodiments, an anti-beta klotho antibody variant binds beta klotho and/or is antagonistic to beta klotho activity. In specific embodiments, an anti-beta klotho antibody variant binds beta klotho and/or is agonistic to beta klotho activity. In certain embodiments, the variant is encoded by a single nucleotide polymorphism (SNP) variant of a nucleic acid molecule that encodes beta klotho or anti-beta klotho antibody VH or VL regions or subregions, such as one or more CDRs.

The term "vector" refers to a substance that is used to carry or include a nucleic acid sequences, including for example, in order to introduce a nucleic acid sequence into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain or an antibody VH and VL) both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g. an anti-beta klotho antibody as described herein), and it is further understood that expression levels can be optimized to obtain sufficient expression using methods well known in the art.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is known (see, e.g., Table 3, page 464, Ravetch and Kinet, Annu. Rev. Immunol. 9:457-92 (1991)). To assess ADCC activity of a molecule of interest, an in vitro ADCC assay, (see, e.g., U.S. Pat. No. 5,500,362 or 5,821,337) may be performed. Useful effector cells for such assays include peripheral blood mononuclear cells (PBMC) and Natural Killer (NK) cells. Alternatively, or additionally, ADCC activity of the molecule of interest may be assessed in vivo, for example, in a animal model (see, e.g., Clynes et al. (USA) 95:652-656 (1998)). Antibodies with little or no ADCC activity may be selected for use.

"Fc receptor" or "FcR" describes a receptor that binds to the Fc region of an antibody. The preferred FcR is a native sequence human FcR. Moreover, a preferred FcR is one that binds an IgG antibody (e.g., a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof (see, e.g., review Daëron, Annu. Rev. Immunol. 15:203-234 (1997)). FcRs are known (see, e.g., Ravetch and Kinet, Annu. Rev. Immunol. 9:457-492 (1991); Capel et al., Immunomethods 4:25-34 (1994); and de Haas et al., J. Lab. Clin. Med. 126:330-41 (1995)). Other FcRs, including those to be identified in the future, are encompassed by the term "FcR" herein. The term also includes the neonatal receptor, FcRn, which is responsible for the transfer of maternal IgGs to the fetus (see, e.g., Guyer et al., J. Immunol. 117:587 (1976) and Kim et al., J. Immunol. 24:249 (1994)). Antibody variants with improved or diminished binding to FcRs have been described (see, e.g., in WO 2000/42072; U.S. Pat. Nos. 7,183,387, 7,332, 581 and 7.335,742; Shields et al. J. Biol. Chem. 9(2):6591-6604 (2001)).

"Complement dependent cytotoxicity" or "CDC" refers to the lysis of a target cell in the presence of complement. Activation of the classical complement pathway is initiated by the binding of the first component of the complement system (Cl q) to antibodies (of the appropriate subclass) which are bound to their cognate antigen. To assess complement activation, a CDC assay, (see, e.g., Gazzano-Santoro et al., J. Immunol. Methods 202:163 (1996)), may be performed. Polypeptide variants with altered Fc region amino acid sequences (polypeptides with a variant Fc region) and increased or decreased Cl q binding capability have been described, (see, e.g., U.S. Pat. No. 6,194,551, WO 1999/51642, Idusogie et al. J. Immunol. 164: 4178-4184 (2000)). Antibodies with little or no CDC activity may be selected for use.

A beta klotho polypeptide "extracellular domain" or "ECD" refers to a form of the beta klotho polypeptide that is essentially free of the transmembrane and cytoplasmic domains. For example, a beta klotho polypeptide ECD may have less than 1% of such transmembrane and/or cytoplasmic domains and preferably, may have less than 0.5% of such domains. The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (e.g., an "algorithm"). Methods that can be used to calculate the identity of the aligned nucleic acids or polypeptides include those described in Computational Molecular Biology, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) SIAM J. Applied Math. 48:1073.

In calculating percent identity, the sequences being compared may be aligned in a way that gives the largest match between the sequences. Computer program may be used to determine percent identity is the GCG program package, which includes GAP (Devereux et al., (1984) Nucl. Acid Res. 12:387; Genetics Computer Group, University of Wisconsin, Madison, Wis.). The computer algorithm GAP used to align the two polypeptides or polynucleotides for which the percent sequence identity is to be determined. The sequences may be aligned for optimal matching of their respective amino acid or nucleotide (the "matched span", as determined by the algorithm). A gap opening penalty (which is calculated as 3.times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992) Proc. Natl. Acad. Sci. U.S.A. 89:10915-10919 for the BLOSUM 62 comparison matrix) is also used by the algorithm.

Exemplary parameters for determining percent identity for polypeptides or nucleotide sequences using the GAP program are the following: (i) Algorithm: Needleman et al., 1970, J. Mol. Biol. 48:443-453; (ii) Comparison matrix: BLOSUM 62 from Henikoff et al., 1992, supra; (iii) Gap Penalty: 12 (but with no penalty for end gaps) (iv) Gap Length Penalty: 4; and (v) Threshold of Similarity: 0.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (e.g., the GAP program) can be adjusted if so desired to result in an alignment that spans a number of amino acids, for example, at least 50 contiguous amino acids of the target polypeptide.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

A "modification" of an amino acid residue/position refers to a change of a primary amino acid sequence as compared to a starting amino acid sequence, wherein the change results from a sequence alteration involving said amino acid residue/positions. For example, typical modifications include substitution of the residue with another amino acid (e.g., a conservative or non-conservative substitution), insertion of one or more (e.g., generally fewer than 5, 4 or 3) amino acids adjacent to said residue/position, and/or deletion of said residue/position.

An "epitope" is the site on the surface of an antigen molecule to which a single antibody molecule binds, such as a localized region on the surface of an antigen, such as a beta klotho polypeptide, a beta klotho polypeptide fragment or a beta klotho epitope, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. The term, "epitope" specifically includes linear epitopes and conformational epitopes. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a beta klotho epitope is a three-dimensional surface feature of a beta klotho polypeptide. In other embodiments, a beta klotho epitope is linear feature of a beta klotho polypeptide. Generally an antigen has several or many different epitopes and may react with many different antibodies.

An antibody binds "an epitope" or "essentially the same epitope" or "the same epitope" as a reference antibody, when the two antibodies recognize identical, overlapping or adjacent epitopes in a three-dimensional space. The most widely used and rapid methods for determining whether two antibodies bind to identical, overlapping or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies is measured using radioactive, fluorescent or enzyme labels.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three dimensional structure of the protein is in an altered confirmation, such as following activation or binding of another protein or ligand (e.g., the binding of beta klotho to an FCF receptor such as FGRFR1c, FGFR2c, FGFR3c, or FGFR4c.

"Epitope binning" is the process of grouping antibodies based on the epitopes they recognize. More particularly, epitope binning comprises methods and systems for discriminating the epitope recognition properties of different antibodies, using competition assays combined with computational processes for clustering antibodies based on their epitope recognition properties and identifying antibodies having distinct binding specificities.

A "beta klotho-mediated disease" and "beta klotho-mediated disorder" and "beta klotho-mediated condition" are used interchangeably and refer to any disease, disorder or condition that is completely or partially caused by or is the result of beta klotho or the interaction of a beta klotho with an FGF receptor such as FGFR1c, FGFR2c, FGFR3c, or FGFR4 and/or alternatively any disease, disorder, or condition in which it is desirable to mimic or augment the in vivo effects of FGF19 and/or FGF21.

The term "therapeutically effective amount" as used herein refers to the amount of an agent (e.g., an antibody described herein or any other agent described herein) that is sufficient to reduce and/or ameliorate the severity and/or duration of a given disease, disorder or condition, and/or a symptom related thereto. A therapeutically effective amount of a agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody provided herein). A "therapeutically effective amount" of a substance/molecule/agent of the present disclosure (e.g., an anti-beta klotho antibody) may vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of an antibody or other agent (e.g., or drug) effective to "treat" a disease, disorder, or condition, in a subject or mammal.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition, including, for example, diabetes, obesity, dyslipidemia, cardiovascular disease, metabolic syndrome or broadly any disease, disorder, or condition in which it is desirable to mimic or augment the in vivo effects of FGF19 and/or FGF21. In some embodiments, the effective amount is a therapeutically effective amount or a prophylactically effective amount. A "therapeutically effective amount" is an amount sufficient to remedy a disease, disorder, or condition (e.g., Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21) or symptoms, particularly a disease, disorder, or condition, or symptoms associated with such a disease, disorder, or condition, or otherwise prevent, hinder, retard or reverse the progression of the disease, disorder, or condition, or any other undesirable symptom associated with such a disease, disorder, or condition, in any way whatsoever. A "prophylactically effective amount" is an amount of a pharmaceutical composition that, when administered to a subject, will have the intended prophylactic effect, e.g., preventing or delaying the onset (or reoccurrence) of diabetes, obesity or dyslipidemia, or reducing the likelihood of the onset (or reoccurrence) of a disease, disorder, or condition or associated symptom(s), including, for example, diabetes, obesity, dyslipidemia, cardiovascular disease, metabolic syndrome or broadly any disease, disorder, or condition in which it is desirable to mimic or augment the in vivo effects of FGF19 and/or FGF21) or associated symptoms. The full therapeutic or prophylactic effect does not necessarily occur by administration of one dose, and may occur only after administration of a series of doses. Thus, a therapeutically or prophylactically effective amount may be administered in one or more administrations.

A "prophylactically effective amount" refers to an amount effective, at dosages and for periods of time necessary, to achieve the desired prophylactic result. Typically, but not necessarily, since a prophylactic dose is used in subjects prior to or at an earlier stage of a disease, disorder, or condition, a prophylactically effective amount may be less than a therapeutically effective amount.

"Chronic" administration refers to administration of the agent(s) in a continuous mode (e.g., for a period of time such as days, weeks, months or years) as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (e.g., concurrent) and consecutive administration in any order. The term "in combination" in the context of the administration of other therapies (e.g., other agents) includes the use of more than one therapy (e.g., one agent). The use of the term "in combination" does not restrict the order in which therapies are administered to a subject. A first therapy (e.g., agent) can be administered before (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 8 weeks, 8 weeks, 9 weeks, 10 weeks, 11 weeks, or 12 weeks), concurrently, or after (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 7 weeks, 8 weeks, 9 weeks, 10 weeks, 11 weeks, or 12 weeks) the administration of a second therapy (e.g., agent) to a subject which had, has, or is susceptible to a beta klotho-mediated disease.

Any additional therapy (e.g., agent) can be administered in any order with the other additional therapies (e.g., agents). In certain embodiments, the antibodies can be administered in combination with one or more therapies such as agents (e.g., therapies, including agents, that are not the antibodies that are currently administered) to prevent, treat, manage, and/or ameliorate a beta klotho-mediated disease. Non-limiting examples of therapies (e.g., agents) that can be administered in combination with an antibody include, for example, analgesic agents, anesthetic agents, antibiotics, or immunomodulatory agents or any other agent listed in the *U.S. Pharmacopoeia* and/or *Physician's Desk Reference*. Examples of agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors. Other agents for combination include steroids such as prednisolone, prednisone, methylprednisolone, betamethasone, dexamethasone, or hydrocortisone. Such a combination may be especially advantageous, since one or more side-effects of the steroid can be reduced or even eliminated by tapering the steroid dose required when treating patients in combination with the present antibodies. Additional examples of agents for combinations include cytokine suppressive anti-inflammatory drug(s) (CSAIDs), antibodies to or antagonists of other human cytokines or growth factors, for example, TNF, LT, IL-1β, IL-2, IL-6, IL-7, IL-8, IL-15, IL-16, IL-18, EMAP-II, GM-CSF, FGF, or PDGF. Combinations of agents may include TNF antagonists like chimeric, humanized or human TNF antibodies, REMICADE, anti-TNF antibody fragments (e.g., CDP870), and soluble p55 or p75 TNF receptors, derivatives thereof, p75TNFRIgG (ENBREL®) or p55TNFR1gG (LENERCEPT®), soluble IL-13 receptor (sIL-13), and also TNFα converting enzyme (TACE) inhibitors; similarly IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination therapy include interferon-β1a (AVONEX); interferon-β1b (BETASERON®); copaxone; hyperbaric oxygen; intravenous immunoglobulin; clabribine; and antibodies to or antagonists of other human cytokines or growth factors (e.g., antibodies to CD40 ligand and CD80).

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The term "carrier" can also refer to a diluent, adjuvant (e.g., Freund's adjuvant (complete or incomplete)), excipient, or vehicle with which the therapeutic is administered. Such carriers, including pharmaceutical carriers, can be sterile liquids, such as water and oils, including those of petroleum, animal, vegetable or synthetic origin, such as peanut oil, soybean oil, mineral oil, sesame oil and the like. Water is a exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Compositions can take the form of solutions, suspensions, emulsion, tablets, pills, capsules, powders, sustained-release formulations and the like. Oral compositions, including formulations, can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990) Mack Publishing Co., Easton, Pa. Compositions, including pharmaceutical compounds, may contain a prophylactically or therapeutically effective amount of an anti-beta klotho antibody, for example, in isolated or purified form, together with a suitable amount of carrier so as to provide the form for proper administration to the subject (e.g., patient). The formulation should suit the mode of administration.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

The term "pharmaceutical formulation" refers to a preparation which is in such form as to permit the biological activity of the active ingredient (e.g., an anti-beta klotho antibody) to be effective, and which contains no additional components which are unacceptably toxic to a subject to which the formulation would be administered. Such formulation may be sterile.

A "sterile" formulation is aseptic or free from all living microorganisms and their spores.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., Chapter 11 in: *Short Protocols in Molecular Biology*, (2002) 5th Ed., Ausubel et al., eds., John Wiley and Sons, New York).

An "isolated nucleic acid" is a nucleic acid, for example, an RNA, DNA, or a mixed polymer, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides. A cell that produces an anti-beta klotho antibody of the present disclosure may include a parent hybridoma cell, as well as bacterial and eukaryotic host cells into which nucleic acid encoding the antibodies have been introduced. Suitable host cells are disclosed below.

Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "package insert" is used to refer to instructions customarily included in commercial packages of therapeutic products, that contain information about the indications, usage, dosage, administration, contraindications and/or warnings concerning the use of such therapeutic products.

The terms "prevent," "preventing," and "prevention" refer to the total or partial inhibition of the development, recurrence, onset or spread of a beta klotho-mediated disease and/or symptom related thereto, resulting from the administration of a therapy or combination of therapies provided herein (e.g., a combination of prophylactic or therapeutic agents, such as an antibody provided herein).

The term "prophylactic agent" refers to any agent that can totally or partially inhibit the development, recurrence, onset or spread of a beta klotho-mediated disease and/or symptom related thereto in a subject. In certain embodiments, the term "prophylactic agent" refers to an anti-beta klotho antibody as described herein. In certain other embodiments, the term "prophylactic agent" refers to an agent other than an anti-beta klotho antibody as described herein. In certain embodiments, a prophylactic agent is an agent which is known to be useful to or has been or is currently being used to prevent a beta klotho-mediated disease, disorder, or condition, and/or a symptom related thereto or impede the onset, development, progression and/or severity of a beta klotho-mediated disease, disorder, or condition, and/or a symptom related thereto. In specific embodiments, the prophylactic agent is a humanized anti-beta klotho antibody, such as a humanized anti-beta klotho monoclonal antibody.

In certain embodiments, a "prophylactically effective serum titer" is the serum titer in a subject, preferably a human, that totally or partially inhibits the development, recurrence, onset or spread of a beta klotho-mediated disease, disorder, or condition, and/or symptom related thereto in the subject.

In certain embodiments, a "therapeutically effective serum titer" is the serum titer in a subject, preferably a human, that reduces the severity, the duration and/or the symptoms associated with a beta klotho-mediated disease, disorder, or condition, in the subject.

The term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created or isolated by any other means that involves splicing of immunoglobulin gene sequences to other DNA sequences. Such recombinant antibodies can have variable and constant regions, including those derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant antibodies may be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "serum titer" refers to an average serum titer in a subject from multiple samples (e.g., at one time present or multiple time points) or in a population of least 10, such as at least 20, or at least 40 subjects, up to about 100, 1000 or more.

The term "side effects" encompasses unwanted and/or adverse effects of a therapy (e.g., a prophylactic or therapeutic agent). Unwanted effects are not necessarily adverse. An adverse effect from a therapy (e.g., a prophylactic or therapeutic agent) might be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspnea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (68th ed., 2014).

The terms "subject" and "patient" may be used interchangeably. As used herein, in certain embodiments, a subject is a mammal, such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a beta klotho-mediated disease, disorder or condition. In another embodiment, the subject is a mammal (e.g., a human) at risk of developing a beta klotho-mediated disease, disorder, or condition.

"Substantially all" refers to refers to at least about 60%, at least about 65%, at least about 70%, at least about 75%, at least about 80%, at least about 85%, at least about 90%, at least about 95%, at least about 98%, at least about 99%, or about 100%.

The term "therapeutic agent" refers to any agent that can be used in treating, preventing or alleviating a disease, disorder or condition, including in the treatment, prevention or alleviation of one or more symptoms of a beta klotho-mediated disease, disorder, or condition and/or a symptom related thereto. In certain embodiments, a therapeutic agent refers to an anti-beta klotho antibody as described herein. In certain other embodiments, a therapeutic agent refers to an agent other than an antibody provided herein. In certain embodiments, a therapeutic agent is an agent which is known to be useful for, or has been or is currently being used for the treatment, prevention or alleviation of one or more symptoms of a beta klotho-mediated disease, disorder, or condition, or a symptom related thereto.

The combination of therapies (e.g., use of agents, including therapeutic agents) can be more effective than the additive effects of any two or more single therapy (e.g., synergistic). A synergetic effect is unexpected and can not be predicted. For example, a synergistic effect of a combination of therapeutic agents permits the use of lower dosages of one or more of the agents and/or less frequent administration of the agents to a subject with a beta klotho-mediated disease. The ability to utilize lower dosages of therapeutic therapies and/or to administer the therapies less frequently reduces the toxicity associated with the administration of the therapies to a subject without reducing the efficacy of the therapies in the prevention, treatment or alleviation of one or more symptom of a beta klotho-mediated disease. In addition, a synergistic effect can result in improved efficacy of therapies in the prevention, treatment or alleviation of one or more symptom of a beta klotho-mediated disease. Finally, synergistic effect of a combination of therapies (e.g., therapeutic agents) may avoid or reduce adverse or unwanted side effects associated with the use of any single therapy.

The term "therapy" refers to any protocol, method and/or agent that can be used in the prevention, management, treatment and/or amelioration of a beta klotho-mediated disease, disorder, or conditions. In certain embodiments, the terms "therapies" and "therapy" refer to a biological therapy, supportive therapy, and/or other therapies useful in the prevention, management, treatment and/or amelioration of a beta klotho-mediated disease, disorder or condition, known to one of skill in the art such as medical personnel.

The term "detectable probe" refers to a composition that provides a detectable signal. The term includes, without limitation, any fluorophore, chromophore, radiolabel, enzyme, antibody or antibody fragment, and the like, that provide a detectable signal via its activity.

The term "diagnostic agent" refers to a substance administered to a subject that aids in the diagnosis of a disease, disorder, or conditions. Such substances can be used to reveal, pinpoint, and/or define the localization of a disease causing process. In certain embodiments, a diagnostic agent includes a substance that is conjugated to an anti-beta klotho antibody as described herein, that when administered to a subject or contacted to a sample from a subject aids in the diagnosis a beta klotho-mediated disease.

The term "detectable agent" refers to a substance that can be used to ascertain the existence or presence of a desired molecule, such as an anti-beta klotho antibody as described herein, in a sample or subject. A detectable agent can be a substance that is capable of being visualized or a substance that is otherwise able to be determined and/or measured (e.g., by quantitation).

The term "encode" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The term "excipient" refers to an inert substance which is commonly used as a diluent, vehicle, preservative, binder, or stabilizing agent, and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, *Remington's Pharmaceutical Sciences* (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, beta klotho fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250, at least 300, at least 350, at least 400, at least 450, at least 500, at least 550, at least 600, at least 650, at least 700, at least 750, at least 800, at least 850, at least 900, or at least 950, contiguous amino acid residues of the amino acid sequence of a beta klotho polypeptide or an antibody that binds to a beta klotho polypeptide. In a specific embodiment, a fragment of a beta klotho polypeptide or an antibody that binds to a beta klotho antigen retains at least 1, at least 2, or at least 3 or more functions of the polypeptide or antibody.

The terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents, such as an antibody provided herein) to "manage" a beta klotho-mediated disease, one or more symptoms thereof, so as to prevent the progression or worsening of the disease.

The terms "about" or "approximately" mean within 20%, within 15%, within 10%, within 9%, within 8%, within 7%, within 6%, within 5%, within 4%, within 3%, within 2%, within or 1% or less of a given value or range.

"Administer" or "administration" refers to the act of injecting or otherwise physically delivering a substance as it exists outside the body (e.g., an anti-beta klotho antibody as described herein) into a patient, such as by mucosal, intradermal, intravenous, intramuscular delivery and/or any other method of physical delivery described herein or known in the art. When a disease, disorder, or condition, or a symptom thereof, is being treated, administration of the substance typically occurs after the onset of the disease, disorder, or condition, or symptoms thereof. When a disease, disorder, or condition or symptoms thereof, are being prevented, administration of the substance typically occurs before the onset of the disease, disorder, or condition, or symptoms thereof.

In the context of a polypeptide, the term "analog" as used herein refers to a polypeptide that possesses a similar or identical function as a beta klotho polypeptide, a fragment of a beta klotho polypeptide, or an anti-beta klotho antibody but does not necessarily comprise a similar or identical amino acid sequence of a beta klotho polypeptide, a fragment of a beta klotho polypeptide, or an anti-beta klotho antibody, or possess a similar or identical structure of a beta klotho polypeptide, a fragment of a beta klotho polypeptide, or an anti-beta klotho antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a beta klotho polypeptide (e.g., SEQ ID NO:297, a fragment of a beta klotho polypeptide, or an anti-beta klotho antibody described herein; (b) a polypeptide encoded by a nucleotide sequence that hybridizes under stringent conditions to a nucleotide sequence encoding a beta klotho polypeptide, a fragment of a beta klotho polypeptide, or an anti-beta klotho antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) *Molecular Cloning: A Laboratory Manual*, Cold Spring Harbor Laboratory Press, Cold Spring Harbor, N.Y.; Maniatis et al. (1982) *Molecular Cloning: A Laboratory Manual*, Cold Spring Harbor Press, Cold Spring Harbor, N.Y.); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a beta klotho polypeptide, a fragment of a beta klotho polypeptide, or an anti-beta klotho antibody (or VH or VL region thereof) described herein. A polypeptide with similar structure to a beta klotho polypeptide, a fragment of a beta klotho polypeptide, or an anti-beta klotho antibody described herein refers to a polypeptide that has a similar secondary, tertiary or quaternary structure of a beta klotho polypeptide, a fragment of a beta klotho, or a beta klotho antibody described herein. The structure of a polypeptide can determined by methods known to those skilled in the art, including but not limited to, X-ray crystallography, nuclear magnetic resonance, and crystallographic electron microscopy.

The term "composition" is intended to encompass a product containing the specified ingredients (e.g., an antibody provided herein) in, optionally, the specified amounts, as well as any product which results, directly or indirectly, from combination of the specified ingredients in, optionally, the specified amounts.

In the context of a polypeptide, the term "derivative" as used herein refers to a polypeptide that comprises an amino acid sequence of a beta klotho polypeptide, a fragment of a beta klotho polypeptide, or an antibody that binds to a beta klotho polypeptide which has been altered by the introduction of amino acid residue substitutions, deletions or additions. The term "derivative" as used herein also refers to a beta klotho polypeptide, a fragment of a beta klotho polypeptide, or an antibody that binds to a beta klotho polypeptide which has been chemically modified, e.g., by the covalent attachment of any type of molecule to the polypeptide. For example, but not by way of limitation, a beta klotho polypeptide, a fragment of a beta klotho polypeptide, or a beta klotho antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a beta klotho polypeptide, a fragment of a beta klotho polypeptide, or a beta klotho antibody may be chemically modified by chemical modifications using techniques known to those of skill in the art, including, but not limited to specific chemical cleavage, acetylation, formulation, metabolic synthesis of tunicamycin, etc. Further, a derivative of a beta klotho polypeptide, a fragment of a beta klotho polypeptide, or a beta klotho antibody may contain one or more non-classical amino acids. A polypeptide derivative possesses a similar or identical function as a beta klotho polypeptide, a fragment of a beta klotho polypeptide, or a beta klotho antibody described herein.

Compositions and Methods of Making the Same

Binding proteins such as antibodies that bind to beta klotho (e.g., human and/or cyno beta klotho) are provided. Antibodies of the present disclosure are useful, for example, for the diagnosis or treatment of diseases, disorders, or conditions associated with expression, of beta klotho. In certain embodiments, antibodies of the present disclosure are useful for the diagnosis or treatment of a diseases, disorder, or condition, such as Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21.

Provided herein are antibodies that bind to a beta klotho polypeptide, a beta klotho polypeptide fragment, beta klotho peptide, or a beta klotho epitope. In some embodiments, the anti-beta klotho antibodies bind to the extracellular domain (ECD) of beta klotho. Also provided are antibodies that competitively block an anti-beta klotho antibody provided herein from binding to a beta klotho polypeptide. The anti-beta klotho antibodies provided herein can also be conjugated or recombinantly fused to a diagnostic agent, detectable agent or therapeutic agent. Further provided are compositions comprising an beta klotho antibody.

Also provided herein are isolated nucleic acid molecules encoding an immunoglobulin heavy chain, light chain, VH region, VL region, VH CDR1, VH CDR2, VH CDR3, VL CDR1, VL CDR2, and/or VL CDR3 of anti-beta klotho antibodies that bind to a beta klotho polypeptide, a beta klotho polypeptide fragment, a beta klotho peptide or a beta klotho epitope. Further provided are vectors and host cells comprising nucleic acid molecules encoding anti-beta klotho antibodies that bind to a beta klotho polypeptide, a beta klotho polypeptide fragment, a beta klotho peptide or a beta klotho epitope. Also provided are methods of making antibodies that bind to a beta klotho polypeptide, a beta klotho polypeptide fragment, a beta klotho peptide or a beta klotho epitope.

Methods of using the anti-beta klotho antibodies are provided. The methods include treating, preventing or alleviating a disease, disorder or condition, including treating, preventing or alleviating one or more symptoms of a disease, disorder or condition in a subject. Non limiting examples of diseases, disorders, or conditions include glucose utilization disorders and the sequelae associated therewith, including diabetes mellitus (Type I and Type-2), gestational diabetes, hyperglycemia, insulin resistance, abnormal glucose metabolism, "pre-diabetes" (Impaired Fasting Glucose (IFG) or Impaired Glucose Tolerance (IGT)), or other physiological disorders associated with, or that result from, the hyperglycemic condition, including, for example, histopathological changes such as pancreatic β-cell destruction. For example subjects with a diseases, disorders, or condition, in need of treatment may have a fasting plasma glucose (FPG) level greater than about 100 mg/dl. Other hyperglycemic-related disorders, include kidney damage (e.g., tubule damage or nephropathy), liver degeneration, eye damage (e.g., diabetic retinopathy or cataracts), and diabetic foot disorders. Other of diseases, disorders, or conditions include dyslipidemias and their sequelae such as, for example, atherosclerosis, coronary artery disease, cerebrovascular disorders and the like or other of diseases, disorders, or conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), or thromboses, hypercoagulable and prothrombotic states (arterial and venous), hypertension, cardiovascular disease, stroke and heart failure. These diseases, disorders, or conditions include atherosclerosis, chronic inflammatory bowel diseases (e.g., Crohn's disease and ulcerative colitis), asthma, lupus erythematosus, arthritis, or other inflammatory rheumatic disorders. Other diseases, disorders, or conditions include adipose cell tumors, lipomatous carcinomas including, for example, liposarcomas, solid tumors, and neoplasms. Other diseases, disorders, or conditions include neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillain-Barre syndrome. Other diseases, disorders, or conditions include skin and dermatological disorders and/or disorders of wound healing processes, including erythemato-squamous dermatoses. Other diseases, disorders, or conditions include syndrome X, osteoarthritis, and acute respiratory distress syndrome. As used herein, the term "hyperglycemic" or "hyperglycemia," when used in reference to a disease, disorder, or condition of a subject refers to a transient or chronic abnormally high level of glucose present in the blood of a subject. The disease, disorder, or condition may be caused by a delay in glucose metabolism or absorption such that the subject exhibits glucose intolerance or a state of elevated glucose not typically found in normal subjects (e.g., in glucose-intolerant pre-diabetic subjects at risk of developing diabetes, or in diabetic subjects). For example, fasting plasma glucose (FPG) levels for normoglycemia may be less than about 100 mg/dl, for impaired glucose metabolism, between about 100 and 126 mg/dl, and for diabetics greater than about 126 mg/dl. Methods of preventing (e.g., in subjects predisposed to having a particular disorder(s)), relate to delaying, slowing or inhibiting progression of, the onset of, or treating (e.g., ameliorating) obesity or an undesirable body mass (e.g., a greater than normal body mass index, or "BMI" relative to an appropriate matched subject of comparable age, gender, race, etc.). Methods of treating obesity or an undesirable body mass (including the co-morbid conditions of obesity, for example, obstructive sleep apnea, arthritis, cancer (e.g., breast, endometrial, and colon), gallstones or hyperglycemia, include contacting or administering a binding protein such as an anti-beta klotho antibody as described herein in an amount effective to treat obesity or an undesirable body mass. For example, a subject may have a body mass index greater than 25, for example, 25-30, 30-35, 35-40, or greater than 40. Methods of preventing (e.g., in subjects predisposed to having a particular disorder(s)), relate to delaying, slowing or inhibiting the progression of, the onset of, or treating undesirable levels or abnormally elevated serum/plasma LDL, VLDL, triglycerides or cholesterol, all of which, alone or in combination, can lead to, for example, plaque formation, narrowing or blockage of blood vessels, and increased risk of hypertension, stroke and coronary artery disease. Such diseases, disorders, or conditions may be due to, for example, genetic predisposition or diet.

Anti-Beta Klotho Antibodies

In one embodiment, the present disclosure provides anti-beta klotho antibodies that may find use herein as therapeutic agents. Exemplary antibodies include polyclonal, monoclonal, humanized, human, bispecific, and heteroconjugate antibodies, as well as variants thereof having improved affinity or other properties.

In some embodiments, provided herein are antibodies that bind to beta klotho, including a beta klotho polypeptide, a beta klotho polypeptide fragment, a beta klotho peptide or a beta klotho epitope. In some embodiments the anti-beta klotho antibodies are humanized antibodies (e.g., comprising human constant regions) that bind beta klotho, including beta klotho polypeptide, a beta klotho polypeptide fragment, a beta klotho peptide or a beta klotho epitope.

In certain embodiments, the anti-beta klotho antibody comprises a VH region, VL region, VH CDR1, VH CDR2, VH CDR3, VL CDR1, VL CDR2, and/or VL CDR3 of any one of the murine monoclonal antibodies described herein, such as an amino acid sequence depicted in Tables 1-10. Accordingly, in some embodiments, the isolated antibody or functional fragment thereof provided herein comprises one, two, and/or three heavy chain CDRs and/or one, two, and/or three light chain CDRs from: (a) the antibody designated 5H23; (b) the antibody designated 1017; (c) the antibody designated 1D19, (d) the antibody designated 2L12; (e) the antibody designated 3L3; (f) the antibody designated 3N20; (g) the antibody designated 4P5; (h) the antibody designated 5O23; (i) the antibody designated 5F7; (j) the antibody designated 1G19, as shown in Tables 1-10.

The antibody designated 5H23 comprises a VH sequence that is SEQ ID NO:25 and a VL sequence that is SEQ ID NO:26.

The antibody designated 1017 comprises a VH sequence that is SEQ ID NO:51 and a VL sequence that is SEQ ID NO:52.

The antibody designated 1D19 comprises a VH sequence that is SEQ ID NO:77 and a VL sequence that is SEQ ID NO:78.

The antibody designated 2L12 comprises a VH sequence that is SEQ ID NO:103 and a VL sequence that is SEQ ID NO:104.

The antibody designated 3L3 comprises a VH sequence that is SEQ ID NO:129 and a VL sequence that is SEQ ID NO:130.

The antibody designated 3N20 comprises a VH sequence that is SEQ ID NO:155 and a VL sequence that is SEQ ID NO:156.

The antibody designated 4P5 comprises a VH sequence that is SEQ ID NO:181 and a VL sequence that is SEQ ID NO:182.

The antibody designated 5O23 comprises a VH sequence that is SEQ ID NO:207 and a VL sequence that is SEQ ID NO:208.

The antibody designated 5F7 comprises a VH sequence that is SEQ ID NO:233 and a VL sequence that is SEQ ID NO:234.

The antibody designated IG19 comprises a VH sequence that is SEQ ID NO:259 and a VL sequence that is SEQ ID NO:260.

TABLE 1

Antibody 5H23 CDR Sequences

| | | Exemplary | IMGT | Kabat | Chothia | Contact | AbM |
|---|---|---|---|---|---|---|---|
| VH CDR seq. | VH CDR1 | GYTFTSYDIN (SEQ ID NO: 1) | GYTFTSYD (SEQ ID NO: 7) | SYDIN (SEQ ID NO: 12) | GYTFTSY (SEQ ID NO: 13) | TSYDIN (SEQ ID NO: 18) | GYTFTSYDIN (SEQ ID NO: 1) |
| | VH CDR2 | WIYPGDGSTKYNEKFKG (SEQ ID NO: 2) | IYPGDGST (SEQ ID NO: 8) | WIYPGDGSTKYNEKFKG (SEQ ID NO: 2) | PGDG (SEQ ID NO: 14) | WIGWIYPGDGSTK (SEQ ID NO: 19) | WIYPGDGSTK (SEQ ID NO: 24) |
| | VH CDR3 | SDYYGSRSFAY (SEQ ID NO: 3) | ARSDYYGSRSFAY (SEQ ID NO: 9) | SDYYGSRSFAY (SEQ ID NO: 3) | DYYGSRSFA (SEQ ID NO: 15) | ARSDYYGSRSFA (SEQ ID NO: 20) | SDYYGSRSFAY (SEQ ID NO: 3) |
| VL CDR seq. | VL CDR1 | RASKSVSTSGYVYMH (SEQ ID NO: 4) | KSVSTSGYVY (SEQ ID NO: 10) | RASKSVSTSGYVYMH (SEQ ID NO: 4) | SKSVSTSGYVY (SEQ ID NO: 16) | STSGYVYMHWN (SEQ ID NO: 21) | RASKSVSTSGYVYMH (SEQ ID NO: 4) |
| | VL CDR2 | LASYLES (SEQ ID NO: 5) | LAS (SEQ ID NO: 11) | LASYLES (SEQ ID NO: 5) | LAS (SEQ ID NO: 11) | LLIYLASYLE (SEQ ID NO: 22) | LASYLES (SEQ ID NO: 5) |
| | VL CDR3 | QHSRDLTFP (SEQ ID NO: 6) | QHSRDLTFP (SEQ ID NO: 6) | QHSRDLTFP (SEQ ID NO: 6) | SRDLTF (SEQ ID NO: 17) | QHSRDLTF (SEQ ID NO: 23) | QHSRDLTFP (SEQ ID NO: 6) |

VH Sequence:
QVQLQQSGPELVKPGALVKISCKASGYTFTSYDINWVKQRPGQGLEWIGWIYPGDGSTKYNEKFKGKATLTADKSSRTAYMQLSSLTSENSAVYFCARSDYYGSRS
FAYWGQGTLVTVSA (SEQ ID NO: 25)

VL Sequence:
DIVLTQSPASLAVSLGQRATISCRASKSVSTSGYVYMHWNQQKPGQPPKLLIYLASYLESGVPARFSGSGSGTDFTLNIHPVEEEDAAIYYCQHSRDLTFPFGGGTKL
EIK (SEQ ID NO: 26)

TABLE 2

Antibody 1C17 CDR Sequences

| | | Exemplary | IMGT | Kabat | Chothia | Contact | AbM |
|---|---|---|---|---|---|---|---|
| VH CDR seq. | VH CDR1 | GYSITSGYYWN (SEQ ID NO: 27) | GYSITSGYY (SEQ ID NO: 33) | SGYYWN (SEQ ID NO: 38) | GYSITSGY (SEQ ID NO: 39) | TSGYYWN (SEQ ID NO: 44) | GYSITSGYYWN (SEQ ID NO: 27) |
| | VH CDR2 | YINYDGNSNYTPSLKN (SEQ ID NO: 28) | INYDGNS (SEQ ID NO: 34) | YINYDGNSNYTPSLKN (SEQ ID NO: 28) | YDG | WMGYINYDGNSN (SEQ ID NO: 45) | YINYDGNSN (SEQ ID NO: 50) |
| | VH CDR3 | KGAYYSNYDSFDV (SEQ ID NO: 29) | ARKGAYYSNYDSFDV (SEQ ID NO: 35) | KGAYYSNYDSFDV (SEQ ID NO: 29) | GAYYSNYDSFD (SEQ ID NO: 40) | ARKGAYYSNYDSFD (SEQ ID NO: 46) | KGAYYSNYDSFDV (SEQ ID NO: 29) |
| VL CDR seq. | VL CDR1 | KASQDINSYLS (SEQ ID NO: 30) | QDINSY (SEQ ID NO: 36) | KASQDINSYLS (SEQ ID NO: 30) | SQDINSY (SEQ ID NO: 41) | NSYLSWV (SEQ ID NO: 47) | KASQDINSYLS (SEQ ID NO: 30) |
| | VL CDR2 | RANRLVD (SEQ ID NO: 31) | RAN | RANRLVD (SEQ ID NO: 31) | RAN (SEQ ID NO: 42) | TLIYRANRLV (SEQ ID NO: 48) | RANRLVD (SEQ ID NO: 31) |
| | VL CDR3 | LQYDEFPFT (SEQ ID NO: 32) | LQYDEFPFT (SEQ ID NO: 32) | LQYDEFPFT (SEQ ID NO: 32) | YDEFPF (SEQ ID NO: 37) | LQYDEFPF (SEQ ID NO: 43) | LQYDEFPFT (SEQ ID NO: 32) |

VH Sequence:
QVQLQESGPGLVKPSQSLSLTCSVTGYSITSGYYWNWIRQFPGNKLEWMGYINYDGNSNYTPSLKNRISITRDTSKNQFFLKLNSVTPEDTATYYCARKGAYYSNYD
SFDVWGTGTTVTVSS (SEQ ID NO: 51)

VL Sequence:
DIKMTQSPSSMYASLGERVTITCKASQDINSYLSWVQQKPGKSPKTLIYRANRLVDGVPSRFSGSGSGQDYSLTISSLEYEDMGIYYCLQYDEFPFTFGSGTKLEIK
(SEQ ID NO: 52)

TABLE 3

Antibody 1D19 CDR Sequences

| VH CDR seq. | | Exemplary | IMGT | Kabat | Chothia | Contact | AbM |
|---|---|---|---|---|---|---|---|
| | VH CDR1 | GYTFTRYDIN (SEQ ID NO: 53) | GYTFTRYD (SEQ ID NO: 59) | RYDIN (SEQ ID NO: 64) | GYTFTRY (SEQ ID NO: 65) | TRYDIN (SEQ ID NO: 70) | GYTFTRYDIN (SEQ ID NO: 53) |
| | VH CDR2 | WIYPGDSSTKFNENFKD (SEQ ID NO: 54) | IYPGDSST (SEQ ID NO: 60) | WIYPGDSSTKFNENFKD (SEQ ID NO: 54) | PGDS (SEQ ID NO: 66) | WIGWIYPGDSSTK (SEQ ID NO: 71) | WIYPGDSSTK (SEQ ID NO: 76) |
| | VH CDR3 | SDYYGSRSFTY (SEQ ID NO: 55) | ARSDYYGSRSFTY (SEQ ID NO: 61) | SDYYGSRSFTY (SEQ ID NO: 55) | DYYGSRSFT (SEQ ID NO: 67) | ARSDYYGSRSFT (SEQ ID NO: 72) | SDYYGSRSFTY (SEQ ID NO: 55) |
| VL CDR seq. | VL CDR1 | RASKSVSTSGYSYMH (SEQ ID NO: 56) | KSVSTSGYSY (SEQ ID NO: 62) | RASKSVSTSGYSYMH (SEQ ID NO: 56) | SKSVSTSGYSY (SEQ ID NO: 68) | STSGYSYMHWY (SEQ ID NO: 73) | RASKSVSTSGYSYMH (SEQ ID NO: 56) |
| | VL CDR2 | LASNLES (SEQ ID NO: 57) | LAS (SEQ ID NO: 63) | LASNLES (SEQ ID NO: 57) | LAS (SEQ ID NO: 63) | LLIYLASNLE (SEQ ID NO: 74) | LASNLES (SEQ ID NO: 57) |
| | VL CDR3 | QHSRELPYT (SEQ ID NO: 58) | QHSRELPYT (SEQ ID NO: 58) | QHSRELPYT (SEQ ID NO: 58) | SRELPY (SEQ ID NO: 69) | QHSRELPY (SEQ ID NO: 75) | QHSRELPYT (SEQ ID NO: 58) |

VH Sequence:
QVQPQESGPELVKPGALVKISCKASGYTFTRYDINWMKQRPGQGLEWIGWIYPGDSSTKFNENFKDKATLTADKSSSTAYMQLSSLTSENSTVYFCARSDYYGSRS
FTYWGQGTLVTVSA (SEQ ID NO: 77)

VL Sequence:
DIVLTQSPASLAVSLGQRATISCRASKSVSTSGYSYMHWYQQKPGQPPKLLIYLASNLESGVPARFSGSGSGTDFTLNIHPVEEEDAATYYCQHSRELPYTFGGGTKL
EIK (SEQ ID NO: 78)

TABLE 4

Antibody 2L12 CDR Sequences

| VH CDR seq. | | Exemplary | IMGT | Kabat | Chothia | Contact | AbM |
|---|---|---|---|---|---|---|---|
| | VH CDR1 | GYTFTRYDIN (SEQ ID NO: 79) | GYTFTRYD (SEQ ID NO: 85) | RYDIN (SEQ ID NO: 90) | GYTFTRY (SEQ ID NO: 91) | TRYDIN (SEQ ID NO: 96) | GYTFTRYDIN (SEQ ID NO: 79) |
| | VH CDR2 | WIYPGDDSTKYNEKPKG (SEQ ID NO: 80) | IYPGDDST (SEQ ID NO: 86) | WIYPGDDSTKYNEKPKG (SEQ ID NO: 80) | PGDD (SEQ ID NO: 92) | WIGWIYPGDDSTK (SEQ ID NO: 97) | WIYPGDDSTK (SEQ ID NO: 102) |
| | VH CDR3 | SDYYGSRSFVY (SEQ ID NO: 81) | ARSDYYGSRSFVY (SEQ ID NO: 87) | SDYYGSRSFVY (SEQ ID NO: 81) | DYYGSRSFV (SEQ ID NO: 93) | ARSDYYGSRSFV (SEQ ID NO: 98) | SDYYGSRSFVY (SEQ ID NO: 81) |
| VL CDR seq. | VL CDR1 | RASKSVSTSGYSYLH (SEQ ID NO: 82) | KSVSTSGYSY (SEQ ID NO: 88) | RASKSVSTSGYSYLH (SEQ ID NO: 82) | SKSVSTSGYSY (SEQ ID NO: 94) | STSGYSYLHWY (SEQ ID NO: 99) | RASKSVSTSGYSYLH (SEQ ID NO: 82) |
| | VL CDR2 | LASNLES (SEQ ID NO: 83) | LAS | LASNLES (SEQ ID NO: 83) | LAS (SEQ ID NO: 89) | LLIYLASNLE (SEQ ID NO: 100) | LASNLES (SEQ ID NO: 83) |
| | VL CDR3 | QHSGELPYT (SEQ ID NO: 84) | QHSGELPYT (SEQ ID NO: 84) | QHSGELPYT (SEQ ID NO: 84) | SGELPY (SEQ ID NO: 95) | QHSGELPY (SEQ ID NO: 101) | QHSGELPYT (SEQ ID NO: 84) |

VH Sequence:
QVQLQQSGPELVKPGALVKISCKASGYTFTRYDINWVKKRPGQGLEWIGWIYPGDDSTKYNEKPKGKATLTADKSSSTAYMQLSSLTSENSAVYFCARSDYYGSRSFVYWGQGTLVTVSA (SEQ ID NO: 103)

VL Sequence:
DIVLTQSPASLPVSLGQRATISCRASKSVSTSGYSYLHWYQQKPGQPPKLLIYLASNLESGVPARFSGSGSGTDFTLNIHPVEEDAATYYCQHSGELPYTFGGGTKLEIK (SEQ ID NO: 104)

TABLE 5

| | | Antibody 3L3 CDR Sequences | | | | |
|---|---|---|---|---|---|---|
| | | Exemplary | IMGT | Kabat | Chothia | Contact | AbM |
| VH CDR seq. | VH CDR1 | GYTFTSYDIN (SEQ ID NO: 105) | GYTFTSYD (SEQ ID NO: 111) | SYDIN (SEQ ID NO: 116) | GYTFTSY (SEQ ID NO: 117) | TSYDIN (SEQ ID NO: 122) | GYTFTSYDIN (SEQ ID NO: 105) |
| | VH CDR2 | WIYPGDGSPKYDEKFKG (SEQ ID NO: 106) | IYPGDGSP (SEQ ID NO: 112) | WIYPGDGSPKYDEKFKG (SEQ ID NO: 106) | PGDG (SEQ ID NO: 118) | WIGWIYPGDGSPK (SEQ ID NO: 123) | WIYPGDGSPK (SEQ ID NO: 128) |
| | VH CDR3 | SDYYGSRSFVY (SEQ ID NO: 107) | ARSDYYGSRSFVY (SEQ ID NO: 113) | SDYYGSRSFVY (SEQ ID NO: 107) | DYYGSRSFV (SEQ ID NO: 119) | ARSDYYGSRSFV (SEQ ID NO: 124) | SDYYGSRSFVY (SEQ ID NO: 107) |
| VL CDR seq. | VL CDR1 | RASKSVSTSGYSYVH (SEQ ID NO: 108) | KSVSTSGYSY (SEQ ID NO: 114) | RASKSVSTSGYSYVH (SEQ ID NO: 108) | SKSVSTSGYSY (SEQ ID NO: 120) | STSGYSYVHWY (SEQ ID NO: 125) | RASKSVSTSGYSYVH (SEQ ID NO: 108) |
| | VL CDR2 | LASNLES (SEQ ID NO: 109) | LAS (SEQ ID NO: 115) | LASNLES (SEQ ID NO: 109) | LAS (SEQ ID NO: 115) | LLIYLASNLE (SEQ ID NO: 126) | LASNLES (SEQ ID NO: 109) |
| | VL CDR3 | QHSGELPYT (SEQ ID NO: 110) | QHSGELPYT (SEQ ID NO: 110) | QHSGELPYT (SEQ ID NO: 110) | SGELPY (SEQ ID NO: 121) | QHSGELPY (SEQ ID NO: 127) | QHSGELPYT (SEQ ID NO: 110) |

VH Sequence:
QVQPQESGPELVKPGTLVKISCKASGYTFTSYDINWVKQRPGQGLEWIGWIYPGDGSPKYDEKFKGKATLTADKSSSTAYMQLSSLTSENSAVYFCARSDYYGSRSFVYWGQGTLVTVSA (SEQ ID NO: 129)

VL Sequence:
DIVLTQSPASLAVSLGQRATISCRASKSVSTSGYSYVHWYQQKPGQPPKLLIYLASNLESGVPARFSGRGSGTDFTLNIHPVEEEDAATYYCQHSGELPYTFGGGTKLEIK (SEQ ID NO: 130)

TABLE 6

Antibody 3N20 CDR Sequences

|  |  | Exemplary | IMGT | Kabat | Chothia | Contact | AbM |
|---|---|---|---|---|---|---|---|
| VH CDR seq. | VH CDR1 | GYIFTNYGIS (SEQ ID NO: 131) | GYIFTNYG (SEQ ID NO: 137) | NYGIS (SEQ ID NO: 142) | GYIFTNY (SEQ ID NO: 143) | TNYGIS (SEQ ID NO: 148) | GYIFTNYGIS (SEQ ID NO: 131) |
|  | VH CDR2 | EIYPRSGNTYYNEKFKG (SEQ ID NO: 132) | IYPRSGNT (SEQ ID NO: 138) | EIYPRSGNTYYNEKFKG (SEQ ID NO: 132) | PRSG (SEQ ID NO: 144) | WIGEIYPRSGNTY (SEQ ID NO: 149) | EIYPRSGNTY (SEQ ID NO: 154) |
|  | VH CDR3 | HWDGVLDYFDY (SEQ ID NO: 133) | ARHWDGVLDYFDY (SEQ ID NO: 139) | HWDGVLDYFDY (SEQ ID NO: 133) | WDGVLDYFD (SEQ ID NO: 145) | ARHWDGVLDYFD (SEQ ID NO: 150) | HWDGVLDYFDY (SEQ ID NO: 133) |
| VL CDR sequences | VL CDR1 | KSSQSLLNSGNQKNYLA (SEQ ID NO: 134) | QSLLNSGNQKNY (SEQ ID NO: 140) | KSSQSLLNSGNQKNYLA (SEQ ID NO: 134) | SQSLLNSGNQKNY (SEQ ID NO: 146) | LNSGNQKNYLAWY (SEQ ID NO: 151) | KSSQSLLNSGNQKNYLA (SEQ ID NO: 134) |
|  | VL CDR2 | GASTRES (SEQ ID NO: 135) | GAS | GASTRES (SEQ ID NO: 135) | GAS (SEQ ID NO: 141) | LLIYGASTRE (SEQ ID NO: 152) | GASTRES (SEQ ID NO: 135) |
|  | VL CDR3 | LNDHSYPFT (SEQ ID NO: 136) | LNDHSYPFT (SEQ ID NO: 141) | LNDHSYPFT (SEQ ID NO: 136) | DHSYPF (SEQ ID NO: 147) | LNDHSYPF (SEQ ID NO: 153) | LNDHSYPFT (SEQ ID NO: 136) |

VH Sequence:
QVQLQESGAELARPGASVKLSCKASGYIFTNYGISWVKQRTGQGLEWIGEIYPRSGNTYYNEKFKGKATLTADMSSSTAYMDLRSLTSEDSAVYFCARHWDGVLDYFDYWGQGTSLTVSS (SEQ ID NO: 155)

VL Sequence:
DIVMTQSPSSLSVSAGEKVTMSCKSSQSLLNSGNQKNYLAWYQQKPGQPPKLLIYGASTRESGVPDRFTGSGSGTDFTLTISSVQAEDLAVYYCLNDHSYPFTFGAGTKLELK (SEQ ID NO: 156)

TABLE 7

Antibody 4P5 CDR Sequences

| VH CDR seq. | | Exemplary | IMGT | Kabat | Chothia | Contact | AbM |
|---|---|---|---|---|---|---|---|
| | VH CDR1 | GYTFTRYDIN (SEQ ID NO: 157) | GYTFTRYD (SEQ ID NO: 163) | RYDIN (SEQ ID NO: 168) | GYTFTRY (SEQ ID NO: 169) | TRYDIN (SEQ ID NO: 174) | GYTFTRYDIN (SEQ ID NO: 157) |
| | VH CDR2 | WIYPGDDSTKYNEKFKG (SEQ ID NO: 158) | IYPGDDST (SEQ ID NO: 164) | WIYPGDDSTKYNEKFKG (SEQ ID NO: 158) | PGDD (SEQ ID NO: 170) | WIGWIYPGDDSTK (SEQ ID NO: 175) | WIYPGDDSTK (SEQ ID NO: 180) |
| | VH CDR3 | SDYYGSRSFVY (SEQ ID NO: 159) | ARSDYYGSRSFVY (SEQ ID NO: 165) | SDYYGSRSFVY (SEQ ID NO: 159) | DYYGSRSFV (SEQ ID NO: 171) | ARSDYYGSRSFV (SEQ ID NO: 176) | SDYYGSRSFVY (SEQ ID NO: 159) |
| VL CDR seq. | VL CDR1 | RASKSVSTSGYSYMH (SEQ ID NO: 160) | KSVSTSGYSY (SEQ ID NO: 166) | RASKSVSTSGYSYMH (SEQ ID NO: 160) | SKSVSTSGYSY (SEQ ID NO: 172) | STSGYSYMHWY (SEQ ID NO: 177) | RASKSVSTSGYSYMH (SEQ ID NO: 160) |
| | VL CDR2 | LASNLES (SEQ ID NO: 161) | LAS (SEQ ID NO: 167) | LASNLES (SEQ ID NO: 161) | LAS (SEQ ID NO: 167) | LLIYLASNLE (SEQ ID NO: 178) | LASNLES (SEQ ID NO: 161) |
| | VL CDR3 | HHSGELPYT (SEQ ID NO: 162) | HHSGELPYT (SEQ ID NO: 162) | HHSGELPYT (SEQ ID NO: 162) | SGELPY (SEQ ID NO: 173) | HHSGELPY (SEQ ID NO: 179) | HHSGELPYT (SEQ ID NO: 162) |

VH Sequence:
QVQLQQSGPELVKPGALVKISCKASGYTFTRYDINWVKKRPGQGLEWIGWIYPGDDSTKYNEKFKGKATLTADKSSSTAYMQLSSLTSENSAVYFCARSDYYGSRSFVYWGQGTLVTVSA (SEQ ID NO: 181)

VL Sequence:
DILLTQSPASLAVSLGQRATISCRASKSVSTSGYSYMHWYQQKPGQPPKLLIYLASNLESGVPARFSGRGSGTDFTLNIHPVEEEDAATYYCHHSGELPYTFGGGTKLEIK (SEQ ID NO: 182)

TABLE 8

Antibody 5C23 CDR Sequences

| | | Exemplary | IMGT | Kabat | Chothia | Contact | AbM |
|---|---|---|---|---|---|---|---|
| VH CDR seq. | VH CDR1 | GYTFTRYDIN (SEQ ID NO: 183) | GYTFTRYD (SEQ ID NO: 189) | RYDIN (SEQ ID NO: 194) | GYTFTRY (SEQ ID NO: 195) | TRYDIN (SEQ ID NO: 200) | GYTFTRYDIN (SEQ ID NO: 183) |
| | VH CDR2 | WIYPGDGSTKYNEKFEG (SEQ ID NO: 184) | IYPGDGST (SEQ ID NO: 190) | WIYPGDGSTKYNEKFEG (SEQ ID NO: 184) | PGDG (SEQ ID NO: 196) | WIGWIYPGDGSTK (SEQ ID NO: 201) | WIYPGDGSTK (SEQ ID NO: 206) |
| | VH CDR3 | SDYYGSRSFVY (SEQ ID NO: 185) | ARSDYYGSRSFVY (SEQ ID NO: 191) | SDYYGSRSFVY (SEQ ID NO: 185) | DYYGSRSFV (SEQ ID NO: 197) | ARSDYYGSRSFV (SEQ ID NO: 202) | SDYYGSRSFVY (SEQ ID NO: 185) |
| VL CDR seq. | VL CDR1 | RASKSVSTSGYSYMH (SEQ ID NO: 186) | KSVSTSGYSY (SEQ ID NO: 192) | RASKSVSTSGYSYMH (SEQ ID NO: 186) | SKSVSTSGYSY (SEQ ID NO: 198) | STSGYSYMHWY (SEQ ID NO: 203) | RASKSVSTSGYSYMH (SEQ ID NO: 186) |
| | VL CDR2 | LASNLES (SEQ ID NO: 187) | LAS (SEQ ID NO: 193) | LASNLES (SEQ ID NO: 187) | LAS (SEQ ID NO: 193) | LLIYLASNLE (SEQ ID NO: 204) | LASNLES (SEQ ID NO: 187) |
| | VL CDR3 | QHSRELPYT (SEQ ID NO: 188) | QHSRELPYT (SEQ ID NO: 188) | QHSRELPYT (SEQ ID NO: 188) | SRELPY (SEQ ID NO: 199) | QHSRELPY (SEQ ID NO: 205) | QHSRELPYT (SEQ ID NO: 188) |

VH Sequence:
QVQPQESGPELVKPGALVKLSCKASGYTFTRYDINWVKKRPGQGLEWIGWIYPGDGSTKYNEKFEGKATLTADKSSSTAYMQLSSLTSENSAVYFCARSDYYGSRSF
VYWGQGTLVTVSA (SEQ ID NO: 207)

VL Sequence:
DIVLTQSPDSLTVSLGQRATISCRASKSVSTSGYSYMHWYQQKPGQPPKLLIYLASNLESGVPARFSGSGSGTDFTLNIHPVEEDAATYYCQHSRELPYTFGGGTKL
EIK (SEQ ID NO: 208)

TABLE 9

Antibody 5F7 CDR Sequences

| | | Exemplary | IMGT | Kabat | Chothia | Contact | AbM |
|---|---|---|---|---|---|---|---|
| VH CDR seq. | VH CDR1 | GYTFTRYDIN (SEQ ID NO: 209) | GYTFTRYD (SEQ ID NO: 215) | RYDIN (SEQ ID NO: 220) | GYTFTRY (SEQ ID NO: 221) | TRYDIN (SEQ ID NO: 226) | GYTFTRYDIN (SEQ ID NO: 209) |
| | VH CDR2 | WIYPGDISTKYNEKFKG (SEQ ID NO: 210) | IYPGDIST (SEQ ID NO: 216) | WIYPGDISTKYNEKFKG (SEQ ID NO: 210) | WIGWIYPGDISTK PGDI (SEQ ID NO: 222) | WIGWIYPGDISTK (SEQ ID NO: 227) | WIYPGDISTK (SEQ ID NO: 232) |
| | VH CDR3 | SDYYGSRSFVY (SEQ ID NO: 211) | ARSDYYGSRSFVY (SEQ ID NO: 217) | SDYYGSRSFVY (SEQ ID NO: 211) | DYYGSRSFV (SEQ ID NO: 223) | ARSDYYGSRSFV (SEQ ID NO: 228) | SDYYGSRSFVY (SEQ ID NO: 211) |
| VL CDR seq. | VL CDR1 | RASKSVSTSGYSYMH (SEQ ID NO: 212) | KSVSTSGYSY (SEQ ID NO: 218) | RASKSVSTSGYSYMH (SEQ ID NO: 212) | SKSVSTSGYSY (SEQ ID NO: 224) | STSGYSYMHWY (SEQ ID NO: 229) | RASKSVSTSGYSYMH (SEQ ID NO: 212) |
| | VL CDR2 | LASNLES (SEQ ID NO: 213) | LAS (SEQ ID NO: 219) | LASNLES (SEQ ID NO: 213) | LAS (SEQ ID NO: 219) | LLIYLASNLE (SEQ ID NO: 230) | LASNLES (SEQ ID NO: 213) |
| | VL CDR3 | QHSRELPYT (SEQ ID NO: 214) | QHSRELPYT (SEQ ID NO: 214) | QHSRELPYT (SEQ ID NO: 214) | SRELPY (SEQ ID NO: 225) | QHSRELPY (SEQ ID NO: 231) | QHSRELPYT (SEQ ID NO: 214) |

VH Sequence:
QVQPQESGPELVKPGALVKISCKASGYTFTRYDINWVKQRPGQGLEWIGWIYPGDISTKYNEKFKGKATLTADKSSSTAYMQLNSLTSENSAVYFCARSDYYGSRSFVYWGQGTLVTVSA (SEQ ID NO: 233)

VL Sequence:
DIVLTQSPASLAVSLGQRATISCRASKSVSTSGYSYMHWYQQKPGQPPKLLIYLASNLESGVPARFSGSGSGTDFTLNIHPVEEDAATYYCQHSRELPYTFGGGTKVEIK (SEQ ID NO: 234)

TABLE 10

Antibody 1G19 CDR Sequences

| | | Exemplary | IMGT | Kabat | Chothia | Contact | AbM |
|---|---|---|---|---|---|---|---|
| VH CDR seq. | VH CDR1 | GYSITSGYYWN (SEQ ID NO: 235) | GYSITSGYY (SEQ ID NO: 241) | SGYYWN (SEQ ID NO: 246) | GYSITSGY (SEQ ID NO: 247) | TSGYYWN (SEQ ID NO: 252) | GYSITSGYYWN (SEQ ID NO: 235) |
| | VH CDR2 | YINYGGSNNYNPSLKN (SEQ ID NO: 236) | INYGGSN (SEQ ID NO: 242) | YINYGGSNNYNPSLKN (SEQ ID NO: 236) | YGG (SEQ ID NO: 248) | WMGYINYGGSNN (SEQ ID NO: 253) | YINYGGSNN (SEQ ID NO: 258) |
| | VH CDR3 | RGAYYSNYDSFDV (SEQ ID NO: 237) | ARRGAYYSNYDSFDV (SEQ ID NO: 243) | RGAYYSNYDSFDV (SEQ ID NO: 237) | GAYYSNYDSFD (SEQ ID NO: 249) | ARRGAYYSNYDSFD (SEQ ID NO: 254) | RGAYYSNYDSFDV (SEQ ID NO: 237) |
| VL CDR seq. | VL CDR1 | KASQDINSYLS (SEQ ID NO: 238) | QDINSY (SEQ ID NO: 244) | KASQDINSYLS (SEQ ID NO: 238) | SQDINSY (SEQ ID NO: 250) | NSYLSWF (SEQ ID NO: 255) | KASQDINSYLS (SEQ ID NO: 238) |
| | VL CDR2 | RANRLVD (SEQ ID NO: 239) | RAN (SEQ ID NO: 245) | RANRLVD (SEQ ID NO: 239) | RAN (SEQ ID NO: 245) | TLIYRANRLV (SEQ ID NO: 256) | RANRLVD (SEQ ID NO: 239) |
| | VL CDR3 | LQYDEFPYT (SEQ ID NO: 240) | LQYDEFPYT (SEQ ID NO: 240) | LQYDEFPYT (SEQ ID NO: 240) | YDEFPY (SEQ ID NO: 251) | LQYDEFPY (SEQ ID NO: 257) | LQYDEFPYT (SEQ ID NO: 240) |

VH Sequence:
QVQLQESGPGLVKPSQSLSLTCSVTGYSITSGYYWNWIRQFPGNKLEWMGYINYGGSNNYNPSLKNRISITRDTSKNQFFLKLTSVTTEDTATYYCARRGAYYSNYD
SFDVWGTGTTVTVSS (SEQ ID NO: 259)

VL Sequence:
DIKMTQSPSSMYASLGERVTITCKASQDINSYLSWFQQKPGKSPKTLIYRANRLVDGVPSRFSGSGSGQDYSLTISSLEYEEMGIYYCLQYDEFPYTFGGGTKLEIK
(SEQ ID NO: 260)

In some embodiments, the antibodies provided herein comprise a VH region or VH domain In other embodiments, the antibodies provided herein comprise a VL region or VL chain. In some embodiments, the antibodies provided herein have a combination of (i) a VH domain or VH region; and/or (ii) a VL domain or VL region.

In some embodiments, an antibody provided herein comprises or consists of six CDRs, for example, VH CDR1, VH CDR2, VH CDR3, VL CDR1, VL CDR2, and/or VL CDR3 identified in Tables 1-10. In some embodiments, an antibody provided herein can comprise less than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3 identified in tables 1-10. In some embodiments, the antibody comprises or consists of one, two, three, four, or five CDRs selected from the group consisting of VH CDR1, VH CDR2, VH CDR3, VL CDR1, VL CDR2, and/or VL CDR3 of the murine monoclonal antibody selected from the group consisting of: (a) the antibody designated 5H23; (b) the antibody designated 1O17; (c) the antibody designated 1D19, (d) the antibody designated 2L12; (e) the antibody designated 3L3; (f) the antibody designated 3N20; (g) the antibody designated 4P5; (h) the antibody designated 5O23; (i) the antibody designated 5F7, (j) the antibody designated 1G19; described herein. Accordingly, in some embodiments, the antibody comprises or consists of one, two, three four or five CDRs of anyone of the VH CDR1, VH CDR2, VH CDR3, VL CDR1, VL CDR2, and/or VL CDR3 identified in Tables 1-10.

In some embodiments, the antibodies provided herein comprise one or more (e.g., one, two or three) VH CDRs listed in Tables 1-10. In other embodiments, the antibodies provided herein comprise one or more (e.g., one, two or three) VL CDRs listed in Tables 1-10. In yet other embodiments, the antibodies provided herein comprise one or more (e.g., one, two or three) VH CDRs listed in Tables 1-10 and one or more VL CDRs listed in Tables 1-10. Accordingly, in some embodiments, the antibodies comprise a VH CDR1 having the amino acid sequence of any one of SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252. In some embodiments, the antibodies comprise a VH CDR2 having the amino acid sequence of any one of SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258. In some embodiments, the antibodies comprise a VH CDR3 having the amino acid sequence of any one of SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254. In some embodiments, the antibodies comprise a VH CDR1 and/or a VH CDR2 and/or a VH CDR3 independently selected from a VH CDR1, VH CDR2, VH CDR3 as depicted in any one of the amino acid sequences depicted in Table 1-10. In some embodiments, the antibodies comprise a VL CDR1 having the amino acid sequence of any one of SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255. In another embodiment, the antibodies comprise a VL CDR2 having the amino acid sequence of any one of SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256. In some embodiments, the antibodies comprise a VL CDR3 having the amino acid sequence of any one of SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257. In some embodiments, the antibodies comprise a VL CDR1 and/or a VL CDR2 and/or a VL CDR3 independently selected from a VL CDR1, VL CDR2, VL CDR3 as depicted in any one of the amino acid sequences depicted in Tables 1-10.

In some embodiments, the antibodies provided herein comprise a heavy chain variable (VH) region comprising: (1) a VH CDR1 having an amino acid sequence of selected from the group consisting of: (i) SEQ ID NO:1, 27, 53, 79, 105, 131, 157, 183, 209, and or 235, (ii) SEQ ID NO:7, 33, 59, 85, 111, 137, 163, 189, 215 or 241, (iii) SEQ ID NO:12, 38, 64, 90, 116, 142, 168, 194, 220 or 246, (iv) SEQ ID NO:13, 39, 65, 91, 117, 143, 169, 195, 221 or 247, and (v) SEQ ID NO:18, 44, 70, 96, 122, 148, 174, 200, 226 or 252; (2) a VH CDR2 having an amino acid sequence of selected from the group consisting of: (i) SEQ ID NO:2, 28, 54, 80, 106, 132, 158, 184, 210, and or 236, (ii) SEQ ID NO:8, 34, 60, 86, 112, 138, 164, 190, 216 or 242, (iii) SEQ ID NO:14, 40, 66, 92, 118, 144, 170, 196, 222 or 248, (iv) SEQ ID NO:19, 45, 71, 97, 123, 149, 175, 201, 227 or 253, and (v) SEQ ID NO:24, 50, 76, 102, 128, 154, 180, 206, 232 or 258; and (3) a VH CDR3 having an amino acid sequence of selected from the group consisting of: (i) SEQ ID NO: 3, 29, 55, 81, 107, 133, 159, 185, 211, and or 237, (ii) SEQ ID NO:9, 35, 61, 87, 113, 139, 165, 191, 217 or 243, (iii) SEQ ID NO:15, 41, 67, 93, 119, 145, 171, 197, 223 or 249, and (iv) SEQ ID NO:20, 46, 72, 98, 124, 150, 176, 202, 228 or 254; and/or a light chain variable (VL) region comprising: (1) a VL CDR1 having an amino acid sequence of selected from the group consisting of: (i) SEQ ID NO:4, 30, 56, 82, 108, 134, 160, 186, 212, and or 238, (ii) SEQ ID NO:10, 36, 52, 88, 114, 140, 166, 192, 218 or 244, (iii) SEQ ID NO:16, 42, 68, 94, 120, 146, 172, 198, 224 or 250, and (iv) SEQ ID NO:21, 47, 73, 99, 125, 151, 177, 203, 229 or 255; (2) a VL CDR2 having an amino acid sequence of selected from the group consisting of: (i) SEQ ID NO:5, 31, 57, 83, 109, 135, 161, 187, 213, and or 239, (ii) SEQ ID NO:11, 37, 63, 89, 115, 141, 167, 193, 219 or 245, and (iii) SEQ ID NO:22, 48, 74, 100, 126, 152, 178, 204, 230 or 256; and (3) a VL CDR3 having an amino acid sequence of selected from the group consisting of: (i) SEQ ID NO:6, 32, 58, 84, 110, 136, 162, 188, 214, and or 240, (ii) SEQ ID NO:17, 43, 69, 95, 121, 147, 173, 199, 225 or 251, and (iii) SEQ ID NO:23, 49, 75, 101, 127, 153, 179, 205, 231 or 257.

In some embodiments, the antibodies provided herein comprise a heavy chain variable (VH) region comprising: (1) a VH CDR1 having an amino acid sequence of selected from the group consisting of: (i) SEQ ID NO:1, 27, 53, 79, 105, 131, 157, 183, 209, and or 235, (ii) SEQ ID NO:7, 33, 59, 85, 111, 137, 163, 189, 215 or 241, (iii) SEQ ID NO:12, 38, 64, 90, 116, 142, 168, 194, 220 or 246, (iv) SEQ ID NO:13, 39, 65, 91, 117, 143, 169, 195, 221 or 247, and (v) SEQ ID NO:18, 44, 70, 96, 122, 148, 174, 200, 226 or 252; (2) a VH CDR2 having an amino acid sequence of selected from the group consisting of: (i) SEQ ID NO:2, 28, 54, 80, 106, 132, 158, 184, 210, and or 236, (ii) SEQ ID NO:8, 34, 60, 86, 112, 138, 164, 190, 216 or 242, (iii) SEQ ID NO:14, 40, 66, 92, 118, 144, 170, 196, 222 or 248, (iv) SEQ ID NO:19, 45, 71, 97, 123, 149, 175, 201, 227 or 253, and (v) SEQ ID NO:24, 50, 76, 102, 128, 154, 180, 206, 232 or 258; and (3) a VH CDR3 having an amino acid sequence of selected from the group consisting of: (i) SEQ ID NO: 3, 29, 55, 81, 107, 133, 159, 185, 211, and or 237, (ii) SEQ ID NO:9, 35, 61, 87, 113, 139, 165, 191, 217 or 243, (iii) SEQ ID NO:15, 41, 67, 93, 119, 145, 171, 197, 223 or 249, and (iv) SEQ ID NO:20, 46, 72, 98, 124, 150, 176, 202, 228 or 254.

In some embodiments, the antibodies provided herein comprise a light chain variable (VL) region comprising: (1) a VL CDR1 having an amino acid sequence of selected from the group consisting of: (i) SEQ ID NO:4, 30, 56, 82, 108, 134, 160, 186, 212, and or 238, (ii) SEQ ID NO:10, 36, 52, 88, 114, 140, 166, 192, 218 or 244, (iii) SEQ ID NO:16, 42, 68, 94, 120, 146, 172, 198, 224 or 250, and (iv) SEQ ID NO:21, 47, 73, 99, 125, 151, 177, 203, 229 or 255; (2) a VL CDR2 having an amino acid sequence of selected from the group consisting of: (i) SEQ ID NO:5, 31, 57, 83, 109, 135, 161, 187, 213, and or 239, (ii) SEQ ID NO:11, 37, 63, 89, 115, 141, 167, 193, 219 or 245, and (iii) SEQ ID NO:22, 48, 74, 100, 126, 152, 178, 204, 230 or 256; and (3) a VL CDR3 having an amino acid sequence of selected from the group consisting of: (i) SEQ ID NO:6, 32, 58, 84, 110, 136, 162, 188, 214, and or 240, (ii) SEQ ID NO:17, 43, 69, 95, 121, 147, 173, 199, 225 or 251, and (iii) SEQ ID NO:23, 49, 75, 101, 127, 153, 179, 205, 231 or 257.

Also provided herein are antibodies comprising one or more VH CDRs and one or more (e.g., one, two or three) VL CDRs listed in Tables 1-10. In particular, provided herein is an antibody comprising a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252.) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252); a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VH CDR1 (SEQ ID NOS 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252) VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257) and a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258); a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VH CDR2 (SEQ ID NOS: 2, 8, 14, 19, 24, 28, 34, 40, 45, 50, 54, 60, 66, 71, 76, 80, 86,92, 97,102,106,112,118,123,128,132,138,144,149, 154,158,164,170, 175, 180, 184, 190, 196, 201, 206, 210, 216, 222, 227, 232, 236, 242, 248, 253, and 258); and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252.), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, and 257); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117,122,131,137,142,143,148,157,163,168,169,174, 183,189,194,195,200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117,122,131,137,142,143, 148,157,163,168,169,174,183,189,194,195,200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR2 (SEQ ID NOS:2, 8, 14, 19, 24, 28, 34, 40, 45, 50, 54, 60, 66, 71, 76, 80, 86,92, 97,102,106,112,118, 123,128,132,138,144,149,154,158,164,170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86,92, 97,102,106,112,118,123,128,132,138,144, 149,154,158,164,170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256), and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117,122,131,137,142,143,148,157,163, 168,169,174,183,189,194,195,200, 209, 215, 220, 221, 226, 235, 241, 246, 247, and 252), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256), and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) or any combination thereof of the VH CDRs and VL CDRs listed in Tables 1-10.

In yet another aspect, the CDRs disclosed herein include consensus sequences derived from groups of related antibodies (see, e.g., Tables 1-10). As described herein, a "consensus sequence" refers to amino acid sequences having conserved amino acids common among a number of sequences and variable amino acids that vary within a given amino acid sequences. The CDR consensus sequences provided include CDRs corresponding to CDRH1, CDRH2, CDRH3, CDRL1, CDRL2 and/or CDRL3. Consensus sequences of CDRs of anti-beta klotho antibodies are shown in FIG. 2.

In certain embodiments, an antibody of fragment thereof described herein comprises a VH region that comprises: (1) a VH FR1 having an amino acid sequence selected from the group consisting of SEQ ID NOS: 278, 279, 280 and 378;

(2) a VH FR2 having an amino acid sequence selected from the group consisting of SEQ ID NOS: 281, 282, and 283; (3) a VH FR3 having an amino acid sequence selected from the group consisting of SEQ ID NOS: 284, 285, 286, 287 and 379-381; and/or (4) a VH FR4 having an amino acid of SEQ ID NO: 288. Accordingly, in some aspects, the humanized antibody comprises a VH region that includes a VH FR1 having an amino acid sequence selected from the group consisting of SEQ ID NOS: 278, 279, 280 and 378. In some aspects, the humanized antibody comprises a VH region that includes a VH FR2 having an amino acid sequence selected from the group consisting of SEQ ID NOS: 281, 282, and 283. In some aspects, the humanized antibody comprises a VH region that includes a VH FR3 having an amino acid sequence selected from the group consisting of SEQ ID NOS: 284, 285, 286, 287 and 379-381. In some aspects, the humanized antibody comprises a VH region that includes a VH FR4 having an amino acid of SEQ ID NO: 288.

In certain embodiments, an antibody of fragment thereof described herein comprises a VL region that comprises: (1) a VL FR1 having an amino acid sequence selected from the group consisting of SEQ ID NOS: 289, 290 and 382-384; (2) a VL FR2 having an amino acid sequence selected from the group consisting of SEQ ID NOS: 291, 292 and 385-392; (3) a VL FR3 having an amino acid sequence selected from the group consisting of SEQ ID NOS: 293, 294, 295 and 393-404; and/or (4) a VL FR4 having an amino acid of SEQ ID NO: 296 and 405-407. Accordingly, in some aspects, the humanized antibody comprises a VL region that includes a VL FR1 having an amino acid sequence selected from the group consisting of SEQ ID NOS: 289, 290 and 382-384. In some aspects, the humanized antibody comprises a VL region that includes a VL FR2 having an amino acid sequence selected from the group consisting of SEQ ID NOS: 291, 292 and 385-392. In some aspects, the humanized antibody comprises a VL region that includes a VL FR3 having an amino acid sequence selected from the group consisting of SEQ ID NOS: 293, 294, 295 and 393-404. In some aspects, the humanized antibody comprises a VL region that includes a VL FR4 having an amino acid of SEQ ID NO: 296 and 405-407.

In certain embodiments, an antibody of fragment thereof described herein comprises a VH region and a VL region, wherein the VH region further comprises: (1) a VH FR1 having an amino acid sequence selected from the group consisting of SEQ ID NOS: 278, 279, 280 and 378; (2) a VH FR2 having an amino acid sequence selected from the group consisting of SEQ ID NOS: 281, 282, and 283; (3) a VH FR3 having an amino acid sequence selected from the group consisting of SEQ ID NOS: 284, 285, 286, 287 and 379-381; and/or (4) a VH FR4 having an amino acid sequence of SEQ ID NO: 288; and wherein the VL region further comprises: (1) a VL FR1 having an amino acid sequence selected from the group consisting of SEQ ID NOS: 289, 290 and 382-384; (2) a VL FR2 having an amino acid sequence selected from the group consisting of SEQ ID NOS: 291, 292 and 385-392; (3) a VL FR3 having an amino acid sequence selected from the group consisting of SEQ ID NOS: 293, 294, 295 and 393-404; and/or (4) a VL FR4 having an amino acid of SEQ ID NO: 296 and 405-407.

Also provided herein are antibodies comprising one or more (e.g., one, two, three or four) VH FRs and one or more VL FRs listed in Table 19. In particular, provided herein is an antibody comprising a VH FR1 (SEQ ID NOS:278, 279, 280 and 378) and a VL FR1 (SEQ ID NOS:289, 290 and 382-384); a VH FR1 (SEQ ID NOS:278, 279, 280 and 378) and a VL FR2 (SEQ ID NOS:291, 292 and 385-392); a VH FR1 (SEQ ID NOS:278, 279, 280 and 378) and a VL FR3 (SEQ ID NOS:293, 294, 295 and 393-404); a VH FR1 (SEQ ID NOS:278, 279, 280 and 378) and a VL FR4 (SEQ ID NO:296 and 405-407); a VH FR2 (SEQ ID NOS:281, 282, and 283) and a VL FR1 (SEQ ID NOS:289, 290 and 382-384); a VH FR2 (SEQ ID NOS:281, 282, and 283) and a VL FR2 (SEQ ID NOS:291, 292 and 385-392); a VH FR2 (SEQ ID NOS:281, 282, and 283) and a VL FR3 (SEQ ID NOS:293, 294, 295 and 393-404); a VH FR2 (SEQ ID NOS:281, 282, and 283) and a VL FR4 (SEQ ID NO:296 and 405-407); a VH FR3 (SEQ ID NOS:284, 285, 286, 287 and 379-381) and a VH FR1 (SEQ ID NOS:278, 279, 280 and 378); a VH FR3 (SEQ ID NOS:284, 285, 286, 287 and 379-381) and a VL FR2 (SEQ ID NOS:291, 292 and 385-392); a VH FR3 (SEQ ID NOS:284, 285, 286, 287 and 379-381) and a VL FR3 (SEQ ID NOS:293, 294, 295 and 393-404); a VH FR3 (SEQ ID NOS:284, 285, 286, 287 and 379-381) and a VL FR4 (SEQ ID NO:296 and 405-407); a VH FR1 (SEQ ID NOS:278, 279, 280 and 378), a VH FR2 (SEQ ID NOS:281, 282, and 283) and a VL FR1 (SEQ ID NOS:289, 290 and 382-384); a VH FR1 (SEQ ID NOS:278, 279, 280 and 378), a VH FR2 (SEQ ID NOS:281, 282, and 283) and a VL FR2 (SEQ ID NOS:291, 292 and 385-392); a VH FR1 (SEQ ID NOS:278, 279, 280 and 378), a VH FR2 (SEQ ID NOS:281, 282, and 283) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283) and a VL FR4 (SEQ ID NO:296 and 405-407); a VH FR2 (SEQ ID NOS:281, 282, and 283), a VH FR3 (SEQ ID NOS:284, 285, 286, 287 and 379-381) and a VL FR1 (SEQ ID NOS:289, 290 and 382-384), a VH FR2 (SEQ ID NOS:281, 282, and 283), a VH FR3 (SEQ ID NOS:284, 285, 286, 287 and 379-381) and a VL FR2 (SEQ ID NOS:291, 292 and 385-392); a VH FR2 (SEQ ID NOS:281, 282, and 283), a VH FR3 (SEQ ID NOS:284, 285, 286, 287 and 379-381) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381) and a VL FR4 (SEQ ID NO:296 and 405-407); a VH FR1 (SEQ ID NOS:278, 279, 280 and 378), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VL FR1 (SEQ ID NOS:289, 290 and 382-384) and a VL FR4 (SEQ ID NO:296 and 405-407); a VH FR1 (SEQ ID NOS:278, 279, 280 and 378), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VL FR2 (SEQ ID NOS:291, 292 and 385-392) and a VL FR4 (SEQ ID NO:296 and 405-407); a VH FR2 (SEQ ID NOS:281, 282, and 283), a VL FR1 (SEQ ID NOS:289, 290 and 382-384) and a VL FR2 (SEQ ID NOS:291, 292 and 385-392); a VH FR2 (SEQ ID NOS:281, 282, and 283), a VL FR1 (SEQ ID NOS:289, 290 and 382-384) and a VL FR3 (SEQ ID NOS:293, 294, 295 and 393-404); a VH FR2 (SEQ ID NOS:281, 282, and 283), a VL FR1 (SEQ ID NOS:289, 290 and 382-384) and a VL FR4 (SEQ ID NO:296 and 405-407); a VH FR2 (SEQ ID NOS:281, 282, and 283), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VL FR2 (SEQ ID NOS:291, 292 and 385-392) and a VL FR4 (SEQ ID NO:296 and 405-407); a VH FR3 (SEQ ID NOS:284, 285, 286, 287 and 379-381), a VL FR1 (SEQ ID NOS:289, 290 and 382-384) and a VL FR2 (SEQ ID NOS:291, 292 and 385-392); a VH FR3 (SEQ ID NOS:284, 285, 286, 287 and 379-381), a VL FR1 (SEQ ID NOS:289, 290 and 382-384) and a VL FR3 (SEQ ID NOS:293, 294, 295 and 393-404); a VH FR3 (SEQ ID NOS:284, 285, 286, 287 and 379-381), a VL FR1 (SEQ ID NOS:289, 290 and 382-384) and a VL FR4 (SEQ ID NO:296 and 405-407); a VH FR3 (SEQ ID NOS:284, 285, 286, 287 and 379-381), a VL FR2 (SEQ ID NOS:291, 292 and 385-392) and a VL FR3 (SEQ ID NOS:293, 294, 295 and 393-404); a VH FR3 (SEQ ID NOS:284, 285, 286, 287 and 379-381), a VL FR2 (SEQ ID NOS:291, 292 and 385-392) and a VL FR4 (SEQ ID NO:296 and 405-407); a VH FR4 (SEQ ID NO:288), a VL FR1 (SEQ ID NOS:289, 290 and 382-384) and a VL FR2 (SEQ ID NOS:291, 292 and 385-392); a VH FR4 (SEQ ID NO:288), a VL FR1 (SEQ ID NOS:289, 290 and 382-384) and a VL FR3 (SEQ ID NOS:293, 294, 295 and 393-404); a VH FR4 (SEQ ID NO:288), a VL FR1 (SEQ ID NOS:289, 290 and 382-384) and a VL FR4 (SEQ ID NO:296 and 405-407); a VH FR4 (SEQ ID NO:288), a VL FR2 (SEQ ID NOS:291, 292 and 385-392) and a VL FR3 (SEQ ID NOS:293, 294, 295 and 393-404); a VH FR4 (SEQ ID NO:288), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381) and a VL FR1 (SEQ ID NOS:289, 290 and 382-384); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288) and a VL FR1 (SEQ ID NOS:289, 290 and 382-384); a VH FR1 (SEQ ID NOS:278, 279, 280 and 378), a VH FR2 (SEQ ID NOS:281, 282, and 283), a VH FR4 (SEQ ID NO:288) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR4 (SEQ ID NO:288) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR4 (SEQ ID NO:288) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VH FR4 (SEQ ID NO:288) and a VL FR1 (SEQ ID NOS:289, 290 and 382-384); a VH FR1 (SEQ ID NOS:278, 279, 280 and 378), a VH FR3 (SEQ ID NOS:284, 285, 286, 287 and 379-381), a VH FR4 (SEQ ID NO:288) and a VL FR2 (SEQ ID NOS:291, 292 and 385-392); a VH FR1 (SEQ ID NOS:278, 279, 280 and 378), a VH FR3 (SEQ ID NOS:284, 285, 286, 287 and 379-381), a VH FR4 (SEQ ID NO:288) and a VL FR3 (SEQ ID NOS:293, 294, 295 and 393-404); a VH FR1 (SEQ ID NOS:278, 279, 280 and 378), a VH FR3 (SEQ ID NOS:284, 285, 286, 287 and 379-381), a VH FR4 (SEQ ID NO:288) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288) and a VL FR1 (SEQ ID NOS:289, 290 and 382-384); a VH FR2 (SEQ ID NOS:281, 282, and 283), a VH FR3 (SEQ ID NOS:284, 285, 286, 287 and 379-381), a VH FR4 (SEQ ID NO:288) and a VL FR2 (SEQ ID NOS:291, 292 and 385-392); a VH FR2 (SEQ ID NOS:281, 282, and 283), a VH FR3 (SEQ ID NOS:284, 285, 286, 287 and 379-381), a VH FR4 (SEQ ID NO:288) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VH FR4 (SEQ ID NO:288) and a VL FR4 (SEQ ID NO:296 and 405-407); a VH FR1 (SEQ ID NOS:278, 279, 280 and 378), a VH FR2 (SEQ ID NOS:281, 282, and 283), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR4 (SEQ ID NO:288), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR4 (SEQ ID NO:288), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR4 (SEQ ID NO:288), a VL FR1 (SEQ ID NOS:289, 290 and 382-384) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR2 (SEQ ID NOS:291, 292 and 385-392); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR4 (SEQ ID NO:296 and 405-407); a VH FR2 (SEQ ID NOS:281, 282, and 283), a VH FR4 (SEQ ID NO:288), a VL FR1 (SEQ ID NOS:289, 290 and 382-384) and a VL FR2 (SEQ ID NOS:291, 292 and 385-392); a VH FR2 (SEQ ID NOS:281, 282, and 283), a VH FR4 (SEQ ID NO:288), a VL FR1 (SEQ ID NOS:289, 290 and 382-384) and a VL FR3 (SEQ ID NOS:293, 294, 295 and 393-404); a VH FR2 (SEQ ID NOS:281, 282, and 283), a VH FR4 (SEQ ID NO:288), a VL FR1 (SEQ ID NOS:289, 290 and 382-384) and a VL FR4 (SEQ ID NO:296 and 405-407); a VH FR3 (SEQ ID NOS:284, 285, 286, 287 and 379-381), a VH FR4 (SEQ ID NO:288), a VL FR1 (SEQ ID NOS:289, 290 and 382-384) and a VL FR2 (SEQ ID NOS:291, 292 and 385-392); a VH FR3 (SEQ ID NOS:284, 285, 286, 287 and 379-381), a VH FR4 (SEQ ID NO:288), a VL FR1 (SEQ ID NOS:289, 290 and 382-384) and a VL FR3 (SEQ ID NOS:293, 294, 295 and 393-404); a VH FR3 (SEQ ID NOS:284, 285, 286, 287 and 379-381), a VH FR4 (SEQ ID NO:288), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR2 (SEQ ID NOS:281, 282, and 283), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR3 (SEQ ID NOS:284, 285, 286, 287 and 379-381), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR4 (SEQ ID NO:288), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR4 (SEQ ID NO:288), a VL FR2 (SEQ ID NOS:291, 292 and 385-392) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392) and a VL FR4 (SEQ ID NO:296 and 405-407); a VH FR2 (SEQ ID NOS:281, 282, and 283), a VH FR4 (SEQ ID NO:288), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VH FR4 (SEQ ID NO:288), a VL FR2 (SEQ ID NOS:291, 292 and 385-392) and a VL FR4 (SEQ ID NO:296 and 405-407); a VH FR3 (SEQ ID NOS:284, 285, 286, 287 and 379-381), a VH FR4 (SEQ ID NO:288), a VL FR2 (SEQ ID NOS:291, 292 and 385-392) and a VL FR3 (SEQ ID NOS:293, 294, 295 and 393-404); a VH FR3 (SEQ ID NOS:284, 285, 286, 287 and 379-381), a VH FR4 (SEQ ID NO:288), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR4 (SEQ ID NO:288), a VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR3 (SEQ ID NOS:293, 294, 295 and 393-404) and a VL FR4 (SEQ ID NO:296 and 405-407); a VH FR2 (SEQ ID NOS:281, 282, and 283), a VH FR4 (SEQ ID NO:288), a VL FR3 (SEQ ID NOS:293, 294, 295 and 393-404) and a VL FR4 (SEQ ID NO:296 and 405-407); a VH FR3 (SEQ ID NOS:284, 285, 286, 287 and 379-381), a VH FR4 (SEQ ID NO:288), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VL FR1 (SEQ ID NOS:289, 290 and 382-384), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VL FR1 (SEQ ID NOS:289, 290 and 382-384), a VL FR2 (SEQ ID NOS:291, 292 and 385-392) and a VL FR4 (SEQ ID NO:296 and 405-407); a VH FR1 (SEQ ID NOS:278, 279, 280 and 378), a VL FR1 (SEQ ID NOS:289, 290 and 382-384), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VL FR2 (SEQ ID NOS:291, 292 and 385-392), a VL FR3 (SEQ ID NOS:293, 294, 295 and 393-404) and a VL FR4 (SEQ ID NO:296 and 405-407); a VH FR2 (SEQ ID NOS:281, 282, and 283), a VL FR1 (SEQ ID NOS:289, 290 and 382-384), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VL FR1 (SEQ ID NOS:289, 290 and 382-384), a VL FR2 (SEQ ID NOS:291, 292 and 385-392) and a VL FR4 (SEQ ID NO:296 and 405-407); a VH FR2 (SEQ ID NOS:281, 282, and 283), a VL FR1 (SEQ ID NOS:289, 290 and 382-384), a VL FR3 (SEQ ID NOS:293, 294, 295 and 393-404) and a VL FR4 (SEQ ID NO:296 and 405-407); a VH FR2 (SEQ ID NOS:281, 282, and 283), a VL FR2 (SEQ ID NOS:291, 292 and 385-392), a VL FR3 (SEQ ID NOS:293, 294, 295 and 393-404) and a VL FR4 (SEQ ID NO:296 and 405-407); a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392) and a VL FR3 (SEQ ID NOS:293, 294, 295 and 393-404); a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392) and a VL FR4 (SEQ ID NO:296 and 405-407); a VH FR3 (SEQ ID NOS:284, 285, 286, 287 and 379-381), a VL FR1 (SEQ ID NOS:289, 290 and 382-384), a VL FR3 (SEQ ID NOS:293, 294, 295 and 393-404) and a VL FR4 (SEQ ID NO:296 and 405-407); a VH FR3 (SEQ ID NOS:284, 285, 286, 287 and 379-381), a VL FR2 (SEQ ID NOS:291, 292 and 385-392), a VL FR3 (SEQ ID NOS:293, 294, 295 and 393-404) and a VL FR4 (SEQ ID NO:296 and 405-407); a VH FR4 (SEQ ID NO:288), a VL FR1 (SEQ ID NOS:289, 290 and 382-384), a VL FR2 (SEQ ID NOS:291, 292 and 385-392) and a VL FR3 (SEQ ID NOS:293, 294, 295 and 393-404); a VH FR4 (SEQ ID NO:288), a VL FR1 (SEQ ID NOS:289, 290 and 382-384), a VL FR2 (SEQ ID NOS:291, 292 and 385-392) and a VL FR4 (SEQ ID NO:296 and 405-407); a VH FR4 (SEQ ID NO:288), a VL FR1 (SEQ ID NOS:289, 290 and 382-384), a VL FR3 (SEQ ID NOS:293, 294, 295 and 393-404) and a VL FR4 (SEQ ID NO:296 and 405-407); a VH FR4 (SEQ ID NO:288), a VL FR2 (SEQ ID NOS:291, 292 and 385-392), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288) and a VL FR1 (SEQ ID NOS:289, 290 and 382-384); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR4 (SEQ ID NO:288), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384) and a VL FR2 (SEQ ID NOS:291, 292 and 385-392); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VH FR4 (SEQ ID NO:288), a VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR1 (SEQ ID NOS:278, 279, 280 and 378), a VH FR2 (SEQ ID NOS:281, 282, and 283), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR2 (SEQ ID NOS:281, 282, and 283), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR4 (SEQ ID NO:288), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR1 (SEQ ID NOS:278, 279, 280 and 378), a VH FR4 (SEQ ID NO:288), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR1 (SEQ ID NOS:278, 279, 280 and 378), a VH FR4 (SEQ ID NO:288), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR4 (SEQ ID NO:288), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), a VL FR3

(SEQ ID NOS:293, 294, 295 and 393-404), and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR2 (SEQ ID NOS:281, 282, and 283), a VH FR4 (SEQ ID NO:288), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR2 (SEQ ID NOS:281, 282, and 283), a VH FR4 (SEQ ID NO:288), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR2 (SEQ ID NOS:281, 282, and 283), a VH FR4 (SEQ ID NO:288), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR2 (SEQ ID NOS:281, 282, and 283), a VH FR4 (SEQ ID NO:288), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR3 (SEQ ID NOS:284, 285, 286, 287 and 379-381), a VH FR4 (SEQ ID NO:288), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR3 (SEQ ID NOS:284, 285, 286, 287 and 379-381), a VH FR4 (SEQ ID NO:288), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR3 (SEQ ID NOS:284, 285, 286, 287 and 379-381), a VH FR4 (SEQ ID NO:288), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR3 (SEQ ID NOS:284, 285, 286, 287 and 379-381), a VH FR4 (SEQ ID NO:288), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VL FR1 (SEQ ID NOS:289, 290 and 382-384), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR2 (SEQ ID NOS:281, 282, and 283), a VL FR1 (SEQ ID NOS:289, 290 and 382-384), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR4 (SEQ ID NO:288), a VL FR1 (SEQ ID NOS:289, 290 and 382-384), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VH FR4 (SEQ ID NO:288), a VL FR1 (SEQ ID NOS:289, 290 and 382-384), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VH FR4 (SEQ ID NO:288), a VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VH FR4 (SEQ ID NO:288), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384), VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384), VL FR2 (SEQ ID NOS:291, 292 and 385-392) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR4 (SEQ ID NO:288), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR2 (SEQ ID NOS:281, 282, and 283), a VH FR4 (SEQ ID NO:288), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR3 (SEQ ID NOS:284, 285, 286, 287 and 379-381), a VH FR4 (SEQ ID NO:288), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384), VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384), VL FR2 (SEQ ID NOS:291, 292 and 385-392), VL FR3 (SEQ ID NOS:293, 294, 295 and 393-404) and a VL FR4 (SEQ ID NO:296 and 405-407); or any combination thereof of the VH FRs (SEQ ID NOS: 278, 279, 280, 378, 281, 282, 283, 284, 285, 286, 287, 379-381 and 288) and VL FRs (SEQ ID NOS: 289, 290, 382-384, 291, 292, 385-392, 293, 294, 295, 393-404, 296, 405-407) listed in Table 19.

In yet another aspect, antibodies are provided that compete with one of the exemplified antibodies or functional fragments for binding to (i) beta klotho or (ii) a complex comprising beta klotho and one of FGFR1c, FGFR2c, FGFR3c, and FGFR4. Such antibodies may also bind to the same epitope as one of the herein exemplified antibodies, or an overlapping epitope. Antibodies and fragments that compete with or bind to the same epitope as the exemplified antibodies are expected to show similar functional properties. The exemplified antigen binding proteins and fragments include those with the VH and VL regions, and CDRs provided herein, including those in Tables 1-10. Thus, as a specific example, the antibodies that are provided include those that compete with an antibody comprising: (a) 1, 2, 3, 4, 5 or all 6 of the CDRs listed for an antibody listed in Tables 1-10; (b) a VH and a VL selected from the VH and a VL regions listed for an antibody listed in Tables 1-10, such as for antibody 5H23 (Table 1) or (c) two light chains and two heavy chains comprising a VH and a VL as specified for an antibody listed in Tables 1-10.

In still yet another aspect, antibodies are provided herein that bind to a region, including an epitope, of human beta klotho or cyno beta klotho. For example, in some embodiments, an antibody provided herein binds to a KLB2 domain of human beta klotho comprising amino acid residues 509 to 1044 of SEQ ID NO:297. As another example, in some embodiments, an antibody provided herein binds to a glycosyl hydrolase 1 region of a KLB2 domain of human beta klotho comprising amino acid residues 517 to 967 of SEQ ID NO:297. As yet another example, in some embodiments, an antibody provided herein binds to a region of human beta klotho comprising amino acid residues 657 to 703 of SEQ ID NO:297. As still another example, in some embodiments, an antibody provided herein binds to a region of cyno beta klotho comprising amino acid residues 657 to 703 of SEQ ID NO:299.

In another aspect, antibodies are provided herein that bind to a specific epitope of human beta klotho. For example, in some embodiments, an antibody provided herein binds an epitope of human beta klotho comprising at least one of amino acid residues 657, 701 and/or 703 of human beta klotho (SEQ ID NO: 297). Accordingly, in some embodiments, an antibody provided herein binds to an epitope of human beta klotho, wherein the epitope of human beta klotho comprise at least amino acid residue 657 of SEQ ID NO: 297. In some embodiments, an antibody provided herein binds to an epitope of human beta klotho, wherein the epitope of human beta klotho comprise at least amino acid residue 701 of SEQ ID NO: 297. In some embodiments, an antibody provided herein binds to an epitope of human beta klotho, wherein the epitope of human beta klotho comprise at least amino acid residue 703 of SEQ ID NO: 297. In some embodiments, an antibody provided herein binds to an epitope of human beta klotho, wherein the epitope of human beta klotho comprise at least amino acid residues 657 and 701 of SEQ ID NO: 297. In some embodiments, an antibody provided herein binds to an epitope of human beta klotho, wherein the epitope of human beta klotho comprise at least amino acid residues 657 and 703 of SEQ ID NO: 297. In some embodiments, an antibody provided herein binds to an epitope of human beta klotho, wherein the epitope of human beta klotho comprise at least amino acid residues 701 and 703 of SEQ ID NO: 297. In some embodiments, an antibody provided herein binds to an epitope of human beta klotho, wherein the epitope of human beta klotho comprise at least amino acid residues 657, 701 and 703 of SEQ ID NO: 297. Such antibodies provided above can, in some embodiments, induce FGF19-like signaling and/or FGF21-like signaling in a cell that expresses human beta klotho and an FGF receptor. Additionally, in some embodiments, the antibody is a humanized, human or chimeric antibody.

1. Polyclonal Antibodies

The antibodies of the present disclosure may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a beta klotho polypeptide or a fusion protein thereof. It may be useful to conjugate the immunizing agent to a protein known to be immunogenic in the mammal being immunized or to immunize the mammal with the protein and one or more adjuvants. Examples of such immunogenic proteins include but are not limited to keyhole limpet hemocyanin, serum albumin, bovine thyroglobulin, and soybean trypsin inhibitor. Examples of adjuvants which may be employed include Ribi, CpG, Poly 10, Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for beta klotho antibody titer. If desired, the mammal can be boosted until the antibody titer increases or plateaus. Additionally or alternatively, lymphocytes may be obtained from the immunized animal for fusion and the preparation of monoclonal antibodies from hybridoma as described below.

2. Monoclonal Antibodies

The antibodies of the present disclosure may alternatively be monoclonal antibodies. Monoclonal antibodies may be made using the hybridoma method first described by Kohler et al., Nature, 256:495 (1975), or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as SP-2 and derivatives, for example, X63-Ag8-653 cells available from the American Type Culture Collection, Manassas, Va., USA and those derived from MOPC-21 and MPC-11 mouse tumors available from the Salk Institute Cell Distribution Center, San Diego, Calif. USA. Human myeloma and mouse-human heteromyeloma cell lines also have been described for the production of human monoclonal antibodies (Kozbor, J., Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., Anal. Biochem., 107: 220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In some embodiments, an antibody that binds a beta klotho epitope comprises an amino acid sequence of a VH domain and/or an amino acid sequence of a VL domain encoded by a nucleotide sequence that hybridizes to (1) the complement of a nucleotide sequence encoding any one of the VH and/or VL domain described herein under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In some embodiments, an antibody that binds a beta klotho epitope comprises an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Tables 1-10 under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3)

In a further embodiment, monoclonal antibodies or antibody fragments can be isolated from antibody phage libraries generated using the techniques described in, for example, *Antibody Phage Display: Methods and Protocols*, P. M. O'Brien and R. Aitken, eds, Humana Press, Totawa N.J., 2002. In principle, synthetic antibody clones are selected by screening phage libraries containing phage that display various fragments of antibody variable region (Fv) fused to phage coat protein. Such phage libraries are screened for against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., *Ann. Rev. Immunol.*, 12: 433-455 (1994).

Repertoires of VH and VL genes can be separately cloned by polymerase chain reaction (PCR) and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, *J. Mol. Biol.*, 227: 381-388 (1992).

Screening of the libraries can be accomplished by various techniques known in the art. For example, beta klotho, (e.g., a beta klotho polypeptide, fragment or epitope) can be used to coat the wells of adsorption plates, expressed on host cells affixed to adsorption plates or used in cell sorting, or conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

Anti-beta klotho antibodies can be obtained by designing a suitable antigen screening procedure to select for the phage clone of interest followed by construction of a full length anti-beta klotho antibody clone using VH and/or VL sequences (e.g., the Fv sequences), or various CDR sequences from VH and VL sequences, from the phage clone of interest and suitable constant region (e.g., Fc) sequences described in Kabat et al., Sequences of Proteins of Immunological Interest, Fifth Edition, NIH Publication 91-3242, Bethesda Md. (1991), vols. 1-3.

3. Antibody Fragments

The present disclosure provides antibodies and antibody fragments that bind to beta klotho. In certain circumstances there are advantages of using antibody fragments, rather than whole antibodies. The smaller size of the fragments allows for rapid clearance, and may lead to improved access to cells, tissues or organs. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli or yeast cells, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising salvage receptor binding epitope residues are described, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894; and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. (See, e.g., Antibody Engineering, ed. Borrebaeck, supra). The antibody fragment may also be a "linear antibody", for example, as described, for example, in the references cited above. Such linear antibodies may be mono-specific or multi-specific, such as bispecific.

Smaller antibody-derived binding structures are the separate variable domains (V domains) also termed single variable domain antibodies (SdAbs). Certain types of organisms, the camelids and cartilaginous fish, possess high affinity single V-like domains mounted on an Fc equivalent domain structure as part of their immune system. (Woolven et al., Immunogenetics 50: 98-101, 1999; Streltsov et al., *Proc Natl Acad Sci USA*. 101:12444-12449, 2004). The V-like domains (called VhH in camelids and V-NAR in sharks) typically display long surface loops, which allow penetration of cavities of target antigens. They also stabilize isolated VH domains by masking hydrophobic surface patches.

These VhH and V-NAR domains have been used to engineer sdAbs. Human V domain variants have been designed using selection from phage libraries and other approaches that have resulted in stable, high binding VL- and VH-derived domains.

Antibodies that bind to beta klotho as provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments, (e.g., beta klotho binding fragments) of any of the above. Non-limiting examples of functional fragments (e.g., fragments that bind to beta klotho) include single-chain Fvs (scFv) (e.g., including monospecific, bispecific, etc.), Fab fragments, F(ab') fragments, F(ab)2 fragments, F(ab')2 fragments, disulfide-linked Fvs (sdFv), Fd fragments, Fv fragments, diabody, triabody, tetrabody and minibody.

Antibodies provided herein include, but are not limited to, immunoglobulin molecules and immunologically active portions of immunoglobulin molecules, for example, molecules that contain an antigen binding site that bind to a beta klotho epitope. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

Variants and derivatives of antibodies include antibody functional fragments that retain the ability to bind to a beta klotho epitope. Exemplary functional fragments include Fab fragments (e.g., an antibody fragment that contains the antigen-binding domain and comprises a light chain and part of a heavy chain bridged by a disulfide bond); Fab' (e.g., an antibody fragment containing a single anti-binding domain comprising an Fab and an additional portion of the heavy chain through the hinge region); F(ab')2 (e.g., two Fab' molecules joined by interchain disulfide bonds in the hinge regions of the heavy chains; the Fab' molecules may be directed toward the same or different epitopes); a bispecific Fab (e.g., a Fab molecule having two antigen binding domains, each of which may be directed to a different epitope); a single chain Fab chain comprising a variable region, also known as, a sFv (e.g., the variable, antigen-binding determinative region of a single light and heavy chain of an antibody linked together by a chain of 10-25 amino acids); a disulfide-linked Fv, or dsFv (e.g., the variable, antigen-binding determinative region of a single light and heavy chain of an antibody linked together by a disulfide bond); a camelized VH (e.g., the variable, antigen-binding determinative region of a single heavy chain of an antibody in which some amino acids at the VH interface are those found in the heavy chain of naturally occurring camel antibodies); a bispecific sFv (e.g., a sFv or a dsFv molecule having two antigen-binding domains, each of which may be directed to a different epitope); a diabody (e.g., a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (e.g., a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody comprises a single-chain Fv ("scFv"). scFvs are antibody fragments comprising the VH and VL domains of an antibody, wherein these domains are present in a single polypeptide chain. The scFv polypeptide may further comprise a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

4. Humanized Antibodies

The present disclosure provides humanized antibodies that bind beta klotho, including human and/or cyno beta klotho. Humanized antibodies of the present disclosure may comprise one or more CDRs as shown in Tables 1-10. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody.

In some cases, the humanized antibodies are constructed by CDR grafting, in which the amino acid sequences of the six complementarity determining regions (CDRs) of the parent non-human antibody (e.g., rodent) are grafted onto a human antibody framework. For example, Padlan et al. (*FASEB J.* 9:133-139, 1995) determined that only about one third of the residues in the CDRs actually contact the antigen, and termed these the "specificity determining residues," or SDRs. In the technique of SDR grafting, only the SDR residues are grafted onto the human antibody framework (see, e.g., Kashmiri et al., *Methods* 36: 25-34, 2005).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence which is closest to that of the rodent may be selected as the human framework for the humanized antibody (Sims et al. (1993) *J. Immunol.* 151:2296; Chothia et al. (1987) J. Mol. 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, 89:4285; Presta et al. (1993) *J. Immunol.*, 151:2623. In some cases, the framework is derived from the consensus sequences of the most abundant human subclasses, VL6 subgroup I (VL61) and VH subgroup III (VHIII). In another method, human germline genes are used at the source of the framework regions.

In an alternative paradigm based on comparison of CDRs, called Superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., *J. Immunol.* 169: 1119-1125, 2002).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, *Protein Eng.* 13: 819-824, 2000), Modeller (Sali and Blundell, *J. Mol. Biol.* 234: 779-815, 1993), and Swiss PDB Viewer (Guex and Peitsch, Electrophoresis 18: 2714-2713, 1997). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes and the differences are scored as HSC. The target sequence is then humanized by maximizing its HSC rather than using a global identity measure to generate multiple diverse humanized variants. (Lazar et al., *Mol. Immunol.* 44: 1986-1998, 2007).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome and yeast display libraries as well as by bacterial colony screening (see, e.g., Hoogenboom, *Nat. Biotechnol.* 23: 1105-1116, 2005; Dufner et al., *Trends Biotechnol.* 24: 523-529, 2006; Feldhaus et al., *Nat. Biotechnol.* 21: 163-70, 2003; Schlapschy et al., *Protein Eng. Des. Sel.* 17: 847-60, 2004).

In the FR library approach, a collection of residue variants are introduced at specific positions in the FR followed by selection of the library to select the FR that best supports the grafted CDR. The residues to be substituted may include some or all of the "Vernier" residues identified as potentially contributing to CDR structure (see, e.g., Foote and Winter, *J. Mol. Biol.* 224: 487-499, 1992), or from the more limited set of target residues identified by Baca et al. (*J. Biol. Chem.* 272: 10678-10684, 1997).

In FR shuffling, whole FRs are combined with the non-human CDRs instead of creating combinatorial libraries of selected residue variants (see, e.g., Dall'Acqua et al., Methods 36: 43-60, 2005). The libraries may be screened for binding in a two-step selection process, first humanizing VL, followed by VH. Alternatively, a one-step FR shuffling process may be used. Such a process has been shown to be more efficient than the two-step screening, as the resulting antibodies exhibited improved biochemical and physico-chemical properties including enhanced expression, increased affinity and thermal stability (see, e.g., Damschroder et al., *Mol. Immunol.* 44: 3049-60, 2007).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple sub-classes with distinct human V-segment CDRs. Humaneering allows for isolation of antibodies that are 91-96% homologous to human germline gene antibodies. (see, e.g., Alfenito, Cambridge Healthtech Institute's Third Annual PEGS, The Protein Engineering Summit, 2007).

The "human engineering" method involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or are substituted with human residues. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering, 7: 805-814 (1994), U.S. Pat. Nos. 5,766,886, 5,770,196, 5,821,123, and 5,869,619, and PCT Application Publication WO 93/11794.

5. Human Antibodies

Human anti-beta klotho antibodies can be constructed by combining Fv clone variable domain sequence(s) selected from human-derived phage display libraries with known human constant domain sequences(s). Alternatively, human monoclonal anti-beta klotho antibodies of the present disclosure can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is also possible to produce transgenic animals (e.g., mice) that are capable, upon immunization, of producing a full repertoire of human antibodies in the absence of endogenous immunoglobulin production. Transgenic mice that express human antibody repertoires have been used to generate high-affinity human sequence monoclonal antibodies against a wide variety of potential drug targets (see, e.g., Jakobovits, A., *Curr. Opin. Biotechnol.* 1995, 6(5):561-6; Bruggemann and Taussing, *Curr. Opin. Biotechnol.* 1997, 8(4):455-8; U.S. Pat. Nos. 6,075,181 and 6,150,584; and Lonberg et al., *Nature Biotechnol.* 23: 1117-1125, 2005).

Alternatively, the human antibody may be prepared via immortalization of human B lymphocytes producing an antibody directed against a target antigen (e.g., such B lymphocytes may be recovered from an individual or may have been immunized in vitro) (see, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373).

Gene shuffling can also be used to derive human antibodies from non-human, for example, rodent, antibodies, where the human antibody has similar affinities and specificities to the starting non-human antibody. According to this method, which is also called "epitope imprinting" or "guided selection", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, (e.g., the epitope guides (imprints) the choice of the human chain partner). When the process is repeated in order to replace the remaining non-human chain, a human antibody is obtained (see, e.g., PCT WO 93/06213; and Osbourn et al., Methods., 36, 61-68, 2005). Unlike traditional humanization of non-human antibodies by CDR grafting, this technique provides completely human antibodies, which have no FR or CDR residues of non-human origin. Examples of guided selection to humanize mouse antibodies towards cell surface antigens include the folate-binding protein present on ovarian cancer cells (see, e.g., Figini et al., *Cancer Res.*, 58, 991-996, 1998) and CD147, which is highly expressed on hepatocellular carcinoma (see, e.g., Bao et al., *Cancer Biol. Ther.*, 4, 1374-1380, 2005).

A potential disadvantage of the guided selection approach is that shuffling of one antibody chain while keeping the other constant could result in epitope drift. In order to maintain the epitope recognized by the non-human antibody, CDR retention can be applied (see, e.g., Klimka et al., *Br. J. Cancer.*, 83, 252-260, 2000; VH CDR2 Beiboer et al., *J. Mol. Biol.*, 296, 833-49, 2000) In this method, the non-human VH CDR3 is commonly retained, as this CDR may be at the center of the antigen-binding site and may be to be the most important region of the antibody for antigen recognition. In some instances, however, VH CDR3 and VL CDR3, as well as VH CDR3, VL CDR3 and VL CFR1, of the non-human antibody may be retained.

6. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for beta klotho and the other is for any other antigen. In some embodiments, one of the binding specificities is for beta klotho, and the other is for another surface antigen expressed on cells expressing beta klotho and a FGF receptor (e.g., FGFR1c, FGFR2c, FGFR3c, FGFR4). In certain embodiments, bispecific antibodies may bind to two different epitopes of beta klotho. Bispecific antibodies can be prepared as full length antibodies or antibody fragments (e.g., F(ab')2 bispecific antibodies).

Methods for making bispecific antibodies are known in the art, such as, for example, by co-expression of two immunoglobulin heavy chain-light chain pairs, where the two heavy chains have different specificities (see, e.g., Milstein and Cuello, *Nature,* 305: 537 (1983)). For further details of generating bispecific antibodies see, for example, Bispecific Antibodies, Kontermann, ed., Springer-Verlag, Hiedelberg (2011).

7. Multivalent Antibodies

A multivalent antibody may be internalized (and/or catabolized) faster than a bivalent antibody by a cell expressing an antigen to which the antibodies bind. The antibodies of the present disclosure can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Fc Engineering

It may be desirable to modify an antibody to beta klotho via Fc engineering, including, with respect to effector function, for example, so as to decrease or remove antigen-dependent cell-mediated cyotoxicity (ADCC) and/or complement dependent cytotoxicity (CDC) of the antibody. This may be achieved by introducing one or more amino acid substitutions in an Fc region of the antibody. For example, substitutions into human IgG1 using IgG2 residues as positions 233-236 and IgG4 residues at positions 327, 330 and 331 were shown to greatly reduce ADCC and CDC (see, e.g., Armour et al., *Eur. J. Immunol.* 29:(8):2613-24 (1999); Shields et al., *J. Biol. Chem.* 276(9): 6591-604 (2001).

To increase the serum half life of the antibody, one may incorporate a salvage receptor binding epitope into the antibody (especially an antibody fragment), for example, as described in U.S. Pat. No. 5,739,277. Term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

9. Alternative Binding Agents

The present disclosure encompasses non-immunoglobulin binding agents that specifically bind to the same epitope as an anti-beta klotho antibody disclosed herein. In some embodiments, a non-immunoglobulin binding agent is identified an agent that displaces or is displaced by an anti-beta klotho antibody of the present disclosure in a competitive binding assay. These alternative binding agents may include, for example, any of the engineered protein scaffolds known in the art. Such scaffolds may comprise one or more CDRs as shown in Tables 1-10. Such scaffolds include, for example, anticalins, which are based upon the lipocalin scaffold, a protein structure characterized by a rigid beta-barrel that supports four hypervariable loops which form the ligand binding site. Novel binding specificities may be engineered by targeted random mutagenesis in the loop regions, in combination with functional display and guided selection (see, e.g., Skerra (2008) *FEBS J.* 275: 2677-2683). Other suitable scaffolds may include, for example, adnectins, or monobodies, based on the tenth extracellular domain of human fibronectin III (see, e.g., Koide and Koide (2007) *Methods Mol. Biol.* 352: 95-109); affibodies, based on the Z domain of staphylococcal protein A (see, e.g., Nygren et al. (2008) *FEBS J.* 275: 2668-2676)); DARPins, based on ankyrin repeat proteins (see, e.g., Stumpp et al. (2008) *Drug. Discov. Today* 13: 695-701); fynomers, based on the SH3 domain of the human Fyn protein kinase Grabulovski et al. (2007) *J. Biol. Chem.* 282: 3196-3204); affitins, based on Sac7d from *Sulfolobus* acidolarius (see, e.g., Krehenbrink et al. (2008) *J. Mol. Biol.* 383: 1058-1068); affilins, based on human y-B-crystallin (see, e.g., Ebersbach et al. (2007) *J. Mol. Biol.* 372: 172-185); avimers, based on the A domains of membrane receptor proteins (see, e.g., Silverman et al. (2005) *Biotechnol.* 23: 1556-1561); cysteine-rich knottin peptides (see, e.g., Kolmar (2008) *FEBS J.* 275: 2684-2690); and engineered Kunitz-type inhibitors (see, e.g., Nixon and Wood (2006) *Curr. Opin. Drug. Discov. Dev.* 9: 261-268) For a review, see, for example, Gebauer and Skerra (2009) *Curr. Opin. Chem. Biol.* 13: 245-255.

Antibody Variants

In some embodiments, amino acid sequence modification(s) of the antibodies that bind to beta klotho or described herein are contemplated. For example, it may be desirable to improve the binding affinity and/or other biological properties of the antibody, including but not limited to specificity, thermostability, expression level, effector functions, glycosylation, reduced immunogenicity or solubility. This, in addition to the anti-beta klotho antibodies described herein, it is contemplated that anti-beta klotho antibody variants can be prepared. For example, anti-beta klotho antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-beta klotho antibody, such as changing the number or position of glycosylation sites or altering the membrane anchoring characteristics.

In some embodiments, antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited, to specific chemical cleavage, acetylation, formulation, metabolic synthesis of tunicamycin, etc. Additionally, the antibody may contain one or more non-classical amino acids.

Variations may be a substitution, deletion or insertion of one or more codons encoding the antibody or polypeptide that results in a change in the amino acid sequence as compared with the native sequence antibody or polypeptide. Amino acid substitutions can be the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In certain embodiments, the substitution, deletion or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the substitution is a conservative amino acid substitution made at one or more predicted non-essential amino acid residues. The variation allowed may be determined by systematically making insertions, deletions or substitutions of amino acids in the sequence and testing the resulting variants for activity exhibited by the full-length or mature native sequence.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for antibody-directed enzyme prodrug therapy) or a polypeptide which increases the serum half-life of the antibody.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Alternatively, conservative (e.g., within an amino acid group with similar properties and/or sidechains) substitutions may be made, so as to maintain or not significantly change the properties. Amino acids may be grouped according to similarities in the properties of their side chains (see, e.g., A. L. Lehninger, in *Biochemistry*, 2nd Ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His(H).

Alternatively, naturally occurring residues may be divided into groups based on common side-chain properties: (1) hydrophobic: Norleucine, Met, Ala, Val, Leu, Ile, (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions entail exchanging a member of one of these classes for another class. Such substituted residues also may be introduced into the conservative substitution sites or, into the remaining (non-conserved) sites. Accordingly, in one embodiment, an antibody or fragment thereof that binds to a beta klotho epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a murine monoclonal antibody described herein. In one embodiment, an antibody or fragment thereof that binds to a beta klotho epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in Tables 1-10. In yet another embodiment, an antibody or fragment thereof that binds to a beta klotho epitope comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence depicted in Tables 1-10 and/or a VL CDR amino acid sequence depicted in Tables 1-10. The variations can be made using methods known in the art such as oligonucleotide-mediated (site-directed) mutagenesis, alanine scanning, and PCR mutagenesis. Site-directed mutagenesis (see, e.g., Carter et al., *Nucl. Acids Res.*, 13:4331 (1986); Zoller et al., *Nucl. Acids Res.*, 10:6487 (1987)), cassette mutagenesis (see, e.g., Wells et al., *Gene,* 34:315 (1985)), restriction selection mutagenesis (see, e.g., Wells et al., *Philos. Trans. R. Soc. London SerA,* 317:415 (1986)) or other known techniques can be performed on the cloned DNA to produce the anti-beta klotho antibody variant DNA.

Any cysteine residue not involved in maintaining the proper conformation of the anti-beta klotho antibody also may be substituted, for example, with another amino acid such as alanine or serine, to improve the oxidative stability of the molecule and prevent aberrant crosslinking. Conversely, cysteine bond(s) may be added to the anti-beta klotho antibody to improve its stability (e.g., where the antibody is an antibody fragment such as an Fv fragment).

In some embodiments, an anti-beta klotho antibody molecule of the present disclosure is a "de-immunized" antibody. A "de-immunized" anti-beta klotho antibody is an antibody derived from a humanized or chimeric anti-beta klotho antibody, that has one or more alterations in its amino acid sequence resulting in a reduction of immunogenicity of the antibody, compared to the respective original non-de-immunized antibody. One of the procedures for generating such antibody mutants involves the identification and removal of T-cell epitopes of the antibody molecule. In a first step, the immunogenicity of the antibody molecule can be determined by several methods, for example, by in vitro determination of T-cell epitopes or in silico prediction of such epitopes, as known in the art. Once the critical residues for T-cell epitope function have been identified, mutations can be made to remove immunogenicity and retain antibody activity. For review, see, for example, Jones et al., Methods in Molecular Biology 525: 405-423, 2009.

1. In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed as Fab, scFv or V domain fragments either on the surface of an organism (e.g., phage, bacteria, yeast or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Preferred affinity matured antibodies will have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and infected in bacteria to produce phage for further rounds of selection. For review, see, for example, Hoogenboom, Methods. Mol. Biol. 178: 1-37, 2002; Bradbury and Marks, *J. Immuno. Methods* 290: 29-49, 2004).

In a yeast display system (see, e.g., Boder et al., *Nat. Biotech.* 15: 553-57, 1997; Chao et al., *Nat. Protocols* 1:755-768, 2006), the antibody may be displayed as single-chain variable fusions (scFv) in which the heavy and light chains are connected by a flexible linker. The scFv is fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the scFv. Expression has been shown to correlate with the stability of the displayed protein, and thus antibodies can be selected for improved stability as well as affinity (see, e.g., Shusta et al., *J. Mol. Biol.* 292: 949-956, 1999). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently 'titrated' while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., US Patent Publication 2003/0186,374; Blaise et al., *Gene* 342: 211-218, 2004).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reversed transcribed back into cDNA, which can then undergo mutagenesis and be used in the next round of selection (see, e.g., Fukuda et al., *Nucleic Acids Res.* 34, e127, 2006). In mRNA display, a covalent bond between antibody and mRNA is established using puromycin as an adaptor molecule (Wilson et al., *Proc. Natl. Acad. Sci. USA* 98, 3750-3755, 2001).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

Diversity may be introduced into the CDRs or the whole V genes of the antibody libraries in a targeted manner or via random introduction. The former approach includes sequentially targeting all the CDRs of an antibody via a high or low level of mutagenesis or targeting isolated hot spots of somatic hypermutations (see, e.g., Ho, et al., *J. Biol. Chem.* 280: 607-617, 2005) or residues suspected of affecting affinity on experimental basis or structural reasons. Random mutations can be introduced throughout the whole V gene using *E. coli* mutator strains, error-prone replication with DNA polymerases (see, e.g., Hawkins et al., *J. Mol. Biol.* 226: 889-896, 1992) or RNA replicases. Diversity may also be introduced by replacement of regions that are naturally diverse via DNA shuffling or similar techniques (see, e.g., Lu et al., *J. Biol. Chem.* 278: 43496-43507, 2003; U.S. Pat. Nos. 5,565,332; 6,989,250). Alternative techniques target hypervariable loops extending into framework-region residues (see, e.g., Bond et al., *J. Mol. Biol.* 348: 699-709, 2005) employ loop deletions and insertions in CDRs or use hybridization-based diversification (see, e.g., US Patent Publication No. 2004/0005709). Additional methods of generating diversity in CDRs are disclosed, for example, in U.S. Pat. No. 7,985,840.

Screening of the libraries can be accomplished by various techniques known in the art. For example, beta klotho can be immobilized onto solid supports, columns, pins or cellulose/poly(vinylidene fluoride) membranes/other filters, expressed on host cells affixed to adsorption plates or used in cell sorting, or conjugated to biotin for capture with streptavidin-coated beads, or used in any other method for panning display libraries.

For review of in vitro affinity maturation methods, see, e.g., Hoogenboom, *Nature Biotechnology* 23: 1105-1116, 2005 and Quiroz and Sinclair, Revista Ingeneria Biomedia 4: 39-51, 2010 and references therein.

2. Modifications of Anti-Beta Klotho Antibodies

Covalent modifications of anti-beta klotho antibodies are included within the scope of the present disclosure. Covalent modifications include reacting targeted amino acid residues of an anti-beta klotho antibody with an organic derivatizing agent that is capable of reacting with selected side chains or the N- or C-terminal residues of the anti-beta klotho antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., T. E. Creighton, *Proteins: Structure and Molecular Properties*, W. H. Freeman & Co., San Francisco, pp. 79-86 (1983)), acetylation of the N-terminal amine, and amidation of any C-terminal carboxyl group.

Other types of covalent modification of the anti-beta klotho antibody included within the scope of this present disclosure include altering the native glycosylation pattern of the antibody or polypeptide (see, e.g., Beck et al., *Curr. Pharm. Biotechnol.* 9: 482-501, 2008; Walsh, *Drug Discov. Today* 15: 773-780, 2010), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192 or 4,179,337.

An anti-beta klotho antibody of the present disclosure may also be modified to form chimeric molecules comprising an anti-beta klotho antibody fused to another, heterologous polypeptide or amino acid sequence, for example, an epitope tag (see, e.g., Terpe, *Appl. Microbiol. Biotechnol.* 60: 523-533, 2003) or the Fc region of an IgG molecule (see, e.g., Aruffo, "Immunoglobulin fusion proteins" in Antibody Fusion Proteins, S. M. Chamow and A. Ashkenazi, eds., Wiley-Liss, New York, 1999, pp. 221-242).

Also provided herein are fusion proteins comprising an antibody provided herein that binds to a beta klotho antigen and a heterologous polypeptide. In some embodiments, the heterologous polypeptide to which the antibody is fused is useful for targeting the antibody to cells having cell surface-expressed beta klotho.

Also provided herein are panels of antibodies that bind to a beta klotho antigen. In specific embodiments, panels of antibodies have different association rate constants different dissociation rate constants, different affinities for beta klotho antigen, and/or different specificities for a beta klotho antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96 well or 384 well plates, such as for assays such as ELISAs.

Preparation of Anti-Beta Klotho Antibodies

Anti-beta klotho antibodies may be produced by culturing cells transformed or transfected with a vector containing anti-beta klotho antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression and purification are further described, in Plückthun et al., (1996) in *Antibody Engineering: Producing antibodies in Escherichia coli: From PCR to fermentation* (McCafferty, J., Hoogenboom, H. R., and Chiswell, D. J., eds), 1 Ed., pp. 203-252, IRL Press, Oxford; Kwong, K. & Rader, C., E. coli expression and purification of Fab antibody fragments, Current protocols in protein science editorial board John E Coligan et al., Chapter 6, Unit 6.10 (2009); Tachibana and Takekoshi, "Production of Antibody Fab Fragments in *Escherichia coli*," in *Antibody Expression and Production*, M. Al-Rubeai, Ed., Springer, New York, 2011; *Therapeutic Monoclonal Antibodies: From Bench to Clinic* (ed Z. An), John Wiley & Sons, Inc., Hoboken, N.J., USA.

It is, of course, contemplated that alternative methods, which are well known in the art, may be employed to prepare anti-beta klotho antibodies. For instance, the appropriate amino acid sequence, or portions thereof, may be produced by direct peptide synthesis using solid-phase techniques (see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)). In vitro protein synthesis may be performed using manual techniques or by automation. Various portions of the anti-beta klotho antibody may be chemically synthesized separately and combined using chemical or enzymatic methods to produce the desired anti-beta klotho antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

Immunoconjugates

The present disclosure also provides conjugates comprising any one of the anti-beta klotho antibodies of the present disclosure covalently bound by a synthetic linker to one or more non-antibody agents.

A variety of radioactive isotopes are available for the production of radioconjugated antibodies. Examples include $At^{211}$, I4, I4, Y4, Re4, Re4, Sm4, Bi4, P4, Pb4 and radioactive isotopes of Lu. When the conjugate is used for detection, it may comprise a radioactive atom for scintigraphic studies, for example tc4 or I4, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron. The radioisotopes may be incorporated in the conjugate in known ways as described, e.g., in Reilly, "The radiochemistry of monoclonal antibodies and peptides," in Monoclonal Antibody and Peptide-Targeted Radiotherapy of Cancer, R. M. Reilly, ed., Wiley, Hoboken N.J., 2010.

In some embodiments, antibodies provided herein are conjugated or recombinantly fused to a diagnostic, detectable or therapeutic agent or any other molecule. The conjugated or recombinantly fused antibodies can be useful, for example, for monitoring or prognosing the onset, development, progression and/or severity of a beta klotho-mediated disease as part of a clinical testing procedure, such as determining the efficacy of a particular therapy.

Such diagnosis and detection can accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; chemiluminescent material, such as but not limited to, an acridinium based compound or a HALOTAG; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium (Ti), gallium ($^{68}$Ga, $^{67}$Ga), palladium ($^{193}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$5c, $^{186}$Re, $^{188}$Re, $^{142}$Pr, $^{105}$Rh, $^{97}$Ru, $^{68}$Ge, $^{57}$Co, $^{65}$Zn, $^{86}$Sr, $^{32}$P, $^{153}$Gd, $^{169}$Yb, $^{51}$Cr, $^{54}$Mn, $^{75}$Se, $^{113}$Sn, and $^{117}$Sn, and positron emitting metals using various positron emission tomographies, and non-radioactive paramagnetic metal ions.

Also provided herein are antibodies that are conjugated or recombinantly fused to a therapeutic moiety (or one or more therapeutic moieties), as well as uses thereof. The antibody may be conjugated or recombinantly fused to a therapeutic moiety, including a cytotoxin such as a cytostatic or cytocidal agent, a therapeutic agent or a radioactive metal ion such as alpha-emitters. A cytotoxin or cytotoxic agent includes any agent that is detrimental to cells.

Further, an antibody provided herein may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, e.g., International Publication No. WO 97/33899), AIM II (see, e.g., International Publication No. WO 97/34911), Fas Ligand (see, e.g., Takahashi et al., 1994, J. Immunol., 6:1567-1574), and VEGF (see, e.g., International Publication No. WO 99/23105), an anti-angiogenic agent, including, for example angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90 or about 100 amino acids) to generate fusion proteins, as well as uses thereof. In particular, provided herein are fusion proteins comprising an antigen-binding fragment of an antibody provided herein (e.g., a Fab fragment, Fd fragment, Fv fragment, F(ab)$_2$ fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses beta klotho or an beta klotho receptor. For example, an antibody that binds to a cell surface receptor expressed by a particular cell type (e.g., an immune cell) may be fused or conjugated to a modified antibody provided herein.

In addition, an antibody provided herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7, 10-tetraazacyclododecane-N,N',N'',N'''-tetraacetic acid (DOTA) which can be attached to the antibody via a linker molecule. Such linker molecules are commonly known in the art and described, for example, in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50.

Moreover, antibodies provided herein can be fused to marker or "tag" sequences, such as a peptide to facilitate purification. In specific embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-824, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of anti-beta klotho antibodies as provided herein, including, for example, antibodies with higher affinities and lower dissociation rates (see, e.g., U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313). Antibodies, or the encoded antibodies, may be altered by being subjected to random mutagenesis by error-prone PCR, random nucleotide insertion or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described, for example, in U.S. Pat. No. 4,676,980.

The therapeutic moiety or drug conjugated or recombinantly fused to an antibody provided herein that binds to beta klotho (e.g., a beta klotho polypeptide, fragment, epitope) should be chosen to achieve the desired prophylactic or therapeutic effect(s). In certain embodiments, the antibody is a modified antibody. A clinician or other medical personnel may consider, for example, the following when deciding on which therapeutic moiety or drug to conjugate or recombinantly fuse to an antibody provided herein: the nature of the disease, the severity of the disease, and the condition of the subject.

Antibodies that bind to beta klotho as provided herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The linker may be a "cleavable linker" facilitating release of the conjugated agent in the cell, but non-cleavable linkers are also contemplated herein. Linkers for use in the conjugates of the present disclosure include without limitation acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (see, e.g., Chari et al., Cancer Research 52:127-131 (1992); U.S. Pat. No. 5,208,020), thioether linkers, or hydrophilic linkers designed to evade multidrug transporter-mediated resistance (see, e.g. Kovtun et al., Cancer Res. 70: 2528-2537, 2010).

Conjugates of the antibody and agent may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate). The present disclosure further contemplates that conjugates of antibodies and agents may be prepared using any suitable methods as disclosed in the art, (see, e.g., in Bioconjugate Techniques, 2nd Ed., G. T. Hermanson, ed., Elsevier, San Francisco, 2008).

Conventional conjugation strategies for antibodies and agents have been based on random conjugation chemistries involving the ε-amino group of Lys residues or the thiol group of Cys residues, which results in heterogenous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding or assembly or alter antigen binding (see, e.g., Junutula et al., J. Immunol. Meth. 332: 41-52 (2008); Junutula et al., Nat. Biotechnol. 26: 925-932, 2008). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., Proc. Natl. Acad. Sci. USA 105: 12451-12456 (2008); Hofer et al., Biochemistry 48(50): 12047-12057, 2009).

Pharmaceutical Formulations

Anti-beta klotho antibodies of the present disclosure may be administered by any route appropriate to the condition to be treated. The antibody will typically be administered parenterally, for example, infusion, subcutaneous, intramuscular, intravenous, intradermal, intrathecal and epidural. The antibody dose will vary, including depending on the nature and/or severity of the disease as well as the condition of the subject, may include doses between 1 mg and 100 mg. Doses may also include those between 1 mg/kg and 15 mg/kg. In some embodiments, the dose is between about 5 mg/kg and about 7.5 mg/kg. In some embodiments, the dose is about 5 mg/kg. In some embodiments, the dose is about 7.5 mg/kg. Flat doses selected from the group consisting of: (a) 375-400 mg every two weeks and (b) 550-600 mg every three weeks. In some embodiments, the flat dose is 375-400 mg every two weeks. In some embodiments, the flat dose is 550-600 mg every three weeks. In some embodiments the flat dose is 400 mg every two weeks. In some embodiments the flat dose is 600 mg every three weeks. In some embodiments of sequential dosing, a first dose and a second dose are each between 1 mg/kg and 15 mg/kg with the second dose following the first does by between 1 and 4 weeks. In some embodiments, the first dose and the second dose are each between 5 mg/kg and 7.5 mg/kg and the second dose follows the first dose by between 2 and 3 weeks. In some embodiments, the first dose and the second dose are each 5 mg/kg and the second dose follows the first dose by 2 weeks. In some embodiments, the first dose and the second dose are each 7.5 mg/kg and the second dose follows the first dose by 3 weeks.

For treating diseases, disorders and conditions, the antibody in some embodiments is administered via intravenous infusion. The dosage administered via infusion is in the range of about 1 $\mu g/m^2$ to about 10,000 $\mu g/m^2$ per dose, generally one dose per week for a total of one, two, three or four doses. Alternatively, the dosage range is of about 1 $\mu g/m^2$ to about 1000 $\mu g/m^2$, about 1 $\mu g/m^2$ to about 800 $\mu g/m^2$, about 1 $\mu g/m^2$ to about 600 $\mu g/m^2$, about 1 $\mu g/m^2$ to about 400 $\mu g/m^2$; alternatively, about 10 $\mu g/m^2$ to about 500 $\mu g/m^2$, about 10 $\mu g/m^2$ to about 300 $\mu g/m^2$, about 10 $\mu g/m^2$ to about 200 $\mu g/m^2$, and about 1 $\mu g/m^2$ to about 200 $\mu g/m^2$. The dose may be administered once per day, once per week, multiple times per week, but less than once per day, multiple times per month but less than once per day, multiple times per month but less than once per week, once per month or intermittently to relieve or alleviate symptoms of the disease, disorder, or condition. Administration may continue at any of the disclosed intervals until amelioration of the disease, disorder or condition, or amelioration of symptoms of the disease, disorder or condition being treated. Administration may continue after remission or relief of symptoms is achieved where such remission or relief is prolonged by such continued administration.

In one aspect, the present disclosure further provides pharmaceutical formulations comprising at least one anti-beta klotho antibody of the present disclosure. In some embodiments, a pharmaceutical formulation comprises 1) an anti-beta klotho antibody, and 2) a pharmaceutically acceptable carrier. In some embodiments, a pharmaceutical formulation comprises 1) an anti-beta klotho antibody and/or an immunoconjugate thereof, and optionally, 2) at least one additional therapeutic agent.

Pharmaceutical formulations comprising an antibody is prepared for storage by mixing the antibody having the desired degree of purity with optional physiologically acceptable carriers, excipients or stabilizers (see, e.g., Remington's Pharmaceutical Sciences 16th edition, Osol, A. Ed. (1980)) in the form of aqueous solutions or lyophilized or other dried formulations. The formulations herein may also contain more than one active compound as necessary for the particular indication being treated, preferably those with complementary activities that do not adversely affect each other. For example, in addition to an anti-beta klotho antibody, it may be desirable to include in the one formulation, an additional antibody, e.g., a second anti-beta klotho antibody which binds a different epitope on the beta klotho polypeptide, or an antibody to some other target. Alternatively, or additionally, the composition may further comprise another agent, including, for example, a chemotherapeutic agent, cytotoxic agent, cytokine, growth inhibitory agent, anti-hormonal agent, and/or cardioprotectant. In some embodiments the formulation includes an alkylating agent (e.g., chlorambucil, bendamustine hydrochloride or cyclophosphamide) a nucleoside analog (e.g., fludurabine, pentostatin, cladribine or cytarabine) a corticosteroid (e.g., prednisone, prednisolone or methylprednisolone), an immunomodulatory agent (e.g., lenalidomide), an antibiotic (e.g., doxorubicin, daunorubicin idarubicin or mitoxentrone), a synthetic flavon (e.g., flavopiridol), a Bcl2 antagonist, (e.g., oblimersen or ABT-263), a hypomethylating agent (e.g., azacytidine or decitabine), an FLT3 inhibitor (e.g., midostaurin, sorafenib and AC220). Such molecules are suitably present in combination in amounts that are effective for the purpose intended.

The antibodies of the present disclosure may be formulated in any suitable form for delivery to a target cell/tissue, e.g., as microcapsules or macroemulsions (Remington's *Pharmaceutical Sciences,* 16th edition, Osol, A. Ed. (1980); Park et al., *Molecules* 10: 146-161 (2005); Malik et al., *Curr. Drug. Deliv.* 4: 141-151 (2007)); as sustained release formulations (Putney and Burke, *Nature Biotechnol.* 16: 153-157, (1998)) or in liposomes (Maclean et al., *Int. J. Oncol.* 11: 235-332 (1997); Kontermann, *Curr. Opin. Mol. Ther.* 8: 39-45 (2006)).

An antibody provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed, for example, in Remington's Pharmaceutical Sciences (1990) Mack Publishing Co., Easton, Pa.

Various delivery systems are known and can be used to administer a prophylactic or therapeutic agent (e.g., an antibody that binds to beta klotho as described herein), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. In another embodiment, a prophylactic or therapeutic agent, or a composition provided herein can be delivered in a controlled release or sustained release system. In one embodiment, a pump may be used to achieve controlled or sustained release (see, e.g., Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibody that binds to beta klotho as described herein) or a composition of the invention (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of the therapeutic target, for example, the nasal passages or lungs, thus requiring only a fraction of the systemic dose (see, e.g., Goodson, in Medical Applications of Controlled Release, supra, vol. 2, pp. 115-138 (1984)). Controlled release systems are discussed, for example, by Langer (1990, Science 249:1527-1533). Any technique known to one of skill in the art can be used to produce sustained release formulations comprising one or more antibodies that bind to beta klotho as described herein. (See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760).

Therapeutic Methods

An antibody of the present disclosure may be used in, for example, in vitro, ex vivo, and in vivo therapeutic methods. In one aspect, the present disclosure provides methods for treating or preventing a disease, disorder, or condition, either in vivo or in vitro, the method comprising exposing a cell to an anti-beta klotho antibody.

In one aspect, an antibody of the present disclosure is used to treat or prevent a disease, disorder, or condition, including, for example, Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21.

In one aspect, methods are provided for treating a disease, disorder or condition comprising administering to an individual an effective amount of an anti-beta klotho antibody or fragment thereof. In certain embodiments, a method for treating a disease, disorder, or condition comprises administering to an individual an effective amount of a pharmaceutical formulation comprising an anti-beta klotho antibody and, optionally, at least one additional therapeutic agent, such as those described herein.

An anti-beta klotho antibody or fragment thereof can be administered to a human for therapeutic purposes. Moreover, an anti-beta klotho antibody or fragment thereof can be administered to a non-human mammal expressing beta klotho with which the antibody cross-reacts (e.g., a primate, pig, rat, or mouse) for veterinary purposes or as an animal model of human disease. Regarding the latter, such animal models may be useful for evaluating the therapeutic efficacy of antibodies of the present disclosure (e.g., testing of dosages and time courses of administration).

Antibodies of the present disclosure can be used either alone or in combination with other compositions in a therapy. For example, an anti-beta klotho antibody of the present disclosure may be co-administered with at least one additional therapeutic agent and/or adjuvant. In some embodiments, the additional compound is a therapeutic antibody other than an anti-beta klotho antibody.

Such combination therapies noted above encompass combined administration (where two or more therapeutic agents are included in the same or separate formulations), and separate administration, in which case, administration of an anti-beta klotho antibody or fragment thereof of the present disclosure can occur prior to, simultaneously, and/or following, administration of the additional therapeutic agent and/or adjuvant. Antibodies of the present disclosure can also be used in combination with additional therapeutic regimens including, without limitation, those described herein.

An antibody of the present disclosure (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody or conjugate is suitably administered by pulse infusion, particularly with declining doses of the antibody or fragment thereof. Dosing can be by any suitable route, for example, by injections, such as intravenous or subcutaneous injections, depending in part on whether the administration is brief or chronic.

Antibodies of the present disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The anti-beta klotho antibody need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a disease, disorder, or condition, the appropriate dosage of an anti-beta klotho antibody of the present disclosure (when used alone or in combination with one or more other additional therapeutic agents, such as agents described herein) will depend on the type of disease, disorder, or condition, to be treated, the type of antibody, the severity and course of the disease, disorder, or condition, whether the antibody is administered for preventive or therapeutic purposes, previous therapy, the patient's clinical history and response to the antibody, and the discretion of the attending physician. The anti-beta klotho antibody is suitably administered to the patient at one time or over a series of treatments. Depending on the type and severity of the disease, about 1 µg/kg to 100 mg/kg (e.g., 0.1 mg/kg-20 mg/kg, 1 mg/kg-15 mg/kg, etc.) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Exemplary dosages of the antibody may be in the range from about 0.05 mg/kg to about 10.0 mg/kg. Thus, one or more doses of about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, or 10.0 mg/kg (or any combination thereof) of antibody may be administered to the patient. Such doses may be administered intermittently, e.g., every week or every three weeks (e.g., such that the patient receives from about two to about twenty, or e.g., about six doses of the antibody). An initial higher loading dose, followed by one or more lower doses may be administered. An exemplary dosing regimen comprises administering an initial loading dose, followed by a maintenance dose (e.g., weekly) of the antibody. The initial loading dose may be greater than the maintenance dose. However, other dosage regimens may be useful. The progress of this therapy is easily monitored by conventional techniques and assays.

Diagnostic Methods and Methods of Detection

In one aspect, anti-beta klotho antibodies and fragments thereof of the present disclosure are useful for detecting the presence of beta klotho in a biological sample. Such anti-beta klotho antibodies may include those that bind to human and/or cyno beta klotho, but do not induce FGF19-like signaling and/or FGF21-like signaling activity. The term "detecting" as used herein encompasses quantitative or qualitative detection. In certain embodiments, a biological sample comprises a cell or tissue.

In one aspect, the present disclosure provides a method of detecting the presence of beta klotho in a biological sample. In certain embodiments, the method comprises contacting the biological sample with an anti-beta klotho antibody under conditions permissive for binding of the anti-beta klotho antibody to beta klotho, and detecting whether a complex is formed between the anti-beta klotho antibody and beta klotho.

In one aspect, the present disclosure provides a method of diagnosing a disorder associated with expression of beta klotho. In certain embodiments, the method comprises contacting a test cell with an anti-beta klotho antibody; determining the level of expression (either quantitatively or qualitatively) of beta klotho by the test cell by detecting binding of the anti-beta klotho antibody to beta klotho; and comparing the level of expression of beta klotho by the test cell with the level of expression of beta klotho by a control cell (e.g., a normal cell of the same tissue origin as the test cell or a cell that expresses beta klotho at levels comparable to such a normal cell), wherein a higher level of expression of beta klotho by the test cell as compared to the control cell indicates the presence of a disorder associated with increased expression of beta klotho. In certain embodiments, the test cell is obtained from an individual suspected of having a disease, disorder or condition associated with expression of beta klotho and/or a disease, disorder or condition in which it is desirable to mimic or augment the in vivo effects of FGF19 and/or FGF21. In certain embodiments, the disease, disorder or condition is, for example, Type 2 diabetes, obesity, dyslipidemia, NASH, cardiovascular disease or metabolic syndrome. Such exemplary diseases, disorders or conditions may be diagnosed using an anti-beta klotho antibody of the present disclosure.

In certain embodiments, a method of diagnosis or detection, such as those described above, comprises detecting binding of an anti-beta klotho antibody to beta klotho expressed on the surface of a cell or in a membrane preparation obtained from a cell expressing beta klotho on its surface. In certain embodiments, the method comprises contacting a cell with an anti-beta klotho antibody under conditions permissive for binding of the anti-beta klotho antibody to beta klotho, and detecting whether a complex is formed between the anti-beta klotho antibody and beta klotho on the cell surface. An exemplary assay for detecting binding of an anti-beta klotho antibody to beta klotho expressed beta klotho on the surface of a cell is a "FACS" assay.

Certain other methods can be used to detect binding of anti-beta klotho antibodies to beta klotho. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-beta klotho antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, for example, through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, for example, firefly luciferase and bacterial luciferase (see, e.g., U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, anti-beta klotho antibodies are immobilized on an insoluble matrix. Immobilization entails separating the anti-beta klotho antibody from any beta klotho that remains free in solution. This conventionally is accomplished by either insolubilizing the anti-beta klotho antibody before the assay procedure, as by adsorption to a water-insoluble matrix or surface (see, e.g., Bennich et al., U.S. Pat. No. 3,720,760), or by covalent coupling (for example, using glutaraldehyde cross-linking), or by insolubilizing the anti-beta klotho antibody after formation of a complex between the anti-beta klotho antibody and beta klotho, for example, by immunoprecipitation.

Any of the above embodiments of diagnosis or detection may be carried out using an immunoconjugate of the present disclosure in place of or in addition to an anti-beta klotho antibody.

Assays

Anti-beta klotho antibodies of the present disclosure may be characterized for their physical/chemical properties and/or biological activities by various assays known in the art.

1. Activity Assays

In one aspect, assays are provided for identifying anti-beta klotho antibodies thereof having biological activity. Biological activity may include, for example, assays which measure effects on glucose and/or lipid metabolism. For example, a blood glucose assay may be used. Blood glucose (e.g., in mouse tail snip or in a human blood sample) may be measured using ACCU-CHEK Active test strips read by ACCU-CHEK Active meter (Roche Diagnostics, Indianapolis, Ind.) following manufacturer's instruction. In addition, for example, a lipid profile assay may be used. Whole blood (e.g., from mouse tail snips or from a human blood sample) may be collected into plain capillary tubes (BD Clay Adams SurePrep, Becton Dickenson and Co. Sparks, Md.). Serum and blood cells can be separated by spinning the tubes in an Autocrit Ultra 3 (Becton Dickinson and Co. Sparks, Md.). Serum samples can be assayed for lipid profile (triglyceride, total cholesterol, HDL, and non-HDL) using Integra 400 Clinical Analyzer (Roche Diagnostics, Indianapolis, Ind.) following the manufacturer's instructions.

2. Binding Assays and Other Assays

In one aspect, an anti-beta klotho antibody is tested for its antigen binding activity. For example, in certain embodiments, an anti-beta klotho antibody is tested for its ability to bind to exogenous or endogenous beta klotho expressed on the surface of a cell. A FACS assay may be used for such testing.

A panel of monoclonal antibodies raised against beta klotho may be grouped based upon the epitiopes they recognize, a process known as epitope binning. Epitope binning is typically carried out using competition assays, which evaluate an antibody's ability to bind to an antigen in the presence of another antibody. In an exemplary competition assay, immobilized beta klotho is incubated in a solution comprising a first labeled antibody that binds to beta klotho and a second unlabeled antibody that is being tested for its ability to compete with the first antibody for binding to beta klotho. The second antibody may be present in a hybridoma supernatant. As a control, immobilized beta klotho is incubated in a solution comprising the first labeled antibody but not the second unlabeled antibody. After incubation under conditions permissive for binding of the first antibody to beta klotho, excess unbound antibody is removed, and the amount of label associated with immobilized beta klotho is measured. If the amount of label associated with immobilized beta klotho is substantially reduced in the test sample relative to the control sample, then that indicates that the second antibody is competing with the first antibody for binding to beta klotho. In certain embodiments, immobilized beta klotho is present on the surface of a cell or in a membrane preparation obtained from a cell expressing beta klotho on its surface.

High-throughput methods of epitope binning are also known in the art (see, e.g., Jia et al., *J. Immunol. Methods* 2004, 288(1-2):91-98, describing a method of multiplexed competitive antibody binning for the characterization of monoclonal antibodies; and Miller et al., *J. Immunol. Methods* 2011, 365(1-2):118-25, describing epitope binning of murine monoclonal antibodies by a multiplexed pairing assay).

3. Epitope Mapping

Epitope mapping is the process of identifying the binding sites, or epitopes, of an antibody on its target protein antigen. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

A variety of methods are known in the art for mapping antibody epitopes on target protein antigens. These include mutagenesis methods, peptide scanning methods, display methods, methods involving and mass spectroscopy, and structural determination.

The site directed mutagenesis method involves targeted site-directed mutagenesis where critical amino acids are identified by systematically introducing substitutions along the protein sequence and then determining the effects of each substitution on antibody binding. This may be done by "alanine scanning mutagenesis," as described, for example, by Cunningham and Wells (1989) *Science* 244: 1081-1085, or some other form of point mutagenesis of amino acid residues in human beta klotho. Mutagenesis studies, however, may also reveal amino acid residues that are crucial to the overall three-dimensional structure of beta klotho but that are not directly involved in antibody-antigen contacts, and thus other methods may be necessary to confirm a functional epitope determined using this method.

Shotgun mutagenesis mapping utilizes a comprehensive plasmid-mutation library for the target gene, with each clone in the library bearing a unique amino acid mutation and the entire library covering every amino acid in the target protein. The clones that constitute the mutation library are individually arranged in microplates, expressed within living mammalian cells, and tested for immunoreactivity with antibodies of interest. Amino acids critical for antibody epitopes are identified by a loss of reactivity and are then mapped onto a protein structure to visualize epitopes. By automating the analysis, new epitope maps can be derived within days to weeks. Because it uses the native structure of proteins within mammalian cells, the technique allows both linear and conformational epitope structures to be mapped on complex proteins. (See, e.g., Paes et al., *J. Am. Chem. Soc.* 131(20): 6952-6954 (2009); Banik and Doranz, *Genetic Engineering and Biotechnology News* 3(2): 25-28 (2010)).

The epitope bound by an anti-beta klotho antibody may also be determined using peptide scanning methods. In peptide scanning, libraries of short peptide sequences from overlapping segments of the target protein, beta klotho, are tested for their ability to bind antibodies of interest. The peptides are synthesized and screened for binding, e.g., using ELISA or BIACORE, or on a chip, by any of the multiple methods for solid-phase screening (see, e.g., Reineke et al., *Curr. Opin. Biotechnol.* 12: 59-64, 2001) as in the "pepscan" methodology (see, e.g., WO 84/03564; WO 93/09872). Such peptide screening methods may not be capable of detecting some discontinuous functional epitopes, i.e. functional epitopes that involve amino acid residues that are not contiguous along the primary sequence of the beta klotho polypeptide chain.

A recently developed technology termed CLIPS (chemical linkage of peptides onto scaffolds) may be used to map conformational epitopes. The loose ends of the peptides are affixed onto synthetic scaffolds, so that the scaffolded peptide may be able to adopt the same spatial structure as the corresponding sequence in the intact protein. CLIPS technology is used to fix linear peptides into cyclic structures ('single-loop' format), and to bring together different parts of a protein binding site ('double-loop', 'triple-loop', etc. format), so as to create conformational epitopes that may be assayed for antibody binding (see, e.g., U.S. Pat. No. 7,972, 993).

The epitopes bound by antibodies of the present disclosure may also be mapped using display techniques, including, for example, phage display, microbial display, and ribosome/mRNA display as described above. In these methods, libraries of peptide fragments are displayed on the surface of the phage or cell. Epitopes are then mapped by screening mAbs against these fragments using selective binding assays. A number of computational tools have been developed which allow the prediction of conformational epitopes based upon linear affinity-selected peptides obtained using phage display (see, e.g., Mayrose et al., *Bioinformatics* 23: 3244-3246, 2007). Methods are also available for the detection of conformational epitopes by phage display. Microbial display systems may also be used to express properly folded antigenic fragments on the cell surface for identification of conformational epitopes (see, e.g., Cochran et al., *J. Immunol. Meth.* 287: 147-158, 2004; Rockberg et al., *Nature Methods* 5: 1039-1045, 2008).

Methods involving proteolysis and mass spectroscopy may also be used to determine antibody epitopes (see, e.g., Baerga-Ortiz et al., *Protein Sci.* 2002 June; 11(6): 1300-1308). In limited proteolysis, the antigen is cleaved by different proteases, in the presence and in the absence of the antibody, and the fragments are identified by mass spectrometry. The epitope is the region of the antigen that becomes protected from proteolysis upon binding of the antibody (see, e.g., Suckau et al., *Proc. Natl. Acad. Sci. USA* 87:9848-9852, 1990). Additional proteolysis based methods include, for example, selective chemical modification (see, e.g., Fiedler et al., *Bioconjugate Chemistry* 1998, 9(2): 236-234, 1998), epitope excision (see, e.g., Van de Water et al., *Clin. Immunol. Immunopathol.* 1997, 85(3): 229-235, 1997), and the recently developed method of hydrogen-deuterium (H/D) exchange (see, e.g., Flanagan, N., *Genetic Engineering and Biotechnology News* 3(2): 25-28, 2010).

The epitope bound by antibodies of the present disclosure may also be determined by structural methods, such as X-ray crystal structure determination (see, e.g., WO 2005/044853), molecular modeling and nuclear magnetic resonance (NMR) spectroscopy, including NMR determination of the H-D exchange rates of labile amide hydrogens when free and when bound in a complex with an antibody of interest (see, e.g., Zinn-Justin et al. (1992) *Biochemistry* 31:11335-11347; Zinn-Justin et al. (1993) *Biochemistry* 32:6884-6891).

Additional antibodies binding to the same epitope as an antibody of the present disclosure may be obtained, for example, by screening of antibodies raised against beta klotho for binding to the epitope, by immunization of an animal with a peptide comprising a fragment of human beta klotho comprising the epitope sequence, or by selection of antibodies using phage display for binding to the epitope sequence. Antibodies that bind to the same functional epitope might be expected to exhibit similar biological activities, such as blocking a biological activity of beta klotho, and such activities can be confirmed by functional assays of the antibodies.

Additional Activity Assays

In one embodiment, an anti-beta klotho antibody of the present disclosure is an antagonist antibody that inhibits a biological activity of beta klotho. The anti-beta klotho antibodies of the present disclosure may be assayed to determine if they inhibit a biological activity of beta klotho.

In one aspect, purified anti-beta klotho antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In one embodiment, the present disclosure contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. An in vitro assay to assess ADCC activity of a molecule of interest is described, for example, in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, for example, in a animal model such as that disclosed in Clynes et al. PNAS (USA) 95:652-656 (1998). C1 q binding assays may also be carried out to confirm that the antibody is unable to bind C1 q and hence lacks CDC activity. To assess complement activation, a CDC assay, for example, as described in Gazzano-Santoro et al., *J. Immunol. Methods* 202:163 (1996), may be performed. FcRn binding and in vivo clearance/half life determinations can also be performed using methods known in the art.

Although the foregoing present disclosure has been described in some detail by way of illustration and example for purposes of clarity of understanding, the descriptions and examples should not be construed as limiting the scope of the present disclosure. The disclosures of all patent and scientific literatures cited herein are expressly incorporated in their entirety by reference.

EXAMPLES

The following are examples of methods and compositions of the present disclosure.

Example 1: Generation of Antibodies to Beta Klotho

Antibodies to beta klotho were generated, for example, by immunizations of mice (i) with cells expressing human beta klotho (HuKLB) and FGF receptor 1c (FGFR1c or R1c) and (ii) with HuKLB and cynomologous beta klotho (cyno KLB) protein.

For example, beta klotho expressing cells were prepared as follows. 293EXPI (Invitrogen) cells were transiently co-transfected with nucleic acid sequences encoding a variant of FGFR1c with a mutation at amino acid position 623 (see, e.g., SEQ ID NO:308 but with a mutation D623N) and HuKLB (SEQ ID NO:297). Cells were analyzed for expression of R1c and HuKLB by the respective specific antibodies by FACS. Cells were washed 2 times in PBS, pelleted by centrifugation and frozen in individual vials at $6\times10^7$ cells for immunization. 129/B6 animals were immunized with $1\times10^7$ cells with adjuvants (Ribi, CpG, and PolyIC). Animals were boosted every 2 weeks for the duration necessary to induce a suitable titer. Animals were boosted with HuKLB and CyKLB protein after 4 boosts with R1c and HuKLB overexpressing-293EXP1 cells. Titers were determined by ELISA and FACS. Single cell suspensions of lymphocytes were obtained from spleen and draining lymph nodes of animals with suitable titers. Cells were fused with SP2/0 myeloma cells at a ratio of 1:2 by electrofusion. Fused cells were plated at $2.5\times10^6$ cells per plate in 70 µL into twenty-four×384-well plates in the presence of HAT selection. After 7 days, 50 µL of supernatant were removed and replaced with fresh HAT containing media. After 10-14 days of culture, supernatants were collected and subjected to screening by FACS using R1c and HuKLB overexpressing-293EXP1 cells or by Biacore using HuKLB protein to confirm binding. Positive clones were further selected and subjected to subcloning.

In a first campaign of immunizations and fusions, at least 25-30 384 well plates were screened for binding to HuKLB (e.g., HuKLB protein and/or cells expressing HuKLB). In a second campaign for immunizations and fusions, a similar number of plates were screened as described for the first campaign. Thousands of clones were screened and hundreds of clones were selected for additional study, including in assays for binding, affinity and epitope specificity as described in Examples 2 and 3. Hundreds of hybridoma supernatants were also tested in functional assays as described, in Examples 4 and 5, including for agonist activity similar to FGF receptor ligands FGF19 and/or FGF21 (e.g., FGF19-like and/or FGF21-like signaling activity).

Example 2: Screening and Selection of Antibodies to Beta Klotho

Antibodies to beta klotho were generated from hybridomas, for example, such as described in Example 1. Hybridoma supernatants were screened for binding to beta klotho (e.g., human and/or cyno beta klotho) in FACS-based and/or Biacore-based assays.

For example, after 2 weeks of culture, hybridoma supernatants were screened for monoclonal antibodies binding to human beta klotho by a FACS based binding screen. Briefly, hybridoma supernatants were co-incubated with human beta klotho over-expressing cells for 30 minutes at 4° C. After washing with PBS/1% BSA/0.1% azide, human beta klotho over-expressing cells were co-incubated with labeled anti-mouse Fc (Jackson Immunoresearch) for 30 minutes at 4° C. After washing with PBS/1% BSA/0.1% azide, cells were acquired on flow cytometer (FACS Calibur) and analyzed by cytometric analytical software (FlowJo). A binding antibody is one that shows a shift from cells incubated with labeled anti-mouse Fc only.

For example, after 2 weeks of culture, hybridoma supernatants were screened for monoclonal antibodies binding to human beta klotho by a Biacore based binding screen. Briefly, anti-mouse Fc antibody (Sigma-Aldrich, St. Louis, Mo.) was immobilized on all four flow cells of a CM5 chip using amine coupling reagents (GE Healthcare LifeSciences, Piscataway, N.J.). Hybridoma supernatants were diluted three fold with PBS-P buffer (PBS containing 0.005% P20) and injected for 30 seconds on flow cells 2,3 and 4 to capture the antibody (flow cell 1 was used as a reference). This was followed by a short injection of human beta klotho (25 nM, R&D Systems, Minneapolis, Minn.) for 60 seconds at a flow rate of 30 µL/min to test for binding to captured antibody on each flow cell.

From two immunization and fusion campaigns as described in Example 1, fifty-sixty 384 well plates of hybridoma supernatants were assayed for binding by FACS and/or Biacore. From these assays, approximately of 250 antibodies were identified as binders to human beta klotho. These antibodies were purified and subsequently tested for their binding affinity to human beta klotho and cyno beta klotho by Biacore and for their functional activity by reporter assays as described in Example 3.

In additional Biacore-based binding/screening assays, the binding affinity of antibodies to human and cyno beta klotho were measured. For example, antibodies were rank ordered based on their binding affinity to human beta klotho and cyno beta klotho by low resolution $K_D$ measurement by Biacore. Briefly, anti-mouse Fc antibody (Sigma-Aldrich, St. Louis, Mo.) was immobilized on all four flow cells of a CM5 chip using amine coupling reagents (GE Healthcare LifeSciences, Piscataway, N.J.). Purified antibodies were captured (~100 RUs) on flow cells 2, 3 and 4 using flow cell 1 as a reference. This was followed by injection of human or cyno beta klotho (25 nM in PBS-P buffer) at a flow rate of 70 µL/min and monitoring the binding kinetics at 25° C.

Binding affinity measurements were also made in additional Biacore based assays. For example, equilibrium dissociation constant ($K_D$) measurements were carried out with purified antibodies to evaluate their binding to human beta klotho and cyno beta klotho. As mentioned above, anti-mouse Fc antibody (Sigma-Aldrich, St. Louis, Mo.) was immobilized on all four flow cells of a CM5 chip using amine coupling reagents (GE Healthcare LifeSciences, Piscataway, N.J.). Purified antibodies were captured (~100 RUs) on flow cells 2, 3 and 4 using flow cell 1 as a reference. This was followed by injection of different concentrations of human or cyno beta klotho (1.56 nM to 25 nM, two-fold dilutions in PBS-P buffer) at a flow rate of 70 µL/min and the binding kinetics were evaluated at 25° C.

Representative results are reported as $K_D$ (nM) values as shown in Table 11 below.

TABLE 11

| Affinity KD (nM) | | |
|---|---|---|
|  | HuKLB | Cyno KLB |
| 5H23 | ~pM | 0.72 |
| 1C17 | 0.89 | 3.1 |
| 1D19 | 1.25 | 2.9 |
| 2L12 | 0.22 | 1.42 |
| 3L3 | 1.14 | 2.2 |
| 3N20 | 3.3 | 3.52 |
| 4P5 | 0.26 | 0.44 |
| 5F7 | 1.7 | 2.5 |
| 1G19 | N/A | N/A |
| 5C23 | 1.2 | 2.4 |

Example 3: Screening and Selection of Antibodies to Beta Klotho

Antibodies that were selected for binding to beta klotho, for example, such as described in Example 2, were evaluated in competition binding assays and epitope binning experiments.

For example, for competition binding assays by FACS analysis, antibody standards were prepared that were conjugated to a fluorochrome using either A488 or A647 antibody labeling kit (Invitrogen) following manufacturer's instructions. A dose titration of the conjugated antibody standard was evaluated using HuKLB overexpressing cells. The plateau of the maximal signal of antibody binding is EC=100 and the background signal is EC=0. Competition by FACS against the fluorochrome labeled antibody was performed by pre-incubating HuKLB overexpressing cells with hybridoma supernatants for 15 minutes at room temperature. Without washing, an EC=10 concentration of A488 or A647 labelled antibody standard was added. EC=10 for an individual antibody was determined by 10% of signal using the maximum signal as (100%) and background signal as (0%). After 30 minutes at 4° C., cells are washed and analyzed by FACS. In these assays, a competing antibody is one that shows signal comparable to the competition by 5H23. A non-competing antibody is one that shows signal equal to labelled antibody alone. A partial competing antibody is one sample that show signal between labelled antibody alone and background. Antibodies that show complete competition against the same standard antibody are considered to be in the same bin.

In exemplary competition binding experiments by FACS, antibody 5H23 or 3I13 was used as an antibody standard for a positive control (competing antibody) or a negative control (non-competing antibody), respectively. Representative results are shown in Table 12 below reported as mean fluorescence intensity (MFI). For these experiments, signal comparable to labeled antibody alone is a non-competing antibody, while signal comparable to the competition by 5H23 is a competing antibody.

TABLE 12

| | Mean Florescence Intensity (MFI) | |
|---|---|---|
| Antibody | 5H23 - Alexa647 | 3I13- Alexa488 |
| 5H23 | 2.3 | 29.8 |
| 1C17 | 2.4 | 26.7 |
| 1D19 | 2.5 | 30.6 |
| 2L12 | 3.1 | 30.9 |
| 3L3 | 4.2 | 28.7 |
| 3N20 | 2.4 | 30.5 |
| 4P5 | 2.4 | 30.1 |
| 5C23 | 2.4 | 29.3 |
| 5F7 | 2.3 | 28.5 |
| 1G19 | 2.2 | 29.0 |
| 3I13 | 9.4 | 7.4 |
| Labeled antibody alone | 10.8 | 32.4 |

To further evaluate the binding sites of the antibodies on human beta klotho, competition experiments were also set up on the Biacore. For example, two antibodies were immobilized on two flow cells of a CM5 chip. Human beta klotho-antibody complexes were prepared with different antibodies (antibody concentration was titrated from 0.1-50 nM while keeping beta klotho concentration constant at 5 nM) in a 96-well micro plate and injected on the antibody surfaces. The measured signal (Response Unit, RU) was plotted against the solution antibody concentration [nM]. If the antibody in solution recognized the same epitope as the antibody immobilized on the chip surface, then a decrease in RU was observed with increase in concentration of antibody in solution (demonstrating competition for the binding site on beta klotho). However, if the antibody in solution recognized a distinct epitope relative to the immobilized antibody, an increase in RU was observed. In the latter scenario, the antibody-klotho complex could bind to the immobilized antibody surface leading to the observed increase in signal.

In exemplary competition binding experiments by Biacore, antibody 5H23 competed with itself for binding to HuKLB and additional antibodies 1C17, 1D19, 2L12, 3L3, 3N20, 4P5, 5C23, 5F7 and 1G19 competed with 5H23. These antibodies were designated as members of the 5H23 epitope bin. The sequences for these epitope-related antibodies are aligned and shown in FIGS. 1 and 2. FIG. 2 also shows conserved amino acid sequences for the CDRs of these related antibodies.

Example 4: Functional Assays

Antibodies to beta klotho generated, for example, such as described in Example 1, were tested for their functional activity in cell-based reporter assays.

For example, ELK1-luciferase reporter assays, which measure FGFR1c/beta klotho signaling, were performed using transiently transfected HEK293, HEK293T, or L6 cells (ATCC). The transfecting plasmids consisted of two reporter plasmids Gal4-Elk1 and 5×UAS-Luc (Agilent Technologies PathDetect Elk1 trans-reporting system Cat #219005), and plasmids encoding human beta klotho (GeneCopoeia Cat #EX-E1104-M02) or cynomolgus monkey beta klotho (cyno beta klotho) and human FGFR1c (GeneCopoeia Cat #EX-A0260-M02). In these assays, activation of recombinantly expressed FGFR1c/beta klotho receptor complex in the cells induces intracellular signaling transduction, which leads to ERK and then Elk1 phosphorylation. Once Gal4-Elk1 is phosphorylated, Gal4-Elk1 binds to the 5×UAS promoter region and turns on luciferase reporter gene transcription. The activity of luciferase is then measured in luciferase enzymatic assays.

For these experiments, the above mentioned four plasmids (e.g., 2 reporter plasmids, beta klotho, R1c) were transfected into newly harvested cells in suspension using FuGene6 or Fugene HD transfection reagent (Promega). Cell density and transfection reagent amount were optimized for each cell type and each Fugene batch. Beta klotho and FGFR1c DNA ratio in transfection was optimized for each cell line and varied between 6:1 to 27:1. Transfected cells were seeded into 96-well (30,000 cells/100 µL/well), or 384-well plate (7500 cells/25 µL/well) in normal growth medium. After overnight incubation at 37° C., a variety of antibodies to beta klotho were added. After 6 hrs of 37° C. incubation with the antibodies, an equal volume of Bright-Glo reagent (Promega) was added and luminescence signal was read using Enspire reader (Perkin Elmer).

Representative results using human beta klotho and cyno beta klotho, transfected into HEK 293 cells, are reported as EC50 values as shown in Table 13 and Table 14, respectively, below.

TABLE 13

| mAb | Experiment - A HEK293 huKLB/R1c reporter assay EC50 (pM) | Experiment - B HEK293 huKLB/R1c reporter assay EC50 (pM) |
|---|---|---|
| control* | 45.3 | 27.9 |
| 5H23 | 102 | 34.2 |
| 1D19 | 620 | |
| 2L12 | 373 | |
| 3L3 | 773 | |
| 3N20 | 527 | |
| 4P5 | 600 | 78.3 |
| 1G19 | 231 | 127 |

*Control mAB comprises SEQ ID NO: 358 and SEQ ID NO: 360

TABLE 14

| mAb | Experiment - A HEK293 cynoKLB/R1c reporter assay EC50 (pM) | Experiment - B HEK293 cynoKLB/R1c reporter assay EC50 (pM) |
|---|---|---|
| control* | 108 | 227 |
|  | 178 |  |
| 5H23 | 165 | 218 |
| 1D19 |  | 954 |
| 2L12 | 260 | 410 |
| 3L3 | 3576 | 1672 |
| 3N20 | 2464 | >10000 |
| 4P5 | 347 | 465 |
| 1G19 | 2354 | 2447 |

*Control mAB comprises SEQ ID NO: 358 and SEQ ID NO: 360

Representative results using human beta klotho, transfected into L6 cells, are reported as EC50 values as shown in Table 15 below.

TABLE 15

| mAb | L6 huKLB/R1c reporter assay EC50 (nM) | L6 huKLB/R2c reporter assay EC50 (nM) | L6 huKLB/R3c reporter assay EC50 (nM) | L6 huKLB/R4 reporter assay EC50 (nM) |
|---|---|---|---|---|
| control | FGF19: 2.66 | FGF19: 0.16 | FGF19: 2.1 | FGF19: 0.05 |
| 5H23 | 0.28 | >67 | >67 | >67 |
| 2L12 | 4.65 | >67 | >67 | >67 |
| 4P5 | 0.39 | >67 | >67 | >67 |

L6 cells lack endogenous receptors and are often used to investigate antibody specificity to various transfected FGF receptor subtypes. Activation of the receptor via FGFR1c/beta klotho signaling in the absence of ligand (e.g., FGF19 (e.g., SEQ ID NO: 304) or FGF21 (e.g., SEQ ID NO: 429)) by the exemplary anti-beta klotho antibodies of the present disclosure was observed with L6 cells transfected with FGFR1c (R1c), but not with L6 cells transfected with FGFR2c (R2c), FGFR3c (R3c), or FGFR4 (R4), whereas activation by the FGF19 control was observed with L6 cells transfected with R1c, R2c, R3c and R4.

Example 5: Additional Functional Assays

Antibodies to beta klotho generated, for example, as described in Example 1, were tested for their functional activity in a cell-based assay, such as an adipocyte assay, which measures endogenous FGFR1c/beta klotho signaling. FGF19 or FGF21 stimulate ERK phosphorylation, increase glucose uptake and lipolyses in cultured adipocytes. Adipocytes are considered physiologically relevant for demonstrating the functional activity of receptor ligands or agonist antibodies which mimic the function of ligands (e.g., signaling of the receptor by the ligands).

For example, frozen human preadipocytes (Lonza Cat #PT-5005) were thawed on day 1, differentiated on day 3 and maintained in differentiation medium for about two weeks before the experiment (e.g., then starved on day 17, and assayed on day 18). The seeding medium was 1:1 DMEM/F12K+10% FBS. Seeding cell density was 25,000 cells/100 µL/well in 96-well plate. On day 3, medium was replaced with human adipocytes differentiation medium (Cell Applications Inc). From then on, fresh differentiation medium was added onto cells every 2-3 days. On day 17 (the day before the assay), the cells were rinsed two times and left with DMEM/0.1% BSA (Sigma cat #A3803 essential fatty acids free BSA) overnight. The next day, fresh DMEM/0.1% BSA medium was added for 1 hour before the cells were treated with test anti-beta klotho antibodies for 15 minutes at 37° C. Cis-bio Cellul'erk assay kit (Cat #64ERKPEH) was used to assay for ERK phosphorylation level following the manufacturer's protocol.

Representative results using human adipocytes are reported as EC50 values as shown in Table 16 below:

TABLE 16

| mAb | Experiment - A hAdip pERK assay | Experiment - B hAdip pERK assay EC50 (nM) |
|---|---|---|
| Control | +++ | FGF19 5.49 |
| 5H23 | +++ | 1.66 |
| 1C17 | ++ | >>67 |
| 1D19 | +++ | >67 |
| 2L12 | +++ | 1.23 |
| 3L3 | +++ | ~30~ |
| 3N20 | +++ | >67 |
| 4P5 | +++ | 0.89 |
| 5F7 | ++ | >67 |
| 5C23 | ++ | >>67 |
| 1G19 | +++ | 1.3 |

Example 6: Ligand Competition

Ligand (FGF19 or FGF21) competition assays were conducted to evaluate whether antibody-human beta klotho interaction influences the binding of beta klotho to its natural ligand, FGF19 or FGF21.

For example, Biacore-based competition assays were set up in which FGF19 (e.g., SEQ ID NO: 304) or FGF21 (e.g., SEQ ID NO: 429) was immobilized on a flow cell (Fc2) of a CM5 chip (using Fc1 as a reference surface). Human beta klotho-antibody complexes were prepared with exemplary antibodies of the present disclosure, such as 5H23 (e.g., VH SEQ ID NO: 25 and VL SEQ ID NO: 26) or a humanized 5H23 (e.g., VH SEQ ID NO: 271 and VL SEQ ID NO: 276)). For example, concentrations of 5H23 and a control antibody were titrated from 0.1-67 nM while keeping beta klotho concentration constant at 5 nM in a 96-well micro plate and injected on the FGF19 surface. For another example, concentrations of a humanized 5H23 (e.g., VH SEQ ID NO: 271 and VL SEQ ID NO: 276) were titrated from 0.001-67 nM while keeping beta klotho concentration constant at 2.5 nM in a 96-well micro plate and injected on the FGF 21 surface. The measured signal (Response Unit, RU) was plotted against the solution antibody concentration [nM]. If the antibody in solution recognized the same epitope as FGF19 ligand or FGF21 ligand immobilized on the chip surface, then a decrease in RU was observed with increase in concentration of antibody in solution, demonstrating competition with FGF19 ligand or FGF21 ligand for the binding site on beta klotho. However, if the antibody in solution recognized a distinct epitope relative to the immobilized FGF19 ligand or FGF21 ligand, an increase in RU was observed. In the latter scenario, the antibody-klotho complex could bind to the immobilized FGF19 ligand surface or immobilized FGF21 ligand surface leading to the observed increase in signal. In the exemplary data shown below in Table 17A, a control antibody partially competed with the FGF19 ligand resulting in a significant reduction of RU signal, where 5H23 did not compete with the FGF19 ligand for binding to beta klotho. In the exemplary data shown below in Table 17B, a control antibody competed with the FGF21 ligand resulting in a significant reduction in RU signal, where a humanized 5H23 did not compete with the FGF21 ligand for binding to beta klotho.

TABLE 17A

| Experiment 1 | RU | % Change | Remark |
|---|---|---|---|
| RU signal for 5 nM β-Klotho (no complex) | 127 | 100% | Control antibody* |
| RU signal for klotho-Control antibody complex | 60 | 47% reduction | Partial competition between Control antibody* and FGF19 for binding to β-klotho |
| RU signal for 5 nM β-Klotho (no complex) | 109 | 100% | Control antibody* |
| RU signal for klotho-5H23 complex | 125 | 114% increase | 5H23-klotho complex binds to FGF19, hence no competition |

*Control antibody comprises SEQ ID NO: 358 and SEQ ID NO: 360

TABLE 17B

| Experiment 1 | Normalized RU | % Change | Remark |
|---|---|---|---|
| RU signal for 2.5 nM β-Klotho (no complex) | 1 | 100% | Control antibody* |
| RU signal for klotho-FGF21 complex | 0.03 | 97% reduction | FGF21 competes with itself for binding to β-klotho |
| RU signal for 2.5 nM β-Klotho (no complex) | 1 | 100% | Control antibody* |
| RU signal for klotho-humanized 5H23 complex | 1.1 | 110% increase | Humanized 5H23-klotho complex binds to FGF21, hence no competition |

*Control antibody comprises SEQ ID NO: 358 and SEQ ID NO: 360

Because 5H23 and a humanized 5H23 antibody bind to a different epitope of beta klotho as compared to endogenous ligands, such as FGF19 and FGF21, experiments were conducted to test if there were synergistic effects between FGF21 and 5H23 or a humanized 5H23 antibody. In a HEK293 reporter assay (see, e.g., Example 4), combinations of FGF21 and a humanized 5H23 antibody (e.g., VH SEQ ID NO: 271 and VL SEQ ID NO: 276) were tested in a 1:1 molar ratio or fixing one and titrating the concentration of the other. No evidence of synergistic effects was observed; the maximum effect of FGF21 was not enhanced by the humanized 5H23 antibody, and vice versa.

Example 7: Humanization

Humanized anti-beta klotho antibodies were generated, including from antibodies selected as described in Examples 1-6.

A number of anti-beta klotho antibodies were selected for sequencing and their VH and VL regions, including their CDRs, are shown in Tables 1-10 and in FIGS. 1 and 2. An exemplary anti-beta klotho antibody, 5H23, was selected for humanization. Several methods of humanization were utilized. For some of the humanized antibodies, the method for humanization was empirical and based in part on structural information related to immunoglobulin variable regions including molecular models and requirements of antibody structural stability (see, e.g., Ewert et al., 2004, Methods 34:184-199; Honegger, 2008, Handb. Exp. Pharmacol. 181: 47-68; Kügler et al., 2009, Protein Eng. Des. Sel. 22: 135-147). The method was also based in part on considerations of antigen contact residues and/or framework stability residues. For example, consideration of typical antigen contact residues depends on the size of the antigen particularly residues outside CDRs which can contact the antigen, upper core, central core and lower core divisions, VH:VL interface residues, conserved Pro/Gly (positive phi angles) and VH subtype correlated residues match (see, e.g., Ewert et al., supra; Honegger, supra; Kügler et al., supra).

For example, human VH sequences homologous to the 5H23 VH framework sequences were searched for and the VH sequence encoded by the human germline IGHV1-3*01 (see, e.g., Ehrenmann et al., 2011, Cold Spring Harbor Protoc. G:737-749) was chosen as an acceptor for humanization. For some of the humanized antibodies, the CDR sequences of 5H23 VH were first transferred to the corresponding positions of IGHV1-3*01. Next, a number of amino acid residues of 5H23 VH were substituted for the corresponding human residues individually or in combinations.

Also, for example, human VL sequences homologous to the 5H23 VL framework sequences, were searched for and the human VK region encoded by the IGKV4-1*01 (see, e.g., Ehrennmann et al., supra) was chosen as an acceptor for humanization. For some of the humanized antibodies, the CDR sequences of 5H23 VL were first transferred to the corresponding positions of IGKV4-1*01. Next, a number of amino acid residues of 5H23 VL were substituted for the corresponding human residues individually or in combinations.

For some of the humanized antibodies, the method of humanization used an algorithm to construct a three-dimensional map of the mouse variable regions. This method also identified framework amino acids and residues important for the formation of CDR structure or necessary for binding to beta klotho. In addition, human VH and VL amino acid sequences with high homology to the mouse sequences were selected for possible framework sequences for humanization. As described above, the CDR sequences of 5H23 antibody may be transferred to such additional human framework sequences. A variety of human framework sequences, including germline sequences (e.g., IGHV1-3, IGHV1-46, IGHV1-69, IGKV4-1, IGKV1-39 or IGKV3-20) and mature individual sequences, may be suitable for the method of humanization. Next, a number of amino acid residues of 5H23 VH and/or 5H23 VL may be substituted for the corresponding human residues individually or in combination.

For some of the humanized light chains, IG BLAST searches were used to identify human germline sequences that were close matches in sequence with 5H23 VL and/or that were commonly used sequences, including, for example, IGKV1-39 and IGKV3-20. For some of the humanized light chains, the CDR sequences of 5H23 VL were first transferred to the corresponding positions of IGKV1-39 or IGKV3-20 and then certain amino acids were selected empirically for substation.

The amino acid sequences of the resulting humanized VH (vH1-vH9) and VL (vL1 to vL5, v1-39a to v1-39p and v3-20a to v3-20j) sequences are shown with 5H23 VH and VL sequences in FIG. 3A-3D. For example, using the various humanization methods described in this Example, a number of amino acid residues of 5H23 VH and VL were substituted for the corresponding human residue to obtain humanized sequences as shown in FIG. 3A-3D.

Humanized beta klotho antibodies may be prepared using any of the CDR sequences in Table 18 in combination with any of the framework sequences in Table 19.

TABLE 18

CDR Sequences for Humanized Anti-Beta Klotho Antibodies

| VH CDR1 |
| --- |
| SEQ ID NO: 1 GYTFTSYDIN |
| SEQ ID NO: 27 GYSITSGYYWN |
| SEQ ID NO: 53 GYTFTRYDIN |
| SEQ ID NO: 79 GYTFTRYDIN |
| SEQ ID NO: 105 GYTFTSYDIN |
| SEQ ID NO: 131 GYIFTNYGIS |
| SEQ ID NO: 157 GYTFTRYDIN |
| SEQ ID NO: 183 GYTFTRYDIN |
| SEQ ID NO: 209 GYTFTRYDIN |
| SEQ ID NO: 235 GYSITSGYYWN |

| VH CDR2 |
| --- |
| SEQ ID NO: 2 WIYPGDGSTKYNEKFKG |
| SEQ ID NO: 28 YINYDGNSNYTPSLKN |
| SEQ ID NO: 54 WIYPGDSSTKFNENFKD |
| SEQ ID NO: 80 WIYPGDDSTKYNEKFKG |
| SEQ ID NO: 106 WIYPGDSPKYDEKFKG |
| SEQ ID NO: 132 EIYPRSGNTYYNEKFKG |
| SEQ ID NO: 158 WIYPGDDSTKYNEKFKG |
| SEQ ID NO: 184 WIYPGDGSTKYNEKFEG |
| SEQ ID NO: 210 WIYPGDISTKYNEKFKG |
| SEQ ID NO: 236 YINYGGSNNYNPSLKN |

| VH CDR3 |
| --- |
| SEQ ID NO: 3 SDYYGSRSFAY |
| SEQ ID NO: 29 KGAYYSNYDSFDV |
| SEQ ID NO: 55 SDYYGSRSFTY |
| SEQ ID NO: 81 SDYYGSRSFVY |
| SEQ ID NO: 107 SDYYGSRSFVY |
| SEQ ID NO: 133 HWDGVLDYFDY |
| SEQ ID NO: 159 SDYYGSRSFVY |
| SEQ ID NO: 185 SDYYGSRSFVY |
| SEQ ID NO: 211 SDYYGSRSFVY |
| SEQ ID NO: 237 RGAYYSNYDSFDV |

| VL CDR1 |
| --- |
| SEQ ID NO: 4 RASKSVSTSGYVYMH |
| SEQ ID NO: 30 KASQDINSYLS |
| SEQ ID NO: 56 RASKSVSTSGYSYMH |
| SEQ ID NO: 82 RASKSVSTSGYSYLH |
| SEQ ID NO: 108 RASKSVSTSGYSYVH |

TABLE 18-continued

CDR Sequences for Humanized Anti-Beta Klotho Antibodies

SEQ ID NO: 134 KSSQSLLNSGNQKNYLA

SEQ ID NO: 160 RASKSVSTSGYSYMH

SEQ ID NO: 186 RASKSVSTSGYSYMH

SEQ ID NO: 212 RASKSVSTSGYSYMH

SEQ ID NO: 238 KASQDINSYLS

VL CDR2

SEQ ID NO: 5 LASYLES

SEQ ID NO: 31 RANRLVD

SEQ ID NO: 57 LASNLES

SEQ ID NO: 83 LASNLES

SEQ ID NO: 109 LASNLES

SEQ ID NO: 135 GASTRES

SEQ ID NO: 161 LASNLES

SEQ ID NO: 187 LASNLES

SEQ ID NO: 213 LASNLES

SEQ ID NO: 239 RANRLVD

VL CDR3

SEQ ID NO: 6 QHSRDLTFP

SEQ ID NO: 32 LQYDEFPFT

SEQ ID NO: 58 QHSRELPYT

SEQ ID NO: 84 QHSGELPYT

SEQ ID NO: 110 QHSGELPYT

SEQ ID NO: 136 LNDHSYPFT

SEQ ID NO: 162 HHSGELPYT

SEQ ID NO: 188 QHSRELPYT

SEQ ID NO: 214 QHSRELPYT

SEQ ID NO: 240 LQYDEFPYT

TABLE 19

Framework Sequences for Humanized Anti-Beta Klotho Antibodies

VH
Framework 1 (FR1)

SEQ ID NO: 278 QVQLVQSGAEVKKPGASVKVSCKAS

SEQ ID NO: 279 QVQLQQSGAEVKKPGASVKVSCKAS

SEQ ID NO: 280 QVQLVQSGPEVKKPGASVKVSCKAS

SEQ ID NO: 378 QVQLVQSGAEVKKPGSSVKVSCKAS

TABLE 19-continued

Framework Sequences for Humanized Anti-Beta Klotho Antibodies

Framework 2 (FR2)

SEQ ID NO: 281 WVRQAPGQGLEWMG

SEQ ID NO: 282 WVRQAPGQGLEWIG

SEQ ID NO: 283 WVKQAPGQGLEWIG

Framework 3 (FR3)

SEQ ID NO: 284 RVTITRDTSASTAYMELSSLRSEDTAVYYCAR

SEQ ID NO: 285 KATITRDTSASTAYMELSSLRSEDTAVYFCAR

SEQ ID NO: 286 KATLTADTSASTAYMELSSLRSENTAVYFCAR

SEQ ID NO: 287 KATLTADKSARTAYMELSSLRSENTAVYFCAR

SEQ ID NO: 379 RATLTADKSTSTAYMELSSLRSEDTAVYYCAR

SEQ ID NO: 380 RATLTADKSTRTAYMELSSLRSEDTAVYYCAR

SEQ ID NO: 381 RATITADKSTSTAYMELSSLRSEDTAVYYCAR

Framework 4 (FR4)

SEQ ID NO: 288 WGQGTLVTVSS

VL
Framework 1 (FR1)

SEQ ID NO: 289 DIVLTQSPDSLAVSLGERATINC

SEQ ID NO: 290 DIVMTQSPDSLAVSLGERATINC

SEQ ID NO: 382 DIQMTQSPSSLSASVGDRVTITC

SEQ ID NO: 383 DIQLTQSPSSLSASVGDRVTITC

SEQ ID NO: 384 EIVLTQSPATLSLSPGERATLSC

Framework 2 (FR2)

SEQ ID NO: 291 WNQQKPGQPPKLLIY

SEQ ID NO: 292 WYQQKPGQPPKLLIY

SEQ ID NO: 385 WYQQKPGKAPKLLIY

SEQ ID NO: 386 WNQQKPGKAPKLLIY

SEQ ID NO: 387 WYQQKPGKPPKLLIY

SEQ ID NO: 388 WNQQKPGKPPKLLIY

SEQ ID NO: 389 WYQQKPGQAPRLLIY

SEQ ID NO: 390 WNQQKPGQAPRLLIY

SEQ ID NO: 391 WYQQKPGQPPRLLIY

SEQ ID NO: 392 WNQQKPGQPPRLLIY

Framework 3 (FR3)

SEQ ID NO: 293 GVPDRFSGSGSGTDFTLTISSVQAEDAAIYYC

SEQ ID NO: 294 GVPDRFSGSGSGTDFTLTISSVQAEDVAVYYC

SEQ ID NO: 295 GVPDRFSGSGSGTDFTLTISSVQAEDVAIYYC

SEQ ID NO: 393 GVPDRFSGSGSGTDFTLTISSLQAEDVAVYYC

SEQ ID NO: 394 GVPSRFSGSGSGTDFTLTISSLQPEDFATYYC

SEQ ID NO: 395 GVPSRFSGSGSGTDFTLTISSVQPEDFATYYC

TABLE 19-continued

Framework Sequences for Humanized Anti-Beta Klotho Antibodies

SEQ ID NO: 396 GVPSRFSGSGSGTDFTLTISSLQEEDFATYYC

SEQ ID NO: 397 GVPSRFSGSGSGTDFTLTISSVQEEDFATYYC

SEQ ID NO: 398 GVPSRFSGSGSGTDFTLTISSVQEEDAATYYC

SEQ ID NO: 399 GIPARFSGSGSGTDFTLTISRLEPEDFAVYYC

SEQ ID NO: 400 GIPARFSGSGSGTDFTLTISRVEPEDFAVYYC

SEQ ID NO: 401 GIPARFSGSGSGTDFTLTISRLEPEDAAVYYC

SEQ ID NO: 402 GIPARFSGSGSGTDFTLTISRLEEEDFAVYYC

SEQ ID NO: 403 GIPARFSGSGSGTDFTLTISRVEEEDFAVYYC

SEQ ID NO: 404 GIPARFSGSGSGTDFTLTISRVEEEDAAVYYC

Framework 4 (FR4)

SEQ ID NO: 296 FGGGTKLEIK

SEQ ID NO: 405 FGGGTKVEIK

SEQ ID NO: 406 FGQGTKLEIK

SEQ ID NO: 407 FGGQTKLEIK

For example, a humanized anti-beta klotho antibody may comprise a heavy chain variable region (VH) comprising: FR1 (e.g., SEQ ID NO:278, 279, 280, or 378); CDR1 (e.g., SEQ ID NO:1, 27, 53, 79, 105, 131, 157, 183, 209, 235); FR2 (e.g., SEQ ID NO:281, 282, or 283); CDR2 (e.g., SEQ ID NO:2, 28, 54, 80, 106, 132, 158, 184, 210, or 236); FR3 (e.g., SEQ ID NO:284, 285, 286, 287, 379, 380, or 381); CDR3 (e.g., SEQ ID NO:3, 29, 55, 81, 107, 133, 159, 185, 211, or 237); and/or FR4 (e.g., SEQ ID NO:288); and/or a light chain variable region (VL) comprising: FR1 (e.g., SEQ ID NO:289, 290, 382, 383, or 384); CDR1 (e.g., SEQ ID NO:4, 30, 56, 82, 108, 134, 160, 186, 212, or 238); FR2 (e.g., SEQ ID NO:291, 292, or 385-392); CDR2 (e.g., SEQ ID NO:5, 31, 57, 83, 109, 135, 161, 187, 213, or 239); FR3 (e.g., SEQ ID NO:293, 294, 295, or 393-404); CDR3 (e.g., SEQ ID NO:6, 32, 58, 84, 110, 136, 162, 188, 214, 240); and/or FR4 (e.g., SEQ ID NO:296, 405, 406, or 407).

As described in this Example, humanized anti-beta klotho antibodies were empirically designed and expressed as beta klotho binding proteins, including nine humanized variants of the VH region of antibody 5H23 and thirty-one humanized variants of the VL region of antibody 5H23 that were created. The sequences of these exemplary humanized 5H23 VH and VL regions are shown in FIG. 3A-3D.

Humanized antibodies were prepared with humanized VH and humanized VL regions with sequences as shown in FIG. 3A-3D. For example, eighteen (6×3) combinations of vH 1-6 and vL1-3 were constructed using an IgG1 (ala-ala) constant region (SEQ ID NO:316) and a kappa constant region (SEQ ID NO:318): vH1-VL1, vH1-vL2, vH1-vL3, vH2-vL1, vH2-vL2, vH2-vL3, vH3-vL1, vH3-vL2, vH3-vL3, vH4-vL1, vH4-vL2, vH4-vL3, vH5-vL1, vH5-vL2, vH5-vL3, vH6-vL1, vH6-vL2, vH6-vL3, with sequences as shown in FIG. 3A-3D. Additionally, humanized antibodies were constructed with an exemplary humanized VH region (e.g., vH3) and twenty-six humanized VL regions (v1-39a to v1-39p and v3-20a to v3-20j) with sequences as shown in FIG. 3A-3D.

The humanized antibodies were tested from their activity in a variety of assays, including, for example, as described in Examples 2-6. Expression of the humanized antibodies with light chains comprising vL3 or v1-39c was low and those antibodies were not further tested. Exemplary results with a variety of humanized anti-beta klotho antibodies are shown in Table 20A and 20B below.

TABLE 20A

| Antibody | Expression (mg/L) | KD-huKLB (nM) | KD-cyKLB (nM) | EC50 reporter assay (nM) | EC50-adipocyte (nM) |
|---|---|---|---|---|---|
| Control mAb | | 0.08 | 0.7 | 0.2, 0.54 | 3.4 |
| 5H23 | | 0.05 | 0.7 | 0.27, 0.51 | 3.4 |
| vL1 | | | | | |
| vH1 | 80 | 1.5 | ≥50 | 2.7 | ND |
| vH2 | 80 | 1.7 | ≥50 | 3.2 | ND |
| vH3 | 50 | 0.43 | ≥50 | 1.1 | ND |
| vH4 | 80 | 2.26 | ≥50 | 3.0 | ND |
| vH5 | 20 | 0.81 | ≥50 | 8.2 | ND |
| vH6 | | | | NA | |
| vL2 | | | | | |
| vH1 | 200 | 0.21 | 0.95 | NA | 8.4 |
| vH2 | 66 | 0.41 | 0.75 | 1.3 | 13.3 |
| vH3 | 50-60 | 0.23 | 0.59 | 0.68 | 5.5 |
| vH4 | 66 | 0.33 | 0.61 | 3.5 | 16.4 |
| vH5 | 30 | 0.19 | 0.61 | 1.1 | 8.1 |
| vH6 | 20 | 0.4 | 0.83 | 1.7 | 15.3 |

TABLE 20B

| Antibody | Estimated Titer (mg/L) | KD-huKLB (nM) | EC50 reporter assay (nM) | EC50 adipocyte (nM) |
|---|---|---|---|---|
| h5H23 (Prep 1) | — | 0.64 | — | — |
| h5H23 (Prep 2) | — | 0.58 | 0.6 | 11.2 |
| vH3 | | | | |
| VL v1-39a | 50 | 0.90 | — | — |
| VL v1-39b | 50 | 0.53 | 1.03 | — |
| VL v1-39c | 10 | — | — | — |
| VL v1-39d | 50 | 0.73 | 1.49 | — |
| VL v1-39e | >100 | 1.00 | — | — |
| VL v1-39f | >100 | 0.28 | 0.80 | 21.4 |
| VL v1-39g | >100 | 1.10 | — | — |
| VL v1-39h | 10 | 2.10 | — | — |
| VL v1-39i | 50 | 0.63 | 1.12 | — |
| VL v1-39j | 100 | 0.70 | — | — |
| VL v1-39k | 100 | 1.50 | — | — |
| VL v1-39l | 100 | — | — | — |
| VL v1-39m | 50 | <0.1 | — | — |
| VL v1-39n | >100 | <0.1 | — | — |
| VL v1-39o | 25 | 0.36 | — | — |
| VL v1-39p | 10 | 0.36 | — | — |
| VL v3-20a | 25 | 0.64 | — | — |
| VL v3-20b | 50 | 1.90 | — | — |
| VL v3-20c | 0 | 1.60 | — | — |
| VL v3-20d | 50 | — | — | — |
| VL v3-20e | 50 | 1.60 | — | — |
| VL v3-20f | 10 | 1.80 | — | — |
| VL v3-20g | — | — | — | — |
| VL v3-20h | 25 | 1.50 | — | — |
| VL v3-20i | 10 | — | — | — |
| VL v3-20j | 10 | — | — | — |

Prep 1 = humanized 5H23 antibody (e.g., VH SEQ ID NO: 271 and VL SEQ ID NO: 276) preparation expressed at the same time as LC variants;
Prep 2 = humanized 5H23 antibody (e.g., VH SEQ ID NO: 271 and VL SEQ ID NO: 276) purified preparation.
Control antibody = VH SEQ ID NO: 358 and VL SEQ ID NO: 360.

In additional assays, for example, reporter assays with HEK293T cells as described in Example 4, wherein the cells were transfected with plasmids encoding mouse beta klotho (e.g., SEQ ID NO: 301), rat beta klotho (e.g., SEQ ID NO: 356), hamster beta klotho (e.g., SEQ ID NO: 408), rabbit beta klotho (e.g., SEQ ID NO: 410), or dog beta klotho (e.g., SEQ ID NO: 412) and were also transfected with plasmids encoding chimeric mouse FGFR1-13111c receptor (e.g., SEQ ID NO: 416), chimeric rat FGFR1-13111c receptor (e.g., SEQ ID NO: 419), chimeric hamster FGFR1-6111c receptor (e.g., SEQ ID NO: 417), chimeric rabbit FGFR1-13111c receptor (e.g., SEQ ID NO: 420), or dog FGFR1-βIIIc receptor (e.g., SEQ ID NO: 418), respectively, when treated with an anti-beta klotho antibody such as a humanized 5H23 antibody (e.g., VH SEQ ID NO: 271 and VL SEQ ID NO: 276), did not activate the chimeric mouse, rat, hamster, rabbit or dog beta klotho-FGFR1c receptor complex, respectively. The anti-beta klotho antibodies as described herein, including 5H23 and humanized 5H23 antibodies, as well as antibodies that compete with 5H23 (e.g., 1C17, 1 D19, 2L12, 3L3, 3N20, 4P5, 5C23, 5F7 and 1G19 as described in Example 3) with CDR sequences as shown in Tables 1-10, activate a human and cyno beta klotho/FGF receptor complex, but not mouse, rat, hamster, rabbit, or dog beta klotho/FGF receptor complexes as demonstrated by reporter assays described above. When a monovalent Fab of anti-beta klotho antibody prepared from a papain digestion of an anti-beta klotho antibody, such as a humanized 5H23 antibody (e.g., VH SEQ ID NO: 271 and VL SEQ ID NO: 276), was tested in a HEK293 reporter assay for its ability to activate human FGFR1c/KLB receptor complex, the Fab showed no antibody activity up to 67 nM, whereas the humanized 5H23 antibody showed activity with low nanomolar concentrations similar to that shown in Table 20B.

Example 8: Animal Studies

Effects of anti-beta klotho antibodies are evaluated in animal studies, including with cynomolgus monkeys.

In obese cynomolgus monkey studies, an exemplary anti-beta klotho antibody that binds to human beta klotho and cyno beta klotho (e.g., antibody 5H23 or humanized variant thereof), as well as an antibody comprising one or more of the CDRs of 5H23 as shown in Table 1 or alternatively, an antibody comprising one or more of the CDRs of an antibody or humanized variant thereof shown in Tables 2-10 that compete for the binding of 5H23 to human beta klotho as described in Example 3, is administered. Effects on a variety of metabolic parameters may be measured. Exemplary parameters include food intake, body weight, body mass index (BMI), abdominal circumference (AC), skin fold thickness (SFT), oral glucose tolerance test (OGTT), fasting and/or fed (e.g., postprandial) blood (e.g., serum) glucose levels, insulin levels, and/or triglyceride levels.

In an actual study, twenty spontaneous obese cynomolgus monkeys with body mass index equal to or above 40 are selected and randomized into vehicle (n=10) and antibody treatment (n=10) groups. Animals receive subcutaneous injection of either vehicle or anti-beta klotho antibody on days 1 and 14. Food intake for each meal is recorded and body weight is measured once a week. Blood samples are taken once a week for 7 weeks for the measurements of plasma (alternatively, serum) glucose, insulin, lipids and parameters of interest. On days 14, 28 and 49, an oral glucose tolerance test is conducted.

Exemplary treatment effects may include reduced food intake, decreased body weight, decreased BMI, AC and/or SFT, improved glucose tolerance, decreased insulin levels, decreased fasting and/or fed (e.g., postprandial) plasma (alternatively, serum) glucose levels, insulin levels, and/or reduced triglyceride levels. These effects indicate improved metabolic parameters with treatment with anti-beta klotho antibodies.

For example, twenty male cynomolgus monkeys were selected for treatment with a humanized 5H23 antibody (e.g., VH SEQ ID NO: 271 and VL SEQ ID NO: 276) or a vehicle control based on their BMI (>40) and were trained for chair restraint, subcutaneous injection, blood draw, and oral gavage. A routine feeding schedule was established.

Baseline values of various parameters of interest were measured prior to the treatments. For example, on day −7, baseline body weight, BMI, abdominal circumference, and skin fold thickness were measured, and a dual energy X-ray absorptiometry ("DEXA") scan was conducted to the cynomolgus monkeys under ketamine anesthesia to measure bone mineral density. Blood samples were taken on day −3, following an overnight fast. Baseline levels of serum glucose, insulin, total cholesterol, LDL, HDL, triglyceride, and a panel of hematology and clinical chemistry parameters were measured and analyzed. Immediately after the baseline samples, animals were subjected to oral glucose tolerance test (OGTT) by receiving a gavage of 4 g/kg glucose and were sampled at 5, 15, 30, 60, 120 and 180 minutes after the glucose challenge, and serum glucose and insulin were measured. Based on the baseline data, the animals were assigned into two groups with 10 animals in each group (e.g., one group for antibody treatment and the other group as a vehicle control group) to achieve similar baseline levels of the various parameters, e.g., body weight, BMI, and levels of serum glucose, insulin, and triglyceride.

Starting from day 0, one group of animals (n=10) received a dose of subcutaneous injection of 10 mg/kg of an anti-beta klotho antibody, such as a humanized 5H23 antibody (e.g., VH SEQ ID NO: 271 and VL SEQ ID NO: 276) biweekly (e.g., on days 0, 14, 28, and 42) for 4 doses. The vehicle control group received matched vehicles on the same days. The treatments were carried out in the morning 30 minutes before the morning meal, and the dosing volume was 0.1 to 0.2 mL/kg.

Parameters of interest, e.g., food intake, body weight, clinical chemistry, and OGTT, were monitored throughout the study. For example, food intake was measured daily. Body weight, BMI, abdominal circumference, and skin fold thickness were measured weekly, e.g., on days 7, 14, 21, 28, 35, 42, 49, 56, 63, 70, 77, 84, 91, and 98. Blood samples were collected weekly, e.g., on days 7, 14, 21, 28, 35, 42, 49, 56, 63, and 70, following an overnight fast, to measure glucose, insulin, and lipids, such as triglyceride. An additional blood sample was taken on day 98, following an overnight fast. OGTTs were conducted after the initiation of the study, e.g., on days 14, 28, and 56, in which animals received a gavage of 4 g/kg glucose and were sampled at 5, 15, 30, 60, 120 and 180 minutes after the glucose challenge, and serum glucose and insulin were measured. A DEXA scan was conducted on days 30 and 72. In addition, a hematology and clinical chemistry panel was analyzed on days 28 and 70. Two animals from vehicle group and two animals from the anti-beta klotho antibody group were euthanized and necropsy was performed on day 50 for safety assessment. During the study, all animals were closely monitored for their health.

Exemplary results from this study are shown in Tables 21 to 25 below. As shown in Table 21, the body weight of animals treated with vehicle remained constant (with slight increase over the course); while the body weight of animals treated with the anti-beta klotho antibody progressively decreased, and the body weight did not return to baseline level during weeks 8-14 (e.g., recovery phase). Similarly, as shown in Table 22, animals treated with vehicle showed relatively stable BMI throughout the study, while animals treated with the anti-beta klotho antibody showed decreased level of BMI over the course of the study. BMI level also did not come back to baseline values (e.g., during the recovery phase). These results suggest that the anti-beta klotho antibody treatment resulted in reduction of fat mass.

As shown in Table 23, the serum insulin levels in animals treated with vehicle increased over the course of the study; while the serum insulin levels in animals treated with the anti-beta klotho antibody significantly decreased. The serum glucose levels were also reduced in animals treated the anti-beta klotho antibody, as shown in Table 24. Similarly, as shown in Table 25, the triglyceride levels in animals treated with vehicle increased over the course of the study; while the triglyceride levels in animals treated with the anti-beta klotho antibody were significantly reduced.

Results of OGTTs demonstrated that before treatments, baseline levels of insulin were not significantly different between the vehicle and the anti-beta klotho antibody groups. In contrast, after treatment, there was a trend towards glucose reduction and insulin levels were reduced in animals treated with the anti-beta klotho antibody compared with animals treated with vehicle.

TABLE 21A

Body Weight (kg)

| | Week | −1 | 0 | 1 | 2 | 3 | 4 | 5 | 6 |
|---|---|---|---|---|---|---|---|---|---|
| Vehicle | Mean | 10.84 | 10.75 | 10.66 | 10.63 | 10.61 | 10.75 | 10.67 | 10.66 |
| | sem | 0.49 | 0.50 | 0.50 | 0.48 | 0.48 | 0.47 | 0.48 | 0.46 |
| h5H23 | Mean | 10.87 | 10.84 | 10.60 | 10.45 | 10.27 | 10.21 | 10.00 | 9.86 |
| | sem | 0.33 | 0.36 | 0.36 | 0.38 | 0.37 | 0.40 | 0.41 | 0.41 |
| | Week | 7 | 8 | 9 | 10 | 11 | 12 | 13 | 14 |
| Vehicle | Mean | 10.75 | 10.98 | 10.96 | 11.08 | 11.09 | 11.12 | 11.23 | 11.18 |
| | sem | 0.47 | 0.59 | 0.59 | 0.61 | 0.60 | 0.59 | 0.58 | 0.59 |
| h5H23 | Mean | 9.76 | 9.58 | 9.52 | 9.46 | 9.43 | 9.43 | 9.39 | 9.27 |
| | sem | 0.42 | 0.50 | 0.51 | 0.51 | 0.53 | 0.56 | 0.53 | 0.56 |

TABLE 21B

Body Weight Change (kg)

| | | Week | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|
| Vehicle | Mean | | 0.00 | −0.09 | −0.12 | −0.14 | 0.00 | −0.08 | −0.09 | 0.00 | 0.14 | 0.13 | 0.24 | 0.26 | 0.28 | 0.39 | 0.34 |
| | sem | | 0.00 | 0.05 | 0.07 | 0.09 | 0.09 | 0.09 | 0.10 | 0.10 | 0.12 | 0.13 | 0.13 | 0.14 | 0.17 | 0.18 | 0.17 |
| h5H23 | Mean | | 0.00 | −0.24 | −0.39 | −0.57 | −0.63 | −0.84 | −0.98 | −1.08 | −1.07 | −1.13 | −1.19 | −1.22 | −1.22 | −1.25 | −1.38 |
| | sem | | 0.00 | 0.05 | 0.08 | 0.10 | 0.13 | 0.15 | 0.17 | 0.19 | 0.26 | 0.27 | 0.28 | 0.31 | 0.34 | 0.31 | 0.34 |

TABLE 22

BMI

| | Week | −1 | 0 | 1 | 2 | 3 | 4 | 5 | 6 |
|---|---|---|---|---|---|---|---|---|---|
| Vehicle | Mean | 57.59 | 57.06 | 56.59 | 56.44 | 56.33 | 57.08 | 56.63 | 56.59 |
| | sem | 2.41 | 2.45 | 2.45 | 2.33 | 2.31 | 2.28 | 2.30 | 2.23 |
| h5H23 | Mean | 57.52 | 57.32 | 56.03 | 55.24 | 54.28 | 53.95 | 52.82 | 52.07 |
| | sem | 2.53 | 2.61 | 2.50 | 2.51 | 2.44 | 2.50 | 2.52 | 2.54 |
| | Week | 7 | 8 | 9 | 10 | 11 | 12 | 13 | 14 |
| Vehicle | Mean | 57.06 | 58.27 | 58.17 | 58.76 | 58.86 | 59.00 | 59.60 | 59.33 |
| | sem | 2.25 | 2.55 | 2.52 | 2.60 | 2.60 | 2.53 | 2.46 | 2.51 |
| h5H23 | Mean | 51.54 | 48.85 | 48.56 | 48.24 | 48.09 | 48.07 | 47.94 | 47.28 |
| | sem | 2.48 | 2.29 | 2.30 | 2.32 | 2.44 | 2.54 | 2.46 | 2.60 |

TABLE 23

| | | Insulin (uU/mL) | | | | | | | | | | |
|---|---|---|---|---|---|---|---|---|---|---|---|---|
| Week | | −1 to 0 | 1 | 2 | 3 | 4 | 5 | 6 | 7 | 8 | 9 | 10 |
| Vehicle | Mean | 114.85 | 100.09 | 91.06 | 124.79 | 187.36 | 159.20 | 226.53 | 145.78 | 186.75 | 204.96 | 181.32 |
| | sem | 32.75 | 19.94 | 26.33 | 37.48 | 62.09 | 51.60 | 130.94 | 34.74 | 39.85 | 52.63 | 52.28 |
| h5H23 | Mean | 89.18 | 34.73 | 36.19 | 38.11 | 46.75 | 48.28 | 35.42 | 37.95 | 57.29 | 63.23 | 55.30 |
| | sem | 9.51 | 4.91 | 4.14 | 7.24 | 6.54 | 6.80 | 4.98 | 5.03 | 12.99 | 12.43 | 13.62 |

TABLE 24

| | | Glucose (mg/dL) | | | | | | | | | | |
|---|---|---|---|---|---|---|---|---|---|---|---|---|
| Week | | −1 to 0 | 1 | 2 | 3 | 4 | 5 | 6 | 7 | 8 | 9 | 10 |
| Vehicle | Mean | 90.81 | 93.69 | 95.41 | 90.21 | 94.51 | 98.31 | 97.70 | 95.78 | 94.73 | 93.53 | 90.06 |
| | sem | 10.00 | 9.07 | 9.73 | 7.93 | 9.17 | 10.46 | 13.12 | 10.21 | 11.62 | 12.09 | 12.49 |
| h5H23 | Mean | 90.85 | 87.37 | 83.19 | 84.92 | 85.62 | 80.52 | 80.97 | 79.60 | 81.90 | 78.20 | 76.60 |
| | sem | 11.67 | 6.61 | 6.92 | 8.02 | 6.75 | 5.67 | 6.32 | 4.30 | 4.97 | 7.07 | 5.49 |

TABLE 25

| | | Triglyceride (mmol/L) | | | | | | | | | | |
|---|---|---|---|---|---|---|---|---|---|---|---|---|
| Week | | −1 to 0 | 1 | 2 | 3 | 4 | 5 | 6 | 7 | 8 | 9 | 10 |
| Vehicle | Mean | 0.93 | 0.76 | 0.92 | 0.70 | 1.36 | 0.90 | 1.15 | 1.20 | 1.54 | 1.35 | 1.26 |
| | sem | 0.25 | 0.08 | 0.16 | 0.10 | 0.27 | 0.14 | 0.38 | 0.22 | 0.35 | 0.38 | 0.37 |
| h5H23 | Mean | 1.05 | 0.65 | 0.65 | 0.59 | 0.70 | 0.59 | 0.56 | 0.70 | 0.90 | 0.73 | 0.71 |
| | sem | 0.17 | 0.09 | 0.12 | 0.08 | 0.10 | 0.05 | 0.07 | 0.12 | 0.13 | 0.08 | 0.10 |

In another exemplary study, forty spontaneous obese male cynomolgus were selected, trained and fed as described above.

Baseline values of various parameters were measured prior to the treatments as discussed above. For example, baseline body weight, BMI, abdominal circumference and skin fold thickness were measured on day −4, and baseline blood samples were taken for measurements of serum glucose, insulin, total cholesterol, LDL, HDL and triglyceride on day −3, following an overnight fast. Based on these baseline data, animals were assigned into 5 groups (8 animals in each group) with 4 groups to receive various doses of an anti-beta klotho antibody such as a humanized 5H23 antibody (e.g., VH SEQ ID NO: 271 and VL SEQ ID NO: 276) and one group to receive a vehicle control.

On day 0, the first group of animals (n=8) received a single dose of subcutaneous injection of 0.1 mg/kg of the anti-beta klotho antibody; the second group of animals (n=8) received a single dose of subcutaneous injection of 1 mg/kg the anti-beta klotho antibody, and the third group of animals (n=8) received a single dose of subcutaneous injection of 10 mg/kg the anti-beta klotho antibody. Starting from day 0, the fourth group of animals (n=8) received a dose of subcutaneous injection of 0.1 mg/kg of the anti-beta klotho antibody once every 4 weeks for a duration of 12 weeks. As a control, the fifth group of animals (n=8) received a dose of vehicle once every 4 weeks for 12 weeks. The treatments were carried out in the morning 30 minutes before the morning meal, and the dosing volume was 0.2 mL/kg.

Parameters of interest were monitored throughout the study. For example, food intake was measured for each meal. Body weight, BMI, abdominal circumference, and skin fold thickness were measured weekly. Blood examples were taken at, e.g., 3, 6, 12 and 24 hours and 3, 4, 7, 10, 14, 21, 28, 35, 42, 49, 56, 63, 70, 77, 84, and 112 days after the dose(s), and parameters of interest, e.g., serum glucose, insulin, total cholesterol, LDL, HDL and triglyceride, were measured. During the study, all animals were closely monitored for their health as described above.

Exemplary results of this dose-response study are shown in Tables 26-29. Table 26 shows the relative body weight changes in animals treated with the anti-beta klotho antibody compared with the body weight changes in animals treated with vehicle. As shown, a single dose of subcutaneous injection of 0.1 mg/kg, 1 mg/kg, or 10 mg/kg the anti-beta klotho antibody, or four doses of subcutaneous injection of 1 mg/kg the anti-beta klotho antibody significantly reduced body weight. In addition, the reduced body weight was maintained on day 112 for animals receiving a single dose of 10 mg/kg the anti-beta klotho antibody, or for animals receiving four doses of 1 mg/kg the anti-beta klotho antibody compared with vehicle.

As shown in Table 27, a single dose of subcutaneous injection of 0.1 mg/kg, 1 mg/kg, or 10 mg/kg the anti-beta klotho antibody, or four doses of subcutaneous injection of 1 mg/kg the anti-beta klotho antibody reduced serum insulin level compared with the vehicle control group. In addition, four doses of subcutaneous injection of 1 mg/kg the anti-beta klotho antibody significantly reduced serum glucose level, as shown in Table 28. Furthermore, serum triglyceride levels in animals treated with a single dose of subcutaneous injection of 1 mg/kg, or 10 mg/kg the anti-beta klotho antibody, or four doses of subcutaneous injection of 1 mg/kg the anti-beta klotho antibody, were reduced compared the animals treated with vehicle, as shown in Table 29.

TABLE 26A

Body Weight

| Days | | −4 | 4 | 10 | 14 | 21 | 28 | 35 | 42 | 49 | 56 | 63 | 70 | 77 | 84 | 112 |
|---|---|---|---|---|---|---|---|---|---|---|---|---|---|---|---|---|
| Vehicle | Mean | 10.17 | 10.07 | 9.89 | 9.87 | 9.91 | 9.83 | 9.82 | 9.73 | 9.71 | 9.63 | 9.61 | 9.57 | 9.53 | 9.45 | 9.24 |
|  | sem | 0.78 | 0.80 | 0.77 | 0.79 | 0.81 | 0.81 | 0.82 | 0.82 | 0.83 | 0.83 | 0.83 | 0.83 | 0.83 | 0.83 | 0.81 |
| 5H23 (0.1 mg/ | Mean | 10.00 | 9.92 | 9.70 | 9.62 | 9.52 | 9.47 | 9.37 | 9.28 | 9.27 | 9.36 | 9.34 | 9.27 | 9.34 | 9.34 | 9.21 |
| kg SD) | sem | 0.67 | 0.71 | 0.69 | 0.71 | 0.73 | 0.76 | 0.76 | 0.79 | 0.79 | 0.81 | 0.83 | 0.85 | 0.86 | 0.87 | 0.85 |
| 5H23 (1 mg/ | Mean | 9.84 | 9.69 | 9.49 | 9.36 | 9.28 | 9.19 | 9.05 | 8.92 | 8.90 | 8.85 | 8.85 | 8.83 | 8.89 | 8.93 | 9.24 |
| kg SD) | sem | 0.54 | 0.55 | 0.54 | 0.53 | 0.54 | 0.55 | 0.55 | 0.55 | 0.55 | 0.54 | 0.55 | 0.55 | 0.55 | 0.55 | 0.56 |
| 5H23 (10 mg/ | Mean | 10.07 | 9.95 | 9.73 | 9.61 | 9.49 | 9.33 | 9.20 | 9.07 | 8.98 | 8.88 | 8.80 | 8.73 | 8.74 | 8.67 | 8.51 |
| kg SD) | sem | 0.58 | 0.56 | 0.57 | 0.57 | 0.59 | 0.59 | 0.58 | 0.58 | 0.56 | 0.56 | 0.58 | 0.55 | 0.55 | 0.54 | 0.50 |
| 5H23 (1 mg/ | Mean | 10.05 | 9.86 | 9.66 | 9.51 | 9.40 | 9.31 | 9.14 | 8.92 | 8.84 | 8.74 | 8.63 | 8.53 | 8.45 | 8.41 | 8.29 |
| kg q4w) | sem | 0.42 | 0.45 | 0.43 | 0.42 | 0.44 | 0.44 | 0.43 | 0.43 | 0.42 | 0.41 | 0.42 | 0.40 | 0.40 | 0.39 | 0.38 |

TABLE 26B

Body Weight Change (kg)

| Days | | −4 | 4 | 10 | 14 | 21 | 28 | 35 | 42 |
|---|---|---|---|---|---|---|---|---|---|
| Vehicle | Mean | 0.00 | −0.09 | −0.28 | −0.30 | −0.26 | −0.34 | −0.35 | −0.44 |
|  | sem | 0.00 | 0.05 | 0.05 | 0.04 | 0.06 | 0.08 | 0.10 | 0.13 |
| 5H23 (0.1 mg/ | Mean | 0.00 | −0.08 | −0.30 | −0.38 | −0.49 | −0.54 | −0.64 | −0.72 |
| kg SD) | sem | 0.00 | 0.08 | 0.06 | 0.09 | 0.11 | 0.15 | 0.17 | 0.20 |
| 5H23 (1 mg/ | Mean | 0.00 | −0.16 | −0.35 | −0.48 | −0.56 | −0.65 | −0.79 | −0.93 |
| kg SD) | sem | 0.00 | 0.03 | 0.04 | 0.04 | 0.05 | 0.07 | 0.08 | 0.09 |
| 5H23 (10 mg/ | Mean | 0.00 | −0.12 | −0.34 | −0.47 | −0.59 | −0.74 | −0.88 | −1.00 |
| kg SD) | sem | 0.00 | 0.05 | 0.07 | 0.08 | 0.10 | 0.12 | 0.12 | 0.11 |
| 5H23 (1 mg/ | Mean | 0.00 | −0.18 | −0.38 | −0.54 | −0.65 | −0.74 | −0.90 | −1.13 |
| kg q4w) | sem | 0.00 | 0.08 | 0.06 | 0.05 | 0.05 | 0.06 | 0.08 | 0.10 |

| Days | | 49 | 56 | 63 | 70 | 77 | 84 | 112 |
|---|---|---|---|---|---|---|---|---|
| Vehicle | Mean | −0.45 | −0.53 | −0.56 | −0.60 | −0.64 | −0.71 | −0.93 |
|  | sem | 0.14 | 0.16 | 0.18 | 0.19 | 0.22 | 0.23 | 0.27 |
| 5H23 (0.1 mg/ | Mean | −0.74 | −0.65 | −0.66 | −0.74 | −0.66 | −0.66 | −0.80 |
| kg SD) | sem | 0.22 | 0.24 | 0.26 | 0.28 | 0.30 | 0.31 | 0.28 |
| 5H23 (1 mg/ | Mean | −0.95 | −0.99 | −1.00 | −1.01 | −0.95 | −0.91 | −0.60 |
| kg SD) | sem | 0.11 | 0.13 | 0.15 | 0.19 | 0.21 | 0.22 | 0.20 |
| 5H23 (10 mg/ | Mean | −1.10 | −1.20 | −1.27 | −1.35 | −1.34 | −1.40 | −1.56 |
| kg SD) | sem | 0.15 | 0.15 | 0.16 | 0.17 | 0.15 | 0.16 | 0.23 |
| 5H23 (1 mg/ | Mean | −1.20 | −1.30 | −1.41 | −1.52 | −1.60 | −1.64 | −1.75 |
| kg q4w) | sem | 0.11 | 0.13 | 0.15 | 0.15 | 0.16 | 0.17 | 0.26 |

TABLE 27

Insulin

| Days | | −3 d | 7 d | 14 d | 21 d | 28 d | 35 d | 42 d | 49 d | 56 d | 70 d | 84 d | 112 d |
|---|---|---|---|---|---|---|---|---|---|---|---|---|---|
| Vehicle | Mean | 78.96 | 75.44 | 85.96 | 98.23 | 90.35 | 80.65 | 71.70 | 76.54 | 80.11 | 80.61 | 70.61 | 51.41 |
|  | sem | 17.16 | 16.65 | 15.18 | 23.76 | 21.01 | 15.17 | 13.01 | 12.82 | 16.32 | 20.81 | 17.91 | 11.05 |
| 5H23 (0.1 mg/ | Mean | 118.28 | 64.70 | 65.09 | 65.83 | 61.15 | 62.26 | 84.34 | 68.17 | 85.20 | 82.99 | 95.31 | 57.32 |
| kg SD) | sem | 62.16 | 20.06 | 22.84 | 20.26 | 22.41 | 19.93 | 37.61 | 24.82 | 41.19 | 45.77 | 46.91 | 20.74 |
| 5H23 (1 mg/ | Mean | 74.75 | 54.52 | 51.50 | 54.88 | 42.31 | 46.42 | 46.28 | 38.83 | 56.57 | 40.89 | 51.84 | 64.91 |
| kg SD) | sem | 14.42 | 15.27 | 10.80 | 15.55 | 13.92 | 11.97 | 10.53 | 7.93 | 16.04 | 7.15 | 14.73 | 21.66 |
| 5H23 (10 mg/ | Mean | 84.03 | 51.57 | 46.50 | 54.45 | 53.42 | 38.67 | 37.25 | 34.70 | 32.83 | 25.49 | 33.33 | 22.38 |
| kg SD) | sem | 18.06 | 10.75 | 7.19 | 14.43 | 15.43 | 7.95 | 5.16 | 5.04 | 6.61 | 3.18 | 7.10 | 2.46 |
| 5H23 (1 mg/ | Mean | 133.82 | 52.88 | 61.67 | 109.20 | 49.94 | 38.83 | 37.60 | 47.85 | 40.18 | 32.42 | 30.58 | 22.14 |
| kg q4w) | sem | 57.35 | 18.45 | 14.30 | 40.07 | 13.96 | 9.93 | 12.32 | 13.85 | 11.96 | 8.21 | 10.73 | 4.17 |

TABLE 28

| | | \-3 d | 7 d | 14 d | 21 d | 28 d | 35 d | 42 d | 49 d | 56 d | 70 d | 84 d | 112 d |
|---|---|---|---|---|---|---|---|---|---|---|---|---|---|
| | | | | | | Glucose | | | | | | | |
| Vehicle | Mean | 90.95 | 76.41 | 69.57 | 68.60 | 63.90 | 59.94 | 68.27 | 70.79 | 58.12 | 70.16 | 73.60 | 71.46 |
| | sem | 8.29 | 9.37 | 5.55 | 7.89 | 6.31 | 3.46 | 6.14 | 7.93 | 4.42 | 7.37 | 7.52 | 11.33 |
| 5H23 (0.1 mg/ kg SD) | Mean | 92.54 | 72.59 | 67.10 | 63.23 | 54.14 | 58.19 | 62.37 | 62.53 | 62.46 | 64.24 | 79.27 | 73.80 |
| | sem | 15.41 | 5.49 | 4.54 | 4.52 | 4.82 | 3.37 | 3.69 | 3.39 | 5.17 | 3.60 | 10.90 | 6.91 |
| 5H23 (1 mg/ kg SD) | Mean | 97.67 | 73.82 | 64.51 | 57.74 | 54.72 | 67.07 | 62.39 | 62.96 | 65.25 | 65.88 | 68.56 | 70.02 |
| | sem | 11.08 | 4.64 | 2.69 | 3.29 | 4.38 | 4.98 | 3.91 | 2.36 | 2.59 | 8.34 | 5.21 | 6.84 |
| 5H23 (10 mg/ kg SD) | Mean | 89.71 | 73.24 | 68.74 | 61.13 | 58.93 | 60.55 | 66.49 | 61.11 | 63.14 | 59.11 | 69.59 | 66.49 |
| | sem | 11.76 | 5.56 | 3.10 | 5.11 | 1.92 | 2.68 | 2.14 | 3.56 | 2.21 | 2.52 | 3.98 | 3.11 |
| 5H23 (1 mg/ kg q4w) | Mean | 130.01 | 87.28 | 81.11 | 77.56 | 71.89 | 67.82 | 67.79 | 66.98 | 65.34 | 63.23 | 72.56 | 69.50 |
| | sem | 21.21 | 15.15 | 10.15 | 13.41 | 6.83 | 7.05 | 7.56 | 4.99 | 6.98 | 3.75 | 6.66 | 4.98 |

TABLE 29

| | | \-3 d | 7 d | 14 d | 21 d | 28 d | 35 d | 42 d | 49 d | 56 d | 70 d | 84 d | 112 d |
|---|---|---|---|---|---|---|---|---|---|---|---|---|---|
| | | | | | | Triglycerides | | | | | | | |
| Vehicle | Mean | 0.90 | 0.61 | 1.00 | 1.45 | 1.04 | 1.51 | 1.03 | 1.30 | 0.99 | 1.10 | 1.12 | 0.79 |
| | sem | 0.18 | 0.12 | 0.19 | 0.33 | 0.23 | 0.32 | 0.17 | 0.23 | 0.19 | 0.25 | 0.30 | 0.13 |
| 5H23 (0.1 mg/ kg SD) | Mean | 0.69 | 0.54 | 0.57 | 0.67 | 0.59 | 0.70 | 0.78 | 0.85 | 1.09 | 0.89 | 1.18 | 0.98 |
| | sem | 0.13 | 0.10 | 0.11 | 0.17 | 0.15 | 0.14 | 0.22 | 0.20 | 0.40 | 0.25 | 0.39 | 0.27 |
| 5H23 (1 mg/ kg SD) | Mean | 1.27 | 0.58 | 0.76 | 0.91 | 0.73 | 0.59 | 0.59 | 0.72 | 0.83 | 0.95 | 1.33 | 1.61 |
| | sem | 0.37 | 0.06 | 0.20 | 0.22 | 0.21 | 0.06 | 0.14 | 0.17 | 0.27 | 0.30 | 0.36 | 0.24 |
| 5H23 (10 mg/ kg SD) | Mean | 1.12 | 0.61 | 0.64 | 0.68 | 0.54 | 0.97 | 0.55 | 0.64 | 0.65 | 0.59 | 0.65 | 0.71 |
| | sem | 0.18 | 0.09 | 0.12 | 0.15 | 0.09 | 0.38 | 0.09 | 0.13 | 0.12 | 0.12 | 0.11 | 0.12 |
| 5H23 (1 mg/ kg q4w) | Mean | 1.24 | 0.65 | 0.68 | 0.77 | 0.65 | 0.57 | 0.56 | 0.55 | 0.57 | 0.49 | 0.53 | 0.53 |
| | sem | 0.36 | 0.18 | 0.19 | 0.28 | 0.11 | 0.11 | 0.09 | 0.13 | 0.14 | 0.10 | 0.08 | 0.07 |

The results from these animal studies demonstrate improved metabolic parameters with treatment with anti-beta klotho antibodies provided herein, for example, such as decreases in body weight, body mass index, abdominal circumference, skinfold thickness, glucose (e.g., serum glucose), insulin (e.g., serum insulin) and/or triglycerides (e.g., serum triglycerides).

Example 9: Epitope and Domain Mapping

Studies were performed in order to localize the binding site on human KLB of anti-beta klotho antibodies in the 5H23 epitope bin, including 5H23 as described in Example 3, with sequences shown in Tables 1-10 and FIGS. 1-3, and human anti-beta klotho antibodies in the 5H23 epitope bin, such as humanized 5H23 antibodies (e.g., VH SEQ ID NO: 271 and VL SEQ ID NO: 276). For example, FACS-based binding assays for domain mapping were performed on Expi293 cells (Life Technologies, A14635) that were transiently transfected with plasmids encoding variants of KLB: human, mouse, cynomolgus, a chimeric version in which the KL1 domain sequence of mouse KLB (M1-F506) replaces the KL1 domain of human KLB (M1-F508) to create mouse-human KLB (SEQ ID NO: 376), and a second chimera in which the human KL1 sequence (M1-F508) replaces the KL1 domain of mouse KLB (M1-F506) to create human-mouse KLB (SEQ ID NO: 374). Additionally, the expression vector pYD7 harboring no KLB sequence was transfected as a negative control.

In some studies, binding of a purified sample of a humanized 5H23 antibody (e.g., VH SEQ ID NO: 271 and VL SEQ ID NO: 276) to KLB variants was determined by FACS analysis. Two day post-transfection cells were co-incubated with purified antibodies: humanized 5H23 antibody (e.g., VH SEQ ID NO: 271 and VL SEQ ID NO: 276), a control antibody (e.g., VH SEQ ID NO: 358 and VL SEQ ID NO: 360), and a negative control antibody (e.g., anti-keyhole limpet hemocyanin (KLH) antibody expressed from a construct comprising SEQ ID NO: 424 and 425) diluted to 1 μg/ml in PBS/1% BSA/0.1% azide for 30 minutes at 4° C. After washing with PBS/1% BSA/0.1% azide, transfected cells were then co-incubated with labeled anti-human Fc (Jackson Immunoresearch) for 30 minutes at 4° C. After washing with PBS/1% BSA/0.1% azide, cells were acquired on flow cytometer (FACS Calibur) and analyzed by cytometric software (FlowJo). To display the resulting data, graphs plotting the number of cells as a function of fluorescence intensity were generated, and the median fluorescence intensity (MFI) was determined for each sample as shown in Table 30.

TABLE 30

| Antibody | Mouse KLB | Mouse-Human chimeric KLB | Human-Mouse chimeric KLB | Human KLB | Cynomolgus KLB | Empty Vector (-control) |
|---|---|---|---|---|---|---|
| h5H23 | 14.2 | 26.1 | 9.29 | 865 | 1909 | 8.29 |
| Control | 10.6 | 5.6 | 71.9 | 620 | 1757 | 6.82 |
| Neg. Control | 9.59 | 5.44 | 6.01 | 6.2 | 9.26 | 5.41 |

\* Mean Fluorescence intensity calculated from FACS data using FlowJo analysis software; Neg. Control is anti-KLH antibody.

An exemplary humanized 5H23 antibody (e.g., VH SEQ ID NO: 271 and VL SEQ ID NO: 276) bound to human KLB and cynomolgus KLB, as indicated by a large proportion of cells having high-fluorescence intensity compared to cells treated with the anti-KLH negative control antibody, but the exemplary humanized 5H23 antibody did not bind to mouse KLB. The exemplary humanized 5H23 antibody also bound to the mouse-human KLB chimeric protein, but not the human-mouse KLB chimeric protein indicating that anti-beta klotho antibodies in the 5H23 epitope bin, including 5H23 as described in Example 3, with sequences shown in Tables 1-10 and FIGS. 1-3, and human anti-beta klotho antibodies in the 5H23 epitope bin, such as humanized 5H23 antibodies (e.g., VH SEQ ID NO: 271 and VL SEQ ID NO: 276) bind to the KL2 domain of human KLB. In contrast, the control antibody bound to the KL1 domain of human KLB as demonstrated by its binding to cells transfected with the human-mouse KLB chimeric protein, but not the mouse-human KLB chimeric protein.

In order to further identify specific binding residues within human beta klotho KL2 domain, shotgun mutagenesis was used to separately mutate individual residues of the KL2 domain of human beta klotho to an alanine (e.g., residues F508A-L1008A). The resulting beta klotho mutant proteins were expressed within HEK-293T cells and assayed by fluorescence-activated cell sorting (FACS) for binding to anti-beta klotho antibodies in the 5H23 epitope bin, including 5H23 as described in Example 3, with sequences shown in Tables 1-10 and FIGS. 1-3, and human anti-beta klotho antibodies in the 5H23 epitope bin, such as a humanized 5H23 antibody (e.g., VH SEQ ID NO: 271 and VL SEQ ID NO: 276), or a monovalent Fab fragment of the humanized 5H23 antibody. For example, screening of the beta klotho mutant proteins was conducted at a concentration of 0.5 μg/ml for the humanized 5H23 antibody, 1.0 μg/ml for the Fab fragment, and 2.0 μg/ml for a positive control polyclonal anti-beta klotho antibodies.

The resulting mapping identified three specific binding residues, H657, Y701 and R703, which were negative for binding by the humanized 5H23 antibody, but were positive for the control polyclonal anti-beta klotho antibodies. These residues represented amino acids whose side changes made the highest energetic contributions to the antibody-epitope interaction as shown in Table 31. The locations of the three identified residues were modeled by showing them (dark spheres) at the equivalent positions on human cytosolic beta-glucosidase (PDB ID #2JFE; Tribolo et al., J. Mol. Biol. 370, 964-975 (2007)), identified by BLAST alignment of the two proteins as shown in FIG. 6. The structure shows the equivalent of beta klotho residues 521-963. Lower reactivity of the Y701A and R703A mutations with the humanized 5H23 antibody indicates that Y701 and R703 are major energetic contributors to binding.

TABLE 31

| Protein Mutation | Binding Reactivity (% WT) | |
| --- | --- | --- |
| | Humanized 5H23 Antibody | Control Polyclonal Antibody |
| H657A | 16.88 (±11.93) | 120.35 (±55.21) |
| Y701A | 0.64 (±0.09) | 43.37 (±5.78) |
| R703A | 1.64 (±1.69) | 131.59 (±19.98) |

Thus, the anti-beta klotho antibodies provided herein, including 5H23 and antibodies in the 5H23 epitope bin recognize an epitope in the KLB2 domain that comprises residues H657, Y701 and/or R703. Such antibodies, as described in Example 3 and respresed by and comprising CDR sequences in Tables 1-10 and FIGS. 1-3, are useful as agonist antibodies to induce FGF19-mediate and/or FGF21-mediated signaling, including, for example, to reduce body weight, food intake, BMI, insulin, glucose and/or triglycerides.

Additionally, the anti-beta klotho antibodies provided herein share the common feature of competing with each other for the binding of beta klotho (see, e.g., Example 3 describing antibodies in the 5H23 epitope bin). This competitive inhibition indicates that each antibody binds to the same region of beta klotho (e.g., the same epitope), thereby asserting similar effects. As further exemplified herein, the anti-beta klotho antibodies include humanized anti-beta klotho antibodies, including humanized anti-beta klotho antibodies derived from or based on 5H23, 1C17, 1D19, 2L12, 3L3, 3N20, 4P5, 5C23, 5F7 and/or 1G19 having CDR sequence as described in Tables 1-10 or FIGS. 1-3, such as anti-beta klotho antibodies, including humanized anti-beta klotho antibodies, bind to a specific domain of human beta klotho (e.g., KL2 (residues S509-S1044) as described above). Moreover, such binding can be largely attributed to particular amino acid residues within the KL2 region (e.g., H657, Y701 and R703 as described above), which comprise the epitope recognized by the anti-beta klotho antibodies described herein. Taken together, these results demonstrate that the effects observed for an anti-beta klotho antibody that is derived from or based on 5H23 or an antibody in the 5H23 eptitope bin, including an antibody having one or more CDRs described in Tables 1-10 or FIGS. 1-3, can be extrapolated to other anti-beta klotho antibodies described herein having the same or similar eptitope specificity (e.g., the same or similar CDRs). For example, the in vitro activities of antibodies as shown in Examples 4-7 and above, as well as the in vivo effects demonstrated in Example 8 for an exemplary humanized anti-beta klotho antibody, are representative of the activities and effects of the anti-beta klotho antibodies described herein.

The embodiments of the present disclosure described above are intended to be merely exemplary, and those skilled in the art will recognize, or be able to ascertain using no more than routine experimentation, numerous equivalents to the specific procedures described herein. All such equivalents are considered to be within the scope of the present disclosure and are covered by the following claims. Furthermore, as used in this specification and claims, the singular forms "a," "an" and "the" include plural forms unless the content clearly dictates otherwise. Thus, for example, reference to "an antibody" may include a mixture of two or more such antibodies, and the like. Additionally, ordinarily skilled artisans will recognize that operational sequences must be set forth in some specific order for the purpose of explanation and claiming, but the present disclosure contemplates various changes beyond such specific order.

The contents of all references described herein are hereby incorporated by reference.

Other embodiments are within the following claims.

What is claimed:

1. A method of treating nonalcoholic steatohepatitis (NASH) in a human subject, the method comprising administering to the human subject an effective amount of an antibody or binding fragment thereof that binds human beta klotho, wherein the antibody or binding fragment comprises:

(a) a heavy chain variable region (VH) comprising a VH complementarity determining region (CDR)1 comprising the amino acid sequence of SEQ ID NO:12, a VH CDR2 comprising the amino acid sequence of SEQ ID NO:2, and a VH CDR3 comprising the amino acid sequence of SEQ ID NO:3; and (b) a light chain variable region (VL) comprising a VL CDR1 comprising the amino acid sequence of SEQ ID NO:4, a VL CDR2 comprising the amino acid sequence of SEQ ID NO:5, and a VL CDR3 comprising the amino acid sequence of SEQ ID NO:6.

2. The method of claim 1, wherein the VH comprises an amino acid sequence that is at least 90% identical to the amino acid sequence of SEQ ID NO:271 and the VL comprises an amino acid sequence that is at least 90% identical to the amino acid sequence of SEQ ID NO:276.

3. The method of claim 1, wherein the VH comprises the amino acid sequence of SEQ ID NO:271 and the VL comprises the amino acid sequence of SEQ ID NO:276.

4. The method of claim 1, wherein the antibody or binding fragment thereof is a humanized antibody.

5. The method of claim 1, wherein the antibody is an IgG1 antibody, an IgG2 antibody, or an IgG4 antibody.

6. The method of claim 1, wherein the human subject has Type 2 diabetes, obesity, dyslipidemia, cardiovascular disease, and/or metabolic syndrome.

7. The method of claim 1, wherein the method further comprises administering at least one additional therapeutic agent.

8. The method of claim 7, wherein the at least one additional therapeutic agent is selected from the group consisting of: biguanides, sulphonylureas, thiazolidinediones, GLP-1 analogs, PPAR gamma agonists, dipeptidyl peptidase-4 (DPP-4) inhibitors, bromocriptine, bile acid sequestrants, insulin, alpha glucosidase inhibitors, metformin, SGLT-2 inhibitors, appetite suppressants, and weight loss drugs.

9. A method of treating NASH in a human subject, the method comprising administering to the human subject an effective amount of an antibody that binds human beta klotho, wherein the antibody comprises a heavy chain comprising amino acids 23-472 of SEQ ID NO:317 and a light chain comprising amino acids 23-240 of SEQ ID NO:319.

10. The method of claim 9, wherein the human subject has Type 2 diabetes, obesity, dyslipidemia, cardiovascular disease, and/or metabolic syndrome.

11. The method of claim 9, wherein the method further comprises administering at least one additional therapeutic agent.

12. The method of claim 11, wherein the at least one additional therapeutic agent is selected from the group consisting of: biguanides, sulphonylureas, thiazolidinediones, GLP-1 analogs, PPAR gamma agonists, dipeptidyl peptidase-4 (DPP-4) inhibitors, bromocriptine, bile acid sequestrants, insulin, alpha glucosidase inhibitors, metformin, SGLT-2 inhibitors, appetite suppressants, and weight loss drugs.

13. A method of treating NASH in a human subject, the method comprising administering to the human subject an effective amount of an antibody or binding fragment thereof that binds human beta klotho, wherein the antibody or binding fragment thereof comprises a VH comprising a VH CDR1, a VH CDR2, and a VH CDR3 from the amino acid sequence of SEQ ID NO:271 and a VL comprising a VL CDR1, a VL CDR2, and a VL CDR3 from the amino acid sequence of SEQ ID NO:276.

14. The method of claim 13, wherein the method further comprises administering at least one additional therapeutic agent.

15. The method of claim 14, wherein the at least one additional therapeutic agent is selected from the group consisting of: biguanides, sulphonylureas, thiazolidinediones, GLP-1 analogues, PPAR gamma agonists, dipeptidyl peptidase-4 (DPP-4) inhibitors, bromocriptine, bile acid sequestrants, insulin, alpha glucosidase inhibitors, metformin, SGLT-2 inhibitors, appetite suppressants, and weight loss drugs.

16. The method of claim 13, wherein:
(a) the VH CDR1 comprises the amino acid sequence of SEQ ID NO:1, the VH CDR2 comprises the amino acid sequence of SEQ ID NO:2, the VH CDR3 comprises the amino acid sequence of SEQ ID NO:3, the VL CDR1 comprises the amino acid sequence of SEQ ID NO:4, the VL CDR2 comprises the amino acid sequence of SEQ ID NO:5, and the VL CDR3 comprises the amino acid sequence of SEQ ID NO:6;
(b) the VH CDR1 comprises the amino acid sequence of SEQ ID NO:7, the VH CDR2 comprises the amino acid sequence of SEQ ID NO:8, the VH CDR3 comprises the amino acid sequence of SEQ ID NO:9, the VL CDR1 comprises the amino acid sequence of SEQ ID NO:10, the VL CDR2 comprises the amino acid sequence of SEQ ID NO:11, and the VL CDR3 comprises the amino acid sequence of SEQ ID NO:6;
(c) the VH CDR1 comprises the amino acid sequence of SEQ ID NO:13, the VH CDR2 comprises the amino acid sequence of SEQ ID NO:14, the VH CDR3 comprises the amino acid sequence of SEQ ID NO:15, the VL CDR1 comprises the amino acid sequence of SEQ ID NO:16, the VL CDR2 comprises the amino acid sequence of SEQ ID NO:11, and the VL CDR3 comprises the amino acid sequence of SEQ ID NO:17;
(d) the VH CDR1 comprises the amino acid sequence of SEQ ID NO:18, the VH CDR2 comprises the amino acid sequence of SEQ ID NO:19, the VH CDR3 comprises the amino acid sequence of SEQ ID NO:20, the VL CDR1 comprises the amino acid sequence of SEQ ID NO:21, the VL CDR2 comprises the amino acid sequence of SEQ ID NO:22, and the VL CDR3 comprises the amino acid sequence of SEQ ID NO:23; or
(e) the VH CDR1 comprises the amino acid sequence of SEQ ID NO:1, the VH CDR2 comprises the amino acid sequence of SEQ ID NO:24, the VH CDR3 comprises the amino acid sequence of SEQ ID NO:3, the VL CDR1 comprises the amino acid sequence of SEQ ID NO:4, the VL CDR2 comprises the amino acid sequence of SEQ ID NO:5, and the VL CDR3 comprises the amino acid sequence of SEQ ID NO:6.

17. The method of claim 13, wherein:
the VH CDR1 comprises the amino acid sequence of SEQ ID NO:1, the VH CDR2 comprises the amino acid sequence of SEQ ID NO:2, the VH CDR3 comprises the amino acid sequence of SEQ ID NO:3, the VL CDR1 comprises the amino acid sequence of SEQ ID NO:4, the VL CDR2 comprises the amino acid sequence of SEQ ID NO:5, and the VL CDR3 comprises the amino acid sequence of SEQ ID NO:6.

18. The method of claim 13, wherein the VH comprises an amino acid sequence that is at least 90% identical to the amino acid sequence of SEQ ID NO:271 and the VL comprises an amino acid sequence that is at least 90% identical to the amino acid sequence of SEQ ID NO:276.

19. The method of claim 13, wherein the antibody or binding fragment thereof is a humanized antibody.

20. The method of claim 13, wherein the antibody is an IgG1 antibody, an IgG2 antibody, or an IgG4 antibody.

21. The method of claim 13, wherein the human subject has Type 2 diabetes, obesity, dyslipidemia, cardiovascular disease, and/or metabolic syndrome.

* * * * *

SEQUENCE LISTING

<160> NUMBER OF SEQ ID NOS: 431

<210> SEQ ID NO 1
<211> LENGTH: 10
<212> TYPE: PRT

```
<213> ORGANISM: Artificial Sequence
<220> FEATURE:
<223> OTHER INFORMATION: 5H23 VH CDR1 - Exemplary

<400> SEQUENCE: 1

Gly Tyr Thr Phe Thr Ser Tyr Asp Ile Asn
1               5                   10

<210> SEQ ID NO 2
<211> LENGTH: 17
<212> TYPE: PRT
<213> ORGANISM: Artificial Sequence
<220> FEATURE:
<223> OTHER INFORMATION: 5H23 VH CDR2- Exemplary

<400> SEQUENCE: 2

Trp Ile Tyr Pro Gly Asp Gly Ser Thr Lys Tyr Asn Glu Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: 5H23 VH CDR3- Exemplary

<400> SEQUENCE: 3

Ser Asp Tyr Tyr Gly Ser Arg Ser Phe Ala Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: 5H23 VL CDR1- Exemplary

<400> SEQUENCE: 4

Arg Ala Ser Lys Ser Val Ser Thr Ser Gly Tyr Val Tyr Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: 5H23 VL CDR2- Exemplary

<400> SEQUENCE: 5

Leu Ala Ser Tyr Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: 5H23 VL CDR3- Exemplary

<400> SEQUENCE: 6

Gln His Ser Arg Asp Leu Thr Phe Pro
1               5

<210> SEQ ID NO 7
<211> LENGTH: 8
```

```
<212> TYPE: PRT
<213> ORGANISM: Artificial Sequence
<220> FEATURE:
<223> OTHER INFORMATION: 5H23 VH CDR1 - IMGT

<400> SEQUENCE: 7

Gly Tyr Thr Phe Thr Ser Tyr Asp
1               5

<210> SEQ ID NO 8
<211> LENGTH: 8
<212> TYPE: PRT
<213> ORGANISM: Artificial Sequence
<220> FEATURE:
<223> OTHER INFORMATION: 5H23 VH CDR2 - IMGT

<400> SEQUENCE: 8

Ile Tyr Pro Gly Asp Gly Ser Thr
1               5

<210> SEQ ID NO 9
<211> LENGTH: 13
<212> TYPE: PRT
<213> ORGANISM: Artificial Sequence
<220> FEATURE:
<223> OTHER INFORMATION: 5H23 VH CDR3 - IMGT

<400> SEQUENCE: 9

Ala Arg Ser Asp Tyr Tyr Gly Ser Arg Ser Phe Ala Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: 5H23 VL CDR1- IMGT

<400> SEQUENCE: 10

Lys Ser Val Ser Thr Ser Gly Tyr Val Tyr
1               5                   10

<210> SEQ ID NO 11
<211> LENGTH: 3
<212> TYPE: PRT
<213> ORGANISM: Artificial Sequence
<220> FEATURE:
<223> OTHER INFORMATION: 5H23 VL CDR2- IMGT

<400> SEQUENCE: 11

Leu Ala Ser
1

<210> SEQ ID NO 12
<211> LENGTH: 5
<212> TYPE: PRT
<213> ORGANISM: Artificial Sequence
<220> FEATURE:
<223> OTHER INFORMATION: 5H23 VH CDR1 - Kabat

<400> SEQUENCE: 12

Ser Tyr Asp Ile Asn
1               5

<210> SEQ ID NO 13
<211> LENGTH: 7
<212> TYPE: PRT
```

```
<213> ORGANISM: Artificial Sequence
<220> FEATURE:
<223> OTHER INFORMATION: 5H23 VH CDR1 - Chothia

<400> SEQUENCE: 13

Gly Tyr Thr Phe Thr Ser Tyr
1               5

<210> SEQ ID NO 14
<211> LENGTH: 4
<212> TYPE: PRT
<213> ORGANISM: Artificial Sequence
<220> FEATURE:
<223> OTHER INFORMATION: 5H23 VH CDR2 - Chothia

<400> SEQUENCE: 14

Pro Gly Asp Gly
1

<210> SEQ ID NO 15
<211> LENGTH: 9
<212> TYPE: PRT
<213> ORGANISM: Artificial Sequence
<220> FEATURE:
<223> OTHER INFORMATION: 5H23 VH CDR3 - Chothia

<400> SEQUENCE: 15

Asp Tyr Tyr Gly Ser Arg Ser Phe Ala
1               5

<210> SEQ ID NO 16
<211> LENGTH: 11
<212> TYPE: PRT
<213> ORGANISM: Artificial Sequence
<220> FEATURE:
<223> OTHER INFORMATION: 5H23 VL CDR1- Chothia

<400> SEQUENCE: 16

Ser Lys Ser Val Ser Thr Ser Gly Tyr Val Tyr
1               5                   10

<210> SEQ ID NO 17
<211> LENGTH: 6
<212> TYPE: PRT
<213> ORGANISM: Artificial Sequence
<220> FEATURE:
<223> OTHER INFORMATION: 5H23 VL CDR3- Chothia

<400> SEQUENCE: 17

Ser Arg Asp Leu Thr Phe
1               5

<210> SEQ ID NO 18
<211> LENGTH: 6
<212> TYPE: PRT
<213> ORGANISM: Artificial Sequence
<220> FEATURE:
<223> OTHER INFORMATION: 5H23 VH CDR1 - Contact

<400> SEQUENCE: 18

Thr Ser Tyr Asp Ile Asn
1               5

<210> SEQ ID NO 19
<211> LENGTH: 13
<212> TYPE: PRT
<213> ORGANISM: Artificial Sequence
```

```
<220> FEATURE:
<223> OTHER INFORMATION: 5H23 VH CDR2 - Contact

<400> SEQUENCE: 19

Trp Ile Gly Trp Ile Tyr Pro Gly Asp Gly Ser Thr Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: 5H23 VH CDR3 - Contact

<400> SEQUENCE: 20

Ala Arg Ser Asp Tyr Tyr Gly Ser Arg Ser Phe Ala
1               5                   10

<210> SEQ ID NO 21
<211> LENGTH: 11
<212> TYPE: PRT
<213> ORGANISM: Artificial Sequence
<220> FEATURE:
<223> OTHER INFORMATION: 5H23 VL CDR1 - Contact

<400> SEQUENCE: 21

Ser Thr Ser Gly Tyr Val Tyr Met His Trp Asn
1               5                   10

<210> SEQ ID NO 22
<211> LENGTH: 10
<212> TYPE: PRT
<213> ORGANISM: Artificial Sequence
<220> FEATURE:
<223> OTHER INFORMATION: 5H23 VL CDR2 - Contact

<400> SEQUENCE: 22

Leu Leu Ile Tyr Leu Ala Ser Tyr Leu Glu
1               5                   10

<210> SEQ ID NO 23
<211> LENGTH: 8
<212> TYPE: PRT
<213> ORGANISM: Artificial Sequence
<220> FEATURE:
<223> OTHER INFORMATION: 5H23 VL CDR3 - Contact

<400> SEQUENCE: 23

Gln His Ser Arg Asp Leu Thr Phe
1               5

<210> SEQ ID NO 24
<211> LENGTH: 10
<212> TYPE: PRT
<213> ORGANISM: Artificial Sequence
<220> FEATURE:
<223> OTHER INFORMATION: 5H23 VH CDR2 - AbM

<400> SEQUENCE: 24

Trp Ile Tyr Pro Gly Asp Gly Ser Thr Lys
1               5                   10

<210> SEQ ID NO 25
<211> LENGTH: 120
<212> TYPE: PRT
<213> ORGANISM: Artificial Sequence
<220> FEATURE:
```

<223> OTHER INFORMATION: 5H23 VH Sequence

<400> SEQUENCE: 25

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ser Arg Thr Ala Tyr
65                  70                  75                  80

Met Gln Leu Ser Ser Leu Thr Ser Glu Asn Ser Ala Val Tyr Phe Cys
            85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ala
        115                 120

<210> SEQ ID NO 26
<211> LENGTH: 111
<212> TYPE: PRT
<213> ORGANISM: Artificial Sequence
<220> FEATURE:
<223> OTHER INFORMATION: 5H23 VL Sequence

<400> SEQUENCE: 26

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Val Tyr Met His Trp Asn Gln Gln Lys Pro Gly Gln Pro Pro
        35                  40                  45

Lys Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Ile Tyr Tyr Cys Gln His Ser Arg
            85                  90                  95

Asp Leu Thr Phe Pro Phe Gly Gly Gly Thr Lys Leu Glu Ile Lys
            100                 105                 110

<210> SEQ ID NO 27
<211> LENGTH: 11
<212> TYPE: PRT
<213> ORGANISM: Artificial Sequence
<220> FEATURE:
<223> OTHER INFORMATION: 1C17 VH CDR1 - Exemplary

<400> SEQUENCE: 27

Gly Tyr Ser Ile Thr Ser Gly Tyr Tyr Trp Asn
1               5                   10

<210> SEQ ID NO 28
<211> LENGTH: 16
<212> TYPE: PRT
<213> ORGANISM: Artificial Sequence
<220> FEATURE:
<223> OTHER INFORMATION: 1C17 VH CDR2 - Exemplary

```
<400> SEQUENCE: 28

Tyr Ile Asn Tyr Asp Gly Asn Ser Asn Tyr Thr Pro Ser Leu Lys Asn
1               5                   10                  15

<210> SEQ ID NO 29
<211> LENGTH: 13
<212> TYPE: PRT
<213> ORGANISM: Artificial Sequence
<220> FEATURE:
<223> OTHER INFORMATION: 1C17 VH CDR3 - Exemplary

<400> SEQUENCE: 29

Lys Gly Ala Tyr Tyr Ser Asn Tyr Asp Ser Phe Asp Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: 1C17 VL CDR1 - Exemplary

<400> SEQUENCE: 30

Lys Ala Ser Gln Asp Ile Asn Ser Tyr Leu Ser
1               5                   10

<210> SEQ ID NO 31
<211> LENGTH: 7
<212> TYPE: PRT
<213> ORGANISM: Artificial Sequence
<220> FEATURE:
<223> OTHER INFORMATION: 1C17 VL CDR2 - Exemplary

<400> SEQUENCE: 31

Arg Ala Asn Arg Leu Val Asp
1               5

<210> SEQ ID NO 32
<211> LENGTH: 9
<212> TYPE: PRT
<213> ORGANISM: Artificial Sequence
<220> FEATURE:
<223> OTHER INFORMATION: 1C17 VL CDR3 - Exemplary

<400> SEQUENCE: 32

Leu Gln Tyr Asp Glu Phe Pro Phe Thr
1               5

<210> SEQ ID NO 33
<211> LENGTH: 9
<212> TYPE: PRT
<213> ORGANISM: Artificial Sequence
<220> FEATURE:
<223> OTHER INFORMATION: 1C17 VH CDR1 - IMGT

<400> SEQUENCE: 33

Gly Tyr Ser Ile Thr Ser Gly Tyr Tyr
1               5

<210> SEQ ID NO 34
<211> LENGTH: 7
<212> TYPE: PRT
<213> ORGANISM: Artificial Sequence
<220> FEATURE:
<223> OTHER INFORMATION: 1C17 VH CDR2 - IMGT
```

```
<400> SEQUENCE: 34

Ile Asn Tyr Asp Gly Asn Ser
1               5

<210> SEQ ID NO 35
<211> LENGTH: 15
<212> TYPE: PRT
<213> ORGANISM: Artificial Sequence
<220> FEATURE:
<223> OTHER INFORMATION: 1C17 VH CDR3 - IMGT

<400> SEQUENCE: 35

Ala Arg Lys Gly Ala Tyr Tyr Ser Asn Tyr Asp Ser Phe Asp Val
1               5                   10                  15

<210> SEQ ID NO 36
<211> LENGTH: 6
<212> TYPE: PRT
<213> ORGANISM: Artificial Sequence
<220> FEATURE:
<223> OTHER INFORMATION: 1C17 VL CDR1 - IMGT

<400> SEQUENCE: 36

Gln Asp Ile Asn Ser Tyr
1               5

<210> SEQ ID NO 37
<211> LENGTH: 3
<212> TYPE: PRT
<213> ORGANISM: Artificial Sequence
<220> FEATURE:
<223> OTHER INFORMATION: 1C17 VL CDR2 - IMGT

<400> SEQUENCE: 37

Arg Ala Asn
1

<210> SEQ ID NO 38
<211> LENGTH: 6
<212> TYPE: PRT
<213> ORGANISM: Artificial Sequence
<220> FEATURE:
<223> OTHER INFORMATION: 1C17 VH CDR1 - Kabat

<400> SEQUENCE: 38

Ser Gly Tyr Tyr Trp Asn
1               5

<210> SEQ ID NO 39
<211> LENGTH: 8
<212> TYPE: PRT
<213> ORGANISM: Artificial Sequence
<220> FEATURE:
<223> OTHER INFORMATION: 1C17 VH CDR1 - Chothia

<400> SEQUENCE: 39

Gly Tyr Ser Ile Thr Ser Gly Tyr
1               5

<210> SEQ ID NO 40
<211> LENGTH: 3
<212> TYPE: PRT
<213> ORGANISM: Artificial Sequence
<220> FEATURE:
<223> OTHER INFORMATION: 1C17 VH CDR2 - Chothia

<400> SEQUENCE: 40
```

```
Tyr Asp Gly
1

<210> SEQ ID NO 41
<211> LENGTH: 11
<212> TYPE: PRT
<213> ORGANISM: Artificial Sequence
<220> FEATURE:
<223> OTHER INFORMATION: 1C17 VH CDR3 - Chothia

<400> SEQUENCE: 41

Gly Ala Tyr Tyr Ser Asn Tyr Asp Ser Phe Asp
1               5                   10

<210> SEQ ID NO 42
<211> LENGTH: 7
<212> TYPE: PRT
<213> ORGANISM: Artificial Sequence
<220> FEATURE:
<223> OTHER INFORMATION: 1C17 VL CDR1 - Chothia

<400> SEQUENCE: 42

Ser Gln Asp Ile Asn Ser Tyr
1               5

<210> SEQ ID NO 43
<211> LENGTH: 6
<212> TYPE: PRT
<213> ORGANISM: Artificial Sequence
<220> FEATURE:
<223> OTHER INFORMATION: 1C17 VL CDR3 - Chothia

<400> SEQUENCE: 43

Tyr Asp Glu Phe Pro Phe
1               5

<210> SEQ ID NO 44
<211> LENGTH: 7
<212> TYPE: PRT
<213> ORGANISM: Artificial Sequence
<220> FEATURE:
<223> OTHER INFORMATION: 1C17 VH CDR1 - Contact

<400> SEQUENCE: 44

Thr Ser Gly Tyr Tyr Trp Asn
1               5

<210> SEQ ID NO 45
<211> LENGTH: 12
<212> TYPE: PRT
<213> ORGANISM: Artificial Sequence
<220> FEATURE:
<223> OTHER INFORMATION: 1C17 VH CDR2 - Contact

<400> SEQUENCE: 45

Trp Met Gly Tyr Ile Asn Tyr Asp Gly Asn Ser Asn
1               5                   10

<210> SEQ ID NO 46
<211> LENGTH: 14
<212> TYPE: PRT
<213> ORGANISM: Artificial Sequence
<220> FEATURE:
<223> OTHER INFORMATION: 1C17 VH CDR3 - Contact

<400> SEQUENCE: 46
```

```
Ala Arg Lys Gly Ala Tyr Tyr Ser Asn Tyr Asp Ser Phe Asp
1               5                   10
```

<210> SEQ ID NO 47
<211> LENGTH: 7
<212> TYPE: PRT
<213> ORGANISM: Artificial Sequence
<220> FEATURE:
<223> OTHER INFORMATION: 1C17 VL CDR1 - Contact

<400> SEQUENCE: 47

```
Asn Ser Tyr Leu Ser Trp Val
1               5
```

<210> SEQ ID NO 48
<211> LENGTH: 10
<212> TYPE: PRT
<213> ORGANISM: Artificial Sequence
<220> FEATURE:
<223> OTHER INFORMATION: 1C17 VL CDR2 - Contact

<400> SEQUENCE: 48

```
Thr Leu Ile Tyr Arg Ala Asn Arg Leu Val
1               5                   10
```

<210> SEQ ID NO 49
<211> LENGTH: 8
<212> TYPE: PRT
<213> ORGANISM: Artificial Sequence
<220> FEATURE:
<223> OTHER INFORMATION: 1C17 VL CDR3 - Contact

<400> SEQUENCE: 49

```
Leu Gln Tyr Asp Glu Phe Pro Phe
1               5
```

<210> SEQ ID NO 50
<211> LENGTH: 9
<212> TYPE: PRT
<213> ORGANISM: Artificial Sequence
<220> FEATURE:
<223> OTHER INFORMATION: 1C17 VH CDR2 - AbM

<400> SEQUENCE: 50

```
Tyr Ile Asn Tyr Asp Gly Asn Ser Asn
1               5
```

<210> SEQ ID NO 51
<211> LENGTH: 122
<212> TYPE: PRT
<213> ORGANISM: Artificial Sequence
<220> FEATURE:
<223> OTHER INFORMATION: 1C17 VH Sequence

<400> SEQUENCE: 51

```
Gln Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Tyr Ile Asn Tyr Asp Gly Asn Ser Asn Tyr Thr Pro Ser Leu
    50                  55                  60

Lys Asn Arg Ile Ser Ile Thr Arg Asp Thr Ser Lys Asn Gln Phe Phe
65                  70                  75                  80
```

```
Leu Lys Leu Asn Ser Val Thr Pro Glu Asp Thr Ala Thr Tyr Tyr Cys
                85                  90                  95

Ala Arg Lys Gly Ala Tyr Tyr Ser Asn Tyr Asp Ser Phe Asp Val Trp
            100                 105                 110

Gly Thr Gly Thr Thr Val Thr Val Ser Ser
        115                 120

<210> SEQ ID NO 52
<211> LENGTH: 107
<212> TYPE: PRT
<213> ORGANISM: Artificial Sequence
<220> FEATURE:
<223> OTHER INFORMATION: 1C17 VL Sequence

<400> SEQUENCE: 52

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Val Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105

<210> SEQ ID NO 53
<211> LENGTH: 10
<212> TYPE: PRT
<213> ORGANISM: Artificial Sequence
<220> FEATURE:
<223> OTHER INFORMATION: 1D19 VH CDR1- Exemplary

<400> SEQUENCE: 53

Gly Tyr Thr Phe Thr Arg Tyr Asp Ile Asn
1               5                   10

<210> SEQ ID NO 54
<211> LENGTH: 17
<212> TYPE: PRT
<213> ORGANISM: Artificial Sequence
<220> FEATURE:
<223> OTHER INFORMATION: 1D19 VH CDR2- Exemplary

<400> SEQUENCE: 54

Trp Ile Tyr Pro Gly Asp Ser Ser Thr Lys Phe Asn Glu Asn Phe Lys
1               5                   10                  15

Asp

<210> SEQ ID NO 55
<211> LENGTH: 11
<212> TYPE: PRT
<213> ORGANISM: Artificial Sequence
<220> FEATURE:
<223> OTHER INFORMATION: 1D19 VH CDR3- Exemplary

<400> SEQUENCE: 55
```

Ser Asp Tyr Tyr Gly Ser Arg Ser Phe Thr Tyr
1               5                   10

<210> SEQ ID NO 56
<211> LENGTH: 15
<212> TYPE: PRT
<213> ORGANISM: Artificial Sequence
<220> FEATURE:
<223> OTHER INFORMATION: 1D19 VL CDR1- Exemplary

<400> SEQUENCE: 56

Arg Ala Ser Lys Ser Val Ser Thr Ser Gly Tyr Ser Tyr Met His
1               5                   10                  15

<210> SEQ ID NO 57
<211> LENGTH: 7
<212> TYPE: PRT
<213> ORGANISM: Artificial Sequence
<220> FEATURE:
<223> OTHER INFORMATION: 1D19 VL CDR2- Exemplary

<400> SEQUENCE: 57

Leu Ala Ser Asn Leu Glu Ser
1               5

<210> SEQ ID NO 58
<211> LENGTH: 9
<212> TYPE: PRT
<213> ORGANISM: Artificial Sequence
<220> FEATURE:
<223> OTHER INFORMATION: 1D19 VL CDR3- Exemplary

<400> SEQUENCE: 58

Gln His Ser Arg Glu Leu Pro Tyr Thr
1               5

<210> SEQ ID NO 59
<211> LENGTH: 8
<212> TYPE: PRT
<213> ORGANISM: Artificial Sequence
<220> FEATURE:
<223> OTHER INFORMATION: 1D19 VH CDR1 - IMGT

<400> SEQUENCE: 59

Gly Tyr Thr Phe Thr Arg Tyr Asp
1               5

<210> SEQ ID NO 60
<211> LENGTH: 8
<212> TYPE: PRT
<213> ORGANISM: Artificial Sequence
<220> FEATURE:
<223> OTHER INFORMATION: 1D19 VH CDR2 - IMGT

<400> SEQUENCE: 60

Ile Tyr Pro Gly Asp Ser Ser Thr
1               5

<210> SEQ ID NO 61
<211> LENGTH: 13
<212> TYPE: PRT
<213> ORGANISM: Artificial Sequence
<220> FEATURE:
<223> OTHER INFORMATION: 1D19 VH CDR3 - IMGT

<400> SEQUENCE: 61

Ala Arg Ser Asp Tyr Tyr Gly Ser Arg Ser Phe Thr Tyr

```
1               5                  10
```

<210> SEQ ID NO 62
<211> LENGTH: 10
<212> TYPE: PRT
<213> ORGANISM: Artificial Sequence
<220> FEATURE:
<223> OTHER INFORMATION: 1D19 VL CDR1 - IMGT

<400> SEQUENCE: 62

```
Lys Ser Val Ser Thr Ser Gly Tyr Ser Tyr
1               5                   10
```

<210> SEQ ID NO 63
<211> LENGTH: 3
<212> TYPE: PRT
<213> ORGANISM: Artificial Sequence
<220> FEATURE:
<223> OTHER INFORMATION: 1D19 VL CDR2 - IMGT

<400> SEQUENCE: 63

```
Leu Ala Ser
1
```

<210> SEQ ID NO 64
<211> LENGTH: 5
<212> TYPE: PRT
<213> ORGANISM: Artificial Sequence
<220> FEATURE:
<223> OTHER INFORMATION: 1D19 VH CDR1 - Kabat

<400> SEQUENCE: 64

```
Arg Tyr Asp Ile Asn
1               5
```

<210> SEQ ID NO 65
<211> LENGTH: 7
<212> TYPE: PRT
<213> ORGANISM: Artificial Sequence
<220> FEATURE:
<223> OTHER INFORMATION: 1D19 VH CDR1 - Chothia

<400> SEQUENCE: 65

```
Gly Tyr Thr Phe Thr Arg Tyr
1               5
```

<210> SEQ ID NO 66
<211> LENGTH: 4
<212> TYPE: PRT
<213> ORGANISM: Artificial Sequence
<220> FEATURE:
<223> OTHER INFORMATION: 1D19 VH CDR2 - Chothia

<400> SEQUENCE: 66

```
Pro Gly Asp Ser
1
```

<210> SEQ ID NO 67
<211> LENGTH: 9
<212> TYPE: PRT
<213> ORGANISM: Artificial Sequence
<220> FEATURE:
<223> OTHER INFORMATION: 1D19 VH CDR3 - Chothia

<400> SEQUENCE: 67

```
Asp Tyr Tyr Gly Ser Arg Ser Phe Thr
1               5
```

```
<210> SEQ ID NO 68
<211> LENGTH: 11
<212> TYPE: PRT
<213> ORGANISM: Artificial Sequence
<220> FEATURE:
<223> OTHER INFORMATION: 1D19 VL CDR1 - Chothia

<400> SEQUENCE: 68

Ser Lys Ser Val Ser Thr Ser Gly Tyr Ser Tyr
1               5                   10

<210> SEQ ID NO 69
<211> LENGTH: 6
<212> TYPE: PRT
<213> ORGANISM: Artificial Sequence
<220> FEATURE:
<223> OTHER INFORMATION: 1D19 VL CDR3 - Chothia

<400> SEQUENCE: 69

Ser Arg Glu Leu Pro Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: 1D19 VH CDR1 - Contact

<400> SEQUENCE: 70

Thr Arg Tyr Asp Ile Asn
1               5

<210> SEQ ID NO 71
<211> LENGTH: 13
<212> TYPE: PRT
<213> ORGANISM: Artificial Sequence
<220> FEATURE:
<223> OTHER INFORMATION: 1D19 VH CDR2 - Contact

<400> SEQUENCE: 71

Trp Ile Gly Trp Ile Tyr Pro Gly Asp Ser Ser Thr Lys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: 1D19 VH CDR3 - Contact

<400> SEQUENCE: 72

Ala Arg Ser Asp Tyr Tyr Gly Ser Arg Ser Phe Thr
1               5                   10

<210> SEQ ID NO 73
<211> LENGTH: 11
<212> TYPE: PRT
<213> ORGANISM: Artificial Sequence
<220> FEATURE:
<223> OTHER INFORMATION: 1D19 VL CDR1 - Contact

<400> SEQUENCE: 73

Ser Thr Ser Gly Tyr Ser Tyr Met His Trp Tyr
1               5                   10
```

```
<210> SEQ ID NO 74
<211> LENGTH: 10
<212> TYPE: PRT
<213> ORGANISM: Artificial Sequence
<220> FEATURE:
<223> OTHER INFORMATION: 1D19 VL CDR2 - Contact

<400> SEQUENCE: 74

Leu Leu Ile Tyr Leu Ala Ser Asn Leu Glu
1               5                   10

<210> SEQ ID NO 75
<211> LENGTH: 8
<212> TYPE: PRT
<213> ORGANISM: Artificial Sequence
<220> FEATURE:
<223> OTHER INFORMATION: 1D19 VL CDR3 - Contact

<400> SEQUENCE: 75

Gln His Ser Arg Glu Leu Pro Tyr
1               5

<210> SEQ ID NO 76
<211> LENGTH: 10
<212> TYPE: PRT
<213> ORGANISM: Artificial Sequence
<220> FEATURE:
<223> OTHER INFORMATION: 1D19 VH CDR2 - AbM

<400> SEQUENCE: 76

Trp Ile Tyr Pro Gly Asp Ser Ser Thr Lys
1               5                   10

<210> SEQ ID NO 77
<211> LENGTH: 120
<212> TYPE: PRT
<213> ORGANISM: Artificial Sequence
<220> FEATURE:
<223> OTHER INFORMATION: 1D19 VH Sequence

<400> SEQUENCE: 77

Gln Val Gln Pro Gln Glu Ser Gly Pro Glu Leu Val Lys Pro Gly Ala
1               5                   10                  15

Leu Val Lys Ile Ser Cys Lys Ala Ser Gly Tyr Thr Phe Thr Arg Tyr
            20                  25                  30

Asp Ile Asn Trp Met Lys Gln Arg Pro Gly Gln Gly Leu Glu Trp Ile
        35                  40                  45

Gly Trp Ile Tyr Pro Gly Asp Ser Ser Thr Lys Phe Asn Glu Asn Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asn Ser Thr Val Tyr Phe Cys
                85                  90                  95

Ala Arg Ser Asp Tyr Tyr Gly Ser Arg Ser Phe Thr Tyr Trp Gly Gln
            100                 105                 110

Gly Thr Leu Val Thr Val Ser Ala
        115                 120

<210> SEQ ID NO 78
<211> LENGTH: 111
<212> TYPE: PRT
<213> ORGANISM: Artificial Sequence
<220> FEATURE:
```

<223> OTHER INFORMATION: 1D19 VL Sequence

<400> SEQUENCE: 78

Asp Ile Val Leu Thr Gln Ser Pro Ala Ser Leu Ala Val Ser Leu Gly
1               5                   10                  15
Gln Arg Ala Thr Ile Ser Cys Arg Ala Ser Lys Ser Val Ser Thr Ser
            20                  25                  30
Gly Tyr Ser Tyr Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ser Arg
                85                  90                  95
Glu Leu Pro Tyr Thr Phe Gly Gly Gly Thr Lys Leu Glu Ile Lys
            100                 105                 110

<210> SEQ ID NO 79
<211> LENGTH: 10
<212> TYPE: PRT
<213> ORGANISM: Artificial Sequence
<220> FEATURE:
<223> OTHER INFORMATION: 2L12 VH CDR1- Exemplary

<400> SEQUENCE: 79

Gly Tyr Thr Phe Thr Arg Tyr Asp Ile Asn
1               5                   10

<210> SEQ ID NO 80
<211> LENGTH: 17
<212> TYPE: PRT
<213> ORGANISM: Artificial Sequence
<220> FEATURE:
<223> OTHER INFORMATION: 2L12 VH CDR2- Exemplary

<400> SEQUENCE: 80

Trp Ile Tyr Pro Gly Asp Asp Ser Thr Lys Tyr Asn Glu Lys Phe Lys
1               5                   10                  15
Gly

<210> SEQ ID NO 81
<211> LENGTH: 11
<212> TYPE: PRT
<213> ORGANISM: Artificial Sequence
<220> FEATURE:
<223> OTHER INFORMATION: 2L12 VH CDR3- Exemplary

<400> SEQUENCE: 81

Ser Asp Tyr Tyr Gly Ser Arg Ser Phe Val Tyr
1               5                   10

<210> SEQ ID NO 82
<211> LENGTH: 15
<212> TYPE: PRT
<213> ORGANISM: Artificial Sequence
<220> FEATURE:
<223> OTHER INFORMATION: 2L12 VL CDR1- Exemplary

<400> SEQUENCE: 82

Arg Ala Ser Lys Ser Val Ser Thr Ser Gly Tyr Ser Tyr Leu His
1               5                   10                  15

<210> SEQ ID NO 83
<211> LENGTH: 7
<212> TYPE: PRT
<213> ORGANISM: Artificial Sequence
<220> FEATURE:
<223> OTHER INFORMATION: 2L12 VL CDR2- Exemplary

<400> SEQUENCE: 83

Leu Ala Ser Asn Leu Glu Ser
1               5

<210> SEQ ID NO 84
<211> LENGTH: 9
<212> TYPE: PRT
<213> ORGANISM: Artificial Sequence
<220> FEATURE:
<223> OTHER INFORMATION: 2L12 VL CDR3- Exemplary

<400> SEQUENCE: 84

Gln His Ser Gly Glu Leu Pro Tyr Thr
1               5

<210> SEQ ID NO 85
<211> LENGTH: 8
<212> TYPE: PRT
<213> ORGANISM: Artificial Sequence
<220> FEATURE:
<223> OTHER INFORMATION: 2L12 VH CDR1 - IMGT

<400> SEQUENCE: 85

Gly Tyr Thr Phe Thr Arg Tyr Asp
1               5

<210> SEQ ID NO 86
<211> LENGTH: 8
<212> TYPE: PRT
<213> ORGANISM: Artificial Sequence
<220> FEATURE:
<223> OTHER INFORMATION: 2L12 VH CDR2 - IMGT

<400> SEQUENCE: 86

Ile Tyr Pro Gly Asp Asp Ser Thr
1               5

<210> SEQ ID NO 87
<211> LENGTH: 13
<212> TYPE: PRT
<213> ORGANISM: Artificial Sequence
<220> FEATURE:
<223> OTHER INFORMATION: 2L12 VH CDR3 - IMGT

<400> SEQUENCE: 87

Ala Arg Ser Asp Tyr Tyr Gly Ser Arg Ser Phe Val Tyr
1               5                   10

<210> SEQ ID NO 88
<211> LENGTH: 10
<212> TYPE: PRT
<213> ORGANISM: Artificial Sequence
<220> FEATURE:
<223> OTHER INFORMATION: 2L12 VL CDR1 - IMGT

<400> SEQUENCE: 88

Lys Ser Val Ser Thr Ser Gly Tyr Ser Tyr
1               5                   10

```
<210> SEQ ID NO 89
<211> LENGTH: 3
<212> TYPE: PRT
<213> ORGANISM: Artificial Sequence
<220> FEATURE:
<223> OTHER INFORMATION: 2L12 VL CDR2 - IMGT

<400> SEQUENCE: 89

Leu Ala Ser
1

<210> SEQ ID NO 90
<211> LENGTH: 5
<212> TYPE: PRT
<213> ORGANISM: Artificial Sequence
<220> FEATURE:
<223> OTHER INFORMATION: 2L12 VH CDR1 - Kabat

<400> SEQUENCE: 90

Arg Tyr Asp Ile Asn
1               5

<210> SEQ ID NO 91
<211> LENGTH: 7
<212> TYPE: PRT
<213> ORGANISM: Artificial Sequence
<220> FEATURE:
<223> OTHER INFORMATION: 2L12 VH CDR1 - Chothia

<400> SEQUENCE: 91

Gly Tyr Thr Phe Thr Arg Tyr
1               5

<210> SEQ ID NO 92
<211> LENGTH: 4
<212> TYPE: PRT
<213> ORGANISM: Artificial Sequence
<220> FEATURE:
<223> OTHER INFORMATION: 2L12 VH CDR2 - Chothia

<400> SEQUENCE: 92

Pro Gly Asp Asp
1

<210> SEQ ID NO 93
<211> LENGTH: 9
<212> TYPE: PRT
<213> ORGANISM: Artificial Sequence
<220> FEATURE:
<223> OTHER INFORMATION: 2L12 VH CDR3 - Chothia

<400> SEQUENCE: 93

Asp Tyr Tyr Gly Ser Arg Ser Phe Val
1               5

<210> SEQ ID NO 94
<211> LENGTH: 11
<212> TYPE: PRT
<213> ORGANISM: Artificial Sequence
<220> FEATURE:
<223> OTHER INFORMATION: 2L12 VL CDR1- Chothia

<400> SEQUENCE: 94

Ser Lys Ser Val Ser Thr Ser Gly Tyr Ser Tyr
1               5                   10

<210> SEQ ID NO 95
```

```
<211> LENGTH: 6
<212> TYPE: PRT
<213> ORGANISM: Artificial Sequence
<220> FEATURE:
<223> OTHER INFORMATION: 2L12 VL CDR3- Chothia

<400> SEQUENCE: 95

Ser Gly Glu Leu Pro Tyr
1               5

<210> SEQ ID NO 96
<211> LENGTH: 6
<212> TYPE: PRT
<213> ORGANISM: Artificial Sequence
<220> FEATURE:
<223> OTHER INFORMATION: 2L12 VH CDR1 - Contact

<400> SEQUENCE: 96

Thr Arg Tyr Asp Ile Asn
1               5

<210> SEQ ID NO 97
<211> LENGTH: 13
<212> TYPE: PRT
<213> ORGANISM: Artificial Sequence
<220> FEATURE:
<223> OTHER INFORMATION: 2L12 VH CDR2 - Contact

<400> SEQUENCE: 97

Trp Ile Gly Trp Ile Tyr Pro Gly Asp Asp Ser Thr Lys
1               5                   10

<210> SEQ ID NO 98
<211> LENGTH: 12
<212> TYPE: PRT
<213> ORGANISM: Artificial Sequence
<220> FEATURE:
<223> OTHER INFORMATION: 2L12 VH CDR3 - Contact

<400> SEQUENCE: 98

Ala Arg Ser Asp Tyr Tyr Gly Ser Arg Ser Phe Val
1               5                   10

<210> SEQ ID NO 99
<211> LENGTH: 11
<212> TYPE: PRT
<213> ORGANISM: Artificial Sequence
<220> FEATURE:
<223> OTHER INFORMATION: 2L12 VL CDR1 - Contact

<400> SEQUENCE: 99

Ser Thr Ser Gly Tyr Ser Tyr Leu His Trp Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: 2L12 VL CDR2 - Contact

<400> SEQUENCE: 100

Leu Leu Ile Tyr Leu Ala Ser Asn Leu Glu
1               5                   10

<210> SEQ ID NO 101
<211> LENGTH: 8
```

```
<212> TYPE: PRT
<213> ORGANISM: Artificial Sequence
<220> FEATURE:
<223> OTHER INFORMATION: 2L12 VL CDR3 - Contact

<400> SEQUENCE: 101

Gln His Ser Gly Glu Leu Pro Tyr
1               5

<210> SEQ ID NO 102
<211> LENGTH: 10
<212> TYPE: PRT
<213> ORGANISM: Artificial Sequence
<220> FEATURE:
<223> OTHER INFORMATION: 2L12 VH CDR2 - AbM

<400> SEQUENCE: 102

Trp Ile Tyr Pro Gly Asp Asp Ser Thr Lys
1               5                   10

<210> SEQ ID NO 103
<211> LENGTH: 120
<212> TYPE: PRT
<213> ORGANISM: Artificial Sequence
<220> FEATURE:
<223> OTHER INFORMATION: 2L12 VH Sequence

<400> SEQUENCE: 103

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Arg Tyr
                20                  25                  30

Asp Ile Asn Trp Val Lys Lys Arg Pro Gly Gln Gly Leu Glu Trp Ile
            35                  40                  45

Gly Trp Ile Tyr Pro Gly Asp Asp Ser Thr Lys Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Ser Asp Tyr Tyr Gly Ser Arg Ser Phe Val Tyr Trp Gly Gln
            100                 105                 110

Gly Thr Leu Val Thr Val Ser Ala
        115                 120

<210> SEQ ID NO 104
<211> LENGTH: 111
<212> TYPE: PRT
<213> ORGANISM: Artificial Sequence
<220> FEATURE:
<223> OTHER INFORMATION: 2L12 VL Sequence

<400> SEQUENCE: 104

Asp Ile Val Leu Thr Gln Ser Pro Ala Ser Leu Pro Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Leu His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60
```

```
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Gly
                 85                  90                  95

Glu Leu Pro Tyr Thr Phe Gly Gly Gly Thr Lys Leu Glu Ile Lys
            100                 105                 110

<210> SEQ ID NO 105
<211> LENGTH: 10
<212> TYPE: PRT
<213> ORGANISM: Artificial Sequence
<220> FEATURE:
<223> OTHER INFORMATION: 3L3 VH CDR1 - Exemplary

<400> SEQUENCE: 105

Gly Tyr Thr Phe Thr Ser Tyr Asp Ile Asn
 1               5                  10

<210> SEQ ID NO 106
<211> LENGTH: 17
<212> TYPE: PRT
<213> ORGANISM: Artificial Sequence
<220> FEATURE:
<223> OTHER INFORMATION: 3L3 VH CDR2 - Exemplary

<400> SEQUENCE: 106

Trp Ile Tyr Pro Gly Asp Gly Ser Pro Lys Tyr Asp Glu Lys Phe Lys
 1               5                  10                  15

Gly

<210> SEQ ID NO 107
<211> LENGTH: 11
<212> TYPE: PRT
<213> ORGANISM: Artificial Sequence
<220> FEATURE:
<223> OTHER INFORMATION: 3L3 VH CDR3 - Exemplary

<400> SEQUENCE: 107

Ser Asp Tyr Tyr Gly Ser Arg Ser Phe Val Tyr
 1               5                  10

<210> SEQ ID NO 108
<211> LENGTH: 15
<212> TYPE: PRT
<213> ORGANISM: Artificial Sequence
<220> FEATURE:
<223> OTHER INFORMATION: 3L3 VL CDR1- Exemplary

<400> SEQUENCE: 108

Arg Ala Ser Lys Ser Val Ser Thr Ser Gly Tyr Ser Tyr Val His
 1               5                  10                  15

<210> SEQ ID NO 109
<211> LENGTH: 7
<212> TYPE: PRT
<213> ORGANISM: Artificial Sequence
<220> FEATURE:
<223> OTHER INFORMATION: 3L3 VL CDR2- Exemplary

<400> SEQUENCE: 109

Leu Ala Ser Asn Leu Glu Ser
 1               5

<210> SEQ ID NO 110
<211> LENGTH: 9
```

```
<212> TYPE: PRT
<213> ORGANISM: Artificial Sequence
<220> FEATURE:
<223> OTHER INFORMATION: 3L3 VL CDR3- Exemplary

<400> SEQUENCE: 110

Gln His Ser Gly Glu Leu Pro Tyr Thr
1               5

<210> SEQ ID NO 111
<211> LENGTH: 8
<212> TYPE: PRT
<213> ORGANISM: Artificial Sequence
<220> FEATURE:
<223> OTHER INFORMATION: 3L3 VH CDR1 - IMGT

<400> SEQUENCE: 111

Gly Tyr Thr Phe Thr Ser Tyr Asp
1               5

<210> SEQ ID NO 112
<211> LENGTH: 8
<212> TYPE: PRT
<213> ORGANISM: Artificial Sequence
<220> FEATURE:
<223> OTHER INFORMATION: 3L3 VH CDR2 - IMGT

<400> SEQUENCE: 112

Ile Tyr Pro Gly Asp Gly Ser Pro
1               5

<210> SEQ ID NO 113
<211> LENGTH: 13
<212> TYPE: PRT
<213> ORGANISM: Artificial Sequence
<220> FEATURE:
<223> OTHER INFORMATION: 3L3 VH CDR3 - IMGT

<400> SEQUENCE: 113

Ala Arg Ser Asp Tyr Tyr Gly Ser Arg Ser Phe Val Tyr
1               5                   10

<210> SEQ ID NO 114
<211> LENGTH: 10
<212> TYPE: PRT
<213> ORGANISM: Artificial Sequence
<220> FEATURE:
<223> OTHER INFORMATION: 3L3 VL CDR1- IMGT

<400> SEQUENCE: 114

Lys Ser Val Ser Thr Ser Gly Tyr Ser Tyr
1               5                   10

<210> SEQ ID NO 115
<211> LENGTH: 3
<212> TYPE: PRT
<213> ORGANISM: Artificial Sequence
<220> FEATURE:
<223> OTHER INFORMATION: 3L3 VL CDR2- IMGT

<400> SEQUENCE: 115

Leu Ala Ser
1

<210> SEQ ID NO 116
<211> LENGTH: 5
<212> TYPE: PRT
```

```
<213> ORGANISM: Artificial Sequence
<220> FEATURE:
<223> OTHER INFORMATION: 3L3 VH CDR1 - Kabat

<400> SEQUENCE: 116

Ser Tyr Asp Ile Asn
1               5

<210> SEQ ID NO 117
<211> LENGTH: 7
<212> TYPE: PRT
<213> ORGANISM: Artificial Sequence
<220> FEATURE:
<223> OTHER INFORMATION: 3L3 VH CDR1 - Chothia

<400> SEQUENCE: 117

Gly Tyr Thr Phe Thr Ser Tyr
1               5

<210> SEQ ID NO 118
<211> LENGTH: 4
<212> TYPE: PRT
<213> ORGANISM: Artificial Sequence
<220> FEATURE:
<223> OTHER INFORMATION: 3L3 VH CDR2 - Chothia

<400> SEQUENCE: 118

Pro Gly Asp Gly
1

<210> SEQ ID NO 119
<211> LENGTH: 9
<212> TYPE: PRT
<213> ORGANISM: Artificial Sequence
<220> FEATURE:
<223> OTHER INFORMATION: 3L3 VH CDR3 - Chothia

<400> SEQUENCE: 119

Asp Tyr Tyr Gly Ser Arg Ser Phe Val
1               5

<210> SEQ ID NO 120
<211> LENGTH: 11
<212> TYPE: PRT
<213> ORGANISM: Artificial Sequence
<220> FEATURE:
<223> OTHER INFORMATION: 3L3 VL CDR1- Chothia

<400> SEQUENCE: 120

Ser Lys Ser Val Ser Thr Ser Gly Tyr Ser Tyr
1               5                   10

<210> SEQ ID NO 121
<211> LENGTH: 6
<212> TYPE: PRT
<213> ORGANISM: Artificial Sequence
<220> FEATURE:
<223> OTHER INFORMATION: 3L3 VL CDR3- Chothia

<400> SEQUENCE: 121

Ser Gly Glu Leu Pro Tyr
1               5

<210> SEQ ID NO 122
<211> LENGTH: 6
<212> TYPE: PRT
<213> ORGANISM: Artificial Sequence
```

```
<220> FEATURE:
<223> OTHER INFORMATION: 3L3 VH CDR1 - Contact

<400> SEQUENCE: 122

Thr Ser Tyr Asp Ile Asn
1               5

<210> SEQ ID NO 123
<211> LENGTH: 13
<212> TYPE: PRT
<213> ORGANISM: Artificial Sequence
<220> FEATURE:
<223> OTHER INFORMATION: 3L3 VH CDR2 - Contact

<400> SEQUENCE: 123

Trp Ile Gly Trp Ile Tyr Pro Gly Asp Gly Ser Pro Lys
1               5                   10

<210> SEQ ID NO 124
<211> LENGTH: 12
<212> TYPE: PRT
<213> ORGANISM: Artificial Sequence
<220> FEATURE:
<223> OTHER INFORMATION: 3L3 VH CDR3 - Contact

<400> SEQUENCE: 124

Ala Arg Ser Asp Tyr Tyr Gly Ser Arg Ser Phe Val
1               5                   10

<210> SEQ ID NO 125
<211> LENGTH: 11
<212> TYPE: PRT
<213> ORGANISM: Artificial Sequence
<220> FEATURE:
<223> OTHER INFORMATION: 3L3 VL CDR1- Contact

<400> SEQUENCE: 125

Ser Thr Ser Gly Tyr Ser Tyr Val His Trp Tyr
1               5                   10

<210> SEQ ID NO 126
<211> LENGTH: 10
<212> TYPE: PRT
<213> ORGANISM: Artificial Sequence
<220> FEATURE:
<223> OTHER INFORMATION: 3L3 VL CDR2- Contact

<400> SEQUENCE: 126

Leu Leu Ile Tyr Leu Ala Ser Asn Leu Glu
1               5                   10

<210> SEQ ID NO 127
<211> LENGTH: 8
<212> TYPE: PRT
<213> ORGANISM: Artificial Sequence
<220> FEATURE:
<223> OTHER INFORMATION: 3L3 VL CDR3- Contact

<400> SEQUENCE: 127

Gln His Ser Gly Glu Leu Pro Tyr
1               5

<210> SEQ ID NO 128
<211> LENGTH: 10
<212> TYPE: PRT
<213> ORGANISM: Artificial Sequence
<220> FEATURE:
```

<223> OTHER INFORMATION: 3L3 VH CDR2 - AbM

<400> SEQUENCE: 128

Trp Ile Tyr Pro Gly Asp Gly Ser Pro Lys
1               5                   10

<210> SEQ ID NO 129
<211> LENGTH: 120
<212> TYPE: PRT
<213> ORGANISM: Artificial Sequence
<220> FEATURE:
<223> OTHER INFORMATION: 3L3 VH Sequence

<400> SEQUENCE: 129

Gln Val Gln Pro Gln Glu Ser Gly Pro Glu Leu Val Lys Pro Gly Thr
1               5                   10                  15

Leu Val Lys Ile Ser Cys Lys Ala Ser Gly Tyr Thr Phe Thr Ser Tyr
                20                  25                  30

Asp Ile Asn Trp Val Lys Gln Arg Pro Gly Gln Gly Leu Glu Trp Ile
            35                  40                  45

Gly Trp Ile Tyr Pro Gly Asp Gly Ser Pro Lys Tyr Asp Glu Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Ser Asp Tyr Tyr Gly Ser Arg Ser Phe Val Tyr Trp Gly Gln
            100                 105                 110

Gly Thr Leu Val Thr Val Ser Ala
        115                 120

<210> SEQ ID NO 130
<211> LENGTH: 111
<212> TYPE: PRT
<213> ORGANISM: Artificial Sequence
<220> FEATURE:
<223> OTHER INFORMATION: 3L3 VL Sequence

<400> SEQUENCE: 130

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Val His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
50                  55                  60

Arg Phe Ser Gly Arg Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Tyr Thr Phe Gly Gly Gly Thr Lys Leu Glu Ile Lys
            100                 105                 110

<210> SEQ ID NO 131
<211> LENGTH: 10
<212> TYPE: PRT
<213> ORGANISM: Artificial Sequence
<220> FEATURE:
<223> OTHER INFORMATION: 3N20 VH CDR1- Exemplary

```
<400> SEQUENCE: 131

Gly Tyr Ile Phe Thr Asn Tyr Gly Ile Ser
1               5                   10

<210> SEQ ID NO 132
<211> LENGTH: 17
<212> TYPE: PRT
<213> ORGANISM: Artificial Sequence
<220> FEATURE:
<223> OTHER INFORMATION: 3N20 VH CDR2- Exemplary

<400> SEQUENCE: 132

Glu Ile Tyr Pro Arg Ser Gly Asn Thr Tyr Tyr Asn Glu Lys Phe Lys
1               5                   10                  15

Gly

<210> SEQ ID NO 133
<211> LENGTH: 11
<212> TYPE: PRT
<213> ORGANISM: Artificial Sequence
<220> FEATURE:
<223> OTHER INFORMATION: 3N20 VH CDR3- Exemplary

<400> SEQUENCE: 133

His Trp Asp Gly Val Leu Asp Tyr Phe Asp Tyr
1               5                   10

<210> SEQ ID NO 134
<211> LENGTH: 17
<212> TYPE: PRT
<213> ORGANISM: Artificial Sequence
<220> FEATURE:
<223> OTHER INFORMATION: 3N20 VL CDR1- Exemplary

<400> SEQUENCE: 134

Lys Ser Ser Gln Ser Leu Leu Asn Ser Gly Asn Gln Lys Asn Tyr Leu
1               5                   10                  15

Ala

<210> SEQ ID NO 135
<211> LENGTH: 7
<212> TYPE: PRT
<213> ORGANISM: Artificial Sequence
<220> FEATURE:
<223> OTHER INFORMATION: 3N20 VL CDR2- Exemplary

<400> SEQUENCE: 135

Gly Ala Ser Thr Arg Glu Ser
1               5

<210> SEQ ID NO 136
<211> LENGTH: 9
<212> TYPE: PRT
<213> ORGANISM: Artificial Sequence
<220> FEATURE:
<223> OTHER INFORMATION: 3N20 VL CDR3- Exemplary

<400> SEQUENCE: 136

Leu Asn Asp His Ser Tyr Pro Phe Thr
1               5

<210> SEQ ID NO 137
<211> LENGTH: 8
<212> TYPE: PRT
```

```
<213> ORGANISM: Artificial Sequence
<220> FEATURE:
<223> OTHER INFORMATION: 3N20 VH CDR1 - IMGT

<400> SEQUENCE: 137

Gly Tyr Ile Phe Thr Asn Tyr Gly
1               5

<210> SEQ ID NO 138
<211> LENGTH: 8
<212> TYPE: PRT
<213> ORGANISM: Artificial Sequence
<220> FEATURE:
<223> OTHER INFORMATION: 3N20 VH CDR2 - IMGT

<400> SEQUENCE: 138

Ile Tyr Pro Arg Ser Gly Asn Thr
1               5

<210> SEQ ID NO 139
<211> LENGTH: 13
<212> TYPE: PRT
<213> ORGANISM: Artificial Sequence
<220> FEATURE:
<223> OTHER INFORMATION: 3N20 VH CDR3 - IMGT

<400> SEQUENCE: 139

Ala Arg His Trp Asp Gly Val Leu Asp Tyr Phe Asp Tyr
1               5                   10

<210> SEQ ID NO 140
<211> LENGTH: 12
<212> TYPE: PRT
<213> ORGANISM: Artificial Sequence
<220> FEATURE:
<223> OTHER INFORMATION: 3N20 VL CDR1 - IMGT

<400> SEQUENCE: 140

Gln Ser Leu Leu Asn Ser Gly Asn Gln Lys Asn Tyr
1               5                   10

<210> SEQ ID NO 141
<211> LENGTH: 3
<212> TYPE: PRT
<213> ORGANISM: Artificial Sequence
<220> FEATURE:
<223> OTHER INFORMATION: 3N20 VL CDR2 - IMGT

<400> SEQUENCE: 141

Gly Ala Ser
1

<210> SEQ ID NO 142
<211> LENGTH: 5
<212> TYPE: PRT
<213> ORGANISM: Artificial Sequence
<220> FEATURE:
<223> OTHER INFORMATION: 3N20 VH CDR1 - Kabat

<400> SEQUENCE: 142

Asn Tyr Gly Ile Ser
1               5

<210> SEQ ID NO 143
<211> LENGTH: 7
<212> TYPE: PRT
<213> ORGANISM: Artificial Sequence
```

```
<220> FEATURE:
<223> OTHER INFORMATION: 3N20 VH CDR1 - Chothia

<400> SEQUENCE: 143

Gly Tyr Ile Phe Thr Asn Tyr
1               5

<210> SEQ ID NO 144
<211> LENGTH: 4
<212> TYPE: PRT
<213> ORGANISM: Artificial Sequence
<220> FEATURE:
<223> OTHER INFORMATION: 3N20 VH CDR2 - Chothia

<400> SEQUENCE: 144

Pro Arg Ser Gly
1

<210> SEQ ID NO 145
<211> LENGTH: 9
<212> TYPE: PRT
<213> ORGANISM: Artificial Sequence
<220> FEATURE:
<223> OTHER INFORMATION: 3N20 VH CDR3 - Chothia

<400> SEQUENCE: 145

Trp Asp Gly Val Leu Asp Tyr Phe Asp
1               5

<210> SEQ ID NO 146
<211> LENGTH: 13
<212> TYPE: PRT
<213> ORGANISM: Artificial Sequence
<220> FEATURE:
<223> OTHER INFORMATION: 3N20 VL CDR1- Chothia

<400> SEQUENCE: 146

Ser Gln Ser Leu Leu Asn Ser Gly Asn Gln Lys Asn Tyr
1               5                   10

<210> SEQ ID NO 147
<211> LENGTH: 6
<212> TYPE: PRT
<213> ORGANISM: Artificial Sequence
<220> FEATURE:
<223> OTHER INFORMATION: 3N20 VL CDR3- Chothia

<400> SEQUENCE: 147

Asp His Ser Tyr Pro Phe
1               5

<210> SEQ ID NO 148
<211> LENGTH: 6
<212> TYPE: PRT
<213> ORGANISM: Artificial Sequence
<220> FEATURE:
<223> OTHER INFORMATION: 3N20 VH CDR1 - Contact

<400> SEQUENCE: 148

Thr Asn Tyr Gly Ile Ser
1               5

<210> SEQ ID NO 149
<211> LENGTH: 13
<212> TYPE: PRT
<213> ORGANISM: Artificial Sequence
<220> FEATURE:
```

```
<223> OTHER INFORMATION: 3N20 VH CDR2 - Contact

<400> SEQUENCE: 149

Trp Ile Gly Glu Ile Tyr Pro Arg Ser Gly Asn Thr Tyr
1               5                   10

<210> SEQ ID NO 150
<211> LENGTH: 12
<212> TYPE: PRT
<213> ORGANISM: Artificial Sequence
<220> FEATURE:
<223> OTHER INFORMATION: 3N20 VH CDR3 - Contact

<400> SEQUENCE: 150

Ala Arg His Trp Asp Gly Val Leu Asp Tyr Phe Asp
1               5                   10

<210> SEQ ID NO 151
<211> LENGTH: 13
<212> TYPE: PRT
<213> ORGANISM: Artificial Sequence
<220> FEATURE:
<223> OTHER INFORMATION: 3N20 VL CDR1 - Contact

<400> SEQUENCE: 151

Leu Asn Ser Gly Asn Gln Lys Asn Tyr Leu Ala Trp Tyr
1               5                   10

<210> SEQ ID NO 152
<211> LENGTH: 10
<212> TYPE: PRT
<213> ORGANISM: Artificial Sequence
<220> FEATURE:
<223> OTHER INFORMATION: 3N20 VL CDR2 - Contact

<400> SEQUENCE: 152

Leu Leu Ile Tyr Gly Ala Ser Thr Arg Glu
1               5                   10

<210> SEQ ID NO 153
<211> LENGTH: 8
<212> TYPE: PRT
<213> ORGANISM: Artificial Sequence
<220> FEATURE:
<223> OTHER INFORMATION: 3N20 VL CDR3 - Contact

<400> SEQUENCE: 153

Leu Asn Asp His Ser Tyr Pro Phe
1               5

<210> SEQ ID NO 154
<211> LENGTH: 10
<212> TYPE: PRT
<213> ORGANISM: Artificial Sequence
<220> FEATURE:
<223> OTHER INFORMATION: 3N20 VH CDR2 - AbM

<400> SEQUENCE: 154

Glu Ile Tyr Pro Arg Ser Gly Asn Thr Tyr
1               5                   10

<210> SEQ ID NO 155
<211> LENGTH: 120
<212> TYPE: PRT
<213> ORGANISM: Artificial Sequence
<220> FEATURE:
<223> OTHER INFORMATION: 3N20 VH Sequence
```

<400> SEQUENCE: 155

```
Gln Val Gln Leu Gln Glu Ser Gly Ala Glu Leu Ala Arg Pro Gly Ala
1               5                   10                  15

Ser Val Lys Leu Ser Cys Lys Val Ser Gly Tyr Ile Phe Thr Asn Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Met Ser Ser Thr Ala Tyr
65                  70                  75                  80

Met Asp Leu Arg Ser Leu Thr Ser Glu Asp Ser Ala Val Tyr Phe Cys
                85                  90                  95

Ala Arg His Trp Asp Gly Val Leu Asp Tyr Phe Asp Tyr Trp Gly Gln
            100                 105                 110

Gly Thr Ser Leu Thr Val Ser Ser
            115                 120
```

<210> SEQ ID NO 156
<211> LENGTH: 113
<212> TYPE: PRT
<213> ORGANISM: Artificial Sequence
<220> FEATURE:
<223> OTHER INFORMATION: 3N20 VL Sequence

<400> SEQUENCE: 156

```
Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Leu Asn
                85                  90                  95

Asp His Ser Tyr Pro Phe Thr Phe Gly Ala Gly Thr Lys Leu Glu Leu
            100                 105                 110

Lys
```

<210> SEQ ID NO 157
<211> LENGTH: 10
<212> TYPE: PRT
<213> ORGANISM: Artificial Sequence
<220> FEATURE:
<223> OTHER INFORMATION: 4P5 VH CDR1 - Exemplary

<400> SEQUENCE: 157

```
Gly Tyr Thr Phe Thr Arg Tyr Asp Ile Asn
1               5                   10
```

<210> SEQ ID NO 158
<211> LENGTH: 17
<212> TYPE: PRT
<213> ORGANISM: Artificial Sequence
<220> FEATURE:

<223> OTHER INFORMATION: 4P5 VH CDR2 - Exemplary

<400> SEQUENCE: 158

Trp Ile Tyr Pro Gly Asp Asp Ser Thr Lys Tyr Asn Glu Lys Phe Lys
1               5                   10                  15

Gly

<210> SEQ ID NO 159
<211> LENGTH: 11
<212> TYPE: PRT
<213> ORGANISM: Artificial Sequence
<220> FEATURE:
<223> OTHER INFORMATION: 4P5 VH CDR3 - Exemplary

<400> SEQUENCE: 159

Ser Asp Tyr Tyr Gly Ser Arg Ser Phe Val Tyr
1               5                   10

<210> SEQ ID NO 160
<211> LENGTH: 15
<212> TYPE: PRT
<213> ORGANISM: Artificial Sequence
<220> FEATURE:
<223> OTHER INFORMATION: 4P5 VL CDR1 - Exemplary

<400> SEQUENCE: 160

Arg Ala Ser Lys Ser Val Ser Thr Ser Gly Tyr Ser Tyr Met His
1               5                   10                  15

<210> SEQ ID NO 161
<211> LENGTH: 7
<212> TYPE: PRT
<213> ORGANISM: Artificial Sequence
<220> FEATURE:
<223> OTHER INFORMATION: 4P5 VL CDR2 - Exemplary

<400> SEQUENCE: 161

Leu Ala Ser Asn Leu Glu Ser
1               5

<210> SEQ ID NO 162
<211> LENGTH: 9
<212> TYPE: PRT
<213> ORGANISM: Artificial Sequence
<220> FEATURE:
<223> OTHER INFORMATION: 4P5 VL CDR3 - Exemplary

<400> SEQUENCE: 162

His His Ser Gly Glu Leu Pro Tyr Thr
1               5

<210> SEQ ID NO 163
<211> LENGTH: 8
<212> TYPE: PRT
<213> ORGANISM: Artificial Sequence
<220> FEATURE:
<223> OTHER INFORMATION: 4P5 VH CDR1 - IMGT

<400> SEQUENCE: 163

Gly Tyr Thr Phe Thr Arg Tyr Asp
1               5

<210> SEQ ID NO 164
<211> LENGTH: 8
<212> TYPE: PRT
<213> ORGANISM: Artificial Sequence

```
<220> FEATURE:
<223> OTHER INFORMATION: 4P5 VH CDR2 - IMGT

<400> SEQUENCE: 164

Ile Tyr Pro Gly Asp Asp Ser Thr
1               5

<210> SEQ ID NO 165
<211> LENGTH: 13
<212> TYPE: PRT
<213> ORGANISM: Artificial Sequence
<220> FEATURE:
<223> OTHER INFORMATION: 4P5 VH CDR3 - IMGT

<400> SEQUENCE: 165

Ala Arg Ser Asp Tyr Tyr Gly Ser Arg Ser Phe Val Tyr
1               5                   10

<210> SEQ ID NO 166
<211> LENGTH: 10
<212> TYPE: PRT
<213> ORGANISM: Artificial Sequence
<220> FEATURE:
<223> OTHER INFORMATION: 4P5 VL CDR1- IMGT

<400> SEQUENCE: 166

Lys Ser Val Ser Thr Ser Gly Tyr Ser Tyr
1               5                   10

<210> SEQ ID NO 167
<211> LENGTH: 3
<212> TYPE: PRT
<213> ORGANISM: Artificial Sequence
<220> FEATURE:
<223> OTHER INFORMATION: 4P5 VL CDR2- IMGT

<400> SEQUENCE: 167

Leu Ala Ser
1

<210> SEQ ID NO 168
<211> LENGTH: 5
<212> TYPE: PRT
<213> ORGANISM: Artificial Sequence
<220> FEATURE:
<223> OTHER INFORMATION: 4P5 VH CDR1 - Kabat

<400> SEQUENCE: 168

Arg Tyr Asp Ile Asn
1               5

<210> SEQ ID NO 169
<211> LENGTH: 7
<212> TYPE: PRT
<213> ORGANISM: Artificial Sequence
<220> FEATURE:
<223> OTHER INFORMATION: 4P5 VH CDR1 - Chothia

<400> SEQUENCE: 169

Gly Tyr Thr Phe Thr Arg Tyr
1               5

<210> SEQ ID NO 170
<211> LENGTH: 4
<212> TYPE: PRT
<213> ORGANISM: Artificial Sequence
<220> FEATURE:
```

```
<223> OTHER INFORMATION: 4P5 VH CDR2 - Chothia

<400> SEQUENCE: 170

Pro Gly Asp Asp
1

<210> SEQ ID NO 171
<211> LENGTH: 9
<212> TYPE: PRT
<213> ORGANISM: Artificial Sequence
<220> FEATURE:
<223> OTHER INFORMATION: 4P5 VH CDR3 - Chothia

<400> SEQUENCE: 171

Asp Tyr Tyr Gly Ser Arg Ser Phe Val
1               5

<210> SEQ ID NO 172
<211> LENGTH: 11
<212> TYPE: PRT
<213> ORGANISM: Artificial Sequence
<220> FEATURE:
<223> OTHER INFORMATION: 4P5 VL CDR1- Chothia

<400> SEQUENCE: 172

Ser Lys Ser Val Ser Thr Ser Gly Tyr Ser Tyr
1               5                   10

<210> SEQ ID NO 173
<211> LENGTH: 6
<212> TYPE: PRT
<213> ORGANISM: Artificial Sequence
<220> FEATURE:
<223> OTHER INFORMATION: 4P5 VL CDR3- Chothia

<400> SEQUENCE: 173

Ser Gly Glu Leu Pro Tyr
1               5

<210> SEQ ID NO 174
<211> LENGTH: 6
<212> TYPE: PRT
<213> ORGANISM: Artificial Sequence
<220> FEATURE:
<223> OTHER INFORMATION: 4P5 VH CDR1 - Contact

<400> SEQUENCE: 174

Thr Arg Tyr Asp Ile Asn
1               5

<210> SEQ ID NO 175
<211> LENGTH: 13
<212> TYPE: PRT
<213> ORGANISM: Artificial Sequence
<220> FEATURE:
<223> OTHER INFORMATION: 4P5 VH CDR2 - Contact

<400> SEQUENCE: 175

Trp Ile Gly Trp Ile Tyr Pro Gly Asp Asp Ser Thr Lys
1               5                   10

<210> SEQ ID NO 176
<211> LENGTH: 12
<212> TYPE: PRT
<213> ORGANISM: Artificial Sequence
<220> FEATURE:
<223> OTHER INFORMATION: 4P5 VH CDR3 - Contact
```

```
<400> SEQUENCE: 176

Ala Arg Ser Asp Tyr Tyr Gly Ser Arg Ser Phe Val
1               5                   10

<210> SEQ ID NO 177
<211> LENGTH: 11
<212> TYPE: PRT
<213> ORGANISM: Artificial Sequence
<220> FEATURE:
<223> OTHER INFORMATION: 4P5 VL CDR1- Contact

<400> SEQUENCE: 177

Ser Thr Ser Gly Tyr Ser Tyr Met His Trp Tyr
1               5                   10

<210> SEQ ID NO 178
<211> LENGTH: 10
<212> TYPE: PRT
<213> ORGANISM: Artificial Sequence
<220> FEATURE:
<223> OTHER INFORMATION: 4P5 VL CDR2- Contact

<400> SEQUENCE: 178

Leu Leu Ile Tyr Leu Ala Ser Asn Leu Glu
1               5                   10

<210> SEQ ID NO 179
<211> LENGTH: 8
<212> TYPE: PRT
<213> ORGANISM: Artificial Sequence
<220> FEATURE:
<223> OTHER INFORMATION: 4P5 VL CDR3- Contact

<400> SEQUENCE: 179

His His Ser Gly Glu Leu Pro Tyr
1               5

<210> SEQ ID NO 180
<211> LENGTH: 10
<212> TYPE: PRT
<213> ORGANISM: Artificial Sequence
<220> FEATURE:
<223> OTHER INFORMATION: 4P5 VH CDR2 - AbM

<400> SEQUENCE: 180

Trp Ile Tyr Pro Gly Asp Asp Ser Thr Lys
1               5                   10

<210> SEQ ID NO 181
<211> LENGTH: 120
<212> TYPE: PRT
<213> ORGANISM: Artificial Sequence
<220> FEATURE:
<223> OTHER INFORMATION: 4P5 VH Sequence

<400> SEQUENCE: 181

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Arg Tyr
            20                  25                  30

Asp Ile Asn Trp Val Lys Lys Arg Pro Gly Gln Gly Leu Glu Trp Ile
        35                  40                  45

Gly Trp Ile Tyr Pro Gly Asp Asp Ser Thr Lys Tyr Asn Glu Lys Phe
    50                  55                  60
```

Lys Gly Lys Ala Thr Leu Thr Ala Asp Lys Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Ser Asp Tyr Tyr Gly Ser Arg Ser Phe Val Tyr Trp Gly Gln
            100                 105                 110

Gly Thr Leu Val Thr Val Ser Ala
        115                 120

<210> SEQ ID NO 182
<211> LENGTH: 111
<212> TYPE: PRT
<213> ORGANISM: Artificial Sequence
<220> FEATURE:
<223> OTHER INFORMATION: 4P5 VL Sequence

<400> SEQUENCE: 182

Asp Ile Leu Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Arg Gly Ser Gly Thr Asp Phe Thr Leu Asn Ile His
65                  70                  75                  80

Pro Val Glu Glu Glu Asp Ala Ala Thr Tyr Tyr Cys His His Ser Gly
                85                  90                  95

Glu Leu Pro Tyr Thr Phe Gly Gly Gly Thr Lys Leu Glu Ile Lys
            100                 105                 110

<210> SEQ ID NO 183
<211> LENGTH: 10
<212> TYPE: PRT
<213> ORGANISM: Artificial Sequence
<220> FEATURE:
<223> OTHER INFORMATION: 5C23 VH CDR1- Exemplary

<400> SEQUENCE: 183

Gly Tyr Thr Phe Thr Arg Tyr Asp Ile Asn
1               5                   10

<210> SEQ ID NO 184
<211> LENGTH: 17
<212> TYPE: PRT
<213> ORGANISM: Artificial Sequence
<220> FEATURE:
<223> OTHER INFORMATION: 5C23 VH CDR2- Exemplary

<400> SEQUENCE: 184

Trp Ile Tyr Pro Gly Asp Gly Ser Thr Lys Tyr Asn Glu Lys Phe Glu
1               5                   10                  15

Gly

<210> SEQ ID NO 185
<211> LENGTH: 11
<212> TYPE: PRT
<213> ORGANISM: Artificial Sequence
<220> FEATURE:
<223> OTHER INFORMATION: 5C23 VH CDR3- Exemplary

<400> SEQUENCE: 185

Ser Asp Tyr Tyr Gly Ser Arg Ser Phe Val Tyr
1               5                   10

<210> SEQ ID NO 186
<211> LENGTH: 15
<212> TYPE: PRT
<213> ORGANISM: Artificial Sequence
<220> FEATURE:
<223> OTHER INFORMATION: 5C23 VL CDR1- Exemplary

<400> SEQUENCE: 186

Arg Ala Ser Lys Ser Val Ser Thr Ser Gly Tyr Ser Tyr Met His
1               5                   10                  15

<210> SEQ ID NO 187
<211> LENGTH: 7
<212> TYPE: PRT
<213> ORGANISM: Artificial Sequence
<220> FEATURE:
<223> OTHER INFORMATION: 5C23 VL CDR2- Exemplary

<400> SEQUENCE: 187

Leu Ala Ser Asn Leu Glu Ser
1               5

<210> SEQ ID NO 188
<211> LENGTH: 9
<212> TYPE: PRT
<213> ORGANISM: Artificial Sequence
<220> FEATURE:
<223> OTHER INFORMATION: 5C23 VL CDR3- Exemplary

<400> SEQUENCE: 188

Gln His Ser Arg Glu Leu Pro Tyr Thr
1               5

<210> SEQ ID NO 189
<211> LENGTH: 8
<212> TYPE: PRT
<213> ORGANISM: Artificial Sequence
<220> FEATURE:
<223> OTHER INFORMATION: 5C23 VH CDR1 - IMGT

<400> SEQUENCE: 189

Gly Tyr Thr Phe Thr Arg Tyr Asp
1               5

<210> SEQ ID NO 190
<211> LENGTH: 8
<212> TYPE: PRT
<213> ORGANISM: Artificial Sequence
<220> FEATURE:
<223> OTHER INFORMATION: 5C23 VH CDR2 - IMGT

<400> SEQUENCE: 190

Ile Tyr Pro Gly Asp Gly Ser Thr
1               5

<210> SEQ ID NO 191
<211> LENGTH: 13
<212> TYPE: PRT
<213> ORGANISM: Artificial Sequence
<220> FEATURE:
<223> OTHER INFORMATION: 5C23 VH CDR3 - IMGT

```
<400> SEQUENCE: 191

Ala Arg Ser Asp Tyr Tyr Gly Ser Arg Ser Phe Val Tyr
1               5                   10

<210> SEQ ID NO 192
<211> LENGTH: 10
<212> TYPE: PRT
<213> ORGANISM: Artificial Sequence
<220> FEATURE:
<223> OTHER INFORMATION: 5C23 VL CDR1- IMGT

<400> SEQUENCE: 192

Lys Ser Val Ser Thr Ser Gly Tyr Ser Tyr
1               5                   10

<210> SEQ ID NO 193
<211> LENGTH: 3
<212> TYPE: PRT
<213> ORGANISM: Artificial Sequence
<220> FEATURE:
<223> OTHER INFORMATION: 5C23 VL CDR2- IMGT

<400> SEQUENCE: 193

Leu Ala Ser
1

<210> SEQ ID NO 194
<211> LENGTH: 5
<212> TYPE: PRT
<213> ORGANISM: Artificial Sequence
<220> FEATURE:
<223> OTHER INFORMATION: 5C23 VH CDR1 - Kabat

<400> SEQUENCE: 194

Arg Tyr Asp Ile Asn
1               5

<210> SEQ ID NO 195
<211> LENGTH: 7
<212> TYPE: PRT
<213> ORGANISM: Artificial Sequence
<220> FEATURE:
<223> OTHER INFORMATION: 5C23 VH CDR1 - Chothia

<400> SEQUENCE: 195

Gly Tyr Thr Phe Thr Arg Tyr
1               5

<210> SEQ ID NO 196
<211> LENGTH: 4
<212> TYPE: PRT
<213> ORGANISM: Artificial Sequence
<220> FEATURE:
<223> OTHER INFORMATION: 5C23 VH CDR2 - Chothia

<400> SEQUENCE: 196

Pro Gly Asp Gly
1

<210> SEQ ID NO 197
<211> LENGTH: 9
<212> TYPE: PRT
<213> ORGANISM: Artificial Sequence
<220> FEATURE:
<223> OTHER INFORMATION: 5C23 VH CDR3 - Chothia

<400> SEQUENCE: 197
```

```
Asp Tyr Tyr Gly Ser Arg Ser Phe Val
1               5
```

<210> SEQ ID NO 198
<211> LENGTH: 11
<212> TYPE: PRT
<213> ORGANISM: Artificial Sequence
<220> FEATURE:
<223> OTHER INFORMATION: 5C23 VL CDR1- Chothia

<400> SEQUENCE: 198

```
Ser Lys Ser Val Ser Thr Ser Gly Tyr Ser Tyr
1               5                   10
```

<210> SEQ ID NO 199
<211> LENGTH: 6
<212> TYPE: PRT
<213> ORGANISM: Artificial Sequence
<220> FEATURE:
<223> OTHER INFORMATION: 5C23 VL CDR3- Chothia

<400> SEQUENCE: 199

```
Ser Arg Glu Leu Pro Tyr
1               5
```

<210> SEQ ID NO 200
<211> LENGTH: 6
<212> TYPE: PRT
<213> ORGANISM: Artificial Sequence
<220> FEATURE:
<223> OTHER INFORMATION: 5C23 VH CDR1 - Contact

<400> SEQUENCE: 200

```
Thr Arg Tyr Asp Ile Asn
1               5
```

<210> SEQ ID NO 201
<211> LENGTH: 13
<212> TYPE: PRT
<213> ORGANISM: Artificial Sequence
<220> FEATURE:
<223> OTHER INFORMATION: 5C23 VH CDR2 - Contact

<400> SEQUENCE: 201

```
Trp Ile Gly Trp Ile Tyr Pro Gly Asp Gly Ser Thr Lys
1               5                   10
```

<210> SEQ ID NO 202
<211> LENGTH: 12
<212> TYPE: PRT
<213> ORGANISM: Artificial Sequence
<220> FEATURE:
<223> OTHER INFORMATION: 5C23 VH CDR3 - Contact

<400> SEQUENCE: 202

```
Ala Arg Ser Asp Tyr Tyr Gly Ser Arg Ser Phe Val
1               5                   10
```

<210> SEQ ID NO 203
<211> LENGTH: 11
<212> TYPE: PRT
<213> ORGANISM: Artificial Sequence
<220> FEATURE:
<223> OTHER INFORMATION: 5C23 VL CDR1 - Contact

<400> SEQUENCE: 203

Ser Thr Ser Gly Tyr Ser Tyr Met His Trp Tyr
1               5                   10

<210> SEQ ID NO 204
<211> LENGTH: 10
<212> TYPE: PRT
<213> ORGANISM: Artificial Sequence
<220> FEATURE:
<223> OTHER INFORMATION: 5C23 VL CDR2 - Contact

<400> SEQUENCE: 204

Leu Leu Ile Tyr Leu Ala Ser Asn Leu Glu
1               5                   10

<210> SEQ ID NO 205
<211> LENGTH: 8
<212> TYPE: PRT
<213> ORGANISM: Artificial Sequence
<220> FEATURE:
<223> OTHER INFORMATION: 5C23 VL CDR3 - Contact

<400> SEQUENCE: 205

Gln His Ser Arg Glu Leu Pro Tyr
1               5

<210> SEQ ID NO 206
<211> LENGTH: 10
<212> TYPE: PRT
<213> ORGANISM: Artificial Sequence
<220> FEATURE:
<223> OTHER INFORMATION: 5C23 VH CDR2 - AbM

<400> SEQUENCE: 206

Trp Ile Tyr Pro Gly Asp Gly Ser Thr Lys
1               5                   10

<210> SEQ ID NO 207
<211> LENGTH: 120
<212> TYPE: PRT
<213> ORGANISM: Artificial Sequence
<220> FEATURE:
<223> OTHER INFORMATION: 5C23 VH Sequence

<400> SEQUENCE: 207

Gln Val Gln Pro Gln Glu Ser Gly Pro Glu Leu Val Lys Pro Gly Ala
1               5                   10                  15

Leu Val Lys Ile Ser Cys Lys Ala Ser Gly Tyr Thr Phe Thr Arg Tyr
            20                  25                  30

Asp Ile Asn Trp Val Lys Lys Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Glu Gly Lys Ala Thr Leu Thr Ala Asp Lys Ser Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Ser Asp Tyr Tyr Gly Ser Arg Ser Phe Val Tyr Trp Gly Gln
            100                 105                 110

Gly Thr Leu Val Thr Val Ser Ala
        115                 120

<210> SEQ ID NO 208
<211> LENGTH: 111

<212> TYPE: PRT
<213> ORGANISM: Artificial Sequence
<220> FEATURE:
<223> OTHER INFORMATION: 5C23 VL Sequence

<400> SEQUENCE: 208

Asp Ile Val Leu Thr Gln Ser Pro Asp Ser Leu Thr Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110

<210> SEQ ID NO 209
<211> LENGTH: 10
<212> TYPE: PRT
<213> ORGANISM: Artificial Sequence
<220> FEATURE:
<223> OTHER INFORMATION: 5F7 VH CDR1 - Exemplary

<400> SEQUENCE: 209

Gly Tyr Thr Phe Thr Arg Tyr Asp Ile Asn
1               5                   10

<210> SEQ ID NO 210
<211> LENGTH: 17
<212> TYPE: PRT
<213> ORGANISM: Artificial Sequence
<220> FEATURE:
<223> OTHER INFORMATION: 5F7 VH CDR2 - Exemplary

<400> SEQUENCE: 210

Trp Ile Tyr Pro Gly Asp Ile Ser Thr Lys Tyr Asn Glu Lys Phe Lys
1               5                   10                  15

Gly

<210> SEQ ID NO 211
<211> LENGTH: 11
<212> TYPE: PRT
<213> ORGANISM: Artificial Sequence
<220> FEATURE:
<223> OTHER INFORMATION: 5F7 VH CDR3 - Exemplary

<400> SEQUENCE: 211

Ser Asp Tyr Tyr Gly Ser Arg Ser Phe Val Tyr
1               5                   10

<210> SEQ ID NO 212
<211> LENGTH: 15
<212> TYPE: PRT
<213> ORGANISM: Artificial Sequence
<220> FEATURE:
<223> OTHER INFORMATION: 5F7 VL CDR1- Exemplary

<400> SEQUENCE: 212

```
Arg Ala Ser Lys Ser Val Ser Thr Ser Gly Tyr Ser Tyr Met His
1               5                   10                  15

<210> SEQ ID NO 213
<211> LENGTH: 7
<212> TYPE: PRT
<213> ORGANISM: Artificial Sequence
<220> FEATURE:
<223> OTHER INFORMATION: 5F7 VL CDR2- Exemplary

<400> SEQUENCE: 213

Leu Ala Ser Asn Leu Glu Ser
1               5

<210> SEQ ID NO 214
<211> LENGTH: 9
<212> TYPE: PRT
<213> ORGANISM: Artificial Sequence
<220> FEATURE:
<223> OTHER INFORMATION: 5F7 VL CDR3- Exemplary

<400> SEQUENCE: 214

Gln His Ser Arg Glu Leu Pro Tyr Thr
1               5

<210> SEQ ID NO 215
<211> LENGTH: 8
<212> TYPE: PRT
<213> ORGANISM: Artificial Sequence
<220> FEATURE:
<223> OTHER INFORMATION: 5F7 VH CDR1 - IMGT

<400> SEQUENCE: 215

Gly Tyr Thr Phe Thr Arg Tyr Asp
1               5

<210> SEQ ID NO 216
<211> LENGTH: 8
<212> TYPE: PRT
<213> ORGANISM: Artificial Sequence
<220> FEATURE:
<223> OTHER INFORMATION: 5F7 VH CDR2 - IMGT

<400> SEQUENCE: 216

Ile Tyr Pro Gly Asp Ile Ser Thr
1               5

<210> SEQ ID NO 217
<211> LENGTH: 13
<212> TYPE: PRT
<213> ORGANISM: Artificial Sequence
<220> FEATURE:
<223> OTHER INFORMATION: 5F7 VH CDR3 - IMGT

<400> SEQUENCE: 217

Ala Arg Ser Asp Tyr Tyr Gly Ser Arg Ser Phe Val Tyr
1               5                   10

<210> SEQ ID NO 218
<211> LENGTH: 10
<212> TYPE: PRT
<213> ORGANISM: Artificial Sequence
<220> FEATURE:
<223> OTHER INFORMATION: 5F7 VL CDR1- IMGT

<400> SEQUENCE: 218

Lys Ser Val Ser Thr Ser Gly Tyr Ser Tyr
```

```
1               5               10

<210> SEQ ID NO 219
<211> LENGTH: 3
<212> TYPE: PRT
<213> ORGANISM: Artificial Sequence
<220> FEATURE:
<223> OTHER INFORMATION: 5F7 VL CDR2- IMGT

<400> SEQUENCE: 219

Leu Ala Ser
1

<210> SEQ ID NO 220
<211> LENGTH: 5
<212> TYPE: PRT
<213> ORGANISM: Artificial Sequence
<220> FEATURE:
<223> OTHER INFORMATION: 5F7 VH CDR1 - Kabat

<400> SEQUENCE: 220

Arg Tyr Asp Ile Asn
1               5

<210> SEQ ID NO 221
<211> LENGTH: 7
<212> TYPE: PRT
<213> ORGANISM: Artificial Sequence
<220> FEATURE:
<223> OTHER INFORMATION: 5F7 VH CDR1 - Chothia

<400> SEQUENCE: 221

Gly Tyr Thr Phe Thr Arg Tyr
1               5

<210> SEQ ID NO 222
<211> LENGTH: 4
<212> TYPE: PRT
<213> ORGANISM: Artificial Sequence
<220> FEATURE:
<223> OTHER INFORMATION: 5F7 VH CDR2 - Chothia

<400> SEQUENCE: 222

Pro Gly Asp Ile
1

<210> SEQ ID NO 223
<211> LENGTH: 9
<212> TYPE: PRT
<213> ORGANISM: Artificial Sequence
<220> FEATURE:
<223> OTHER INFORMATION: 5F7 VH CDR3 - Chothia

<400> SEQUENCE: 223

Asp Tyr Tyr Gly Ser Arg Ser Phe Val
1               5

<210> SEQ ID NO 224
<211> LENGTH: 11
<212> TYPE: PRT
<213> ORGANISM: Artificial Sequence
<220> FEATURE:
<223> OTHER INFORMATION: 5F7 VL CDR1 - Chothia

<400> SEQUENCE: 224

Ser Lys Ser Val Ser Thr Ser Gly Tyr Ser Tyr
1               5               10
```

```
<210> SEQ ID NO 225
<211> LENGTH: 6
<212> TYPE: PRT
<213> ORGANISM: Artificial Sequence
<220> FEATURE:
<223> OTHER INFORMATION: 5F7 VL CDR3 - Chothia

<400> SEQUENCE: 225

Ser Arg Glu Leu Pro Tyr
1               5

<210> SEQ ID NO 226
<211> LENGTH: 6
<212> TYPE: PRT
<213> ORGANISM: Artificial Sequence
<220> FEATURE:
<223> OTHER INFORMATION: 5F7 VH CDR1 - Contact

<400> SEQUENCE: 226

Thr Arg Tyr Asp Ile Asn
1               5

<210> SEQ ID NO 227
<211> LENGTH: 13
<212> TYPE: PRT
<213> ORGANISM: Artificial Sequence
<220> FEATURE:
<223> OTHER INFORMATION: 5F7 VH CDR2 - Contact

<400> SEQUENCE: 227

Trp Ile Gly Trp Ile Tyr Pro Gly Asp Ile Ser Thr Lys
1               5                   10

<210> SEQ ID NO 228
<211> LENGTH: 12
<212> TYPE: PRT
<213> ORGANISM: Artificial Sequence
<220> FEATURE:
<223> OTHER INFORMATION: 5F7 VH CDR3 - Contact

<400> SEQUENCE: 228

Ala Arg Ser Asp Tyr Tyr Gly Ser Arg Ser Phe Val
1               5                   10

<210> SEQ ID NO 229
<211> LENGTH: 11
<212> TYPE: PRT
<213> ORGANISM: Artificial Sequence
<220> FEATURE:
<223> OTHER INFORMATION: 5F7 VL CDR1- Contact

<400> SEQUENCE: 229

Ser Thr Ser Gly Tyr Ser Tyr Met His Trp Tyr
1               5                   10

<210> SEQ ID NO 230
<211> LENGTH: 10
<212> TYPE: PRT
<213> ORGANISM: Artificial Sequence
<220> FEATURE:
<223> OTHER INFORMATION: 5F7 VL CDR2- Contact

<400> SEQUENCE: 230

Leu Leu Ile Tyr Leu Ala Ser Asn Leu Glu
1               5                   10
```

```
<210> SEQ ID NO 231
<211> LENGTH: 8
<212> TYPE: PRT
<213> ORGANISM: Artificial Sequence
<220> FEATURE:
<223> OTHER INFORMATION: 5F7 VL CDR3- Contact

<400> SEQUENCE: 231

Gln His Ser Arg Glu Leu Pro Tyr
1               5

<210> SEQ ID NO 232
<211> LENGTH: 10
<212> TYPE: PRT
<213> ORGANISM: Artificial Sequence
<220> FEATURE:
<223> OTHER INFORMATION: 5F7 VH CDR2 - AbM

<400> SEQUENCE: 232

Trp Ile Tyr Pro Gly Asp Ile Ser Thr Lys
1               5                   10

<210> SEQ ID NO 233
<211> LENGTH: 120
<212> TYPE: PRT
<213> ORGANISM: Artificial Sequence
<220> FEATURE:
<223> OTHER INFORMATION: 5F7 VH Sequence

<400> SEQUENCE: 233

Gln Val Gln Pro Gln Glu Ser Gly Pro Glu Leu Val Lys Pro Gly Ala
1               5                   10                  15

Leu Val Lys Ile Ser Cys Lys Ala Ser Gly Tyr Thr Phe Thr Arg Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Ile Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asn Ser Ala Val Tyr Phe Cys
                85                  90                  95

Ala Arg Ser Asp Tyr Tyr Gly Ser Arg Ser Phe Val Tyr Trp Gly Gln
            100                 105                 110

Gly Thr Leu Val Thr Val Ser Ala
        115                 120

<210> SEQ ID NO 234
<211> LENGTH: 111
<212> TYPE: PRT
<213> ORGANISM: Artificial Sequence
<220> FEATURE:
<223> OTHER INFORMATION: 5F7 VL Sequence

<400> SEQUENCE: 234

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45
```

```
Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Tyr Thr Phe Gly Gly Gly Thr Lys Val Glu Ile Lys
            100                 105                 110

<210> SEQ ID NO 235
<211> LENGTH: 11
<212> TYPE: PRT
<213> ORGANISM: Artificial Sequence
<220> FEATURE:
<223> OTHER INFORMATION: 1G19 VH CDR1- Exemplary

<400> SEQUENCE: 235

Gly Tyr Ser Ile Thr Ser Gly Tyr Tyr Trp Asn
1               5                   10

<210> SEQ ID NO 236
<211> LENGTH: 16
<212> TYPE: PRT
<213> ORGANISM: Artificial Sequence
<220> FEATURE:
<223> OTHER INFORMATION: 1G19 VH CDR2- Exemplary

<400> SEQUENCE: 236

Tyr Ile Asn Tyr Gly Gly Ser Asn Asn Tyr Asn Pro Ser Leu Lys Asn
1               5                   10                  15

<210> SEQ ID NO 237
<211> LENGTH: 13
<212> TYPE: PRT
<213> ORGANISM: Artificial Sequence
<220> FEATURE:
<223> OTHER INFORMATION: 1G19 VH CDR3- Exemplary

<400> SEQUENCE: 237

Arg Gly Ala Tyr Tyr Ser Asn Tyr Asp Ser Phe Asp Val
1               5                   10

<210> SEQ ID NO 238
<211> LENGTH: 11
<212> TYPE: PRT
<213> ORGANISM: Artificial Sequence
<220> FEATURE:
<223> OTHER INFORMATION: 1G19 VL CDR1- Exemplary

<400> SEQUENCE: 238

Lys Ala Ser Gln Asp Ile Asn Ser Tyr Leu Ser
1               5                   10

<210> SEQ ID NO 239
<211> LENGTH: 7
<212> TYPE: PRT
<213> ORGANISM: Artificial Sequence
<220> FEATURE:
<223> OTHER INFORMATION: 1G19 VL CDR2- Exemplary

<400> SEQUENCE: 239

Arg Ala Asn Arg Leu Val Asp
1               5

<210> SEQ ID NO 240
```

```
<211> LENGTH: 9
<212> TYPE: PRT
<213> ORGANISM: Artificial Sequence
<220> FEATURE:
<223> OTHER INFORMATION: 1G19 VL CDR3- Exemplary

<400> SEQUENCE: 240

Leu Gln Tyr Asp Glu Phe Pro Tyr Thr
1               5

<210> SEQ ID NO 241
<211> LENGTH: 9
<212> TYPE: PRT
<213> ORGANISM: Artificial Sequence
<220> FEATURE:
<223> OTHER INFORMATION: 1G19 VH CDR1 - IMGT

<400> SEQUENCE: 241

Gly Tyr Ser Ile Thr Ser Gly Tyr Tyr
1               5

<210> SEQ ID NO 242
<211> LENGTH: 7
<212> TYPE: PRT
<213> ORGANISM: Artificial Sequence
<220> FEATURE:
<223> OTHER INFORMATION: 1G19 VH CDR2 - IMGT

<400> SEQUENCE: 242

Ile Asn Tyr Gly Gly Ser Asn
1               5

<210> SEQ ID NO 243
<211> LENGTH: 15
<212> TYPE: PRT
<213> ORGANISM: Artificial Sequence
<220> FEATURE:
<223> OTHER INFORMATION: 1G19 VH CDR3 - IMGT

<400> SEQUENCE: 243

Ala Arg Arg Gly Ala Tyr Tyr Ser Asn Tyr Asp Ser Phe Asp Val
1               5                   10                  15

<210> SEQ ID NO 244
<211> LENGTH: 6
<212> TYPE: PRT
<213> ORGANISM: Artificial Sequence
<220> FEATURE:
<223> OTHER INFORMATION: 1G19 VL CDR1 - IMGT

<400> SEQUENCE: 244

Gln Asp Ile Asn Ser Tyr
1               5

<210> SEQ ID NO 245
<211> LENGTH: 3
<212> TYPE: PRT
<213> ORGANISM: Artificial Sequence
<220> FEATURE:
<223> OTHER INFORMATION: 1G19 VL CDR2 - IMGT

<400> SEQUENCE: 245

Arg Ala Asn
1

<210> SEQ ID NO 246
<211> LENGTH: 6
```

```
<212> TYPE: PRT
<213> ORGANISM: Artificial Sequence
<220> FEATURE:
<223> OTHER INFORMATION: 1G19 VH CDR1 - Kabat

<400> SEQUENCE: 246

Ser Gly Tyr Tyr Trp Asn
1               5

<210> SEQ ID NO 247
<211> LENGTH: 8
<212> TYPE: PRT
<213> ORGANISM: Artificial Sequence
<220> FEATURE:
<223> OTHER INFORMATION: 1G19 VH CDR1 - Chothia

<400> SEQUENCE: 247

Gly Tyr Ser Ile Thr Ser Gly Tyr
1               5

<210> SEQ ID NO 248
<211> LENGTH: 3
<212> TYPE: PRT
<213> ORGANISM: Artificial Sequence
<220> FEATURE:
<223> OTHER INFORMATION: 1G19 VH CDR2 - Chothia

<400> SEQUENCE: 248

Tyr Gly Gly
1

<210> SEQ ID NO 249
<211> LENGTH: 11
<212> TYPE: PRT
<213> ORGANISM: Artificial Sequence
<220> FEATURE:
<223> OTHER INFORMATION: 1G19 VH CDR3 - Chothia

<400> SEQUENCE: 249

Gly Ala Tyr Tyr Ser Asn Tyr Asp Ser Phe Asp
1               5                   10

<210> SEQ ID NO 250
<211> LENGTH: 7
<212> TYPE: PRT
<213> ORGANISM: Artificial Sequence
<220> FEATURE:
<223> OTHER INFORMATION: 1G19 VL CDR1- Chothia

<400> SEQUENCE: 250

Ser Gln Asp Ile Asn Ser Tyr
1               5

<210> SEQ ID NO 251
<211> LENGTH: 6
<212> TYPE: PRT
<213> ORGANISM: Artificial Sequence
<220> FEATURE:
<223> OTHER INFORMATION: 1G19 VL CDR3- Chothia

<400> SEQUENCE: 251

Tyr Asp Glu Phe Pro Tyr
1               5

<210> SEQ ID NO 252
<211> LENGTH: 7
<212> TYPE: PRT
```

```
<213> ORGANISM: Artificial Sequence
<220> FEATURE:
<223> OTHER INFORMATION: 1G19 VH CDR1 - Contact

<400> SEQUENCE: 252

Thr Ser Gly Tyr Tyr Trp Asn
1               5

<210> SEQ ID NO 253
<211> LENGTH: 12
<212> TYPE: PRT
<213> ORGANISM: Artificial Sequence
<220> FEATURE:
<223> OTHER INFORMATION: 1G19 VH CDR2 - Contact

<400> SEQUENCE: 253

Trp Met Gly Tyr Ile Asn Tyr Gly Gly Ser Asn Asn
1               5                   10

<210> SEQ ID NO 254
<211> LENGTH: 14
<212> TYPE: PRT
<213> ORGANISM: Artificial Sequence
<220> FEATURE:
<223> OTHER INFORMATION: 1G19 VH CDR3 - Contact

<400> SEQUENCE: 254

Ala Arg Arg Gly Ala Tyr Tyr Ser Asn Tyr Asp Ser Phe Asp
1               5                   10

<210> SEQ ID NO 255
<211> LENGTH: 7
<212> TYPE: PRT
<213> ORGANISM: Artificial Sequence
<220> FEATURE:
<223> OTHER INFORMATION: 1G19 VL CDR1 - Contact

<400> SEQUENCE: 255

Asn Ser Tyr Leu Ser Trp Phe
1               5

<210> SEQ ID NO 256
<211> LENGTH: 10
<212> TYPE: PRT
<213> ORGANISM: Artificial Sequence
<220> FEATURE:
<223> OTHER INFORMATION: 1G19 VL CDR2 - Contact

<400> SEQUENCE: 256

Thr Leu Ile Tyr Arg Ala Asn Arg Leu Val
1               5                   10

<210> SEQ ID NO 257
<211> LENGTH: 8
<212> TYPE: PRT
<213> ORGANISM: Artificial Sequence
<220> FEATURE:
<223> OTHER INFORMATION: 1G19 VL CDR3 - Contact

<400> SEQUENCE: 257

Leu Gln Tyr Asp Glu Phe Pro Tyr
1               5

<210> SEQ ID NO 258
<211> LENGTH: 9
<212> TYPE: PRT
<213> ORGANISM: Artificial Sequence
```

<220> FEATURE:
<223> OTHER INFORMATION: 1G19 VH CDR2 - AbM

<400> SEQUENCE: 258

Tyr Ile Asn Tyr Gly Gly Ser Asn Asn
1               5

<210> SEQ ID NO 259
<211> LENGTH: 122
<212> TYPE: PRT
<213> ORGANISM: Artificial Sequence
<220> FEATURE:
<223> OTHER INFORMATION: 1G19 VH Sequence

<400> SEQUENCE: 259

Gln Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Asn Tyr Gly Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Thr Ser Val Thr Thr Glu Asp Thr Ala Thr Tyr Tyr Cys
                85                  90                  95

Ala Arg Arg Gly Ala Tyr Tyr Ser Asn Tyr Asp Ser Phe Asp Val Trp
            100                 105                 110

Gly Thr Gly Thr Thr Val Thr Val Ser Ser
        115                 120

<210> SEQ ID NO 260
<211> LENGTH: 107
<212> TYPE: PRT
<213> ORGANISM: Artificial Sequence
<220> FEATURE:
<223> OTHER INFORMATION: 1G19 VL Sequence

<400> SEQUENCE: 260

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Glu Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 261
<211> LENGTH: 10
<212> TYPE: PRT
<213> ORGANISM: Artificial Sequence
<220> FEATURE:

<223> OTHER INFORMATION: consensus CDR1 sequence of anti-beta klotho
      antibodies VH domain
<220> FEATURE:
<221> NAME/KEY: VARIANT
<222> LOCATION: 6
<223> OTHER INFORMATION: Xaa = Arg or Ser

<400> SEQUENCE: 261

Gly Tyr Thr Phe Thr Xaa Tyr Asp Ile Asn
1               5                   10

<210> SEQ ID NO 262
<211> LENGTH: 17
<212> TYPE: PRT
<213> ORGANISM: Artificial Sequence
<220> FEATURE:
<223> OTHER INFORMATION: consensus CDR2 sequence of anti-beta klotho
      antibodies VH domain
<220> FEATURE:
<221> NAME/KEY: VARIANT
<222> LOCATION: 7
<223> OTHER INFORMATION: Xaa = Gly, Asp, Ser or Ile

<400> SEQUENCE: 262

Trp Ile Tyr Pro Gly Asp Xaa Ser Thr Lys Tyr Asn Glu Lys Phe Lys
1               5                   10                  15

Gly

<210> SEQ ID NO 263
<211> LENGTH: 11
<212> TYPE: PRT
<213> ORGANISM: Artificial Sequence
<220> FEATURE:
<223> OTHER INFORMATION: consensus CDR2 sequence of anti-beta klotho
      antibodies VH domain
<220> FEATURE:
<221> NAME/KEY: VARIANT
<222> LOCATION: 10
<223> OTHER INFORMATION: Xaa = Val, Thr or Ala

<400> SEQUENCE: 263

Ser Asp Tyr Tyr Gly Ser Arg Ser Phe Xaa Tyr
1               5                   10

<210> SEQ ID NO 264
<211> LENGTH: 16
<212> TYPE: PRT
<213> ORGANISM: Artificial Sequence
<220> FEATURE:
<223> OTHER INFORMATION: consensus CDR3 sequence of anti-beta klotho
      antibodies VH domain
<220> FEATURE:
<221> NAME/KEY: VARIANT
<222> LOCATION: 5
<223> OTHER INFORMATION: Xaa = Asp or Gly
<220> FEATURE:
<221> NAME/KEY: VARIANT
<222> LOCATION: 7
<223> OTHER INFORMATION: Xaa = Asn or Ser
<220> FEATURE:
<221> NAME/KEY: VARIANT
<222> LOCATION: 8
<223> OTHER INFORMATION: Xaa = Ser or Asn
<220> FEATURE:
<221> NAME/KEY: VARIANT
<222> LOCATION: 11
<223> OTHER INFORMATION: Xaa = Thr or Asn

<400> SEQUENCE: 264

Tyr Ile Asn Tyr Xaa Gly Xaa Xaa Asn Tyr Xaa Pro Ser Leu Lys Asn
1               5                   10                  15

```
<210> SEQ ID NO 265
<211> LENGTH: 13
<212> TYPE: PRT
<213> ORGANISM: Artificial Sequence
<220> FEATURE:
<223> OTHER INFORMATION: consensus CDR3 sequence of anti-beta klotho
      antibodies VH domain
<220> FEATURE:
<221> NAME/KEY: VARIANT
<222> LOCATION: 1
<223> OTHER INFORMATION: Xaa = Lys or Arg

<400> SEQUENCE: 265

Xaa Gly Ala Tyr Tyr Ser Asn Tyr Asp Ser Phe Asp Val
1               5                   10

<210> SEQ ID NO 266
<211> LENGTH: 15
<212> TYPE: PRT
<213> ORGANISM: Artificial Sequence
<220> FEATURE:
<223> OTHER INFORMATION: consensus CDR1 sequence of anti-beta klotho
      antibodies VL domain
<220> FEATURE:
<221> NAME/KEY: VARIANT
<222> LOCATION: 14
<223> OTHER INFORMATION: Xaa = Met, Leu or Val

<400> SEQUENCE: 266

Arg Ala Ser Lys Ser Val Ser Thr Ser Gly Tyr Ser Tyr Xaa His
1               5                   10                  15

<210> SEQ ID NO 267
<211> LENGTH: 9
<212> TYPE: PRT
<213> ORGANISM: Artificial Sequence
<220> FEATURE:
<223> OTHER INFORMATION: consensus CDR3 sequence of anti-beta klotho
      antibodies VL domain
<220> FEATURE:
<221> NAME/KEY: VARIANT
<222> LOCATION: 1
<223> OTHER INFORMATION: Xaa = Gln or His
<220> FEATURE:
<221> NAME/KEY: VARIANT
<222> LOCATION: 4
<223> OTHER INFORMATION: Xaa = Arg or Gly

<400> SEQUENCE: 267

Xaa His Ser Xaa Glu Leu Pro Tyr Thr
1               5

<210> SEQ ID NO 268
<211> LENGTH: 9
<212> TYPE: PRT
<213> ORGANISM: Artificial Sequence
<220> FEATURE:
<223> OTHER INFORMATION: consensus CDR3 sequence of anti-beta klotho
      antibodies VL domain
<220> FEATURE:
<221> NAME/KEY: VARIANT
<222> LOCATION: 8
<223> OTHER INFORMATION: Xaa = Phe or Tyr

<400> SEQUENCE: 268

Leu Gln Tyr Asp Glu Phe Pro Xaa Thr
1               5

<210> SEQ ID NO 269
```

```
<211> LENGTH: 120
<212> TYPE: PRT
<213> ORGANISM: Artificial Sequence
<220> FEATURE:
<223> OTHER INFORMATION: vH1

<400> SEQUENCE: 269

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 270
<211> LENGTH: 120
<212> TYPE: PRT
<213> ORGANISM: Artificial Sequence
<220> FEATURE:
<223> OTHER INFORMATION: vH2

<400> SEQUENCE: 270

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Arg Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Gly Arg Val Thr Ile Thr Ala Asp Lys Ser Ala Arg Thr Ala Tyr
65                  70                  75                  80

Met Glu Leu Ser Ser Leu Thr Ser Glu Asp Thr Ala Val Tyr Tyr Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 271
<211> LENGTH: 120
<212> TYPE: PRT
<213> ORGANISM: Artificial Sequence
<220> FEATURE:
<223> OTHER INFORMATION: vH3

<400> SEQUENCE: 271

Gln Val Gln Leu Gln Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
            115                 120

<210> SEQ ID NO 272
<211> LENGTH: 120
<212> TYPE: PRT
<213> ORGANISM: Artificial Sequence
<220> FEATURE:
<223> OTHER INFORMATION: vH4

<400> SEQUENCE: 272

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Arg Val Thr Ile Thr Ala Asp Lys Ser Ala Arg Thr Ala Tyr
65                  70                  75                  80

Met Glu Leu Ser Ser Leu Thr Ser Glu Asp Thr Ala Val Tyr Tyr Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
            115                 120

<210> SEQ ID NO 273
<211> LENGTH: 120
<212> TYPE: PRT
<213> ORGANISM: Artificial Sequence
<220> FEATURE:
<223> OTHER INFORMATION: vH5

<400> SEQUENCE: 273

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Thr Ser Ala Ser Thr Ala Tyr
65                  70                  75                  80

-continued

Met Glu Leu Ser Ser Leu Arg Ser Glu Asn Thr Ala Val Tyr Phe Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 274
<211> LENGTH: 120
<212> TYPE: PRT
<213> ORGANISM: Artificial Sequence
<220> FEATURE:
<223> OTHER INFORMATION: vH6

<400> SEQUENCE: 274

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Lys Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Leu Thr Ala Asp Lys Ser Ala Arg Thr Ala Tyr
65                  70                  75                  80

Met Glu Leu Ser Ser Leu Arg Ser Glu Asn Thr Ala Val Tyr Phe Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 275
<211> LENGTH: 111
<212> TYPE: PRT
<213> ORGANISM: Artificial Sequence
<220> FEATURE:
<223> OTHER INFORMATION: vL1

<400> SEQUENCE: 275

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Val Tyr Met His Trp Asn Gln Gln Lys Pro Gly Gln Pro Pro
        35                  40                  45

Lys Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Ala Ala Ile Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 276
<211> LENGTH: 111
<212> TYPE: PRT

```
<213> ORGANISM: Artificial Sequence
<220> FEATURE:
<223> OTHER INFORMATION: vL2

<400> SEQUENCE: 276

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Val Tyr Met His Trp Tyr Gln Gln Lys Pro Gly Gln Pro Pro
        35                  40                  45

Lys Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 277
<211> LENGTH: 111
<212> TYPE: PRT
<213> ORGANISM: Artificial Sequence
<220> FEATURE:
<223> OTHER INFORMATION: vL3

<400> SEQUENCE: 277

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Val Tyr Met His Trp Asn Gln Gln Lys Pro Gly Gln Pro Pro
        35                  40                  45

Lys Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Ile Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 278
<211> LENGTH: 25
<212> TYPE: PRT
<213> ORGANISM: Artificial Sequence
<220> FEATURE:
<223> OTHER INFORMATION: Humanized Anti-Beta Klotho VH FR1

<400> SEQUENCE: 278

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 279
<211> LENGTH: 25
<212> TYPE: PRT
<213> ORGANISM: Artificial Sequence
```

```
<220> FEATURE:
<223> OTHER INFORMATION: Humanized Anti-Beta Klotho VH FR1

<400> SEQUENCE: 279

Gln Val Gln Leu Gln Gln Ser Gly Ala Glu Val Lys Lys Pro Gly Ala
1               5                   10                  15

Ser Val Lys Val Ser Cys Lys Ala Ser
            20                  25

<210> SEQ ID NO 280
<211> LENGTH: 25
<212> TYPE: PRT
<213> ORGANISM: Artificial Sequence
<220> FEATURE:
<223> OTHER INFORMATION: Humanized Anti-Beta Klotho VH FR1

<400> SEQUENCE: 280

Gln Val Gln Leu Val Gln Ser Gly Pro Glu Val Lys Lys Pro Gly Ala
1               5                   10                  15

Ser Val Lys Val Ser Cys Lys Ala Ser
            20                  25

<210> SEQ ID NO 281
<211> LENGTH: 14
<212> TYPE: PRT
<213> ORGANISM: Artificial Sequence
<220> FEATURE:
<223> OTHER INFORMATION: Humanized Anti-Beta Klotho VH FR2

<400> SEQUENCE: 281

Trp Val Arg Gln Ala Pro Gly Gln Gly Leu Glu Trp Met Gly
1               5                   10

<210> SEQ ID NO 282
<211> LENGTH: 14
<212> TYPE: PRT
<213> ORGANISM: Artificial Sequence
<220> FEATURE:
<223> OTHER INFORMATION: Humanized Anti-Beta Klotho VH FR2

<400> SEQUENCE: 282

Trp Val Arg Gln Ala Pro Gly Gln Gly Leu Glu Trp Ile Gly
1               5                   10

<210> SEQ ID NO 283
<211> LENGTH: 14
<212> TYPE: PRT
<213> ORGANISM: Artificial Sequence
<220> FEATURE:
<223> OTHER INFORMATION: Humanized Anti-Beta Klotho VH FR2

<400> SEQUENCE: 283

Trp Val Lys Gln Ala Pro Gly Gln Gly Leu Glu Trp Ile Gly
1               5                   10

<210> SEQ ID NO 284
<211> LENGTH: 32
<212> TYPE: PRT
<213> ORGANISM: Artificial Sequence
<220> FEATURE:
<223> OTHER INFORMATION: Humanized Anti-Beta Klotho VH FR3

<400> SEQUENCE: 284

Arg Val Thr Ile Thr Arg Asp Thr Ser Ala Ser Thr Ala Tyr Met Glu
1               5                   10                  15
```

Leu Ser Ser Leu Arg Ser Glu Asp Thr Ala Val Tyr Tyr Cys Ala Arg
            20                  25                  30

<210> SEQ ID NO 285
<211> LENGTH: 32
<212> TYPE: PRT
<213> ORGANISM: Artificial Sequence
<220> FEATURE:
<223> OTHER INFORMATION: Humanized Anti-Beta Klotho VH FR3

<400> SEQUENCE: 285

Lys Ala Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 286
<211> LENGTH: 32
<212> TYPE: PRT
<213> ORGANISM: Artificial Sequence
<220> FEATURE:
<223> OTHER INFORMATION: Humanized Anti-Beta Klotho VH FR3

<400> SEQUENCE: 286

Lys Ala Thr Leu Thr Ala Asp Thr Ser Ala Ser Thr Ala Tyr Met Glu
1               5                   10                  15

Leu Ser Ser Leu Arg Ser Glu Asn Thr Ala Val Tyr Phe Cys Ala Arg
            20                  25                  30

<210> SEQ ID NO 287
<211> LENGTH: 32
<212> TYPE: PRT
<213> ORGANISM: Artificial Sequence
<220> FEATURE:
<223> OTHER INFORMATION: Humanized Anti-Beta Klotho VH FR3

<400> SEQUENCE: 287

Lys Ala Thr Leu Thr Ala Asp Lys Ser Ala Arg Thr Ala Tyr Met Glu
1               5                   10                  15

Leu Ser Ser Leu Arg Ser Glu Asn Thr Ala Val Tyr Phe Cys Ala Arg
            20                  25                  30

<210> SEQ ID NO 288
<211> LENGTH: 11
<212> TYPE: PRT
<213> ORGANISM: Artificial Sequence
<220> FEATURE:
<223> OTHER INFORMATION: Humanized Anti-Beta Klotho VH FR4

<400> SEQUENCE: 288

Trp Gly Gln Gly Thr Leu Val Thr Val Ser Ser
1               5                   10

<210> SEQ ID NO 289
<211> LENGTH: 23
<212> TYPE: PRT
<213> ORGANISM: Artificial Sequence
<220> FEATURE:
<223> OTHER INFORMATION: Humanized Anti-Beta Klotho VL FR1

<400> SEQUENCE: 289

Asp Ile Val Leu Thr Gln Ser Pro Asp Ser Leu Ala Val Ser Leu Gly
1               5                   10                  15

Glu Arg Ala Thr Ile Asn Cys
            20

<210> SEQ ID NO 290
<211> LENGTH: 23
<212> TYPE: PRT
<213> ORGANISM: Artificial Sequence
<220> FEATURE:
<223> OTHER INFORMATION: Humanized Anti-Beta Klotho VL FR1

<400> SEQUENCE: 290

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 291
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 291

Trp Asn Gln Gln Lys Pro Gly Gln Pro Pro Lys Leu Leu Ile Tyr
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 292

Trp Tyr Gln Gln Lys Pro Gly Gln Pro Pro Lys Leu Leu Ile Tyr
1               5                   10                  15

<210> SEQ ID NO 293
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 293

Gly Val Pro Asp Arg Phe Ser Gly Ser Gly Ser Gly Thr Asp Phe Thr
1               5                   10                  15

Leu Thr Ile Ser Ser Val Gln Ala Glu Asp Ala Ala Ile Tyr Tyr Cys
            20                  25                  30

<210> SEQ ID NO 294
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 294

Gly Val Pro Asp Arg Phe Ser Gly Ser Gly Ser Gly Thr Asp Phe Thr
1               5                   10                  15

Leu Thr Ile Ser Ser Val Gln Ala Glu Asp Val Ala Val Tyr Tyr Cys
            20                  25                  30

<210> SEQ ID NO 295
<211> LENGTH: 32
<212> TYPE: PRT

```
<213> ORGANISM: Artificial Sequence
<220> FEATURE:
<223> OTHER INFORMATION: Humanized Anti-Beta Klotho VL FR3

<400> SEQUENCE: 295

Gly Val Pro Asp Arg Phe Ser Gly Ser Gly Ser Gly Thr Asp Phe Thr
1               5                   10                  15

Leu Thr Ile Ser Ser Val Gln Ala Glu Asp Val Ala Ile Tyr Tyr Cys
            20                  25                  30

<210> SEQ ID NO 296
<211> LENGTH: 10
<212> TYPE: PRT
<213> ORGANISM: Artificial Sequence
<220> FEATURE:
<223> OTHER INFORMATION: Humanized Anti-Beta Klotho VL FR4

<400> SEQUENCE: 296

Phe Gly Gly Gly Thr Lys Leu Glu Ile Lys
1               5                   10

<210> SEQ ID NO 297
<211> LENGTH: 1044
<212> TYPE: PRT
<213> ORGANISM: Homo sapiens
<220> FEATURE:
<223> OTHER INFORMATION: human beta klotho

<400> SEQUENCE: 297

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240
```

```
Asn Pro Tyr Leu Val Ala Trp His Gly Tyr Gly Thr Gly Met His Ala
            245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
            275                 280                 285

Arg Pro His Gln Lys Gly Trp Leu Ser Ile Thr Leu Gly Ser His Trp
            290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
            325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
            355                 360                 365

Phe Phe Ala Phe Ser Phe Gly Pro Asn Asn Phe Lys Pro Leu Asn Thr
            370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
            405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
            435                 440                 445

Leu Asp Glu Ile Arg Val Phe Gly Tyr Thr Ala Trp Ser Leu Leu Asp
            450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
            485                 490                 495

His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
            515                 520                 525

Val Thr Glu Ser Val Leu Lys Pro Glu Ser Val Ala Ser Ser Pro Gln
            530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
            565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
            595                 600                 605

Thr Gly Asn Leu Ser Ala Val Asn Arg Gln Ala Leu Arg Tyr Tyr Arg
            610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
            645                 650                 655
```

His Ala Asp Gly Trp Leu Asn Pro Ser Thr Ala Glu Ala Phe Gln Ala
                660                 665                 670

Tyr Ala Gly Leu Cys Phe Gln Glu Leu Gly Asp Leu Val Lys Leu Trp
            675                 680                 685

Ile Thr Ile Asn Glu Pro Asn Arg Leu Ser Asp Ile Tyr Asn Arg Ser
        690                 695                 700

Gly Asn Asp Thr Tyr Gly Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
    850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu Leu Leu Ser Ile Ala Ile Phe Gln Arg Gln Lys Arg Arg Lys
    1010                1015                1020

Phe Trp Lys Ala Lys Asn Leu Gln His Ile Pro Leu Lys Lys Gly Lys
1025                1030                1035                1040

Arg Val Val Ser

<210> SEQ ID NO 298
<211> LENGTH: 3132
<212> TYPE: DNA
<213> ORGANISM: Homo sapiens
<220> FEATURE:
<223> OTHER INFORMATION: human beta klotho coding sequence

<400> SEQUENCE: 298

| | | | | | |
|---|---|---|---|---|---|
| atgaagccag | gctgtgcggc | aggatctcca | gggaatgaat | ggattttctt | cagcactgat | 60 |
| gaaataacca | cacgctatag | aatacaatg | tccaacgggg | gattgcaaag | atctgtcatc | 120 |
| ctgtcagcac | ttattctgct | acgagctgtt | actggattct | ctggagatgg | aagagctata | 180 |
| tggtctaaaa | atcctaattt | tactccggta | aatgaaagtc | agctgtttct | ctatgacact | 240 |
| ttccctaaaa | acttttttctg | gggtattggg | actggagcat | tgcaagtgga | agggagttgg | 300 |
| aagaaggatg | gaaaaggacc | ttctatatgg | gatcatttca | tccacacaca | ccttaaaaat | 360 |
| gtcagcagca | cgaatggttc | cagtgacagt | tatattttc | tggaaaaaga | cttatcagcc | 420 |
| ctggatttta | taggagtttc | tttttatcaa | tttcaattt | cctggccaag | gcttttcccc | 480 |
| gatggaatag | taacagttgc | caacgcaaaa | ggtctgcagt | actacagtac | tcttctggac | 540 |
| gctctagtgc | ttagaaacat | tgaacctata | gttactttat | accactggga | tttgccttg | 600 |
| gcactacaag | aaaaatatgg | ggggtggaaa | aatgatacca | atagatat | cttcaatgac | 660 |
| tatgccacat | actgttttcca | gatgtttggg | accgtgtca | aatattggat | tacaattcac | 720 |
| aacccatatc | tagtggcttg | gcatgggtat | gggacaggta | tgcatgcccc | tggagagaag | 780 |
| ggaaatttag | cagctgtcta | cactgtggga | cacaacttga | tcaaggctca | ctcgaaagtt | 840 |
| tggcataact | acaacacaca | tttccgccca | catcagaagg | gttggttatc | gatcacgttg | 900 |
| ggatctcatt | ggatcgagcc | aaaccggtcg | gaaaacacga | tggatatatt | caaatgtcaa | 960 |
| caatccatgg | tttctgtgct | tggatggttt | gccaacccta | tccatgggga | tggcgactat | 1020 |
| ccagagggga | tgagaaagaa | gttgttctcc | gttctaccca | ttttctctga | agcagagaag | 1080 |
| catgagatga | gaggcacagc | tgatttcttt | gccttttctt | ttggacccaa | caacttcaag | 1140 |
| cccctaaaca | ccatggctaa | aatgggacaa | aatgtttcac | ttaatttaag | agaagcgctg | 1200 |
| aactggatta | aactggaata | caacaaccct | cgaatcttga | ttgctgagaa | tggctggttc | 1260 |
| acagacagtc | gtgtgaaaac | agaagacacc | acggccatct | acatgatgaa | gaatttcctc | 1320 |
| agccaggtgc | ttcaagcaat | aaggttagat | gaaatacgag | tgtttggtta | tactgcctgg | 1380 |
| tctctcctgg | atggctttga | atggcaggat | gcttacacca | tccgccgagg | attattttat | 1440 |
| gtggatttta | acagtaaaca | gaaagagcgg | aaacctaagt | cttcagcaca | ctactacaaa | 1500 |
| cagatcatac | gagaaaatgg | ttttcttta | aaagagtcca | cgccagatgt | gcagggccag | 1560 |
| tttccctgtg | acttctcctg | gggtgtcact | gaatctgttc | ttaagcccga | gtctgtggct | 1620 |
| tcgtccccac | agttcagcga | tcctcatctg | tacgtgtgga | acgccactgg | caacagactg | 1680 |
| ttgcaccgag | tggaaggggt | gaggctgaaa | acacgacccg | ctcaatgcac | agattttgta | 1740 |
| aacatcaaaa | aacaacttga | gatgttggca | agaatgaaag | tcacccacta | ccggttttgct | 1800 |
| ctggattggg | cctcggtcct | tcccactggc | aacctgtccg | cggtgaaccg | acaggccctg | 1860 |
| aggtactaca | ggtgcgtggt | cagtgagggg | ctgaagcttg | gcatctccgc | gatggtcacc | 1920 |
| ctgtattatc | cgacccacgc | ccacctaggc | ctccccgagc | ctctgttgca | tgccgacggg | 1980 |
| tggctgaacc | catcgacggc | cgaggccttc | caggcctacg | ctgggctgtg | cttccaggag | 2040 |
| ctggggacc | tggtgaagct | ctggatcacc | atcaacgagc | ctaaccggct | aagtgacatc | 2100 |
| tacaaccgct | ctggcaacga | cacctacggg | cggcgcaca | acctgctggt | ggcccacgcc | 2160 |
| ctggcctggc | gcctctacga | ccggcagttc | aggcccctcac | agcgcggggc | cgtgtcgctg | 2220 |

```
tcgctgcacg cggactgggc ggaacccgcc aaccccctatg ctgactcgca ctggagggcg   2280
gccgagcgct tcctgcagtt cgagatcgcc tggttcgccg agccgctctt caagaccggg   2340
gactaccccg cggccatgag ggaatacatt gcctccaagc accgacgggg gctttccagc   2400
tcggccctgc cgcgcctcac cgaggccgaa aggaggctgc tcaagggcac ggtcgacttc   2460
tgcgcgctca accacttcac cactaggttc gtgatgcacg agcagctggc cggcagccgc   2520
tacgactcgg acagggacat ccagtttctg caggacatca cccgcctgag ctcccccacg   2580
cgcctggctg tgattccctg gggggtgcgc aagctgctgc ggtgggtccg gaggaactac   2640
ggcgacatgg acatttacat caccgccagt ggcatcgacg accaggctct ggaggatgac   2700
cggctccgga agtactacct agggaagtac cttcaggagg tgctgaaagc atacctgatt   2760
gataaagtca gaatcaaagg ctattatgca ttcaaactgg ctgaagagaa atctaaaccc   2820
agatttggat tcttcacatc tgattttaaa gctaaatcct caatacaatt ttacaacaaa   2880
gtgatcagca gcaggggctt ccctttttgag aacagtagtt ctagatgcag tcagacccaa   2940
```

```
tcgctgcacg cggactgggc ggaacccgcc aaccccctatg ctgactcgca ctggagggcg   2280
gccgagcgct tcctgcagtt cgagatcgcc tggttcgccg agccgctctt caagaccggg   2340
gactaccccg cggccatgag ggaatacatt gcctccaagc accgacgggg gctttccagc   2400
tcggccctgc cgcgcctcac cgaggccgaa aggaggctgc tcaagggcac ggtcgacttc   2460
tgcgcgctca accacttcac cactaggttc gtgatgcacg agcagctggc cggcagccgc   2520
tacgactcgg acagggacat ccagtttctg caggacatca cccgcctgag ctcccccacg   2580
cgcctggctg tgattccctg gggggtgcgc aagctgctgc ggtgggtccg gaggaactac   2640
ggcgacatgg acatttacat caccgccagt ggcatcgacg accaggctct ggaggatgac   2700
cggctccgga agtactacct agggaagtac cttcaggagg tgctgaaagc atacctgatt   2760
gataaagtca gaatcaaagg ctattatgca ttcaaactgg ctgaagagaa atctaaaccc   2820
agatttggat tcttcacatc tgattttaaa gctaaatcct caatacaatt ttacaacaaa   2880
gtgatcagca gcaggggctt ccctttgag aacagtagtt ctagatgcag tcagacccaa   2940
gaaaatacag agtgcactgt ctgcttattc cttgtgcaga agaaaccact gatattcctg   3000
ggttgttgct tcttctccac cctggttcta ctcttatcaa ttgccatttt tcaaaggcag   3060
aagagaagaa agttttggaa agcaaaaaac ttacaacaca taccattaaa gaaaggcaag   3120
agagttgtta gc                                                        3132
```

<210> SEQ ID NO 299
<211> LENGTH: 1044
<212> TYPE: PRT
<213> ORGANISM: Macaca fascicularis
<220> FEATURE:
<223> OTHER INFORMATION: cynomolgus monkey (cyno) beta klotho

<400> SEQUENCE: 299

```
Met Lys Pro Gly Cys Ala Ala Gly Ser Pro Gly Asn Glu Trp Ile Phe
1               5                   10                  15

Phe Ser Thr Asp Glu Ile Thr Ile Arg Tyr Arg Asn Thr Met Ser Asn
            20                  25                  30

Gly Gly Leu Gln Arg Ser Val Ile Leu Ser Ala Leu Thr Leu Leu Arg
        35                  40                  45

Ala Val Thr Gly Phe Ser Gly Asp Gly Arg Ala Val Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Val Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Val His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Asn
                165                 170                 175

Thr Leu Leu Asp Ser Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
```

-continued

```
            195                 200                 205
Trp Lys Asn Asp Thr Ile Ile Asp Ile Phe Asn Asp Tyr Ala Thr Tyr
210                 215                 220
Cys Phe Gln Thr Phe Gly Asp Arg Val Lys Tyr Trp Ile Thr Ile His
225                 230                 235                 240
Asn Pro Tyr Leu Val Ala Trp His Gly Tyr Gly Thr Gly Met His Ala
            245                 250                 255
Pro Gly Glu Lys Gly Asn Leu Ala Ala Val Tyr Thr Val Gly His Asn
            260                 265                 270
Leu Ile Lys Ala His Ser Lys Val Trp His Asn Tyr Asn Thr His Phe
            275                 280                 285
Arg Pro His Gln Lys Gly Trp Leu Ser Ile Thr Leu Gly Ser His Trp
            290                 295                 300
Ile Glu Pro Asn Arg Ser Glu Asn Thr Met Asp Ile Leu Lys Cys Gln
305                 310                 315                 320
Gln Ser Met Val Ser Val Leu Gly Trp Phe Ala Asn Pro Ile His Gly
            325                 330                 335
Asp Gly Asp Tyr Pro Glu Gly Met Lys Lys Leu Leu Ser Ile Leu
            340                 345                 350
Pro Leu Phe Ser Glu Ala Glu Lys Asn Glu Val Arg Gly Thr Ala Asp
            355                 360                 365
Phe Phe Ala Phe Ser Phe Gly Pro Asn Asn Phe Lys Pro Leu Asn Thr
370                 375                 380
Met Ala Lys Met Gly Gln Asn Val Ser Leu Asn Leu Arg Glu Ala Leu
385                 390                 395                 400
Asn Trp Ile Lys Leu Glu Tyr Asn Asn Pro Arg Ile Leu Ile Ala Glu
            405                 410                 415
Asn Gly Trp Phe Thr Asp Ser His Val Lys Thr Glu Asp Thr Thr Ala
            420                 425                 430
Ile Tyr Met Met Lys Asn Phe Leu Ser Gln Val Leu Gln Ala Ile Arg
            435                 440                 445
Leu Asp Glu Ile Arg Val Phe Gly Tyr Thr Ala Trp Ser Leu Leu Asp
            450                 455                 460
Gly Phe Glu Trp Gln Asp Ala Tyr Thr Ile Arg Arg Gly Leu Phe Tyr
465                 470                 475                 480
Val Asp Phe Asn Ser Lys Gln Lys Glu Arg Lys Pro Lys Ser Ser Ala
            485                 490                 495
His Tyr Tyr Lys Gln Ile Ile Arg Glu Asn Gly Phe Ser Leu Lys Glu
            500                 505                 510
Ala Thr Pro Asp Val Gln Gly Gln Phe Pro Cys Asp Phe Ser Trp Gly
            515                 520                 525
Val Thr Glu Ser Val Leu Lys Pro Glu Ser Val Ala Ser Ser Pro Gln
            530                 535                 540
Phe Ser Asp Pro Tyr Leu Tyr Val Trp Asn Ala Thr Gly Asn Arg Leu
545                 550                 555                 560
Leu His Arg Val Glu Gly Val Arg Leu Lys Thr Arg Pro Ala Gln Cys
            565                 570                 575
Thr Asp Phe Val Asn Ile Lys Lys Gln Leu Glu Met Leu Ala Arg Met
            580                 585                 590
Lys Val Thr His Tyr Arg Phe Ala Leu Asp Trp Ala Ser Val Leu Pro
            595                 600                 605
Thr Gly Asn Leu Ser Ala Val Asn Arg Gln Ala Leu Arg Tyr Tyr Arg
            610                 615                 620
```

```
Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
        645                 650                 655

His Ala Gly Gly Trp Leu Asn Pro Ser Thr Val Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
            725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
            805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
            885                 890                 895

Leu Glu Asp Asp Arg Leu Arg Lys Tyr Tyr Leu Glu Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
930                 935                 940

Phe Thr Ser Asp Phe Lys Ala Lys Ser Ser Ile Gln Phe Tyr Asn Lys
945                 950                 955                 960

Met Ile Ser Ser Ser Gly Phe Pro Ser Glu Asn Ser Ser Arg Cys
            965                 970                 975

Ser Gln Thr Gln Lys Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu Leu Leu Ser Ile Thr Ile Phe His Arg Gln Lys Arg Lys
            1010                1015                1020

Phe Trp Lys Ala Lys Asn Leu Gln His Ile Pro Leu Lys Gly Lys
1025                1030                1035                1040
```

Arg Val Leu Ser

<210> SEQ ID NO 300
<211> LENGTH: 3135
<212> TYPE: DNA
<213> ORGANISM: Macaca fascicularis
<220> FEATURE:
<223> OTHER INFORMATION: cynomolgus monkey (cyno) beta klotho

<400> SEQUENCE: 300

| | |
|---|---|
| atgaagcctg gatgtgccgc cggaagcccc ggcaacgagt ggatcttctt cagcaccgac | 60 |
| gagatcacca tccggtacag aaacaccatg agcaacggcg ccctgcagcg gagcgtgatc | 120 |
| ctgtctgctc tgaccctgct gagagccgtg accggcttca gcggagatgg cagagccgtg | 180 |
| tggtccaaga cccccaactt caccccccgtg aacgagagcc agctgttcct gtacgatacc | 240 |
| ttccccaaga acttcttctg gggcgtgggc acaggcgccc tgcaggtgga aggatcctgg | 300 |
| aagaaggacg gcaagggccc cagcatctgg gaccactttg cacacccca cctgaagaac | 360 |
| gtgtccagca ccaacggcag cagcgacagc tacatctttc tggaaaagga cctgagcgcc | 420 |
| ctggacttca tcggcgtgtc cttctaccag ttcagcatca gctggcccag actgttcccc | 480 |
| gacggcatcg tgacagtggc caatgccaag ggcctgcagt actacaacac cctgctggac | 540 |
| agcctggtgc tgcggaacat cgagcccatc gtgaccctgt accactggga cctgccactg | 600 |
| gctctgcagg agaaatacgg cggctggaag aacgacacca tcatcgacat cttcaacgac | 660 |
| tacgccacct actgcttcca gaccttcggc gacagagtga agtactggat cacaatccac | 720 |
| aacccctacc tggtggcctg gcacggctat ggcaccggaa tgcatgcccc tggcgagaag | 780 |
| ggaaatctgg ccgccgtgta caccgtgggc cacaacctga tcaaggccca gcaaagtg | 840 |
| tggcacaact acaataccca cttccggccc caccagaagg gctggctgtc tatcacactg | 900 |
| ggcagccact ggatcgagcc taaccgcagc gagaacacca tggacatcct gaagtgccag | 960 |
| cagagcatgg tgtccgtgct gggatggttc gccaaccccca ttcacggcga cggcgattac | 1020 |
| cccgagggca tgaagaagaa gctgctgagc atcctgcccc tgttcagcga ggccgagaag | 1080 |
| aacgaagtgc ggggcaccgc cgatttcttc gcctttagct tcggccccca aacttcaag | 1140 |
| cccctgaata ccatggccaa gatgggccag aatgtgtccc tgaacctgag agaggccctg | 1200 |
| aactggatca gctggagta caacaacccc cggatcctga tcgccgagaa cggctggttc | 1260 |
| accgacagcc acgtgaaaac cgaggacacc accgccatct atatgatgaa gaacttcctg | 1320 |
| agccaggtgc tgcaggctat ccggctggat gagatccggg tgttcggcta caccgcctgg | 1380 |
| tcactgctgg acggcttcga atggcaggac gcctacacca tcagacgggg cctgttctac | 1440 |
| gtggacttca cagcaagca gaaagagcgg aagcccaaga gcagcgccca ctactacaag | 1500 |
| cagatcatca gagagaatgg cttcagcctg aaagaggcca cccccgacgt gcagggccag | 1560 |
| ttcccttgtg atttctcttg gggcgtgacc gagagcgtgc tgaagcctga aagcgtggcc | 1620 |
| agcagccccc agttcagcga cccttacctg tacgtgtgga acgccaccgg caaccggctg | 1680 |
| ctgcatagag tggaaggcgt gcggctgaaa accagacccg cccagtgcac cgacttcgtg | 1740 |
| aacatcaaga acagctgga atgctgcc cggatgaaag tgacccacta cagattcgcc | 1800 |
| ctggactggg ccagcgtgct gcctaccgga aatctgagcg ccgtgaacag acaggccctg | 1860 |
| cggtactaca gatgcgtggt gtccgagggc ctgaagctgg catcagcgc catggtcacc | 1920 |
| ctgtactacc ctacccacgc ccacctggga ctgcctgaac tctgctgca tgctggcggc | 1980 |
| tggctgaacc ctagcaccgt ggaagccttt caggcctacg ccgggctgtg cttccaggaa | 2040 |

```
ctgggcgacc tcgtgaagct gtggatcacc atcaacgagc ccaacagact gagcgacatc    2100
tacaacagaa gcggcaacga cacctacggc gctgcccaca atctgctggt ggctcatgcc    2160
ctggcttggc ggctgtacga cagacagttc cggccttctc agcggggagc cgtgtctctg    2220
tctctgcatg ccgattgggc cgagcccgcc aaccctacg ccgactctca ttggagagcc    2280
gccgagcggt tcctgcagtt cgagatcgct tggtttgccg agcccctgtt caagaccggc    2340
gattaccctg ccgccatgag agagtatatc gccagcaagc acagacgggg cctgagcagc    2400
tctgccctgc ctagactgac cgaggccgag cggagactgc tgaagggaac cgtggatttc    2460
tgcgccctga accacttcac caccagattc gtgatgcacg agcagctggc cggcagcaga    2520
tacgacagcg accgggacat ccagtttctg caggacatca cccggctgag cagccctaca    2580
agactggccg tgatcccttg gggagtgcgc aagctgctga gatgggtgcg cagaaactac    2640
ggcgacatgg atatctacat caccgccagc ggcatcgacg accaggccct ggaagatgac    2700
cggctgcgga gtactacct ggaaaagtac ctgcaggaag tgctgaaggc ctacctgatc    2760
gacaaagtgc ggatcaaggg ctactacgcc ttcaagctgg ccgaggaaaa gagcaagccc    2820
agattcggct tcttcaccag cgacttcaag gccaagagca gcatccagtt ctacaacaag    2880
atgatcagca gcagcggctt ccccagcgag aacagcagct ccagatgcag ccagacccag    2940
aaaaacaccg agtgtaccgt gtgcctgttc ctggtgcaga gaagcccct gatcttcctg    3000 ggctgctgct tctttagcac cctggtgctg ctgctgtcca tcaccatctt ccaccggcag    3060
aagcggagaa agttctggaa ggccaaaaac ctgcagcaca tcccctgaa gaaaggcaag    3120 cgggtgctga gctga                                                    3135
```

<210> SEQ ID NO 301
<211> LENGTH: 1043
<212> TYPE: PRT
<213> ORGANISM: Mus musculus
<220> FEATURE:
<223> OTHER INFORMATION: Mouse beta klotho

<400> SEQUENCE: 301

```
Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
                20                  25                  30

Arg Ala Leu Gln Arg Ser Ala Val Leu Ser Ala Phe Val Leu Leu Arg
            35                  40                  45

Ala Val Thr Gly Phe Ser Gly Asp Gly Lys Ala Ile Trp Asp Lys Lys
        50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
    130                 135                 140

Gly Val Ser Phe Tyr Gln Phe Ser Ile Ser Trp Pro Arg Leu Phe Pro
145                 150                 155                 160
```

```
Asn Gly Thr Val Ala Val Asn Ala Gln Gly Leu Arg Tyr Tyr Arg
            165                 170                 175
Ala Leu Leu Asp Ser Leu Val Leu Arg Asn Ile Glu Pro Ile Val Thr
        180                 185                 190
Leu Tyr His Trp Asp Leu Pro Leu Thr Leu Gln Glu Glu Tyr Gly Gly
        195                 200                 205
Trp Lys Asn Ala Thr Met Ile Asp Leu Phe Asn Asp Tyr Ala Thr Tyr
    210                 215                 220
Cys Phe Gln Thr Phe Gly Asp Arg Val Lys Tyr Trp Ile Thr Ile His
225                 230                 235                 240
Asn Pro Tyr Leu Val Ala Trp His Gly Phe Gly Thr Gly Met His Ala
                245                 250                 255
Pro Gly Glu Lys Gly Asn Leu Thr Ala Val Tyr Thr Val Gly His Asn
            260                 265                 270
Leu Ile Lys Ala His Ser Lys Val Trp His Asn Tyr Asp Lys Asn Phe
        275                 280                 285
Arg Pro His Gln Lys Gly Trp Leu Ser Ile Thr Leu Gly Ser His Trp
    290                 295                 300
Ile Glu Pro Asn Arg Thr Asp Asn Met Glu Asp Val Ile Asn Cys Gln
305                 310                 315                 320
His Ser Met Ser Ser Val Leu Gly Trp Phe Ala Asn Pro Ile His Gly
                325                 330                 335
Asp Gly Asp Tyr Pro Glu Phe Met Lys Thr Gly Ala Met Ile Pro Glu
            340                 345                 350
Phe Ser Glu Ala Glu Lys Glu Glu Val Arg Gly Thr Ala Asp Phe Phe
        355                 360                 365
Ala Phe Ser Phe Gly Pro Asn Asn Phe Arg Pro Ser Asn Thr Val Val
    370                 375                 380
Lys Met Gly Gln Asn Val Ser Leu Asn Leu Arg Gln Val Leu Asn Trp
385                 390                 395                 400
Ile Lys Leu Glu Tyr Asp Asp Pro Gln Ile Leu Ile Ser Glu Asn Gly
                405                 410                 415
Trp Phe Thr Asp Ser Tyr Ile Lys Thr Glu Asp Thr Thr Ala Ile Tyr
            420                 425                 430
Met Met Lys Asn Phe Leu Asn Gln Val Leu Gln Ala Ile Lys Phe Asp
        435                 440                 445
Glu Ile Arg Val Phe Gly Tyr Thr Ala Trp Thr Leu Leu Asp Gly Phe
    450                 455                 460
Glu Trp Gln Asp Ala Tyr Thr Thr Arg Arg Gly Leu Phe Tyr Val Asp
465                 470                 475                 480
Phe Asn Ser Glu Gln Lys Glu Arg Lys Pro Lys Ser Ser Ala His Tyr
                485                 490                 495
Tyr Lys Gln Ile Ile Gln Asp Asn Gly Phe Pro Leu Lys Glu Ser Thr
            500                 505                 510
Pro Asp Met Lys Gly Arg Phe Pro Cys Asp Phe Ser Trp Gly Val Thr
        515                 520                 525
Glu Ser Val Leu Lys Pro Glu Phe Thr Val Ser Ser Pro Gln Phe Thr
    530                 535                 540
Asp Pro His Leu Tyr Val Trp Asn Val Thr Gly Asn Arg Leu Leu Tyr
545                 550                 555                 560
Arg Val Glu Gly Val Arg Leu Lys Thr Arg Pro Ser Gln Cys Thr Asp
                565                 570                 575
Tyr Val Ser Ile Lys Lys Arg Val Glu Met Leu Ala Lys Met Lys Val
```

-continued

```
                580             585             590
Thr His Tyr Gln Phe Ala Leu Asp Trp Thr Ser Ile Leu Pro Thr Gly
            595                 600             605
Asn Leu Ser Lys Val Asn Arg Gln Val Leu Arg Tyr Tyr Arg Cys Val
    610             615             620
Val Ser Glu Gly Leu Lys Leu Gly Val Phe Pro Met Val Thr Leu Tyr
625                 630             635             640
His Pro Thr His Ser His Leu Gly Leu Pro Leu Pro Leu Leu Ser Ser
                645             650             655
Gly Gly Trp Leu Asn Met Asn Thr Ala Lys Ala Phe Gln Asp Tyr Ala
            660             665             670
Glu Leu Cys Phe Arg Glu Leu Gly Asp Leu Val Lys Leu Trp Ile Thr
        675             680             685
Ile Asn Glu Pro Asn Arg Leu Ser Asp Met Tyr Asn Arg Thr Ser Asn
    690             695             700
Asp Thr Tyr Arg Ala Ala His Asn Leu Met Ile Ala His Ala Gln Val
705             710             715             720
Trp His Leu Tyr Asp Arg Gln Tyr Arg Pro Val Gln His Gly Ala Val
                725             730             735
Ser Leu Ser Leu His Cys Asp Trp Ala Glu Pro Ala Asn Pro Phe Val
            740             745             750
Asp Ser His Trp Lys Ala Ala Glu Arg Phe Leu Gln Phe Glu Ile Ala
        755             760             765
Trp Phe Ala Asp Pro Leu Phe Lys Thr Gly Asp Tyr Pro Ser Val Met
    770             775             780
Lys Glu Tyr Ile Ala Ser Lys Asn Gln Arg Gly Leu Ser Ser Ser Val
785             790             795             800
Leu Pro Arg Phe Thr Ala Lys Glu Ser Arg Leu Val Lys Gly Thr Val
                805             810             815
Asp Phe Tyr Ala Leu Asn His Phe Thr Thr Arg Phe Val Ile His Lys
            820             825             830
Gln Leu Asn Thr Asn Arg Ser Val Ala Asp Arg Asp Val Gln Phe Leu
        835             840             845
Gln Asp Ile Thr Arg Leu Ser Ser Pro Ser Arg Leu Ala Val Thr Pro
    850             855             860
Trp Gly Val Arg Lys Leu Leu Ala Trp Ile Arg Arg Asn Tyr Arg Asp
865             870             875             880
Arg Asp Ile Tyr Ile Thr Ala Asn Gly Ile Asp Asp Leu Ala Leu Glu
                885             890             895
Asp Asp Gln Ile Arg Lys Tyr Tyr Leu Glu Lys Tyr Val Gln Glu Ala
            900             905             910
Leu Lys Ala Tyr Leu Ile Asp Lys Val Lys Ile Lys Gly Tyr Tyr Ala
        915             920             925
Phe Lys Leu Thr Glu Glu Lys Ser Lys Pro Arg Phe Gly Phe Phe Thr
    930             935             940
Ser Asp Phe Arg Ala Lys Ser Ser Val Gln Phe Tyr Ser Lys Leu Ile
945             950             955             960
Ser Ser Ser Gly Leu Pro Ala Glu Asn Arg Ser Pro Ala Cys Gly Gln
                965             970             975
Pro Ala Glu Asp Thr Asp Cys Thr Ile Cys Ser Phe Leu Val Glu Lys
            980             985             990
Lys Pro Leu Ile Phe Phe Gly Cys Cys Phe Ile Ser Thr Leu Ala Val
        995             1000            1005
```

```
Leu Leu Ser Ile Thr Val Phe His His Gln Lys Arg Arg Lys Phe Gln
   1010                1015                1020

Lys Ala Arg Asn Leu Gln Asn Ile Pro Leu Lys Lys Gly His Ser Arg
1025                1030                1035                1040

Val Phe Ser

<210> SEQ ID NO 302
<211> LENGTH: 3129
<212> TYPE: DNA
<213> ORGANISM: Mus musculus
<220> FEATURE:
<223> OTHER INFORMATION: Mouse beta klotho

<400> SEQUENCE: 302
```

| | | | | |
|---|---|---|---|---|
| atgaagacag | gctgtgcagc | agggtctccg | gggaatgaat | ggattttctt | cagctctgat | 60 |
| gaaagaaaca | cacgctctag | gaaaacaatg | tccaacaggg | cactgcaaag | atctgccgtg | 120 |
| ctgtctgcgt | ttgttctgct | gcgagctgtt | accggcttct | ccggagacgg | aaagcaata | 180 |
| tgggataaaa | aacagtacgt | gagtccggta | aacccaagtc | agctgttcct | ctatgacact | 240 |
| ttccctaaaa | acttttcctg | gggcgttggg | accggagcat | ttcaagtgga | agggagttgg | 300 |
| aagacagatg | gaagaggacc | ctcgatctgg | gatcggtacg | tctactcaca | cctgagaggt | 360 |
| gtcaacggca | cagacagatc | cactgacagt | tacatctttc | tggaaaaaga | cttgttggct | 420 |
| ctggattttt | taggagtttc | tttttatcag | ttctcaatct | cctggccacg | gttgtttccc | 480 |
| aatggaacag | tagcagcagt | gaatgcgcaa | ggtctccggt | actaccgtgc | acttctggac | 540 |
| tcgctggtac | ttaggaatat | cgagcccatt | gttaccttgt | accattggga | tttgcctctg | 600 |
| acgctccagg | aagaatatgg | gggctggaaa | aatgcaacta | tgatagatct | cttcaacgac | 660 |
| tatgccacat | actgcttcca | gaccctttgga | gaccgtgtca | atattggat | tacaattcac | 720 |
| aacccttacc | ttgttgcttg | gcatgggttt | ggcacaggta | tgcatgcacc | aggagagaag | 780 |
| ggaaatttaa | cagctgtcta | cactgtggga | cacaacctga | tcaaggcaca | ttcgaaagtg | 840 |
| tggcataact | acgacaaaaa | cttccgccct | catcagaagg | gttggctctc | catcaccttg | 900 |
| gggtcccatt | ggatagagcc | aaacagaaca | gacaacatgg | aggacgtgat | caactgccag | 960 |
| cactccatgt | cctctgtgct | tggatggttc | gccaaccccca | tccacgggga | cggcgactac | 1020 |
| cctgagttca | tgaagacggg | cgccatgatc | cccgagttct | ctgaggcaga | aaggaggag | 1080 |
| gtgaggggca | cggctgattt | ctttgccttt | tccttcgggc | caacaacttc | aggccctca | 1140 |
| aacaccgtgg | tgaaaatggg | acaaaatgta | tcactcaact | taaggcaggt | gctgaactgg | 1200 |
| attaaactgg | aatacgatga | ccctcaaatc | ttgatttcgg | agaacggctg | gttcacagat | 1260 |
| agctatataa | agacagagga | caccacggcc | atctacatga | tgaagaattt | cctaaaccag | 1320 |
| gttcttcaag | caataaaatt | tgatgaaatc | cgcgtgtttg | ttatacggc | tggactctc | 1380 |
| ctggatggct | ttgagtggca | ggatgcctat | acgacccgac | gagggctgtt | ttatgtggac | 1440 |
| tttaacagtg | agcagaaaga | gaggaaaccc | aagtcctcgg | ctcattacta | caagcagatc | 1500 |
| atacaagaca | acggcttccc | tttgaaagag | tccacgccag | acatgaaggg | tcggttcccc | 1560 |
| tgtgatttct | cttggggagt | cactgagtct | gttcttaagc | ccgagtttac | ggtctcctcc | 1620 |
| ccgcagttta | ccgatcctca | cctgtatgtg | tggaatgtca | ctggcaacag | attgctctac | 1680 |
| cgagtggaag | gggtaaggct | gaaaacaaga | ccatcccagt | gcacagatta | tgtgagcatc | 1740 |
| aaaaaacgag | ttgaaatgtt | ggcaaaaatg | aaagtcaccc | actaccagtt | tgctctggac | 1800 |

| | |
|---|---|
| tggacctcta tccttcccac tggcaatctg tccaaagtta acagacaagt gttaaggtac | 1860 |
| tataggtgtg tggtgagcga aggactgaag ctgggcgtct tccccatggt gacgttgtac | 1920 |
| cacccaaccc actcccatct cggcctcccc ctgccacttc tgagcagtgg ggggtggcta | 1980 |
| aacatgaaca cagccaaggc cttccaggac tacgctgagc tgtgcttccg ggagttgggg | 2040 |
| gacttggtga agctctggat caccatcaat gagcctaaca ggctgagtga catgtacaac | 2100 |
| cgcacgagta atgacaccta ccgtgcagcc acaacctga tgatcgccca tgcccaggtc | 2160 |
| tggcacctct atgataggca gtataggccg gtccagcatg gggctgtgtc gctgtcctta | 2220 |
| cattgcgact gggcagaacc tgccaacccc tttgtggatt cacactgaa ggcagccgag | 2280 |
| cgcttcctcc agtttgagat cgcctggttt gcagatccgc tcttcaagac tggcgactat | 2340 |
| ccatcggtta tgaaggaata catcgcctcc aagaaccagc gagggctgtc tagctcagtc | 2400 |
| ctgccgcgct tcaccgcgaa ggagagcagg ctggtgaagg gtaccgtcga cttctacgca | 2460 |
| ctgaaccact tcactacgag gttcgtgata cacaagcagc tgaacaccaa ccgctcagtt | 2520 |
| gcagacaggg acgtccagtt cctgcaggac atcacccgcc taagctcgcc cagccgcctg | 2580 |
| gctgtaacac cctggggagt gcgcaagctc cttgcgtgga tccggaggaa ctacagagac | 2640 |
| agggatatct acatcacagc caatggcatc gatgacctgg ctctagagga tgatcagatc | 2700 |
| cgaaagtact acttggagaa gtatgtccag gaggctctga agcatatct cattgacaag | 2760 |
| gtcaaaatca aaggctacta tgcattcaaa ctgactgaag agaaatctaa gcctagattt | 2820 |
| ggattttca cctctgactt cagagctaag tcctctgtcc agttttacag caagctgatc | 2880 |
| agcagcagtg gcctccccgc tgagaacaga agtcctgcgt gtggtcagcc tgcggaagac | 2940 |
| acagactgca ccatttgctc atttctcgtg gagaagaaac cactcatctt cttcggttgc | 3000 |
| tgcttcatct ccactctggc tgtactgcta tccatcaccg ttttcatca tcaaaagaga | 3060 |
| agaaaattcc agaaagcaag gaacttacaa aatataccat tgaagaaagg ccacagcaga | 3120 |
| gttttcagc | 3129 |

<210> SEQ ID NO 303
<211> LENGTH: 651
<212> TYPE: DNA
<213> ORGANISM: Artificial Sequence
<220> FEATURE:
<223> OTHER INFORMATION: full length FGF19 (NM_005117.2)

<400> SEQUENCE: 303

| | |
|---|---|
| atgcggagcg ggtgtgtggt ggtccacgta tggatcctgg ccggcctctg gctggccgtg | 60 |
| gccgggcgcc ccctcgcctt ctcggacgcg gggccccacg tgcactacgg ctggggcgac | 120 |
| cccatccgcc tgcggcacct gtacacctcc ggccccacg ggctctccag ctgcttcctg | 180 |
| cgcatccgtg ccgacggcgt cgtggactgc gcgcggggcc agagcgcgca cagtttgctg | 240 |
| gagatcaagg cagtcgctct gcggaccgtg gccatcaagg gcgtgcacag cgtgcggtac | 300 |
| ctctgcatgg gcgccgacgg caagatgcag gggctgcttc agtactcgga ggaagactgt | 360 |
| gctttcgagg aggagatccg cccagatggc tacaatgtgt accgatccga gaagcaccgc | 420 |
| ctcccggtct ccctgagcag tgccaaacag cggcagctgt acaagaacag aggctttctt | 480 |
| ccactctctc atttcctgcc catgctgccc atggtcccag aggagcctga ggacctcagg | 540 |
| ggccacttgg aatctgacat gttctcttcg ccccctggaga ccgacagcat ggacccattt | 600 |
| gggcttgtca ccggactgga ggccgtgagg agtcccagct ttgagaagta a | 651 |

<210> SEQ ID NO 304
<211> LENGTH: 216
<212> TYPE: PRT
<213> ORGANISM: Artificial Sequence
<220> FEATURE:
<223> OTHER INFORMATION: full length FGF19 (NP_005108.1)

<400> SEQUENCE: 304

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 305
<211> LENGTH: 630
<212> TYPE: DNA
<213> ORGANISM: Artificial Sequence
<220> FEATURE:
<223> OTHER INFORMATION: A full length FGF21

<400> SEQUENCE: 305

```
atggactcgg acgagaccgg gttcgagcac tcaggactgt gggtttctgt gctggctggt     60
cttctgctgg agcctgcca ggcacacccc atccctgact ccagtcctct cctgcaattc    120
gggggccaag tccggcagcg gtacctctac acagatgatg cccagcagac agaagcccac    180
ctggagatca gggaggatgg gacggtgggg ggcgctgctg accagagccc cgaaagtctc    240
ctgcagctga aagccttgaa gccgggagtt attcaaatct gggagtcaa gacatccagg    300 ttcctgtgcc agcggccaga tgggccctg tatggatcgc tccactttga ccctgaggcc    360
tgcagcttcc gggagctgct tcttgaggac ggatacaatg tttaccagtc gaagcccac    420 ggcctcccgc tgcacctgcc agggaacaag tccccacacc gggaccctgc accccgagga    480
ccagctcgct tcctgccact accaggcctg cccccgcac ccccggagcc acccggaatc    540
```

```
ctggcccccc agccccccga tgtgggctcc tcggaccctc tgagcatggt gggaccttcc    600
cagggccgaa gccccagcta cgcttcctga                                      630
```

```
<210> SEQ ID NO 306
<211> LENGTH: 209
<212> TYPE: PRT
<213> ORGANISM: Artificial Sequence
<220> FEATURE:
<223> OTHER INFORMATION: A full length FGF21

<400> SEQUENCE: 306
```

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

```
<210> SEQ ID NO 307
<211> LENGTH: 2469
<212> TYPE: DNA
<213> ORGANISM: Homo sapiens
<220> FEATURE:
<223> OTHER INFORMATION: human FGFR1c NM_023110.2 (also designated FGFR
      alpha-IIIc)

<400> SEQUENCE: 307
```

```
atgtggagct ggaagtgcct cctcttctgg gctgtgctgg tcacagccac actctgcacc    60
gctaggccgt ccccgacctt gcctgaacaa gcccagcct ggggagcccc tgtggaagtg    120
gagtccttcc tggtccaccc cggtgacctg ctgcagcttc gctgtcggct gcgggacgat    180
gtgcagagca tcaactggct gcgggacggg gtgcagctgg cggaaagcaa ccgcacccgc    240
atcacagggg aggaggtgga ggtgcaggac tccgtgccgg cagactccgg cctctatgct    300
tgcgtaacca gcagcccctc gggcagtgac accacctact ctccgtcaa tgtttcagat    360 gctctcccct cctcggagga tgatgatgat gatgatgact cctcttcaga ggagaaagaa    420
```

```
acagataaca ccaaaccaaa ccgtatgccc gtagctccat attggacatc accagaaaag    480
atggaaaaga aattgcatgc agtgccggct gccaagacag tgaagttcaa atgcccttcc    540
agtgggacac caaacccaac actgcgctgg ttgaaaaatg gcaaagaatt caaacctgac    600
cacagaattg gaggctacaa ggtccgttat gccacctgga gcatcataat ggactctgtg    660
gtgccctctg acaagggcaa ctacacctgc attgtggaga atgagtacgg cagcatcaac    720
cacacatacc agctggatgt cgtggagcgg tcccctcacc ggcccatcct gcaagcaggg    780
ttgcccgcca acaaaacagt ggccctgggt agcaacgtgg agttcatgtg taaggtgtac    840
agtgacccgc agccgcacat ccagtggcta aagcacatcg aggtgaatgg gagcaagatt    900
ggcccagaca acctgcctta tgtccagatc ttgaagactg ctggagttaa taccaccgac    960
aaagagatgg aggtgcttca cttaagaaat gtctcctttg aggacgcagg ggagtatacg   1020
tgcttggcgg gtaactctat cggactctcc catcactctg catggttgac cgttctggaa   1080
gccctggaag agaggccggc agtgatgacc tcgcccctgt acctggagat catcatctat   1140
tgcacagggg ccttcctcat ctcctgcatg gtggggtcgg tcatcgtcta caagatgaag   1200
agtggtacca agaagagtga cttccacagc cagatggctg tgcacaagct ggccaagagc   1260
atccctctgc gcagacaggt aacagtgtct gctgactcca gtgcatccat gaactctggg   1320
gttcttctgg ttcggccatc acggctctcc tccagtggga ctcccatgct agcaggggtc   1380
tctgagtatg agcttcccga agaccctcgc tgggagctgc ctcgggacag actggtctta   1440
ggcaaacccc tgggagaggg ctgctttggg caggtggtgt tggcagaggc tatcgggctg   1500
gacaaggaca aacccaaccg tgtgaccaaa gtggctgtga agatgttgaa gtcggacgca   1560
acagagaaag acttgtcaga cctgatctca gaaatggaga tgatgaagat gatcgggaag   1620
cataagaata tcatcaacct gctggggcc tgcacgcagg atggtccctt gtatgtcatc   1680
gtggagtatg cctccaaggg caacctgcgg gagtacctgc aggcccggag gccccccagg   1740
ctggaatact gctacaaccc cagccacaac ccagaggagc agctctcctc caaggacctg   1800
gtgtcctgcg cctaccaggt ggcccgagc atggagtatc tggcctccaa gaagtgcata   1860
caccgagacc tggcagccag gaatgtcctg gtgacagagc acaatgtgat gaagatagca   1920
gactttggcc tcgcacggga cattcaccac atcgactact ataaaaagac aaccaacggc   1980
cgactgcctg tgaagtggat ggcacccgag gcattatttg accggatcta cacccaccag   2040
agtgatgtgt ggtctttcgg ggtgctcctg tgggagatct tcactctggg cggctcccca   2100
taccccggtg tgcctgtgga ggaacttttc aagctgctga ggagggtca ccgcatggac   2160 aagcccagta actgcaccaa cgagctgtac atgatgatgc gggactgctg gcatgcagtg   2220
ccctcacaga gacccacctt caagcagctg gtggaagacc tggaccgcat cgtggccttg   2280
acctccaacc aggagtacct ggacctgtcc atgcccctgg accagtactc ccccagcttt   2340
cccgacaccc ggagctctac gtgctcctca ggggaggatt ccgtcttctc tcatgagccg   2400
ctgcccgagg agccctgcct gccccgacac ccagcccagc ttgccaatgg cggactcaaa   2460
cgccgctga                                                           2469
```

<210> SEQ ID NO 308
<211> LENGTH: 822
<212> TYPE: PRT
<213> ORGANISM: Homo sapiens
<220> FEATURE:
<223> OTHER INFORMATION: human FGFR1c NP_075598.2 (also designated FGFR alpha-IIIc)

<400> SEQUENCE: 308

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys

```
            405                 410                 415
Leu Ala Lys Ser Ile Pro Leu Arg Arg Gln Val Thr Val Ser Ala Asp
            420                 425                 430
Ser Ser Ala Ser Met Asn Ser Gly Val Leu Leu Val Arg Pro Ser Arg
            435                 440                 445
Leu Ser Ser Ser Gly Thr Pro Met Leu Ala Gly Val Ser Glu Tyr Glu
450                 455                 460
Leu Pro Glu Asp Pro Arg Trp Glu Leu Pro Arg Asp Arg Leu Val Leu
465                 470                 475                 480
Gly Lys Pro Leu Gly Glu Gly Cys Phe Gly Gln Val Val Leu Ala Glu
            485                 490                 495
Ala Ile Gly Leu Asp Lys Asp Lys Pro Asn Arg Val Thr Lys Val Ala
            500                 505                 510
Val Lys Met Leu Lys Ser Asp Ala Thr Glu Lys Asp Leu Ser Asp Leu
            515                 520                 525
Ile Ser Glu Met Glu Met Met Lys Met Ile Gly Lys His Lys Asn Ile
        530                 535                 540
Ile Asn Leu Leu Gly Ala Cys Thr Gln Asp Gly Pro Leu Tyr Val Ile
545                 550                 555                 560
Val Glu Tyr Ala Ser Lys Gly Asn Leu Arg Glu Tyr Leu Gln Ala Arg
            565                 570                 575
Arg Pro Pro Gly Leu Glu Tyr Cys Tyr Asn Pro Ser His Asn Pro Glu
            580                 585                 590
Glu Gln Leu Ser Ser Lys Asp Leu Val Ser Cys Ala Tyr Gln Val Ala
            595                 600                 605
Arg Gly Met Glu Tyr Leu Ala Ser Lys Lys Cys Ile His Arg Asp Leu
        610                 615                 620
Ala Ala Arg Asn Val Leu Val Thr Glu Asp Asn Val Met Lys Ile Ala
625                 630                 635                 640
Asp Phe Gly Leu Ala Arg Asp Ile His His Ile Asp Tyr Tyr Lys Lys
            645                 650                 655
Thr Thr Asn Gly Arg Leu Pro Val Lys Trp Met Ala Pro Glu Ala Leu
        660                 665                 670
Phe Asp Arg Ile Tyr Thr His Gln Ser Asp Val Trp Ser Phe Gly Val
        675                 680                 685
Leu Leu Trp Glu Ile Phe Thr Leu Gly Gly Ser Pro Tyr Pro Gly Val
    690                 695                 700
Pro Val Glu Glu Leu Phe Lys Leu Leu Lys Glu Gly His Arg Met Asp
705                 710                 715                 720
Lys Pro Ser Asn Cys Thr Asn Glu Leu Tyr Met Met Met Arg Asp Cys
                725                 730                 735
Trp His Ala Val Pro Ser Gln Arg Pro Thr Phe Lys Gln Leu Val Glu
            740                 745                 750
Asp Leu Asp Arg Ile Val Ala Leu Thr Ser Asn Gln Glu Tyr Leu Asp
            755                 760                 765
Leu Ser Met Pro Leu Asp Gln Tyr Ser Pro Ser Phe Pro Asp Thr Arg
        770                 775                 780
Ser Ser Thr Cys Ser Ser Gly Glu Asp Ser Val Phe Ser His Glu Pro
785                 790                 795                 800
Leu Pro Glu Glu Pro Cys Leu Pro Arg His Pro Ala Gln Leu Ala Asn
            805                 810                 815
Gly Gly Leu Lys Arg Arg
            820
```

<210> SEQ ID NO 309
<211> LENGTH: 374
<212> TYPE: PRT
<213> ORGANISM: Artificial Sequence
<220> FEATURE:
<223> OTHER INFORMATION: example of extracellular region of FGFR1c

<400> SEQUENCE: 309

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365
```

Met Thr Ser Pro Leu Tyr
    370

<210> SEQ ID NO 310
<211> LENGTH: 2466
<212> TYPE: DNA
<213> ORGANISM: Homo sapiens
<220> FEATURE:
<223> OTHER INFORMATION: Coding sequence of human FGFR2c (NM_000141.4)

<400> SEQUENCE: 310

| | | | | | |
|---|---|---|---|---|---|
| atggtcagct | ggggtcgttt | catctgcctg | gtcgtggtca | ccatggcaac | cttgtccctg | 60 |
| gcccggccct | ccttcagttt | agttgaggat | accacattag | agccagaaga | gccaccaacc | 120 |
| aaataccaaa | tctctcaacc | agaagtgtac | gtggctgcgc | caggggagtc | gctagaggtg | 180 |
| cgctgcctgt | tgaaagatgc | cgccgtgatc | agttggacta | aggatggggt | gcacttgggg | 240 |
| cccaacaata | ggacagtgct | tattggggag | tacttgcaga | taaagggcgc | cacgcctaga | 300 |
| gactccggcc | tctatgcttg | tactgccagt | aggactgtag | acagtgaaac | ttggtacttc | 360 |
| atggtgaatg | tcacagatgc | catctcatcc | ggagatgatg | aggatgacac | cgatggtgcg | 420 |
| gaagattttg | tcagtgagaa | cagtaacaac | aagagagcac | catactggac | caacacagaa | 480 |
| aagatggaaa | agcggctcca | tgctgtgcct | gcggccaaca | ctgtcaagtt | cgctgcccca | 540 |
| gccgggggga | acccaatgcc | aaccatgcgg | tggctgaaaa | acgggaagga | gtttaagcag | 600 |
| gagcatcgca | ttggaggcta | caaggtacga | aaccagcact | ggagcctcat | tatggaaagt | 660 |
| gtggtcccat | ctgacaaggg | aaattatacc | tgtgtagtgg | agaatgaata | cgggtccatc | 720 |
| aatcacacgt | accacctgga | tgttgtggag | cgatcgcctc | accggccat | cctccaagcc | 780 |
| ggactgccgg | caaatgcctc | cacagtggtc | ggaggagacg | tagagtttgt | ctgcaaggtt | 840 |
| tacagtgatg | cccagcccca | catccagtgg | atcaagcacg | tggaaaagaa | cggcagtaaa | 900 |
| tacgggcccg | acgggctgcc | ctacctcaag | gttctcaagg | ccgccggtgt | aaccaccacg | 960 |
| gacaaagaga | ttgaggttct | ctatattcgg | aatgtaactt | ttgaggacgc | tggggaatat | 1020 |
| acgtgcttgg | cgggtaattc | tattgggata | tcctttcact | ctgcatggtt | gacagttctg | 1080 |
| ccagcgcctg | gaagagaaaa | ggagattaca | gcttccccag | actacctgga | gatagccatt | 1140 |
| tactgcatag | ggtcttctt | aatcgcctgt | atggtggtaa | cagtcatcct | gtgccgaatg | 1200 |
| aagaacacga | ccaagaagcc | agacttcagc | agccagccgg | ctgtgcacaa | gctgaccaaa | 1260 |
| cgtatccccc | tgcggagaca | ggtaacagtt | tcggctgagt | ccagctcctc | catgaactcc | 1320 |
| aacacccgc | tggtgaggat | aacaacacgc | ctctcttcaa | cggcagacac | ccccatgctg | 1380 |
| gcagggtct | ccgagtatga | acttccagag | gacccaaaat | gggagtttcc | aagagataag | 1440 |
| ctgacactgg | gcaagcccct | gggagaaggt | tgctttgggc | aagtggtcat | ggcggaagca | 1500 |
| gtgggaattg | acaaagacaa | gcccaaggag | gcggtcaccg | tggccgtgaa | gatgttgaaa | 1560 |
| gatgatgcca | cagagaaaga | cctttctgat | ctggtgtcag | agatggagat | gatgaagatg | 1620 |
| attgggaaac | acaagaatat | cataaatctt | cttggagcct | gcacacagga | tgggcctctc | 1680 |
| tatgtcatag | ttgagtatgc | ctctaaaggc | aacctccgag | aatacctccg | agcccggagg | 1740 |
| ccacccggga | tggagtactc | ctatgacatt | aaccgtgttc | ctgaggagca | gatgaccttc | 1800 |
| aaggacttgg | tgtcatgcac | ctaccagctg | gccagaggca | tggagtactt | ggcttcccaa | 1860 |
| aaatgtattc | atcgagattt | agcagccaga | aatgttttgg | taacagaaaa | caatgtgatg | 1920 |
| aaaatagcag | actttggact | cgccagagat | atcaacaata | tagactatta | caaaaagacc | 1980 |

-continued

```
accaatgggc ggcttccagt caagtggatg gctccagaag ccctgtttga tagagtatac    2040
actcatcaga gtgatgtctg gtccttcggg gtgttaatgt gggagatctt cactttaggg    2100
ggctcgccct acccagggat tcccgtggag gaactttta agctgctgaa ggaaggacac     2160
agaatggata agccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga ggaatacttg gacctcagcc aacctctcga acagtattca    2340
cctagttacc ctgacacaag aagttcttgt tcttcaggag atgattctgt ttttctccca    2400
gaccccatgc cttacgaacc atgccttcct cagtatccac acataaacgg cagtgttaaa    2460
acatga                                                               2466
```

<210> SEQ ID NO 311
<211> LENGTH: 821
<212> TYPE: PRT
<213> ORGANISM: Homo sapiens
<220> FEATURE:
<223> OTHER INFORMATION: human FGFR2c (NP_000132.3)

<400> SEQUENCE: 311

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270
```

```
Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
        290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
                340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
        370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
    610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685
```

```
    Phe Gly Val Leu Met Trp Glu Ile Phe Thr Leu Gly Gly Ser Pro Tyr
            690                 695                 700

Pro Gly Ile Pro Val Glu Glu Leu Phe Lys Leu Leu Lys Glu Gly His
    705                 710                 715                 720

Arg Met Asp Lys Pro Ala Asn Cys Thr Asn Glu Leu Tyr Met Met Met
                    725                 730                 735

Arg Asp Cys Trp His Ala Val Pro Ser Gln Arg Pro Thr Phe Lys Gln
                    740                 745                 750

Leu Val Glu Asp Leu Asp Arg Ile Leu Thr Leu Thr Thr Asn Glu Glu
                755                 760                 765

Tyr Leu Asp Leu Ser Gln Pro Leu Glu Gln Tyr Ser Pro Ser Tyr Pro
            770                 775                 780

Asp Thr Arg Ser Ser Cys Ser Ser Gly Asp Asp Ser Val Phe Ser Pro
    785                 790                 795                 800

Asp Pro Met Pro Tyr Glu Pro Cys Leu Pro Gln Tyr Pro His Ile Asn
                    805                 810                 815

Gly Ser Val Lys Thr
                820

<210> SEQ ID NO 312
<211> LENGTH: 2421
<212> TYPE: DNA
<213> ORGANISM: Homo sapiens
<220> FEATURE:
<223> OTHER INFORMATION: human FGFR3c (NM_000142.4)

<400> SEQUENCE: 312
atgggcgccc ctgcctgcgc cctcgcgctc tgcgtggccg tggccatcgt ggccggcgcc      60
tcctcggagt ccttggggac ggagcagcgc gtcgtgggc gagcggcaga agtcccgggc      120
ccagagcccg ccagcaggag gcagttggtc ttcggcagcg gggatgctgt ggagctgagc      180 tgtccccgc ccggggggtgg tcccatgggg cccactgtct gggtcaagga tggcacaggg      240
ctggtgccct cggagcgtgt cctggtgggg ccccagcggc tgcaggtgct gaatgcctcc      300
cacgaggact ccgggggccta cagctgccgg cagcggctca gcagcgcgt actgtgccac      360 ttcagtgtgc gggtgacaga cgctccatcc tcgggagatg acgaagacgg ggaggacgag      420
gctgaggaca caggtgtgga cacaggggcc ccttactgga cacggcccga gcggatggac      480
aagaagctgc tggccgtgcc ggccgccaac accgtccgct ccgctgccc agccgctggc      540 aaccccactc cctccatctc ctggctgaag aacggcaggg agttccgcgg cgagcaccgc      600
attggaggca tcaagctgcg gcatcagcag tggagcctgg tcatggaaag cgtggtgccc      660
tcggaccgcg gcaactacac ctgcgtcgtg gagaacaagt tggcagcat ccggcagacg      720 tacacgctgg acgtgctgga gcgctccccg caccggccca tcctgcaggc ggggctgccg      780
gccaaccaga cggcggtgct gggcagcgac gtggagttcc actgcaaggt gtacagtgac      840
gcacagcccc acatccagtg gctcaagcac gtggaggtga atggcagcaa ggtgggcccg      900
gacggcacac cctacgttac cgtgctcaag acggcgggcg ctaacaccac cgacaaggag      960
ctagaggttc tctccttgca caacgtcacc tttgaggacg ccggggagta cacctgcctg      1020
gcgggcaatt ctattgggtt ttctcatcac tctgcgtggc tggtggtgct gccagccgag      1080
gaggagctgg tggaggctga cgaggcgggc agtgtgtatg caggcatcct cagctacggg      1140
gtgggcttct tcctgttcat cctggtggtg cggctgtga cgctctgccg cctgcgcagc      1200
ccccccaaga aaggcctggg ctcccccacc gtgcacaaga tctcccgctt cccgctcaag      1260
```

-continued

```
cgacaggtgt ccctggagtc caacgcgtcc atgagctcca acacaccact ggtgcgcatc    1320
gcaaggctgt cctcagggga gggcccacg ctggccaatg tctccgagct cgagctgcct    1380
gccgacccca atgggagct gtctcgggcc cggctgaccc tgggcaagcc ccttggggag    1440
ggctgcttcg gccaggtggt catggcgag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga acacaaaaa catcatcaac    1620 ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acaaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctccc cgtaccccgg catccctgtg    2100
gaggagctct tcaagctgct gaaggagggc accgcatgg acaagccgc caactgcaca    2160 cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg ccaggacac ccccagctcc    2340 agctcctcag gggacgactc cgtgtttgcc cacgacctgc tgcccccggc cccacccagc    2400
agtgggggct cgcggacgtg a    2421
```

<210> SEQ ID NO 313
<211> LENGTH: 806
<212> TYPE: PRT
<213> ORGANISM: Homo sapiens
<220> FEATURE:
<223> OTHER INFORMATION: human FGFR3c (NP_000133.1)

<400> SEQUENCE: 313

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160
```

```
Lys Lys Leu Leu Ala Val Pro Ala Ala Asn Thr Val Arg Phe Arg Cys
            165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
            325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
            370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
            405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
            450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
            530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
            565                 570                 575
```

```
Tyr Ser Phe Asp Thr Cys Lys Pro Pro Glu Glu Gln Leu Thr Phe Lys
                580                 585                 590
Asp Leu Val Ser Cys Ala Tyr Gln Val Ala Arg Gly Met Glu Tyr Leu
            595                 600                 605
Ala Ser Gln Lys Cys Ile His Arg Asp Leu Ala Ala Arg Asn Val Leu
        610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
            660                 665                 670
His Gln Ser Asp Val Trp Ser Phe Gly Val Leu Leu Trp Glu Ile Phe
        675                 680                 685
Thr Leu Gly Gly Ser Pro Tyr Pro Gly Ile Pro Val Glu Glu Leu Phe
690                 695                 700
Lys Leu Leu Lys Glu Gly His Arg Met Asp Lys Pro Ala Asn Cys Thr
705                 710                 715                 720
His Asp Leu Tyr Met Ile Met Arg Glu Cys Trp His Ala Ala Pro Ser
                725                 730                 735
Gln Arg Pro Thr Phe Lys Gln Leu Val Glu Asp Leu Asp Arg Val Leu
            740                 745                 750
Thr Val Thr Ser Thr Asp Glu Tyr Leu Asp Leu Ser Ala Pro Phe Glu
        755                 760                 765
Gln Tyr Ser Pro Gly Gly Gln Asp Thr Pro Ser Ser Ser Ser Ser Gly
770                 775                 780
Asp Asp Ser Val Phe Ala His Asp Leu Leu Pro Pro Ala Pro Pro Ser
785                 790                 795                 800
Ser Gly Gly Ser Arg Thr
                805

<210> SEQ ID NO 314
<211> LENGTH: 2409
<212> TYPE: DNA
<213> ORGANISM: Homo sapiens
<220> FEATURE:
<223> OTHER INFORMATION: human FGFR4 (NM_002011.4)

<400> SEQUENCE: 314
atgcggctgc tgctggccct gttgggggtc ctgctgagtg tgcctgggcc tccagtcttg      60
tccctggagg cctctgagga agtggagctt gagccctgcc tggctcccag cctggagcag     120
caagagcagg agctgacagt agcccttggg cagcctgtgc gtctgtgctg tgggcgggct     180
gagcgtggtg ccactggta caaggagggc agtcgcctgg cacctgctgg ccgtgtacgg     240
ggctggaggg gccgcctaga gattgccagc ttcctacctg aggatgctgg ccgctacctc     300
tgcctggcac gaggctccat gatcgtcctg cagaatctca cttgattac aggtgactcc      360
ttgacctcca gcaacgatga tgaggacccc aagtcccata gggacccctc gaataggcac     420
agttaccccc agcaagcacc ctactggaca caccccagc gcatggagaa gaaactgcat     480
gcagtacctg cggggaacac cgtcaagttc cgctgtccag ctgcaggcaa ccccacgccc     540
accatccgct ggcttaagga tggacaggcc tttcatgggg agaaccgcat tggaggcatt     600
cggctgcgcc atcagcactg gagtctcgtg atggagagcg tggtgccctc ggaccgcggc     660
acatacacct gcctggtaga gaacgctgtg ggcagcatcc gctataacta cctgctagat     720
```

```
gtgctggagc ggtccccgca ccggcccatc ctgcaggccg ggctcccggc caacaccaca    780
gccgtggtgg gcagcgacgt ggagctgctg tgcaaggtgt acagcgatgc ccagccccac    840
atccagtggc tgaagcacat cgtcatcaac ggcagcagct tcggagccga cggtttcccc    900
tatgtgcaag tcctaaagac tgcagacatc aatagctcag aggtggaggt cctgtacctg    960
cggaacgtgt cagccgagga cgcaggcgag tacacctgcc tcgcaggcaa ttccatcggc   1020
ctctcctacc agtctgcctg gctcacggtg ctgccagagg aggacccac atggaccgca    1080 gcagcgcccg aggccaggta tacggacatc atcctgtacg cgtcgggctc cctggccttg   1140
gctgtgctcc tgctgctggc cgggctgtat cgagggcagg cgctccacgg ccggcacccc   1200
cgccccgccg ccactgtgca gaagctctcc cgcttccctc tggcccgaca gttctccctg   1260
gagtcaggct cttccggcaa gtcaagctca tccctggtac gaggcgtgcg tctctcctcc   1320
agcggccccg ccttgctcgc cggcctcgtg agtctagatc tacctctcga cccactatgg   1380
gagttccccc gggacaggct ggtgcttggg aagcccctag gcgagggctg ctttggccag   1440
gtagtacgtg cagaggcctt tggcatggac cctgccccggc ctgaccaagc cagcactgtg   1500
gccgtcaaga tgctcaaaga caacgcctct gacaaggacc tggccgacct ggtctcggag   1560
atggaggtga tgaagctgat cggccgacac aagaacatca tcaacctgct tggtgtctgc   1620
acccaggaag ggccctgta cgtgatcgtg gagtgcgccg ccaagggaaa cctgcgggag   1680
ttcctgcggg cccggcgccc cccaggcccc gacctcagcc ccgacggtcc tcggagcagt   1740
gaggggccgc tctccttccc agtcctggtc tcctgcgcct accaggtggc ccgaggcatg   1800
cagtatctgg agtcccggaa gtgtatccac cgggacctgg ctgcccgcaa tgtgctggtg   1860
actgaggaca atgtgatgaa gattgctgac tttgggctgg cccgcggcgt ccaccacatt   1920
gactactata agaaaaccag caacggccgc ctgcctgtga gtggatggc gcccgaggcc   1980 ttgtttgacc gggtgtacac acaccagagt gacgtgtggt cttttgggat cctgctatgg   2040
gagatcttca ccctcggggg ctccccgtat cctggcatcc cggtggagga gctgttctcg   2100
ctgctgcggg agggacatcg gatggaccga cccccacact gccccccaga gctgtacggg   2160
ctgatgcgtg agtgctggca cgcagcgccc tcccagaggc taccttcaa gcagctggtg   2220 gaggcgctgg acaaggtcct gctggccgtc tctgaggagt acctcgacct ccgcctgacc   2280
ttcggaccct attccccctc tggtggggac gccagcagca cctgctcctc cagcgattct   2340
gtcttcagcc acgaccccct gccattggga tccagctcct tcccttcgg gtctggggtg   2400 cagacatga                                                           2409
```

<210> SEQ ID NO 315  
<211> LENGTH: 802  
<212> TYPE: PRT  
<213> ORGANISM: Homo sapiens  
<220> FEATURE:  
<223> OTHER INFORMATION: human FGFR4 (NP_002002.3)

<400> SEQUENCE: 315

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

-continued

```
His Trp Tyr Lys Glu Gly Ser Arg Leu Ala Pro Ala Gly Arg Val Arg
 65                  70                  75                  80

Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Pro Glu Ala Arg Tyr Thr
        355                 360                 365

Asp Ile Ile Leu Tyr Ala Ser Gly Ser Leu Ala Leu Ala Val Leu Leu
        370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
            420                 425                 430

Val Arg Gly Val Arg Leu Ser Ser Ser Gly Pro Ala Leu Leu Ala Gly
        435                 440                 445

Leu Val Ser Leu Asp Leu Pro Leu Asp Pro Leu Trp Glu Phe Pro Arg
        450                 455                 460

Asp Arg Leu Val Leu Gly Lys Pro Leu Gly Glu Gly Cys Phe Gly Gln
465                 470                 475                 480
```

```
Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
    770                 775                 780

Asp Pro Leu Pro Leu Gly Ser Ser Phe Pro Phe Gly Ser Gly Val
785                 790                 795                 800

Gln Thr

<210> SEQ ID NO 316
<211> LENGTH: 330
<212> TYPE: PRT
<213> ORGANISM: Artificial Sequence
<220> FEATURE:
<223> OTHER INFORMATION: human IgG1 Fc with two amino acid changes to
      alanine

<400> SEQUENCE: 316

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 317
<211> LENGTH: 472
<212> TYPE: PRT
<213> ORGANISM: Artificial Sequence
<220> FEATURE:
<223> OTHER INFORMATION: Humanized 5H23-vH3-human IgG1 (E233A)(L235A)

<400> SEQUENCE: 317

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Gln Ser Gly Ala Glu
            20                  25                  30

Val Lys Lys Pro Gly Ala Ser Val Lys Val Ser Cys Lys Ala Ser Gly
            35                  40                  45

Tyr Thr Phe Thr Ser Tyr Asp Ile Asn Trp Val Arg Gln Ala Pro Gly
 50                  55                  60
```

```
Gln Gly Leu Glu Trp Ile Gly Trp Ile Tyr Pro Gly Asp Gly Ser Thr
 65                  70                  75                  80

Lys Tyr Asn Glu Lys Phe Lys Gly Lys Ala Thr Ile Thr Arg Asp Thr
                 85                  90                  95

Ser Ala Ser Thr Ala Tyr Met Glu Leu Ser Ser Leu Arg Ser Glu Asp
            100                 105                 110

Thr Ala Val Tyr Phe Cys Ala Arg Ser Asp Tyr Tyr Gly Ser Arg Ser
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Ala Leu Ala Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

```
<210> SEQ ID NO 318
<211> LENGTH: 107
<212> TYPE: PRT
<213> ORGANISM: Homo sapiens
<220> FEATURE:
<223> OTHER INFORMATION: Human kappa constant region of light chain

<400> SEQUENCE: 318

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 319
<211> LENGTH: 240
<212> TYPE: PRT
<213> ORGANISM: Artificial Sequence
<220> FEATURE:
<223> OTHER INFORMATION: humanized 5H23-vL2-human kappa constant region
      of light chain

<400> SEQUENCE: 319

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Asp Ser
            20                  25                  30

Leu Ala Val Ser Leu Gly Glu Arg Ala Thr Ile Asn Cys Arg Ala Ser
        35                  40                  45

Lys Ser Val Ser Thr Ser Gly Tyr Val Tyr Met His Trp Tyr Gln Gln
    50                  55                  60

Lys Pro Gly Gln Pro Pro Lys Leu Leu Ile Tyr Leu Ala Ser Tyr Leu
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Val Gln Ala Glu Asp Val Ala Val Tyr
            100                 105                 110

Tyr Cys Gln His Ser Arg Asp Leu Thr Phe Pro Phe Gly Gly Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205
```

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240

<210> SEQ ID NO 320
<211> LENGTH: 120
<212> TYPE: PRT
<213> ORGANISM: Artificial Sequence
<220> FEATURE:
<223> OTHER INFORMATION: vH7

<400> SEQUENCE: 320

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Ile
            35                  40                  45

Gly Trp Ile Tyr Pro Gly Asp Gly Ser Thr Lys Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 321
<211> LENGTH: 120
<212> TYPE: PRT
<213> ORGANISM: Artificial Sequence
<220> FEATURE:
<223> OTHER INFORMATION: vH8

<400> SEQUENCE: 321

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Ile
            35                  40                  45

Gly Trp Ile Tyr Pro Gly Asp Gly Ser Thr Lys Tyr Asn Glu Lys Phe
    50                  55                  60

Lys Gly Arg Ala Thr Leu Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 322
<211> LENGTH: 120
<212> TYPE: PRT

<213> ORGANISM: Artificial Sequence
<220> FEATURE:
<223> OTHER INFORMATION: vH9

<400> SEQUENCE: 322

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 323
<211> LENGTH: 120
<212> TYPE: PRT
<213> ORGANISM: Artificial Sequence
<220> FEATURE:
<223> OTHER INFORMATION: 5H23v1-3

<400> SEQUENCE: 323

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Arg Leu Glu Trp Met
        35                  40                  45

Gly Trp Ile Tyr Pro Gly Asp Gly Ser Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 324
<211> LENGTH: 120
<212> TYPE: PRT
<213> ORGANISM: Artificial Sequence
<220> FEATURE:
<223> OTHER INFORMATION: 5H23v1-46

<400> SEQUENCE: 324

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Asp Ile Asn Trp Val Arg Gln Ala Pro Gly Gln Gly Leu Glu Trp Met
            35                  40                  45

Gly Trp Ile Tyr Pro Gly Asp Gly Ser Thr Lys Tyr Asn Glu Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
            115                 120

<210> SEQ ID NO 325
<211> LENGTH: 111
<212> TYPE: PRT
<213> ORGANISM: Artificial Sequence
<220> FEATURE:
<223> OTHER INFORMATION: vL4

<400> SEQUENCE: 325

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
             20                  25                  30

Gly Tyr Val Tyr Met His Trp Asn Gln Gln Lys Pro Gly Gln Pro Pro
         35                  40                  45

Lys Leu Leu Ile Tyr Leu Ala Ser Tyr Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Asp Leu Thr Phe Pro Phe Gly Gly Gly Thr Lys Val Glu Ile Lys
            100                 105                 110

<210> SEQ ID NO 326
<211> LENGTH: 111
<212> TYPE: PRT
<213> ORGANISM: Artificial Sequence
<220> FEATURE:
<223> OTHER INFORMATION: vL5

<400> SEQUENCE: 326

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
             20                  25                  30

Gly Tyr Val Tyr Met His Trp Asn Gln Gln Lys Pro Gly Gln Pro Pro
         35                  40                  45

Lys Leu Leu Ile Tyr Leu Ala Ser Tyr Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Asp Leu Thr Phe Pro Phe Gly Gly Gly Thr Lys Val Glu Ile Lys
```

```
                    100                 105                 110

<210> SEQ ID NO 327
<211> LENGTH: 111
<212> TYPE: PRT
<213> ORGANISM: Artificial Sequence
<220> FEATURE:
<223> OTHER INFORMATION: v1-39a

<400> SEQUENCE: 327

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Tyr Gln Gln Lys Pro Gly Lys Ala Pro
        35                  40                  45

Lys Leu Leu Ile Tyr Leu Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Asp Leu Thr Phe Pro Phe Gly Gln Gly Thr Lys Leu Glu Ile Lys
            100                 105                 110

<210> SEQ ID NO 328
<211> LENGTH: 111
<212> TYPE: PRT
<213> ORGANISM: Artificial Sequence
<220> FEATURE:
<223> OTHER INFORMATION: v1-39b

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Tyr Gln Gln Lys Pro Gly Lys Ala Pro
        35                  40                  45

Lys Leu Leu Ile Tyr Leu Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Val Gln Pro Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 329
<211> LENGTH: 111
<212> TYPE: PRT
<213> ORGANISM: Artificial Sequence
<220> FEATURE:
<223> OTHER INFORMATION: v1-39c

<400> SEQUENCE: 329

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30
```

```
Gly Tyr Val Tyr Met His Trp Asn Gln Gln Lys Pro Gly Lys Ala Pro
            35                  40                  45

Lys Leu Leu Ile Tyr Leu Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 330
<211> LENGTH: 111
<212> TYPE: PRT
<213> ORGANISM: Artificial Sequence
<220> FEATURE:
<223> OTHER INFORMATION: v1-39d

<400> SEQUENCE: 330

Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Ser Val Ser Thr Ser
                20                  25                  30

Gly Tyr Val Tyr Met His Trp Tyr Gln Gln Lys Pro Gly Lys Pro Pro
            35                  40                  45

Lys Leu Leu Ile Tyr Leu Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 331
<211> LENGTH: 111
<212> TYPE: PRT
<213> ORGANISM: Artificial Sequence
<220> FEATURE:
<223> OTHER INFORMATION: v1-39e

<400> SEQUENCE: 331

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Lys Ser Val Ser Thr Ser
                20                  25                  30

Gly Tyr Val Tyr Met His Trp Tyr Gln Gln Lys Pro Gly Lys Ala Pro
            35                  40                  45

Lys Leu Leu Ile Tyr Leu Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
            100                 105                 110
```

```
<210> SEQ ID NO 332
<211> LENGTH: 111
<212> TYPE: PRT
<213> ORGANISM: Artificial Sequence
<220> FEATURE:
<223> OTHER INFORMATION: v1-39f

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Tyr Gln Gln Lys Pro Gly Lys Pro Pro
        35                  40                  45

Lys Leu Leu Ile Tyr Leu Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Val Gln Pro Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 333
<211> LENGTH: 111
<212> TYPE: PRT
<213> ORGANISM: Artificial Sequence
<220> FEATURE:
<223> OTHER INFORMATION: v1-39g

<400> SEQUENCE: 333

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Tyr Gln Gln Lys Pro Gly Lys Pro Pro
        35                  40                  45

Lys Leu Leu Ile Tyr Leu Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Val Gln Pro Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 334
<211> LENGTH: 111
<212> TYPE: PRT
<213> ORGANISM: Artificial Sequence
<220> FEATURE:
<223> OTHER INFORMATION: v1-39h

<400> SEQUENCE: 334

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Asn Gln Gln Lys Pro Gly Lys Pro Pro
        35                  40                  45
```

Lys Leu Leu Ile Tyr Leu Ala Ser Tyr Leu Glu Ser Gly Val Pro Ser
            50                  55                  60

Arg Phe Ser Gly Ser Gly Ser Gly Thr Asp Phe Thr Leu Thr Ile Ser
 65                  70                  75                  80

Ser Val Gln Pro Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
                100                 105                 110

<210> SEQ ID NO 335
<211> LENGTH: 111
<212> TYPE: PRT
<213> ORGANISM: Artificial Sequence
<220> FEATURE:
<223> OTHER INFORMATION: v1-39i

<400> SEQUENCE: 335

Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Ser Val Ser Thr Ser
                20                  25                  30

Gly Tyr Val Tyr Met His Trp Tyr Gln Gln Lys Pro Gly Lys Ala Pro
            35                  40                  45

Lys Leu Leu Ile Tyr Leu Ala Ser Tyr Leu Glu Ser Gly Val Pro Ser
            50                  55                  60

Arg Phe Ser Gly Ser Gly Ser Gly Thr Asp Phe Thr Leu Thr Ile Ser
 65                  70                  75                  80

Ser Leu Gln Glu Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
                100                 105                 110

<210> SEQ ID NO 336
<211> LENGTH: 111
<212> TYPE: PRT
<213> ORGANISM: Artificial Sequence
<220> FEATURE:
<223> OTHER INFORMATION: v1-39j

<400> SEQUENCE: 336

Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Ser Val Ser Thr Ser
                20                  25                  30

Gly Tyr Val Tyr Met His Trp Tyr Gln Gln Lys Pro Gly Lys Ala Pro
            35                  40                  45

Lys Leu Leu Ile Tyr Leu Ala Ser Tyr Leu Glu Ser Gly Val Pro Ser
            50                  55                  60

Arg Phe Ser Gly Ser Gly Ser Gly Thr Asp Phe Thr Leu Thr Ile Ser
 65                  70                  75                  80

Ser Val Gln Glu Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
                100                 105                 110

<210> SEQ ID NO 337
<211> LENGTH: 111
<212> TYPE: PRT

```
<213> ORGANISM: Artificial Sequence
<220> FEATURE:
<223> OTHER INFORMATION: v1-39k

<400> SEQUENCE: 337

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Asn Gln Gln Lys Pro Gly Lys Pro Pro
        35                  40                  45

Lys Leu Leu Ile Tyr Leu Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Val Gln Glu Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 338
<211> LENGTH: 111
<212> TYPE: PRT
<213> ORGANISM: Artificial Sequence
<220> FEATURE:
<223> OTHER INFORMATION: v1-39l

<400> SEQUENCE: 338

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Asn Gln Gln Lys Pro Gly Lys Pro Pro
        35                  40                  45

Lys Leu Leu Ile Tyr Leu Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Val Gln Glu Glu Asp Ala Ala Thr Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 339
<211> LENGTH: 111
<212> TYPE: PRT
<213> ORGANISM: Artificial Sequence
<220> FEATURE:
<223> OTHER INFORMATION: v1-39m

<400> SEQUENCE: 339

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Tyr Gln Gln Lys Pro Gly Lys Pro Pro
        35                  40                  45

Lys Leu Leu Ile Tyr Leu Ala Ser Tyr Leu Glu Ser Gly Val Pro Ser
    50                  55                  60
```

```
Arg Phe Ser Gly Ser Gly Ser Gly Thr Asp Phe Thr Leu Thr Ile Ser
 65                  70                  75                  80

Ser Val Gln Glu Glu Asp Phe Ala Thr Tyr Tyr Cys Gln His Ser Arg
                 85                  90                  95

Asp Leu Thr Phe Pro Phe Gly Gly Gly Thr Lys Leu Glu Ile Lys
            100                 105                 110
```

<210> SEQ ID NO 340
<211> LENGTH: 111
<212> TYPE: PRT
<213> ORGANISM: Artificial Sequence
<220> FEATURE:
<223> OTHER INFORMATION: v1-39n

<400> SEQUENCE: 340

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Lys Ser Val Ser Thr Ser
                 20                  25                  30

Gly Tyr Val Tyr Met His Trp Tyr Gln Gln Lys Pro Gly Lys Pro Pro
             35                  40                  45

Lys Leu Leu Ile Tyr Leu Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Val Gln Glu Glu Asp Ala Ala Thr Tyr Tyr Cys Gln His Ser Arg
                 85                  90                  95

Asp Leu Thr Phe Pro Phe Gly Gly Gly Thr Lys Leu Glu Ile Lys
            100                 105                 110
```

<210> SEQ ID NO 341
<211> LENGTH: 111
<212> TYPE: PRT
<213> ORGANISM: Artificial Sequence
<220> FEATURE:
<223> OTHER INFORMATION: v1-39o

<400> SEQUENCE: 341

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Lys Ser Val Ser Thr Ser
                 20                  25                  30

Gly Tyr Val Tyr Met His Trp Tyr Gln Gln Lys Pro Gly Lys Pro Pro
             35                  40                  45

Lys Leu Leu Ile Tyr Leu Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Val Gln Pro Glu Asp Phe Ala Thr Tyr Tyr Cys Gln His Ser Arg
                 85                  90                  95

Asp Leu Thr Phe Pro Phe Gly Gly Gln Thr Lys Leu Glu Ile Lys
            100                 105                 110
```

<210> SEQ ID NO 342
<211> LENGTH: 111
<212> TYPE: PRT
<213> ORGANISM: Artificial Sequence
<220> FEATURE:
<223> OTHER INFORMATION: v1-39p

<400> SEQUENCE: 342

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Val Tyr Met His Trp Tyr Gln Gln Lys Pro Gly Lys Pro Pro
        35                  40                  45

Lys Leu Leu Ile Tyr Leu Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Val Gln Glu Glu Asp Phe Ala Thr Tyr Tyr Cys Gln His Ser Arg
                85                  90                  95

Asp Leu Thr Phe Pro Phe Gly Gly Gln Thr Lys Leu Glu Ile Lys
            100                 105                 110

<210> SEQ ID NO 343
<211> LENGTH: 111
<212> TYPE: PRT
<213> ORGANISM: Artificial Sequence
<220> FEATURE:
<223> OTHER INFORMATION: v3-20a

<400> SEQUENCE: 343

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Val Tyr Met His Trp Tyr Gln Gln Lys Pro Gly Gln Ala Pro
        35                  40                  45

Arg Leu Leu Ile Tyr Leu Ala Ser Tyr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Ser Arg
                85                  90                  95

Asp Leu Thr Phe Pro Phe Gly Gln Gly Thr Lys Leu Glu Ile Lys
            100                 105                 110

<210> SEQ ID NO 344
<211> LENGTH: 111
<212> TYPE: PRT
<213> ORGANISM: Artificial Sequence
<220> FEATURE:
<223> OTHER INFORMATION: v3-20b

<400> SEQUENCE: 344

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Val Tyr Met His Trp Tyr Gln Gln Lys Pro Gly Gln Ala Pro
        35                  40                  45

Arg Leu Leu Ile Tyr Leu Ala Ser Tyr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Val Glu Pro Glu Asp Phe Ala Val Tyr Tyr Cys Gln His Ser Arg
                85                  90                  95

Asp Leu Thr Phe Pro Phe Gly Gly Gly Thr Lys Leu Glu Ile Lys
                100                 105                 110

<210> SEQ ID NO 345
<211> LENGTH: 111
<212> TYPE: PRT
<213> ORGANISM: Artificial Sequence
<220> FEATURE:
<223> OTHER INFORMATION: v3-20c

<400> SEQUENCE: 345

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
                20                  25                  30

Gly Tyr Val Tyr Met His Trp Asn Gln Gln Lys Pro Gly Gln Ala Pro
            35                  40                  45

Arg Leu Leu Ile Tyr Leu Ala Ser Tyr Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Ser Arg
                85                  90                  95

Asp Leu Thr Phe Pro Phe Gly Gly Gly Thr Lys Leu Glu Ile Lys
                100                 105                 110

<210> SEQ ID NO 346
<211> LENGTH: 111
<212> TYPE: PRT
<213> ORGANISM: Artificial Sequence
<220> FEATURE:
<223> OTHER INFORMATION: v3-20d

<400> SEQUENCE: 346

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
                20                  25                  30

Gly Tyr Val Tyr Met His Trp Tyr Gln Gln Lys Pro Gly Gln Pro Pro
            35                  40                  45

Arg Leu Leu Ile Tyr Leu Ala Ser Tyr Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Ser Arg
                85                  90                  95

Asp Leu Thr Phe Pro Phe Gly Gly Gly Thr Lys Leu Glu Ile Lys
                100                 105                 110

<210> SEQ ID NO 347
<211> LENGTH: 111
<212> TYPE: PRT
<213> ORGANISM: Artificial Sequence
<220> FEATURE:
<223> OTHER INFORMATION: v3-20e

<400> SEQUENCE: 347

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Val Tyr Met His Trp Tyr Gln Gln Lys Pro Gly Gln Ala Pro
        35                  40                  45

Arg Leu Leu Ile Tyr Leu Ala Ser Tyr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Ala Ala Val Tyr Tyr Cys Gln His Ser Arg
                85                  90                  95

Asp Leu Thr Phe Pro Phe Gly Gly Gly Thr Lys Leu Glu Ile Lys
            100                 105                 110
```

<210> SEQ ID NO 348
<211> LENGTH: 111
<212> TYPE: PRT
<213> ORGANISM: Artificial Sequence
<220> FEATURE:
<223> OTHER INFORMATION: v3-20f

<400> SEQUENCE: 348

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Val Tyr Met His Trp Asn Gln Gln Lys Pro Gly Gln Ala Pro
        35                  40                  45

Arg Leu Leu Ile Tyr Leu Ala Ser Tyr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Val Glu Pro Glu Asp Phe Ala Val Tyr Tyr Cys Gln His Ser Arg
                85                  90                  95

Asp Leu Thr Phe Pro Phe Gly Gly Gly Thr Lys Leu Glu Ile Lys
            100                 105                 110
```

<210> SEQ ID NO 349
<211> LENGTH: 111
<212> TYPE: PRT
<213> ORGANISM: Artificial Sequence
<220> FEATURE:
<223> OTHER INFORMATION: v3-20g

<400> SEQUENCE: 349

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Val Tyr Met His Trp Tyr Gln Gln Lys Pro Gly Gln Pro Pro
        35                  40                  45

Arg Leu Leu Ile Tyr Leu Ala Ser Tyr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Val Glu Pro Glu Asp Phe Ala Val Tyr Tyr Cys Gln His Ser Arg
                85                  90                  95
```

Asp Leu Thr Phe Pro Phe Gly Gly Gly Thr Lys Leu Glu Ile Lys
            100                 105                 110

<210> SEQ ID NO 350
<211> LENGTH: 111
<212> TYPE: PRT
<213> ORGANISM: Artificial Sequence
<220> FEATURE:
<223> OTHER INFORMATION: v3-20h

<400> SEQUENCE: 350

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Val Tyr Met His Trp Tyr Gln Gln Lys Pro Gly Gln Ala Pro
        35                  40                  45

Arg Leu Leu Ile Tyr Leu Ala Ser Tyr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Glu Glu Asp Phe Ala Val Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 351
<211> LENGTH: 111
<212> TYPE: PRT
<213> ORGANISM: Artificial Sequence
<220> FEATURE:
<223> OTHER INFORMATION: v3-20i

<400> SEQUENCE: 351

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Val Tyr Met His Trp Asn Gln Gln Lys Pro Gly Gln Ala Pro
        35                  40                  45

Arg Leu Leu Ile Tyr Leu Ala Ser Tyr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Val Glu Glu Glu Asp Phe Ala Val Tyr Tyr Cys Gln His Ser Arg
                85                  90                  95

Asp Leu Thr Phe Pro Phe Gly Gly Gly Thr Lys Leu Glu Ile Lys
            100                 105                 110

<210> SEQ ID NO 352
<211> LENGTH: 111
<212> TYPE: PRT
<213> ORGANISM: Artificial Sequence
<220> FEATURE:
<223> OTHER INFORMATION: v3-20j

<400> SEQUENCE: 352

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Lys Ser Val Ser Thr Ser
                20                  25                  30

Gly Tyr Val Tyr Met His Trp Asn Gln Gln Lys Pro Gly Gln Pro Pro
            35                  40                  45

Arg Leu Leu Ile Tyr Leu Ala Ser Tyr Leu Glu Ser Gly Ile Pro Ala
        50                  55                  60

Arg Phe Ser Gly Ser Gly Ser Gly Thr Asp Phe Thr Leu Thr Ile Ser
 65                 70                  75                  80

Arg Val Glu Glu Glu Asp Ala Ala Val Tyr Tyr Cys Gln His Ser Arg
                85                  90                  95

Asp Leu Thr Phe Pro Phe Gly Gly Gly Thr Lys Leu Glu Ile Lys
                100                 105                 110
```

<210> SEQ ID NO 353
<211> LENGTH: 111
<212> TYPE: PRT
<213> ORGANISM: Artificial Sequence
<220> FEATURE:
<223> OTHER INFORMATION: hz5H23v1-39

<400> SEQUENCE: 353

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Ser Val Ser Thr Ser
                20                  25                  30

Gly Tyr Val Tyr Met His Trp Tyr Gln Gln Lys Pro Gly Lys Ala Pro
            35                  40                  45

Lys Leu Leu Ile Tyr Leu Ala Ser Tyr Leu Glu Ser Gly Val Pro Ser
        50                  55                  60

Arg Phe Ser Gly Ser Gly Ser Gly Thr Asp Phe Thr Leu Thr Ile Ser
 65                 70                  75                  80

Ser Leu Gln Pro Glu Asp Phe Ala Thr Tyr Tyr Cys Gln His Ser Arg
                85                  90                  95

Asp Leu Thr Phe Pro Phe Gly Gly Gly Thr Lys Leu Glu Ile Lys
                100                 105                 110
```

<210> SEQ ID NO 354
<211> LENGTH: 111
<212> TYPE: PRT
<213> ORGANISM: Artificial Sequence
<220> FEATURE:
<223> OTHER INFORMATION: hz5H23v3-20

<400> SEQUENCE: 354

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Lys Ser Val Ser Thr Ser
                20                  25                  30

Gly Tyr Val Tyr Met His Trp Tyr Gln Gln Lys Pro Gly Gln Ala Pro
            35                  40                  45

Arg Leu Leu Ile Tyr Leu Ala Ser Tyr Leu Glu Ser Gly Ile Pro Ala
        50                  55                  60

Arg Phe Ser Gly Ser Gly Ser Gly Thr Asp Phe Thr Leu Thr Ile Ser
 65                 70                  75                  80

Arg Leu Glu Pro Glu Asp Phe Ala Val Tyr Tyr Cys Gln His Ser Arg
                85                  90                  95

Asp Leu Thr Phe Pro Phe Gly Gly Gly Thr Lys Leu Glu Ile Lys
                100                 105                 110
```

<210> SEQ ID NO 355
<211> LENGTH: 111
<212> TYPE: PRT
<213> ORGANISM: Artificial Sequence
<220> FEATURE:
<223> OTHER INFORMATION: hz5H23v4-1

<400> SEQUENCE: 355

```
Asp Ile Val Met Thr Gln Ser Pro Asp Ser Leu Ala Val Ser Leu Gly
1               5                   10                  15
Glu Arg Ala Thr Ile Asn Cys Arg Ala Ser Lys Ser Val Ser Thr Ser
            20                  25                  30
Gly Tyr Val Tyr Met His Trp Tyr Gln Gln Lys Pro Gly Gln Pro Pro
        35                  40                  45
Lys Leu Leu Ile Tyr Leu Ala Ser Tyr Leu Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln His Ser Arg
                85                  90                  95
Asp Leu Thr Phe Pro Phe Gly Gly Gly Thr Lys Leu Glu Ile Lys
            100                 105                 110
```

<210> SEQ ID NO 356
<211> LENGTH: 1043
<212> TYPE: PRT
<213> ORGANISM: Rattus
<220> FEATURE:
<223> OTHER INFORMATION: Rat beta klotho

<400> SEQUENCE: 356

```
Met Lys Thr Gly Cys Ala Ala Gly Ser Pro Gly Asn Glu Trp Val Phe
1               5                   10                  15
Phe Ser Ser Asp Glu Arg Ser Thr Arg Ser Arg Lys Thr Met Ser Asn
            20                  25                  30
Gly Ala Leu Gln Arg Ser Ala Val Leu Ser Ala Leu Val Leu Leu Arg
        35                  40                  45
Ala Val Thr Gly Phe Ser Gly Asp Gly Lys Ala Ile Trp Asp Lys Lys
    50                  55                  60
Gln Tyr Val Ser Pro Val Asn Pro Gly Gln Leu Phe Leu Tyr Asp Thr
65                  70                  75                  80
Phe Pro Lys Asn Phe Ser Trp Gly Val Gly Thr Gly Ala Phe Gln Val
                85                  90                  95
Glu Gly Ser Trp Lys Ala Asp Gly Arg Gly Pro Ser Ile Trp Asp Arg
            100                 105                 110
Tyr Val Asp Ser His Leu Arg Gly Val Asn Ser Thr Asp Arg Ser Thr
        115                 120                 125
Asp Ser Tyr Val Phe Leu Glu Lys Asp Leu Leu Ala Leu Asp Phe Leu
    130                 135                 140
Gly Val Ser Phe Tyr Gln Phe Ser Ile Ser Trp Pro Arg Leu Phe Pro
145                 150                 155                 160
Asn Gly Thr Val Ala Ala Val Asn Ala Lys Gly Leu Gln Tyr Tyr Arg
                165                 170                 175
Ala Leu Leu Asp Ser Leu Val Leu Arg Asn Ile Glu Pro Ile Val Thr
            180                 185                 190
Leu Tyr His Trp Asp Leu Pro Leu Thr Leu Gln Glu Glu Tyr Gly Gly
```

-continued

```
            195                 200                 205
Trp Lys Asn Ala Thr Met Ile Asp Leu Phe Asn Asp Tyr Ala Thr Tyr
210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                    245                 250                 255

Pro Gly Glu Lys Gly Asn Leu Thr Ala Val Tyr Thr Val Gly His Asn
                260                 265                 270

Leu Ile Lys Ala His Ser Lys Val Trp His Asn Tyr Asp Lys Asn Phe
            275                 280                 285

Arg Pro His Gln Lys Gly Trp Leu Ser Ile Thr Leu Gly Ser His Trp
        290                 295                 300

Ile Glu Pro Asn Arg Thr Glu Asn Met Glu Asp Val Ile Asn Cys Gln
305                 310                 315                 320

His Ser Met Ser Ser Val Leu Gly Trp Phe Ala Asn Pro Ile His Gly
                    325                 330                 335

Asp Gly Asp Tyr Pro Glu Phe Met Lys Thr Ser Ser Val Ile Pro Glu
                340                 345                 350

Phe Ser Glu Ala Glu Lys Glu Val Arg Gly Thr Ala Asp Phe Phe
            355                 360                 365

Ala Phe Ser Phe Gly Pro Asn Asn Phe Arg Pro Ser Asn Thr Val Val
        370                 375                 380

Lys Met Gly Gln Asn Val Ser Leu Asn Leu Arg Gln Val Leu Asn Trp
385                 390                 395                 400

Ile Lys Leu Glu Tyr Asp Asn Pro Arg Ile Leu Ile Ser Glu Asn Gly
                    405                 410                 415

Trp Phe Thr Asp Ser Tyr Ile Lys Thr Glu Asp Thr Thr Ala Ile Tyr
                420                 425                 430

Met Met Lys Asn Phe Leu Asn Gln Val Leu Gln Ala Ile Lys Phe Asp
            435                 440                 445

Glu Ile Gln Val Phe Gly Tyr Thr Ala Trp Thr Leu Leu Asp Gly Phe
        450                 455                 460

Glu Trp Gln Asp Ala Tyr Thr Thr Arg Arg Gly Leu Phe Tyr Val Asp
465                 470                 475                 480

Phe Asn Ser Glu Gln Lys Glu Arg Lys Pro Lys Ser Ser Ala His Tyr
                    485                 490                 495

Tyr Lys Gln Ile Ile Gln Asp Asn Gly Phe Pro Leu Gln Glu Ser Thr
                500                 505                 510

Pro Asp Met Lys Gly Gln Phe Pro Cys Asp Phe Ser Trp Gly Val Thr
            515                 520                 525

Glu Ser Val Leu Lys Pro Glu Phe Thr Val Ser Ser Pro Gln Phe Thr
        530                 535                 540

Asp Pro His Leu Tyr Val Trp Asn Val Thr Gly Asn Arg Leu Leu Tyr
545                 550                 555                 560

Arg Val Glu Gly Val Arg Leu Lys Thr Arg Pro Ser Gln Cys Thr Asp
                    565                 570                 575

Tyr Val Ser Ile Lys Lys Arg Val Glu Met Leu Ala Lys Met Lys Val
                580                 585                 590

Thr His Tyr Gln Phe Ala Leu Asp Trp Thr Ser Ile Leu Pro Thr Gly
            595                 600                 605

Asn Leu Ser Lys Ile Asn Arg Gln Val Leu Arg Tyr Tyr Arg Cys Val
        610                 615                 620
```

```
Val Ser Glu Gly Leu Lys Leu Gly Ile Ser Pro Met Val Thr Leu Tyr
625                 630                 635                 640

His Pro Thr His Ser His Leu Gly Leu Pro Met Pro Leu Leu Ser Ser
            645                 650                 655

Gly Gly Trp Leu Asn Thr Asn Thr Ala Lys Ala Phe Gln Asp Tyr Ala
            660                 665                 670

Gly Leu Cys Phe Lys Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
            725                 730                 735

Ser Leu Ser Leu His Ser Asp Trp Ala Glu Pro Ala Asn Pro Tyr Val
            740                 745                 750

Glu Ser His Trp Lys Ala Ala Glu Arg Phe Leu Gln Phe Glu Ile Ala
            755                 760                 765

Trp Phe Ala Asp Pro Leu Phe Lys Thr Gly Asp Tyr Pro Leu Ala Met
770                 775                 780

Lys Glu Tyr Ile Ala Ser Lys Lys Gln Arg Gly Leu Ser Ser Ser Val
785                 790                 795                 800

Leu Pro Arg Phe Thr Leu Lys Glu Ser Arg Leu Val Lys Gly Thr Ile
            805                 810                 815

Asp Phe Tyr Ala Leu Asn His Phe Thr Thr Arg Phe Val Ile His Lys
            820                 825                 830

Gln Leu Asn Thr Asn Cys Ser Val Ala Asp Arg Asp Val Gln Phe Leu
            835                 840                 845

Gln Asp Ile Thr Arg Leu Ser Ser Pro Ser Arg Leu Ala Val Thr Pro
850                 855                 860

Trp Gly Met Arg Lys Leu Leu Gly Trp Ile Arg Arg Asn Tyr Arg Asp
865                 870                 875                 880

Met Asp Ile Tyr Val Thr Ala Asn Gly Ile Asp Asp Leu Ala Leu Glu
            885                 890                 895

Asp Asp Gln Ile Arg Lys Tyr Tyr Leu Glu Lys Tyr Val Gln Glu Ala
            900                 905                 910

Leu Lys Ala Tyr Leu Ile Asp Lys Val Lys Ile Lys Gly Tyr Tyr Ala
            915                 920                 925

Phe Lys Leu Thr Glu Glu Lys Ser Lys Pro Arg Phe Gly Phe Phe Thr
            930                 935                 940

Ser Asp Phe Lys Ala Lys Ser Ser Val Gln Phe Tyr Ser Lys Leu Ile
945                 950                 955                 960

Ser Ser Ser Gly Phe Ser Ser Glu Asn Arg Ser Pro Ala Cys Gly Gln
            965                 970                 975

Pro Pro Glu Asp Thr Glu Cys Ala Ile Cys Ser Phe Leu Thr Gln Lys
            980                 985                 990

Lys Pro Leu Ile Phe Phe Gly Cys Cys Phe Ile Ser Thr Leu Ala Ala
            995                 1000                1005

Leu Leu Ser Ile Thr Ile Phe His His Arg Lys Arg Lys Phe Gln
      1010                1015                1020

Lys Ala Arg Asn Leu Gln Asn Ile Pro Leu Lys Lys Gly His Ser Arg
1025                1030                1035                1040
```

Val Phe Ser

<210> SEQ ID NO 357
<211> LENGTH: 3132
<212> TYPE: DNA
<213> ORGANISM: Rattus
<220> FEATURE:
<223> OTHER INFORMATION: Rat beta klotho

<400> SEQUENCE: 357

```
atgaagacag gctgtgcagc agggtctcca gggaatgaat gggttttctt cagctctgat      60
gaaagaagca cacgctctag gaaaacaatg tccaacggag cactgcaaag atctgccgtg     120
ctgtctgcat tggttctgct gcgagctgtt accggcttct ctggagacgg aaaagcaata     180
tgggataaaa acaatacgt gagtccggta acccaggtc agctgttcct ctatgacact       240
ttccctaaaa acttttcctg gggcgttggg accggagcat tcaagtgga agggagttgg     300
aaggcagatg aagaggacc ctcgatctgg gaccgttatg tcgactcaca cctgagaggt      360
gtcaacagca cagacagatc cactgacagt tatgtctttc tggaaaagga cttgctggct    420
ctggattttt taggagtttc tttttatcag ttctcaatct cctggccgcg gttgttcccc     480
aacgaaacag tagcagctgt gaatgcaaaa ggtctccagt actacagagc acttctggac    540
tcgctggtac ttaggaatat cgaacccatt gttaccttat accattggga tttgcctttg    600
acgctacagg aagaatatgg gggctggaaa aatgcaacta tgatagatct cttcaatgac    660
tatgccacat actgcttcca gacctttgga gaccgtgtca atattggat tacaattcac     720
aacccttacc tcgttgcttg catgggtttt ggcacaggta tgcatgcgcc aggagagaag    780
ggaaatttaa cagctgtcta cactgtggga cacaacctga tcaaggcgca ttcgaaagtg    840
tggcataact acgacaaaaa cttccgcccct catcagaagg gttggctctc catcaccttg    900
gggtcccatt ggatagaacc aaacagaaca gaaaacatgg aggacgtgat caactgccag    960
cactccatgt cttctgtgct cggatggttt gccaacccca tccacggaga cggcgactac   1020
cccgagttca tgaagacgag ctccgtaatc cctgagttct ctgaggcaga aggaggag     1080
gtgcggggca ctgctgactt cttttgcctttt tccttcgggc caacaatttt caggccctcg   1140
aacaccgtgg taaaaatggg acaaaatgta tcactcaact taagacaggt gctgaactgg   1200
attaaactag aatatgacaa ccctcgaatc ttgatttcgg agaacggctg gttcacagat    1260
agttatataa agacggaaga taccacggcc atctacatga tgaagaattt cctcaaccag   1320
gttcttcaag caataaagtt tgatgaaata caagtgtttg ttatacggc ttggactctc     1380
ctggatggct ttgagtggca ggatgcctac acgacccgac gagggctgtt ttatgtggac    1440
tttaatagtg agcagaaaga gaggaaaccc aagtcctccg ctcattacta caaacagatt    1500
atacaagaca acggttttcc tttgcaagaa tccacaccag acatgaaggg tcagttttcc    1560
tgtgacttct cctggggagt cactgagtct gttcttaagc cggagtttac ggtgtcctcc    1620
ccacagttta ctgatcctca cctgtatgtg tggaatgtca ctggcaacag attgctatac    1680
cgagtggaag gagtcaggct aaaaacaaga ccgtcccaat gcacagatta tgtgagcatc    1740
aaaaaacgag ttgaaatgtt ggccaaaatg aaagtcaccc actaccagtt tgctctggac    1800
tggacctcta tcctccctac cggaaatctg tctaaaatta atagacaagt gttgaggtac    1860
tataggtgtg tggtgagcga aggactgaag ctgggcatct cccctatggt gacgttgtac    1920
cacccgaccc actcccatct aggcctcccc atgccacttt tgagcagtgg gggatggcta    1980
aacaccaaca cagccaaggc cttccaggac tacgcaggcc tgtgcttcaa ggagctgggg   2040
```

```
gacttggtaa agctctggat caccatcaat gaacccaata ggctgagtga catgtacaac    2100
cgcacgagta acgacaccta ccgtgcggcc cacaacctga tgatcgccca tgcccaggtc    2160
tggcacctct atgataggca gtataggccg gtccagcacg gggctgtgtc gctgtcctta    2220
cattccgact gggcagaacc tgccaacccc tatgtggagt ctcactggaa ggcagccgag    2280
cgcttcctcc agtttgagat cgcctggttt gcggatccac tcttcaagac tggtgactac    2340
ccgctggcca tgaaggaata catcgcctcc aagaagcagc gagggctgtc tagctcagtc    2400
ctgccgcgct ttaccttgaa ggagagcagg ctggtgaagg ggaccatcga cttttacgca    2460
ctgaaccact tcactactag attcgtgata cacaagcagt tgaataccaa ctgctcagtg    2520
gcagacaggg acgtccagtt cctgcaggac atcacccgcc tgagctcgcc cagtcgccta    2580
gccgtaacgc cctggggaat gcgcaagctc cttgggtgga tccggaggaa ctacagagac    2640
atggatatct acgtcacagc caatggcatt gatgatcttg ctctagagga cgatcagatt    2700
agaaagtact acttggagaa gtacgtccag gaggctctga agcatatct gattgacaag    2760 gtcaaaatca aggctacta tgcattcaaa ctgactgaag agaaatctaa gcctagattt    2820
ggatttttca catctgactt caaagctaaa tcttctgtac agttttatag caagctgatc    2880
agcagcagcg gcttctcctc tgagaacaga agtcctgcct gtggtcagcc tccagaagac    2940
acagaatgcg ccatttgctc cttccttaca cagaagaaac cactcatctt ctttggttgt    3000
tgcttcatct ccactctggc tgcactgcta tcaatcacta ttttttcatca tcggaagaga    3060 agaaaattcc agaaagcaag gaacttacaa aatataccat tgaagaaagg gcacagcaga    3120 gttttttagct aa                                                      3132
```

<210> SEQ ID NO 358
<211> LENGTH: 472
<212> TYPE: PRT
<213> ORGANISM: Artificial Sequence
<220> FEATURE:
<223> OTHER INFORMATION: Heavy Chain SEQ ID NO: 32 in U.S. Publication
      US20110135657

<400> SEQUENCE: 358

```
Met Asp Met Arg Val Pro Ala Gln Leu Leu Gly Leu Leu Leu Leu Trp
1               5                   10                  15

Leu Arg Gly Ala Arg Cys Gln Val Thr Leu Lys Glu Ser Gly Pro Val
            20                  25                  30

Leu Val Lys Pro Thr Glu Thr Leu Thr Leu Thr Cys Thr Val Ser Gly
        35                  40                  45

Phe Ser Leu Asn Asn Ala Arg Met Gly Val Ser Trp Ile Arg Gln Pro
    50                  55                  60

Pro Gly Lys Ala Leu Glu Trp Leu Ala His Ile Phe Ser Asn Asp Glu
65                  70                  75                  80

Lys Ser Tyr Ser Thr Ser Leu Lys Ser Arg Leu Thr Ile Ser Lys Asp
                85                  90                  95

Thr Ser Lys Ser Gln Val Val Leu Ile Met Thr Asn Met Asp Pro Val
            100                 105                 110

Asp Thr Ala Thr Tyr Tyr Cys Ala Arg Ser Val Thr Gly Gly Tyr
        115                 120                 125

Tyr Tyr Asp Gly Met Asp Val Trp Gly Gln Gly Thr Thr Val Thr Val
    130                 135                 140

Ser Ser Ala Ser Thr Lys Gly Pro Ser Val Phe Pro Leu Ala Pro Cys
145                 150                 155                 160
```

```
Ser Arg Ser Thr Ser Glu Ser Thr Ala Ala Leu Gly Cys Leu Val Lys
            165                 170                 175

Asp Tyr Phe Pro Glu Pro Val Thr Val Ser Trp Asn Ser Gly Ala Leu
        180                 185                 190

Thr Ser Gly Val His Thr Phe Pro Ala Val Leu Gln Ser Ser Gly Leu
    195                 200                 205

Tyr Ser Leu Ser Ser Val Val Thr Val Pro Ser Ser Asn Phe Gly Thr
210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
            245                 250                 255

Ala Pro Pro Val Ala Gly Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285

Val Asp Val Ser His Glu Asp Pro Glu Val Gln Phe Asn Trp Tyr Val
290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
            325                 330                 335

Asp Trp Leu Asn Gly Lys Glu Tyr Lys Cys Lys Val Ser Asn Lys Gly
        340                 345                 350

Leu Pro Ala Pro Ile Glu Lys Thr Ile Ser Lys Thr Lys Gly Gln Pro
    355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Met Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Lys
465                 470
```

<210> SEQ ID NO 359
<211> LENGTH: 1419
<212> TYPE: DNA
<213> ORGANISM: Artificial Sequence
<220> FEATURE:
<223> OTHER INFORMATION: Coding sequence of Heavy Chain SEQ ID NO: 32
      in U.S. Publication US20110135657

<400> SEQUENCE: 359
atggacatga gggtccccgc tcagctcctg gggctcctgc tactctggct ccgaggtgcc      60
agatgtcagg tgacgctgaa agagtccgga ccggtcctgg tgaaaccaac tgaaacccta     120
actctcacgt gcactgtcag cggcttctct ctcaacaacg caagaatggg tgtgtcttgg     180
atcagacagc caccaggtaa agcgcttgag tggctggcac acatcttctc caacgatgag     240

-continued

```
aagagctact ctaccagcct caagtctcgt ctgaccatca gtaaagatac gtccaagtcc      300
caagtagtcc tcatcatgac taacatggac cccgtggata ccgcgaccta ctactgtgcg      360
aggagcgtcg tgaccggtgg ctactactac gacggcatgg atgtgtgggg tcagggtacg      420
acggtgaccg tcagcagcgc gagcaccaag ggtccgtccg tgtttccgct cgcccttgt       480 agccggagca cctcagagtc tactgccgca ctaggctgcc tggtgaagga ctacttccct      540
gaacccgtga cagtgagctg gaactccgga gcactgacta cggcgtgca caccttcccc      600 gctgtcttgc agtctagcgg cctgtattcg ctctccagcg tggtcactgt accgtccagc     660
aatttcggaa cccagaccta cacatgtaac gtcgatcata accgtccaa cactaaggta      720 gacaaaaccg tggaaaggaa atgctgcgtg gagtgtcccc cctgcccagc tccgccagtg     780
gcaggcccca gcgtgttcct gttcccccca aagccaaaag acaccctgat gatctcgaga    840 accccgagg tgacttgcgt cgtcgtcgat gtctcccatg aggatccaga agtacagttc     900
aactggtacg tggacggcgt ggaagtgcac aatgcaaaaa cgaagcccg agaagagcag     960 ttcaactcca cattccgggt ggtatcagtc ctgactgtgg tccaccagga ttggctgaac    1020
gggaaggaat acaaatgtaa agtgagcaat aagggtctgc ccgcaccgat cgagaaaact    1080
atctcaaaaa ctaagggtca gcctcgcgag cctcaagtgt atacgctgcc gccaagtagg    1140
gaggagatga ccaaaaacca ggtgtcactg acatgtctgg tgaaaggctt ctaccccagc    1200
gacatcgccg tggagtggga gtcaaatggc cagccggaga caactacaa gaccacaccg     1260 ccgatgctgg actcagacgg gtccttttc ctctattcca agctcaccgt cgacaaaagc     1320
cgttggcagc agggaaacgt attctcatgc tctgtgatgc acgaggccct tcacaaccat    1380
tacactcaga aatcgttgtc cctttctccc ggaaaatga                            1419
```

<210> SEQ ID NO 360
<211> LENGTH: 236
<212> TYPE: PRT
<213> ORGANISM: Artificial Sequence
<220> FEATURE:
<223> OTHER INFORMATION: Light Chain SEQ ID No: 14 in U.S. Publication
    US20110135657

<400> SEQUENCE: 360

```
Met Asp Met Arg Val Pro Ala Gln Leu Leu Gly Leu Leu Leu Leu Trp
1               5                   10                  15

Leu Arg Gly Ala Arg Cys Ser Tyr Val Leu Thr Gln Pro Pro Ser Val
            20                  25                  30

Ser Val Ala Pro Gly Gln Thr Ala Arg Ile Thr Cys Gly Gly Asn Asn
        35                  40                  45

Ile Gly Ser Glu Ser Val His Trp Tyr Gln Gln Lys Pro Gly Gln Ala
    50                  55                  60

Pro Val Leu Val Val Tyr Asp Asp Ser Asp Arg Pro Ser Gly Ile Pro
65                  70                  75                  80

Glu Arg Phe Ser Gly Ser Asn Ser Gly Asn Thr Ala Thr Leu Thr Ile
                85                  90                  95

Ser Arg Val Glu Ala Gly Asp Glu Ala Asp Tyr Tyr Cys Gln Val Trp
            100                 105                 110

Asp Gly Asn Ser Asp His Val Val Phe Gly Gly Gly Thr Lys Leu Thr
        115                 120                 125

Val Leu Gly Gln Pro Lys Ala Asn Pro Thr Val Thr Leu Phe Pro Pro
    130                 135                 140
```

| Ser | Ser | Glu | Glu | Leu | Gln | Ala | Asn | Lys | Ala | Thr | Leu | Val | Cys | Leu | Ile |
| 145 | | | | 150 | | | | | 155 | | | | | 160 | |

Ser Asp Phe Tyr Pro Gly Ala Val Thr Val Ala Trp Lys Ala Asp Gly
            165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
        210                 215                 220

Thr Val Glu Lys Thr Val Ala Pro Thr Glu Cys Ser
225                 230                 235

<210> SEQ ID NO 361
<211> LENGTH: 711
<212> TYPE: DNA
<213> ORGANISM: Artificial Sequence
<220> FEATURE:
<223> OTHER INFORMATION: Coding sequence for Light Chain SEQ ID No: 14
      in U.S. Publication US20110135657

<400> SEQUENCE: 361

```
atggacatga gggtccccgc tcagctcctg ggctcctgc tactctggct ccgaggtgcc      60
agatgttcat acgtgctgac tcagccccca tccgtgtctg tggcacccgg acaaactgcc    120
aggatcactt gcggagggaa taacatcggt agcgagagcg tccactggta ccagcaaaaa    180
ccaggccagg caccggtcct cgtggtatac gacgattctg accgaccgtc cggcatccca    240
gaaagattct cgggtagcaa ctctggcaac acggctaccc tgaccatcag ccgtgtcgag    300
gccggtgacg aggcggatta ctactgccag gtgtgggacg ggaactccga tcatgtggtg    360
ttcggcggag gcactaagct gaccgtattg ggtcagccca agcaaatcc accgtgacg      420
ctctttcccc ctagctccga ggagctgcag gcgaacaagg caactcttgt ctgtctcatc    480
tcggacttct atccgggagc ggtgaccgtc gcatggaaag cagatggttc tccggtcaaa    540
gcaggcgtgg aaacgaccaa gccttccaaa cagagtaaca acaagtatgc tgccagctcc    600
tacctaagcc tgacaccgga gcagtggaag agccaccggt catacagctg ccaggtaact    660
catgaaggct aacagtgga gaaaaccgtg gcgccaaccg agtgttcctg a             711
```

<210> SEQ ID NO 362
<211> LENGTH: 98
<212> TYPE: PRT
<213> ORGANISM: Artificial Sequence
<220> FEATURE:
<223> OTHER INFORMATION: IGHV1-3

<400> SEQUENCE: 362

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys

```
                85                  90                  95

Ala Arg

<210> SEQ ID NO 363
<211> LENGTH: 98
<212> TYPE: PRT
<213> ORGANISM: Artificial Sequence
<220> FEATURE:
<223> OTHER INFORMATION: IGHV1-18

<400> SEQUENCE: 363

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 364
<211> LENGTH: 98
<212> TYPE: PRT
<213> ORGANISM: Artificial Sequence
<220> FEATURE:
<223> OTHER INFORMATION: IGHV1-46

<400> SEQUENCE: 364

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 365
<211> LENGTH: 98
<212> TYPE: PRT
<213> ORGANISM: Artificial Sequence
<220> FEATURE:
<223> OTHER INFORMATION: IGHV1-69

<400> SEQUENCE: 365

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
                20                  25                  30
```

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 366
<211> LENGTH: 121
<212> TYPE: PRT
<213> ORGANISM: Artificial Sequence
<220> FEATURE:
<223> OTHER INFORMATION: U00583

<400> SEQUENCE: 366

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Ile Leu Thr Gly Leu Asn Trp Phe Asp Pro Trp Gly
            100                 105                 110

Gln Gly Thr Leu Val Thr Val Ser Ser
        115                 120

<210> SEQ ID NO 367
<211> LENGTH: 101
<212> TYPE: PRT
<213> ORGANISM: Artificial Sequence
<220> FEATURE:
<223> OTHER INFORMATION: IGKV4-1

<400> SEQUENCE: 367

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

```
<210> SEQ ID NO 368
<211> LENGTH: 95
<212> TYPE: PRT
<213> ORGANISM: Artificial Sequence
<220> FEATURE:
<223> OTHER INFORMATION: IGKV1-39

<400> SEQUENCE: 368

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 369
<211> LENGTH: 90
<212> TYPE: PRT
<213> ORGANISM: Artificial Sequence
<220> FEATURE:
<223> OTHER INFORMATION: IGKV3-20

<400> SEQUENCE: 369

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Ala Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln
                85                  90

<210> SEQ ID NO 370
<211> LENGTH: 450
<212> TYPE: PRT
<213> ORGANISM: Artificial Sequence
<220> FEATURE:
<223> OTHER INFORMATION: hIgK-5H23(VH)-hIgG1(E233A)(L235A) (5H23
      chimera)

<400> SEQUENCE: 370

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60
```

```
Lys Gly Lys Ala Thr Leu Thr Ala Asp Lys Ser Ser Arg Thr Ala Tyr
 65                  70                  75                  80

Met Gln Leu Ser Ser Leu Thr Ser Glu Asn Ser Ala Val Tyr Phe Cys
                 85                  90                  95

Ala Arg Ser Asp Tyr Tyr Gly Ser Arg Ser Phe Ala Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
     210                 215                 220

Lys Thr His Thr Cys Pro Pro Cys Pro Ala Pro Ala Leu Ala Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

Gly Lys
    450

<210> SEQ ID NO 371
<211> LENGTH: 1419
```

<212> TYPE: DNA
<213> ORGANISM: Artificial Sequence
<220> FEATURE:
<223> OTHER INFORMATION: Coding sequence of hIgK-5H23(VH)-hIgG1(E233A)
      (L235A) (5H23 chimera)

<400> SEQUENCE: 371

```
atggacatga gggtccccgc tcagctcctg gggctcctgc tactctggct ccgaggtgcc    60
agatgtcaag tgcaacttca acagtcaggc ccagaactcg tcaaacccgg agcactcgtg   120
aagatctcgt gcaaggcgtc gggttacact ttcacgtcct acgacatcaa ttgggtgaag   180
cagaggcctg acagggcctg gagtggattg gatggatctt accgggggga tgggtctacc   240
aagtacaacg aaaagttcaa aggcaaagcc actctgaccg cagacaagag cagcagaacc   300
gcgtacatgc agttgtcatc cctgaccagc gagaactcgg ccgtctactt ttgtgctcgc   360
tccgattact atggatcccg gagcttcgcc tactggggac agggaactct ggtgactgtg   420
tcatcggcta gcaccaaggg cccatcggtc ttccccctgg cacccctcct caagagcacc   480
tctgggggca gcgcggccct gggctgcctg gtcaaggact acttccccga accggtgacg   540
gtgtcgtgga actcaggcgc cctgaccagc ggcgtgcaca ccttcccggc tgtcctacag   600
tcctcaggac tctactccct cagcagcgtg gtgaccgtgc cctccagcag cttgggcacc   660
cagacctaca tctgcaacgt gaatcacaag cccagcaaca ccaaggtgga caagaaagtt   720
gagcccaaat cttgtgacaa aactcacaca tgcccaccgt gcccagcacc tgcactcgcg   780
gggggaccgt cagtcttcct cttccccca aaacccaagg acaccctcat gatctcccgg   840
accccctgagg tcacatgcgt ggtggtggac gtgagccacg aagaccctga ggtcaagttc   900
aactggtacg tggacggcgt ggaggtgcat aatgccaaga caaagccgcg ggaggagcag   960
tacaacagca cgtaccgtgt ggtcagcgtc ctcaccgtcc tgcaccagga ctggctgaat  1020
ggcaaggagt acaagtgcaa ggtctccaac aaagccctcc cagcccccat cgagaaaacc  1080
atctccaaag ccaaagggca gccccgagaa ccacaggtgt acaccctgcc cccatcccgg  1140
gaggagatga ccaagaacca ggtcagcctg acctgcctgg tcaaaggctt ctatcccagc  1200
gacatcgccg tggagtggga gagcaatggg cagccggaga caactacaa gaccacgcct  1260
cccgtgctgg actccgacgg ctccttcttc ctctacagca agctcaccgt ggacaagagc  1320
aggtggcagc aggggaacgt cttctcatgc tccgtgatgc atgaggctct gcacaaccac  1380
tacacgcaga agagcctctc cctgtctccg ggtaaatga                         1419
```

<210> SEQ ID NO 372
<211> LENGTH: 218
<212> TYPE: PRT
<213> ORGANISM: Artificial Sequence
<220> FEATURE:
<223> OTHER INFORMATION: hIgK-5H23(VL)-hIgK (5H23 chimera)

<400> SEQUENCE: 372

```
Asp Ile Val Leu Thr Gln Ser Pro Ala Ser Leu Ala Val Ser Leu Gly
  1               5                  10                  15

Gln Arg Ala Thr Ile Ser Cys Arg Ala Ser Lys Ser Val Ser Thr Ser
             20                  25                  30

Gly Tyr Val Tyr Met His Trp Asn Gln Gln Lys Pro Gly Gln Pro Pro
         35                  40                  45

Lys Leu Leu Ile Tyr Leu Ala Ser Tyr Leu Glu Ser Gly Val Pro Ala
     50                  55                  60

Arg Phe Ser Gly Ser Gly Ser Gly Thr Asp Phe Thr Leu Asn Ile His
```

```
                65                  70                  75                  80
Pro Val Glu Glu Glu Asp Ala Ala Ile Tyr Tyr Cys Gln His Ser Arg
                    85                  90                  95

Asp Leu Thr Phe Pro Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 373
<211> LENGTH: 723
<212> TYPE: DNA
<213> ORGANISM: Artificial Sequence
<220> FEATURE:
<223> OTHER INFORMATION: Coding sequence of hIgK-5H23(VL)-hIgK (5H23
      chimera)

<400> SEQUENCE: 373
atggacatga gggtccccgc tcagctcctg gggctcctgc tactctggct ccgaggtgcc      60
agatgtgaca tcgtcctgac tcagagcccc gcatccctcg ccgtgtcact tggtcaaaga    120
gctaccattt cctgccgcgc atcgaagtct gtgagcactt ccggctacgt ctacatgcac    180
tggaaccagc agaagccagg acaaccgccg aagctgctga tctatctcgc gtcataccta    240
gaatcgggag tgccggcgag ttttcgggga tcgggctccg gaaccgactt caccctgaat    300
atccatccag tggaagagga ggatgccgcc atctactact gtcagcacag ccgggatctc    360
actttccctt tcggcggagg gacgaaattg gaaatcaaac gtacggtggc tgcaccatct    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagctcgccc gtcacaaaga gcttcaacag gggagagtgt    720
tag                                                                  723

<210> SEQ ID NO 374
<211> LENGTH: 1045
<212> TYPE: PRT
<213> ORGANISM: Artificial Sequence
<220> FEATURE:
<223> OTHER INFORMATION: human KLB (M1-F508)- mouse KLB (P507-S1043)

<400> SEQUENCE: 374

Met Lys Pro Gly Cys Ala Ala Gly Ser Pro Gly Asn Glu Trp Ile Phe
1               5                   10                  15
```

-continued

```
Phe Ser Thr Asp Glu Ile Thr Thr Arg Tyr Arg Asn Thr Met Ser Asn
             20                  25                  30

Gly Gly Leu Gln Arg Ser Val Ile Leu Ser Ala Leu Ile Leu Leu Arg
         35                  40                  45

Ala Val Thr Gly Phe Ser Gly Asp Gly Arg Ala Ile Trp Ser Lys Asn
 50                  55                  60

Pro Asn Phe Thr Pro Val Asn Glu Ser Gln Leu Phe Leu Tyr Asp Thr
 65                  70                  75                  80

Phe Pro Lys Asn Phe Phe Trp Gly Ile Gly Thr Gly Ala Leu Gln Val
                 85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
```

```
              435                 440                 445
Leu Asp Glu Ile Arg Val Phe Gly Tyr Thr Ala Trp Ser Leu Leu Asp
450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Pro Leu Lys Glu
            500                 505                 510

Ser Thr Pro Asp Met Lys Gly Arg Phe Pro Cys Asp Phe Ser Trp Gly
        515                 520                 525

Val Thr Glu Ser Val Leu Lys Pro Glu Phe Thr Val Ser Ser Pro Gln
    530                 535                 540

Phe Thr Asp Pro His Leu Tyr Val Trp Asn Val Thr Gly Asn Arg Leu
545                 550                 555                 560

Leu Tyr Arg Val Glu Gly Val Arg Leu Lys Thr Arg Pro Ser Gln Cys
                565                 570                 575

Thr Asp Tyr Val Ser Ile Lys Lys Arg Val Glu Met Leu Ala Lys Met
            580                 585                 590

Lys Val Thr His Tyr Gln Phe Ala Leu Asp Trp Thr Ser Ile Leu Pro
        595                 600                 605

Thr Gly Asn Leu Ser Lys Val Asn Arg Gln Val Leu Arg Tyr Tyr Arg
    610                 615                 620

Cys Val Val Ser Glu Gly Leu Lys Leu Gly Val Phe Pro Met Val Thr
625                 630                 635                 640

Leu Tyr His Pro Thr His Ser His Leu Gly Leu Pro Leu Pro Leu Leu
                645                 650                 655

Ser Ser Gly Gly Trp Leu Asn Met Asn Thr Ala Lys Ala Phe Gln Asp
            660                 665                 670

Tyr Ala Glu Leu Cys Phe Arg Glu Leu Gly Asp Leu Val Lys Leu Trp
        675                 680                 685

Ile Thr Ile Asn Glu Pro Asn Arg Leu Ser Asp Met Tyr Asn Arg Thr
    690                 695                 700

Ser Asn Asp Thr Tyr Arg Ala Ala His Asn Leu Met Ile Ala His Ala
705                 710                 715                 720

Gln Val Trp His Leu Tyr Asp Arg Gln Tyr Arg Pro Val Gln His Gly
                725                 730                 735

Ala Val Ser Leu Ser Leu His Cys Asp Trp Ala Glu Pro Ala Asn Pro
            740                 745                 750

Phe Val Asp Ser His Trp Lys Ala Ala Glu Arg Phe Leu Gln Phe Glu
        755                 760                 765

Ile Ala Trp Phe Ala Asp Pro Leu Phe Lys Thr Gly Asp Tyr Pro Ser
    770                 775                 780

Val Met Lys Glu Tyr Ile Ala Ser Lys Asn Gln Arg Gly Leu Ser Ser
785                 790                 795                 800

Ser Val Leu Pro Arg Phe Thr Ala Lys Glu Ser Arg Leu Val Lys Gly
                805                 810                 815

Thr Val Asp Phe Tyr Ala Leu Asn His Phe Thr Thr Arg Phe Val Ile
            820                 825                 830

His Lys Gln Leu Asn Thr Asn Arg Ser Val Ala Asp Arg Asp Val Gln
        835                 840                 845

Phe Leu Gln Asp Ile Thr Arg Leu Ser Ser Pro Ser Arg Leu Ala Val
    850                 855                 860
```

| | | | | | | | | | | | |
|---|---|---|---|---|---|---|---|---|---|---|---|
|Thr|Pro|Trp|Gly|Val|Arg|Lys|Leu|Leu|Ala|Trp|Ile|Arg|Arg|Asn|Tyr
865| | | | |870| | | | |875| | | | |880

Arg Asp Arg Asp Ile Tyr Ile Thr Ala Asn Gly Ile Asp Leu Ala
            885                 890                 895

Leu Glu Asp Asp Gln Ile Arg Lys Tyr Tyr Leu Glu Lys Tyr Val Gln
            900                 905                 910

Glu Ala Leu Lys Ala Tyr Leu Ile Asp Lys Val Lys Ile Lys Gly Tyr
            915                 920                 925

Tyr Ala Phe Lys Leu Thr Glu Glu Lys Ser Lys Pro Arg Phe Gly Phe
930             935                 940

Phe Thr Ser Asp Phe Arg Ala Lys Ser Ser Val Gln Phe Tyr Ser Lys
945             950                 955                 960

Leu Ile Ser Ser Ser Gly Leu Pro Ala Glu Asn Arg Ser Pro Ala Cys
                965                 970                 975

Gly Gln Pro Ala Glu Asp Thr Asp Cys Thr Ile Cys Ser Phe Leu Val
                980                 985                 990

Glu Lys Lys Pro Leu Ile Phe Phe Gly Cys Cys Phe Ile Ser Thr Leu
            995                 1000                1005

Ala Val Leu Leu Ser Ile Thr Val Phe His His Gln Lys Arg Arg Lys
        1010                1015                1020

Phe Gln Lys Ala Arg Asn Leu Gln Asn Ile Pro Leu Lys Lys Gly His
1025                1030                1035                1040

Ser Arg Val Phe Ser
                1045

<210> SEQ ID NO 375
<211> LENGTH: 3138
<212> TYPE: DNA
<213> ORGANISM: Artificial Sequence
<220> FEATURE:
<223> OTHER INFORMATION: Coding sequence of human KLB (M1-F508)- mouse
      KLB (P507-S1043)

<400> SEQUENCE: 375
atgaagccag gctgtgcggc aggatctcca gggaatgaat ggatttctt cagcactgat      60 gaaataacca cacgctatag aatacaatg tccaacgggg gattgcaaag atctgtcatc     120
ctgtcagcac ttattctgct acgagctgtt actggattct ctggagatgg aagagctata     180
tggtctaaaa atcctaattt tactccggta atgaaagtc agctgtttct ctatgacact      240
ttccctaaaa acttttttctg gggtattggg actggagcat gcaagtgga agggagttgg     300 aagaaggatg gaaaaggacc ttctatatgg gatcatttca tccacacaca ccttaaaaat     360
gtcagcagca cgaatggttc cagtgacagt tatatttttc tggaaaaaga cttatcagcc     420
ctggatttta taggagtttc ttttttatcaa ttttcaattt cctggccaag gcttttcccc     480
gatggaatag taacagttgc caacgcaaaa ggtctgcagt actacagtac tcttctggac     540
gctctagtgc ttagaaacat tgaacctata gttactttat accactggga tttgcctttg     600
gcactacaag aaaaatatgg ggggtggaaa atgatacca atagatat cttcaatgac       660 tatgccacat actgtttcca gatgtttggg gaccgtgtca atattggat tacaattcac     720 aacccatatc tagtggcttg gcatgggtat gggacaggta tgcatgcccc tggagagaag     780
ggaaatttag cagctgtcta cactgtggga cacaacttga tcaaggctca ctcgaaagtt     840
tggcataact acaacacaca tttccgccca catcagaagg gttggttatc gatcacgttg     900
ggatctcatt ggatcgagcc aaaccggtcg gaaaacacga tggatatatt caatgtcaa      960

```
caatccatgg tttctgtgct tggatggttt gccaacccta tccatgggga tggcgactat    1020
ccagagggga tgagaaagaa gttgttctcc gttctaccca tttctctga agcagagaag     1080 catgagatga gaggcacagc tgatttcttt gccttttctt ttggacccaa caacttcaag    1140
cccctaaaca ccatggctaa aatgggacaa aatgtttcac ttaatttaag agaagcgctg    1200
aactggatta aactggaata caacaaccct cgaatcttga ttgctgagaa tggctggttc    1260
acagacagtc gtgtgaaaac agaagacacc acggccatct acatgatgaa gaatttcctc    1320
agccaggtgc ttcaagcaat aaggttagat gaaatacgag tgtttggtta tactgcctgg    1380
tctctcctgg atggctttga atggcaggat gcttacacca tccgccgagg attattttat    1440
gtggatttta acagtaaaca gaaagagcgg aaacctaagt cttcagcaca ctactacaaa    1500
cagatcatac gagaaaatgg ttttcctttg aaagagtcca cgccagacat gaagggtcgg    1560
ttcccctgtg atttctcttg gggagtcact gagtctgttc ttaagcccga gtttacggtc    1620
tcctccccgc agtttaccga tcctcacctg tatgtgtgga atgtcactgg caacagattg    1680
ctctaccgag tggaaggggt aaggctgaaa acaagaccat cccagtgcac agattatgtg    1740
agcatcaaaa aacgagttga aatgttggca aaaatgaaag tcacccacta ccagtttgct    1800
ctggactgga cctctatcct tcccactggc aatctgtcca agttaacag acaagtgtta     1860 aggtactata ggtgtgtggt gagcgaagga ctgaagctgg gcgtcttccc catggtgacg    1920
ttgtaccacc caacccactc ccatctcggc ctcccctgc cacttctgag cagtgggggg     1980
tggctaaaca tgaacacagc caaggccttc caggactacg ctgagctgtg cttccgggag    2040
ttgggggact tggtgaagct ctggatcacc atcaatgagc ctaacaggct gagtgacatg    2100
tacaaccgca cgagtaatga cacctaccgt gcagcccaca acctgatgat cgcccatgcc    2160
caggtctggc acctctatga taggcagtat aggccggtcc agcatggggc tgtgtcgctg    2220
tccttacatt gcgactgggc agaacctgcc aaccccttg tggattcaca ctggaaggca     2280
gccgagcgct tcctccagtt tgagatcgcc tggtttgcag atccgctctt caagactggc    2340
gactatccat cggttatgaa ggaatacatc gcctccaaga accagcgagg gctgtctagc    2400
tcagtcctgc cgcgcttcac cgcgaaggag agcaggctgg tgaagggtac cgtcgacttc    2460
tacgcactga accacttcac tacgaggttc gtgatacaca gcagctgaa caccaaccgc     2520 tcagttgcag acagggacgt ccagttcctg caggacatca cccgcctaag ctcgcccagc    2580
cgcctggctg taacaccctg gggagtgcgc aagctccttg cgtggatccg gaggaactac    2640
agagacaggg atatctacat cacagccaat ggcatcgatg acctggctct agaggatgat    2700
cagatccgaa agtactactt ggagaagtat gtccaggagg ctctgaaagc atatctcatt    2760
gacaaggtca aaatcaaagg ctactatgca ttcaaactga ctgaagagaa atctaagcct    2820
agatttggat ttttcaccctc tgacttcaga gctaagtcct ctgtccagtt ttacagcaag    2880
ctgatcagca gcagtggcct ccccgctgag aacagaagtc ctgcgtgtgg tcagcctgcg    2940
gaagacacag actgcaccat ttgctcattt ctcgtggaga agaaaccact catcttcttc    3000
ggttgctgct tcatctccac tctggctgta ctgctatcca tcaccgtttt tcatcatcaa    3060
aagagaagaa aattccagaa agcaaggaac ttacaaaata taccattgaa gaaaggccac    3120
agcagagttt tcagctga                                                  3138

<210> SEQ ID NO 376
<211> LENGTH: 1042
<212> TYPE: PRT
```

<213> ORGANISM: Artificial Sequence
<220> FEATURE:
<223> OTHER INFORMATION: Mouse KLB (M1-F506) - human KLB(S509-S1044)

<400> SEQUENCE: 376

```
Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
            20                  25                  30

Arg Ala Leu Gln Arg Ser Ala Val Leu Ser Ala Phe Val Leu Leu Arg
        35                  40                  45

Ala Val Thr Gly Phe Ser Gly Asp Gly Lys Ala Ile Trp Asp Lys Lys
    50                  55                  60

Gln Tyr Val Ser Pro Val Asn Pro Ser Gln Leu Phe Leu Tyr Asp Thr
65              70                  75                  80

Phe Pro Lys Asn Phe Ser Trp Gly Val Gly Thr Gly Ala Phe Gln Val
            85                  90                  95

Glu Gly Ser Trp Lys Thr Asp Gly Arg Gly Pro Ser Ile Trp Asp Arg
        100                 105                 110

Tyr Val Tyr Ser His Leu Arg Gly Val Asn Gly Thr Asp Arg Ser Thr
    115                 120                 125

Asp Ser Tyr Ile Phe Leu Glu Lys Asp Leu Leu Ala Leu Asp Phe Leu
130             135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
            165                 170                 175

Ala Leu Leu Asp Ser Leu Val Leu Arg Asn Ile Glu Pro Ile Val Thr
        180                 185                 190

Leu Tyr His Trp Asp Leu Pro Leu Thr Leu Gln Glu Glu Tyr Gly Gly
    195                 200                 205

Trp Lys Asn Ala Thr Met Ile Asp Leu Phe Asn Asp Tyr Ala Thr Tyr
    210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
            245                 250                 255

Pro Gly Glu Lys Gly Asn Leu Thr Ala Val Tyr Thr Val Gly His Asn
        260                 265                 270

Leu Ile Lys Ala His Ser Lys Val Trp His Asn Tyr Asp Lys Asn Phe
    275                 280                 285

Arg Pro His Gln Lys Gly Trp Leu Ser Ile Thr Leu Gly Ser His Trp
290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
            325                 330                 335

Asp Gly Asp Tyr Pro Glu Phe Met Lys Thr Gly Ala Met Ile Pro Glu
        340                 345                 350

Phe Ser Glu Ala Glu Lys Glu Val Arg Gly Thr Ala Asp Phe Phe
    355                 360                 365

Ala Phe Ser Phe Gly Pro Asn Asn Phe Arg Pro Ser Asn Thr Val Val
    370                 375                 380

Lys Met Gly Gln Asn Val Ser Leu Asn Leu Arg Gln Val Leu Asn Trp
```

```
                385                 390                 395                 400
            Ile Lys Leu Glu Tyr Asp Asp Pro Gln Ile Leu Ile Ser Glu Asn Gly
                            405                 410                 415

Trp Phe Thr Asp Ser Tyr Ile Lys Thr Glu Asp Thr Thr Ala Ile Tyr
                            420                 425                 430

Met Met Lys Asn Phe Leu Asn Gln Val Leu Gln Ala Ile Lys Phe Asp
                            435                 440                 445

Glu Ile Arg Val Phe Gly Tyr Thr Ala Trp Thr Leu Leu Asp Gly Phe
                450                 455                 460

Glu Trp Gln Asp Ala Tyr Thr Thr Arg Gly Leu Phe Tyr Val Asp
            465                 470                 475                 480

Phe Asn Ser Glu Gln Lys Glu Arg Lys Pro Lys Ser Ser Ala His Tyr
                            485                 490                 495

Tyr Lys Gln Ile Ile Gln Asp Asn Gly Phe Ser Leu Lys Glu Ser Thr
                            500                 505                 510

Pro Asp Val Gln Gly Gln Phe Pro Cys Asp Phe Ser Trp Gly Val Thr
                            515                 520                 525

Glu Ser Val Leu Lys Pro Glu Ser Val Ala Ser Ser Pro Gln Phe Ser
                530                 535                 540

Asp Pro His Leu Tyr Val Trp Asn Ala Thr Gly Asn Arg Leu Leu His
            545                 550                 555                 560

Arg Val Glu Gly Val Arg Leu Lys Thr Arg Pro Ala Gln Cys Thr Asp
                            565                 570                 575

Phe Val Asn Ile Lys Lys Gln Leu Glu Met Leu Ala Arg Met Lys Val
                            580                 585                 590

Thr His Tyr Arg Phe Ala Leu Asp Trp Ala Ser Val Leu Pro Thr Gly
                            595                 600                 605

Asn Leu Ser Ala Val Asn Arg Gln Ala Leu Arg Tyr Tyr Arg Cys Val
                            610                 615                 620

Val Ser Glu Gly Leu Lys Leu Gly Ile Ser Ala Met Val Thr Leu Tyr
            625                 630                 635                 640

Tyr Pro Thr His Ala His Leu Gly Leu Pro Glu Pro Leu Leu His Ala
                            645                 650                 655

Asp Gly Trp Leu Asn Pro Ser Thr Ala Glu Ala Phe Gln Ala Tyr Ala
                            660                 665                 670

Gly Leu Cys Phe Gln Glu Leu Gly Asp Leu Val Lys Leu Trp Ile Thr
                            675                 680                 685

Ile Asn Glu Pro Asn Arg Leu Ser Asp Ile Tyr Asn Arg Ser Gly Asn
                690                 695                 700

Asp Thr Tyr Gly Ala Ala His Asn Leu Leu Val Ala His Ala Leu Ala
            705                 710                 715                 720

Trp Arg Leu Tyr Asp Arg Gln Phe Arg Pro Ser Gln Arg Gly Ala Val
                            725                 730                 735

Ser Leu Ser Leu His Ala Asp Trp Ala Glu Pro Ala Asn Pro Tyr Ala
                            740                 745                 750

Asp Ser His Trp Arg Ala Ala Glu Arg Phe Leu Gln Phe Glu Ile Ala
                            755                 760                 765

Trp Phe Ala Glu Pro Leu Phe Lys Thr Gly Asp Tyr Pro Ala Ala Met
                770                 775                 780

Arg Glu Tyr Ile Ala Ser Lys His Arg Gly Leu Ser Ser Ser Ala
            785                 790                 795                 800

Leu Pro Arg Leu Thr Glu Ala Glu Arg Arg Leu Leu Lys Gly Thr Val
                            805                 810                 815
```

-continued

```
Asp Phe Cys Ala Leu Asn His Phe Thr Thr Arg Phe Val Met His Glu
                820                 825                 830
Gln Leu Ala Gly Ser Arg Tyr Asp Ser Asp Arg Asp Ile Gln Phe Leu
            835                 840                 845
Gln Asp Ile Thr Arg Leu Ser Ser Pro Thr Arg Leu Ala Val Ile Pro
        850                 855                 860
Trp Gly Val Arg Lys Leu Leu Arg Trp Val Arg Arg Asn Tyr Gly Asp
865                 870                 875                 880
Met Asp Ile Tyr Ile Thr Ala Ser Gly Ile Asp Asp Gln Ala Leu Glu
                885                 890                 895
Asp Asp Arg Leu Arg Lys Tyr Tyr Leu Gly Lys Tyr Leu Gln Glu Val
            900                 905                 910
Leu Lys Ala Tyr Leu Ile Asp Lys Val Arg Ile Lys Gly Tyr Tyr Ala
        915                 920                 925
Phe Lys Leu Ala Glu Glu Lys Ser Lys Pro Arg Phe Gly Phe Phe Thr
930                 935                 940
Ser Asp Phe Lys Ala Lys Ser Ser Ile Gln Phe Tyr Asn Lys Val Ile
945                 950                 955                 960
Ser Ser Arg Gly Phe Pro Phe Glu Asn Ser Ser Ser Arg Cys Ser Gln
                965                 970                 975
Thr Gln Glu Asn Thr Glu Cys Thr Val Cys Leu Phe Leu Val Gln Lys
            980                 985                 990
Lys Pro Leu Ile Phe Leu Gly Cys Cys Phe Phe Ser Thr Leu Val Leu
        995                 1000                1005
Leu Leu Ser Ile Ala Ile Phe Gln Arg Gln Lys Arg Arg Lys Phe Trp
    1010                1015                1020
Lys Ala Lys Asn Leu Gln His Ile Pro Leu Lys Lys Gly Lys Arg Val
1025                1030                1035                1040
Val Ser
```

```
<210> SEQ ID NO 377
<211> LENGTH: 3129
<212> TYPE: DNA
<213> ORGANISM: Artificial Sequence
<220> FEATURE:
<223> OTHER INFORMATION: Coding sequence of Mouse KLB (M1-F506) - human
      KLB(S509-S1044)

<400> SEQUENCE: 377
```

| | | | | | |
|---|---|---|---|---|---|
| atgaagacag | gctgtgcagc | agggtctccg | gggaatgaat | ggattttctt | cagctctgat | 60 |
| gaaagaaaca | cacgctctag | gaaaacaatg | tccaacaggg | cactgcaaag | atctgccgtg | 120 |
| ctgtctgcgt | tgttctgct | gcgagctgtt | accggcttct | ccggagacgg | aaagcaata | 180 |
| tgggataaaa | aacagtacgt | gagtccggta | aacccaagtc | agctgttcct | ctatgacact | 240 |
| ttccctaaaa | acttttcctg | gggcgttggg | accggagcat | tcaagtgga | agggagttgg | 300 |
| aagacagatg | gaaaggacc | ctcgatctgg | gatcggtacg | tctactcaca | cctgagaggt | 360 |
| gtcaacggca | cagacagatc | cactgacagt | tacatctttc | tggaaaaaga | cttgttggct | 420 |
| ctggattttt | taggagtttc | ttttatcag | ttctcaatct | cctggccacg | gttgtttccc | 480 |
| aatggaacag | tagcagcagt | gaatgcgcaa | ggtctccggt | actaccgtgc | acttctggac | 540 |
| tcgctggtac | ttaggaatat | cgagcccatt | gttaccttgt | accattggga | tttgcctctg | 600 |
| acgtccagg | aagaatatgg | gggctggaaa | aatgcaacta | tgatagatct | cttcaacgac | 660 |
| tatgccacat | actgcttcca | gacctttgga | gaccgtgtca | aatattggat | tacaattcac | 720 |

```
aacccttacc ttgttgcttg gcatgggttt ggcacaggta tgcatgcacc aggagagaag     780
ggaaatttaa cagctgtcta cactgtggga cacaacctga tcaaggcaca ttcgaaagtg     840
tggcataact acgacaaaaa cttccgccct catcagaagg gttggctctc catcaccttg     900
gggtcccatt ggatagagcc aaacagaaca gacaacatgg aggacgtgat caactgccag     960
cactccatgt cctctgtgct tggatggttc gccaacccca tccacgggga cggcgactac    1020
cctgagttca tgaagacggg cgccatgatc cccgagttct ctgaggcaga aaggaggag     1080 gtgaggggca cggctgattt ctttgccttt tccttcgggc ccaacaactt caggccctca    1140
aacaccgtgg tgaaaatggg acaaaatgta tcactcaact taaggcaggt gctgaactgg    1200
attaaactgg aatacgatga ccctcaaatc ttgatttcgg agaacggctg gttcacagat    1260
agctatataa agacagagga caccacggcc atctacatga tgaagaattt cctaaaccag    1320
gttcttcaag caataaaatt tgatgaaatc cgcgtgtttg ttatacggc ctggactctc      1380 ctggatggct ttgagtggca ggatgcctat acgacccgac gagggctgtt ttatgtggac    1440
tttaacagtg agcagaaaga gaggaaaccc aagtcctcgg ctcattacta caagcagatc    1500
atacaagaca acggcttctc tttaaaagag tccacgccag atgtgcaggg ccagtttccc    1560
tgtgacttct cctggggtgt cactgaatct gttcttaagc ccgagtctgt ggcttcgtcc    1620
ccacagttca gcgatcctca tctgtacgtg tggaacgcca ctggcaacag actgttgcac    1680
cgagtggaag gggtgaggct gaaaacacga cccgctcaat gcacagattt tgtaaacatc    1740
aaaaaacaac ttgagatgtt ggcaagaatg aaagtcaccc actaccggtt tgctctggat    1800
tgggcctcgg tccttcccac tggcaacctg tccgcggtga accgacaggc cctgaggtac    1860
tacaggtgcg tggtcagtga ggggctgaag cttggcatct ccgcgatggt caccctgtat    1920
tatccgaccc acgccacct aggcctcccc gagcctctgt tgcatgccga cgggtggctg      1980
aacccatcga cggccgaggc cttcaggcc tacgctgggc tgtgcttcca ggagctgggg      2040
gacctggtga agctctggat caccatcaac gagcctaacc ggctaagtga catctacaac    2100
cgctctggca acgacaccta cggggcggcg cacaacctgc tggtggccca cgccctggcc    2160
tggcgcctct acgaccggca gttcaggccc tcacagcgcg gggccgtgtc gctgtcgctg    2220
cacgcggact gggcggaacc cgccaacccc tatgctgact cgcactggag ggcggccgag    2280
cgcttcctgc agttcgagat cgcctggttc gccgagccgc tcttcaagac cggggactac    2340
cccgcggcca tgagggaata cattgcctcc aagcaccgac gggggctttc cagctcggcc    2400
ctgccgcgcc tcaccgaggc cgaaaggagg ctgctcaagg gcacggtcga cttctgcgcg    2460
ctcaaccact tcaccactag gttcgtgatg cacgagcagc tggccggcag ccgctacgac    2520
tcggacaggg acatccagtt tctgcaggac atcacccgcc tgagctcccc cacgcgcctg    2580
gctgtgattc cctgggggt gcgcaagctg ctgcggtggg tccggaggaa ctacggcgac      2640
atggacattt acatcaccgc cagtggcatc gacgaccagg ctctggagga tgaccggctc    2700
cggaagtact acctagggaa gtaccttcag gaggtgctga agcatacct gattgataaa      2760 gtcagaatca aaggctatta tgcattcaaa ctggctgaag agaaatctaa acccagattt    2820
ggattcttca catctgattt taaagctaaa tcctcaatac aattttacaa caaagtgatc    2880
agcagcaggg gcttcccttt tgagaacagt agttctagat gcagtcagac ccaagaaaat    2940
acagagtgca ctgtctgctt attccttgtg cagaagaaac cactgatatt cctgggttgt    3000
tgcttcttct ccaccctggt tctactctta tcaattgcca ttttcaaag gcagaagaga     3060
```

-continued

```
agaaagtttt ggaaagcaaa aaacttacaa cacataccat taaagaaagg caagagagtt   3120
gttagctag                                                           3129
```

<210> SEQ ID NO 378
<211> LENGTH: 25
<212> TYPE: PRT
<213> ORGANISM: Artificial Sequence
<220> FEATURE:
<223> OTHER INFORMATION: Humanized Anti-Beta Klotho VH FR1

<400> SEQUENCE: 378

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 379
<211> LENGTH: 32
<212> TYPE: PRT
<213> ORGANISM: Artificial Sequence
<220> FEATURE:
<223> OTHER INFORMATION: Humanized Anti-Beta Klotho VH FR3

<400> SEQUENCE: 379

Arg Ala Thr Leu Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 380
<211> LENGTH: 32
<212> TYPE: PRT
<213> ORGANISM: Artificial Sequence
<220> FEATURE:
<223> OTHER INFORMATION: Humanized Anti-Beta Klotho VH FR3

<400> SEQUENCE: 380

Arg Ala Thr Leu Thr Ala Asp Lys Ser Thr Arg Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 381
<211> LENGTH: 32
<212> TYPE: PRT
<213> ORGANISM: Artificial Sequence
<220> FEATURE:
<223> OTHER INFORMATION: Humanized Anti-Beta Klotho VH FR3

<400> SEQUENCE: 381

Arg Ala Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 382
<211> LENGTH: 23
<212> TYPE: PRT
<213> ORGANISM: Artificial Sequence
<220> FEATURE:
<223> OTHER INFORMATION: Humanized Anti-Beta Klotho VL FR1

<400> SEQUENCE: 382

Asp Ile Gln Met Thr Gln Ser Pro Ser Ser Leu Ser Ala Ser Val Gly

```
                1               5                  10                  15
Asp Arg Val Thr Ile Thr Cys
                20

<210> SEQ ID NO 383
<211> LENGTH: 23
<212> TYPE: PRT
<213> ORGANISM: Artificial Sequence
<220> FEATURE:
<223> OTHER INFORMATION: Humanized Anti-Beta Klotho VL FR1

<400> SEQUENCE: 383

Asp Ile Gln Leu Thr Gln Ser Pro Ser Ser Leu Ser Ala Ser Val Gly
1               5                   10                  15

Asp Arg Val Thr Ile Thr Cys
                20

<210> SEQ ID NO 384
<211> LENGTH: 23
<212> TYPE: PRT
<213> ORGANISM: Artificial Sequence
<220> FEATURE:
<223> OTHER INFORMATION: Humanized Anti-Beta Klotho VL FR1

<400> SEQUENCE: 384

Glu Ile Val Leu Thr Gln Ser Pro Ala Thr Leu Ser Leu Ser Pro Gly
1               5                   10                  15

Glu Arg Ala Thr Leu Ser Cys
                20

<210> SEQ ID NO 385
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 385

Trp Tyr Gln Gln Lys Pro Gly Lys Ala Pro Lys Leu Leu Ile Tyr
1               5                   10                  15

<210> SEQ ID NO 386
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 386

Trp Asn Gln Gln Lys Pro Gly Lys Ala Pro Lys Leu Leu Ile Tyr
1               5                   10                  15

<210> SEQ ID NO 387
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 387

Trp Tyr Gln Gln Lys Pro Gly Lys Pro Pro Lys Leu Leu Ile Tyr
1               5                   10                  15

<210> SEQ ID NO 388
<211> LENGTH: 15
```

```
<212> TYPE: PRT
<213> ORGANISM: Artificial Sequence
<220> FEATURE:
<223> OTHER INFORMATION: Humanized Anti-Beta Klotho VL FR2

<400> SEQUENCE: 388

Trp Asn Gln Gln Lys Pro Gly Lys Pro Pro Lys Leu Leu Ile Tyr
 1               5                  10                  15

<210> SEQ ID NO 389
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 389

Trp Tyr Gln Gln Lys Pro Gly Gln Ala Pro Arg Leu Leu Ile Tyr
 1               5                  10                  15

<210> SEQ ID NO 390
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 390

Trp Asn Gln Gln Lys Pro Gly Gln Ala Pro Arg Leu Leu Ile Tyr
 1               5                  10                  15

<210> SEQ ID NO 391
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 391

Trp Tyr Gln Gln Lys Pro Gly Gln Pro Pro Arg Leu Leu Ile Tyr
 1               5                  10                  15

<210> SEQ ID NO 392
<211> LENGTH: 15
<212> TYPE: PRT
<213> ORGANISM: Artificial Sequence
<220> FEATURE:
<223> OTHER INFORMATION: Humanized Anti-Beta Klotho VL FR2

<400> SEQUENCE: 392

Trp Asn Gln Gln Lys Pro Gly Gln Pro Pro Arg Leu Leu Ile Tyr
 1               5                  10                  15

<210> SEQ ID NO 393
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 393

Gly Val Pro Asp Arg Phe Ser Gly Ser Gly Ser Gly Thr Asp Phe Thr
 1               5                  10                  15

Leu Thr Ile Ser Ser Leu Gln Ala Glu Asp Val Ala Val Tyr Tyr Cys
                20                  25                  30
```

```
<210> SEQ ID NO 394
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 394

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 395
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 395

Gly Val Pro Ser Arg Phe Ser Gly Ser Gly Ser Gly Thr Asp Phe Thr
1               5                   10                  15

Leu Thr Ile Ser Ser Val Gln Pro Glu Asp Phe Ala Thr Tyr Tyr Cys
            20                  25                  30

<210> SEQ ID NO 396
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 396

Gly Val Pro Ser Arg Phe Ser Gly Ser Gly Ser Gly Thr Asp Phe Thr
1               5                   10                  15

Leu Thr Ile Ser Ser Leu Gln Glu Glu Asp Phe Ala Thr Tyr Tyr Cys
            20                  25                  30

<210> SEQ ID NO 397
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 397

Gly Val Pro Ser Arg Phe Ser Gly Ser Gly Ser Gly Thr Asp Phe Thr
1               5                   10                  15

Leu Thr Ile Ser Ser Val Gln Glu Glu Asp Phe Ala Thr Tyr Tyr Cys
            20                  25                  30

<210> SEQ ID NO 398
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 398

Gly Val Pro Ser Arg Phe Ser Gly Ser Gly Ser Gly Thr Asp Phe Thr
1               5                   10                  15

Leu Thr Ile Ser Ser Val Gln Glu Glu Asp Ala Ala Thr Tyr Tyr Cys
            20                  25                  30
```

<210> SEQ ID NO 399
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 399

Gly Ile Pro Ala Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 400
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 400

Gly Ile Pro Ala Arg Phe Ser Gly Ser Gly Ser Gly Thr Asp Phe Thr
1               5                   10                  15

Leu Thr Ile Ser Arg Val Glu Pro Glu Asp Phe Ala Val Tyr Tyr Cys
            20                  25                  30

<210> SEQ ID NO 401
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 401

Gly Ile Pro Ala Arg Phe Ser Gly Ser Gly Ser Gly Thr Asp Phe Thr
1               5                   10                  15

Leu Thr Ile Ser Arg Leu Glu Pro Glu Asp Ala Ala Val Tyr Tyr Cys
            20                  25                  30

<210> SEQ ID NO 402
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 402

Gly Ile Pro Ala Arg Phe Ser Gly Ser Gly Ser Gly Thr Asp Phe Thr
1               5                   10                  15

Leu Thr Ile Ser Arg Leu Glu Glu Glu Asp Phe Ala Val Tyr Tyr Cys
            20                  25                  30

<210> SEQ ID NO 403
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 403

Gly Ile Pro Ala Arg Phe Ser Gly Ser Gly Ser Gly Thr Asp Phe Thr
1               5                   10                  15

Leu Thr Ile Ser Arg Val Glu Glu Glu Asp Phe Ala Val Tyr Tyr Cys
            20                  25                  30

<210> SEQ ID NO 404
<211> LENGTH: 32
<212> TYPE: PRT
<213> ORGANISM: Artificial Sequence
<220> FEATURE:
<223> OTHER INFORMATION: Humanized Anti-Beta Klotho VL FR3

<400> SEQUENCE: 404

Gly Ile Pro Ala Arg Phe Ser Gly Ser Gly Ser Gly Thr Asp Phe Thr
1               5                   10                  15

Leu Thr Ile Ser Arg Val Glu Glu Asp Ala Ala Val Tyr Tyr Cys
            20                  25                  30

<210> SEQ ID NO 405
<211> LENGTH: 10
<212> TYPE: PRT
<213> ORGANISM: Artificial Sequence
<220> FEATURE:
<223> OTHER INFORMATION: Humanized Anti-Beta Klotho VL FR4

<400> SEQUENCE: 405

Phe Gly Gly Gly Thr Lys Val Glu Ile Lys
1               5                   10

<210> SEQ ID NO 406
<211> LENGTH: 10
<212> TYPE: PRT
<213> ORGANISM: Artificial Sequence
<220> FEATURE:
<223> OTHER INFORMATION: Humanized Anti-Beta Klotho VL FR4

<400> SEQUENCE: 406

Phe Gly Gln Gly Thr Lys Leu Glu Ile Lys
1               5                   10

<210> SEQ ID NO 407
<211> LENGTH: 10
<212> TYPE: PRT
<213> ORGANISM: Artificial Sequence
<220> FEATURE:
<223> OTHER INFORMATION: Humanized Anti-Beta Klotho VL FR4

<400> SEQUENCE: 407

Phe Gly Gly Gln Thr Lys Leu Glu Ile Lys
1               5                   10

<210> SEQ ID NO 408
<211> LENGTH: 1042
<212> TYPE: PRT
<213> ORGANISM: Cricetulus griseus
<220> FEATURE:
<223> OTHER INFORMATION: hamster beta klotho

<400> SEQUENCE: 408

Met Lys Ala Gly Cys Ala Ala Gly Ser Pro Gly Asn Glu Trp Ile Phe
1               5                   10                  15

Leu Ser Ser Tyr Glu Arg Asn Thr Arg Ser Lys Lys Thr Met Ser Asn
            20                  25                  30

Arg Ala Leu Gln Arg Ser Val Leu Ser Ala Phe Val Leu Leu Arg
        35                  40                  45

Ala Val Thr Gly Leu Ser Gly Asp Gly Lys Ala Ile Trp Asp Lys Lys
    50                  55                  60

Gln Tyr Val Ser Pro Val Asn Ala Ser Gln Leu Phe Leu Tyr Asp Thr

-continued

```
            65                  70                  75                  80
Phe Pro Lys Asn Phe Phe Trp Gly Val Gly Thr Gly Ala Phe Gln Val
                85                  90                  95
Glu Gly Asn Trp Gln Ala Asp Gly Arg Gly Pro Ser Ile Trp Asp Arg
            100                 105                 110
Phe Ile Tyr Thr His Leu Arg Asp Val Ser Ile Thr Glu Lys Ser Ala
            115                 120                 125
Asp Ser Tyr Ile Phe Leu Glu Lys Asp Leu Leu Ala Leu Asp Phe Leu
        130                 135                 140
Gly Val Ser Phe Tyr Gln Phe Ser Ile Ser Trp Pro Arg Leu Phe Pro
145                 150                 155                 160
Asn Gly Thr Val Ala Ser Val Asn Ala Lys Gly Leu Gln Tyr Tyr Asn
                165                 170                 175
Lys Leu Leu Asp Ser Leu Ile Leu Arg Asn Ile Glu Pro Val Val Thr
            180                 185                 190
Leu Tyr His Trp Asp Leu Pro Leu Ala Leu Gln Glu Asp Tyr Gly Gly
        195                 200                 205
Trp Lys Asn Ala Thr Met Ile Asp Leu Phe Asn Asp Tyr Ala Thr Tyr
210                 215                 220
Cys Phe Gln Thr Phe Gly Asp Arg Val Lys Tyr Trp Ile Thr Ile His
225                 230                 235                 240
Asn Pro Tyr Leu Val Ala Trp His Gly Phe Ala Thr Gly Met His Ala
                245                 250                 255
Pro Gly Glu Thr Gly Asn Leu Thr Ala Val Tyr Ile Val Gly His Asn
            260                 265                 270
Leu Ile Lys Ala His Ser Lys Val Trp His Asn Tyr Asp Lys Asn Phe
        275                 280                 285
Arg Pro His Gln Lys Gly Leu Leu Ser Ile Thr Leu Gly Ser His Trp
        290                 295                 300
Ile Glu Pro Asn Lys Thr Glu Asn Met Ala Asp Thr Ile Ser Cys Gln
305                 310                 315                 320
His Ser Met Ala Phe Val Leu Gly Trp Phe Ala Asn Pro Ile His Ala
                325                 330                 335
Asp Gly Asp Tyr Pro Glu Phe Met Lys Thr Leu Ser Thr Met Pro Val
            340                 345                 350
Phe Ser Glu Ala Glu Lys Glu Val Arg Gly Thr Ala Asp Phe Phe
        355                 360                 365
Ala Phe Ser Phe Gly Pro Asn Asn Phe Arg Pro Ser Asn Thr Val Val
        370                 375                 380
Lys Met Gly Gln Asn Val Ser Leu Asn Leu Arg Gln Val Leu Asn Trp
385                 390                 395                 400
Ile Lys Leu Glu Tyr Asp Asn Pro Arg Ile Leu Ile Ser Glu Asn Gly
                405                 410                 415
Trp Phe Thr Asp Ser Asp Ile Lys Thr Glu Asp Thr Thr Ala Ile Tyr
            420                 425                 430
Met Met Lys His Phe Leu Asn Gln Val Leu Gln Ala Ile Gln Phe Asp
        435                 440                 445
Glu Ile Arg Val Phe Gly Tyr Thr Ala Trp Ser Leu Leu Asp Gly Phe
        450                 455                 460
Glu Trp Gln Tyr Ala Tyr Thr Ser Arg Arg Gly Leu Phe Tyr Val Asp
465                 470                 475                 480
Phe Asn Ser Glu Gln Lys Glu Arg Lys Pro Lys Thr Ser Ala His Tyr
                485                 490                 495
```

-continued

```
Tyr Lys Gln Ile Ile Gln Glu Asn Gly Phe Pro Leu Lys Glu Ser Thr
            500                 505                 510

Pro Asp Met Gln Gly Gln Phe Pro Cys Asp Phe Ser Trp Gly Val Thr
            515                 520                 525

Glu Ser Val Leu Lys Pro Glu Phe Met Val Ser Ser Pro Gln Phe Thr
            530                 535                 540

Asp Pro His Leu Tyr Val Trp Asn Ala Thr Gly Asn Arg Leu Leu Gln
545                 550                 555                 560

Arg Val Glu Gly Val Arg Leu Lys Thr Lys Pro Ser His Cys Thr Asp
                565                 570                 575

Tyr Val Ser Ile Lys Lys Arg Val Glu Met Leu Ala Lys Met Lys Val
            580                 585                 590

Thr His Tyr Gln Phe Ala Leu Asp Trp Ala Thr Ile Leu Pro Thr Gly
            595                 600                 605

Asn Leu Ser Glu Val Asn Arg Gln Val Leu Arg Tyr Tyr Arg Cys Val
            610                 615                 620

Val Ser Glu Gly Leu Lys Leu Gly Val Ser Pro Met Val Thr Leu Tyr
625                 630                 635                 640

His Pro Thr His Ser His Leu Gly Leu Pro Glu Pro Leu Leu Asn Ser
                645                 650                 655

Gly Gly Trp Leu Asn Thr Tyr Thr Ala Lys Ala Phe Gln Asp Tyr Ala
            660                 665                 670

Gly Leu Cys Phe Gln Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp Arg Leu Tyr Asp Arg Gln Tyr Arg Pro Val Gln His Gly Ala Val
                725                 730                 735

Ser Leu Ser Leu His Ser Asp Trp Val Glu Pro Ala Asn Pro Tyr Val
            740                 745                 750

Asp Ser His Trp Lys Ala Ala Glu Arg Phe Leu Leu Phe Glu Ile Ala
            755                 760                 765

Trp Phe Ala Asp Pro Leu Phe Lys Thr Gly Asp Tyr Pro Leu Ala Met
770                 775                 780

Lys Glu Tyr Ile Ala Ser Lys Asn Gln Gln Gly Leu Ser Arg Ser Val
785                 790                 795                 800

Leu Pro Arg Phe Thr Pro Glu Glu Ser Arg Leu Val Lys Gly Thr Ile
                805                 810                 815

Asp Phe Tyr Ala Leu Asn His Phe Thr Thr Arg Phe Val Ile His Lys
            820                 825                 830

Gln Leu Asn Ser Ser Arg Ser Met Ala Asp Arg Asp Val Gln Phe Leu
            835                 840                 845

Gln Asp Ile Thr Arg Leu Ser Ser Pro Ser Arg Leu Ala Val Met Pro
            850                 855                 860

Trp Gly Ala Arg Lys Leu Leu Gly Trp Ile Gln Arg Asn Tyr Gly Asp
865                 870                 875                 880

Met Asp Ile Tyr Ile Thr Ala Asn Gly Ile Asp Asp Leu Ala Leu Glu
                885                 890                 895

Asn Asp Gly Ile Arg Lys Tyr Tyr Leu Glu Lys Tyr Ile Gln Glu Ala
            900                 905                 910
```

```
Leu Lys Ala Tyr Leu Ile Asp Lys Val Lys Ile Lys Gly Tyr Tyr Ala
            915                 920                 925

Phe Lys Leu Thr Glu Glu Lys Ser Lys Pro Arg Phe Gly Phe Phe Thr
        930                 935                 940

Ser Asp Phe Lys Ala Lys Ser Ser Val Glu Phe Tyr Ser Lys Leu Ile
945                 950                 955                 960

Ser Arg Ser Gly Phe Pro Ser Glu Thr Ser Asn Pro Ala Cys Gly Gln
                965                 970                 975

Pro Pro Glu Asp Thr Asp Cys Thr Ile Cys Ser Phe Phe Thr Gln Lys
            980                 985                 990

Lys Ser Leu Ile Phe Phe Gly Cys Cys Phe Ile Ser Thr Leu Ala Val
        995                 1000                1005

Leu Leu Ser Ile Thr Ile Phe His His Arg Lys Arg Arg Phe His Lys
        1010                1015                1020

Ser Lys Asn Leu Glu Asn Ile Pro Leu Lys Glu Gly His Ser Arg Val
1025                1030                1035                1040

Leu Ser

<210> SEQ ID NO 409
<211> LENGTH: 3042
<212> TYPE: DNA
<213> ORGANISM: Cricetulus griseus
<220> FEATURE:
<223> OTHER INFORMATION: Coding sequence of hamster beta klotho

<400> SEQUENCE: 409
atgtccaaca gggcactgca aagatctgtc gtgctgtcag cgtttgttct gctgcgagct      60
gttaccggat tgtctggaga cgggaaagcg atatgggata aaaaacagta cgtgagtccg     120
gtgaatgcaa gtcagctgtt tctctatgac actttcccta aaactttttt ctggggtgtt     180
ggaactggag catttcaagt ggaagggaat tggcaggcag acggaagagg accctcgatt     240
tgggatcgtt tcatctacac acacctgaga gatgtcagca tcacagagaa atccgccgac     300
agttacattt ttctggaaaa agatttgttg ctctggatt ttttaggagt ttcttttat       360 cagttctcaa tctcctggcc acggttgttc cccaatggaa cagtagcatc cgtgaatgca     420
aaaggtctcc aatactacaa caaacttctg gactcgctga tacttaggaa tattgagccc     480
gttgttacct ataccattg ggatttgcct ttggcgctac aggaagacta tggggttgg       540 aaaaatgcaa ctatgataga tctcttcaat gactatgcca catactgctt ccagaccttt     600
ggagaccgtg tcaagtattg gattacaatt cacaacccttt acctggttgc ttggcatggg     660
tttgccacag gtatgcatgc gccaggagag acgggaaatt taacagctgt ctacattgtg     720
ggacacaacc tgatcaaggc tcattcgaaa gtgtggcata actacgacaa aaacttccgc     780
ccccatcaga agggtttgct gtccattacc ttggggtccc actggatag accaaacaaa     840 acagaaaaca tggccgatac aatcagctgc cagcactcta tggcttttgt gcttgggtgg     900
tttgccaacc ccatccatgc agacggcgac taccctgagt tcatgaaaac attgtccacc     960
atgccagtgt tctctgaggc agagaaggag gaggtgaggg gcacagctga cttcttttgcc    1020 ttttcctttg ggcccaacaa tttcaggccc tcgaacactg tagtgaaaat gggacaaaat    1080
gtatcactca acttaagaca ggtgctgaac tggattaaat agaatatga caaccctcga    1140 atcttgattt cggagaatgg ctggttcaca gatagtgaca taaagacaga ggacaccaca    1200
gccatctaca tgatgaagca tttcctcaac caggttcttc aagcaataca gtttgatgaa    1260
atacgagtgt ttggttacac ggcctggtct ctcctggatg gctttgaatg gcagtatgcc    1320
```

-continued

```
tacacgtctc gccgaggact gttttatgtg gactttaata gtgaacagaa agaaaggaaa    1380
cccaagacct cggcacatta ctacaaacag atcatacaag aaaatggttt ccctttgaaa    1440
gagtccacgc cagacatgca gggtcagttt ccctgtgact tctcctgggg ggtcaccgag    1500
tctgttctta agccggagtt tatggtttcc tccccacagt ttaccgaccc tcacctgtat    1560
gtgtggaatg ccactggcaa cagattgcta cagcgagtag aaggagtaag gctaaaaaca    1620
aaaccatccc actgcacaga ctatgttagc atcaaaaaac gagttgagat gttggccaaa    1680
atgaaagtca cccactacca gtttgctctg actgggccaa ccatccttcc cactggcaat    1740
ctgtctgaag ttaatagaca agtactaagg tactataggt gtgtggtgag cgaaggactg    1800
aagctgggcg tctctcccat ggtgacgttg taccacccca cccactccca tctaggcctc    1860
cctgagccgc ttcttaacag tgggggatgg ctaaacactt acaccgccaa ggccttccag    1920
gactacgcag gactgtgctt ccaggaacta ggggacttgg tgaagctctg gatcaccatc    1980
aatgagccta ataggctgag tgacatgtac aaccgcacga gtaatgacac ctaccgtgca    2040
gcccataacc tgatgattgc ccatgcccag gtctggcgtc tctacgacag gcagtatagg    2100
ccagtccagc atggagctgt gtcgctgtcc ctacattctg actgggtgga acctgccaac    2160
ccctatgtgg actcacactg gaaggcagcg gagcgcttcc tcctgtttga gatcgcctgg    2220
ttcgctgatc cgctcttcaa gactggcgac tatccactgg ccatgaagga gtacatcgcc    2280
tccaagaacc agcaagggct gtcccgctca gtcctgccgc gcttcacccc agaggagagc    2340
aggctggtga agggcaccat cgacttctac gcactgaacc acttcactac taggttcgtg    2400
atacacaaac agctcaacag cagccgctct atggcagaca gggacgtcca gttcctgcag    2460
gacatcaccc gcctgagctc gcccagccgc ctggctgtta tgccctgggg agcacgcaag    2520
ctgcttgggt ggatccagag gaactatggg gacatggaca tctacatcac agccaatggc    2580
atcgatgatc tggctctgga gaatgatggg atccgaaagt actacttgga agtacatc     2640 caggaggctc tgaaaagcata cctcattgac aaagtcaaaa tcaaaggcta ttatgcattc    2700
aaactgactg aagagaaatc taagcctaga tttggatttt tcacatctga cttcaaagct    2760
aagtcatctg tagagtttta tagcaagttg atcagcagaa gtggcttccc ctctgagact    2820
agcaatcccg catgtggtca gcctccagaa gacacagact gcaccatctg ctcattttc    2880 actcagaaga aatctctgat cttctttggt tgttgcttca tctccactct ggctgtactg    2940
ctgtcaatca ccattttttca tcatcgaaag agaagatttc ataaatcaaa gaacttagaa    3000
aatataccat tgaaggaagg ccacagtaga gttcttagct aa                       3042
```

<210> SEQ ID NO 410
<211> LENGTH: 1044
<212> TYPE: PRT
<213> ORGANISM: Oryctolagus cuniculus
<220> FEATURE:
<223> OTHER INFORMATION: Rabbit beta klotho

<400> SEQUENCE: 410

Met Lys Pro Gly Cys Ala Ala Gly Ser Pro Gly Asn Glu Trp Val Ser
1               5                   10                  15

Phe Cys Thr Asp Glu Arg Asn Arg Cys Arg Glu Thr Met Ser Ser
            20                  25                  30

Gly Arg Leu Arg Arg Ser Val Met Leu Ser Ala Phe Ile Leu Leu Arg
        35                  40                  45

Ala Val Thr Gly Phe Pro Gly Asp Gly Arg Ala Val Trp Ser Gln Asn

```
                  50                  55                  60
Pro Asn Leu Ser Pro Val Asn Glu Ser Gln Leu Phe Leu Tyr Asp Thr
65                  70                  75                  80

Phe Pro Lys Asn Phe Phe Trp Gly Val Gly Thr Gly Ala Phe Gln Val
                85                  90                  95

Glu Gly Ser Trp Lys Lys Asp Gly Lys Gly Leu Ser Val Trp Asp His
                100                 105                 110

Phe Ile Ala Thr His Leu Asn Val Ser Ser Arg Asp Gly Ser Ser Asp
                115                 120                 125

Ser Tyr Ile Phe Leu Glu Lys Asp Leu Ser Ala Leu Asp Phe Leu Gly
                130                 135                 140

Val Ser Phe Tyr Gln Phe Ser Ile Ser Trp Pro Arg Leu Phe Pro Asp
145                 150                 155                 160

Gly Thr Val Ala Val Asn Ala Lys Gly Leu Gln Tyr Tyr Asn Arg
                165                 170                 175

Leu Leu Asp Ser Leu Leu Arg Asn Ile Glu Pro Val Val Thr Leu
                180                 185                 190

Tyr His Trp Asp Leu Pro Trp Ala Leu Gln Glu Lys Tyr Gly Gly Trp
                195                 200                 205

Lys Asn Glu Thr Leu Ile Asp Leu Phe Asn Asp Tyr Ala Thr Tyr Cys
                210                 215                 220

Phe Gln Thr Phe Gly Asp Arg Val Lys Tyr Trp Ile Thr Ile His Asn
225                 230                 235                 240

Pro Tyr Leu Val Ala Trp His Gly Tyr Gly Thr Gly Leu His Ala Pro
                245                 250                 255

Gly Glu Lys Gly Asn Val Ala Ala Val Tyr Thr Val Gly His Asn Leu
                260                 265                 270

Leu Lys Ala His Ser Lys Val Trp His Asn Tyr Asn Arg Asn Phe Arg
                275                 280                 285

Pro His Gln Lys Gly Trp Leu Ser Ile Thr Leu Gly Ser His Trp Ile
                290                 295                 300

Glu Pro Asn Arg Ala Glu Ser Ile Val Asp Ile Leu Lys Cys Gln Gln
305                 310                 315                 320

Ser Met Val Ser Val Leu Gly Trp Phe Ala Asn Pro Ile His Gly Asp
                325                 330                 335

Gly Asp Tyr Pro Glu Val Met Thr Lys Lys Leu Leu Ser Val Leu Pro
                340                 345                 350

Ala Phe Ser Glu Ala Glu Lys Asn Glu Val Arg Gly Thr Ala Asp Phe
                355                 360                 365

Phe Ala Phe Ser Phe Gly Pro Asn Asn Phe Lys Pro Leu Asn Thr Met
                370                 375                 380

Ala Lys Met Gly Gln Asn Val Ser Leu Asn Leu Arg Gln Val Leu Asn
385                 390                 395                 400

Trp Ile Lys Leu Glu Tyr Gly Asn Pro Arg Ile Leu Ile Ala Glu Asn
                405                 410                 415

Gly Trp Phe Thr Asp Ser Tyr Val Gln Thr Glu Asp Thr Thr Ala Ile
                420                 425                 430

Tyr Met Met Lys Asn Phe Leu Asn Gln Val Leu Gln Ala Ile Arg Leu
                435                 440                 445

Asp Gly Val Arg Val Phe Gly Tyr Thr Ala Trp Ser Leu Leu Asp Gly
                450                 455                 460

Phe Glu Trp Gln Asp Ala Tyr Asn Thr Arg Arg Gly Leu Phe Tyr Val
465                 470                 475                 480
```

```
Asp Phe Asn Ser Glu Gln Arg Glu Arg Pro Lys Ser Ser Ala His
            485                 490                 495

Tyr Tyr Lys Gln Val Ile Gly Glu Asn Gly Phe Thr Leu Arg Glu Ala
            500                 505                 510

Thr Pro Asp Leu Gln Gly Gln Phe Pro Cys Asp Phe Ser Trp Gly Val
            515                 520                 525

Thr Glu Ser Val Leu Lys Pro Glu Ser Val Ala Ser Ser Pro Gln Phe
            530                 535                 540

Ser Asp Pro His Leu Tyr Val Trp Asn Ala Thr Gly Asn Arg Met Leu
545                 550                 555                 560

His Arg Val Glu Gly Val Arg Leu Lys Thr Arg Pro Ala Gln Cys Thr
                565                 570                 575

Asp Phe Ile Thr Ile Lys Lys Gln Leu Glu Met Leu Ala Arg Met Lys
                580                 585                 590

Val Thr His Phe Arg Phe Ala Leu Asp Trp Ala Ser Val Leu Pro Thr
                595                 600                 605

Gly Asn Leu Ser Glu Val Asn Arg Gln Ala Leu Arg Tyr Tyr Arg Cys
            610                 615                 620

Val Val Thr Glu Gly Leu Lys Leu Asn Ile Ser Pro Met Val Thr Leu
625                 630                 635                 640

Tyr Tyr Pro Thr His Ala His Leu Gly Leu Pro Ala Pro Leu Leu His
                645                 650                 655

Ser Gly Gly Trp Leu Asp Pro Ser Thr Ala Lys Ala Phe Arg Asp Tyr
                660                 665                 670

Ala Gly Leu Cys Phe Arg Glu Leu Gly Asp Leu Val Lys Leu Trp Ile
            675                 680                 685

Thr Ile Asn Glu Pro Asn Arg Leu Ser Asp Val Tyr Asn Arg Thr Ser
690                 695                 700

Asn Asp Thr Tyr Gln Ala Ala His Asn Leu Leu Ile Ala His Ala Leu
705                 710                 715                 720

Val Trp His Leu Tyr Asp Arg Gln Tyr Arg Pro Ser Gln Arg Gly Ala
                725                 730                 735

Leu Ser Leu Ser Leu His Ser Asp Trp Ala Glu Pro Ala Asn Pro Tyr
                740                 745                 750

Val Ala Ser His Trp Gln Ala Ala Glu Arg Phe Leu Gln Phe Glu Ile
            755                 760                 765

Ala Trp Phe Ala Glu Pro Leu Phe Lys Thr Gly Asp Tyr Pro Val Ala
            770                 775                 780

Met Arg Glu Tyr Ile Ala Ser Lys Thr Arg Arg Gly Leu Ser Ser Ser
785                 790                 795                 800

Val Leu Pro Arg Phe Ser Asp Ala Glu Arg Arg Leu Val Lys Gly Ala
                805                 810                 815

Ala Asp Phe Tyr Ala Leu Asn His Phe Thr Thr Arg Phe Val Met His
                820                 825                 830

Glu Gln Gln Asn Gly Ser Arg Tyr Asp Ser Asp Arg Asp Val Gln Phe
            835                 840                 845

Leu Gln Asp Ile Thr Arg Leu Ala Ser Pro Ser Arg Leu Ala Val Met
850                 855                 860

Pro Trp Gly Glu Gly Lys Leu Leu Arg Trp Met Arg Asn Asn Tyr Gly
865                 870                 875                 880

Asp Leu Asp Val Tyr Ile Thr Ala Asn Gly Ile Asp Asp Gln Ala Leu
                885                 890                 895
```

Gln Asn Asp Gln Leu Arg Gln Tyr Tyr Leu Glu Lys Tyr Val Gln Glu
             900                 905                 910

Ala Leu Lys Ala Tyr Leu Ile Asp Lys Ile Lys Ile Lys Gly Tyr Tyr
         915                 920                 925

Ala Phe Lys Leu Thr Glu Glu Lys Ser Lys Pro Arg Phe Gly Phe Phe
     930                 935                 940

Thr Ser Asp Phe Lys Ala Lys Ser Ser Ile Gln Phe Tyr Asn Lys Leu
945                 950                 955                 960

Ile Thr Ser Asn Gly Phe Pro Ser Glu Asn Gly Pro Arg Cys Asn
                 965                 970                 975

Gln Thr Gln Gly Asn Pro Glu Cys Thr Val Cys Leu Leu Leu Gln
             980                 985                 990

Lys Lys Pro Leu Ile Phe Phe Ser Cys Cys Phe Phe Cys Thr Leu Val
         995                 1000                1005

Leu Leu Ser Ser Ile Thr Ile Phe His Arg Arg Lys Arg Arg Lys Phe
     1010                1015                1020

Trp Lys Ala Lys Asp Leu Gln His Ile Pro Leu Lys Lys Gly His Lys
1025                1030                1035                1040

Arg Val Leu Ser

<210> SEQ ID NO 411
<211> LENGTH: 5737
<212> TYPE: DNA
<213> ORGANISM: Oryctolagus cuniculus
<220> FEATURE:
<223> OTHER INFORMATION: Coding sequence of Rabbit beta klotho

<400> SEQUENCE: 411

| | | | | | |
|---|---|---|---|---|---|
| tgaagccgtg | ataagacggt | cccgcagttc | gtggcaaatg | aagccaggct | gtgcggcagg | 60 |
| atctccaggg | aatgaatggg | tttccttctg | caccgatgaa | agaaacagac | gctgtaggga | 120 |
| aacgatgtcc | agcggacgcc | tgcggagatc | tgtcatgctg | tcagccttca | tcctgctgcg | 180 |
| agccgtgact | gggttccccg | gagacggaag | agctgtatgg | tcgcaaaatc | ctaatttgag | 240 |
| tccggtaaac | gaaagtcagc | tgtttctcta | tgacactttc | ccaaaaaact | ttttctgggg | 300 |
| tgtggggact | ggagccttcc | aagtggaagg | gagttggaag | aaggatggga | aaggactctc | 360 |
| tgtatgggat | catttcatcg | ctacacacct | gaacgtcagc | agccgcgatg | gctccagtga | 420 |
| cagctacatt | ttttttggaga | aagacttatc | ggcgctggat | tttttaggag | tctctttta | 480 |
| tcagttttca | atttcctggc | caagactgtt | cccggatggc | acagtagcag | tcgccaatgc | 540 |
| aaaaggtctc | cagtactata | atcggctcct | ggactctctg | ctacttagaa | acattgaacc | 600 |
| tgtagtcact | ttataccatt | gggatctgcc | ttgggcgcta | caagaaaaat | acggggggtg | 660 |
| gaaaaacgag | acgttgattg | atttattcaa | tgactatgcc | acctactgtt | tccagacgtt | 720 |
| tggggaccgt | gtcaaatact | ggatcaccat | tcacaatccc | tatctggtgg | cttggcatgg | 780 |
| ctacgggaca | ggtctgcatg | ctccgggaga | aaggggaat | gtggcagctg | tctacactgt | 840 |
| gggacacaac | ctgcttaagg | ctcattcaaa | agtctggcac | aactacaaca | ggaatttccg | 900 |
| cccgcatcag | aaaggctggc | tgtcgatcac | gctgggatcc | cactggattg | agccaaacag | 960 |
| agcggaaagc | atcgtggaca | tactcaagtg | ccagcagtcc | atggtctcgg | tgctgggctg | 1020 |
| gtttgccaac | ccgatccacg | gggacgggga | ctacccagag | gtgatgacaa | agaagctgct | 1080 |
| ctccgtcctg | cccgctttct | cagaaagcaga | gaagaacgag | gtacgaggca | ccgcagactt | 1140 |
| ctttgccttt | tcgtttggac | ccaacaactt | caagcccctta | aacaccatgg | ctaaaatggg | 1200 |

```
gcagaatgtg tcactcaatc taagacaggt gctgaactgg attaaactgg aatatggcaa    1260
ccctcgaatc ctgatcgctg agaacggctg gttcacagac agttacgtgc aaacagaaga    1320
caccacagcc atctacatga tgaagaattt cctcaaccag gttcttcaag caataaggtt    1380
ggatggagtc cgagtgtttg gctacactgc ctggtctctc ctggatggct tcgaatggca    1440
ggacgcttac aacacccgcc gtggactgtt ttatgtggac ttcaacagcg aacagagaga    1500
aagaaggccc aagtcctcgg cgcattacta taaacaggtc ataggagaaa acggcttcac    1560
gctcagagag gccacccgg atctgcaggg gcagtttccc tgtgacttct cctggggcgt    1620
caccgagtct gttcttaagc ccgagtcggt ggcttcctcg ccacagttca gcgaccctca    1680
cctctacgtg tggaacgcca ctggcaaccg aatgcttcac cgggtggaag gggtgaggct    1740
gaaaacacgg cccgctcagt gcacagattt catcaccatc aagaaacaac tcgagatgtt    1800
ggcaagaatg aaagtcaccc acttccggtt tgctctggac tgggcctcgg tccttcccac    1860
gggcaacctg tccgaggtga accgacaagc cctgaggtac tacaggtgtg tggtcaccga    1920
ggggctgaag ctcaacatct cgcccatggt caccttgtac tacccgaccc atgcccacct    1980
gggcctgccc gcgccgctgc tgcacagcgg ggggtggctg gacccatcca cggccaaggc    2040
cttccgcgac tacgcagggc tgtgcttccg ggagctgggg gacctggtga agctctggat    2100
caccatcaac gagcccaacc ggctgagcga cgtctacaac cgcaccagca acgacaccta    2160
ccaggccgcc cacaacctgc tgatcgcgca cgcgctcgtg tggcacctgt acgaccgcca    2220
gtaccggccg tcgcagcgcg gggcgctgtc gctgtccctg cactcggact gggccgagcc    2280
cgccaacccc tacgtggcct cgcactggca ggcggccgag cgcttcctgc agttcgagat    2340
tgcgtggttc gccgagcccc tgttcaagac cggggactac ccgqtggcca tgagggagta    2400 catcgcctcc aagacccggc gcgggctctc cagctccgtg ctgccccgct cagcgacgc    2460 cgagcggcgg ctggtcaagg gcgccgccga cttctacgcc ctcaaccact tcaccaccag    2520
gttcgtgatg cacgagcagc agaacggcag ccgctacgac tcggacaggg acgtgcagtt    2580
cctgcaggac atcacccgcc tggcctcacc cagccgcctg gccgtgatgc cctggggcga    2640
gggcaagctg ctgcgcggtgga tgcggaacaa ctacggagac ctggacgtct acatcacggc    2700
caatggcatc gacgaccagg ccctgcagaa cgaccagctt cgccagtact acctggagaa    2760
gtacgtccag gaggctctga agcatatct gatagataaa ataaaaatca aaggctatta    2820
tgcattcaaa ctgactgaag aaaaatctaa acccaggttt ggattcttca cctctgattt    2880
caaagccaag tcttcaatac agttttacaa caaactaatt accagcaacg gcttcccgtc    2940
tgagaacggc ggtcctagat gcaatcagac tcaaggaaat cccgagtgca ccgtctgctt    3000
actcctcctg cagaagaagc cgctgatatt ctttagctgc tgcttcttct gcaccctggt    3060
tctactctca tcaattacca tctttcacag acggaagaga agaaaatttt ggaaagcaaa    3120
ggacttacaa cacataccat taagaaaagg ccacaagaga gtccttagct aaagtgaact    3180
tatttctctc tgaagagttt agaaattcac tccagttcca tatgctggta acacaaaaga    3240 cataccgta ttgtacacag agtatttgag atactgtgct aaccaaggcg atgacaatca    3300
aaacctctgc catgtggttg aatgcatttt cccttaagcg tgacaatca gcgaactcag    3360 ttcttggttc taaaggaggc ttcgcactgc cactaggcta tgagtattac ctgacgcatt    3420
gctttgtcaa gtttgatgag ctgtttcgca tcattctcta gctttctta gataccaata    3480 gctactatgg taaaagttgt ttttaaaagt caaactctgt aaggcttcac agcagattta    3540
aaactattct ttacactgga tctgtgattt tgtcactcgt agcaaggtgc tttccccttt    3600
```

```
tggtcctagt ggctctcaaa tagaaagcaa acacatctta gggtaatcta cttatctata    3660
gccaatcaca gcactgaccc acaactacac aaatccgtta gctcttctcc ataaaacacc    3720
taattttgtg atcttttaag taatctgaaa tgtaaaagta tgacttccgt aacccatctc    3780
atggaaagat cgactaagga gagccatacc cagctgtgag acaatttag tcactaatct     3840 caccgtactg caacttcctc ctttagagca ggcattcctt accattttg taagatgaca     3900 tgatttagca tctagaaccc ctatctgcag tttctttcta tggcttacct acatttcaag    3960
aatattgaac ggaaaatttc agaaagattt ccaagtttta aattgtgtac tagcattagt    4020
gcatgatgaa atctcatttt ctttgctcca tcctgcacag gatgtgaaac atccctctgt    4080
ccagcaagtc caagctacct atattactca cttgatagtc accatggtta tccagctgtt    4140
attacttgct catacccagg taacccttt ttatttaat atagctccaa agtataagac      4200
tagtgatgaa aaggaggtaa gtcatcaaat atggaaggac agattaactc tggcactaag    4260
tgggaatgct gcaggtttta caggaaaaca aaattcagtc agtggtttaa agcatcctct    4320
gaggtacctg gggcacaatc tccacagata aggggaaaga gcactgacaa agactaaaca    4380
tcctaaaaag acgcaatgtt ctacttactg gccatcagaa taatggccaa aggaccctat    4440
acttgcttgc tctctagcca agtttcgctg cacataggtg tagaatgcag cgactgaccc    4500
tggatgcgat tcagaatgct gatctgagtg aactagtttt ttatacagca cttttaaag    4560 cctagaattc ttccatctga acttgggagt tttgacttt ttgaaattaa ttgtgcttaa     4620
gatttattca gtgattctaa acactggagg tagaaaactg tatacccatt atgcctatta   4680 attttcttg attagccaac atttaaataa ccacaaagtg gccagtcgtt gtctttccct    4740
ttcaggaatt taagtcaaag gatgctgctg cctgcgatgc tggcacttca tagggggtgac   4800 agtttgtgtc cctgcggttc cacttcctat ccagctccct gctaatggct tgggagagcc    4860
ctgcacccac atgggagacc caaaagcaga tcctgctgct ttcagcctgc tgcggccact    4920
tggagtatga accagtggat ggaagatcaa tgtctctccc aacaattctt tgaataaatt    4980
ttttcaaaag tcaaaataaa attctccagc tcaaaaagct ttagtagaaa acgatcctac    5040
attaaggcgg ttgtgattgt atcccaagtg catctacgtt acaaaccaaa ttgagtatgc    5100
aattcagtat gctactagac tataaggaga aaacagccaa ttcaaacaaa ataccaaagt    5160
cacgtgcagt taatttgctt tctggttggc caaatgtttt ttttctcttc ttgccaccac    5220
tgttttacat gtactttaga agaaattttg acttttgct tcctttgaga aatcactatt     5280
atcaaaggca attcataatt acaagtggtc cattgtctta agagctcaag attatagccc    5340
ttcaaacttg ccaaactcct caaatagtga agctcctaac gaagggttta caacatcctg    5400
ttccttaggg gttatatttt taagtgactg taatttacct aacaaattta atctggctat    5460
ctattggtaa tacatgtaat attcaggttt atcataaacc cacttaaaaa ctaaaggtta    5520
agtggaagtt gctgcttttc aaagtaacag gcttctcagg ggaaaatatc accttagcgt    5580
ccacctggta ctacatctcg tgtattcact gtaacccatc tttccgaaca tgtctgatat    5640
atatggaaac aacactagtg cttagcctct ggaaatgagg ccaggatttt gtgattaaat    5700
gtctaattta ttccaaataa actgatttac gccaata                            5737

<210> SEQ ID NO 412
<211> LENGTH: 1045
<212> TYPE: PRT
<213> ORGANISM: Canis lupus familiaris
<220> FEATURE:
```

<223> OTHER INFORMATION: Dog beta klotho

<400> SEQUENCE: 412

```
Met Lys Pro Gly Cys Ala Ala Gly Ser Pro Gly Asn Glu Trp Ile Phe
1               5                   10                  15

Leu Ser Thr Asp Glu Ser Asn Thr His Tyr Arg Lys Thr Met Cys Asn
            20                  25                  30

His Gly Leu Gln Arg Ser Val Ile Leu Ser Ala Phe Ile Leu Leu Gly
        35                  40                  45

Ala Val Pro Gly Phe Ser Gly Asp Gly Arg Ala Ile Trp Ser Lys Asn
    50                  55                  60

Pro His Phe Ser Pro Val Asn Glu Ser Gln Leu Phe Leu Tyr Asp Thr
65                  70                  75                  80

Phe Pro Lys Asn Phe Phe Trp Gly Val Gly Thr Gly Ala Phe Gln Val
                85                  90                  95

Glu Gly Asn Trp Lys Thr Asp Gly Lys Gly Pro Ser Ile Trp Asp His
            100                 105                 110

Phe Ile His Thr His Leu Lys Asn Val Asn Ser Met Asn Ser Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Ala Ala Val Ala Asn Ala Lys Gly Leu Gln Tyr Tyr Asn
                165                 170                 175

Ser Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Glu Thr Ile Thr Asp Ile Phe Asn Asp Tyr Ala Thr Tyr
    210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr Asn Phe
        275                 280                 285

Arg Pro Tyr Gln Lys Gly Leu Leu Ser Ile Thr Leu Gly Ser His Trp
    290                 295                 300

Ile Glu Pro Asn Arg Ser Glu Asn Met Met Asp Ile Leu Lys Cys Gln
305                 310                 315                 320

Gln Ser Met Val Ser Val Leu Gly Trp Phe Ala Asn Pro Ile His Gly
                325                 330                 335

Asn Gly Asp Tyr Pro Glu Val Met Lys Lys Leu Leu Ser Thr Leu
            340                 345                 350

Pro Leu Phe Ser Glu Ala Glu Lys Asn Glu Val Arg Gly Thr Ala Asp
        355                 360                 365

Phe Phe Ala Phe Ser Phe Gly Pro Asn Asn Phe Lys Pro Gln Asn Thr
    370                 375                 380

Met Ala Lys Met Gly Gln Asn Val Ser Leu Asn Leu Arg Glu Val Leu
385                 390                 395                 400
```

-continued

```
Asn Trp Ile Lys Leu Glu Tyr Gly Asn Pro Arg Ile Leu Ile Ala Glu
                405                 410                 415
Asn Gly Trp Phe Thr Asp Ser His Val Lys Thr Glu Asp Thr Thr Ala
            420                 425                 430
Ile Tyr Met Met Lys Asn Phe Leu Asn Gln Val Leu Gln Ala Ile Arg
        435                 440                 445
Phe Asp Glu Ile Gln Val Phe Gly Tyr Thr Ala Trp Ser Leu Leu Asp
450                 455                 460
Gly Phe Glu Trp Gln Asp Ala Tyr Ser Thr Arg Arg Gly Leu Phe Tyr
465                 470                 475                 480
Val Asp Phe Asn Ser Lys Gln Lys Glu Arg Lys Pro Lys Ser Ser Ala
                485                 490                 495
Tyr Tyr Tyr Lys Gln Ile Ile Gln Glu Asn Gly Phe Thr Phe Lys Glu
            500                 505                 510
Ser Thr Pro Asp Val Gln Gly Gln Phe Pro Cys Asp Phe Ser Trp Gly
        515                 520                 525
Val Thr Glu Ser Val Leu Lys Pro Lys Val Val Ala Ser Ser Pro Gln
530                 535                 540
Phe Ser Asp Pro His Leu Tyr Val Trp Asn Val Thr Gly Asn Arg Leu
545                 550                 555                 560
Leu His Arg Val Glu Gly Val Arg Leu Lys Thr Arg Pro Ala Gln Cys
                565                 570                 575
Thr Asp Phe Val Ser Ile Lys Arg Gln Leu Glu Met Leu Ala Arg Met
            580                 585                 590
Asn Val Thr His Tyr Arg Phe Ala Leu Asp Trp Pro Ser Ile Leu Pro
        595                 600                 605
Thr Gly Asn Leu Ser Thr Val Asn Arg Gln Ala Leu Arg Tyr Tyr Arg
610                 615                 620
Cys Val Val Ser Glu Ser Leu Lys Leu Ser Ile Ser Pro Met Val Thr
625                 630                 635                 640
Leu Tyr Tyr Pro Thr His Ala His Leu Gly Leu Pro Ser Pro Leu Leu
                645                 650                 655
His Ser Gly Gly Trp Leu Asn Ala Ser Thr Ala Arg Ala Phe Gln Asp
            660                 665                 670
Tyr Ala Gly Leu Cys Phe Gln Glu Leu Gly Asp Leu Val Lys Leu Trp
        675                 680                 685
Ile Thr Ile Asn Glu Pro Asn Arg Leu Ser Asp Val Tyr Ser His Thr
690                 695                 700
Ser Ser Asp Thr Tyr Arg Ala Ala His Asn Leu Leu Ile Ala His Ala
705                 710                 715                 720
Leu Val Trp His Leu Tyr Asp Arg Arg Tyr Arg Pro Ala Gln Arg Gly
                725                 730                 735
Ala Val Ser Leu Ser Leu His Ser Asp Trp Ala Glu Pro Ala Asn Pro
            740                 745                 750
Tyr Ala Asp Ser His Trp Lys Ala Ala Glu Arg Phe Leu Gln Phe Glu
        755                 760                 765
Ile Ala Trp Phe Ala Glu Pro Leu Phe Lys Thr Gly Asp Tyr Pro Pro
770                 775                 780
Ala Met Arg Glu Tyr Ile Ala Ser Lys Asn Arg Gln Gly Leu Ser Arg
785                 790                 795                 800
Ser Thr Leu Pro Arg Phe Thr Asp Glu Glu Arg Arg Leu Val Lys Gly
                805                 810                 815
Ala Ala Asp Phe Tyr Ala Leu Asn His Phe Thr Thr Arg Phe Val Met
```

|  | | 820 | | | 825 | | | 830 | | |
|---|---|---|---|---|---|---|---|---|---|---|

His Ala Arg Gln Asn Gly Ser Arg Tyr Asp Ala Asp Arg Asp Val Gln
835                     840                     845

Phe Leu Gln Asp Ile Thr Cys Leu Ser Ser Pro Ser Arg Leu Ala Val
850                     855                     860

Leu Pro Trp Gly Glu Arg Lys Val Leu Arg Trp Ile Gln Lys Asn Tyr
865                     870                     875                     880

Gly Asp Val Asp Val Tyr Ile Thr Ala Ser Gly Ile Asp Asp Gln Ser
                885                     890                     895

Leu Glu Asn Asp Glu Leu Arg Lys Tyr Tyr Leu Glu Lys Tyr Ile Gln
                900                     905                     910

Glu Ala Leu Lys Ala His Leu Ile Asp Lys Val Lys Val Lys Gly Tyr
                915                     920                     925

Tyr Ala Phe Lys Leu Thr Glu Glu Lys Ser Lys Pro Arg Phe Gly Phe
                930                     935                     940

Phe Thr Ser Glu Phe Lys Ala Lys Ser Ser Val Gln Leu Tyr Asn Lys
945                     950                     955                     960

Leu Ile Ser Asn Ser Gly Phe Pro Ser Glu Asn Arg Ser Pro Arg Cys
                965                     970                     975

Ser Glu Thr Gln Arg Asn Thr Glu Cys Met Val Cys Leu Phe Leu Val
                980                     985                     990

Gln Lys Lys Pro Leu Ile Phe Phe Ser Cys Cys Phe Phe Ser Thr Leu
                995                     1000                    1005

Val Leu Leu Ser Ser Ile Thr Ile Leu His Lys Arg Lys Arg Arg Lys
                1010                    1015                    1020

Ile Trp Lys Ala Lys Asn Leu Gln His Ile Pro Leu Lys Lys Ser Lys
1025                    1030                    1035                    1040

Asn Ser Leu Gln Ser
                1045

```
<210> SEQ ID NO 413
<211> LENGTH: 4350
<212> TYPE: DNA
<213> ORGANISM: Canis lupus familiaris
<220> FEATURE:
<223> OTHER INFORMATION: Coding sequence of dog beta klotho

<400> SEQUENCE: 413
acaatcacaa gcttttactg aagcgttgat aagacaggcg agcagttagt ggcaaatgaa      60
gccaggctgt gcggctggat ctccagggaa tgaatggatt ttcctcagca ccgatgaaag     120
caacacacac tataggaaaa caatgtgcaa ccacgggcta cagagatctg tcatcctgtc     180
agcatttatt ctcctaggag ctgttcctgg attctctgga gacggaagag ctatatggtc     240
taaaaatcct cattttagtc cggtaaatga aagtcagctg tttctctatg cacttttcc      300 taaaactttt ttgggcg ttgggactgg agcatttcaa gtggaaggga attggaagac        360
agatggaaaa ggaccctcta tatgggatca tttcatccac acacacctta aaaatgtcaa    420
cagcatgaat agttccagtg acagttacat ttttctggaa aaagacctat cagccctgga    480
ttttatcgga gttctttttt atcaatttc aatttcctgg ccaaggcttt tccccgatgg     540
aatagcagca gttgccaacg caaaaggtct ccagtactac aattctcttc tcgatgctct    600
agtacttagg aacattgaac ctatagttac tttataccat tgggatttgc ctttggcact    660
acaagaaaaa tatgggggt ggaaaaatga accataacg gatatcttca atgactatgc      720
cacctactgt ttccagacgt cggggatcg tgtcaaatac tggattacaa ttcacaatcc    780
```

-continued

```
atatctagtt gcttggcatg ggtatgggac aggtatgcac gcgcctggag agaagggaaa      840
cttagcagct gtctacactg tgggacacaa cctaatcaag gctcattcga aagtttggca      900
taactacaac acaaatttcc gcccatatca gaagggtttg ttatcaatca cgttgggatc      960
ccattggatt gaaccaaaca gatcagaaaa catgatggat atactcaaat gtcaacaatc     1020
catggtttca gtgctcgggt ggtttgccaa ccccatccat gggaatggag actatccaga     1080
agtgatgaaa aagaagttgc tctccactct accccttttc tctgaagcag agaagaatga     1140
agtgaggggc acagctgact tctttgcctt ttccttggga cccaacaatt tcaagcccca     1200
gaacaccatg gctaaaatgg gacaaaatgt gtcactcaat ttaagagaag tgctgaattg     1260
gattaaactg gaatatggca acccccgaat cttgattgct gagaatggct ggttcacaga     1320
cagtcatgtg aaaacagaag ataccacagc catttacatg atgaagaatt tcctcaacca     1380
ggttcttcaa gcaataaggt ttgacgaaat acaagtgttt ggctacactg cttggtctct     1440
cctggatggc tttgaatggc aggatgctta ctccactcgc cgaggattat tttatgtgga     1500
tttttaatagt aaacaaaaag aaagaaagcc caagtcttcg gcatattact ataaacagat     1560
catacaagaa aatggttttta ctttcaaaga gtccacccca gatgtgcagg gtcagtttcc     1620
ctgtgacttc tcatggggtg tcaccgaatc tgtccttaag cccaaagtcg tggcttcctc     1680
cccacagttc agcgaccctc acctgtacgt gtggaatgtg acaggcaaca gactgttgca     1740
ccgagtggaa ggggtgaggc tgaagacacg gccggctcaa tgcacagatt ttgtcagcat     1800
caaaagacaa cttgagatgt tggcgaggat gaacgtcact cactacaggt ttgctctgga     1860
ctggccctcc atccttccca ccggcaacct gtccacggtt aaccgacaag ccctgaggta     1920
ctacaggtgt gtggtcagcg agtcgctgaa gctcagcatc tccccgatgg tcacgctgta     1980
ctacccgacc cacgcccacc tgggcctccc ctcgccgctg ctgcacagcg ggggctggct     2040
gaacgcgtcc accgcccgcg ccttccagga ctatgccggg ctgtgcttcc aggagctggg     2100
ggacctggtg aagctctgga tcaccatcaa tgagcccaac cggctgagtg acgtctacag     2160
ccacaccagc agcgacacct accgggcagc gcacaacctg ctgatcgccc acgcctggt     2220
gtggcacctg tacgaccggc ggtaccggcc ggcgcagcgc ggggccgtgt cgctgtccct     2280
gcactcggac tgggcggagc ccgccaaccc ctacgccgac tcgcactgga aggcggccga     2340
gcgcttcctg cagttcgaaa tcgcctggtt cgccgagccg ctcttcaaga ccggggacta     2400
cccgccggcc atgagggagt acatcgcctc caagaacagg caggggctct cgcgctccac     2460
cctgccccgc ttcaccgacg aggagaggag gctggtcaag ggcgccgccg acttctacgc     2520
gctgaaccac ttcaccacca ggttcgtgat gcacgcgcgc cagaacggca gccgctacga     2580
cgcggaccgc gacgtccagt tcctgcagga catcacctgc ctgagctccc cagccgcct     2640
ggccgtcctg ccctgggggg agcgcaaggt gctcaggtgg atccagaaga actacggaga     2700
cgtggacgtg tacatcacgg ccagtggcat cgatgaccag tctctggaaa atgatgagct     2760
cagaaaatac tacttggaga atacatcca ggaggctctg aaagcacacc taattgataa     2820
agtcaaagtc aaaggctatt atgcattcaa actgactgaa gaaaaatcta aacccagatt     2880
tggattcttc acgtctgaat tcaaagctaa atcctcagtt cagctttaca acaaactgat     2940
cagcaacagt ggcttcccctt ctgagaacag gagtcctaga tgcagtgaga ctcaaagaaa     3000
cacagagtgc atggtctgct tatttcttgt gcaaaagaaa ccactgatat tctttagttg     3060
ttgcttcttc tctaccctgg ttctactttc atcgattacc attcttcata agcgaaagag     3120
```

```
aagaaaaatt tggaaagcaa agaacttaca acatatacca ttaaagtgag gccacagaaa    3180
gttcttagtg aaactgatcc tatttctgtc tgcatgatag aaagtctaaa aattcactcc    3240
agtcccaaat actggtaaca tagaagacaa tttgaaacac tagtagtaac caaggtgatg    3300
acaatcaagg tctctgctgt gtggtccaaa tgaattttcc attaggtgtt gacatcactg    3360
aatacagttt ttagatctga agactaagat ctagagagta agctaggatt atctgataca    3420
atgcttcatt aagtttaata agctgttatc catcattctt ctctggcttc cttctagaaa    3480
taccaatagc taattatagc aacttagaaa aaagtgcaac ttttgctaga ctccatagca    3540
gaaatctaaa actcttaaca ctggatattc agtgattatt ctatcacttc taacaaggtg    3600 cttttccccct ttagaagata tacaataggg taaatagtgc tcctttatca tccattccag    3660
cacttttttt ttccagcata gactcttaaa cacattgatc ctagtttttc tcaatagaaa    3720
taaaaaatca tttagaaaac atggaatttt gtgaggtctc tccttgcatt agatctgagt    3780 ttttttttaaa aaaaagactt aacttccata acccatctca tgggaagatc acaggactaa    3840
gattaaggag agttagaccc atcaactgcc tgaggagaca gcactcaacc tcacagtaca    3900
gcaaattcct tgggacaaac tgacagcaat cttccgcact tggattgttg aggcagcaca    3960
caagatctta acatacttag gaaagttaaa tattctaaaa agatgtaaag ttttatttt     4020 attatcaagt cttcaaagga ccatattatt ccataagact tgctctctcc tgagttccac    4080
tcttctgaca ctatgtgtat atggggacac tcaaactgca ccttgacatt gcaactttgg    4140
atacaattca gaatgtaaat gtttgaagga cttaaaactt tctccactgc accttttgaa    4200
gctgggatta agtaaatacg aactgggagt ttgacttttt tgaactctgt gcttgattta    4260
ttcactgtat tctaaatttt aaggaaaacc tgaatgtaaa cccattcata cccttctctt    4320
gggttagtaa acatttaacc acccatttca                                     4350
```

<210> SEQ ID NO 414
<211> LENGTH: 120
<212> TYPE: PRT
<213> ORGANISM: Artificial Sequence
<220> FEATURE:
<223> OTHER INFORMATION: 5H23v1-69

<400> SEQUENCE: 414

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Ile Tyr Pro Gly Asp Gly Ser Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120
```

<210> SEQ ID NO 415
<211> LENGTH: 710

```
<212> TYPE: PRT
<213> ORGANISM: Artificial Sequence
<220> FEATURE:
<223> OTHER INFORMATION: Human FGFR1 beta-IIIc, NP_075594.1

<400> SEQUENCE: 415
```

| | | | | | | | | | | | | | | |
|---|---|---|---|---|---|---|---|---|---|---|---|---|---|---|
| Arg | Pro | Ser | Pro | Thr | Leu | Pro | Glu | Gln | Asp | Ala | Leu | Pro | Ser | Ser | Glu |
| 1 | | | | 5 | | | | | 10 | | | | | 15 | |
| Asp | Asp | Asp | Asp | Asp | Asp | Ser | Ser | Glu | Glu | Lys | Glu | Thr | Asp |
| | | | 20 | | | | | 25 | | | | | 30 |
| Asn | Thr | Lys | Pro | Asn | Pro | Val | Ala | Pro | Tyr | Trp | Thr | Ser | Pro | Glu | Lys |
| | | 35 | | | | | 40 | | | | | 45 | | | |
| Met | Glu | Lys | Lys | Leu | His | Ala | Val | Pro | Ala | Ala | Lys | Thr | Val | Lys | Phe |
| 50 | | | | | 55 | | | | | 60 | | | | | |
| Lys | Cys | Pro | Ser | Ser | Gly | Thr | Pro | Asn | Pro | Thr | Leu | Arg | Trp | Leu | Lys |
| 65 | | | | | 70 | | | | | 75 | | | | | 80 |
| Asn | Gly | Lys | Glu | Phe | Lys | Pro | Asp | His | Arg | Ile | Gly | Gly | Tyr | Lys | Val |
| | | | | 85 | | | | | 90 | | | | | 95 | |
| Arg | Tyr | Ala | Thr | Trp | Ser | Ile | Ile | Met | Asp | Ser | Val | Val | Pro | Ser | Asp |
| | | | 100 | | | | | 105 | | | | | 110 | | |
| Lys | Gly | Asn | Tyr | Thr | Cys | Ile | Val | Glu | Asn | Glu | Tyr | Gly | Ser | Ile | Asn |
| | | 115 | | | | | 120 | | | | | 125 | | | |
| His | Thr | Tyr | Gln | Leu | Asp | Val | Val | Glu | Arg | Ser | Pro | His | Arg | Pro | Ile |
| 130 | | | | | 135 | | | | | 140 | | | | | |
| Leu | Gln | Ala | Gly | Leu | Pro | Ala | Asn | Lys | Thr | Val | Ala | Leu | Gly | Ser | Asn |
| 145 | | | | | 150 | | | | | 155 | | | | | 160 |
| Val | Glu | Phe | Met | Cys | Lys | Val | Tyr | Ser | Asp | Pro | Gln | Pro | His | Ile | Gln |
| | | | | 165 | | | | | 170 | | | | | 175 | |
| Trp | Leu | Lys | His | Ile | Glu | Val | Asn | Gly | Ser | Lys | Ile | Gly | Pro | Asp | Asn |
| | | | 180 | | | | | 185 | | | | | 190 | | |
| Leu | Pro | Tyr | Val | Gln | Ile | Leu | Lys | Thr | Ala | Gly | Val | Asn | Thr | Thr | Asp |
| | | 195 | | | | | 200 | | | | | 205 | | | |
| Lys | Glu | Met | Glu | Val | Leu | His | Leu | Arg | Asn | Val | Ser | Phe | Glu | Asp | Ala |
| 210 | | | | | 215 | | | | | 220 | | | | | |
| Gly | Glu | Tyr | Thr | Cys | Leu | Ala | Gly | Asn | Ser | Ile | Gly | Leu | Ser | His | His |
| 225 | | | | | 230 | | | | | 235 | | | | | 240 |
| Ser | Ala | Trp | Leu | Thr | Val | Leu | Glu | Ala | Leu | Glu | Glu | Arg | Pro | Ala | Val |
| | | | | 245 | | | | | 250 | | | | | 255 | |
| Met | Thr | Ser | Pro | Leu | Tyr | Leu | Glu | Ile | Ile | Ile | Tyr | Cys | Thr | Gly | Ala |
| | | | 260 | | | | | 265 | | | | | 270 | | |
| Phe | Leu | Ile | Ser | Cys | Met | Val | Gly | Ser | Val | Ile | Val | Tyr | Lys | Met | Lys |
| | | | 275 | | | | | 280 | | | | | 285 | | |
| Ser | Gly | Thr | Lys | Lys | Ser | Asp | Phe | His | Ser | Gln | Met | Ala | Val | His | Lys |
| | | 290 | | | | | 295 | | | | | 300 | | | |
| Leu | Ala | Lys | Ser | Ile | Pro | Leu | Arg | Arg | Gln | Val | Thr | Val | Ser | Ala | Asp |
| 305 | | | | | 310 | | | | | 315 | | | | | 320 |
| Ser | Ser | Ala | Ser | Met | Asn | Ser | Gly | Val | Leu | Leu | Val | Arg | Pro | Ser | Arg |
| | | | | 325 | | | | | 330 | | | | | 335 | |
| Leu | Ser | Ser | Ser | Gly | Thr | Pro | Met | Leu | Ala | Gly | Val | Ser | Glu | Tyr | Glu |
| | | | 340 | | | | | 345 | | | | | 350 | | |
| Leu | Pro | Glu | Asp | Pro | Arg | Trp | Glu | Leu | Pro | Arg | Asp | Arg | Leu | Val | Leu |
| | | 355 | | | | | 360 | | | | | 365 | | | |
| Gly | Lys | Pro | Leu | Gly | Glu | Gly | Cys | Phe | Gly | Gln | Val | Val | Leu | Ala | Glu |
| 370 | | | | | 375 | | | | | 380 | | | | | |

Ala Ile Gly Leu Asp Lys Asp Lys Pro Asn Arg Val Thr Lys Val Ala
385                 390                 395                 400

Val Lys Met Leu Lys Ser Asp Ala Thr Glu Lys Asp Leu Ser Asp Leu
            405                 410                 415

Ile Ser Glu Met Glu Met Met Lys Met Ile Gly Lys His Lys Asn Ile
                420                 425                 430

Ile Asn Leu Leu Gly Ala Cys Thr Gln Asp Gly Pro Leu Tyr Val Ile
            435                 440                 445

Val Glu Tyr Ala Ser Lys Gly Asn Leu Arg Glu Tyr Leu Gln Ala Arg
    450                 455                 460

Arg Pro Pro Gly Leu Glu Tyr Cys Tyr Asn Pro Ser His Asn Pro Glu
465                 470                 475                 480

Glu Gln Leu Ser Ser Lys Asp Leu Val Ser Cys Ala Tyr Gln Val Ala
            485                 490                 495

Arg Gly Met Glu Tyr Leu Ala Ser Lys Lys Cys Ile His Arg Asp Leu
                500                 505                 510

Ala Ala Arg Asn Val Leu Val Thr Glu Asp Asn Val Met Lys Ile Ala
            515                 520                 525

Asp Phe Gly Leu Ala Arg Asp Ile His His Ile Asp Tyr Tyr Lys Lys
    530                 535                 540

Thr Thr Asn Gly Arg Leu Pro Val Lys Trp Met Ala Pro Glu Ala Leu
545                 550                 555                 560

Phe Asp Arg Ile Tyr Thr His Gln Ser Asp Val Trp Ser Phe Gly Val
            565                 570                 575

Leu Leu Trp Glu Ile Phe Thr Leu Gly Gly Ser Pro Tyr Pro Gly Val
                580                 585                 590

Pro Val Glu Glu Leu Phe Lys Leu Leu Lys Glu Gly His Arg Met Asp
            595                 600                 605

Lys Pro Ser Asn Cys Thr Asn Glu Leu Tyr Met Met Met Arg Asp Cys
    610                 615                 620

Trp His Ala Val Pro Ser Gln Arg Pro Thr Phe Lys Gln Leu Val Glu
625                 630                 635                 640

Asp Leu Asp Arg Ile Val Ala Leu Thr Ser Asn Gln Glu Tyr Leu Asp
            645                 650                 655

Leu Ser Met Pro Leu Asp Gln Tyr Ser Pro Ser Phe Pro Asp Thr Arg
                660                 665                 670

Ser Ser Thr Cys Ser Ser Gly Glu Asp Ser Val Phe Ser His Glu Pro
            675                 680                 685

Leu Pro Glu Glu Pro Cys Leu Pro Arg His Pro Ala Gln Leu Ala Asn
    690                 695                 700

Gly Gly Leu Lys Arg Arg
705                 710

<210> SEQ ID NO 416
<211> LENGTH: 710
<212> TYPE: PRT
<213> ORGANISM: Artificial Sequence
<220> FEATURE:
<223> OTHER INFORMATION: mouse-FGFR1 (R22-E287) (Beta-IIIc,
      NP_001073378) fused to human FGFR1 (I286-R731, NP_075594)

<400> SEQUENCE: 416

Arg Pro Ala Pro Thr Leu Pro Glu Gln Asp Ala Leu Pro Ser Ser Glu
1               5                   10                  15

Asp Asp Asp Asp Asp Asp Asp Ser Ser Ser Glu Glu Lys Glu Thr Asp
            20                  25                  30

-continued

```
Asn Thr Lys Pro Asn Pro Val Ala Pro Tyr Trp Thr Ser Pro Glu Lys
        35                  40                  45

Met Glu Lys Lys Leu His Ala Val Pro Ala Ala Lys Thr Val Lys Phe
    50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
                85                  90                  95

Arg Tyr Ala Thr Trp Ser Ile Ile Met Asp Ser Val Val Pro Ser Asp
                100                 105                 110

Lys Gly Asn Tyr Thr Cys Ile Val Glu Asn Glu Tyr Gly Ser Ile Asn
                115                 120                 125

His Thr Tyr Gln Leu Asp Val Val Glu Arg Ser Pro His Arg Pro Ile
    130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
                180                 185                 190

Leu Pro Tyr Val Gln Ile Leu Lys Thr Ala Gly Val Asn Thr Thr Asp
                195                 200                 205

Lys Glu Met Glu Val Leu His Leu Arg Asn Val Ser Phe Glu Asp Ala
    210                 215                 220

Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Glu Arg Pro Ala Val
                245                 250                 255

Met Thr Ser Pro Leu Tyr Leu Glu Ile Ile Ile Tyr Cys Thr Gly Ala
                260                 265                 270

Phe Leu Ile Ser Cys Met Val Gly Ser Val Ile Val Tyr Lys Met Lys
                275                 280                 285

Ser Gly Thr Lys Lys Ser Asp Phe His Ser Gln Met Ala Val His Lys
    290                 295                 300

Leu Ala Lys Ser Ile Pro Leu Arg Arg Gln Val Thr Val Ser Ala Asp
305                 310                 315                 320

Ser Ser Ala Ser Met Asn Ser Gly Val Leu Leu Val Arg Pro Ser Arg
                325                 330                 335

Leu Ser Ser Ser Gly Thr Pro Met Leu Ala Gly Val Ser Glu Tyr Glu
                340                 345                 350

Leu Pro Glu Asp Pro Arg Trp Glu Leu Pro Arg Asp Arg Leu Val Leu
                355                 360                 365

Gly Lys Pro Leu Gly Glu Gly Cys Phe Gly Gln Val Val Leu Ala Glu
    370                 375                 380

Ala Ile Gly Leu Asp Lys Asp Lys Pro Asn Arg Val Thr Lys Val Ala
385                 390                 395                 400

Val Lys Met Leu Lys Ser Asp Ala Thr Glu Lys Asp Leu Ser Asp Leu
                405                 410                 415

Ile Ser Glu Met Glu Met Met Lys Met Ile Gly Lys His Lys Asn Ile
                420                 425                 430

Ile Asn Leu Leu Gly Ala Cys Thr Gln Asp Gly Pro Leu Tyr Val Ile
                435                 440                 445
```

Val Glu Tyr Ala Ser Lys Gly Asn Leu Arg Glu Tyr Leu Gln Ala Arg
450                 455                 460

Arg Pro Pro Gly Leu Glu Tyr Cys Tyr Asn Pro Ser His Asn Pro Glu
465                 470                 475                 480

Glu Gln Leu Ser Ser Lys Asp Leu Val Ser Cys Ala Tyr Gln Val Ala
                485                 490                 495

Arg Gly Met Glu Tyr Leu Ala Ser Lys Lys Cys Ile His Arg Asp Leu
            500                 505                 510

Ala Ala Arg Asn Val Leu Val Thr Glu Asp Asn Val Met Lys Ile Ala
        515                 520                 525

Asp Phe Gly Leu Ala Arg Asp Ile His His Ile Asp Tyr Tyr Lys Lys
530                 535                 540

Thr Thr Asn Gly Arg Leu Pro Val Lys Trp Met Ala Pro Glu Ala Leu
545                 550                 555                 560

Phe Asp Arg Ile Tyr Thr His Gln Ser Asp Val Trp Ser Phe Gly Val
                565                 570                 575

Leu Leu Trp Glu Ile Phe Thr Leu Gly Gly Ser Pro Tyr Pro Gly Val
            580                 585                 590

Pro Val Glu Glu Leu Phe Lys Leu Leu Lys Glu Gly His Arg Met Asp
        595                 600                 605

Lys Pro Ser Asn Cys Thr Asn Glu Leu Tyr Met Met Met Arg Asp Cys
610                 615                 620

Trp His Ala Val Pro Ser Gln Arg Pro Thr Phe Lys Gln Leu Val Glu
625                 630                 635                 640

Asp Leu Asp Arg Ile Val Ala Leu Thr Ser Asn Gln Glu Tyr Leu Asp
                645                 650                 655

Leu Ser Met Pro Leu Asp Gln Tyr Ser Pro Ser Phe Pro Asp Thr Arg
            660                 665                 670

Ser Ser Thr Cys Ser Ser Gly Glu Asp Ser Val Phe Ser His Glu Pro
        675                 680                 685

Leu Pro Glu Glu Pro Cys Leu Pro Arg His Pro Ala Gln Leu Ala Asn
690                 695                 700

Gly Gly Leu Lys Arg Arg
705                 710

<210> SEQ ID NO 417
<211> LENGTH: 710
<212> TYPE: PRT
<213> ORGANISM: Artificial Sequence
<220> FEATURE:
<223> OTHER INFORMATION: hamster-FGFR1 (R54-E319) (Beta-IIIc)
      XP_007610900.1 fused to human FGFR1 (I286-R731, NP_075594)

<400> SEQUENCE: 417

Arg Pro Ala Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
                20                  25                  30

Asn Thr Lys Pro Asn Pro Val Ala Pro Tyr Trp Thr Ser Pro Glu Lys
            35                  40                  45

Met Glu Lys Lys Leu His Ala Val Pro Ala Ala Lys Thr Val Lys Phe
        50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
                85                  90                  95

```
Arg Tyr Ala Thr Trp Ser Ile Ile Met Asp Ser Val Pro Ser Asp
            100                 105                 110

Lys Gly Asn Tyr Thr Cys Ile Val Glu Asn Glu Tyr Gly Ser Ile Asn
            115                 120                 125

His Thr Tyr Gln Leu Asp Val Val Glu Arg Ser Pro His Arg Pro Ile
            130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
            180                 185                 190

Leu Pro Tyr Val Gln Ile Leu Lys Thr Ala Gly Val Asn Thr Thr Asp
            195                 200                 205

Lys Glu Met Glu Val Leu His Leu Arg Asn Val Ser Phe Glu Asp Ala
210                 215                 220

Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Glu Arg Pro Ala Val
                245                 250                 255

Met Thr Ser Pro Leu Tyr Leu Glu Ile Ile Ile Tyr Cys Thr Gly Ala
            260                 265                 270

Phe Leu Ile Ser Cys Met Val Gly Ser Val Ile Val Tyr Lys Met Lys
            275                 280                 285

Ser Gly Thr Lys Lys Ser Asp Phe His Ser Gln Met Ala Val His Lys
            290                 295                 300

Leu Ala Lys Ser Ile Pro Leu Arg Arg Gln Val Thr Val Ser Ala Asp
305                 310                 315                 320

Ser Ser Ala Ser Met Asn Ser Gly Val Leu Leu Val Arg Pro Ser Arg
                325                 330                 335

Leu Ser Ser Ser Gly Thr Pro Met Leu Ala Gly Val Ser Glu Tyr Glu
            340                 345                 350

Leu Pro Glu Asp Pro Arg Trp Glu Leu Pro Arg Asp Arg Leu Val Leu
            355                 360                 365

Gly Lys Pro Leu Gly Glu Gly Cys Phe Gly Gln Val Val Leu Ala Glu
370                 375                 380

Ala Ile Gly Leu Asp Lys Asp Lys Pro Asn Arg Val Thr Lys Val Ala
385                 390                 395                 400

Val Lys Met Leu Lys Ser Asp Ala Thr Glu Lys Asp Leu Ser Asp Leu
                405                 410                 415

Ile Ser Glu Met Glu Met Met Lys Met Ile Gly Lys His Lys Asn Ile
            420                 425                 430

Ile Asn Leu Leu Gly Ala Cys Thr Gln Asp Gly Pro Leu Tyr Val Ile
            435                 440                 445

Val Glu Tyr Ala Ser Lys Gly Asn Leu Arg Glu Tyr Leu Gln Ala Arg
            450                 455                 460

Arg Pro Pro Gly Leu Glu Tyr Cys Tyr Asn Pro Ser His Asn Pro Glu
465                 470                 475                 480

Glu Gln Leu Ser Ser Lys Asp Leu Val Ser Cys Ala Tyr Gln Val Ala
                485                 490                 495

Arg Gly Met Glu Tyr Leu Ala Ser Lys Lys Cys Ile His Arg Asp Leu
            500                 505                 510
```

Ala Ala Arg Asn Val Leu Val Thr Glu Asp Asn Val Met Lys Ile Ala
            515                 520                 525

Asp Phe Gly Leu Ala Arg Asp Ile His His Ile Asp Tyr Tyr Lys Lys
530                 535                 540

Thr Thr Asn Gly Arg Leu Pro Val Lys Trp Met Ala Pro Glu Ala Leu
545                 550                 555                 560

Phe Asp Arg Ile Tyr Thr His Gln Ser Asp Val Trp Ser Phe Gly Val
                565                 570                 575

Leu Leu Trp Glu Ile Phe Thr Leu Gly Gly Ser Pro Tyr Pro Gly Val
            580                 585                 590

Pro Val Glu Glu Leu Phe Lys Leu Leu Lys Glu Gly His Arg Met Asp
        595                 600                 605

Lys Pro Ser Asn Cys Thr Asn Glu Leu Tyr Met Met Met Arg Asp Cys
    610                 615                 620

Trp His Ala Val Pro Ser Gln Arg Pro Thr Phe Lys Gln Leu Val Glu
625                 630                 635                 640

Asp Leu Asp Arg Ile Val Ala Leu Thr Ser Asn Gln Glu Tyr Leu Asp
                645                 650                 655

Leu Ser Met Pro Leu Asp Gln Tyr Ser Pro Ser Phe Pro Asp Thr Arg
            660                 665                 670

Ser Ser Thr Cys Ser Ser Gly Glu Asp Ser Val Phe Ser His Glu Pro
        675                 680                 685

Leu Pro Glu Glu Pro Cys Leu Pro Arg His Pro Ala Gln Leu Ala Asn
    690                 695                 700

Gly Gly Leu Lys Arg Arg
705                 710

<210> SEQ ID NO 418
<211> LENGTH: 710
<212> TYPE: PRT
<213> ORGANISM: Artificial Sequence
<220> FEATURE:
<223> OTHER INFORMATION: dog-FGFR1 (R22-E287) (Beta-IIIc),
      XP_005629909.1 fused to human FGFR1 (I286-R731, NP_075594)

<400> SEQUENCE: 418

Arg Pro Ala Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
            20                  25                  30

Asn Thr Lys Pro Asn Pro Val Ala Pro Tyr Trp Thr Ser Pro Glu Lys
        35                  40                  45

Met Glu Lys Lys Leu His Ala Val Pro Ala Ala Lys Thr Val Lys Phe
    50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
                85                  90                  95

Arg Tyr Ala Thr Trp Ser Ile Ile Met Asp Ser Val Val Pro Ser Asp
            100                 105                 110

Lys Gly Asn Tyr Thr Cys Ile Val Glu Asn Glu Tyr Gly Ser Ile Asn
        115                 120                 125

His Thr Tyr Gln Leu Asp Val Val Glu Arg Ser Pro His Arg Pro Ile
    130                 135                 140

Leu Gln Ala Gly Leu Pro Ala Asn Lys Thr Val Ala Leu Gly Ser Asn
145                 150                 155                 160

-continued

```
Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
                180                 185                 190

Leu Pro Tyr Val Gln Ile Leu Lys Thr Ala Gly Val Asn Thr Thr Asp
                195                 200                 205

Lys Glu Met Glu Val Leu His Leu Arg Asn Val Ser Phe Glu Asp Ala
                210                 215                 220

Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Glu Arg Pro Ala Ala
                245                 250                 255

Met Thr Ser Pro Leu Tyr Leu Glu Ile Ile Ile Tyr Cys Thr Gly Ala
                260                 265                 270

Phe Leu Ile Ser Cys Met Val Gly Ser Val Ile Val Tyr Lys Met Lys
                275                 280                 285

Ser Gly Thr Lys Lys Ser Asp Phe His Ser Gln Met Ala Val His Lys
                290                 295                 300

Leu Ala Lys Ser Ile Pro Leu Arg Arg Gln Val Thr Val Ser Ala Asp
305                 310                 315                 320

Ser Ser Ala Ser Met Asn Ser Gly Val Leu Leu Val Arg Pro Ser Arg
                325                 330                 335

Leu Ser Ser Ser Gly Thr Pro Met Leu Ala Gly Val Ser Glu Tyr Glu
                340                 345                 350

Leu Pro Glu Asp Pro Arg Trp Glu Leu Pro Arg Asp Arg Leu Val Leu
                355                 360                 365

Gly Lys Pro Leu Gly Glu Gly Cys Phe Gly Gln Val Val Leu Ala Glu
370                 375                 380

Ala Ile Gly Leu Asp Lys Asp Lys Pro Asn Arg Val Thr Lys Val Ala
385                 390                 395                 400

Val Lys Met Leu Lys Ser Asp Ala Thr Glu Lys Asp Leu Ser Asp Leu
                405                 410                 415

Ile Ser Glu Met Glu Met Met Lys Met Ile Gly Lys His Lys Asn Ile
                420                 425                 430

Ile Asn Leu Leu Gly Ala Cys Thr Gln Asp Gly Pro Leu Tyr Val Ile
                435                 440                 445

Val Glu Tyr Ala Ser Lys Gly Asn Leu Arg Glu Tyr Leu Gln Ala Arg
                450                 455                 460

Arg Pro Pro Gly Leu Glu Tyr Cys Tyr Asn Pro Ser His Asn Pro Glu
465                 470                 475                 480

Glu Gln Leu Ser Ser Lys Asp Leu Val Ser Cys Ala Tyr Gln Val Ala
                485                 490                 495

Arg Gly Met Glu Tyr Leu Ala Ser Lys Lys Cys Ile His Arg Asp Leu
                500                 505                 510

Ala Ala Arg Asn Val Leu Val Thr Glu Asp Asn Val Met Lys Ile Ala
                515                 520                 525

Asp Phe Gly Leu Ala Arg Asp Ile His His Ile Asp Tyr Tyr Lys Lys
                530                 535                 540

Thr Thr Asn Gly Arg Leu Pro Val Lys Trp Met Ala Pro Glu Ala Leu
545                 550                 555                 560

Phe Asp Arg Ile Tyr Thr His Gln Ser Asp Val Trp Ser Phe Gly Val
                565                 570                 575
```

```
Leu Leu Trp Glu Ile Phe Thr Leu Gly Gly Ser Pro Tyr Pro Gly Val
            580                 585                 590

Pro Val Glu Glu Leu Phe Lys Leu Leu Lys Glu Gly His Arg Met Asp
        595                 600                 605

Lys Pro Ser Asn Cys Thr Asn Glu Leu Tyr Met Met Met Arg Asp Cys
    610                 615                 620

Trp His Ala Val Pro Ser Gln Arg Pro Thr Phe Lys Gln Leu Val Glu
625                 630                 635                 640

Asp Leu Asp Arg Ile Val Ala Leu Thr Ser Asn Gln Glu Tyr Leu Asp
                645                 650                 655

Leu Ser Met Pro Leu Asp Gln Tyr Ser Pro Ser Phe Pro Asp Thr Arg
            660                 665                 670

Ser Ser Thr Cys Ser Ser Gly Glu Asp Ser Val Phe Ser His Glu Pro
        675                 680                 685

Leu Pro Glu Glu Pro Cys Leu Pro Arg His Pro Ala Gln Leu Ala Asn
    690                 695                 700

Gly Gly Leu Lys Arg Arg
705                 710

<210> SEQ ID NO 419
<211> LENGTH: 710
<212> TYPE: PRT
<213> ORGANISM: Artificial Sequence
<220> FEATURE:
<223> OTHER INFORMATION: rat-FGFR1 (R22-E287) (Beta-IIIc),
      XP_006253387.1 fused to human FGFR1 (I286-R731, NP_075594)

<400> SEQUENCE: 419

Arg Pro Ala Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
                20                  25                  30

Asn Thr Lys Pro Asn Pro Val Ala Pro Tyr Trp Thr Ser Pro Glu Lys
            35                  40                  45

Met Glu Lys Lys Leu His Ala Val Pro Ala Ala Lys Thr Val Lys Phe
        50                  55                  60

Lys Cys Pro Ser Ser Gly Thr Pro Ser Pro Thr Leu Arg Trp Leu Lys
65                  70                  75                  80

Asn Gly Lys Glu Phe Lys Pro Asp His Arg Ile Gly Gly Tyr Lys Val
                85                  90                  95

Arg Tyr Ala Thr Trp Ser Ile Ile Met Asp Ser Val Val Pro Ser Asp
            100                 105                 110

Lys Gly Asn Tyr Thr Cys Ile Val Glu Asn Glu Tyr Gly Ser Ile Asn
        115                 120                 125

His Thr Tyr Gln Leu Asp Val Val Glu Arg Ser Pro His Arg Pro Ile
    130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
            180                 185                 190

Leu Pro Tyr Val Gln Ile Leu Lys Thr Ala Gly Val Asn Thr Thr Asp
        195                 200                 205

Lys Glu Met Glu Val Leu His Leu Arg Asn Val Ser Phe Glu Asp Ala
    210                 215                 220
```

```
Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Arg Pro Ala Val
            245                 250                 255

Met Thr Ser Pro Leu Tyr Leu Glu Ile Ile Tyr Cys Thr Gly Ala
                260                 265                 270

Phe Leu Ile Ser Cys Met Val Gly Ser Val Ile Val Tyr Lys Met Lys
            275                 280                 285

Ser Gly Thr Lys Lys Ser Asp Phe His Ser Gln Met Ala Val His Lys
            290                 295                 300

Leu Ala Lys Ser Ile Pro Leu Arg Arg Gln Val Thr Val Ser Ala Asp
305                 310                 315                 320

Ser Ser Ala Ser Met Asn Ser Gly Val Leu Leu Val Arg Pro Ser Arg
                325                 330                 335

Leu Ser Ser Ser Gly Thr Pro Met Leu Ala Gly Val Ser Glu Tyr Glu
                340                 345                 350

Leu Pro Glu Asp Pro Arg Trp Glu Leu Pro Arg Asp Arg Leu Val Leu
            355                 360                 365

Gly Lys Pro Leu Gly Glu Gly Cys Phe Gly Gln Val Val Leu Ala Glu
370                 375                 380

Ala Ile Gly Leu Asp Lys Asp Lys Pro Asn Arg Val Thr Lys Val Ala
385                 390                 395                 400

Val Lys Met Leu Lys Ser Asp Ala Thr Glu Lys Asp Leu Ser Asp Leu
                405                 410                 415

Ile Ser Glu Met Glu Met Met Lys Met Ile Gly Lys His Lys Asn Ile
                420                 425                 430

Ile Asn Leu Leu Gly Ala Cys Thr Gln Asp Gly Pro Leu Tyr Val Ile
            435                 440                 445

Val Glu Tyr Ala Ser Lys Gly Asn Leu Arg Glu Tyr Leu Gln Ala Arg
450                 455                 460

Arg Pro Pro Gly Leu Glu Tyr Cys Tyr Asn Pro Ser His Asn Pro Glu
465                 470                 475                 480

Glu Gln Leu Ser Ser Lys Asp Leu Val Ser Cys Ala Tyr Gln Val Ala
                485                 490                 495

Arg Gly Met Glu Tyr Leu Ala Ser Lys Lys Cys Ile His Arg Asp Leu
                500                 505                 510

Ala Ala Arg Asn Val Leu Val Thr Glu Asp Asn Val Met Lys Ile Ala
            515                 520                 525

Asp Phe Gly Leu Ala Arg Asp Ile His His Ile Asp Tyr Tyr Lys Lys
            530                 535                 540

Thr Thr Asn Gly Arg Leu Pro Val Lys Trp Met Ala Pro Glu Ala Leu
545                 550                 555                 560

Phe Asp Arg Ile Tyr Thr His Gln Ser Asp Val Trp Ser Phe Gly Val
                565                 570                 575

Leu Leu Trp Glu Ile Phe Thr Leu Gly Gly Ser Pro Tyr Pro Gly Val
            580                 585                 590

Pro Val Glu Glu Leu Phe Lys Leu Leu Lys Glu Gly His Arg Met Asp
            595                 600                 605

Lys Pro Ser Asn Cys Thr Asn Glu Leu Tyr Met Met Met Arg Asp Cys
            610                 615                 620

Trp His Ala Val Pro Ser Gln Arg Pro Thr Phe Lys Gln Leu Val Glu
625                 630                 635                 640
```

```
Asp Leu Asp Arg Ile Val Ala Leu Thr Ser Asn Gln Glu Tyr Leu Asp
                645                 650                 655

Leu Ser Met Pro Leu Asp Gln Tyr Ser Pro Ser Phe Pro Asp Thr Arg
        660                 665                 670

Ser Ser Thr Cys Ser Ser Gly Glu Asp Ser Val Phe Ser His Glu Pro
            675                 680                 685

Leu Pro Glu Glu Pro Cys Leu Pro Arg His Pro Ala Gln Leu Ala Asn
        690                 695                 700

Gly Gly Leu Lys Arg Arg
705                 710

<210> SEQ ID NO 420
<211> LENGTH: 713
<212> TYPE: PRT
<213> ORGANISM: Artificial Sequence
<220> FEATURE:
<223> OTHER INFORMATION: rabbit-FGFR1 (R22-E288) (Beta-IIIc),
      XP_008272198.1 fused to human FGFR1 (I286-R731, NP_075594)

<400> SEQUENCE: 420

Arg Pro Ala Ala Pro Thr Leu Pro Glu Gln Asp Ala Leu Pro Ser Ser
1               5                   10                  15

Glu Asp Asp Asp Asp Asp Asp Ser Ser Glu Glu Lys Glu Thr
                20                  25                  30

Asp Asn Thr Lys Pro Asn Arg Met Pro Val Ala Pro Tyr Trp Thr Ser
            35                  40                  45

Pro Glu Lys Met Glu Lys Lys Leu His Ala Val Pro Ala Ala Lys Thr
        50                  55                  60

Val Lys Phe Lys Cys Pro Ser Ser Gly Thr Pro Asn Pro Thr Leu Arg
65                  70                  75                  80

Trp Leu Lys Asn Gly Lys Glu Phe Lys Pro Asp His Arg Ile Gly Gly
                85                  90                  95

Tyr Lys Val Arg Tyr Ala Thr Trp Ser Ile Ile Met Asp Ser Val Val
            100                 105                 110

Pro Ser Asp Lys Gly Asn Tyr Thr Cys Ile Val Glu Asn Glu Tyr Gly
        115                 120                 125

Ser Ile Asn His Thr Tyr Gln Leu Asp Val Val Glu Arg Ser Pro His
    130                 135                 140

Arg Pro Ile Leu Gln Ala Gly Leu Pro Ala Asn Lys Thr Val Ala Leu
145                 150                 155                 160

Gly Ser Asn Val Glu Phe Met Cys Lys Val Tyr Ser Asp Pro Gln Pro
                165                 170                 175

His Ile Gln Trp Leu Lys His Ile Glu Val Asn Gly Ser Lys Ile Gly
            180                 185                 190

Pro Asp Asn Leu Pro Tyr Val Gln Ile Leu Lys Thr Ala Gly Val Asn
        195                 200                 205

Thr Thr Asp Lys Glu Met Glu Val Leu His Leu Arg Asn Val Ser Phe
    210                 215                 220

Glu Asp Ala Gly Glu Tyr Thr Cys Leu Ala Gly Asn Ser Ile Gly Leu
225                 230                 235                 240

Ser His His Ser Ala Trp Leu Thr Val Leu Glu Ala Leu Glu Glu Arg
                245                 250                 255

Pro Ala Val Met Thr Ser Pro Leu Tyr Leu Glu Ile Ile Ile Tyr Cys
            260                 265                 270

Thr Gly Ala Phe Leu Ile Ser Cys Met Val Gly Ser Val Ile Val Tyr
        275                 280                 285
```

```
Lys Met Lys Ser Gly Thr Lys Ser Asp Phe His Ser Gln Met Ala
    290                 295                 300

Val His Lys Leu Ala Lys Ser Ile Pro Leu Arg Arg Gln Val Thr Val
305                 310                 315                 320

Ser Ala Asp Ser Ala Ser Met Asn Ser Gly Val Leu Leu Val Arg
                325                 330                 335

Pro Ser Arg Leu Ser Ser Ser Gly Thr Pro Met Leu Ala Gly Val Ser
                340                 345                 350

Glu Tyr Glu Leu Pro Glu Asp Pro Arg Trp Glu Leu Pro Arg Asp Arg
            355                 360                 365

Leu Val Leu Gly Lys Pro Leu Gly Glu Gly Cys Phe Gly Gln Val Val
            370                 375                 380

Leu Ala Glu Ala Ile Gly Leu Asp Lys Asp Lys Pro Asn Arg Val Thr
385                 390                 395                 400

Lys Val Ala Val Lys Met Leu Lys Ser Asp Ala Thr Glu Lys Asp Leu
                405                 410                 415

Ser Asp Leu Ile Ser Glu Met Glu Met Met Lys Met Ile Gly Lys His
                420                 425                 430

Lys Asn Ile Ile Asn Leu Leu Gly Ala Cys Thr Gln Asp Gly Pro Leu
            435                 440                 445

Tyr Val Ile Val Glu Tyr Ala Ser Lys Gly Asn Leu Arg Glu Tyr Leu
450                 455                 460

Gln Ala Arg Arg Pro Pro Gly Leu Glu Tyr Cys Tyr Asn Pro Ser His
465                 470                 475                 480

Asn Pro Glu Glu Gln Leu Ser Ser Lys Asp Leu Val Ser Cys Ala Tyr
                485                 490                 495

Gln Val Ala Arg Gly Met Glu Tyr Leu Ala Ser Lys Lys Cys Ile His
                500                 505                 510

Arg Asp Leu Ala Ala Arg Asn Val Leu Val Thr Glu Asp Asn Val Met
            515                 520                 525

Lys Ile Ala Asp Phe Gly Leu Ala Arg Asp Ile His His Ile Asp Tyr
            530                 535                 540

Tyr Lys Lys Thr Thr Asn Gly Arg Leu Pro Val Lys Trp Met Ala Pro
545                 550                 555                 560

Glu Ala Leu Phe Asp Arg Ile Tyr Thr His Gln Ser Asp Val Trp Ser
                565                 570                 575

Phe Gly Val Leu Leu Trp Glu Ile Phe Thr Leu Gly Gly Ser Pro Tyr
            580                 585                 590

Pro Gly Val Pro Val Glu Glu Leu Phe Lys Leu Leu Lys Glu Gly His
            595                 600                 605

Arg Met Asp Lys Pro Ser Asn Cys Thr Asn Glu Leu Tyr Met Met Met
610                 615                 620

Arg Asp Cys Trp His Ala Val Pro Ser Gln Arg Pro Thr Phe Lys Gln
625                 630                 635                 640

Leu Val Glu Asp Leu Asp Arg Ile Val Ala Leu Thr Ser Asn Gln Glu
                645                 650                 655

Tyr Leu Asp Leu Ser Met Pro Leu Asp Gln Tyr Ser Pro Ser Phe Pro
                660                 665                 670

Asp Thr Arg Ser Ser Thr Cys Ser Ser Gly Glu Asp Ser Val Phe Ser
            675                 680                 685

His Glu Pro Leu Pro Glu Glu Pro Cys Leu Pro Arg His Pro Ala Gln
            690                 695                 700
```

Leu Ala Asn Gly Gly Leu Lys Arg Arg
705                 710

<210> SEQ ID NO 421
<211> LENGTH: 465
<212> TYPE: PRT
<213> ORGANISM: Artificial Sequence
<220> FEATURE:
<223> OTHER INFORMATION: hIgK alpha-KLH VH mIgG1

<400> SEQUENCE: 421

Met Asp Met Arg Val Pro Ala Gln Leu Leu Gly Leu Leu Leu Trp
1               5                   10                  15

Leu Arg Gly Ala Arg Cys Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr Gly Tyr His Met His Trp Val Arg Gln Ala Pro Gly
        50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Lys Thr
130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Glu Thr Val Thr Cys Asn
210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Asp Ile Ser Lys Asp Asp
        275                 280                 285

Pro Glu Val Gln Phe Ser Trp Phe Val Asp Asp Val Glu Val His Thr
290                 295                 300

Ala Gln Thr Gln Pro Arg Glu Glu Gln Phe Asn Ser Thr Phe Arg Ser
305                 310                 315                 320

Val Ser Glu Leu Pro Ile Met His Gln Asp Trp Leu Asn Gly Lys Glu
                325                 330                 335

Phe Lys Cys Arg Val Asn Ser Ala Ala Phe Pro Ala Pro Ile Glu Lys
            340                 345                 350

```
Thr Ile Ser Lys Thr Lys Gly Arg Pro Lys Ala Pro Gln Val Tyr Thr
            355                 360                 365
Ile Pro Pro Lys Glu Gln Met Ala Lys Asp Lys Val Ser Leu Thr
370                 375                 380
Cys Met Ile Thr Asp Phe Phe Pro Glu Asp Ile Thr Val Glu Trp Gln
385                 390                 395                 400
Trp Asn Gly Gln Pro Ala Glu Asn Tyr Lys Asn Thr Gln Pro Ile Met
                405                 410                 415
Asp Thr Asp Gly Ser Tyr Phe Val Tyr Ser Lys Leu Asn Val Gln Lys
            420                 425                 430
Ser Asn Trp Glu Ala Gly Asn Thr Phe Thr Cys Ser Val Leu His Glu
        435                 440                 445
Gly Leu His Asn His His Thr Glu Lys Ser Leu Ser His Ser Pro Gly
    450                 455                 460
Lys
465

<210> SEQ ID NO 422
<211> LENGTH: 471
<212> TYPE: PRT
<213> ORGANISM: Artificial Sequence
<220> FEATURE:
<223> OTHER INFORMATION: hIgK alpha-KLH VH mIgG2-alpha

<400> SEQUENCE: 422

Met Asp Met Arg Val Pro Ala Gln Leu Leu Gly Leu Leu Leu Leu Trp
1               5                   10                  15
Leu Arg Gly Ala Arg Cys Gln Val Gln Leu Val Gln Ser Gly Ala Glu
            20                  25                  30
Val Lys Lys Pro Gly Ala Ser Val Lys Val Ser Cys Lys Ala Ser Gly
        35                  40                  45
Tyr Thr Phe Thr Gly Tyr His Met His Trp Val Arg Gln Ala Pro Gly
    50                  55                  60
Gln Gly Leu Glu Trp Met Gly Trp Ile Asn Pro Asn Ser Gly Gly Thr
65                  70                  75                  80
Asn Tyr Ala Gln Lys Phe Gln Gly Arg Val Thr Met Thr Arg Asp Thr
                85                  90                  95
Ser Ile Ser Thr Ala Tyr Met Glu Leu Ser Arg Leu Arg Ser Asp Asp
            100                 105                 110
Thr Ala Val Tyr Tyr Cys Ala Arg Asp Arg Gly Ser Tyr Tyr Trp Phe
        115                 120                 125
Asp Pro Trp Gly Gln Gly Thr Leu Val Thr Val Ser Ser Ala Lys Thr
    130                 135                 140
Thr Ala Pro Ser Val Tyr Pro Leu Ala Pro Val Cys Gly Asp Thr Thr
145                 150                 155                 160
Gly Ser Ser Val Thr Leu Gly Cys Leu Val Lys Gly Tyr Phe Pro Glu
                165                 170                 175
Pro Val Thr Leu Thr Trp Asn Ser Gly Ser Leu Ser Ser Gly Val His
            180                 185                 190
Thr Phe Pro Ala Val Leu Gln Ser Asp Leu Tyr Thr Leu Ser Ser Ser
        195                 200                 205
Val Thr Val Thr Ser Ser Thr Trp Pro Ser Gln Ser Ile Thr Cys Asn
    210                 215                 220
Val Ala His Pro Ala Ser Ser Thr Lys Val Asp Lys Lys Ile Glu Pro
225                 230                 235                 240
```

```
Arg Gly Pro Thr Ile Lys Pro Cys Pro Cys Lys Cys Pro Ala Pro
            245                 250                 255

Asn Leu Leu Gly Gly Pro Ser Val Phe Ile Phe Pro Pro Lys Ile Lys
        260                 265                 270

Asp Val Leu Met Ile Ser Leu Ser Pro Ile Val Thr Cys Val Val Val
        275                 280                 285

Asp Val Ser Glu Asp Asp Pro Asp Val Gln Ile Ser Trp Phe Val Asn
        290                 295                 300

Asn Val Glu Val His Thr Ala Gln Thr Gln Thr His Arg Glu Asp Tyr
305                 310                 315                 320

Asn Ser Thr Leu Arg Val Val Ser Ala Leu Pro Ile Gln His Gln Asp
                325                 330                 335

Trp Met Ser Gly Lys Glu Phe Lys Cys Lys Val Asn Asn Lys Asp Leu
            340                 345                 350

Pro Ala Pro Ile Glu Arg Thr Ile Ser Lys Pro Lys Gly Ser Val Arg
        355                 360                 365

Ala Pro Gln Val Tyr Val Leu Pro Pro Pro Glu Glu Glu Met Thr Lys
        370                 375                 380

Lys Gln Val Thr Leu Thr Cys Met Val Thr Asp Phe Met Pro Glu Asp
385                 390                 395                 400

Ile Tyr Val Glu Trp Thr Asn Asn Gly Lys Thr Glu Leu Asn Tyr Lys
                405                 410                 415

Asn Thr Glu Pro Val Leu Asp Ser Asp Gly Ser Tyr Phe Met Tyr Ser
            420                 425                 430

Lys Leu Arg Val Glu Lys Lys Asn Trp Val Glu Arg Asn Ser Tyr Ser
        435                 440                 445

Cys Ser Val Val His Glu Gly Leu His Asn His His Thr Thr Lys Ser
450                 455                 460

Phe Ser Arg Thr Pro Gly Lys
465                 470

<210> SEQ ID NO 423
<211> LENGTH: 236
<212> TYPE: PRT
<213> ORGANISM: Artificial Sequence
<220> FEATURE:
<223> OTHER INFORMATION: hIgK alpha-KLH VL mKappa

<400> SEQUENCE: 423

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Leu Thr Phe Gly Gly Gly Thr Lys Val Glu Ile
        115                 120                 125
```

```
Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
210                 215                 220

Ser Pro Ile Val Lys Ser Phe Asn Arg Asn Glu Cys
225                 230                 235

<210> SEQ ID NO 424
<211> LENGTH: 471
<212> TYPE: PRT
<213> ORGANISM: Artificial Sequence
<220> FEATURE:
<223> OTHER INFORMATION: hIgK-KLH-(VH)-hIgG1(E233A)(L235A)

<400> SEQUENCE: 424

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255
```

```
Ala Leu Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 425
<211> LENGTH: 236
<212> TYPE: PRT
<213> ORGANISM: Artificial Sequence
<220> FEATURE:
<223> OTHER INFORMATION: hIgK-KLH-(VL)-hIgK

<400> SEQUENCE: 425

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140
```

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 426
<211> LENGTH: 264
<212> TYPE: PRT
<213> ORGANISM: Artificial Sequence
<220> FEATURE:
<223> OTHER INFORMATION: Example of extracellular region of FGFR1c
      (beta-IIIc, NP_075594)

<400> SEQUENCE: 426

Arg Pro Ser Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
            20                  25                  30

Asn Thr Lys Pro Asn Pro Val Ala Pro Tyr Trp Thr Ser Pro Glu Lys
            35                  40                  45

Met Glu Lys Lys Leu His Ala Val Pro Ala Ala Lys Thr Val Lys Phe
50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
            85                  90                  95

Arg Tyr Ala Thr Trp Ser Ile Ile Met Asp Ser Val Val Pro Ser Asp
            100                 105                 110

Lys Gly Asn Tyr Thr Cys Ile Val Glu Asn Glu Tyr Gly Ser Ile Asn
            115                 120                 125

His Thr Tyr Gln Leu Asp Val Val Glu Arg Ser Pro His Arg Pro Ile
            130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
            165                 170                 175

Trp Leu Lys His Ile Glu Val Asn Gly Ser Lys Ile Gly Pro Asp Asn
            180                 185                 190

Leu Pro Tyr Val Gln Ile Leu Lys Thr Ala Gly Val Asn Thr Thr Asp
            195                 200                 205

Lys Glu Met Glu Val Leu His Leu Arg Asn Val Ser Phe Glu Asp Ala
210                 215                 220

Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Glu Arg Pro Ala Val
            245                 250                 255

Met Thr Ser Pro Leu Tyr Leu Glu
            260
```

```
<210> SEQ ID NO 427
<211> LENGTH: 354
<212> TYPE: PRT
<213> ORGANISM: Artificial Sequence
<220> FEATURE:
<223> OTHER INFORMATION: Example of extracellular region of FGFR1c
      (Alpha-IIIc, NP_056934)

<400> SEQUENCE: 427

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Arg Met
        115                 120                 125

Pro Val Ala Pro Tyr Trp Thr Ser Pro Glu Lys Met Glu Lys Lys Leu
    130                 135                 140

His Ala Val Pro Ala Ala Lys Thr Val Lys Phe Lys Cys Pro Ser Ser
145                 150                 155                 160

Gly Thr Pro Asn Pro Thr Leu Arg Trp Leu Lys Asn Gly Lys Glu Phe
                165                 170                 175

Lys Pro Asp His Arg Ile Gly Gly Tyr Lys Val Arg Tyr Ala Thr Trp
            180                 185                 190

Ser Ile Ile Met Asp Ser Val Val Pro Ser Asp Lys Gly Asn Tyr Thr
        195                 200                 205

Cys Ile Val Glu Asn Glu Tyr Gly Ser Ile Asn His Thr Tyr Gln Leu
    210                 215                 220

Asp Val Val Glu Arg Ser Pro His Arg Pro Ile Leu Gln Ala Gly Leu
225                 230                 235                 240

Pro Ala Asn Lys Thr Val Ala Leu Gly Ser Asn Val Glu Phe Met Cys
                245                 250                 255

Lys Val Tyr Ser Asp Pro Gln Pro His Ile Gln Trp Leu Lys His Ile
            260                 265                 270

Glu Val Asn Gly Ser Lys Ile Gly Pro Asp Asn Leu Pro Tyr Val Gln
        275                 280                 285

Ile Leu Lys Thr Ala Gly Val Asn Thr Thr Asp Lys Glu Met Glu Val
    290                 295                 300

Leu His Leu Arg Asn Val Ser Phe Glu Asp Ala Gly Glu Tyr Thr Cys
305                 310                 315                 320

Leu Ala Gly Asn Ser Ile Gly Leu Ser His His Ser Ala Trp Leu Thr
                325                 330                 335

Val Leu Glu Ala Leu Glu Glu Arg Pro Ala Val Met Thr Ser Pro Leu
            340                 345                 350

Tyr Glu
```

<210> SEQ ID NO 428
<211> LENGTH: 630
<212> TYPE: DNA
<213> ORGANISM: Artificial Sequence
<220> FEATURE:
<223> OTHER INFORMATION: A full length FGF21, NM_019113.2

<400> SEQUENCE: 428

| | | |
|---|---|---|
| atggactcgg acgagaccgg gttcgagcac tcaggactgt gggtttctgt gctggctggt | 60 |
| cttctgctgg agcctgcca ggcacacccc atccctgact ccagtcctct cctgcaattc | 120 |
| gggggccaag tccggcagcg gtacctctac acagatgatg cccagcagac agaagcccac | 180 |
| ctggagatca gggaggatgg gacggtgggg ggcgctgctg accagagccc cgaaagtctc | 240 |
| ctgcagctga aagccttgaa gccgggagtt attcaaatct gggagtcaa gacatccagg | 300 |
| ttcctgtgcc agcggccaga tggggccctg tatggatcgc tccactttga ccctgaggcc | 360 |
| tgcagcttcc gggagctgct tcttgaggac ggatacaatg tttaccagtc cgaagcccac | 420 |
| ggcctcccgc tgcacctgcc agggaacaag tccccacacc gggaccctgc accccgagga | 480 |
| ccagctcgct tcctgccact accaggcctg cccccgcac tccggagcc acccggaatc | 540 |
| ctggcccccc agcccccga tgtgggctcc tcggaccctc tgagcatggt gggaccttcc | 600 |
| cagggccgaa gccccagcta cgcttcctga | 630 |

<210> SEQ ID NO 429
<211> LENGTH: 209
<212> TYPE: PRT
<213> ORGANISM: Artificial Sequence
<220> FEATURE:
<223> OTHER INFORMATION: A full length FGF21, NP_061986.1

<400> SEQUENCE: 429

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

```
Pro Leu Ser Met Val Gly Pro Ser Gln Gly Arg Ser Pro Ser Tyr Ala
        195                 200                 205
Ser

<210> SEQ ID NO 430
<211> LENGTH: 124
<212> TYPE: PRT
<213> ORGANISM: Artificial Sequence
<220> FEATURE:
<223> OTHER INFORMATION: VH SEQ ID NO: 68 in U.S. Patent Publication
      20110135657

<400> SEQUENCE: 430

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Ile Met Thr Asn Met Asp Pro Val Asp Thr Ala Thr Tyr Tyr
                85                  90                  95

Cys Ala Arg Ser Val Val Thr Gly Gly Tyr Tyr Tyr Asp Gly Met Asp
            100                 105                 110

Val Trp Gly Gln Gly Thr Thr Val Thr Val Ser Ser
        115                 120

<210> SEQ ID NO 431
<211> LENGTH: 108
<212> TYPE: PRT
<213> ORGANISM: Artificial Sequence
<220> FEATURE:
<223> OTHER INFORMATION: VH SEQ ID NO: 50 in U.S. Patent Publication
      20110135657

<400> SEQUENCE: 431

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Asn Ser Asp His
                85                  90                  95

Val Val Phe Gly Gly Gly Thr Lys Leu Thr Val Leu
            100                 105
```